US010793868B2

(12) United States Patent
Li

(10) Patent No.: US 10,793,868 B2
(45) Date of Patent: Oct. 6, 2020

(54) PLANTS WITH INCREASED SEED SIZE

(71) Applicant: INSTITUTE OF GENETICS AND DEVELOPMENTAL BIOLOGY CHINESE ACADEMY OF SCIENCES, Beijing (CN)

(72) Inventor: Yunhai Li, Beijing (CN)

(73) Assignee: INSTITUTE OF GENETICS AND DEVELOPMENTAL BIOLOGY CHINESE ACADEMY OF SCIENCES, Beijing (CN)

( * ) Notice: Subject to any disclaimer, the term of this patent is extended or adjusted under 35 U.S.C. 154(b) by 69 days.

(21) Appl. No.: 15/548,398

(22) PCT Filed: Feb. 3, 2016

(86) PCT No.: PCT/GB2016/050245
§ 371 (c)(1),
(2) Date: Aug. 2, 2017

(87) PCT Pub. No.: WO2016/124918
PCT Pub. Date: Aug. 11, 2016

(65) Prior Publication Data
US 2018/0265882 A1    Sep. 20, 2018

(30) Foreign Application Priority Data
Feb. 3, 2015    (CN) ............... PCT/CN2015/072143

(51) Int. Cl.
C12N 15/82      (2006.01)
C07K 14/415     (2006.01)
(52) U.S. Cl.
CPC ........ *C12N 15/8218* (2013.01); *C07K 14/415* (2013.01); *C12N 15/8261* (2013.01)
(58) Field of Classification Search
None
See application file for complete search history.

(56) References Cited

U.S. PATENT DOCUMENTS

2005/0193443 A1    9/2005  Rock et al.
2009/0144849 A1*   6/2009  Lutfiyya ............... C07K 14/415
                                                        800/278

FOREIGN PATENT DOCUMENTS

WO    2004031349 A2    4/2004
WO    2016124918 A1    8/2016

OTHER PUBLICATIONS

GenBank Accession NP_187765, dated Aug. 20, 2002. (Year: 2002).*
Rensing et al. (Science 319.5859 (2008): 64-69). (Year: 2008).*
Phypa1_1|37177|e_gw1.135.126.1 sequence. (Year: 2008).*
Ikeda et al. (Plant and cell physiology 50.5 (2009): 970-975). (Year: 2009).*
Calderon-Villalobos et al. (Plant Physiology 141.1 (2006): 3-14). (Year: 2006).*
Hannon (Nature 418.6894 (2002): 244). (Year: 2002).*
Zhang et al. (The Plant Cell 27.3 (2015): 620-632). (Year: 2015).*
Engelhorn et al. (Development 139.14 (2012): 2566-2575). (Year: 2012).*
PCT/GB2016/050245 filed Feb. 3, 2016, "Written Opinion of the International Searching Authority", dated Feb. 3, 2016.
Yamasaki, Kazuhiko et al., "Solution Structure of the B3 DNA Binding Domain of the Arabidopsis Cold-Responsive Transcription Factor RAV1", The Plant Cell, vol. 16, pp. 3448-3459 Dec. 2004.
Zhang, Yueying et al., "Transcription Factors SOD7/NGAL2 and DPA4/NGAL3 Act Redundantly to Regulate Seed Size by Directly Repressing KLU Expression in Arabidopsis thaliana", The Plant Cell, vol. 27, pp. 620-632 Mar. 2015.
Zhang, Xiangqian et al., "Epigenetic Mutation of RAV6 Affects Leaf Angle and Seed Size in Rice", Plant Physiology, vol. 169, pp. 2118-2128 Nov. 2015.
Adamski, Nikolai M., et al., "Local Maternal Control of Seed Size by KLUH/CYP78A5-dependent growth signaling", Plant Biology, vol. 106, No. 47, pp. 20115-20120 Nov. 24, 2009.
Alvarez, John Paul et al., "The NGATHA Distal Organ Development Genes Are Essential for Style Specification in Arabidopsis", The Plant Cell, vol. 21, pp. 1373-1393 May 2009.
Anastasiou, Elena et al., "Control of Plant Organ Size by KLUH/CYP78A5-Dependent Intercellular Signaling", Developmental Cell 13, pp. 843-856 Dec. 2007.
Du, Liang et al., "The Ubiquitin Receptor DA1 Regulates Seed and Organ Size by Modulating the Stability of the Ubiquitin-Specific Protease UBP15/SOD2 in Arabidopsis", The Plant Cell, vol. 26, pp. 665-677 Feb. 2014.
Engelhorn, Julia et al., "Developmental-Related PcG Target in the APEX 4 Controls Leaf Margin Architecture in Arabidopsis thaliana", Development 139, pp. 2566-2575 May 3, 2012.
Fan, Chuchuan et al., "GS3, a Major QTL for Grain Length and Weight and Minor QTL for Grain Width and Thickness in Rice, Encodes a Putative Transmembrane Protein", Theor Appl Genet (2006) 112; pp. 1164-1171 Dec. 16, 2005.
Fang, Wenjuan et al, "Maternal Control of Seed Size by EOD3/CYP78A6 in Arabidopsis thaliana", The Plant Journal, (2012) 70, pp. 929-939 Apr. 2, 2012.
Garcia, Damien et al., "Maternal Control of Integument Cell Elongation and Zygotic Control of Endosperm Growth Are Coordinated to Determine Seed Size in Arabidopsis", The Plant Cell, vol. 17, pp. 52-60 Jan. 2005.
Ikeda, Miho et al., "A Novel Group of Transcriptional Repressors in Arabidopsis", Plant Cell Physiol, 50(5): pp. 70-975 2009.

(Continued)

*Primary Examiner* — Charles Logsdon
(74) *Attorney, Agent, or Firm* — McKee, Voorhees & Sease, PLC

(57) ABSTRACT

The invention relates to genetically modified plants with an altered seed phenotype, in particular increased seed size. The invention relates to a plant that does not produce a functional NGAL2 polypeptide or functional NGAL2 and NGAL3 polypeptides. NGAL2 and NGAL3 are members of the RAV family and comprise a B3 DNA-binding domain and a transcriptional repression motif.

16 Claims, 28 Drawing Sheets

Figure 1:
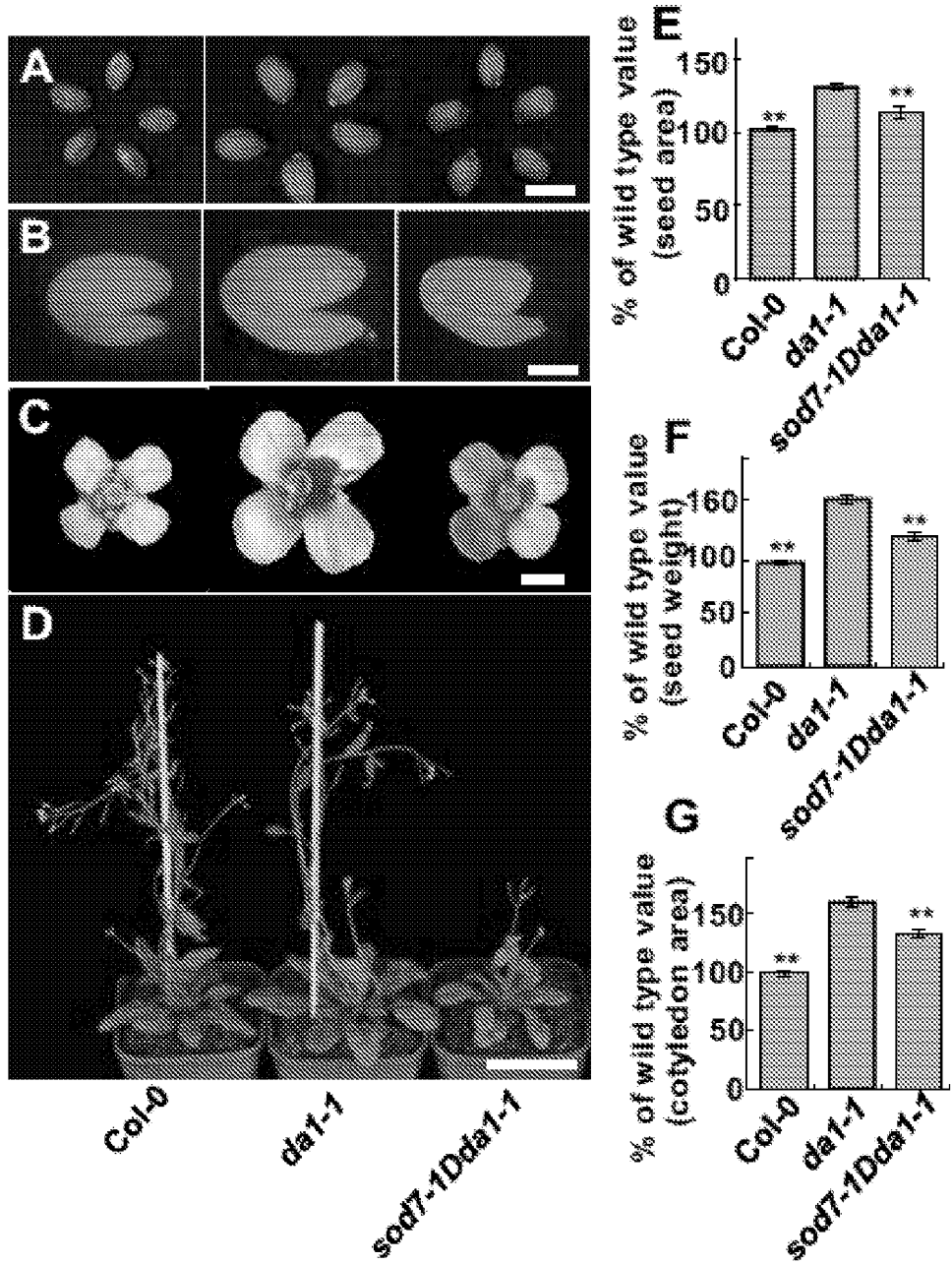

Specification includes a Sequence Listing.

(56) References Cited

OTHER PUBLICATIONS

Jofuku, K. Diane et al., "Control of Seed Mass and Seed Yield by the Floral Homeotic Gene APETALA2", PNAS, vol. 102, No. 8, pp. 3117-3122 Feb. 22, 2005.

Kagaya, Yasuaki et al., "RAV1, A Novel DNA-Binding Protein, Binds to Bipartite Recognition Sequence Through Two Distinct DNA-Binding Domains Uniquely Found in Higher Plants", Nucleic Acids Research, 1999, vol. 27, No. 2, pp. 470-478 Oct. 7, 1998.

Krizek, Beth A., "Making Bigger Plants: Key Regulators of Final Organ Size", Current Opinion in Plant Biology, www.sciencedirect.com, 12: pp. 17-22 2009.

Li, Yunhai et al., "Control of Final Seed and Organ Size by the DA1 Gene Family in Arabidopsis thaliana", Genes & Development, 22: pp. 1331-1336 Mar. 17, 2008.

Ohto, Masa-aki et al.' "Effects of APETALA2 on Embryo, Endosperm, and Seed Coat Development Determine Seed Size in Arabidopsis", Sex Plant Reprod 22: pp. 277-289 Oct. 25, 2009.

Schruff, Marie C. et al., "The Auxin Response Factor 2 gene of Arabidopsis Links Auxin Signalling, Cell Division, and the Size of Seeds and other Organs", Development 133, pp. 251-261 Nov. 1, 2005.

Song, Xian-Jun et al., "A QTL for Rice Grain Width and Weight Encodes a Previously Unknown RING-type E3 Ubiquitin Ligase", Nature Genetics, vol. 39, No. 5, pp. 623-630 Apr. 8, 2007.

Trigueros, Marina et al., "The NGATHA Genes Direct Style Development in the Arabidopsis Gynoecium", The Plant Cell, vol. 21, pp. 1394-1409 May 2009.

Xia, Tian et al., "The Ubiquitin Receptor DA1 Interacts with the E3 Ubiquitin Ligase DA2 to Regulate Seed and Organ Size in Arabidopsis", The Plant Cell, vol. 25, pp. 3347-3359 Sep. 2013.

Xu, Ran et al., "Control of Final Organ Size by Mediator Complex Subunit 25 in Arabidopsis thaliana", Development, 138, pp. 4545-4554 Aug. 15, 2011.

Mendel Biotechnology Inc., PCT/GB2016/050245 filed Apr. 26, 2016, "International Search Report" dated Apr. 26, 2016.

www.pbltechnology.com, "SOD7/NGAL3 Increased seed size, plant growth and grain yield," Tech Release, 2 pages, dated Feb. 9, 2015, updated Oct. 23, 2018.

\* cited by examiner

Fig. 12

A

```
SOD7                              1  PEK-LTPSDVGKLNRLVIPKQHAEKYFP-NNNNNGGSGDDVA----EKG-LLSFEDES
Brassica rapa2                    1  PEK-LTPSDVGKLNRLVIPKQHAE-YFP-NN---CGGCGDVTAE----EKG-LLSFEES
Glycine max.At3g11580-like1       1  PEK-LTPSDVGKLNRLVIPKQHAEKYFP-S--------DSGG-EG---KGLLLSFEDES
Glycine max At5g06250-like1       1  PEK-LTPSDVGKLNRLVIPKQHAEKYFP-SG-------DSG--EG---KGLLLSFEDES
Glycine max At2g36080-like1       1  PEK-LTPSDVGKLNRLVIPKQHAEKYFP-DSS------GGD-AAA---KGLLLSFEDES
Oryza sativa                      1  PEK-LTPSDVGKLNRLVIPKQHAE-YFP-G------------GD-GE-KGLLLSFEDES
At5g06250/NAGL3                   1  PEK-SLTPSDVGKLNRLVIPKQHAEKYFP-VLVS-SAAADT----EKG-LLSFEDES
Hordeum vulgare1                  1  S--V-TPSDVGKLNRLVIPKQHAEKYFP-D-----------AAN-EKGLLLSFE-RG
Zea mays Os02g0683500             1  S--V-TPSDVGKLNRLVIPKQHAEKYFP-D-----------AAN-EKGLLLGFEIRA
Zea mays Os02g0683500-like1       1  S--V-TPSDVGKLNRLVIPKQHAEKYFP-D-----------AAN-EKG-LLSFEIRA
Hordeum vulgare2                  1  S--V-TPSDVGKLNRLVIPKQHAEKYFP-D-----------------KGLLLSFEIRA
Gossypium hirsutum RAV            1  PEK-TPSDVGKLNRLVIPKQHAEKYFP-QS-------------G-AS-EKG-LINFEEV-
Triticum aestivum                 1  PEK-TPSDVGKLNRLV-FKQHAEK-FPIKRTP------ETP----EKG-LINFEEGE
```

```
 58  GK-VK-FRYSYWNSSQSYVLTKGWSR-VK--KRLDAGDVA-L-QERR----FDLHRLFIGW--ERGE  116  SEQ ID NO 260
 56  GK-SR-FRYSYWNSSQSYVLTKGWSR-VK--H-NAGEVV-L-QRRH----FDIR-LFIG-NRREGE  114  SEQ ID NO 261
 50  GR-SR-FRYSYWNSSQSYVLTKGWSR-VK--KRLDAGDVAL-EBRR----VDAQRLFIGWRR----  106  SEQ ID NO 262
 51  GK-SR-FRYSYWNSSQSYVLTKGWSR-VK--KRL-NGDVV-L-QRRR----DAQRLFIGWRRE--  107  SEQ ID NO 263
 51  GK-SP-FRYSYWNSSQSYVLTKGWSR-VK--KRL-NGDVV-L-QRRR----HPQFFLISCTEH--  107  SEQ ID NO 264
 48  GK-VRFRYSYW-SSQSYVLTKGWSR-VK--KRLDAGDVV-HEPRV-GSL-AAD-RLFIGC-RRGE  108  SEQ ID NO 265
 57  GR-SRFRYSYWNSSQSYVLTKGWSR-VK--R-L-EDVV-FR-QRNR--SDSR-RLFIGVRRFCQ  115  SEQ ID NO 266
 47  GK-SRFRYSYWNSSQSYV-TKGWSR-VK--KRLDAGET-VSRC-RGAAD-TRDRLFIDR-RVE   107  SEQ ID NO 267
 47  GR-SRFRYSYWNSSQSYV-TKGWSR-VK--KRLDAGET-VSRC-RGAAD-ARDRLFIDVE--    105  SEQ ID NO 268
 47  GR-SRFRYSYWNSSQSYV-TKGWSR-VK--KRLDAGEY-VSRG-RGAGDTARDRLFIDS-READ  107  SEQ ID NO 269
 47  GR-SRFRYSYWNSSQSYV-TKGWSR-VK--KRLDAGEY-VSRG-RGVGR-ARGRLFINWRR-PD  107  SEQ ID NO 270
 48  GK-VRFRYSYWNSSQSYVL-TKGWSR-VK--N-L-EGE-QSO-RST---PTEKQ-LIDVAS---  104  SEQ ID NO 271
 52  GK-VRFRYSYWNSSQSYVLTKGWSR-V--C-NGTSLL-SCSL--YEQE-QS---------    102  SEQ ID NO 272
```

B

| SEQ ID NO 164 | LOC_Os04g49230  | 1 | DRLFIDWKRR |
| SEQ ID No 165 | Bra007646       | 1 | RLFGVD-    |
| SEQ ID No 166 | sGmLoc100795470 | 1 | RLFGVD-    |
| SEQ ID No 167 | Bra000434       | 1 | RLFGVD-    |
| SEQ ID No 168 | Bra040478       | 1 | RLFGVD-    |
| SEQ ID No 169 | Bra004501       | 1 | RLFGVD-    |
| SEQ ID No 170 | Bra003482       | 1 | RLFGVD-    |
| SEQ ID No 171 | Bra014415       | 1 | RLFGVD-    |
| SEQ ID No 172 | GmLoc100818164  | 1 | RLFGVN-    |
| SEQ ID No 173 | GmLoc100802734  | 1 | RLFGVN-    |
| SEQ ID No 174 | GmLoc100781489  | 1 | RLFGVN-    |
| SEQ ID No 175 | GmLoc100778733  | 1 | RLFGVN-    |
| SEQ ID No 176 | Bra005301       | 1 | RLFGVN-    |
| SEQ ID No 177 | Bra017262       | 1 | RLFGVN-    |
| SEQ ID No 178 | GmLoc102660503  | 1 | RLFGVC-T-  |

Fig. 12
B (continued)

| SEQ ID No 179 | HvMLOC_7940 | 1 | VRLFGV.A- |
|---|---|---|---|
| SEQ ID No 180 | HvMLOC_56567 | 1 | VRLFGV.A- |
| SEQ ID No 181 | Bra038346 | 1 | VRL...F- |
| SEQ ID No 182 | TRAES3BF098300C10CFD_t1 | 1 | VRLFGV.S- |
| SEQ ID No 183 | GmLoc100776987 | 1 | VRLFGV.L- |
| SEQ ID No 184 | GmLoc100801107 | 1 | VRLFGV.L- |
| SEQ ID No 185 | os01g0693400 | 1 | VRL...L- |
| SEQ ID No 186 | GmLoc100789009 | 1 | VRLFGV.L- |
| SEQ ID No 187 | HvMLOC44012 | 1 | VRL...L- |
| SEQ ID No 188 | HvMLOC_38822 | 1 | VRL...L- |
| SEQ ID No 189 | GmLoc732601 | 1 | VRLFGVNL- |
| SEQ ID No 190 | BrLOC103849927 | 1 | VRLFGVNL- |
| SEQ ID No 191 | Bra034828 | 1 | VRLFGVNL- |
| SEQ ID No 192 | Bra005886 | 1 | VRLFGVNL- |
| SEQ ID No 193 | SOD7 | 1 | VRLFGVNL- |
| SEQ ID No 194 | At5g06250/NGAL3 | 1 | VRLGVNL- |
| SEQ ID No 195 | LOC_Os11g05740.1 | 1 | RL...L- |
| SEQ ID No 196 | GRMZM2G328742_T01 | 1 | RLFGVNL- |
| SEQ ID No 197 | os02g0683500 | 1 | VRLFGVNL- |
| SEQ ID No 198 | LOC_Os03g02900 | 1 | VRL...L- |
| SEQ ID No 199 | Os10g0537100 | 1 | VRLFGVNL- |
| SEQ ID No 200 | HvMLOC_66387 | 1 | VRLFGVNL- |
| SEQ ID No 201 | GRMZM2G102059_T01 | 1 | VRLFGVNL- |
| SEQ ID No 202 | GRMZM2G062227_T01 | 1 | VRL...L- |
| SEQ ID No 203 | GRMZM2G024948_T01 | 1 | VRLFGVNL- |
| SEQ ID No 204 | GRMZM2G142999_T01 | 1 | VRLFGVNL- |
| SEQ ID No 205 | GRMZM2G125095_T01 | 1 | VRLFGVNL- |

Fig. 13 (continued)

| Name | Pos | Sequence |
|---|---|---|
| GRMZM2G053808 | 17 | TPPSPWTITDGAISGTLPAAEAPAVHPGYPSSP----ARAARTLGGLPGLAKVESSDPGA |
| HvMLOC_67250 | 1 | |
| Os12g0157000 | 1 | |
| GmLoc100778733 | 1 | |
| Bra004901 | 1 | |
| Bra000634 | 1 | |
| Bra040478 | 1 | |
| Bra014415 | 1 | |
| Bra003482 | 1 | |
| Bra007846 | 1 | |
| GlycinemaxLoc100781489 | 1 | |
| GRMZM2G024948_T01 | 1 | |
| os02g0683500 | 1 | |
| HvMLOC_66387 | 1 | |
| os08g0581400 | 1 | |
| GRMZM2G102059_T01 | 1 | |
| Os10g0537100 | 1 | |
| GRMZM2G142999_T01 | 1 | |
| GRMZM2G125095_T01 | 1 | |
| os03g0120900 | 1 | |
| GRMZM2G098443_T01 | 1 | |
| GRMZM2G082227_T01 | 1 | |
| Os11g0156800 | 1 | |
| GRMZM2G328742_T01 | 1 | |
| GmLoc100802734 | 1 | |
| GmLoc100795478 | 1 | |
| GmLoc100818164 | 1 | |
| Bra017262 | 1 | |
| At2g36080 | 1 | |
| Bra009301 | 1 | |
| At3g11580 | 1 | |
| BraLOC103843927 | 1 | |
| BrassicarapaBra036828 | 1 | |
| At5g06250 | 1 | |
| Bra005886 | 1 | |
| GmLoc102660603 | 24 | LMOC-WQIS-G----------VESSDC-SEIK--------FAFDAVVKRAR----KEENN |
| HvMLOC_38822 | 1 | |
| os01g0693400 | 32 | APLE-RWGS-GA----------SAVVDAAEPGAEADSGSGGRVCGGGGGGAG----GAGGK |
| HvMLOC44012 | 1 | |
| HvMLOC_7940 | 39 | SLP----------VSIAD----ES----------ATSR----SASAQ |
| HvMLOC_75135 | 38 | SLP----------VAITD----ES----------VTSR----SASAQ |
| TRAECDM81004 | 38 | SLP----------VAIAD----ES----------VTS------AQ |
| HvMLOC_56367 | 38 | SLP----------VAIAD----ES----------LTS------R |
| TRAES3BF098300010CFD_t1 | 38 | SLP----------VAIAD----ES----------VTS------R |
| HvMLOC_63261 | 32 | ----------SFVA |
| TRAES3BF062700040CFD_t1 | 34 | SSP----------VL---APPRA |
| TRAES3BF062600010CFD_t1 | 34 | SSP----------VL---APPRA |
| Bra038346 | 38 | LRLN-PMRS-GG----------SNVVLQSKNG----------VD----IDSRK |
| GmLoc732601 | 22 | --PS-RVGS-VA----------SAVVDFDGCCVS----------GE----AESRK |
| GmLoc100789009 | 28 | --LS-LVGS-GA----------TAVVYPDGCCVS----------GE----AESRK |
| GmLoc100778987 | 41 | NRLC-RVGS-GA----------SAVVDSDGGGG----------GETK----VESRK |
| GmLoc100801107 | 49 | NRLC-RVGS-GA----------SAVVDPDGGGSG----------AE----VESRK |

Fig. 13 (continued)

| | | |
|---|---|---|
| GRM2M2G053008 | 74 | RLELRFREDPYCHSAFGQSRAST----GLLIRLSRRGAAAPCAHYVA------- |
| BvMLOC_97250 | 1 | ---------------------------------------------------- |
| Os12g0157000 | 1 | ---------------------------------------------------- |
| GmLoc100778733 | 1 | --------------------MELMQ-KVKG-YSGGSEKEKEEEAAKEII------ |
| Bra004301 | 1 | ---------------------------------------------------- |
| Bra000434 | 1 | ---------------------------------------------------- |
| Bra040478 | 1 | ---------------------------------------------------- |
| Bra014415 | 1 | ---------------------------------------------------- |
| Bra003482 | 1 | ---------------------------------------------------- |
| Bra007646 | 1 | ---------------------------------------------------- |
| GlycinemaxLoc100781489 | 1 | --------------------MELMQ-QVKGNYSGSSEEEK------------ |
| GRM2M2G024948_T01 | 1 | --------------------MDQFA--ASGRFSREEEADE----------- |
| os02g0683500 | 1 | --------------------MEFTT---SSRFSRE--EED----------- |
| BvMLOC_66387 | 1 | --------------------MEFTA--TSSRFSKGEEEVS----------- |
| os04g0581400 | 1 | --------------------MEFAT---TSSRFSKEEEEEEGEQEMEQEQ- |
| GRM2M2G102055_T01 | 1 | --------------------MEFAS--SSSRFSREEDEEEE-------Q-- |
| Os10g0537100 | 1 | ---------------------------------------------------- |
| GRM2M2G142999_T01 | 1 | ---------------------------------------------------- |
| GRM2M2G125099_T01 | 1 | ---------------------------------------------------- |
| os03g0120900 | 1 | ---------------------------------------------------- |
| GRM2M2G098443_T01 | 1 | ---------------------------------------------------- |
| GRM2M2G082227_T01 | 1 | ---------------------------------------------------- |
| Os11g0156000 | 1 | ---------------------------------------------------- |
| GRM2M2G328742_T01 | 1 | ---------------------------------------------------- |
| GmLoc100802734 | 1 | ---------------------------------------------------- |
| GmLoc100799478 | 1 | ---------------------------------------------------- |
| GmLoc100818164 | 1 | ---------------------------------------------------- |
| Bra017262 | 1 | ---------------------------------------------------- |
| At2g36080 | 1 | ---------------------------------------------------- |
| Bra005361 | 1 | ---------------------------------------------------- |
| At3g11580 | 1 | ---------------------------------------------------- |
| BraLOC103849927 | 1 | ---------------------------------------------------- |
| BrassicarapaBra034838 | 1 | ---------------------------------------------------- |
| At5g06350 | 1 | ---------------------------------------------------- |
| Bra003886 | 1 | ---------------------------------------------------- |
| GmLoc102660303 | 60 | AAAQKFKGVVSQQNGNNGAQIYAHQQRINLGTFKSYEAAMAYDSASINLRSGKCESNFP |
| BvMLOC_35822 | 1 | ---------------------------------------------------- |
| os01g0693400 | 77 | LPSSKFKGVVPQPNGRWGAQIYERHQRVWLGTFAGEDDAARAYDVAAQSFSGRDAVTKFE |
| BvMLOC44012 | 1 | ---------------------------------------------------- |
| BvMLOC_7940 | 58 | STSSRFKGVVPQPNGRWGAQIYERHARVWLGTFPDEDSAARAIDVAALRYRGRDAATNFP |
| BvMLOC_79135 | 57 | SASSRFKGVVPQPNGRWGSQIYERHARVWLGTFPDQDSAARAIDVASLRYRGRDAATNFP |
| TRAECHR81004 | 53 | SAPSRFKGVVPQPNGSEWGSQIYERHARVWLGTFPDQDLAASAIDVAALRYRGRDAATNFP |
| BvMLOC_56967 | 52 | SASSRFKGVVPQPNGRWGKQIYERHARVWLGTFEDQDSAARAIDVASLRYRGGDAAFNFP |
| TRABS3BF098300010CFD_t1 | 52 | SASSRFKGVVPQPNGRWGAQIYERHARVWLGTFPDQDSAARAIDVASLRYRGRDAAFNFP |
| BvMLOC_83261 | 36 | APSSRFKGVVPQPNGRWGAQIYERESRVWLGTFSDERAAACAYDVAALEFSGSDAVTRHQ |
| TRAES3BF062700040CFD_t1 | 44 | APSSRFKGVVPQPNGRWGAQIYEKHSRVWLGTFPEEDAAVRAIDVAALEFSGSDAVIRHQ |
| TRAES3BF062600010CFD_t1 | 44 | APSSRFKGVVPQPNGRWGAQIYEKHSRVWLGTFPDEDAAARAIDVAALRFGGSDAVIRHQ |
| Bra038346 | 65 | LSSSKYSGVVPQFNGSEWGAQIYVKHQRVWLGTFCDEEEAAHSYDIAARNFRGRDAVVNFP |
| GmLoc732681 | 49 | LPSSKYKGVVPQPNGRWGAQIYERHQRVWLGTFNEEDSAARAYDIAALRFRGPDAVTNPK |
| GmLoc100789009 | 55 | LPSSKYKGVVPQPNGRWGAQIYERHQRVWLGTFNEEDSAARAYDIAAKRFRGRDAVTNPK |
| GmLoc100776987 | 72 | LPSSKYKGVVPQPNGRWGSQIYERHQRVWLGTFNEEDSAARAYDVAVQSFSGKDAVTNFK |
| GmLoc100801197 | 78 | LPSSKYKGVVPQPNGRWGAQIYERHQRVWLGTFNEEDSAARAYDIAAQSFSGKDAVTNFK |

Fig. 13 (continued)

```
GRMZM2G053008              119 -------------------------------R-PTAY-FEGMADFQ----RVVPVHA
HvMLOC_57250                 1 ----------------------------------------------------------
Os12g0157000                 1 ----------------------------------------------------------
GmLoc100778733              29 ---------------TREESSPLLHQHQEAAGSNFI-NNMHHHQHHHH----------
Bra004501                    1 ----------------------------------------------------------
Bra000434                    1 ----------------------------------------------------------
Bra040478                    1 ----------------------------------------------------------
Bra014415                    1 ----------------------------------------------------------
Bra003482                    1 ----------------------------------------------------------
Bra007646                    1 ----------------------------------------------------------
GlycinemaxLoc100781489      20 -------------------------EE---------------------EAA-------
GRMZM2G024948_T01           19 -------------------------EQE--------------------DAS-------
os02g0683500                16 -------------------------EE---------------------QDE-------
HvMLOC_66387                19 -------------------------EE---------------------QEE-------
os04g0581400                29 -------------------------DEKEE------------------EAE-------
GRMZM2G102059_T01           21 -------------------------EEEEE------------------EEE-------
Os10g0537100                 1 ----------------------------------------------------------
GRMZM2G142999_T01            1 ----------------------------------------------------------
GRMZM2G125095_T01            1 ----------------------------------------------------------
os03g0120900                 1 ----------------------------------------------------------
GRMZM2G098443_T01            1 ----------------------------------------------------------
GRMZM2G082227_T01            1 ----------------------------------------------------------
Os11g0196900                 1 -------------------------------------AMNHPL-FSQEQF---QSWFWGV
GRMZM2G328742_T01            1 -------------------------------------APNHLSQSQHQHP---QAWPWGV
GmLoc100802734               1 -------------------------------------MSSINE----SPFT----LYWTNDQ
GmLoc100795470               1 -------------------------------------SINF-MDLFEPT----LNWPHPH
GmLoc100818164               1 -------------------------------------STNF-MDLP-PT----LNWPHPH
Bra017262                    1 -------------------------------------SINQ-SEFYYH----SLMWQQQQ
At2g36080                    1 -------------------------------------SINQ-SSDFHYH----SLMWQQQQ
Bra005301                    1 -------------------------------------SINQ-SSDFNYH----SLMWQQQQ
At3g11580                    1 -------------------------------------SVNE-HN-----TLS-----LH--
BraLOC103849927              1 -------------------------------------SGNE-SRDIHHPTPS-----V---
BrassicarapaBra034838        1 -------------------------------------SVNE-SNTL-----S------SH--
At5g06250                    1 -------------------------------------SVNE-STDHHSTL----LMQQQQ
Bra005886                    1 -------------------------------------SVNE-STDHHQVHHHHTLFLQ--
GmLoc102669503             120 WNDQ-----------------TVQEFQFQSHYSAETVLN-M-PDGT-PSEFAT-------
HvMLOC_38820                 1 --------------------------------------M-RKHF-PDELAQ--------
os01g0693400               137 PLAEAGE-----------EAAAELRFLATRSKASVVD-M-RKHT-PDELAQ---------
HvMLOC4012                   1 --------------------------------------M-RKHT-PDELAQ---------
HvMLOC_7940                118 CAA----------------AEAELAFLAAHSKAEIVD-M-RKHT-PDELRQ---------
HvMLOC_75135               117 CAA----------------AEAELAFLTAHSKAEIVD-M-RKHT-ADELRQ---------
TRAECDM81004               113 CAA----------------AEAELAFLGAHSKAEIVD-M-RKHT-ADELRQ---------
HvMLOC_56567               112 CVV-----------------VEAELAFLAAHSKAEIVD-M-RKQT-ADELRQ---------
TRAES3BF098300010CFD_t1    112 CAA-----------------VEGELAFLAAHSKAEIVD-M-RKQT-ADELRQ---------
HvMLOC_63261                96 RLPAAEGAGWSS-------TSELAFLADHSKAEIVD-M-RKHT-DDELRQ---------
TRAES3BF062700040CFD_t1    104 RPTAAEEAGSSSSRSELDPELGFLADHSKAEIVD-M-RKHT-DDELRQ---------
TRAES3BF062600010CFD_t1    104 RPTAAEEAGSSSSRSELDPELGFLADHSKAEIVD-M-RKHT-DDELRQ---------
Bra038346                  125 TFLASED------------DNGELCFLEAHSKAEIVD-M-RKHT-ADELAQ---------
GmLoc732601                109 PFAASD-------------DAESEFLNSHSKFEIVD-M-RKHT-DDELQQ---------
GmLoc100789009             115 PLAGAD-------------DAEAEFLSTHSKSEIVD-M-RKHT-DDELQQ---------
GmLoc100776987             132 PLSGTDD------------DDGESEFLNSHSKSEIVD-M-RKHT-NDELEQ---------
GmLoc100801107             138 PLAGADD------------DDGESEFLNSHSKFEIVD-M-RKHT-NDELEQ---------
```

```
GRMZM2G053008              338 -------SESEKWADMCNLETHPSQSFIYLQLYELKDDFIQAEIPKPSVQSVCSRSTGWFS
HvMLOC_37250               109
Os12g0157000               109 ----------NGGWSMCYSTSG-----SSYDT---S-
GmLoc100778733             273 RLYSLPSPTPPRHHEK---------LNYNNNA---------MTK-
Bra004601                  162 RFYSFPTAY----SYNL-------------YNYQQP-
Bra000434                  159 RFYSFQTACTSTSYRP--------------YNHQQP-
Bra040478                  150 RFYSFPTATTSTCYDL--------------YNHQPP-
Bra014415                  160 RFYSYPYPQIQASYER-
Bra003482                  141 RFYSFSHPQH-
Bra007646                  141 RFYSFPHPQMPTSFES-
GlycinemaxLoc100781489     213 RLYSLPPTMPPRTKHDWHFH-----HHLNYNNLF-----------T-
GRMZM2G024948_T01          226 SHYGGPHHYSPWGFGGGGG--------------------------GGGGFPM
os02g0683500               222 --------SHYAPWGIGGG--------------------------GGPFV
HvMLOC_66387               218 --------SHYSPWGLGAG--------------------------ASGFPM
os04g0581400               232 -------SPYGPWGGGA-GA-------------------------SSCRPRR
GRMZM2G102059_T01          219 -------SPYGPWGGGG--GG------------------------GAGGFPM
Os10g0537100               185 --------VPLCPWDYTTAYG----GGYGY-
GRMZM2G142999_T01          170 --------VPLCPWQDYG-
GRMZM2G125095_T01          168 --------VPLCPWQGYG-
os03g0120900               163 -------IPFAPWAHHN----G----H----------G---------AAAAA-AAAAGAPFLI
GRMZM2G098443_T01          165 -------VPYAPWAA--HAHK-----HHYPADGKT--------------KPVTPCLCATLVATEM
GRMZM2G082237_T01          164 -------VPYAPWAAAAHAHK-----HHYPAAGVG--------------AARTTTTTTTVLRHL
Os11g0156000               164 -AAQNAGKQQPWSPMCYSTS----GGGSY-
GRMZM2G328742_T01          166 -DKQQQQQPSPWSPMCYSTS----GSYSY-
GmLoc100802734             183 ---------SSASFYSAH------SP---Y-
GmLoc100795470             202 SNS-----NSGWTRGFYSAH----SP---Y-
GmLoc100818164             204 SSHNEGDVGVGWTPGFYSAH----SP---Y-
Bra017262                  157
At2g36080                  158
Bra005301                  159
At3g11580                  160 -------VHTTAYWSGLT-----TP---Y-
BraLOC103849927            160 -------VHTTAYWSGLT-----TP---Y-
BrassicarapaBra034808      153 -------ANTTAYWNGLT-----TP---Y-
At5g06250                  176 ------SS-----MGA------LS---Y-
Bra005886                  170 ------SS-----MT-
GmLoc102668503             318
HvMLOC_38822               173
os01g0893400               336
HvMLOC44012                172
HvMLOC_7940                305
HvMLOC_79135               298
TRAECIM81004               294
HvMLOC_16167               283
TRAES3BF098300010CFD_t1    283
HvMLOC_63281               280
TRAES3BF062700040CFD_t1    292
TRAES3BF062600010CFD_t1    292
Bra038346                  298
GmLoc732601                301
GmLoc100789069             307
GmLoc100776967             329
GmLoc100801107             341
```

Fig. 13 (continued)

| | | |
|---|---|---|
| GRMZM2G053808 | 392 | KDMIKTL-RLQVSIR----------------------LLSLIHNS------ |
| HvMLOC_57250 | | |
| Os12g0157000 | 127 | ----------------------------AMSTAYHSSV------ |
| GmLoc108778733 | 301 | -------P-FHHHGAGSGINATTHHYHNYHHMSSTTT---SGSAGSVFYHPS-TPPISMPLA |
| Bra004501 | 181 | ---------RHHHHSG----------YNYPQIPPS----------FGYGYLV- |
| Bra000434 | 181 | ---------RS-HHSG----------YCYPQIPPS----------FGYGYVVRS-V- |
| Bra040478 | 172 | ---------RS-SHIG----------YGYPQIPRS----------FGYGYFVSS-V- |
| Bra014415 | 176 | ---------H----------NLYHRYQRD----------IGIGYTVSS-N- |
| Bra003482 | 151 | ---------------------LYHRYQQD---------LGIGYTVSS-N- |
| Bra007646 | 157 | ---------SHH----------LYHHRFQRD----------LGIGYY- |
| GlycinemaxLoc100781469 | 243 | ---------FQQHQYQQLGAATTTHHNNYGY----------QNSGSGSLYYLPSSNSMGG------ |
| GRMZM2G024948_T01 | 252 | PPSPPATLYSK-RLR----Q--------GLDFRSNTTTYSAFTVGPQLLFFGSARMFPHHAPPP |
| os02g0683500 | 238 | QPSPPATLYEH-RLR----Q--------GLDFRAFHPA-A---AMGRQVLLFGSAR-IFPQAF-- |
| HvMLOC_86387 | 235 | PPSPPATLYEH-RLR----Q--------GFDFRGMNPSYP---TMGRQVILFGSAARMFPHGFAP |
| os04g0581400 | 251 | PPSTSI-----TAFA----R---------AST-----SATS--------TPLCRSGSHS-----SSAPQ |
| GRMZM2G102059_T01 | 238 | PPAFPATLYHHHFR----Q--------ALDFRNINAAA---AFARQLLFFGSAGMFPRASMPQ |
| Os10g0537100 | 204 | ----------------GYG---GGSTPASSHHVLFL---------- |
| GRMZM2G142999_T01 | 188 | ----------------ASAPAPNPHVLFL---------- |
| GRMZM2G128095_T01 | 178 | ----------------ASAPAPSRHVLFL---------- |
| os03g0120900 | 191 | PPSST-FIYDHHRHH----------AHAVGYDAYA---------AATSRQVLFY- |
| GRMZM2G098443_T01 | 202 | RASSS-QLSLTPSNLS---RPPQPRIASVDGAQPPPSSSPRQPQSLWC |
| GRMZM2G082227_T01 | 203 | PPSPS-PLYLDTRRR----------NVGYDAY----------GAGTRQLLFY- |
| Os11g0156000 | 186 | -----PT----------SPANSY----------AY- |
| GRMZM2G328742_T01 | 210 | -----PT----------SSPANSQH----------AYH- |
| GmLoc100802734 | 195 | -----PA----------HH----------F- |
| GmLoc100795470 | 220 | -----PT----------HH----------LKH- |
| GmLoc100818164 | 227 | -----PT----------HH |
| Bra017262 | 157 | |
| At2g36080 | 158 | |
| Bra005301 | 159 | |
| At3g11580 | 174 | ---------SQ----------VH----------AST- |
| BraLOC103849927 | 174 | ---------SQ----------VH----------AST- |
| BrassicarapaBra034828 | 167 | ---------SQ----------VH----------AST- |
| At5g06230 | 184 | ---------SQ----------IH----------ATS- |
| Bra003886 | 174 | ---------AP----------PYS- |
| GmLoc102860503 | 318 | |
| HvMLOC_38822 | 173 | |
| os01g0693400 | 336 | |
| HvMLOC44012 | 172 | |
| HvMLOC_7940 | 305 | |
| HvMLOC_75135 | 298 | |
| TRAESCHR1004 | 294 | |
| HvMLOC_58567 | 293 | |
| TRAES3BF098300010CFD_t1 | 293 | |
| HvMLOC_63261 | 288 | |
| TRAES3BF062700040CFD_t1 | 292 | |
| TRAES3BF062600010CFD_t1 | 292 | |
| Bra038346 | 298 | |
| GmLoc732801 | 301 | |
| GmLoc100789009 | 307 | |
| GmLoc100776987 | 325 | |
| GmLoc100801107 | 341 | |

Fig. 13 (continued)

```
GRMZM2G053008            414  ----------EAKNLLRNAHELIER--SKKQEALSRSELSISYNDA--DQVSAAHTGI----------
HvMLOC_57250                  
Os12g0157600             137  --------------------------------------DDHSDHAGSRA-----
GmLoc100778733           351  SKQTLNTRQ----------QQQQQQQQBGAGNVSLSPMIIDSVPVAHHLHKQQHHGGXSSG----
Bra004501                204  -------------------------------DQRAVVADPLVIESVPVMHGG--A----------
Bra000434                206  -------------------------------DQRAVVADPLVIESVPVMMKGG--A----------
Bra040478                197  -------------------------------DQRAVVADPLVIESVPVMMRGS--A----------
Bra014415                196  -------------------------------ERYD----PTAVIESVPVIMQRR--A----------
Bra003482                169  -------------------------------ERND----PTAVIESVPLIMQRPAA---------
Bra007646                175  -------------------------------------PTAVIESVPVIMQREEA----------
GlycinemaxLoc100781489   284  --------------------GDQNLQGRGSNIVPMIIDSVPVNVAHHNNRHQNGG----------
GRMZM2G024948_T01        303  QF---------RFFSLPLHHYTVQP-SAAGVTAASRFVLLDSVPVIESF-----------
os03g0683500             283  -L---------LARAPSPLHHBYTLQP-SGDGVRAAGSFVVLDSVPVIESP-----------
HvMLOC_66367             284  LL---------VPRPPPLHFTYQQQGSDAGGSVTAGSFVVLDSVPVIESP-----------
os04g0581400             285  GRGFISTRPCHRRRRHLRLLT-NSTLRCTTRAF-----------
GRMZM2G102059_T01        287  QQ---QFPPPRPPLRSIMLVQ-FSPAFPTASVPMLLDSVPLVNSF-----------
Os10g0537100             221  --------RPQV---------------------PAAVVLESVPVKVAATSAVQ----------
GRMZM2G142999_T01        193  --------RPQV---------------------PAAVVLESVPVPVAASAV----------
GRMZM2G129095_T01        191  --------RPQV---------------------PAAVVLTSVPVRVAASAV----------
os03g0120900             225  --------RPLPPQQ------------------QHEPAVVLESVPVRMTAGE----A---EP--
GRMZM2G088443_T01        246  ---------RSC---------------------QPQPRRYA---DV-------
GRMZM2G082227_T01        234  ---------RPK---Q-----------------QPSTTVKLDSVPVRLFPTPGQHA---EP--
Os11g0156000             198  --------RRAADHDH-----------------GDHHEAGES---PSD
GRMZM2G328742_T01        223  --------PKSADHDH-----------------SNNHQHAGES---QSD
GmLoc100802734           208  --------PFPYQ--------------------FHSLRAPGGGSGQNE
GmLoc100795470           227  --------HQPSPYQ------------------QQHDCLKAGRGSQGQNQ
GmLoc100818184           231  --------HRPSPYKH-----------------QQDDSLHAVRGSQGQNQ
Bra017262                157  ----------SNSSL------------------QY--YPHAG--AQA---
At2g36080                158  ----------SNASL------------------QY--YPHAG--AQA---
Bra005301                159  ----------SNASL------------------QY--YPHAG--VQA---
At3g11580                181  ----------TVPN-IH----------------QE--YSHYG--AVVDHA
BraLOC103849927          181  ----------SSYPN-IH---------------QE--YSHYG--AVA---
BrassicarapaBra034828    174  ----------SSYPNNIH---------------QE--YSHYG--PVA---
At5g06250                191  ----------NYSNPFSH---------------SS--YSHYG--AAVATA
Bra005886                179  ----------NYSNPAH----------------SK--YSHYG--AAVATA
GmLoc102660503           318  ----------GSEE-------------------GED
HvMLOC_38822             173  
os01g0693400             336  
HvMLOC44012              172  
HvMLOC_7940              389  
HvMLOC_75135             298  
TRAESCIN81004            294  
HvMLOC_56567             293  
TRAES3BF088300010CFD_t1  293  
HvMLOC_63261             280  
TRAES3BF062700040CFD_t1  282  
TRAES3BF066600010CFD_t1  282  
Bra038346                298  
GmLoc732601              301  
GmLoc100789009           307  
GmLoc100776987           325  
GmLoc100801107           341  
```

Fig. 13 (continued)

Fig. 13 (continued)

```
GRMZM2G053008           488  ----------DSP----------   ----PMADDIKEPTLG---DSYAFGSGFSNG
HvMLOC_57250                 .............................................
Os01g0157000            181  YAA---VSTVNY SV-------   ------------------------------
GmLoc100728733          482  ---S-SMANSNSQPPLQLIREDTLSSSS------ARPGD---QRGVGEPSMLFD DPSLQ
Bra004501               261  --G-DASPSSS QLRLGSSEKDD-----------------FSKKGKSSLPFD DQ--
Bra000434               274  --G-GASPSSS QLRLGSSEKDN-----------------LPKKGKSSLPFN DQ--
Bra040478               255  GGG-GASPSSS QLRLGSSCKDDN----------------FSKKGKSSLPFD DQ---
Bra014615               267  GV---SMAGVGSPLQLRIVSSDGDDQSLVARGAARVDEDRHLFT-RKGKSSLSFD DK---
Bra003482               238  GV--SMASVGS LQLRIVSSD---DESLVAMEAASVDKDRHLFT-RKGKSSLSFT DRK--
Bra007646               240  GV--SMAGVGS LQLRIVSSD---DESLVAMEGATVDEDRRLFTTRKGKSSLSFD DI---
GlycinemaxLoc100781189  378  KQR-LRV------PVPVPLEDPLSSSA--AAAARFG----DHKGASTGTSLLFD DPSLQ
GRMZM2G024948_T01       378  GWD-QRTFTLR LELPRNG---GESSA--ASSPSSS---SSSKRKARSALDLD ----
os02g0683300            365  AWM-RRDFTLR LELFPKHKGABSSA--ASSPSSS---SSSKRDAHSALDLD ----
HvMLOC_66367            368  AWS-PRDKTLR LEFPSHGA------S--ASSPSSS---SSSKRKAHSGLDLD ----
os04g0581400                 .............................................
GRMZM2G102059_T01       366  GWD-RFGF-LRE ESPQR----GAKSSA-ASSPSSS----SSSKRKAHSSLDLD ----
Os10g0537100            278  -AS-RTAA-SS LQLPSS-------------SSSTS---SSTAGRKMCSLDLG ----
GRMZM2G142999_T01       243  -RG-RAAS-TT LQLPSF-------------SSSTS---SSTAGRDVCCLDLG ----
GRMZM2G125095_T01       242  -R------YP-ST LQLPSS-------------SSSTS---SSTYGRDVRSLDLG ----
os03g0120900            284  -------YAPP------PLPSP----------P-SSS---SSSGKAHCSLNLD ----
GRMZM2G088443_T01            .............................................
GRMZM2G082027_T01       298  --WR-TSAP------PTQQA---------S-SSS---SYSSGKARCSLNLD ----
Os11g0156000            264  SSYAAMS----A---------V---------PSYWGN---------S-----
GRMZM2G328742_T01       291  PYA----------------------YNNWGS------PYQHDEEI---
GmLoc100802734          269  --------QTSS---------YSSSSN-----------PHHEM PQQF-
GmLoc100789470          303  TQGTDH-SKHNF QQ-QP---------SNSNPS-----------PHHHM KEQFY
GmLoc100818164          308  TQGTDIKSHLNF QQQQT---------SNSKPP-----------PHHHM KEQFY
Bra017262               312  ---NHD---QFR P--KP-----------FPP--------PYYMG SFTGD
At2g36080               313  ---NHD---QFRF QQQH------------YPP--------PYYMG SFTGD
Bra003301               314  ---SHD---QFH PQ-QR------------YPP--------PYYMG SFTGD
At3g11580               232  ---RPDVYNDQH ------Y------------YST-------PKPKN SFAGE
BraLOC103649927         239  ---CPDSYNGQH ------Y------------YST-------PDPRN SFAGK
BrassicarapaBra038828   223  ---CPDAYNGQH ------Y------------YST-------PHPKN SFAGK
At5g08250               258  ----PDGYYGQN ------Y------------YYS-------HPKNM ILTLL
Bra005886               247  ---RQDSYYDQH ------N------------YYT-------PHSSAS-----
GsLoc102660503               .............................................
HvMLOC_38822            219  V-A-APTRARA KRRCV---------------DFALTYR ATTPQ
os01g0693400            373  A-A-TTPPQARA KRQCI---------------ELALV-------
BvMLOC44012             208  V-K-PP-PPKVA KRQCI---------------ELALA-------
BvMLOC_7940             334  ------EQR KRQSV--------------AKS-QK---SPA
HvMLOC_75135            327  ------ELGFPE KRQSV--------------AKGCGRM---NYI
TRAECH81004             323  ------EQGFPE LKKQCV-------------PLPHGQR---SPA
HvMLOC_56567            322  ------EQGPGK KFQCH--------------AHGQH----SPA
TRAES3BF098300010CFD_t1 324  ------RQCLQE KRQCV--------------APGQH----SPA
HvMLOC_83261                 .............................................
TRAES3BF062700040CFD_t1      .............................................
TRAES3BF062600010CFD_t1      .............................................
Bra038316               329  ----SSRDVH ALRCS---------------KKS-------
GmLoc732601             330  ----KRKEHE AFECS---------------KKL-------
GmLoc100789009          341  ----KRKEHE AFECS---------------KKL-------
GmLoc100776987          363  ----KRKEHE SLECS---------------KKP-------
GmLoc100801107          380  ----KRKEHE SLECS---------------KKP-------
```

Fig. 13 (continued)

```
GRMZM2G053068              511 VLEEVLRSLPLQEDGQKEL-CDAFIHADASB
HvMLOC_97250                   ........................................
Os12g0137000                   ........................................
GmLoc100778733             489 YRQ-------------------------------------
Bra004981                      ........................................
Bra000434                      ........................................
Bra040478                      ........................................
Bra014415                      ........................................
Bra003482                      ........................................
Bra007646                      ........................................
GlycinemaxLoc100781489     417 YHRH------------------------------------
GRMZM2G024948_T01              ........................................
os02g0683800                   ........................................
HvMLOC_66387                   ........................................
os04g0581400                   ........................................
GRMZM2G102059_T01              ........................................
Os10g0537100                   ........................................
GRMZM2G142999_T01              ........................................
GRMZM2G125095_T01              ........................................
os03g0120900                   ........................................
GRMZM2G098443_T01              ........................................
GRMZM2G082227_T01              ........................................
Os11g0156000                   ........................................
GRMZM2G328742_T01              ........................................
GmLoc100802734                 ........................................
GmLoc100795470             336 YT--------------------------------------
GmLoc100818164             343 YT--------------------------------------
Bra017262                  237 VRQTSS-Q-------QG-----------------------
At2g36080                  240 MNRTS-----------------------------------
Bra005301                  240 VRQTRS-P-------QG-----------------------
At3g11580                  258 ALRQVGDG-------RG-----------------------
BraLOC103849927            259 AMRQVGDG-------PR-----------------------
BrassicarapaBra034828      249 AMRQVGDG-------RG-----------------------
At5g06250                  283 ........................................
Bra005686                      ........................................
GmLoc102660505                 ........................................
HvMLOC_38822               248 CPRSPDQL-------BGVQAAGSTFAL-------------
os01g0693400                   ........................................
HvMLOC44013                    ........................................
HvMLOC_7940                352 ---------------L-GAFVL------------------
HvMLOC_75135               350 CYSIG----------TI-GPIMLN----------------
TRAECIN81004               346 ---------------L-GAFVL------------------
HvMLOC_96967               343 ---------------L-GDFAL------------------
TRAES3BF098300010CFD_t1    345 ---------------L-GAFAL------------------
HvMLOC_63261                   ........................................
TRAES3BF062700040CFD_t1        ........................................
TRAES3BF062600010CFD_t1        ........................................
Bra038346                  348 ------A--------II-MAL-------------------
GmLoc732601                346 ------K--------VI-GAL-------------------
GmLoc100789009             357 ------K--------VI-GAL-------------------
GmLoc100776987             379 ------K--------II-GAL-------------------
GmLoc100801107             398 ------K--------II-GAL-------------------
```

Figure 14

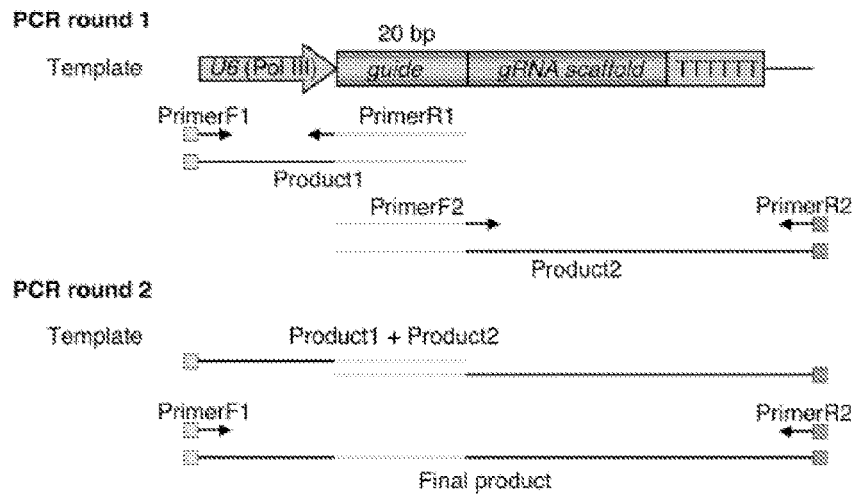

gRNA sequence (SEQ ID NO: 146)

gacggccagtgccaagcttCTCGGATCCACTAGTAACGGCCGCCAGTGTGCTGGAATTGCCCTTGGATCA
TGAACCAACGGCCTGGCTGTATTTGGTGGTTGTGTAGGGAGATGGGGAGAAGAAAAGCCCGATT
CTCTTCGCTGTGATGGGCTGGATGCATGCGGGGGAGCGGGAGGCCCAAGTACGTGCACGGTGAG
CGGCCCACAGGGCGAGTGTGAGCGCGAGAGGCGGGAGGAACAGTTTAGTACCACATTGCCCAG
CTAACTCGAACGCGACCAACTTATAAACCCGCGCGCTGTCGCTTGTGTGGGAAGGAAGAGAC
AGATTGGTTTTAGAGCTAGAAATAGCAAGTTAAAATAAGGCTAGTCCGTTATCAACTTGAAAA
AGTGGCACCGAGTCGGTGCTTTTTTTGTCCCTTCGAAGGGCAATTCTGCAGATATCCATCACACT
GGCGGCCGCTCGAGGTCGaagcttgcatgcctgcagg os11g01560000
A-R1
GGACTGGGGTTGCTCCTGGGACACAAGCGACAGCGCGCGGG (SEQ ID NO: 147)
A-F2
CCCAGGAGCAACCCCAGTCCGTTTTAGAGCTAGAAATAGCA (SEQ ID NO: 148)
B-R1
TGCTATTTCTAGCTCTAAAACACACAAGCGACAGCGCGCGGG (SEQ ID NO: 149)
B-F2
GCCCCTGACGCCCAGTGACGGTTTTAGAGCTAGAAATAGCA (SEQ ID NO: 150)

Os12g0157000
C-R1
GGGGGTGCCCCTGGGCGAGAACACAAGCGACAGCGCGCGGG (SEQ ID NO: 152)
C-F2
TCTCGCCCAGGGGCACCCCCGTTTTAGAGCTAGAAATAGCA (SEQ ID NO: 153)
D-R1
CTCGTAGTGGTGGTGGTAGTACACAAGCGACAGCGCGCGGG (SEQ ID NO: 154)
D-F2
ACTACCACCACCACTACGAGGTTTTAGAGCTAGAAATAGCA (SEQ ID NO: 155)

PLANTS WITH INCREASED SEED SIZE

FIELD OF THE INVENTION

The invention relates to transgenic plants with improved growth and yield-related traits, in particular increased seed size. Also within the scope of the invention are related methods, uses, isolated nucleic acids and vector constructs.

INTRODUCTION

The ever-increasing world population and the dwindling supply of arable land available for agriculture fuels research towards increasing the efficiency of agriculture and providing food security. Conventional means for crop and horticultural improvements utilise selective breeding techniques to identify plants having desirable characteristics. However, such selective breeding techniques have several drawbacks, namely that these techniques are typically labour intensive and result in plants that often contain heterogeneous genetic components that may not always result in the desirable trait being passed on from parent plants. Advances in molecular biology have allowed mankind to modify the germplasm of animals and plants. Genetic engineering of plants entails the isolation and manipulation of genetic material (typically in the form of DNA or RNA) and the subsequent introduction of that genetic material into a plant. Such technology has the capacity to deliver crops or plants having various improved economic, agronomic or horticultural traits, including increased yield. There are a number of methods that can be used, for example genome editing (using CRISPR or TALEN) or mutagenesis.

A trait of particular economic interest is increased seed size. Seed size is an important agronomic trait which increased crop yield, and is also a key ecological trait that influences many aspects of a species' regeneration strategy, such as seedling survival rates and seed dispersal syndrome (Harper et al., 1970; Westoby et al., 2002; Moles et al., 2005; Fan et al., 2006; Orsi and Tanksley, 2009; Gegas et al., 2010). Although the size of seeds is one of the most important agronomic traits in plants, the genetic and molecular mechanisms that set the final size of seeds are almost unknown. In higher plants, seed development starts with a double fertilization process, in which one of the two haploid pollen nuclei fuses with the haploid egg cell to produce the diploid embryo, while the other sperm nucleus fuses with the diploid central cell to form the triploid endosperm (Lopes and Larkins, 1993). The integuments surrounding the ovule are maternal tissues and form the seed coat after fertilization. Therefore, the size of the seed is the result of the growth of the embryo, the endosperm and the maternal tissues. However, the genetic and molecular mechanisms setting the limits of seed growth are almost unknown in plants.

Several factors that function maternally to regulate seed size have been identified in *Arabidopsis*. For example, TRANSPARENT TESTA GLABRA 2 (TTG2) influences seed growth by increasing cell elongation in the maternal integuments (Garcia et al., 2005; Ohto et al., 2009), while APETALA2 (AP2) may control seed growth by limiting cell elongation in the maternal integuments (Jofuku et al., 2005; Ohto et al., 2005; Ohto et al., 2009). By contrast, AUXIN RESPONSE FACTOR 2 (ARF2) acts maternally to control seed growth by restricting cell proliferation (Schruff et al., 2006). Similarly, the ubiquitin receptor DA1 acts synergistically with the E3 ubiquitin ligases DA2 and EOD1/BB to control seed size by limiting cell proliferation in the maternal integuments (Li et al., 2008; Xia et al., 2013). Mutations in the suppressor of da1-1 (SOD2), which encodes the ubiquitin-specific protease (UBP15), suppress the large seed phenotype of da1-1 (Du et al., 2014). DA1 physically associates with UBP15/SOD2 and modulates the stability of UBP15. These studies show that the ubiquitin pathway plays an important part in the maternal control of seed size. KLU/CYTOCHROME P450 78A5 (CYP78A5) regulates seed size by increasing cell proliferation in the maternal integuments of ovules (Adamski et al., 2009). KLU has also been suggested to generate mobile plant-growth substances that promote cell proliferation (Anastasiou et al., 2007; Adamski et al., 2009). By contrast, overexpression of CYP78A6/EOD3 increases both cell proliferation and cell elongation in the integuments, resulting in large seeds (Fang et al., 2012). Seed size is also determined by zygotic tissues. Several factors have been described to influence seed size via the zygotic tissues in *Arabidopsis*, including HAIKU1 (IKU1), IKU2, MINISEED3 (MINI3) and SHORT HYPOCOTYL UNDER BLUE1 (SHB1) (Garcia et al., 2003; Luo et al., 2005; Zhou et al., 2009; Wang et al., 2010; Kang et al., 2013). iku and mini3 mutants form small seeds due to precocious cellularization of the endosperm (Garcia et al., 2003; Luo et al., 2005; Wang et al., 2010). SHB1 associates with MINI3 and IKU2 promoters and regulates expression of MINI3 and IKU2 (Zhou et al., 2009; Kang et al., 2013). ABA INSENSITIVE5 (AB15) has been recently described to repress the expression of SHB1 (Cheng et al., 2014), and MINI3 has been reported to activate expression of the cytokinin oxidase (CKX2) (Li et al., 2013), suggesting the roles of phytohormones in regulating endosperm growth. In addition, the endosperm growth is influenced by parent-of-origin effects (Scott et al., 1998; Xiao et al., 2006).

The invention is aimed at providing plants with improved yield traits that are beneficial to agriculture.

SUMMARY OF THE INVENTION

In a first aspect, the invention relates to a plant generated that does not produce a functional NGAL2 polypeptide or does not produce functional NGAL2 and NGAL3 polypeptides.

In another aspect, the invention relates to a method for altering a plant phenotype comprising reducing or abolishing the expression of a nucleic acid sequence encoding a NGAL2 polypeptide or reducing or abolishing the activity of a NGAL2 or reducing or abolishing the expression of a nucleic acid sequences encoding NGAL2 and NGAL3 polypeptides or reducing or abolishing the activity of a NGAL2 and NGAL3 polypeptide relative to a control plant.

In another aspect, the invention relates to a method for making a plant with an altered phenotype comprising reducing or abolishing the expression of a nucleic acid sequence encoding a NGAL2 polypeptide or reducing or abolishing the activity of a NGAL2 or reducing or abolishing the expression of a nucleic acid sequences encoding NGAL2 and NGAL3 polypeptides or reducing or abolishing the activity of a NGAL2 and NGAL3 polypeptide relative to a control plant.

In another aspect, the invention relates to a plant obtained or obtainable any method described above.

In another aspect, the invention relates to an isolated nucleic acid comprising a sequence comprising or consisting of SEQ ID NO: 1 or 2 or a functional variant or homologue thereof.

In another aspect, the invention relates to a vector comprising an isolated nucleic acid described above.

In another aspect, the invention relates to a silencing nucleic acid construct targeting sequence comprising or consisting of SEQ ID NO: 1, 2 or 3 or a functional variant, part or homologue thereof.

FIGURES

The invention is further described in the following non-limiting figures.

FIG. 1. Isolation of a suppressor of da1-1 (sod7-1D).

(A) Seeds from wild-type, da1-1 and sod7-1D da1-1 plants (from left to right). (B) Mature embryos of the wild type, da1-1 and sod7-1D da1-1 (from left to right). (C) Flowers from wild-type, da1-1 and sod7-1D da1-1 plants (from left to right). (D) 30-day-old plants of the wild type, da1-1 and sod7-1D da1-1 (from left to right). (E) Projective area of wild-type, da1-1 and sod7-1D da1-1 seeds. (F) Weight of wild-type, da1-1 and sod7-1D da1-1 seeds. (G) Cotyledon area of 10-d-old wild-type, da1-1 and sod7-1D da1-1 seedlings. Values (E-G) are given as mean±SD relative to the respective wild-type values, set at 100%. **, $P<0.01$ compared with da1-1 (Student's t-test). Bars=0.5 mm in (A), 0.2 mm in (B), 1 mm in (C) and 5 cm in (D).

Figure 2:
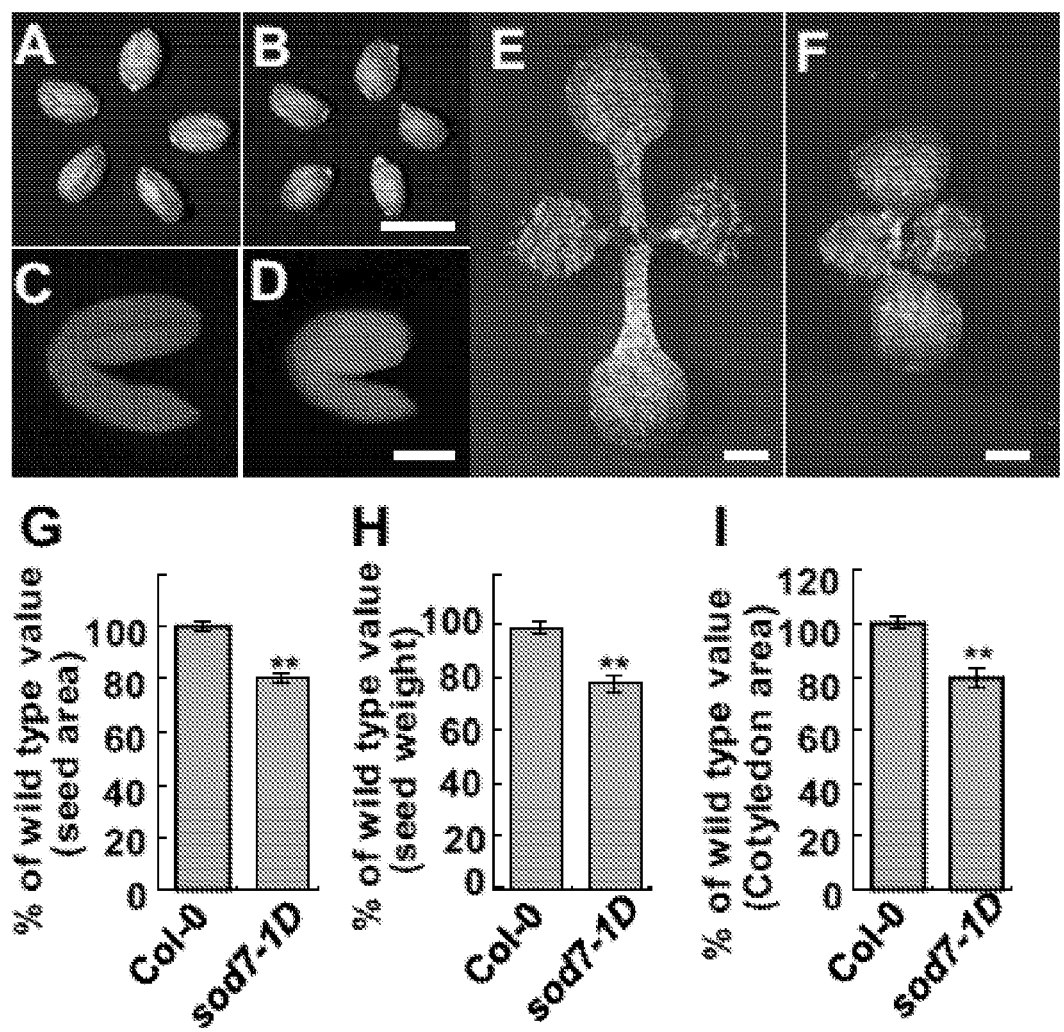

FIG. 2. Seed and organ size in the sod7-1D mutant.

(A and B) Seeds of Col-0 (A) and sod7-1D (B). (C and D) Mature embryos of Col-0 (C) and sod7-1D (D). (E and F) 10-day-old seedlings of Col-0 (E) and sod7-1D (F). (G) Projective area of Col-0 and sod7-1D seeds. (H) Weight of Col-0 and sod7-1D seeds. (I) Cotyledon area of 10-day-old Col-0 and sod7-1D seedlings. Values (G-I) are given as mean±SD relative to the respective wild-type values, set at 100%. **, $P<0.01$ compared with the wild type (Student's t-test). Bars=0.5 mm in (A) and (B), 0.2 mm in (C) and (D), and 1 mm in (E) and (F).

Figure 3:
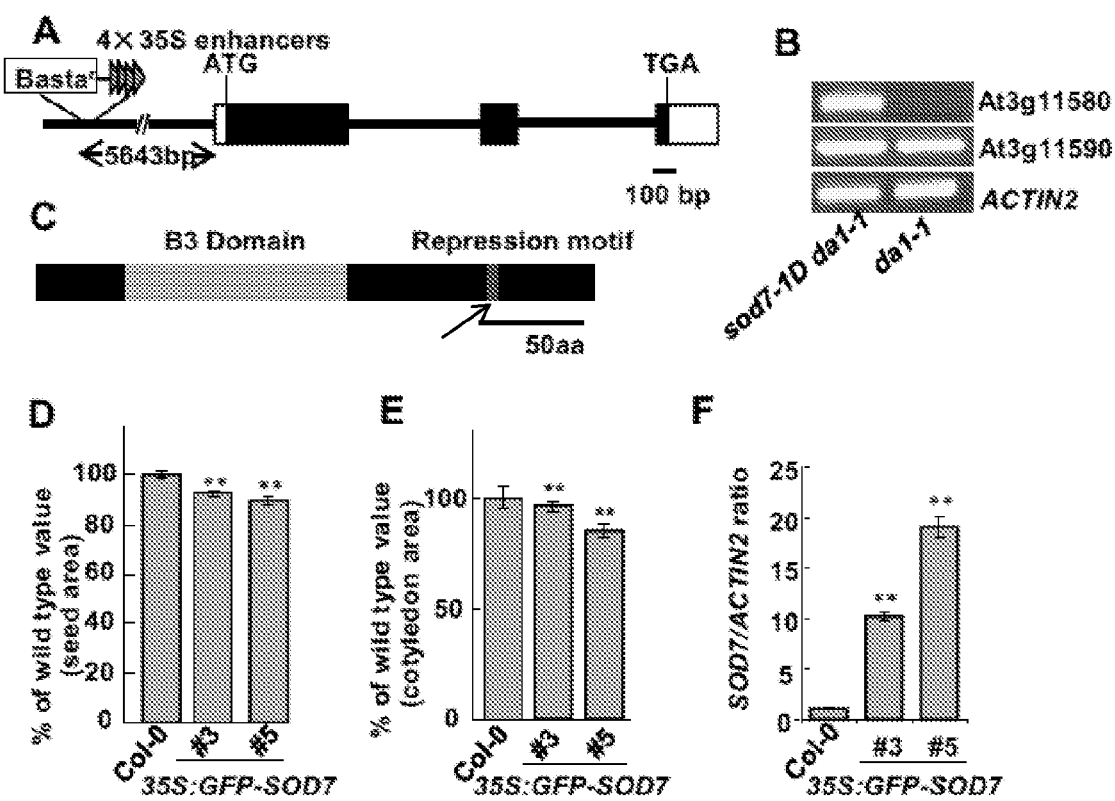

FIG. 3. Cloning of the SOD7 gene.

(A) Structure of the T-DNA insertion in the sod7-1D mutant. (B) Expression levels of At3g11580 (SOD7) and At3g11590 in da1-1 and sod7-1D da1 seedlings.

(C) The SOD7 protein contains a B3 DNA binding domain (second domain in lighter shading) and a transcriptional repression motif (small light box in darker shading, marked with an arrow). (D) Projective area of Col-0, 35S:GFP-SOD7#3 and 35S:GFP-SOD7#5 seeds. (E) Cotyledon area of 10-day-old Col-0, 35S:GFP-SOD7#3 and 35S:GFP-SOD7#5 seedlings. (F) Expression levels of SOD7 in Col-0, 35S:GFP-SOD7#3 and 35S:GFP-SOD7#5 seedlings. Values (D-F) are given as mean±SD relative to the respective wild-type values, set at 100%. **, $P<0.01$ compared with the wild type (Student's t-test).

Figure 4:
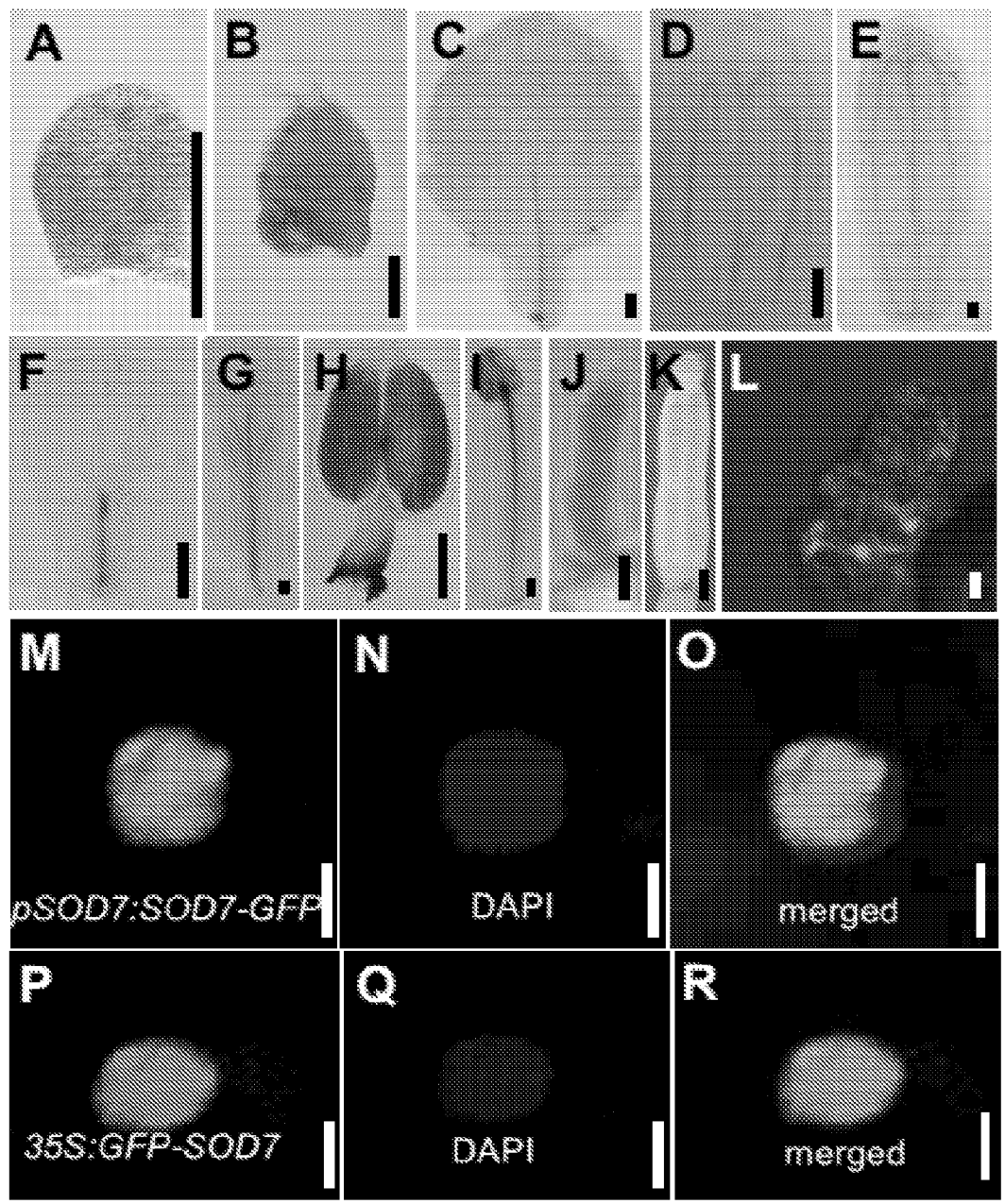

FIG. 4. Expression pattern and subcellular localization of SOD7.

(A-K) SOD7 expression activity was monitored by pSOD7:GUS transgene expression. Histochemical analysis of GUS activity in the developing leaves (A, B and C), the developing sepals (D, E), the developing petals (F, G), the developing stamens (H, I), and the developing carpels (J, K). (L) GFP florescence of SOD7-GFP in a young ovule of pSOD7:SOD7-GFP transgenic plants. (M-O) GFP fluorescence of SOD7-GFP (M), DAPI staining (N), and merged (O) images are shown. Epidermal cells in pSOD7:SOD7-GFP leaves were used to observe GFP signal. (P-R) GFP fluorescence of GFP-SOD7 (P), DAPI staining (Q), and merged (R) images are shown. Epidermal cells in 35S:GFP-SOD7 leaves were used to observe GFP signal. Bars=100 μm in (A-K), 10 μm in (L), and 2 μm in (M-R).

Figure 5:
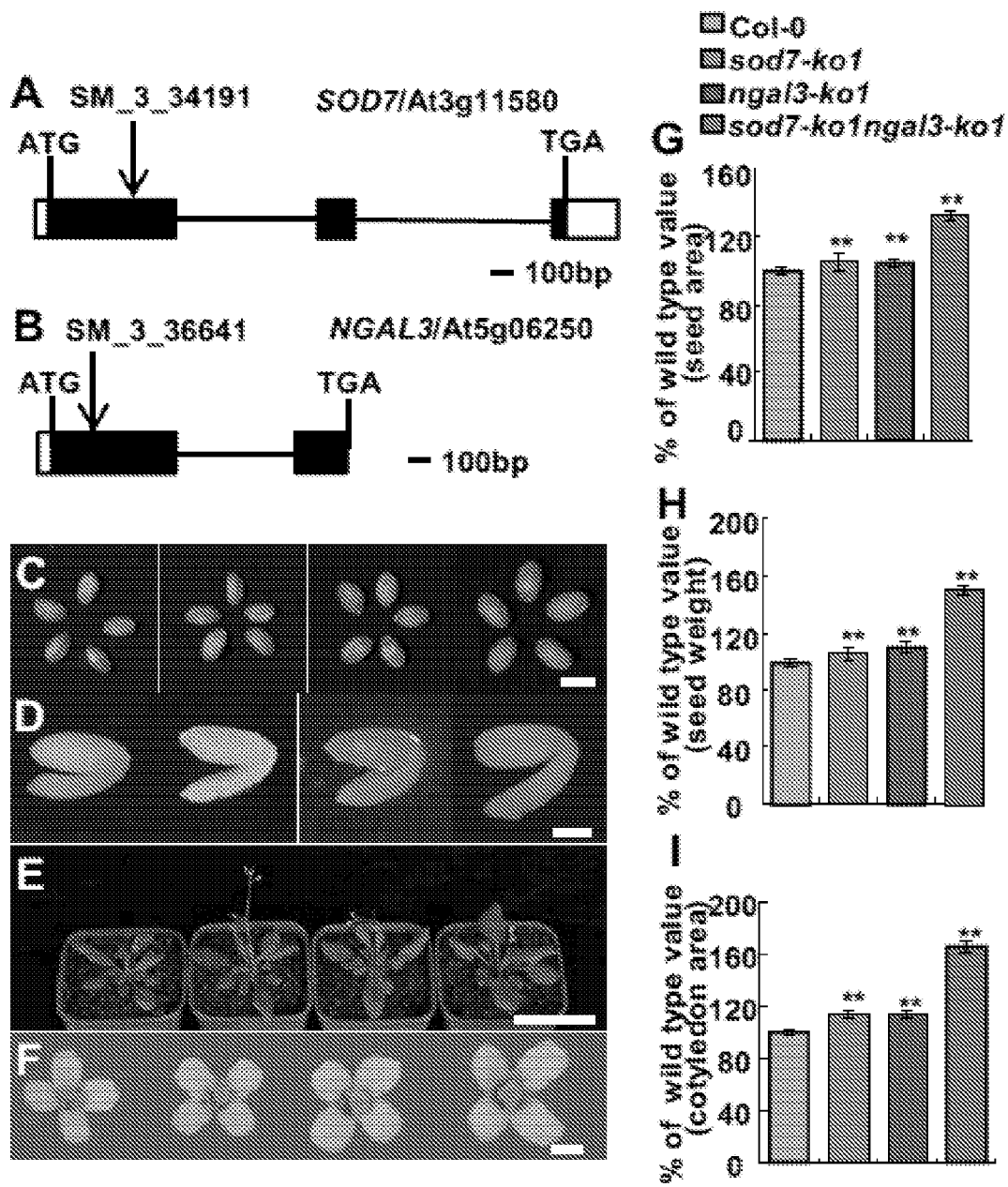

FIG. 5. SOD7 acts redundantly with NGAL3 to control seed size.

(A) The SOD7 gene structure. The start codon (ATG) and the stop codon (TGA) are shown. Closed boxes indicate the coding sequence, and the line between boxes indicates intron. The T-DNA insertion site (sod7-ko1) in the SOD7 gene was indicated. (B) The NGAL3 gene structure. The start codon (ATG) and the stop codon (TGA) are shown. Closed boxes indicate the coding sequence, and the line between boxes indicates intron. The T-DNA insertion site (ngal3-ko1) in the NGAL3 gene was indicated. (C) Seeds from Col-0, sod7-ko1, ngal3-ko1 and sod7-ko1 ngal3-ko1 plants (from left to right). (D) Mature embryos of Col-0, sod7-ko1, ngal3-ko1 and sod7-ko1 ngal3-ko1 (from left to right). (E) 25-day-old plants of Col-0, sod7-ko1, ngal3-ko1 and sod7-ko1 ngal3-ko1 (from left to right). (F) Flowers of Col-0, sod7-ko1, ngal3-ko1 and sod7-ko1 ngal3-ko1 (from left to right). (G) Projective area of Col-0, sod7-ko1, ngal3-ko1 and sod7-ko1 ngal3-ko1 seeds. (H) Weight of Col-0, sod7-ko1, ngal3-ko1 and sod7-ko1 ngal3-ko1 seeds. (I) Cotyledon area of Col-0, sod7-ko1, ngal3-ko1 and sod7-ko1 ngal3-ko1 seedlings. Values (G-I) are given as mean±SD relative to the respective wild-type values, set at 100%. **, $P<0.01$ compared with the wild type (Col-0) (Student's t-test). Bars=0.5 mm in (C), 0.2 mm in (D), 5 cm in (E), and 1 mm in (F).

Figure 6:
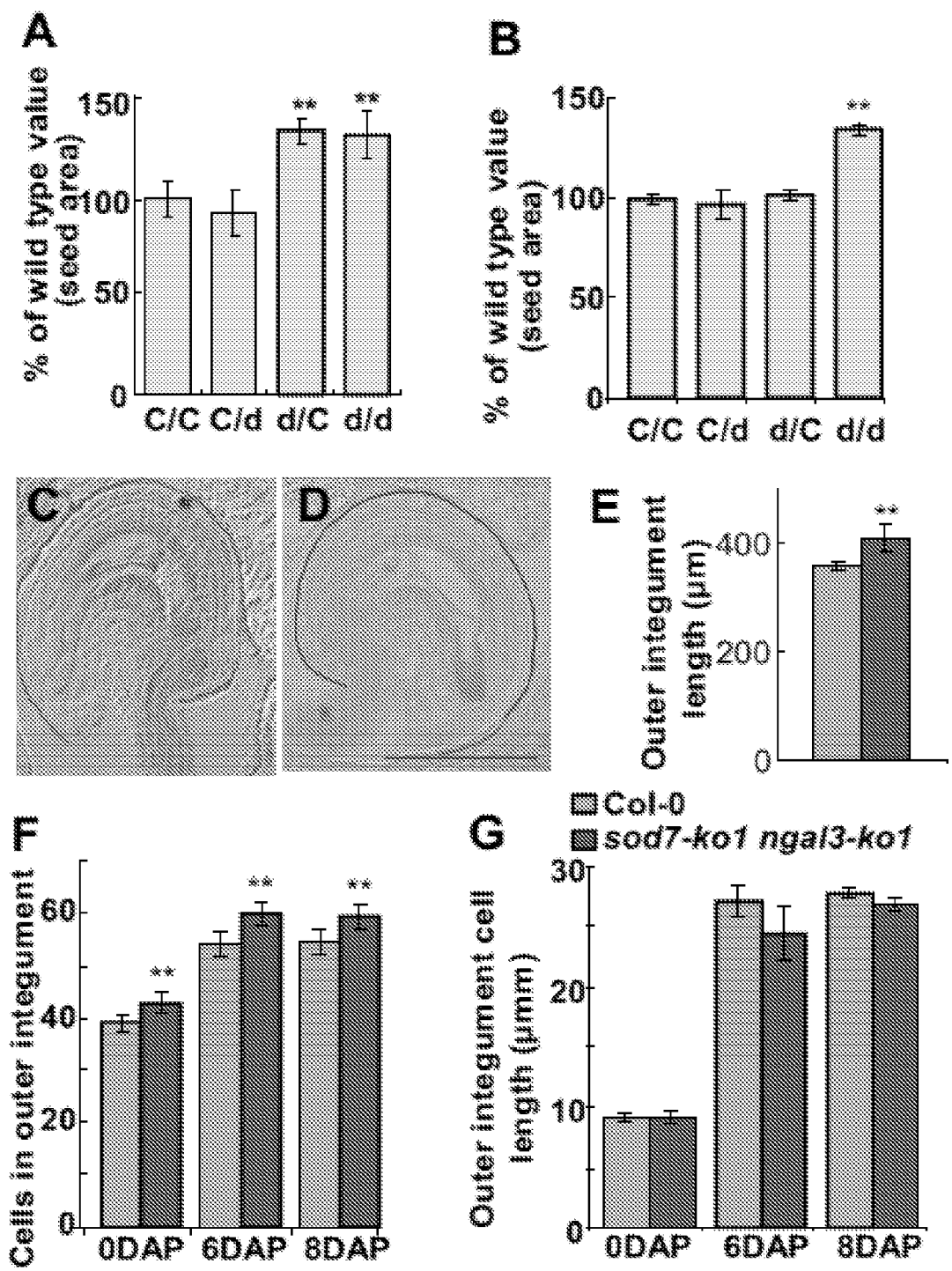

FIG. 6. SOD7 acts maternally to determine seed size.

(A) Projective area of Col-0×Col-0 (C/C) F1, Col-0× sod7-ko1 ngal3-ko1 (C/d) F1, sod7-ko1 ngal3-ko1×Col-0 (d/C) F1 and sod7-ko1 ngal3-ko1×sod7-ko1 ngal3-ko1 (d/d) F1 seeds. Values are given as mean±SD relative to the respective wild-type values, set at 100%. (B) Projective area of Col-0×Col-0 (C/C) F2, Col-0×sod7-ko1 ngal3-ko1 (C/d) F2, sod7-ko1 ngal3-ko1×Col-0 (d/C) F2 and sod7-ko1 ngal3-ko1×sod7-ko1 ngal3-ko1 (d/d) F2 seeds. Values are given as mean±SD relative to the respective wild-type values, set at 100%. (C and D) Mature ovules of Col-0 (C) and sod7-ko1 ngal3-ko1 (D). (E) Outer integument length of mature Col-0 (lighter bar to the left) and sod7-ko1 ngal3-ko1 (darker bar to the right) ovules. Values are given as mean±SD. (F) The number of cells in the outer integuments of Col-0 and sod7-ko1 ngal3-ko1 at 0, 6 and 8 DAP. Values are given as mean±SD. (G) The length of cells in the outer integuments of Col-0 and sod7-ko1 ngal3-ko1 at 0, 6 and 8 DAP. Values are given as mean±SD. **, $P<0.01$ compared with the wild type (Col-0) (Student's t-test). Bars=50 μm in (C) and (D).

Figure 7:
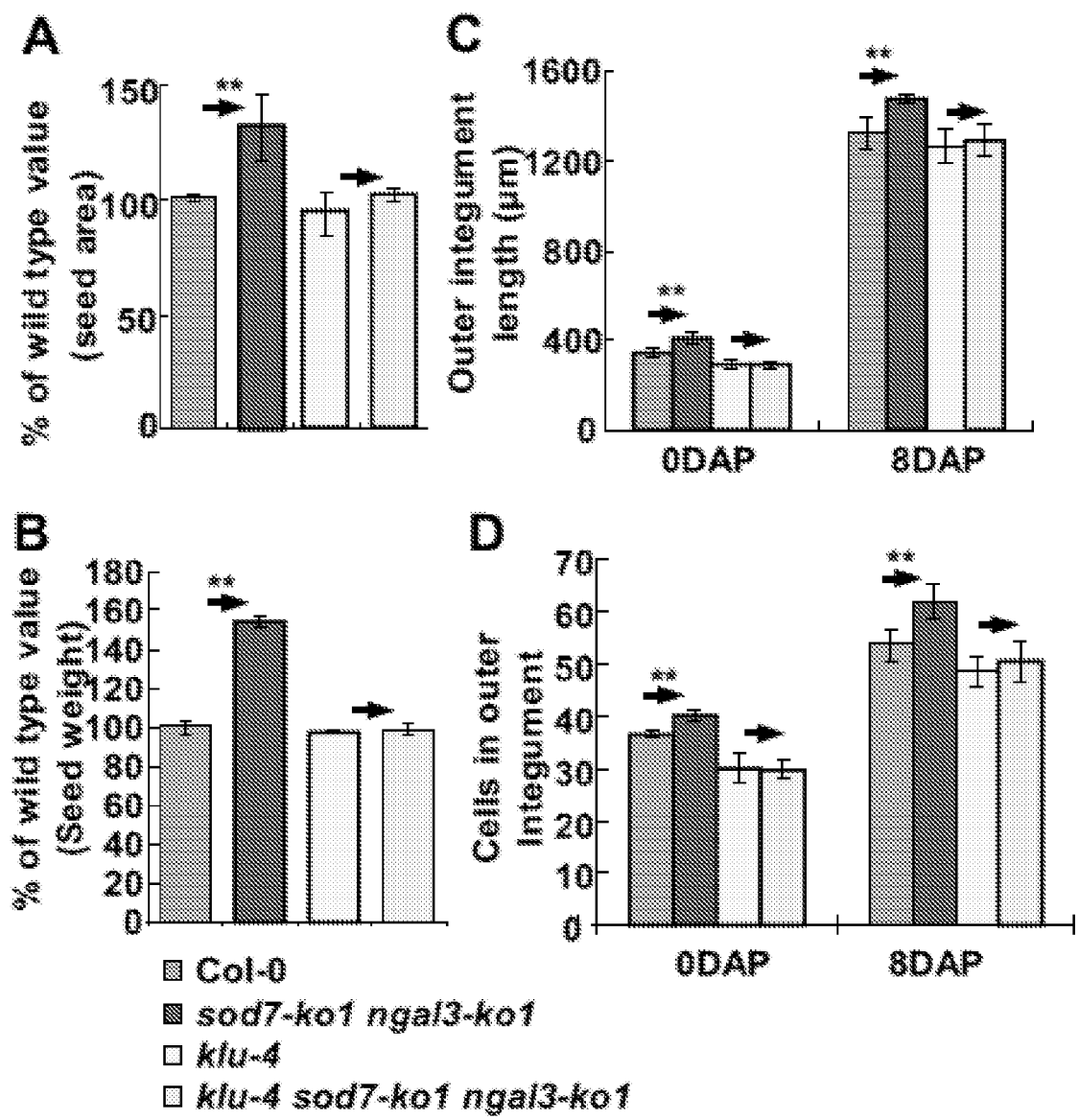

FIG. 7. klu-4 is epistatic to sod7-ko1 ngal3-ko1 with respect to seed size.

(A) Seed area of Col-0, klu-4, sod7-ko1 ngal3-ko1 and klu-4 sod7-ko1 ngal3-ko1 (from left to right). Values are given as mean±SD relative to the respective wild-type values, set at 100%. (B) Seed weight of Col-0, klu-4, sod7-ko1 ngal3-ko1 and klu-4 sod7-ko1 ngal3-ko1 (from left to right). Values are given as mean±SD relative to the respective wild-type values, set at 100%. (C) The outer integument length of Col-0, klu-4, sod7-ko1 ngal3-ko1 and klu-4 sod7-ko1 ngal3-ko1 (from left to right). ngal3-ko1 at 0 and 8 DAP. Values are given as mean±SD. (D) The number of cells in the outer integuments of Col-0, klu-4, sod7-ko1 ngal3-ko1 and klu-4 sod7-ko1 ngal3-ko1 (from left to right) at 0 and 8 DAP. Values are given as mean±SD. **, $P<0.01$ compared with their respective controls (Student's t-test).

Figure 8:
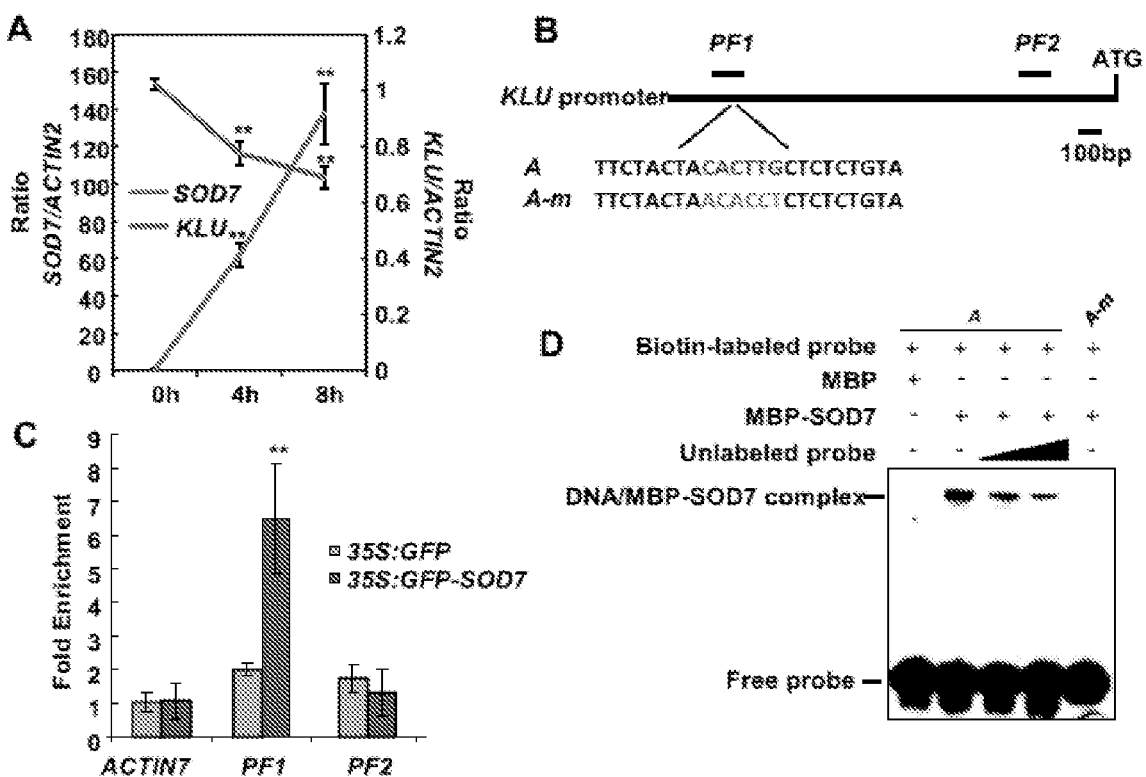

FIG. 8. SOD7 directly binds to the promoter of KLU and represses the expression of KLU.

(A) Expression dynamics of SOD7 and KLU in pER8-SOD7 transgenic plants treated with β-estradiol for 0, 4 and 8 hours. Means were calculated from three biological samples. Values are given as mean±SD. , P<0.01, compared with the expression level of KLU and SOD7 at 0 hour, respectively (Student's t-test). (B) A 2-kb promoter region of KLU upstream of its ATG codon contains a CACTTG sequence. PF1 and PF2 represent PCR fragments used for ChIP-quantitative PCR analysis. A and A-m indicate the wild-type probe and the mutated probe used in the EMSA essay, respectively. (C) ChIP-qPCR analysis shows that SOD7 binds to the promoter fragment PF1 of KLU. Chromatin from 35S:GFP and 35S:GFP-SOD7 transgenic plants was immunoprecipitated by anti-GFP, and the enrichment of the fragments was determined by quantitative real-time PCR. The ACTIN7 promoter was used as a negative control. The fold enrichment was normalized to the ACTIN7 amplicon, set at 1. Means were calculated from three biological samples. Values are given as mean±SD. , P<0.01, compared with 35S:GFP transgenic plants (Student's t-test). (D) Direct interaction between SOD7 and the KLU promoter determined by EMSA. The biotin-labeled probe A and MBP-SOD7 formed the DNA-protein complex, but the mutated probe A-m and MBP-SOD7 did not form the DNA-protein complex. The retarded DNA-protein complex was reduced by competition using the unlabeled probe A.

Figure 9:
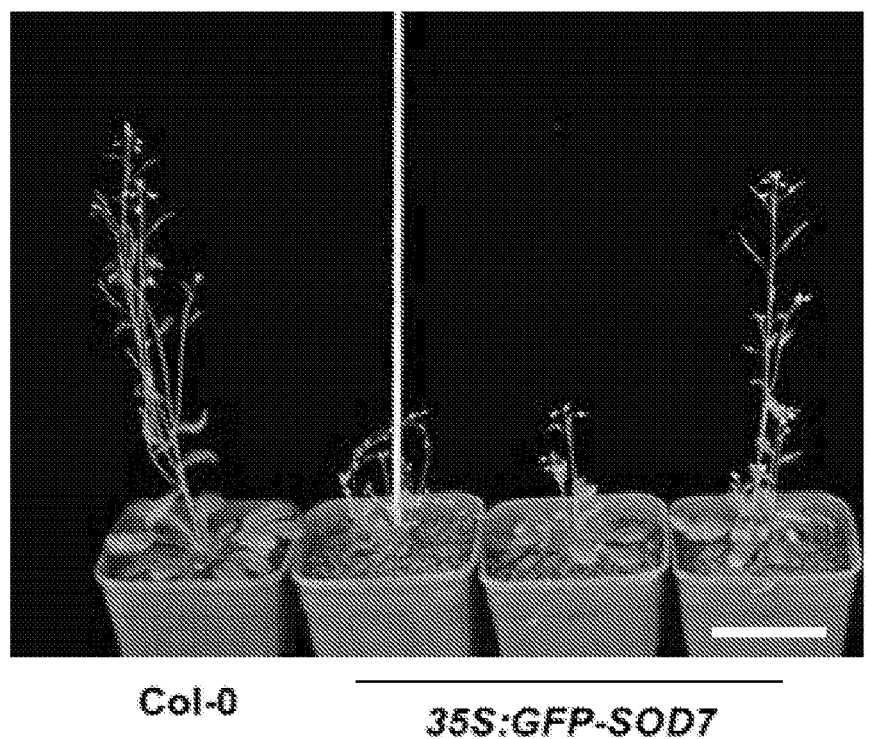

FIG. 9. The organ size phenotype of 35S:GFP-SOD7 transgenic plants. Overexpression of SOD7 results in small plants compared with the wild type. Bar=5 cm.

Figure 10:
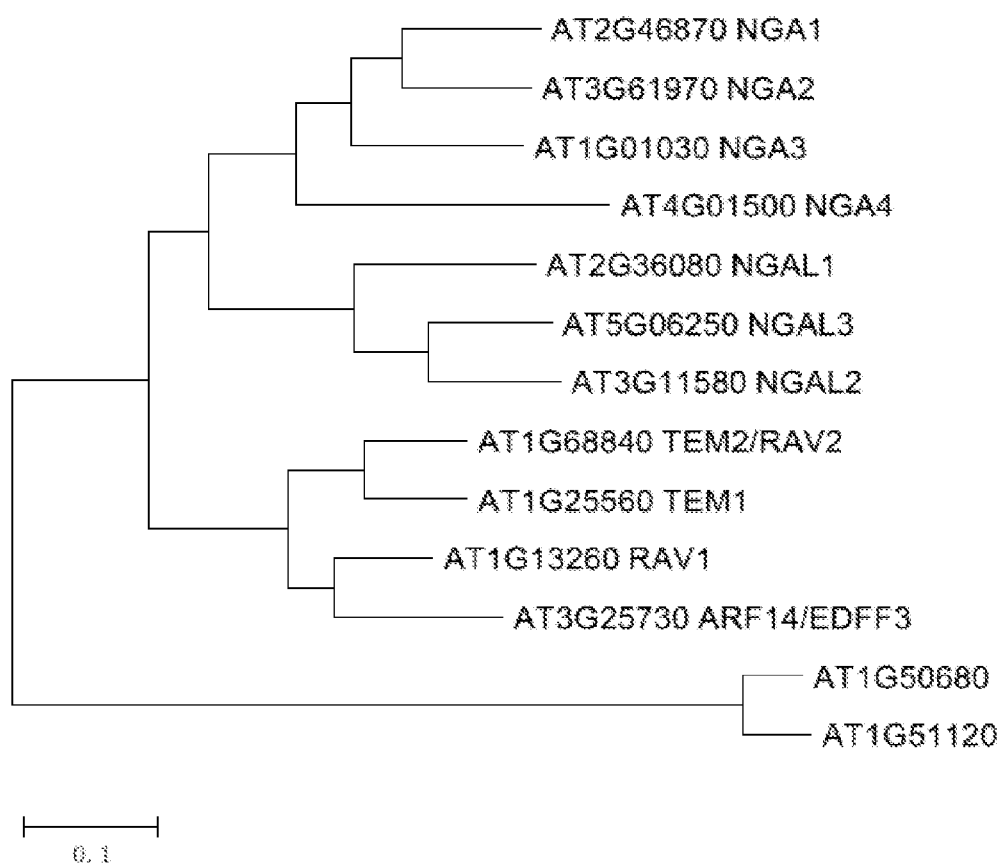

FIG. 10. Phylogenetic tree of the RAV family members in *Arabidopsis*.

Figure 11:
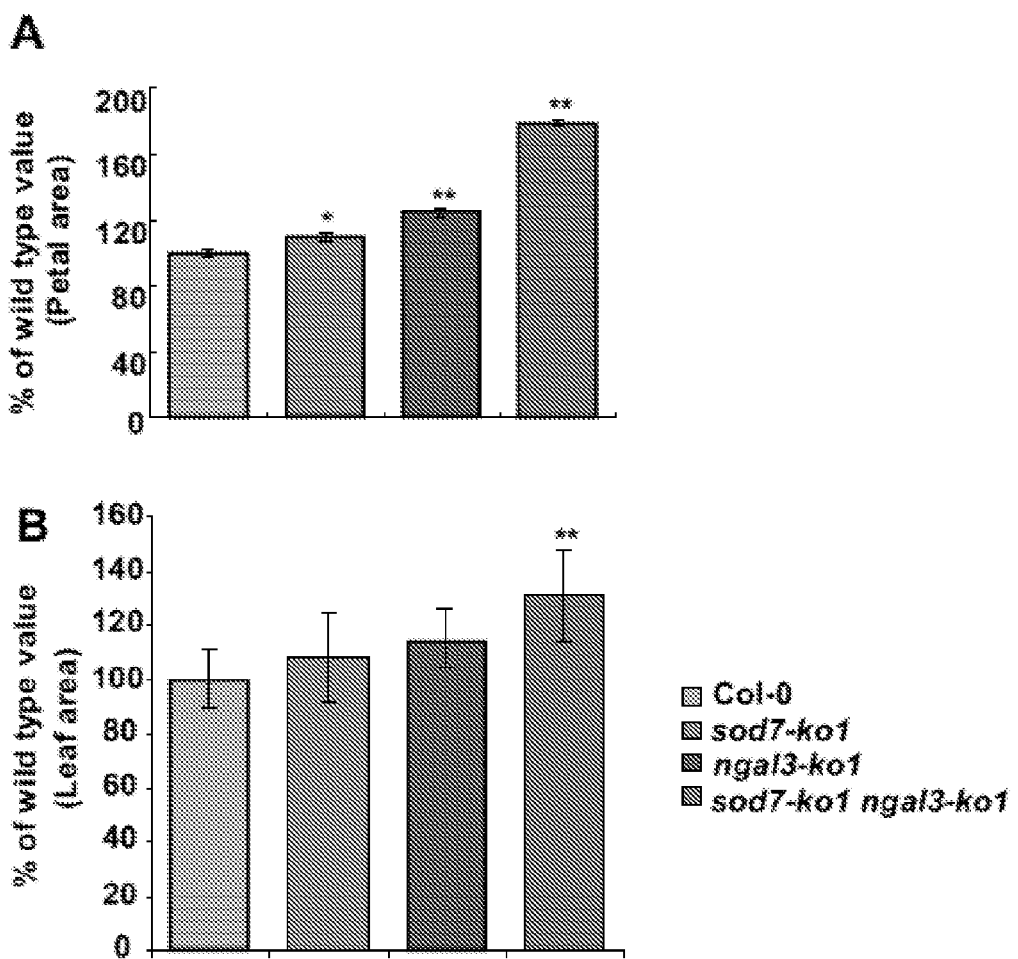

FIG. 11. SOD7 acts redundantly with NGAL3 to influence organ size.

Petal area of Col-0, sod7-ko1, ngal3-ko1 and sod7-ko1 ngal3-ko1. (B) The seventh leaf area of Col-0, sod7-ko1, ngal3-ko1 and sod7-ko1 ngal3-ko1. Values (A and B) are given as mean±SD relative to the respective wild-type values, set at 100%. **, P<0.01 and *, P<0.05 compared with the wild type (Col-0).

FIG. 12: Conserved domains in NGAL2, NGAL3 and homologs. a) B box motif. b) Repressor motif FIG. 13: Alignment of sequences. The following sequences are shown (from top to bottom): RMZM2G053008, HvMLOC_57250, 0 s12g0157000, GmLoc100778733, Bra004501, Bra000434, Bra040478, Bra014415, Bra003482, Bra007646, GmLoc100781489, GRMZM2G024948_T01, 0502g0683500, HvMLOC_66387, 0504 g0581400, GRMZM2G102059_T01, Os10g0537100, GRMZM2G142999_T01, GRMZM2G125095_T01, 0503g0120900, GRMZM2G098443_T01, GRMZM2G082227_T01, Os11g0156000, GRMZM2G328742_T01, GmLoc100802734 GmLoc100795470, GmLoc100818164, Bra017262, At2g36080/NGAL1, Bra005301, At3g11580/SOD7, BraLOC103849927, Bra034828, At5g06250/NGAL3, Bra005886, GmLoc102660503, HvMLOC_38822, os01g0693400, HvMLOC44012, HvMLOC_7940 HvMLOC_75135, TRAECDM81004, HvMLOC_56567, TRAES3BF098300010CFD21 HvMLOC_63261, TRAES3BF062700040CFD21, TRAES3BF062600010CFD21, Bra038346, GmLoc732601, GmLoc100789009, GmLoc100776987, GmLoc100801107. Conserved B3 domain and repressor motif are boxed.

FIG. 14: Genome editing experiments to knock out rice genes Os11g01560000 and Os12g0157000 in rice. gRNA stands for guide RNA, target site linked with gRNA scaffold will recruit CAS9 enzyme to target site in the genome and cause gene-editing.

DETAILED DESCRIPTION

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

The practice of the present invention will employ, unless otherwise indicated, conventional techniques of botany, microbiology, tissue culture, molecular biology, chemistry, biochemistry and recombinant DNA technology, bioinformatics which are within the skill of the art. Such techniques are explained fully in the literature.

As used herein, the words "nucleic acid", "nucleic acid sequence", "nucleotide", "nucleic acid molecule" or "polynucleotide" are intended to include DNA molecules (e.g., cDNA or genomic DNA), RNA molecules (e.g., mRNA), naturally occurring, mutated, synthetic DNA or RNA molecules, and analogues of the DNA or RNA generated using nucleotide analogues. It can be single-stranded or double-stranded. Such nucleic acids or polynucleotides include, but are not limited to, coding sequences of structural genes, anti-sense sequences, and non-coding regulatory sequences that do not encode mRNAs or protein products. These terms also encompass a gene. The term "gene" or "gene sequence" is used broadly to refer to a DNA nucleic acid associated with a biological function. Thus, genes may include introns and exons as in the genomic sequence, or may comprise only a coding sequence as in cDNAs, and/or may include cDNAs in combination with regulatory sequences.

The terms "peptide", "polypeptide" and "protein" are used interchangeably herein and refer to amino acids in a polymeric form of any length, linked together by peptide bonds.

For the purposes of the invention, "transgenic", "transgene" or "recombinant" means with regard to, for example, a nucleic acid sequence, an expression cassette, gene construct or a vector comprising the nucleic acid sequence or an organism transformed with the nucleic acid sequences, expression cassettes or vectors according to the invention, all those constructions brought about by recombinant methods in which either (a) the nucleic acid sequences encoding proteins useful in the methods of the invention, or (b) genetic control sequence(s) which is operably linked with the nucleic acid sequence according to the invention, for example a promoter, or (c) both (a) and (b)

are not located in their natural genetic environment or have been modified by genetic intervention techniques, it being possible for the modification to take the form of, for example, a substitution, addition, deletion, inversion or insertion of one or more nucleotide residues. The natural genetic environment is understood as meaning the natural genomic or chromosomal locus in the original plant or the presence in a genomic library. In the case of a genomic library, the natural genetic environment of the nucleic acid sequence is preferably retained, at least in part. The environment flanks the nucleic acid sequence at least on one side and has a sequence length of at least 50 bp, preferably at least 500 bp, especially preferably at least 1000 bp, most preferably at least 5000 bp. A naturally occurring expression cassette—for example the naturally occurring combination of the natural promoter of the nucleic acid sequences with the corresponding nucleic acid sequence encoding a polypeptide useful in the methods of the present invention, as defined above—becomes a transgenic expression cassette when this expression cassette is modified by non-natural, synthetic ("artificial") methods such as, for example, mutagenic treatment. Suitable methods are described, for example, in U.S. Pat. No. 5,565,350 or WO 00/15815 both incorporated by reference.

In certain embodiments, a transgenic plant for the purposes of the invention is thus understood as meaning, as above, that the nucleic acids used in the method of the invention are not at their natural locus in the genome of said plant, it being possible for the nucleic acids to be expressed homologously or heterologously. Thus, the plant can express a silencing construct transgene. However, as mentioned, in certain embodiments, transgenic also means that, while the nucleic acids according to the different embodiments of the invention are at their natural position in the genome of a plant, the sequence has been modified with regard to the natural sequence, and/or that the regulatory sequences of the natural sequences have been modified, for example by mutagenesis.

Transgenic is preferably understood as meaning the expression of the nucleic acids according to the invention at an unnatural locus in the genome, i.e. homologous or, preferably, heterologous expression of the nucleic acids takes place. According to the invention, the transgene is stably integrated into the plant and the plant is preferably homozygous for the transgene.

The various aspects of the invention use genetic engineering methods. Thus, the plants have been generated using genetic engineering methods, for example transgene expression, mutagenesis, gene targeting, gene silencing or genome editing as detailed below. Thus, the various aspects of the invention can involve recombinant DNA technology. The plants of the invention are thus mutant plants which have been genetically engineered, that is manipulated by human intervention. The plants of the various aspects of the invention do not relate to natural variants which have not been manipulated by genetic engineering methods. The plant may be a transgenic plant in some embodiments, for example a plant which comprises a nucleic acid construct expressing a silencing construct.

In preferred embodiments exclude embodiments that are solely based on generating plants by traditional breeding methods.

The inventor has identified a B3 domain transcriptional repressor termed AtNGAL2, encoded by the suppressor of Atda1-1 (AtSOD7), which acts maternally to control seed size by restricting cell proliferation in the integuments of ovules and developing seeds.

The inventor previously identified the ubiquitin receptor DA1 as a negative regulator of seed size in *Arabidopsis* (Li et al., 2008). The da1-1 mutant formed large seeds due to increased cell proliferation in the maternal integuments (Li et al., 2008; Xia et al., 2013). To identify novel components in the DA1 pathway or other seed size regulators, the inventor initiated a T-DNA activation tagging screen for modifiers of da1-1 (Fang et al., 2012). A dominant suppressor of da1-1 (sod7-1D) was isolated from seeds produced from approximate 16,000 T1 plants (FIG. 1A). Seeds of the sod7-1D da1-1 double mutant were significantly smaller and lighter than da1-1 seeds (FIGS. 1A, E and F). The results show that the sod7-1D mutation suppressed the seed and organ size phenotypes of da1-1. The SOD7 gene was isolated and found to encode a NGATHA like protein (NGAL2) containing a B3 DNA-binding domain and a transcriptional repression motif (FIG. 3C) (Alvarez et al., 2009; Ikeda and Ohme-Takagi, 2009; Trigueros et al., 2009). SOD7 belongs to the RAV gene family that consists of 13 members in *Arabidopsis* (FIG. 10) (Swaminathan et al., 2008). Several members of the RAV family contain the putative transcriptional repression motifs, including NGA1, NGA2, NGA3, NGA4, NGAL1, NGAL2/SOD7 and NGAL3 (FIG. 10) (Ikeda and Ohme-Takagi, 2009). The transcriptional repression motifs in NGA1, NGAL1 and NGAL2/SOD7 have been known to possess the repressive activity (Ikeda and Ohme-Takagi, 2009), indicating that they are transcriptional repressors. SOD7 exhibits the highest similarity to *Arabidopsis* NGAL3/DEVELOPMENT-RELATED PcG TARGET IN THE APEX 4 (DPA4) (FIG. 10), which has known roles in the regulation of leaf serrations (Engelhorn et al., 2012), but no previously identified function in seed size control.

The inventor has shown that overexpression of AtSOD7 significantly decreases seed size of wild-type plants, while the disruption of AtSOD7 increases seed size. The inventors have shown that disruption of AtNGAL3, a close homolog of AtSOD7 also increases seed size. Moreover, the simultaneous disruption of AtSOD7 and AtNGAL3 further increases seed size in a synergistic manner. Genetic analyses carried out by the inventor indicate that AtSOD7 acts in a common pathway with the seed size regulator AtKLU to control seed growth, but does so independently of AtDA1. Further results show that AtSOD7 directly binds to the promoter of AtKLU in vitro and in vivo and represses expression of AtKLU. Therefore, the inventor's findings show that AtSOD7 (aka AtNGAL2) is a target for seed size improvement in crops. The plants of the invention are characterised by increased organ size, for example increased seed size, and also increased petal size, increased embryo size, for example. Increased seed size leads to an increase in seed yield and the plants of the invention are thus characterised by increased seed yield.

Thus, the invention relates to a plant wherein said plant does not produce a functional NGAL2 and/or NGAL3 polypeptide. For example, the plant does not produce a full length transcript of a nucleic acid sequence encoding a NGAL2 and/or NGAL3 protein. In another embodiment, the plant produces a full length transcript of a nucleic acid sequence encoding a NGAL2 and/or NGAL3, but the resulting protein is not functional. In a preferred embodiment, said plant does not produce a functional NGAL2 polypeptide and also does not produce a functional NGAL3 polypeptide. Such plants are double knock-out or knock-down mutants (loss of function mutants) and methods according to the invention as described below relate to making such double mutants.

The plants of the invention are mutant plants which have been genetically modified and are not naturally occurring varieties. Thus, the plants have been generated using genetic engineering methods, for example mutagenesis, gene targeting, gene silencing or genome editing as detailed below. Thus, the various aspects of the invention can involve recombinant DNA technology. The plant may be a transgenic plant in some embodiments, for example a plant which comprises a transgene to silence gene expression of SOD7 and/or NGAL3. In other embodiments, the plant does not carry a transgene, but is a mutant plant wherein the endogenous nucleic acid sequence encoding a NGAL2 and/or NGAL3 polypeptide or the endogenous SOD7 and/or NGAL3 promoter sequence has been manipulated to either reduce or abolish expression of a nucleic acid sequence encoding a NGAL2 and/or NGAL3 polypeptide or reduce or abolish the activity of a NGAL2 and/or NGAL3 polypeptide. The plants of the various aspects of the invention do not relate to natural variants which have not been manipulated by genetic engineering methods.

In one aspect, the invention relates to a plant generated by genetic engineering methods wherein the expression of a nucleic acid sequence encoding a NGAL2 and/or NGAL3 polypeptide and/or the activity of a NGAL2 and/or NGAL3 polypeptide is reduced or abolished relative to a control plant. In one embodiment, expression of a nucleic acid sequence encoding a NGAL2 polypeptide or the activity of a NGAL2 polypeptide is reduced or abolished. In another embodiment, expression of a nucleic acid sequence encoding a NGAL3 polypeptide or the activity of a NGAL3 polypeptide is reduced or abolished. In a preferred embodiment the presence of function of both proteins is affected, in other words, the plant is characterised in that expression of a nucleic acid sequence encoding a NGAL2 polypeptide or the activity of a NGAL2 polypeptide is reduced or abolished and also expression of a nucleic acid sequence encoding a NGAL3 polypeptide or the activity of a NGAL3 polypeptide is reduced or abolished in said plant.

For example, said plant can have reduced or abolished expression of a nucleic acid sequence encoding a NGAL2 polypeptide and reduced or abolished expression of a nucleic acid sequence encoding a NGAL3 polypeptide. In another embodiment, said plant can have reduced or abolished activity of a NGAL2 polypeptide and reduced or abolished activity of a NGAL3 polypeptide. In another embodiment, said plant can have reduced or abolished expression of a nucleic acid sequence encoding a NGAL2 polypeptide and reduced or abolished activity of a NGAL3 polypeptide. In another embodiment, said plant can have reduced or abolished expression of a nucleic acid sequence encoding a NGAL3 polypeptide and reduced or abolished activity of a NGAL2 polypeptide.

A NGAL2 or NGAL3 polypeptide as described in the various aspects of the invention has a characteristic domain structure as explained below.

A NGAL2 OR NGLA3 polypeptide as described in the various aspects of the invention comprises a B3 DNA binding domain which has the structure shown in FIG. 12.

In one embodiment, the domain is: SNNNNNNGGSGD-DVACHFQRFDLHRLFIGWRGE (SEQ ID NO:6) or a domain with at least 80%, at least 95% or at least 95% sequence identity thereto.

A NGAL2 OR NGAL3 polypeptide as described in the various aspects of the invention also comprises a transcriptional repression motif shown in FIG. 12.

In one embodiment, the domain is: VRLFGVNLE (SEQ ID NO:7) or a domain with at least 95% sequence identity thereto.

In one embodiment, the NGAL2 protein is AtNGAL2, a functional variant, part or homologue thereof. AtNGAL2 is encoded by AtSOD7. The term AtSOD7 refers to the wild type AtSOD7 nucleic acid sequence comprising or consisting of SEQ ID NO. 1 (CDNA) or SEQ ID NO 2 (genomic DNA). The protein encoded by AtSOD7 is termed AtNGAL2 SEQ ID NO. 3. In one embodiment, said functional homologue is not AtNGAL3.

In one embodiment, the NGAL3 protein is AtNGAL3, a functional variant, part or homologue thereof. The term AtNGAL3 refers to the wild type AtNGAL3 nucleic acid sequence comprising or consisting of SEQ ID NO. 4. The protein encoded by AtNGAL3 is termed AtNGAL3 SEQ ID NO. 5.

The term "functional" refers to the biological function of the NGAL2 or NGAL3, that is their function in controlling organ size, in particular seed size. The terms "functional variant" or "functional part" as used herein, for example with reference to SEQ ID NOs: 1, 2 or 3, or SEQ ID NOs: 4 or 5 refers to a variant gene or polypeptide sequence or part of the gene or polypeptide sequence which retains the biological function of the full non-variant SOD7/NGAL2 or NGAL2/NGAL3 sequence, that is regulation of seed size. Such sequences complement the Atsod7-1D mutant or Atngal3 mutant respectively.

Thus, it is understood, as those skilled in the art will appreciate, that the aspects of the invention, encompass not only targeting a AtSOD7 and/or AtNGAL3 nucleic acid, for example a nucleic acid sequence comprising or consisting of SEQ ID NO: 1 or SEQ ID NO: 2, or SEQ ID NO: 4 respectively or a polypeptide comprising or consisting of SEQ ID NO: 3, or SEQ ID NO: 5, or a promoter of a AtSOD7 and/or AtNGAL3 nucleic acid. The aspects of the invention encompass also functional variants of AtNGAL2 or AtNGAL3 that do not affect the biological activity and function of the resulting protein.

Alterations in a nucleic acid sequence which result in the production of a different amino acid at a given site that do however not affect the functional properties of the encoded polypeptide, are well known in the art. For example, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also produce a functionally equivalent product. Each of the proposed modifications is well within the routine skill in the art, as is determination of retention of biological activity of the encoded products. Also encompassed is a variant that is substantially identical, i.e. has only some sequence variations, for example in non-conserved residues, to the wild type sequences as shown herein and is biologically active.

Generally, variants of a particular SOD7/NGAL3 nucleotide sequence or NGAL2/NGAL3 polypeptide as described herein will have at least about 60%, preferably at least about 75%, 76%, 77%, 78%, 79%, 80%, 81%, 82%, 83%, 84%, 85%, 86%, 87%, 88%, 89%, 90%, 92%, 94%, 95%, 96%, 97%, 98% or 99% or more sequence identity to that particular non-variant nucleotide sequence, as determined by sequence alignment programs described elsewhere herein.

Furthermore, the various the aspects of the invention encompass not only a AtSOD7 and/or AtNGAL3 nucleic acid, for example a nucleic acid sequence comprising or consisting of SEQ ID NO: 1 or SEQ ID NO: 2, or SEQ ID NO: 4 respectively or a polypeptide comprising or consisting of SEQ ID NO: 3, or SEQ ID NO: 5, or their functional variants but also homologues of AtSOD7 and/or AtNGAL3 in Arabidopsis or other plants. Also within the scope of the invention are functional variants of such homologues as defined above.

The term homologue as used herein also designates an AtSOD7 and/or AtNGAL3 orthologue from other plant species. A homologue of AtNGAL2 or AtNGAL3 polypeptide respectively has, in increasing order of preference, at least 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% overall sequence identity to the amino acid represented by SEQ ID NO: 3 or 5 respectively. Preferably, overall sequence identity is at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%, most preferably 90%, 91%, 92%, 93%, 94%, 95%, 96%, 97%, 98%, or at least 99%.

In another embodiment, the homologue of a AtSOD7 or AtNGAL3 nucleic acid sequence respectively has, in increasing order of preference, at least 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99% overall sequence identity to the nucleic acid represented by SEQ ID NO: 1 or 2 or 4 respectively. Preferably, overall sequence identity is at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%, most preferably 90%, 91%, 92%, 93%, 94%, 95%, 96%, 97%, 98%, or at least 99%. The overall sequence identity is determined using a global alignment algorithm known in the art, such as the Needleman Wunsch algorithm in the program GAP (GCG Wisconsin Package, Accelrys).

In a preferred embodiment, the NGAL2 or NGAL3 homologue is from a plant that is not *Arabidopsis*.

In one embodiment, an AtNGAL2 or a homologue thereof or AtNGAL3 or a homologue thereof comprises a B3 domain having the sequence as defined above In one embodiment, an AtNGAL2 or a homologue thereof or AtNGAL3 or a homologue thereof comprises a transcriptional repression motif having the sequence as defined above Examples of homologues are shown in FIG. 13 and in SEQ ID NO: 49-145. In certain embodiments, if a plant has more than one AtNGAL2 and/or AtNGAL3 homologue, then all homologues are knocked out or knocked down. Suitable homologues can be identified by sequence comparisons and identifications of conserved domains. There are predictors in the art that can be used to identify such sequences. The function of the homologue can be identified as described herein and a skilled person would thus be able to confirm the function, for example when overexpressed in a plant or knocked out in a plant or when expressed in a plant or by expressing the homologous nucleic acid sequence in an *Arabidopsis* gain of function mutant.

Thus, the nucleotide sequences of the invention and described herein can also be used to isolate corresponding sequences from other organisms, particularly other plants, for example crop plants. In this manner, methods such as PCR, hybridization, and the like can be used to identify such sequences based on their sequence homology to the sequences described herein. Topology of the sequences and the characteristic domains structure can also be considered when identifying and isolating homologues. Sequences may be isolated based on their sequence identity to the entire sequence or to fragments thereof. In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen plant. The hybridization probes may be genomic DNA fragments, cDNA fragments, RNA fragments, or other oligonucleotides, and may be labelled with a detectable group, or any other detectable marker. Thus, for example, probes for hybridization can be made by labelling synthetic oligonucleotides based on the ABA-associated sequences of the invention. Methods for preparation of probes for hybridization and for construction of cDNA and genomic libraries are generally known in the art and are disclosed in Sambrook, et al., (1989) Molecular Cloning: A Library Manual (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing).

Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Duration of hybridization is generally less than about 24 hours, usually about 4 to 12. Stringent conditions may also be achieved with the addition of destabilizing agents such as formamide.

According to the invention, preferred homologues of AtSOD7 and AtNGAL3 peptides are selected from crop plants, for example cereal crops. Preferred homologues of AtNGAL2 and AtNGAL3 and their polypeptide sequences are also shown in FIG. 13.

A plant according to the various aspects of the invention, including the transgenic plants, methods and uses described herein may be a monocot or a dicot plant.

A dicot plant may be selected from the families including, but not limited to Asteraceae, Brassicaceae (e.g. *Brassica napus*), Chenopodiaceae, Cucurbitaceae, Leguminosae (Caesalpiniaceae, Aesalpiniaceae Mimosaceae, Papilionaceae or Fabaceae), Malvaceae, Rosaceae or Solanaceae. For example, the plant may be selected from lettuce, sunflower, *Arabidopsis*, broccoli, spinach, water melon, squash, cabbage, tomato, potato, yam, capsicum, tobacco, cotton, okra, apple, rose, strawberry, alfalfa, bean, soybean, field (fava) bean, pea, lentil, peanut, chickpea, apricots, pears, peach, grape vine, bell pepper, chilli or citrus species.

A monocot plant may, for example, be selected from the families Arecaceae, Amaryllidaceae or Poaceae. For example, the plant may be a cereal crop, such as maize, wheat, rice, barley, oat, sorghum, rye, millet, buckwheat, or a grass crop such as *Lolium* species or *Festuca* species, or a crop such as sugar cane, onion, leek, yam or banana.

Also included are biofuel and bioenergy crops such as rape/canola, sugar cane, sweet sorghum, *Panicum virgatum* (switchgrass), linseed, lupin and willow, poplar, poplar hybrids, *Miscanthus* or gymnosperms, such as loblolly pine. Also included are crops for silage (maize), grazing or fodder (grasses, clover, sanfoin, alfalfa), fibres (e.g. cotton, flax), building materials (e.g. pine, oak), pulping (e.g. poplar), feeder stocks for the chemical industry (e.g. high erucic acid oil seed rape, linseed) and for amenity purposes (e.g. turf grasses for golf courses), ornamentals for public and private gardens (e.g. snapdragon, petunia, roses, geranium, *Nicotiana* sp.) and plants and cut flowers for the home (African violets, Begonias, chrysanthemums, geraniums, *Coleus* spider plants, Dracaena, rubber plant).

Preferably, the plant is a crop plant. By crop plant is meant any plant which is grown on a commercial scale for human or animal consumption or use. In a preferred embodiment, the plant is a cereal.

Most preferred plants are maize, rice, wheat, oilseed rape/canola, sorghum, soybean, sunflower, alfalfa, potato, tomato, tobacco, grape, barley, pea, bean, field bean, lettuce, cotton, sugar cane, sugar beet, broccoli or other vegetable brassicas or poplar.

The term "plant" as used herein encompasses whole plants, ancestors and progeny of the plants and plant parts, including seeds, fruit, shoots, stems, leaves, roots (including tubers), flowers, and tissues and organs, wherein each of the aforementioned comprise the gene/nucleic acid of interest. The term "plant" also encompasses plant cells, suspension cultures, callus tissue, embryos, meristematic regions, gametophytes, sporophytes, pollen and microspores, again wherein each of the aforementioned comprises the gene/nucleic acid of interest.

According to the various aspects of the invention, including the plants and methods of the invention, abolishing, inactivating, repressing, reducing or down-regulating the activity of a NGAL2 and/or NGAL3 polypeptide can be achieved through different means. Such means that are within the scope of the various aspects of the invention are methods for abolishing or reducing translation or transcription of the SOD7 and/or NGAL3 gene, destabilizing SOD7 and/or NGAL3 transcript stability, destabilizing NGAL2 and/or NGAL3 polypeptide stability or abolishing or reducing the activation or activity of the NGAL2 and/or NGAL3 or polypeptide. Thus, in one embodiment, endogenous SOD7 and/or NGAL3 gene or its promoter carry a functional mutation so that no full length transcript is made. In another embodiment, the SOD7 and/or NGAL3 gene is silenced in said plant using gene silencing techniques. In another embodiment, the SOD7 and/or NGAL3 nucleic acid sequence has been altered to introduce a mutation which results in a NGAL2/NGAL3 protein with reduced or abolished activity. These embodiments and the techniques used are described in more detail below.

In another aspect, the invention relates to a method for altering a plant phenotype comprising reducing or abolishing the expression of a nucleic acid sequence encoding a NGAL2 and/or NGAL3 polypeptide and/or reducing or abolishing the activity of a NGAL2 and/or NGAL3 polypeptide relative to a control plant.

In another aspect, the invention relates to a method for making a plant with an altered phenotype comprising reducing or abolishing the expression of a nucleic acid sequence encoding a NGAL2 and/or NGAL3 polypeptide and/or reducing or abolishing the activity of a NGAL2 and/or NGAL3 polypeptide relative to a control plant.

As previously described, such methods above use genetic engineering methods.

In this aspect, a wild type plant may be targeted to simultaneously knock out or down both SOD7 and NGAL3 function. Alternatively, the method may comprise the following steps
 a) Knocking out or down SOD7 function in a first plant;
 b) knocking out or down NGAL3 function in a second plant and
 c) crossing plants regenerated from said first plant with plants regenerated from said second plant.

In one embodiment of these methods, expression of a nucleic acid sequence encoding a NGAL2 polypeptide or the activity of a NGAL2 polypeptide is reduced or abolished. In another embodiment, expression of a nucleic acid sequence encoding a NGAL3 polypeptide or the activity of a NGAL3 polypeptide is reduced or abolished. In a preferred embodiment, the method comprises reducing or abolishing expression of a nucleic acid sequence encoding a NGAL2 polypeptide or the activity of a NGAL2 polypeptide and reducing or abolishing expression of a nucleic acid sequence encoding a NGAL3 polypeptide or the activity of a NGAL3 polypeptide to create a double loss of function mutant.

For example, the method comprises reducing or abolishing expression of a nucleic acid sequence encoding a NGAL2 polypeptide and reducing or abolishing expression of a nucleic acid sequence encoding a NGAL3 polypeptide. In another embodiment, the method comprises reducing or abolishing activity of a NGAL2 polypeptide and reducing or abolishing activity of a NGAL3 polypeptide. In another embodiment, the method comprises reducing or abolishing expression of a nucleic acid sequence encoding a NGAL2 polypeptide and reducing or abolishing activity of a NGAL3 polypeptide. In another embodiment the method comprises reducing or abolishing expression of a nucleic acid sequence encoding a NGAL3 polypeptide or reducing or abolishing activity of a NGAL2 polypeptide.

According to these methods, the phenotype is preferably selected from increased organ size, for example increased seed size or increased seed weight. Increased seed size leads to an increase in yield and the methods of the invention also increased yield.

The term "yield" in general means a measurable produce of economic value, typically related to a specified crop, to an area, and to a period of time. Individual plant parts directly contribute to yield based on their number, size and/or weight, or the actual yield is the yield per square meter for a crop and year, which is determined by dividing total production (includes both harvested and appraised production) by planted square meters. The term "yield" as described herein relates to yield-related traits and may relate to vegetative biomass (root and/or shoot biomass), to reproductive organs, and/or to propagules (such as seeds) of that plant. Thus, according to the invention, the term yield refers to organ size, in particular seed size and can be measured by assessing seed size or seed weight or cotyledon size.

The terms "increase", "improve" or "enhance" are interchangeable. Yield or seed size for example is increased by at least a 2%, 3%, 4%, 5%, 6%, 7%, 8%, 9% or 10%, preferably at least 15% or 20%, more preferably 25%, 30%, 35%, 40% or 50% or more in comparison to a control plant.

A control plant as used herein according to all of the aspects of the invention is a plant which has not been modified according to the methods of the invention. Accordingly, the control plant has not been genetically modified to alter either expression of a nucleic acid encoding a NGAL2 or NGAL3 polypeptide or to alter the activity of a NGAL2 or NGAL3 polypeptide as described herein. In one embodiment, the control plant is a wild type plant that has not been genetically altered. In another embodiment, the control plant is a transgenic plant that does not have altered expression of a nucleic acid encoding a NGAL2 or NGAL3 polypeptide or altered activity of a NGAL2 or NGAL3 polypeptide, but has been genetically altered in other ways, for example by expressing a desirable transgene to confer certain traits.

The reduction, decrease, down-regulation or repression of the activity of the NGAL2 and/or NGAL3 polypeptide or corresponding SOD7 and/or NGAL3 nucleic acid sequences according to the aspects of the invention is at least 10%, 20%, 30%, 40% or 50% in comparison to the control plant.

For example, the plant is a reduction (knock down) or loss of function (knock out) mutant wherein the function of the SOD7 and/or NGAL3 nucleic acid sequence is reduced or lost compared to a wild type control plant. To this end, a mutation is introduced into the SOD7 and/or NGAL3 nucleic acid sequence or the corresponding promoter sequence which disrupts the transcription of the gene leading to a gene product which is not functional or has a reduced function. The mutation may be a deletion, insertion or substitution. The expression of active protein may thus be abolished by mutating the nucleic acid sequences in the plant cell which encode the NGAL2 or NGAL3 polypeptide and regenerating a plant from the mutated cell. The nucleic acids may be mutated by insertion or deletion of one or more nucleotides. Techniques for the inactivation or knockout of target genes are well-known in the art. These techniques include gene target using vectors that target the gene of interest and which allow integration allows for integration of transgene at a specific site. The targeting construct is engineered to recombine with the target gene, which is accomplished by incorporating sequences from the gene itself into the construct. Recombination then occurs in the region of that sequence within the gene, resulting in the insertion of a foreign sequence to disrupt the gene. With its sequence interrupted, the altered gene will be translated into a non-functional protein, if it is translated at all. Other techniques include genome editing (targeted genome engineering) as described below. Using either of these techniques, in preferred embodiment, conserved domains which confer function of NGAL2 or NGAL3 respectively are modified.

A skilled person will know further approaches can be used to generate such mutants. In one embodiment, insertional mutagenesis is used, for example using T-DNA mutagenesis (which inserts pieces of the T-DNA from the *Agrobacterium tumefaciens* T-Plasmid into DNA causing either loss of gene function or gain of gene function mutations), site-directed nucleases (SDNs) or transposons as mutagens. Insertional mutagenesis is an alternative means of disrupting gene function and is based on the insertion of foreign DNA into the gene of interest (see Krysan et al, The Plant Cell, Vol. 11, 2283-2290, December 1999).

In one embodiment, as discussed in the examples, T-DNA may be used as an insertional mutagen which disrupts SOD7 and/or NGAL3 gene expression. T-DNA not only disrupts the expression of the gene into which it is inserted, but also acts as a marker for subsequent identification of the mutation. Since the sequence of the inserted element is known, the gene in which the insertion has occurred can be recovered, using various cloning or PCR-based strategies. The insertion of a piece of T-DNA on the order of 5 to 25 kb in length generally produces a disruption of gene function. If a large enough population of T-DNA transformed lines is generated, there are reasonably good chances of finding a transgenic plant carrying a T-DNA insert within any gene of interest. Transformation of spores with T-DNA is achieved by an *Agrobacterium*-mediated method which involves exposing plant cells and tissues to a suspension of *Agrobacterium* cells.

The details of this method are well known to a skilled person. In short, plant transformation by *Agrobacterium* results in the integration into the nuclear genome of a sequence called T-DNA, which is carried on a bacterial plasmid. The use of T-DNA transformation leads to stable single insertions. Further mutant analysis of the resultant transformed lines is straightforward and each individual insertion line can be rapidly characterized by direct sequencing and analysis of DNA flanking the insertion. Gene expression in the mutant is compared to expression of the SOD7 and/or NGAL3 nucleic acid sequence in a wild type plant and phenotypic analysis is also carried out. Other techniques for insertional mutagenesis include the use of transposons.

In another embodiment, mutagenesis is physical mutagenesis, such as application of ultraviolet radiation, X-rays, gamma rays, fast or thermal neutrons or protons. The targeted population can then be screened to identify a SOD7 or NGAL3 loss of function mutant.

In another embodiment of the various aspects of the invention, the plant is a mutant plant derived from a plant population mutagenised with a mutagen. The mutagen may be fast neutron irradiation or a chemical mutagen, for example selected from the following non-limiting list: ethyl methanesulfonate (EMS), methylmethane sulfonate (MMS), N-ethyl-N-nitrosurea (ENU), triethylmelamine (1'EM), N-methyl-N-nitrosourea (MNU), procarbazine, chlorambucil, cyclophosphamide, diethyl sulfate, acrylamide monomer, melphalan, nitrogen mustard, vincristine, dimethylnitosamine, N-methyl-N'-nitro-Nitrosoguanidine (MNNG), nitrosoguanidine, 2-aminopurine, 7,12 dimethyl-benz(a)anthracene (DMBA), ethylene oxide, hexamethylphosphoramide, bisulfan, diepoxyalkanes (diepoxyoctane (DEO), diepoxybutane (BEB), and the like), 2-methoxy-6-chloro-9 [3-(ethyl-2-chloroethyl)aminopropylamino]acridine dihydrochloride (ICR-170) or formaldehyde.

In one embodiment, the method used to create and analyse mutations is targeting induced local lesions in genomes (TLLING), reviewed in Henikoff et al, 2004. In this method, seeds are mutagenised with a chemical mutagen, for example EMS. The resulting M1 plants are self-fertilised and the M2 generation of individuals is used to prepare DNA samples for mutational screening. DNA samples are pooled and arrayed on microtiter plates and subjected to gene specific PCR. The PCR amplification products may be screened for mutations in the SOD7 and/or NGAL3 target gene using any method that identifies heteroduplexes between wild type and mutant genes. For example, but not limited to, denaturing high pressure liquid chromatography (dHPLC), constant denaturant capillary electrophoresis (CDCE), temperature gradient capillary electrophoresis (TGCE), or by fragmentation using chemical cleavage. Preferably the PCR amplification products are incubated with an endonuclease that preferentially cleaves mismatches in heteroduplexes between wild type and mutant sequences. Cleavage products are electrophoresed using an automated sequencing gel apparatus, and gel images are analyzed with the aid of a standard commercial image-processing program. Any primer specific to the SOD7 or NGAL3 nucleic acid sequence may be utilized to amplify the SOD7 or NGAL3 nucleic acid sequence within the pooled DNA sample. Preferably, the primer is designed to amplify the regions of the SOD7 and/or NGAL3 gene where useful mutations are most likely to arise, specifically in the areas of the SOD7 and/or NGAL3 gene that are highly conserved and/or confer activity as explained elsewhere. To facilitate detection of PCR products on a gel, the PCR primer may be labelled using any conventional labelling method.

Rapid high-throughput screening procedures thus allow the analysis of amplification products for identifying a mutation conferring the reduction or inactivation of the expression of the SOD7 and/or NGAL3 gene as compared to a corresponding non-mutagenised wild type plant. Once a mutation is identified in a gene of interest, the seeds of the M2 plant carrying that mutation are grown into adult M3 plants and screened for the phenotypic characteristics associated with the target gene SOD7 or NGAL3. Loss of function or reduced function mutants with increased seed size compared to a control can thus be identified.

Plants obtained or obtainable by such method which carry a functional mutation in the endogenous SOD7 and/or NGAL3 locus are also within the scope of the invention In another embodiment, RNA-mediated gene suppression or RNA silencing may be used to achieve silencing of the SOD7 and/or NGAL3 nucleic acid sequence. "Gene silencing" is a term generally used to refer to suppression of expression of a gene via sequence-specific interactions that are mediated by RNA molecules. The degree of reduction may be so as to totally abolish production of the encoded gene product, but more usually the abolition of expression is partial, with some degree of expression remaining. The term should not therefore be taken to require complete "silencing" of expression.

Transgenes may be used to suppress endogenous plant genes. This was discovered originally when chalcone synthase transgenes in petunia caused suppression of the endogenous chalcone synthase genes and indicated by easily visible pigmentation changes. Subsequently it has been described how many, if not all plant genes can be "silenced" by transgenes. Gene silencing requires sequence similarity between the transgene and the gene that becomes silenced. This sequence homology may involve promoter regions or coding regions of the silenced target gene. When coding regions are involved, the transgene able to cause gene silencing may have been constructed with a promoter that would transcribe either the sense or the antisense orientation of the coding sequence RNA. It is likely that the various examples of gene silencing involve different mechanisms that are not well understood. In different examples there may be transcriptional or post-transcriptional gene silencing and both may be used according to the methods of the invention.

The mechanisms of gene silencing and their application in genetic engineering, which were first discovered in plants in the early 1990s and then shown in *Caenorhabditis elegans* are extensively described in the literature.

RNA-mediated gene suppression or RNA silencing according to the methods of the invention includes co-suppression wherein over-expression of the target sense RNA or mRNA, that is the SOD7 and/or NGAL3 sense RNA or mRNA, leads to a reduction in the level of expression of the genes concerned. RNAs of the transgene and homologous endogenous gene are co-ordinately suppressed. Other techniques used in the methods of the invention include antisense RNA to reduce transcript levels of the endogenous target gene in a plant. In this method, RNA silencing does not affect the transcription of a gene locus, but only causes sequence-specific degradation of target mRNAs. An "antisense" nucleic acid sequence comprises a nucleotide sequence that is complementary to a "sense" nucleic acid sequence encoding a NGAL2 and/or NGAL3 protein, or a part of the protein, i.e. complementary to the coding strand of a double-stranded cDNA molecule or complementary to an mRNA transcript sequence. The antisense nucleic acid sequence is preferably complementary to the endogenous SOD7 and/or NGAL3 gene to be silenced. The complementarity may be located in the "coding region" and/or in the "non-coding region" of a gene. The term "coding region" refers to a region of the nucleotide sequence comprising codons that are translated into amino acid residues. The term "non-coding region" refers to 5' and 3' sequences that flank the coding region that are transcribed but not translated into amino acids (also referred to as 5' and 3' untranslated regions).

Antisense nucleic acid sequences can be designed according to the rules of Watson and Crick base pairing. The antisense nucleic acid sequence may be complementary to the entire SOD7 and/or NGAL3 nucleic acid sequence, but may also be an oligonucleotide that is antisense to only a part of the nucleic acid sequence (including the mRNA 5' and 3' UTR). For example, the antisense oligonucleotide sequence may be complementary to the region surrounding the translation start site of an mRNA transcript encoding a polypeptide. The length of a suitable antisense oligonucleotide sequence is known in the art and may start from about 50, 45, 40, 35, 30, 25, 20, 15 or 10 nucleotides in length or less. An antisense nucleic acid sequence according to the invention may be constructed using chemical synthesis and enzymatic ligation reactions using methods known in the art. For example, an antisense nucleic acid sequence (e.g., an antisense oligonucleotide sequence) may be chemically synthesized using naturally occurring nucleotides or variously modified nucleotides designed to increase the biological stability of the molecules or to increase the physical stability of the duplex formed between the antisense and sense nucleic acid sequences, e.g., phosphorothioate derivatives and acridine-substituted nucleotides may be used. Examples of modified nucleotides that may be used to generate the antisense nucleic acid sequences are well known in the art. The antisense nucleic acid sequence can be produced biologically using an expression vector into which a nucleic acid sequence has been subcloned in an antisense orientation (i.e., RNA transcribed from the inserted nucleic acid will be of an antisense orientation to a target nucleic acid of interest). Preferably, production of antisense nucleic acid sequences in plants occurs by means of a stably integrated nucleic acid construct comprising a promoter, an operably linked antisense oligonucleotide, and a terminator.

The nucleic acid molecules used for silencing in the methods of the invention hybridize with or bind to mRNA transcripts and/or insert into genomic DNA encoding a polypeptide to thereby inhibit expression of the protein, e.g., by inhibiting transcription and/or translation. The hybridization can be by conventional nucleotide complementarity to form a stable duplex, or, for example, in the case of an antisense nucleic acid sequence which binds to DNA duplexes, through specific interactions in the major groove of the double helix. Antisense nucleic acid sequences may be introduced into a plant by transformation or direct injection at a specific tissue site. Alternatively, antisense nucleic acid sequences can be modified to target selected cells and then administered systemically. For example, for systemic administration, antisense nucleic acid sequences can be modified such that they specifically bind to receptors or antigens expressed on a selected cell surface, e.g., by linking the antisense nucleic acid sequence to peptides or antibodies which bind to cell surface receptors or antigens. The antisense nucleic acid sequences can also be delivered to cells using vectors.

RNA interference (RNAi) is another post-transcriptional gene-silencing phenomenon which may be used according to the methods of the invention. This is induced by double-stranded RNA in which mRNA that is homologous to the dsRNA is specifically degraded. It refers to the process of sequence-specific post-transcriptional gene silencing mediated by short interfering RNAs (siRNA). The process of RNAi begins when the enzyme, DICER, encounters dsRNA and chops it into pieces called small-interfering RNAs (siRNA). This enzyme belongs to the RNase III nuclease family. A complex of proteins gathers up these RNA remains and uses their code as a guide to search out and destroy any RNAs in the cell with a matching sequence, such as target mRNA.

Artificial and/or natural microRNAs (miRNAs) may be used to knock out gene expression and/or mRNA translation. MicroRNAs (miRNAs) miRNAs are typically single stranded small RNAs typically 19-24 nucleotides long. Most plant miRNAs have perfect or near-perfect complementarity with their target sequences. However, there are natural targets with up to five mismatches. They are processed from longer non-coding RNAs with characteristic fold-back structures by double-strand specific RNases of the Dicer family. Upon processing, they are integrated in the RNA-induced silencing complex (RISC) by binding to its main component, an Argonaute protein. miRNAs serve as the specificity components of RISC, since they base-pair to target nucleic acids, mostly mRNAs, in the cytoplasm. Subsequent regulatory events include target mRNA cleavage and destruction and/or translational inhibition. Effects of miRNA overexpression are thus often reflected in decreased mRNA levels of target genes. Artificial microRNA (amiRNA) technology has been applied in *Arabidopsis thaliana* and other plants to efficiently silence target genes of interest. The design principles for amiRNAs have been generalized and integrated into a Web-based tool (wmd.weigelworld.org).

Thus, according to the various aspects of the invention a plant may be transformed to introduce a RNAi, shRNA, snRNA, dsRNA, siRNA, miRNA, ta-siRNA, amiRNA or cosuppression molecule that has been designed to target the expression of an SOD7 and/or NGAL3 nucleic acid sequence and selectively decreases or inhibits the expression of the gene or stability of its transcript. Preferably, the RNAi, snRNA, dsRNA, shRNA siRNA, miRNA, amiRNA, ta-siRNA or cosuppression molecule used according to the various aspects of the invention comprises a fragment of at least 17 nt, preferably 22 to 26 nt and can be designed on the basis of the information shown in SEQ ID NO: 1. Guidelines for designing effective siRNAs are known to the skilled person. Briefly, a short fragment of the target gene sequence (e.g., 19-40 nucleotides in length) is chosen as the target sequence of the siRNA of the invention. The short fragment of target gene sequence is a fragment of the target gene mRNA. In preferred embodiments, the criteria for choosing a sequence fragment from the target gene mRNA to be a candidate siRNA molecule include 1) a sequence from the target gene mRNA that is at least 50-100 nucleotides from the 5' or 3' end of the native mRNA molecule, 2) a sequence from the target gene mRNA that has a G/C content of between 30% and 70%, most preferably around 50%, 3) a sequence from the target gene mRNA that does not contain repetitive sequences (e.g., AAA, CCC, GGG, TTT, AAAA, CCCC, GGGG, TTTT), 4) a sequence from the target gene mRNA that is accessible in the mRNA, 5) a sequence from the target gene mRNA that is unique to the target gene, 6) avoids regions within 75 bases of a start codon. The sequence fragment from the target gene mRNA may meet one or more of the criteria identified above. The selected gene is introduced as a nucleotide sequence in a prediction program that takes into account all the variables described above for the design of optimal oligonucleotides. This program scans any mRNA nucleotide sequence for regions susceptible to be targeted by siRNAs. The output of this analysis is a score of possible siRNA oligonucleotides. The highest scores are used to design double stranded RNA oligonucleotides that are typically made by chemical synthesis. In addition to siRNA which is complementary to the mRNA target region, degenerate siRNA sequences may be used to target homologous regions. siRNAs according to the invention can be synthesized by any method known in the art. RNAs are preferably chemically synthesized using appropriately protected ribonucleoside phosphoramidites and a conventional DNA/RNA synthesizer. Additionally, siRNAs can be obtained from commercial RNA oligonucleotide synthesis suppliers.

siRNA molecules according to the aspects of the invention may be double stranded. In one embodiment, double stranded siRNA molecules comprise blunt ends. In another embodiment, double stranded siRNA molecules comprise overhanging nucleotides (e.g., 1-5 nucleotide overhangs, preferably 2 nucleotide overhangs). In some embodiments, the siRNA is a short hairpin RNA (shRNA); and the two strands of the siRNA molecule may be connected by a linker region (e.g., a nucleotide linker or a non-nucleotide linker). The siRNAs of the invention may contain one or more modified nucleotides and/or non-phosphodiester linkages. Chemical modifications well known in the art are capable of increasing stability, availability, and/or cell uptake of the siRNA. The skilled person will be aware of other types of chemical modification which may be incorporated into RNA molecules.

In one embodiment, recombinant DNA constructs as described in U.S. Pat. No. 6,635,805, incorporated herein by reference, may be used.

The silencing RNA molecule is introduced into the plant using conventional methods, for example a vector and *Agrobacterium*-mediated transformation. Stably transformed plants are generated and expression of the SOD7 and/or NGAL3 gene compared to a wild type control plant is analysed.

Silencing of the SOD7 and/or NGAL3 nucleic acid sequence may also be achieved using virus-induced gene silencing.

Thus, in one embodiment of the invention, the plant expresses a nucleic acid construct comprising a RNAi, shRNA snRNA, dsRNA, siRNA, miRNA, ta-siRNA, amiRNA or co-suppression molecule that targets the SOD7 or NGAL3 nucleic acid sequence as described herein and reduces expression of the endogenous SOD7 or NGAL3 nucleic acid sequence. A gene is targeted when, for example, the RNAi, snRNA, dsRNA, siRNA, shRNA miRNA, ta-siRNA, amiRNA or cosuppression molecule selectively decreases or inhibits the expression of the gene compared to a control plant. Alternatively, a RNAi, snRNA, dsRNA, siRNA, miRNA, ta-siRNA, amiRNA or cosuppression molecule targets A SOD7 or NGAL3 nucleic acid sequence when the RNAi, shRNA snRNA, dsRNA, siRNA, miRNA, ta-siRNA, amiRNA or cosuppression molecule hybridises under stringent conditions to the gene transcript.

Gene silencing may also occur if there is a mutation on an endogenous gene and/or a mutation on an isolated gene/nucleic acid subsequently introduced into a plant. The reduction or substantial elimination may be caused by a non-functional polypeptide. For example, the polypeptide may bind to various interacting proteins; one or more mutation(s) and/or truncation(s) may therefore provide for a polypeptide that is still able to bind interacting proteins (such as receptor proteins) but that cannot exhibit its normal function (such as signalling ligand).

A further approach to gene silencing is by targeting nucleic acid sequences complementary to the regulatory region of the gene (e.g., the promoter and/or enhancers) to form triple helical structures that prevent transcription of the gene in target cells. Other methods, such as the use of antibodies directed to an endogenous polypeptide for inhibiting its function in planta, or interference in the signalling pathway in which a polypeptide is involved, will be well known to the skilled man. In particular, it can be envisaged that manmade molecules may be useful for inhibiting the biological function of a target polypeptide, or for interfering with the signalling pathway in which the target polypeptide is involved.

In one embodiment, the suppressor nucleic acids may be anti-sense suppressors of expression of the NGAL2 or NGAL3 polypeptides. In using anti-sense sequences to down-regulate gene expression, a nucleotide sequence is placed under the control of a promoter in a "reverse orientation" such that transcription yields RNA which is complementary to normal mRNA transcribed from the "sense" strand of the target gene.

An anti-sense suppressor nucleic acid may comprise an anti-sense sequence of at least 10 nucleotides from the target nucleotide sequence. It may be preferable that there is complete sequence identity in the sequence used for down-regulation of expression of a target sequence, and the target sequence, although total complementarity or similarity of sequence is not essential. One or more nucleotides may differ in the sequence used from the target gene. Thus, a sequence employed in a down-regulation of gene expression in accordance with the present invention may be a wild-type sequence (e.g. gene) selected from those available, or a variant of such a sequence.

The sequence need not include an open reading frame or specify an RNA that would be translatable. It may be preferred for there to be sufficient homology for the respective anti-sense and sense RNA molecules to hybridise. There may be down regulation of gene expression even where there is about 5%, 10%, 15% or 20% or more mismatch between the sequence used and the target gene. Effectively, the homology should be sufficient for the down-regulation of gene expression to take place.

Suppressor nucleic acids may be operably linked to tissue-specific or inducible promoters. For example, integument and seed specific promoters can be used to specifically down-regulate a SOD7 or NGAL3 nucleic acids in developing ovules and seeds to increase final seed size.

Nucleic acid which suppresses expression of a NGAL2 or NGAL3 polypeptide as described herein may be operably linked to a heterologous regulatory sequence, such as a promoter, for example a constitutive, inducible, tissue-specific or developmental specific promoter. The construct or vector may be transformed into plant cells and expressed as described herein. Plant cells comprising such vectors are also within the scope of the invention.

In another aspect, the invention relates to a silencing construct to silence expression of NGAL2 or NGAL3 obtainable or obtained by a method as described herein and to a plant cell comprising such construct. Accordingly, the invention also relates to the use of a nucleic acid sequence comprising or consisting of SEQ ID NO: 1, 2 or 3 or a part thereof or a homologue of SEQ ID NO: 1, 2 or 3 or a part thereof in silencing expression of NGAL2 or NGAL3. Host cells transformed with such construct are also within the scope of the invention.

Recently, genome editing techniques have emerged as alternative methods to conventional mutagenesis methods (such as physical and chemical mutagenesis) or methods using the expression of transgenes in plants to produce mutant plants with improved phenotypes that are important in agriculture. These techniques employ sequence-specific nucleases (SSNs) including zinc finger nucleases (ZFNs), transcription activator-like effector nucleases (TALENs), and the RNA-guided nuclease Cas9 (CRISPR/Cas9), which generate targeted DNA double-strand breaks (DSBs), which are then repaired mainly by either error-prone non-homologous end joining (NHEJ) or high-fidelity homologous recombination (HR). The SSNs have been used to create targeted knockout plants in various species ranging from the model plants, *Arabidopsis* and tobacco, to important crops, such as barley, soybean, rice and maize. Heritable gene modification has been demonstrated in *Arabidopsis* and rice using the CRISPR/Cas9 system and TALENs.

Targeted genome modification or targeted genome editing is a genome engineering technique that uses targeted DNA double-strand breaks (DSBs) to stimulate genome editing through homologous recombination (HR)-mediated recombination events. To achieve effective genome editing via introduction of site-specific DNA DSBs, four major classes of customizable DNA binding proteins can be used: meganucleases derived from microbial mobile genetic elements, ZF nucleases based on eukaryotic transcription factors, transcription activator-like effectors (TALEs) from *Xanthomonas* bacteria, and the RNA-guided DNA endonuclease Cas9 from the type II bacterial adaptive immune system CRISPR (clustered regularly interspaced short palindromic repeats). Meganuclease, ZF, and TALE proteins all recognize specific DNA sequences through protein-DNA interactions. Although meganucleases integrate its nuclease and DNA-binding domains, ZF and TALE proteins consist of individual modules targeting 3 or 1 nucleotides (nt) of DNA, respectively. ZFs and TALEs can be assembled in desired combinations and attached to the nuclease domain of FokI to direct nucleolytic activity toward specific genomic loci.

Upon delivery into host cells via the bacterial type III secretion system, TAL effectors enter the nucleus, bind to effector-specific sequences in host gene promoters and activate transcription. Their targeting specificity is determined by a central domain of tandem, 33-35 amino acid repeats. This is followed by a single truncated repeat of 20 amino acids. The majority of naturally occurring TAL effectors examined have between 12 and 27 full repeats.

These repeats only differ from each other by two adjacent amino acids, their repeat-variable di-residue (RVD). The RVD that determines which single nucleotide the TAL effector will recognize: one RVD corresponds to one nucleotide, with the four most common RVDs each preferentially associating with one of the four bases. Naturally occurring recognition sites are uniformly preceded by a T that is required for TAL effector activity. TAL effectors can be fused to the catalytic domain of the FokI nuclease to create a TAL effector nuclease (TALEN) which makes targeted DNA double-strand breaks (DSBs) in vivo for genome editing. The use of this technology in genome editing is well described in the art, for example in U.S. Pat. Nos. 8,440,431, 8,440,432 and 8,450,471. Reference 30 describes a set of customized plasmids that can be used with the Golden Gate cloning method to assemble multiple DNA fragments. As described therein, the Golden Gate method uses Type IIS restriction endonucleases, which cleave outside their recognition sites to create unique 4 bp overhangs. Cloning is expedited by digesting and ligating in the same reaction mixture because correct assembly eliminates the enzyme recognition site. Assembly of a custom TALEN or TAL effector construct and involves two steps: (i) assembly of repeat modules into intermediary arrays of 1-10 repeats and (ii) joining of the intermediary arrays into a backbone to make the final construct.

Another genome editing method that can be used according to the various aspects of the invention is CRISPR. The use of this technology in genome editing is well described in the art, for example in U.S. Pat. No. 8,697,359 and references cited herein. In short, CRISPR is a microbial nuclease system involved in defense against invading phages and plasmids. CRISPR loci in microbial hosts contain a combination of CRISPR-associated (Cas) genes as well as non-coding RNA elements capable of programming the specificity of the CRISPR-mediated nucleic acid cleavage (sgRNA). Three types (I-III) of CRISPR systems have been identified across a wide range of bacterial hosts. One key feature of each CRISPR locus is the presence of an array of repetitive sequences (direct repeats) interspaced by short stretches of non-repetitive sequences (spacers). The non-coding CRISPR array is transcribed and cleaved within direct repeats into short crRNAs containing individual spacer sequences, which direct Cas nucleases to the target site (protospacer). The Type II CRISPR is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Watson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer.

Cas9 is thus the hallmark protein of the type II CRISPR-Cas system, and a large monomeric DNA nuclease guided to a DNA target sequence adjacent to the PAM (protospacer adjacent motif) sequence motif by a complex of two non-coding RNAs: CRIPSR RNA (crRNA) and trans-activating crRNA (tracrRNA). The Cas9 protein contains two nuclease domains homologous to RuvC and HNH nucleases. The HNH nuclease domain cleaves the complementary DNA strand whereas the RuvC-like domain cleaves the non-complementary strand and, as a result, a blunt cut is introduced in the target DNA. Heterologous expression of Cas9 together with an sgRNA can introduce site-specific double strand breaks (DSBs) into genomic DNA of live cells from various organisms. For applications in eukaryotic organisms, codon optimized versions of Cas9, which is originally from the bacterium *Streptococcus pyogenes*, have been used.

The single guide RNA (sgRNA) is the second component of the CRISPR/Cas system that forms a complex with the Cas9 nuclease. sgRNA is a synthetic RNA chimera created by fusing crRNA with tracrRNA. The sgRNA guide sequence located at its 5' end confers DNA target specificity. Therefore, by modifying the guide sequence, it is possible to create sgRNAs with different target specificities. The canonical length of the guide sequence is 20 bp. In plants, sgRNAs have been expressed using plant RNA polymerase III promoters, such as U6 and U3.

Using these techniques, it is possible to specifically target conserved domains to abolish the function of the NGAL2 and/or NGAL3 polypeptide.

For example, the conserved B3 domain or repression motif may be targeted.

Thus, in another embodiment of the invention directed to a mutant plant, plant cell, plant or a part thereof characterised in that the activity of a NGAL2 polypeptide is altered and said plant expresses a nucleic acid comprising a mutant SEQ ID NO. 1 or 2 and encoding a mutant NGAL2 polypeptide, a functional homologue or variant thereof, for example one which carries a mutation in the B3 or repressor domain.

Thus, in another embodiment of the invention directed to a mutant plant, plant cell, plant or a part thereof characterised in that the activity of a NGAL3 polypeptide is altered and said plant expresses a nucleic acid comprising a mutant SEQ ID NO. 4 and encoding a mutant NGAL3 polypeptide, a functional homologue or variant thereof which carries a mutation in the B3 or repressor domain.

In a preferred embodiment, the invention directed to a mutant plant, plant cell, plant or a part thereof characterised in that the activity of a NGAL2 and a NGAL3 polypeptide is altered and said plant expresses a nucleic acid comprising a mutant SEQ ID NO. 1 or 2 and encoding a mutant NGAL2 polypeptide, a functional homologue or variant thereof, for example one which carries a mutation in the B3 or repressor domain and said plant expresses a nucleic acid comprising a mutant SEQ ID NO. 4 and encoding a mutant NGAL3 polypeptide which carries a mutation in the B3 or repressor domain.

Mutations in the promoter region of SOD7 and/or NGAL3 resulting in a loss of function are also within the scope of the invention.

Constructs designed using the genome editing technologies to knock out or knock down NGAL2 or NGAL3, for example as shown herein, are also within the scope of the invention as well as host cells comprising these constructs. In one embodiment, the constructs comprise or consist of a sequence selected from SEQ ID NO: 155, 156, 157 or 158. Accordingly, in a further aspect of the invention, there is provided a nucleic acid construct comprising a sequence selected from SEQ ID NO: 155, 156, 157 or 158. In a further aspect of the invention, there is provided a nucleic acid construct comprising at least one CRISPR target sequence, wherein the target sequence is selected from SEQ ID Nos 150, 160, 161, 162 and 163. Preferably, the target sequence comprises at least two CRISPR target sequences, preferably SEQ ID No 159 and 160 or SEQ ID No 161 and 162, or SEQ ID No 161 and 163 or SEQ ID No 159 and 163.

In another embodiment of the methods of the invention, inactivating, repressing or down-regulating the activity of NGAL2 and/or NGAL3 can be achieved by manipulating the expression of SOD7 and/or NGAL3 inhibitors in a plant, for example transgenic plant. For example, a gene expressing a protein that inhibits the expression of the SOD7 and/or NGAL3 gene or activity of the SOD7 and/or NGAL3 protein can be introduced into a plant and over-expressed. The inhibitor may interact with the regulatory sequences that direct SOD7 and/or NGAL3 gene expression to down-regulate or repress SOD7 and/or NGAL3 gene expression. For example, the inhibitor may be a transcriptional repressor. Alternatively, it may interact and repress transcriptional regulators, for example transcription factors, that positively regulate expression of the SOD7 and/or NGAL3 gene. Alternatively, the inhibitor it may directly interact with the NGAL2 and/or NGAL3 protein to inhibit its activity or interact with modulators of the NGAL2 and/or NGAL3 protein. For example, the activity of the NGAL2 and/or NGAL3 protein may be inactivated, repressed or down-regulated by manipulating post-transcriptional modifications, of the NGAL2 and/or NGAL3 protein resulting in a reduced or lost activity.

In one embodiment, the methods of the invention comprise comparing the activity of the NGAL2 and/or NGAL3 polypeptide and/or expression of the SOD7 and/or NGAL3 gene with the activity of the NGAL2 and/or NGAL3 polypeptide and/or expression of the SOD7 and/or NGAL3 gene in a control plant.

In another aspect, the invention relates to a plant obtainable or obtained by a method as described herein.

In another aspect, the invention relates to an expression cassette comprising an isolated nucleic acid sequence comprising or consisting of a sequence as shown in
SEQ ID NO: 1 or 2 a functional part, variant, homologue or orthologue thereof operably linked to a regulatory element. In another aspect, the invention relates to an expression cassette comprising an isolated nucleic acid sequence comprising or consisting of a sequence as shown in SEQ ID NO: 4 or a functional part, variant, homologue or orthologue thereof operably linked to a regulatory element. The regulatory element may be a promoter. The invention also relates to a vector comprising such expression cassette. The invention also relates to a composition comprising the two expression cassettes above.

In the methods described here, plants can be regenerated from plants transformed or genetically altered as described above and the phenotype, specifically the seed phenotype is analysed by known methods.

Transformation methods are known in the art. The nucleic acid sequence is introduced into said plant through a process called transformation. The term "introduction" or "transformation" as referred to herein encompasses the transfer of an exogenous polynucleotide into a host cell, irrespective of the method used for transfer. Plant tissue capable of subsequent clonal propagation, whether by organogenesis or embryogenesis, may be transformed with a genetic construct of the present invention and a whole plant regenerated there from. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The resulting transformed plant cell may then be used to regenerate a transformed plant in a manner known to persons skilled in the art.

The transfer of foreign genes into the genome of a plant is called transformation. Transformation of plants is now a routine technique in many species. Advantageously, any of several transformation methods may be used to introduce the gene of interest into a suitable ancestor cell. The methods described for the transformation and regeneration of plants from plant tissues or plant cells may be utilized for transient or for stable transformation. Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts, electroporation of protoplasts, microinjection into plant material, DNA or RNA-coated particle bombardment, infection with (non-integrative) viruses and the like. Transgenic plants, including transgenic crop plants, are preferably produced via *Agrobacterium tumefaciens* mediated transformation.

To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility is growing the seeds, if appropriate after sterilization, on agar plates using a suitable selection agent so that only the transformed seeds can grow into plants. Alternatively, the transformed plants are screened for the presence of a selectable marker such as the ones described above. Following DNA transfer and regeneration, putatively transformed plants may also be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques. The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

The various aspects of the invention described herein clearly extend to any plant cell or any plant produced, obtained or obtainable by any of the methods described herein, and to all plant parts and propagules thereof unless otherwise specified. The present invention extends further to encompass the progeny of a primary transformed or transfected cell, tissue, organ or whole plant that has been produced by any of the aforementioned methods, the only requirement being that progeny exhibit the same genotypic and/or phenotypic characteristic(s) as those produced by the parent in the methods according to the invention.

The invention also extends to harvestable parts of a plant of the invention as described above such as, but not limited to seeds, leaves, fruits, flowers, stems, roots, rhizomes, tubers and bulbs. The invention furthermore relates to products derived, preferably directly derived, from a harvestable part of such a plant, such as dry pellets or powders, oil, fat and fatty acids, starch or proteins. The invention also relates to food products and food supplements comprising the plant of the invention or parts thereof.

While the foregoing disclosure provides a general description of the subject matter encompassed within the scope of the present invention, including methods, as well as the best mode thereof, of making and using this invention, the following examples are provided to further enable those skilled in the art to practice this invention and to provide a complete written description thereof. However, those skilled in the art will appreciate that the specifics of these examples should not be read as limiting on the invention, the scope of which should be apprehended from the claims and equivalents thereof appended to this disclosure. Various further aspects and embodiments of the present invention will be apparent to those skilled in the art in view of the present disclosure.

All documents mentioned in this specification are incorporated herein by reference in their entirety, including references to gene and protein accession numbers.

"and/or" where used herein is to be taken as specific disclosure of each of the multiple specified features or components with or without the other at each combination unless otherwise dictated. For example "A, B and/or C" is to be taken as specific disclosure of each of (i) A, (ii) B, (iii) C, (iv) A and B, (v) B and C or (vi) A and B and C, just as if each is set out individually herein.

Unless context dictates otherwise, the descriptions and definitions of the features set out above are not limited to any particular aspect or embodiment of the invention and apply equally to all aspects and embodiments which are described.

The invention is further described in the following non-limiting examples.

Examples

Methods
Plant Materials and Growth Conditions

*Arabidopsis thaliana* Columbia (Col-0) was used as wild-type line. The dal-1, sod7-1D, sod7-ko1 and ngal3-ko1 were in the Col-0 background. sod7-1D was identified as a suppressor of dal-1 by using T-DNA activation tagging method. The sod7-ko1 (SM_3_34191) and ngal3-ko1 (SM_3_36641) were identified in AtIDB (atidb.org) and obtained from *Arabidopsis* Stock Centre NASC collection. T-DNA insertions were confirmed by PCR and sequencing by using the primers described in Table 1. *Arabidopsis* plants were grown under long-day conditions (16 h light/8 h dark) at 22° C. Activation tagging screening The activation tagging plasmid pJFAT260 was introduced into the dal-1 mutant plants using *Agrobacterium tumefaciens* strain GV3101 (Fan et al., 2009; Fang et al., 2012), and T1 plants were selected by using the herbicide Basta. Seeds produced from T1 plants were used to isolate modifiers of dal-1.

Morphological and Cellular Analysis

To measure seed size, we photographed dry seeds of the wild type and mutants under a Leica microscope (LEICA S8APO) using Leica CCD (DFC420). The projective area of wild-type and mutant seeds was measured by using Image J software. Average seed weight was determined by weighing mature dry seeds in batches of 100 using an electronic analytical balance (METTLER TOLEDO AL104, China). The weights of five sample batches were measured for each seed lot. Fully expanded cotyledons, petals (stage 14) and leaves were scanned to produce digital images for area measurement. To measure cell number and cell size, petals, leaves, ovules and seeds were placed in a drop of clearing solution [30 ml H2O, 80 g Chloral hydrate (Sigma, C8383), 10 ml 100% Glycerol (Sigma, G6279)]. Cleared Samples were imaged under a Leica microscope (LEICA DM2500) with differential interference contrast (DIC) optics and photographed with a SPOT FLEX Cooled CCD Digital Imaging System. Area measurement was made by using Image J software.

Cloning of the SOD7 Gene

The flanking sequences of the T-DNA insertion of the sod7-1D mutant were identified by the thermal asymmetric interlaced PCR (TAIL-PCR) according to a previously reported method (Liu et al., 1995). Briefly, TAIL-PCR utilizes three nested specific primers (OJF22, OJF23 and OJF24) within the T-DNA region of the pJFAT260 vector and a shorter arbitrary degenerate primer (AD1). Thus, the relative amplification efficiencies of specific and non-specific products can be thermally controlled. TAIL-PCR products were sequenced using the primer OJF24. The specific primers OJF22, OJF23 and OJF24 and an arbitrary degenerate (AD1) primer are described in Table 1.

Constructs and Plant Transformation

The 35S:GFP-SOD7, pSOD7:SOD7-GFP and pSOD7:GUS constructs were made using a PCR-based Gateway system. The coding sequence (CDS) of SOD7 was amplified using the primers SOD7CDS-F and SOD7CDS-R (Table 1). PCR products were cloned into pCR8/TOPO TA cloning vector. The SOD7 CDS was then subcloned into the binary vector pMDC43 with the GFP gene to generate the transformation plasmid 35S:GFP-SOD7. The SOD7 genomic sequence containing 2040-bp promoter sequence and 2104-bp SOD7 gene was amplified using the primers SOD7G-F and SOD7G-R (Table 1). PCR products were cloned into pCR8/TOPO TA cloning vector. The SOD7 genomic sequence was then subcloned into the binary vectors pMDC107 with the GFP gene to generate the transformation plasmid pSOD7:SOD7-GFP. The 2262-bp SOD7 promoter sequence was amplified using the primers SOD7P-F and SOD7P-R (Table 1). PCR products were cloned into pCR8/TOPO TA cloning vector. The SOD7 promoter was then subcloned into the binary vectors pGWB3 with the GUS gene to generate the transformation plasmid pSOD7:GUS. The plasmids 35S:GFP-SOD7, pSOD7:SOD7-GFP and pSOD7:GUS were introduced into Col-0 or sod7-ko1 ngal3ko1 plants using *Agrobacterium tumefaciens* GV3101, respectively, and transformants were selected on hygromycin (30 µg/ml)-containing medium. The SOD7 cDNA was cloned into the ApaI and SpeI sites of the binary vector pER8 to generate a chemically inducible construct pER8-SOD7. The specific primers for the pER8-SOD7 construct were SOP7ER-F and SOD7ER-R. The plasmid pER8-SOD7 was introduced into Col-0 plants using *Agrobacterium tumefaciens* GV3101, and transformants were selected on hygromycin (30 µg/ml)-containing medium. GUS staining Samples (pSOD7:GUS) were stained in a GUS staining solution (1 mM X-gluc, 50 Mm NaPO4 buffer, 0.4 mM each K3Fe(CN)6/K4Fe(CN)6, and 0.1% (v/v) Triton X-100) and incubated at 37° C. for 3 hours. After GUS staining, chlorophyll was removed by 70% ethanol. RT-PCR and quantitative real-time RT-PCR. Total RNA was extracted from *Arabidopsis* seedlings using an RNAprep pure Plant kit (TIANGEN). mRNA was reverse transcribed into cDNA using SuperScriptIII reverse transcriptase (Invitrogen). cDNA samples were standardized on ACTIN2 transcript amount using the primers ACTIN2-F and ACTIN2-R (Table 1). Quantitative real-time RT-PCR analysis was performed with a Lightcycler 480 machine (Roche) using the Lightcycler 480 SYBR Green I Master (Roche). ACTIN2 mRNA was used as an internal control, and relative amounts of mRNA were calculated using the comparative threshold cycle method. The primers used for RT-PCR and quantitative real-time RT-PCR are described in Table 1.

The Chromatin Immunoprecipitation (ChIP) Assay

The chromatin immunoprecipitation (ChIP) assay was performed as described previously with minor modifications (Gendrel et al., 2005). Briefly, 35S:GFP and 35S:GFP- SOD7 transgenic seeds were grown on ½ MS plates for 10 days. The seedlings were cross-linked by 1% formaldehyde for 15 min in vacuum and stopped by 0.125 M Glycine. Samples were ground in liquid nitrogen, and nuclei were isolated. Chromatin was immunoprecipitated by anti-GFP (Roche, 11814460001) and protein A+G beads (Millpore Magna ChIP Protein A+G Magnetic Beads, 16-663). DNA was precipitated by glycogen, NaOAc and ethanol, washed by 70% ethanol, and dissolved in 60 μl of water. Gene-specific primers (PF1-F, PF1-R, PF-2F, PF2-R, ACTIN7-ChIP-F, and ACTIN7-ChIP-R) were used to quantify the enrichment of each fragment (Table 1).

The DNA Electrophoretic Mobility Shift Assay (EMSA)

The coding sequence of SOD7 was cloned into the NdeI and BamHI sites of the pMAL-C2 vector to generate the construct MBP-SOD7. MBP-SOD7 fusion proteins were expressed in *Escherichia coli* BL21 (DE3) (Biomed) and purified by Amylose resins (New England Biolabs). The biotin-labeled and unlabeled probes were synthesized as forward and reverse strands. The forward and reverse strands were then incubated in a solution (50 mM Tris-HCl, 5 mM EDTA and 250 mM NaCl) at 95° C. for 10 min and renatured to double stranded probes at room temperature. The gel-shift assay was performed according to the method described previously (Smaczniak et al., 2012).

Results

Sod7-1D Suppresses the Seed Size Phenotype of Da1-1

We previously identified the ubiquitin receptor DA1 as a negative regulator of seed size in *Arabidopsis* (Li et al., 2008). The da1-1 mutant formed large seeds due to increased cell proliferation in the maternal integuments (Li et al., 2008; Xia et al., 2013). To identify novel components in the DA1 pathway or other seed size regulators, we initiated a T-DNA activation tagging screen for modifiers of da1-1 (Fang et al., 2012). A dominant suppressor of da1-1 (sod7-1D) was isolated from seeds produced from approximate 16,000 T1 plants (FIG. 1A). Seeds of the sod7-1D da1-1 double mutant were significantly smaller and lighter than da1-1 seeds (FIGS. 1A, E and F). The embryo constitutes the major volume of a mature seed in *Arabidopsis*. sod7-1D da1-1 embryos were smaller than da1-1 embryos (FIG. 1B). The size of sod7-1D da1-1 cotyledons was significantly reduced, compared with that of da1-1 cotyledons (FIG. 1G). In addition, sod7-1D da1-1 double mutant formed smaller leaves and flowers than da1-1 (FIGS. 1C and 1D). Thus, these results show that the sod7-1D mutation suppressed the seed and organ size phenotypes of da1-1.

Sod7-1D Produces Small Seeds

We isolated the single sod7-1D mutant among F2 progeny derived from a cross between the wild type (Col-0) and sod7-1D da1-1. The sod7-1D seeds were significantly smaller and lighter than wild-type seeds (FIGS. 2A, B, G and H). We further isolated and visualized embryos from mature wild-type and sod7-1D seeds. The sod7-1D embryos were obviously smaller than wild-type embryos (FIGS. 2C and D). The changes in seed size were also reflected in the size of seedlings (FIGS. 2E and F). The 10-d old sod7-1D cotyledons were significantly smaller than wild-type cotyledons (FIGS. 2E, F and I). In addition, the sod7-1D mutants exhibited small leaves and flowers compared with the wild type. The decreased size of sod7-1D leaves and petals was not caused by smaller cells, indicating that the sod7-1D mutation results in a decrease in cell number. In fact, the average area of epidermal cells in sod7-1D petals was larger than that in wild-type petals, suggesting a possible compensation mechanism between cell number and cell size.

SOD7 Encodes a B3 Domain Transcriptional Repressor NGAL2

To determine whether the seed and organ size phenotypes of sod7-1D was caused by the T-DNA insertion, we firstly analyzed the genetic linkage of the mutant phenotypes with Basta resistance, which is conferred by the selectable marker of the activation tagging vector (Fan et al., 2009). In a T2 population, 181 plants with sod7-1D da1-1 phenotypes were resistant, whereas 55 plants with da1-1 phenotypes were sensitive, indicating that the insertion is cosegregated with the sod7-1D phenotypes. To clone the SOD7 gene, we isolated the T-DNA flanking sequences using thermal asymmetric interlaced PCR (Liu et al., 1995). DNA sequencing revealed that the T-DNA had inserted approximately 5.6 kb upstream of the At3g11580 and about 3.7 kb upstream of the At3g11590 gene (FIG. 3A). To determine which gene is responsible for the sod7-1D phenotypes, we examined the mRNA levels of these two genes. The mRNA of the At3g11590 gene accumulated at a similar level in sod7-1D da1-1 and da1-1, suggesting that At3g11590 is not the SOD7 gene (FIG. 3B). By contrast, expression level of the At3g11580 gene in sod7-1D da1-1 plants was dramatically higher than that in da1-1 plants, suggesting that At3g11580 is the SOD7 gene (FIG. 3B). To further confirm whether the sod7-1D phenotypes were caused by ectopic At3g11580 expression, we overexpressed the At3g11580 gene (35S: GFP-SOD7) in wild-type plants (Col-0) and isolated 37 transgenic plants. Most transgenic lines showed small seeds and organs (FIGS. 3D-F), similar to those observed in the sod7-1D single mutant, indicating that At3g11580 is the SOD7 gene. The SOD7 gene encodes a NGATHA like protein (NGAL2) containing a B3 DNA-binding domain and a transcriptional repression motif (FIG. 3C) (Alvarez et al., 2009; Ikeda and Ohme-Takagi, 2009; Trigueros et al., 2009). SOD7 belongs to the RAV gene family that consists of 13 members in *Arabidopsis* (FIG. 10) (Swaminathan et al., 2008). Several members of the RAV family contain the putative transcriptional repression motifs, including NGA1, NGA2, NGA3, NGA4, NGAL1, NGAL2/SOD7 and NGAL3 (FIG. 10) (Ikeda and Ohme-Takagi, 2009). The transcriptional repression motifs in NGA1, NGAL1 and NGAL2/SOD7 have been known to possess the repressive activity (Ikeda and Ohme-Takagi, 2009), indicating that they are transcriptional repressors. SOD7 exhibits the highest similarity to *Arabidopsis* NGAL3/DEVELOPMENT-RELATED PcG TARGET IN THE APEX 4 (DPA4) (FIG. 10), which has known roles in the regulation of leaf serrations (Engelhorn et al., 2012), but no previously identified function in seed size control.

Expression Pattern and Subcellular Localization of SOD7

To monitor SOD7 expression pattern during development, the pSOD7:GUS and pSOD7:SOD7-GFP vectors were constructed and transformed to wild-type plants, respectively. The tissue-specific expression patterns of SOD7 were examined using a histochemical assay for GUS activity. In seedlings, relatively higher GUS activity was detected in younger leaves than in older leaves (FIGS. 4A-C). In flowers, GUS activity was observed in sepals, petals, stamens and carpels (FIGS. 4D-K). GUS activity was stronger in younger floral organs than in older ones (FIGS. 4D-K). Expression of SOD7 was also detected in ovules (FIG. 4L). Thus, these analyses indicate that SOD7 is a temporally and spatially expressed gene. As SOD7 encodes a B3 domain transcriptional repressor, we speculated that SOD7 is localized in the nucleus. To determine subcellular localization of SOD7, we observed GFP inflorescence in pSOD7:SOD7-GFP transgenic plants. As shown in FIGS. 4M-O, GFP signal was only detected in nuclei. We also expressed a GFP-SOD7 fusion protein under the control of the 35S promoter in wild-type plants. Transgenic lines overexpressing GFP-SOD7 formed smaller seeds than the wild type (FIG. 3D), indicating that the GFP-SOD7 fusion protein is functional. As shown in FIGS. 4P-R, GFP fluorescence in 35S:GFP-SOD7 transgenic plants was exclusively observed in nuclei. Thus, these results show that SOD7 is a nuclear-localized protein.

SOD7/NGAL2 Acts Redundantly with NGAL3 to Control Seed Size

In order to further investigate the function of SOD7 in seed size control, we isolated T-DNA inserted loss-of-function mutants for SOD7 and NGAL3, the most closely related family member. sod7-ko1 (SM_3_34191) was identified with T-DNA insertion in the first exon of the SOD7 gene (FIG. 5A). ngal3-ko1 (SM_3_36641) had T-DNA insertion in the first exon of the NGAL3 gene (FIG. 5B). The T-DNA insertion sites were confirmed by PCR using T-DNA specific and flanking primers and sequencing PCR products. sod7-ko1 and ngal3-ko1 mutants had no detectable full-length transcripts of SOD7 and NGAL3, respectively. Seeds from sod7-ko1 and ngal3-ko1 mutants were slightly larger and heavier than seeds from wild-type plants (FIGS. 5C, G and H). The cotyledon area of sod7-ko1 and ngal3-ko1 mutants was increased, compared with that of the wild type (FIG. 5I). Considering that SOD7 shares the highest similarity with NGAL3, we speculated that SOD7 may act redundantly with NGAL3 to influence seed size. To test this, we generated the sod7-ko1 ngal3-ko1 double mutant. As shown in FIGS. 5C, D, G and H, the seed size and weight phenotypes of sod7-ko1 mutant were synergistically enhanced by the disruption of NGAL3, indicating that SOD7 functions redundantly with NGAL3 to control seed size. We further measured the cotyledon area of 10-d-old seedlings. A synergistic enhancement of cotyledon size of sod7-ko1 by the ngal3-ko1 mutation was also observed (FIG. 5I). In addition, the sod7-ko1 ngal3-ko1 double mutant formed larger leaves and flowers than their parental lines (FIGS. 5E and F; 11). Thus, these results indicate that SOD7 and NGAL3 act redundantly to control seed and organ growth.

SOD7 Acts Maternally to Control Seed Size

As the size of a seed is determined by the zygotic and/or maternal tissues (Garcia et al., 2005; Xia et al., 2013; Du et al., 2014), we asked whether SOD7 functions maternally or zygotically. We therefore performed reciprocal cross experiments between the wild type and sod7-ko1 ngal3-ko1. The effect of sod7-ko1 ngal3-ko1 on seed size was observed only when sod7-ko1 ngal3-ko1 was used as maternal plants (FIG. 6A). The size of seeds from sod7-ko1 ngal3-ko1 plants pollinated with wild-type pollen was similar to that from the self-pollinated sod7-ko1 ngal3-ko1 plants (FIG. 6A). By contrast, the size of seeds from wild-type plants pollinated with sod7-ko1 ngal3-ko1 mutant pollen was similar to that from the self-pollinated wild-type plants (FIG. 6A). These results indicate that sod7-ko1 ngal3-ko1 acts maternally to influence seed size. We further investigated the size of Col-0/Col-0 F2, Col-0/sod7-ko1 ngal3-ko1 F2, sod7-ko1 ngal3-ko1/Col-0 F2 and sod7-ko1 ngal3-ko1/sod7-ko1 ngal3-ko1 F2 seeds. As shown in FIG. 6B, sod7-ko1 ngal3-ko1/sod7-ko1 ngal3-ko1 F2 seeds were larger than wild-type seeds, while the size of Col-0/sod7-ko1 ngal3-ko1 F2 and sod7-ko1 ngal3-ko1/Col-0 F2 seeds was similar to that of wild-type seeds. Thus, these results indicate that the embryo and endosperm genotypes for SOD7 do not determine seed size, and SOD7 is required in the sporophytic tissue of the mother plant to control seed growth.

SOD7 Regulates Cell Proliferation in the Maternal Integuments

The reciprocal crosses showed that SOD7 functions maternally to influence seed size. The integuments surrounding the ovule are maternal tissues, which could set the growth potential of the seed coat after fertilization. Consistent with this idea, several studies showed that the integument size influences the final size of seeds in Arabidopsis (Garcia et al., 2005; Schruff et al., 2006; Adamski et al., 2009; Xia et al., 2013; Du et al., 2014). We therefore asked whether SOD7 acts through the maternal integuments to determine seed size. To test this, we characterized mature ovules of the wild type and sod7-ko1 ngal3-ko1. As shown in FIGS. 6C and D, the sod7-ko1 ngal3-ko1 ovules were obviously larger than wild-type ovules. The outer integument length of sod7-ko1 ngal3-ko1 ovules was significantly increased, compared with that of wild-type ovules (FIG. 6E). As the size of the integument is determined by cell proliferation and cell expansion, we examined the number and size of outer integument cells in wild-type and sod7-ko1 ngal3-ko1 ovules. As shown in FIG. 6F, the number of outer integument cells in sod7-ko1 ngal3-ko1 ovules was increased, compared with that in wild-type ovules. By contrast, the length of outer integument cells in sod7-ko1 ngal3-ko1 ovules was similar to that in wild-type ovules (FIG. 6G). These results showed that SOD7 is required for cell proliferation in the maternal integuments of ovules. After fertilization, cells in the integument mainly undergo expansion but still have division. We further examined the number and size of outer integument cells in wild-type and sod7-ko1 ngal3-ko1 seeds at 6 and 8 day after pollination (DAP). In wild-type seeds, the number of outer integument cells at 6 DAP was comparable with that at 8 DAP (FIG. 6F), indicating that cells in the outer integuments of wild-type seeds completely stop dividing by 6 DAP. Similarly, cells in the outer integuments of sod7-ko1 ngal3-ko1 seeds also cease division by 6 DAP. The number of outer integument cells in sod7-ko1 ngal3-ko1 seeds was significantly increased, compared with that in wild-type seeds (FIG. 6F). By contrast, the length of outer integument cells in sod7-ko1 ngal3-ko1 seeds was not increased in comparison to that in wild-type seeds (FIG. 6G). Thus, these analyses indicate that SOD7 is required for cell proliferation in the maternal integuments of ovules and developing seeds.

SOD7 Acts in a Common Pathway with KLU to Control Seed Size, but does so Independently of DA1

The Arabidopsis klu mutants formed small seeds due to the decreased cell proliferation in the integuments, while plants overexpressing KLU/CYP78A5 produced large seeds as a result of the increased cell proliferation in the integuments (Adamski et al., 2009), suggesting that SOD7 and KLU could function antagonistically in a common pathway to control seed growth. To test for genetic interactions between SOD7 and KLU, we generated the klu-4 sod7-ko1 ngal3-ko1 triple mutant and measured the size of seeds from wild-type, klu-4, sod7-ko1 ngal3-ko1 and klu-4 sod7-ko1 ngal3-ko1 plants. As shown in FIGS. 7A and B, the average size and weight of klu-4 sod7-ko1 ngal3-ko1 seeds were similar to those of the klu-4 single mutant, indicating that klu-4 is epistatic to sod7-ko1 ngal3-ko1 with respect to seed size and weight. We further investigated the mature ovules from wild-type, klu-4, sod7-ko1 ngal3-ko1 and klu-4 sod7-ko1 ngal3-ko1 plants. The outer integument length of klu-4 sod7-ko1 ngal3-ko1 ovules was comparable with that of klu-4 ovules (FIG. 7C). Similarly, the outer integument length of klu-4 sod7-ko1 ngal3-ko1 seeds was indistinguishable from that of klu-4 seeds at 8 DAP (FIG. 7C). In addition, the size of klu-4 sod7-ko1 ngal3-ko1 petals was similar to that of klu-4 petals).

Thus, these genetic analyses show that klu-4 is epistatic to sod7-ko1 ngal3-ko1 with respect to seed and organ size, indicating that SOD7 and KLU act antagonistically in a common pathway to control seed and organ growth. To further understand the cellular basis of epistatic interactions between SOD7 and KLU, we investigated the outer integument cell number of ovules and developing seeds from wild-type, klu-4, sod7-ko1 ngal3-ko1 and klu-4 sod7-ko1 ngal3-ko1 plants. The number of outer integument cells in klu-4 sod7-ko1 ngal3-ko1 ovules was similar to that in klu-4 ovules (FIG. 7D). Similarly, the number of outer integument cells in klu-4 sod7-ko1 ngal3-ko1 seeds was comparable with that in klu-4 seeds (FIG. 7D). These results indicate that klu-4 is epistatic to sod7-ko1 ngal3-ko1 with respect to the number of outer integument cells. We also observed that cells in the outer integuments of klu-4 and klu-4 sod7-ko1 ngal3-ko1 seeds were slightly longer than those in wild-type seeds, suggesting a possible compensation mechanism between cell proliferation and cell expansion. Together, these findings show that SOD7 functions antagonistically in a common pathway with KLU to control cell proliferation in the maternal integuments.

Considering that sod7-1D was identified as a suppressor of da1-1 in seed size, we further asked whether SOD7 and DA1 could act in the same genetic pathway. To test this, we measured the size of wild-type, da1-1, sod7-1D and sod7-1D da1-1 seeds. The genetic interaction between sod7-1D and da1-1 was essentially additive for seed size, compared with that of sod7-1D and da1-1 single mutants, indicating that SOD7 might function independently of DA1 to control seed size. We further crossed sod7-ko1 ngal3-ko1 with da1-1 and generated the sod7-ko1 ngal3-ko1 da1-1 triple mutant and measured its seed size. The genetic interaction between sod7-ko1 ngal3-ko1 and da1-1 was also additive for seed size, compared with their parental lines, further supporting that SOD7 functions to control seed growth separately from DA1.

SOD7 Directly Binds to the Promoter of KLU and Represses the Expression of KLU

Considering that SOD7 acts antagonistically in a common pathway with KLU to control seed size, we asked whether the transcription repressor SOD7 could repress the expression of KLU. We therefore investigated the expression of KLU in the chemically-inducible SOD7 (pER8-SOD7) transgenic plants. After the pER8-SOD7 transgenic plants were treated with the inducer (ß-estradiol), the expression of SOD7 was strongly induced at 4 and 8 hours (FIG. 8A). As expected, the expression of KLU was dramatically repressed at 4 and 8 hours (FIG. 8A). Thus, these results indicate that SOD7 represses the expression of KLU and also suggest that KLU might be a direct target of SOD7.

To determine whether SOD7 can directly bind to the promoter of the KLU gene, we performed a chromatin immunoprecipitation (ChIP) assay with 35S:GFP and 35:GFP-SOD7 transgenic plants. It has been reported that the CACCTG sequence is recognized by the B3 domain of RAV1, one member of the RAV family (Kagaya et al., 1999; Yamasaki et al., 2004). We therefore analyzed the promoter sequence of KLU and did not find an intact CACCTG sequence within 2 kb promoter region of KLU.

However, we found a similar sequence (CACTTG) in the promoter region of KLU (FIG. 8B), which could be the potential SOD7-binding site. To test this, we examined the enrichment of a KLU promoter fragment (PF1) containing the CACTTG sequence by ChIP analyses and found that the fragment PF1 was strongly enriched in the chromatin-immunoprecipitated DNA with anti-GFP antibody (FIGS. 8B and C). By contrast, we did not detect significant enrichment of an ACTIN7 promoter sequence and the KLU promoter fragment PF2, which do not contain the CACTTG sequence (FIGS. 8B and C). This result shows that SOD7 associates with the promoter of KLU in vivo. We further expressed SOD7 as a MBP fusion protein (MBP-SOD7) and performed the DNA electrophoretic mobility shift assays (EMSA). As shown in FIGS. 8B and D, MBP-SOD7 was able to bind to the biotin-labeled probe A containing the CACTTG sequence, and the binding was reduced by the addition of an unlabeled probe A. By contrast, MBP-SOD7 failed to bind to a probe A-m with mutations in the CACTTG sequence (FIGS. 8B and D). Taken together, these results show that SOD7 directly binds to the promoter of KLU and represses KLU expression.

Discussion

Seed size is crucial for plant fitness and agricultural purposes, but little is known about the genetic and molecular mechanisms that set the final size of seeds in plants. In this study, we show that SOD7 acts maternally to control seed size by restricting cell proliferation in the integuments of ovules and developing seeds. SOD7 encodes a B3 domain transcriptional repressor NGAL2 and acts redundantly with its closest homolog NGAL3 to control seed size. Genetic analyses indicate that SOD7 functions in a common pathway with the maternal factor KLU to control seed growth, but does so independently of DA1. Further results reveal that SOD7 directly binds to the promoter region of KLU and represses KLU expression. Thus, our findings identify SOD7 as a negative factor for seed size and define the genetic and molecular mechanisms of SOD7 and KLU in seed size control.

SOD7 Acts Maternally to Regulate Seed Size

The sod7-1D gain-of-function mutant was identified as a suppressor of the large seed phenotype of da1-1. However, genetic analyses showed that SOD7 functions independently of DA1 to control seed growth. The sod7-1D single mutant produced small seeds and organs (FIG. 2), while the simultaneous disruption of SOD7 and the closely related family member NGAL3 resulted in large seeds and organs (FIG. 5), indicating that SOD7 is a negative regulator of seed and organ size. Several previous studies suggest that there is a possible link between seed size and organ growth. For instance, arf2, da1-1, da2-1 and eod3-1D mutants produced large seeds and organs (Schruff et al., 2006; Li et al., 2008; Fang et al., 2012; Xia et al., 2013), whereas klu and sod2/ubp15 mutants formed small seeds and organs (Anastasiou et al., 2007; Adamski et al., 2009; Du et al., 2014). However, seed size is not invariably associated with organ size. For example, eod8/med25 mutants with large organs formed normal-sized seeds (Xu and Li, 2011), while ap2 mutants with normal-sized organs produced large seeds (Jofuku et al., 2005; Ohto et al., 2005). Thus, these findings suggest that seeds and organs not only share common mechanisms but also possess distinct pathways to control their respective size.

Reciprocal cross experiments showed that SOD7 acts maternally to restrict seed growth, and the endosperm and embryo genotypes for SOD7 do not determine seed size (FIG. 6). The integuments surrounding the ovule are maternal tissues and form the seed coat after fertilization. Arabidopsis arf2, ap2, da1-1, da2-1 and eod3-1D mutants with large integuments formed large seeds (Jofuku et al., 2005;

Ohto et al., 2005; Schruff et al., 2006; Li et al., 2008; Fang et al., 2012; Xia et al., 2013), while klu-4 and ubp15/sod2 mutants with small integuments produced small seeds (Adamski et al., 2009; Du et al., 2014), indicating that the maternal integuments are crucial for determining seed size in *Arabidopsis*. Consistent with this notion, mature eod7-ko1 ngal3-ko1 ovules were larger than wild-type ovules (FIGS. 6C and D). The outer integument length of eod7-ko1 ngal3-ko1 ovules and developing seeds was significantly increased, compared with that of wild-type ovules and seeds (FIGS. 6E and 7C). Considering that the maternal integument or seed coat not only acts as a protective structure but also restricts seed growth, the regulation of maternal integument size is one of important mechanisms for seed size control. The size of the integument is determined by cell proliferation and cell expansion; these two processes are assumed to be coordinated. The number of outer integument cells in sod7-ko1 ngal3-ko1 ovules and seeds was significantly increased, compared with that in wild-type ovules and seeds (FIG. 6F), indicating that SOD7 controls seed growth by limiting cell proliferation in the maternal integuments. Similarly, several mutants with the increased number of cells in the maternal integuments produced large seeds in *Arabidopsis* (Schruff et al., 2006; Li et al., 2008; Xia et al., 2013). By contrast, several other mutants with the decreased number of cells in the maternal integuments formed small seeds in *Arabidopsis* (Adamski et al., 2009; Du et al., 2014). Considering that cells in the integuments mainly undergo expansion after fertilization (Garcia et al., 2005), it is possible that the number of cells in the integuments determines the growth potential of the seed coat after fertilization.

The Genetic and Molecular Mechanisms of SOD7 and KLU in Seed Size Control

The sod7-1D mutant had small seeds and organs (FIG. 2), as had been seen in klu mutants (Anastasiou et al., 2007; Adamski et al., 2009). KLU encodes a cytochrome P450 CYP78A5 that has been proposed to generate mobile plant-growth substances (Anastasiou et al., 2007; Adamski et al., 2009). KLU regulates seed size by promoting cell proliferation in the maternal integuments of ovules (Anastasiou et al., 2007; Adamski et al., 2009). By contrast, SOD7 acts maternally to control seed size by limiting cell proliferation in the integuments of ovules and developing seeds (FIG. 6). These results suggest that SOD7 could function antagonistically in a common pathway with KLU to control seed size. In our growth conditions, klu-4 formed slightly smaller seeds than the wild type due to the decreased cell number and the slightly increased cell length in the integuments of developing seeds (FIGS. 7A and D), suggesting a possible compensation mechanism between cell proliferation and cell expansion in klu-4 integuments. Importantly, our genetic analyses showed that klu-4 is epistatic to sod7-ko1 ngal3-ko1 with respect to seed and organ size (FIGS. 7A and B). klu-4 is also epistatic to sod7-ko1 ngal3-ko1 for the outer integument length (FIG. 7C). Further results revealed that the number of cells in the outer integuments of klu-4 sod7-ko1 ngal3-ko1 ovules and developing seeds was similar to that of klu-4 ovules and developing seeds (FIG. 7D). Thus, these genetic results demonstrate that SOD7 act in a common pathway with KLU to control seed size by regulating cell proliferation in the maternal integuments.

SOD7 encodes a B3 domain transcriptional repressor NGAL2 that is localized in nuclei of *Arabidopsis* cells (FIGS. 4M-R). Thus, it is possible that SOD7 could directly bind to the promoter of KLU and repress KLU expression. Supporting this idea, the inducible expression of SOD7 resulted in a strong reduction of KLU expression (FIG. 8A). Our ChIP-qPCR data showed that SOD7 associates with the promoter region of KLU in vivo (FIGS. 8B and C). EMSA experiments revealed that SOD7 directly binds to the CACTTG sequence in the promoter of the KLU gene (FIGS. 8B and D). Thus, these results illustrate that SOD7 directly targets the promoter region of KLU and represses the expression of KLU, thereby determining seed size. Taken together, these findings reveal the genetic and molecular mechanisms of SOD7 and KLU in regulating *Arabidopsis* seed size.

For many plants, the seeds are the main product to be harvested, and an increase in seed size would be beneficial for growers. In this study, we identify SOD7 as a negative regulator of seed size, and demonstrate that SOD7 acts in a common genetic pathway with KLU to control seed size. Our current knowledge of SOD7 functions suggests that the SOD7 gene (and its homologs in other plant species) could be used to engineer large seed size in crops. Considering that crop plants have undergone selection for large seed size during domestication (Fan et al., 2006; Song et al., 2007; Gegas et al., 2010), it will be a worthwhile challenge to know whether beneficial alleles of the SOD7 gene have already been utilized by plant breeders.

Knockout Experiments in Rice Using Genome Editing

Genome editing experiments to knock out os11g01560000 and/or Os12g0157000 in rice are being carried out using the crisper-cas9 system. Four vectors, each with two recognition (CRISPR target) sites, have been constructed, to achieve these knock outs, as described in FIG. 14. In summary, the vectors were obtained as follows:

1. The target sites were identified. The target site should be (or approximately so) 20 nucleotides before a NGG sequence, N being for any nucleotide. The target sequence was then evaluated using the website: http://cbi.hzau.edu.cn/crispr/help.php (incorporated herein by reference). Of note, the target site should be unique in the genome.

2. Using overlap PCR, the target sequence is linked with the U6 sequence, as shown in FIG. 14. U6 is for transcriptional activity.

3. Using infusion technology we connected the U6-guide-gRNA scaffold fragment to the vector pMDC99-cas9 to obtain the pMDC99-cas9-U6-guide-gRNA scaffold constructs. These constructs were named zyy1, zyy2, zyy3, zyy4. The full sequences of these constructs are represented in SEQ ID NO: 155, 156, 157 and 158 respectively. Each construct contains two recognition sites, which are highlighted in the sequence information, and are represented separately as SEQ ID Nos 159, 160, 161, 162 and 163.

4. We then transformed these constructs into Agrobacteria and used an Agrobacteria mediated method to transform rice and obtain gene-edited rice.

Transformation of plants is a routine technique that is well known to the skilled person. Nonetheless, a brief outline of transformation techniques is provided above.

Knock out lines are being analysed to assess the phenotype.

TABLE 1

Primers used in this study

| Primer Name | Primer Sequences |
|---|---|
| *Primers for T-DNA identification* | |
| SM_3_34191-LP | ACCATGACATTCGAGGTTCAC (SEQ ID NO. 8) |
| SM_3_34191-RP | ATCACCACCAAAACGACGTAG (SEQ ID NO. 9) |
| SM_3_36641-RP | TACGTCATGCTTCAAATCGTG (SEQ ID NO. 10) |
| SM_3_36641-RP | AGGACACGAACAATTCATTCG (SEQ ID NO. 11) |
| Spm32 | TACGAATAAGAGCGTCCATTTTAGAGTGA (SEQ ID NO. 12) |
| SM_3_39145-LP | ACCCAAAGAACAGCAATCATG (SEQ ID NO. 13) |
| SM_3_39145-RP | AAAACACTCCGCCATTAAACC (SEQ ID NO. 14) |
| *Primers for TAIL-PCR* | |
| OJF22 | CGAGTATCAATGGAAACTTAACCG (SEQ ID NO.15) |
| OJF23 | AACGGAGAGTGGCTTGAGAT (SEQ ID NO. 16) |
| OJF24 | TGGCCCTTATGGTTTCTGCA (SEQ ID NO. 17) |
| AD1 | NTCGA(G/C)T(A/T)T(G/C)G(A/T)GTT (SEQ ID NO. 18) |
| *Primers for Constructs* | |
| SOD7CDS-F | ATGTCAGTCAACCATTACCAC (SEQ ID NO. 19) |
| SOD7CDS-R | CAGGTAGGAGATGGACGAGGTTGA (SEQ ID NO. 20) |
| SOD7G-F | TGAGAGGAACCATTTCTTAGAGG (SEQ ID NO. 21) |
| SOD7G-R | ACCTCGTCCATCTCCTACCTGC (SEQ ID NO. 22) |
| SOD7P-F | AAACACGTCAAATATAACGAAT (SEQ ID NO. 23) |
| SOD7P-R | CTTTTTTTTGGTTTCTTGGAGTGAGAGAGAGAG (SEQ ID NO. 24) |
| SOD7-ER-F | AGTCTGGGCCCATGTCAGTCAACCATTAC (SEQ ID NO. 25) |
| SOD7-ER-R | GCGACTAGTTTATAAAAGAGTTAAAATTA (SEQ ID NO. 25) |
| MBP-SOD7-FP | CGGGATCCTCAGTCAACCATTACC (SEQ ID NO. 27) |
| MBP-SOD7-RP | ACTAGTCGACTCAACCTCGTCCATCTCC (SEQ ID NO. 28) |
| *Primers for RT-PCR and qRT-PCR* | |
| ACTIN2-F | GAAATCACAGCACTTGCACC (SEQ ID NO. 29) |
| ACTIN2-R | AAGCCTTTGATCTTGAGAGC (SEQ ID NO. 30) |
| SOD7-EX-F | GCGACGACGGAGAAAGGG (SEQ ID NO. 31) |
| SOD7-EX-R | ACGACGGCGCCATAGTGT (SEQ ID NO. 32) |
| NGAL3-EX-F | TTTGAAGACGAGTCAGGCAAGT (SEQ ID NO. 33) |
| NGAL3-EX-R | TACGGCGGCTCCATAGTGGG (SEQ ID NO. 34) |
| SOD7-q-FP | GTATTGGAGCGGCTTGACTACACC (SEQ ID NO. 35) |
| SOD7-q-RP | GACGGCATCACCATGACATTCG (SEQ ID NO. 36) |
| KLU-q-FP | TGATTCTGACATGATTGCTGTTCT (SEQ ID NO. 37) |
| KLU-q-RP | TCGCAACTGTATCTGTCCCTCTA (SEQ ID NO. 38) |
| *Primers for ChIP assay* | |
| ACTIN7-ChIP-FP | CGTTTCGCTTTCCTTAGTGTTAGCT (SEQ ID NO. 29) |
| ACTIN7-ChIP-RP | AGCGAACGGATCTAGAGACTCACCTTG (SEQ ID NO. 40) |

TABLE 1-continued

Primers used in this study

| Primer Name | Primer Sequences |
|---|---|
| PF1-F | CAGGCCTAAGCCTAACAGTAGAC (SEQ ID NO. 41) |
| PF1-R | TGTACTAGGATTTATTTACGTAG (SEQ ID NO. 42) |
| PF2-F | TATTGTTCATAGAAACCCTGCAAA (SEQ ID NO. 43) |
| PF2-R | AGTCAATGGTTTAATGGCGGAGTG (SEQ ID NO. 44) |
| Probes for EMSA | |
| A-Biotin-FP | TTCTACTACACTTGCTCTCTGTA (SEQ ID NO. 45) |
| A-Biotin-RP | TACAGAGAGCAAGTGTAGTAGAA (SEQ ID NO. 46) |
| A-Biotin-m-FP | TTCTACTAACACCTCTCTCTGTA (SEQ ID NO. 47) |
| A-Biotin-m-RP | TACAGAGAGAGGTGTTAGTAGAA (SEQ ID NO. 48) |

REFERENCES

Adamski, N. M., Anastasiou, E., Eriksson, S., O'Neill, C. M., and Lenhard, M. (2009). mLocal maternal control of seed size by KLUH/CYP78A5-dependent growth signaling. Proceedings of the National Academy of Sciences of the United States of America 106, 20115-20120.

Alvarez, J. P., Goldshmidt, A., Efroni, I., Bowman, J. L., and Eshed, Y. (2009). The NGATHA distal organ development genes are essential for style specification in *Arabidopsis*. Plant Cell 21, 1373-1393.

Anastasiou, E., Kenz, S., Gerstung, M., MacLean, D., Timmer, J., Fleck, C., and Lenhard, M. (2007). Control of plant organ size by KLUH/CYP78A5-dependent intercellular signaling. Developmental cell 13, 843-856.

Cheng, Z. J., Zhao, X. Y., Shao, X. X., Wang, F., Zhou, C., Liu, Y. G., Zhang, Y., and Zhang, X. S. (2014). Abscisic Acid Regulates Early Seed Development in *Arabidopsis* by AB15-Mediated Transcription of SHORT HYPOCOTYL UNDER BLUE1. Plant Cell 26, 1053-1068.

Du, L., Li, N., Chen, L., Xu, Y., Li, Y., Zhang, Y., and Li, C. (2014). The Ubiquitin Receptor DA1 Regulates Seed and Organ Size by Modulating the Stability of the Ubiquitin-Specific Protease UBP15/SOD2 in *Arabidopsis*. Plant Cell 26, 665-677.

Engelhorn, J., Reimer, J. J., Leuz, I., Gobel, U., Huettel, B., Farrona, S., and Turck, F. (2012). Development-related PcG target in the apex 4 controls leaf margin architecture in *Arabidopsis thaliana*. Development 139, 2566-2575.

Fan, C., Xing, Y., Mao, H., Lu, T., Han, B., Xu, C., Li, X., and Zhang, Q. (2006). GS3, a major QTL for grain length and weight and minor QTL for grain width and thickness in rice, encodes a putative transmembrane protein. Theor Appl Genet 112, 1164-1171.

Fan, J., Hill, L., Crooks, C., Doerner, P., and Lamb, C. (2009). Abscisic acid has a key role in modulating diverse plant-pathogen interactions. Plant physiology 150, 1750-1761

Fang, W., Wang, Z., Cui, R., Li, J., and Li, Y. (2012). Maternal control of seed size by EOD3/CYP78A6 in *Arabidopsis thaliana*. Plant J 70, 929-939.

Garcia, D., Fitz Gerald, J. N., and Berger, F. (2005). Maternal control of integument cell elongation and zygotic control of endosperm growth are coordinated to determine seed size in *Arabidopsis*. Plant Cell 17, 52-60.

Garcia, D., Saingery, V., Chambrier, P., Mayer, U., Jurgens, G., and Berger, F. (2003). *Arabidopsis* haiku mutants reveal new controls of seed size by endosperm. Plant physiology 131, 1661-1670.

Gegas, V. C., Nazari, A., Griffiths, S., Simmonds, J., Fish, L., Orford, S., Sayers, L., Doonan, J. H., and Snape, J. W. (2010). A genetic framework for grain size and shape variation in wheat. Plant Cell 22, 1046-1056.

Gendrel, A. V., Lippman, Z., Martienssen, R., and Colot, V. (2005). Profiling histone modification patterns in plants using genomic tiling microarrays. Nat Methods 2, 213-218.

Harper, J. L., Lovell, P. H., and Moore, K. G. (1970). The Shapes and Sizes of Seeds. Annual Review of Ecology and Systematics 1, 327-356

Ikeda, M., and Ohme-Takagi, M. (2009). A novel group of transcriptional repressors in *Arabidopsis*. Plant & cell physiology 50, 970-975.

Jofuku, K. D., Omidyar, P. K., Gee, Z., and Okamuro, J. K. (2005). Control of seed mass and seed yield by the floral homeotic gene APETALA2. Proceedings of the National Academy of Sciences of the United States of America 102, 3117-3122.

Kagaya, Y., Ohmiya, K., and Hattori, T. (1999). RAV1, a novel DNA-binding protein, binds to bipartite recognition sequence through two distinct DNA-binding domains uniquely found in higher plants. Nucleic Acids Res 27, 470-478.

Kang, X., Li, W., Zhou, Y., and Ni, M. (2013). A WRKY transcription factor recruits the SYG1-like protein SHB1 to activate gene expression and seed cavity enlargement. PLoS Genet 9, e1003347.

Li, J., Nie, X., Tan, J. L., and Berger, F. (2013). Integration of epigenetic and genetic controls of seed size by cytokinin in *Arabidopsis*. Proceedings of the National Academy of Sciences of the United States of America 110, 15479-15484.

Li, Y., Zheng, L., Corke, F., Smith, C., and Bevan, M. W. (2008). Control of final seed and organ size by the DA1 gene family in *Arabidopsis thaliana*. Genes Dev 22, 1331-1336.

Liu, Y. G., Mitsukawa, N., Oosumi, T., and Whittier, R. F. (1995). Efficient isolation and mapping of *Arabidopsis thaliana* T-DNA insert junctions by thermal asymmetric interlaced PCR. Plant J 8, 457-463.

Lopes, M. A., and Larkins, B. A. (1993). Endosperm origin, development, and function. Plant Cell 5, 1383-1399.

Luo, M., Dennis, E. S., Berger, F., Peacock, W. J., and Chaudhury, A. (2005). MINISEED3 (MINI3), a WRKY family gene, and HAIKU2 (IKU2), a leucine-rich repeat (LRR) KINASE gene, are regulators of seed size in *Arabidopsis*. Proceedings of the National Academy of Sciences of the United States of America 102, 17531-17536.

Moles, A. T., Ackerly, D. D., Webb, C. O., Tweddle, J. C., Dickie, J. B., and Westoby, M. (2005). A brief history of seed size. Science 307, 576-580.

Ohto, M. A., Fischer, R. L., Goldberg, R. B., Nakamura, K., and Harada, J. J. (2005). Control of seed mass by APETALA2. Proceedings of the National Academy of Sciences of the United States of America 102, 3123-3128.

Ohto, M. A., Floyd, S. K., Fischer, R. L., Goldberg, R. B., and Harada, J. J. (2009). Effects of APETALA2 on embryo, endosperm, and seed coat development determine seed size in *Arabidopsis*. Sex Plant Reprod 22, 277-289.

Orsi, C. H., and Tanksley, S. D. (2009). Natural variation in an ABC transporter gene associated with seed size evolution in tomato species. PLoS Genet 5, e1000347.

Schruff, M. C., Spielman, M., Tiwari, S., Adams, S., Fenby, N., and Scott, R. J. (2006). The AUXIN RESPONSE FACTOR 2 gene of *Arabidopsis* links auxin signalling, cell division, and the size of seeds and other organs. Development 133, 251-261. Scott, R. J., Spielman, M., Bailey, J., and Dickinson, H. G. (1998). Parent-of-origin effects on seed development in *Arabidopsis thaliana*. Development 125, 3329-3341.

Smaczniak, C., Immink, R. G., Muino, J. M., Blanvillain, R., Busscher, M., Busscher-Lange, J., Dinh, Q. D., Liu, S., Westphal, A. H., Boeren, S., Parcy, F., Xu, L., Carles, C. C., Angenent, G. C., and Kaufmann, K. (2012). Characterization of MADS-domain transcription factor complexes in *Arabidopsis* flower development. Proceedings of the National Academy of Sciences of the United States of America 109, 1560-1565.

Song, X. J., Huang, W., Shi, M., Zhu, M. Z., and Lin, H. X. (2007). A QTL for rice grain width and weight encodes a previously unknown RING-type E3 ubiquitin ligase. Nat Genet 39, 623-630.

Swaminathan, K., Peterson, K., and Jack, T. (2008). The plant B3 superfamily. Trends Plant Sci 13, 647-655.

Trigueros, M., Navarrete-Gomez, M., Sato, S., Christensen, S. K., Pelaz, S., Weigel, D., Yanofsky, M. F., and Ferrandiz, C. (2009). The NGATHA genes direct style development in the *Arabidopsis* gynoecium. Plant Cell 21, 1394-1409.

Wang, A., Garcia, D., Zhang, H., Feng, K., Chaudhury, A., Berger, F., Peacock, W. J., Dennis, E. S., and Luo, M. (2010). The VQ motif protein IKU1 regulates endosperm growth and seed size in *Arabidopsis*. Plant J 64, 670-679.

Westoby, M., Falster, D. S., Moles, A. T., Vesk, P. A., and Wright, I. J. (2002). PLANT ECOLOGICAL STRATEGIES: Some Leading Dimensions of Variation Between Species. Annual Review of Ecology and Systematics 33, 125-159.

Xia, T., Li, N., Dumenil, J., Li, J., Kamenski, A., Bevan, M. W., Gao, F., and Li, Y. (2013). The Ubiquitin Receptor DA1 Interacts with the E3 Ubiquitin Ligase DA2 to Regulate Seed and Organ Size in *Arabidopsis*. Plant Cell 25, 3347-3359.

Xiao, W., Brown, R. C., Lemmon, B. E., Harada, J. J., Goldberg, R. B., and Fischer, R. L. (2006). Regulation of seed size by hypomethylation of maternal and paternal genomes. Plant physiology 142, 1160-1168.

Xu, R., and Li, Y. (2011). Control of final organ size by Mediator complex subunit 25 in *Arabidopsis thaliana*. Development 138, 4545-4554.

Yamasaki, K., Kigawa, T., Inoue, M., Tateno, M., Yamasaki, T., Yabuki, T., Aoki, M., Seki, E., Matsuda, T., Tomo, Y., Hayami, N., Terada, T., Shirouzu, M., Osanai, T., Tanaka, A., Seki, M., Shinozaki, K., and Yokoyama, S. (2004). Solution structure of the B3 DNA binding domain of the *Arabidopsis* cold-responsive transcription factor RAV1. Plant Cell 16, 3448-3459.

Zhou, Y., Zhang, X., Kang, X., Zhao, X., and Ni, M. (2009). SHORT HYPOCOTYL UNDER BLUE1 associates with MINISEED3 and HAIKU2 promoters in vivo to regulate *Arabidopsis* seed development. Plant Cell 21, 106-117.

SEQUENCE INFORMATION

Identity of homologs to NGAL2 is indicated

AtSOD7 nucleic acid (cDNA) At3g11580

SEQ ID NO. 1

```
ATGTCAGTCAACCATTACCACAACACTCTCTCGTTGCATCATCACCACCAAAACGA

CGTAGCTATAGCACAACGAGAGTCTTTGTTCGAGAAATCACTCACACCAAGCGAC

GTCGGAAAGCTAAACCGCTTAGTCATACCAAAACAACACGCCGAGAAATACTTCC

CTCTCAATAATAATAATAATGGCGGCAGCGGAGATGACGTGGCGACGACGGA

GAAAGGGATGCTTCTTAGCTTCGAGGATGAGTCAGGCAAGTGTTGGAAATTCAGA

TACTCTTATTGGAACAGTAGCCAAAGCTACGTGTTGACCAAAGGATGGAGCAGGT

ACGTCAAAGACAAACACCTCGACGCAGGCGACGTTGTTTTCTTTCAACGTCACCG

TTTTGATCTCCATAGACTCTTCATTGGCTGGCGGAGACGCGGTGAAGCTTCTTCCT

CTCCCGCTGTCTCCGTTGTGTCTCAAGAAGCTCTAGTTAATACGACGGCGTATTG

GAGCGGCTTGACTACACCTTATCGTCAAGTACACGCGTCAACTACTTACCCTAATA

TTCACCAAGAGTATTCACACTATGGCGCCGTCGTTGATCATGCTCAGTCGATACCA

CCGGTGGTCGCAGGTAGCTCGAGGACGGTGAGGCTTTTTGGCGTGAACCTCGAA
```

```
TGTCATGGTGATGCCGTCGAGCCACCACCGCGTCCTGATGTCTATAATGACCAAC

ACATTTACTATTACTCAACTCCTCATCCCATGAATATATCATTTGCTGGGGAAGCAT

TGGAGCAGGTAGGAGATGGACGAGGTTGA
```

AtSOD7 nucleic acid (genomic DNA).

SEQ ID NO. 2

```
ttgtttcggctatttgttatactattgttataacagtcacaagacttgacctcaacgaaaacttttacaaaacgtgaattggaaa ttttttacaaaatatgctcttaatcgttaatgcttcccaattaggtgagttaaattgtgagaggaaccatttcttagaggaaatggt tcatgaaaacaaatatgaaatagtatcactagtcttagttttgcgagaaaattaggaaaaatagaaacgtgtaagcacca atgatattcctgaaagcacgtgacagatatttcatgatcctataattaacaagtgataaagatattaaataaaattaacgata cttgagaaattcgtcaaataaaatagaagaggaccactcacgtaaccatttgcacgtcccattgattttttgtggtagacttgg tatgttatattacttatattcacagaattatatacgaaactcacgacttaagatgcacggtaataactacagatggaaatttac ccatcaaacaagaaaacaacatttactcaagcatctagctagaccaaaatgtttgtttacttgttgacttgcgatccatagat atattagttagaacttttctcttctacaattgatcaaatgtttcacactgttctcaatttctcatctagattcatgacttatatgtttggtc aaatatcacagcttgatgagcattaaatagcgtcgaagtataggatggttacgttgttcaatattgtaaaggaaaaaaga gaaagagtgccaaaaggtcaagtcgatttcacaaataaatcttgaagtctttatccctctcgattataaaatgattaggaaa agaaaaagagagaataaaatgtagataaagagaaagagaaagagagagaggaacataagggatggtatgaagta gaagtgaagatgcatgcgatggtgtgtcggaaaggcaaagcacatgctacacaacttgagcttctcacttgcgtcaggg ataagtatcctctgtaccttcttacttttgcgtaatatgtaccacctcacttctcaaccgtttgatcttttaatccttcattatttcttcatt accttctcttttttgthttgttttcgttttcaatttctcatagattcatttacaaactaaatatcataggaaggtgttatctctagttaatttc ttatcctacttttaacaaaatttaattgtcaaaagattattttttacgtttatagacaaaagatactgacacatcaattccacgaac caaatggttgagaaaaacaaaacgactatctttgtcttgcaaataaattaatggcagttagtaagattctcagctgaaaatt catacaagagtaaatgatcaaataaccatttatgagagaaatttaatccttcagaaccaatgaggatctgatcaagtaat tgcaaaccacatgagtccatgataaaggattgtttgacttacgcaatccacatatttatggctgcttgatatgtaaggtttatct gctttgacagtctatagaatcttgctaatcaatacgtcatatccggtgaatactgaaacttttttaattaagaaaacacaaatc atcttttctccggaggatttcgaatttagttccggcaatgctgaaataacatatgttgaacttataacattccaagacatcaaat tttactaatatataaataattacatattcttcttctacatgatcaaaaccttttcaactttaattaaagggttacgtcgcggcgttttg tgtggcttactctttthttacactataactatagaacactcgtggatccaatgccgtttaggacaagattttatcagacgagaaa aaaaaaaacaataccacatttttaaatatatatggattatggactgcaacaacaatatagaaagaagagaaaaaaat aaaaataatgattgaaaggaaatatcatcacgcaaaaccttaaaagtactatcggtatcgtgtcgtcctctcctcatcaaat agttcccacagttttcacatcaatttaaccattttcaatttttttcactctctgtctctctcctttgtataatactatattagtaccattac ccatctctctttcaccaccaaaccaacacctgcaaatcctctctctctctctcactccaagaaaccaaaaaaaaagATG

TCAGTCAACCATTACCACAACACTCTCTCGTTGCATCATCACCACCAAAACGACGT

AGCTATAGCACAACGAGAGTCTTTGTTCGAGAAATCACTCACACCAAGCGACGTC

GGAAAGCTAAACCGCTTAGTCATACCAAAACAACACGCCGAGAAATACTTCCCTCT

CAATAATAATAATAATAATGGCGGCAGCGGAGATGACGTGGCGACGACGGAGAAA

GGGATGCTTCTTAGCTTCGAGGATGAGTCAGGCAAGTGTTGGAAATTCAGATACT

CTTATTGGAACAGTAGCCAAAGCTACGTGTTGACCAAAGGATGGAGCAGGTACGT

CAAAGACAAACACCTCGACGCAGGCGACGTTGTTTTCTTTCAACGTCACCGTTTTG

ATCTCCATAGACTCTTCATTGGCTGGCGGAGACGCGGTGAAGCTTCTTCCTCTCC

CGCTGTCTCCGTTGTGTCTCAAGAAGCTCTAGTTAATACGACGGCGTATTGGAGC

GGCTTGACTACACCTTATCGTCAAGTACACGCGTCAACTACTTACCCTAATATTCA

CCAAGAGTATTCACACTATGgtaaattcaaacccttttatttcctcttttgttttttctttctctcttatctatatgtcagatt
```

-continued

```
tatactcctctctgttctcttttaagatttgtcttttcataaaaatagatgattcgtaatttgtattgcatatttacatgttctcttaaaa aaagtaatagagattaatattttatgcatggtattttagattatctgcctactttatatggtagtaaacaagaacattcatctttatt tggttttataaacaaaatatgagaattttaaaggttagggcaagcacttggaaagctcaaccattttagttagctggtggaa tatctttcttataaaaagcaaatgagttatctaaaactatatgacaattattttagttgcgtgtgtaatgtatataaataacaac atgaaataacattttgtctttattttgtcattcttattatttaattttggacccgacaattcaaataatcttctccaagttgtaacta atccgttacatgcgcgtgaggagaaccgtccaatccacttagactaacgtgccctttatttcttccttttaattctatgttaaaaa aacaatttaactaaaagatgcgcacgtgtcttgacggtggaaaaaaattgtagGCGCCGTCGTTGATCATG

CTCAGTCGATACCACCGGTGGTCGCAGGTAGCTCGAGGACGGTGAGGCTTTTTG

GCGTGAACCTCGAATGTCATGGTGATGCCGTCGAGCCACCACCGCGTCCTGATG

TCTATAATGACCAACACATTTACTATTACTCAACTCCTCATCCCATGgtaaatattttttttttt acatttttgtcagattcaaattttgcttacgtatgatataattattaaacagatgtcgtggctgtttctcgagacgagacagatg aaaattagtaattttaaaatagacctgaaagagatttttatgthaataaattatataaaggaggaatcagagagaataata ctatacacttgactgtaaaaccacatggccaatttggttttattgattactttgatttgttttgtttactcttttgtctctgtagcctcct tttgttcattaattaatatcagccgtaagtatatagtttcctgtgaaaacagtctctattttggttttactattctaatttgttaggcac cgtcagtttttttgtgaaaccaaattattgactaataagctggaaagcaaaactgactaaaagcattacaaacttatcaatg acataagttttgaatttattaccatgttttgtaatgttcagatataatttgaaatgcttagaattatatatttgtatacttaaattaatg aaataaagtgaatactaaagatagttttattttcatattattctatacaattcggtgtacaatttgttttgatgataataaaata ataaaattgcgtgttggaattgtgaaacagAATATATCATTTGCTGGGGAAGCATTGGAGCAGGT

AGGAGATGGACGAGGT
```

AtNGAL2 (protein encoded by AtSOD7)..

SEQ ID NO. 3

```
MSVNHYHNTLSLHHHHQNDVAIAQRESLFEKSLTPSDVGKLNRLVIPKQHAEKYFPLN

NNNNNGGSGDDVATTEKGMLLSFEDESGKCWKFRYSYWNSSQSYVLTKGWSRYVK

DKHLDAGDVVFFQRHRFDLHRLFIGWRRRGEASSSPAVSVVSQEALVNTTAYWSGL

TTPYRQVHASTTYPNIHQEYSHYGAVVDHAQSIPPVVAGSSRTVRLFGVNLECHGDA

VEPPPRPDVYNDQHIYYYSTPHPMNISFAGEALEQVGDGRG
```

AtNGAL3 nucleic acid sequence (cDNA) at5g06250

SEQ ID NO. 4

```
ATGTCAGTCAACCATTACTCCACAGACCACCACCACACTCTCTTGTGGCAGCAAC

AGCAACACCGCCACACCACCGACACATCGGAGACAACCACCACCGCCACATGGC

TCCACGACGACCTAAAAGAGTCACTCTTCGAGAAGTCTCTCACACCAAGCGACGT

CGGGAAACTCAACCGCCTCGTCATACCAAAACAACACGCAGAGAAATACTTCCCT

CTCAATGCCGTCCTAGTCTCCTCTGCTGCTGCTGACACGTCATCTTCGGAGAAAG

GGATGCTTCTAAGCTTTGAAGACGAGTCAGGCAAGTCATGGAGGTTCAGATACTC

TTACTGGAACAGCAGTCAAAGCTATGTCTTGACTAAAGGATGGAGCAGATTTGTCA

AAGACAAACAGCTCGATCCAGGCGACGTTGTTTTCTTCCAACGACACCGTTCTGA

TTCTAGGAGACTCTTCATTGGCTGGCGCAGACGTGGACAAGGCTCCTCATCCTCC

GTCGCGGCCACTAACTCCGCCGTGAATACGAGTTCTATGGGAGCTCTTTCTTATC

ATCAAATCCACGCCACTAGTAATTACTCTAATCCTCCCTCTCACTCAGAGTATTCC

CACTATGGAGCCGCCGTAGCAACAGCGGCTGAGACTCACAGCACACCGTCGTCT

TCCGTCGTCGGGAGCTCAAGGACGGTGAGGCTTTTCGGTGTGAATCTGGAGTGT

CAAATGGATGAAAACGACGGAGATGATTCTGTTGCAGTTGCCACCACCGTTGAAT
```

```
CTCCCGACGGTTACTACGGCCAAAACATGTACTATTATTACTCTCATCCTCATAAC

ATGGTAATTTTAACTCTTTTATAA
```

AtNGAL3 amino acid                                                          SEQ ID NO. 5

```
MSVNHYSTDHHHTLLWQQQQHRHTTDTSETTTTATWLHDDLKESLFEKSLTPSDVG

KLNRLVIPKQHAEKYFPLNAVLVSSAAADTSSSEKGMLLSFEDESGKSWRFRYSYWN

SSQSYVLTKGWSRFVKDKQLDPGDVVFFQRHRSDSRRLFIGWRRRGQGSSSSVAAT

NSAVNTSSMGALSYHQIHATSNYSNPPSHSEYSHYGAAVATAAETHSTPSSSVVGSS

RTVRLFGVNLECQMDENDGDDSVAVATTVESPDGYYGQNMYYYYSHPHNMVILTLL
```

Oryza sativa
Os12g0157000 LOC_Os12g06080.1
Cover 73% identity 53%
SEQ ID NO: 49
```
MAMHAGHAWWGVAMYTNHYHHHYRHKTSDVGKNRVKHARYGGGDSGKGSDSGKWRRYSYWTSSSYVTKG

WSRYVKKRDAGDVVHRVRGGAADRGCRRRGSAAAVRVTANGGWSMCYSTSGSSYDTSANSYAYHRSVDDHSD

HAGSRADAKSSSAASASRRRGVNDCGADATAMYGYMHHSYAAVSTVNYWSV
```

CDS                                                                         SEQ ID NO: 50

```
ATGGCCATGCACCCTCTCGCCCAGGGGCACCCCCAGGCGTGGCCATGGGGTGTAGCCATG

TACACCAACCTGCACTACCACCACCACTACGAGAGGGAGCACCTGTTCGAGAAGCCGCTG

ACGCCGAGCGACGTCGGCAAGCTCAACAGGCTGGTGATCCCCAAGCAGCACGCCGAGAGG

TACTTCCCGCTCGGCGGCGGCGACTCCGGTGAGAAGGGCCTCCTCCTCTCCTTCGAGGAC

GAGTCCGGCAAGCCATGGCGGTTCCGCTACTCCTACTGGACCAGCAGCCAGAGCTACGTG

CTCACCAAGGGCTGGAGCCGCTACGTCAAGGAGAAGCGCCTCGACGCCGGCGACGTCGTC

CACTTCGAGCGCGTCCGCGGCCTCGGCGCCGCCGACCGCCTCTTCATCGGCTGCAGGCGC

CGCGGCGAGAGCGCGCCCGCGCCGCCGCCCGCCGTTCGCGTCACGCCGCAGCCGCCTGCC

CTCAACGGCGGCGAGCAGCAGCCGTGGAGCCCAATGTGTTACAGCACGTCGGGCTCGTCC

TACGACCCTACCAGCCCTGCCAATTCATATGCCTACCATCGCTCCGTAGACCAAGATCAC

AGCGACATACTACACGCAGGAGAGTCGCAGAGAGAAGCAGACGCCAAGAGCAGCAGCGCG

GCGTCGGCGCCGCCGCCGTCGAGGCGGCTCAGGCTGTTCGGCGTTAACCTCGACTGCGGC

CCGGAGCCGGAGGCGGATCAGGCGACGGCAATGTACGGCTACATGCACCACCAGAGCCCC

TACGCCGCAGTGTCTACAGTGCCAAATTACTGGTCAGTATTTTTTCAGTTTTAA
```

Os11g0156000
LOC_Os11g05740.1
Cover 81% identity 47%                                                      SEQ ID NO: 51

```
MAMNHPLFSQEQPQSWPWGVAMYANFHYHHHYEKEHMFEKPLTPSDVGKLNRLVIPKQHA

ERYFPLGAGDAADKGLILSFEDEAGAPWRFRYSYWTSSQSYVLTKGWSRYVKEKRLDAGD

VVHFERVRGSFGVGDRLFIGCRRRGDAAAAQTPAPPPAVRVAPAAQNAGEQQPWSPMCYS

TSGGGSYPTSPANSYAYRRAADHDHGDMHHADESPRDTDSPSFSAGSAPSRRLRLFGVNL

DCGPEPEADTTAAATMYGYMHQQSSYAAMSAVPSYWGNS
```

CDS                                                                         SEQ ID NO: 52

```
ATGGCCATGAACCACCCTCTCTTCTCCCAGGAGCAACCCCAGTCCTGGCCATGGGGTGTG

GCCATGTACGCCAACTTCCACTACCACCACCACTACGAGAAGGAGCACATGTTTGAGAAG

CCCCTGACGCCCAGTGACGTGGGGAAGCTGAACCGGCTGGTGATCCCCAAGCAGCACGCC

GAGAGGTACTTCCCCCTCGGCGCCGGCGACGCCGCCGACAAGGGCCTGATCCTGTCGTTC

GAGGACGAGGCCGGCGCGCCCGTGGCGGTTCAGGTACTCCTACTGGACGAGCAGCCAGAGC
```

```
TACGTGCTCACCAAGGGCTGGAGCCGCTACGTCAAGGAGAAGCGCCTCGACGCCGGCGAC

GTCGTGCACTTCGAGAGGGTGCGCGGCTCCTTCGGCGTCGGCGACCGTCTCTTCATCGGC

TGCAGGCGCCGCGGCGACGCCGCCGCGCGCAAACACCCGCACCGCCGCCCGCCGTGCGC

GTCGCCCCGGCTGCACAGAACGCCGGCGAGCAGCAGCCGTGGAGCCCAATGTGTTACAGC

ACGTCGGGCGGCGGCTCATACCCTACCAGCCCAGCCAACTCCTACGCCTACCGCCGCGCA

GCAGATCATGATCACGGGGACATGCACCATGCAGACGAGTCTCCGCGCGACACGGACAGC

CCAAGCTTCAGTGCAGGCTCGGCGCCATCGAGGCGGCTCAGGCTGTTCGGCGTCAACCTC

GACTGCGGGCCAGAGCCGGAGGCAGACACCACGGCAGCGGCAACAATGTACGGCTACATG

CACCAGCAGAGCTCCTATGCTGCCATGTCTGCAGTACCCAGTTACTGGGGCAATTCATAA
```

Os02g0683500 LOC_Os02g45850
Cover 47% identity 62%

SEQ ID NO: 53

MEFTTSSRFSKEEEDEEQDEAGRREIPFMTATAEAAPAPTSSSSSPAHHAASASASASAS
GSSTPFRSDDGAGASGSGGGGGGGGEAEVVEKEHMFDKVVTPSDVGKLNRLVIPKQYAEK
YFPLDAAANEKGLLLNFEDRAGKPWRFRYSYWNSSQSYVMTKGWSRFVKEKRLDAGDTVS
FSRGIGDEAARHRLFIDWKRRADTRDPLRLPRGLPLPMPLTSHYAPWGIGGGGGFFVQPS
PPATLYEHRLRQGLDFRAFNPAAAMGRQVLLFGSARIPPQAPLLARAPSPLHHHYTLQPS
GDGVRAAGSPVVLDSVPVIESPTTAAKRVRLFGVNLDNPHAGGGGGAAAGESSNHGNALS
LQTPAWMRRDPTLRLLELPPHHHHGAESSAASSPSSSSSSKRDAHSALDLDL

CDS

SEQ ID NO: 54

```
ATGGAGTTCACTACAAGCAGTAGGTTTTCTAAAGAAGAGGAGGACGAGGAGCAGGATGAG

GCGGGAAGGCGAGAGATCCCCTTCATGACGGCCACGGCCGAAGCCGCGCCTGCGCCCACG

TCGTCGTCGTCGTCTCCTGCTCATCACGCGGCTTCCGCGTCGGCGTCGGCGTCTGCGTCA

GGGAGCAGCACTCCCTTTCGCTCCGACGATGGCGCCGGGGCGTCTGGGAGCGGCGGCGGC

GGCGGCGGCGGCGGAGAAGCGGAGGTGGTGGAGAAGGAGCACATGTTCGACAAGGTGGTG

ACGCCGAGCGACGTTGGGAAGCTGAACCGGCTGGTGATCCCGAAGCAGTACGCCGAGAAG

TACTTCCCGCTGGACGCGGCGGCGAACGAGAAGGGCCTCCTGCTCAACTTCGAGGACCGC

GCGGGGAAGCCATGGCGGTTCCGCTACTCCTACTGGAACAGCAGCCAGAGCTACGTGATG

ACCAAGGGGTGGAGCCGCTTCGTCAAGGAGAAGCGCCTCGACGCCGGGGACACCGTCTCC

TTCTCCCGCGGCATCGGCGACGAGGCGGCGCGGCACCGCCTCTTCATCGACTGGAAGCGC

CGCGCCGACACCCGCGACCCGCTCCGGCTGCCCCGCGGGCTGCCGCTCCCGATGCCGCTC

ACGTCGCACTACGCCCCGTGGGGATCGGCGGCGGAGGGGGATTCTTCGTGCAGCCCTCG

CCGCCGGCCACGCTCTACGAGCACCGCCTCAGGCAAGGCCTCGACTTCCGCGCCTTCAAC

CCCGCCGCCGCGATGGGGAGGCAGGTCCTCCTGTTCGGCTCGGCGAGGATTCCTCCGCAA

GCACCACTGCTGGCGCGCGCGCCGTCGCCGCTGCACCACCACTACACGCTGCAGCCGAGC

GGCGATGGTGTAAGGGCGGCGGGCTCACCGGTGGTGCTCGACTCGGTTCCGGTCATCGAG

AGCCCCACGACGGCCGCGAAGCGCGTGCGGCTGTTCGGCGTGAACCTCGACAACCCGCAT

GCCGGCGGCGGCGGCGGCGCCGCCGCCGGCGAGTCGAGCAATCATGGCAATGCACTGTCA

TTGCAGACGCCCGCGTGGATGAGGAGGGATCCAACACTGCGGCTGCTGGAATTGCCTCCT

CACCACCACCATGGCGCCGAGTCGTCCGCTGCATCGTCTCCGTCGTCGTCGTCTICCTCC

AAGAGGGACGCGCATTCGGCCTTGGATCTCGATCTGTAG
```

Os04g0581400 LOC_Os04g49230
Cover 46% identity 64%
CDS

SEQ ID NO: 55

ATGGAGTTTGCTACAACGAGTAGTAGGTTTTCCAAGGAAGAGGAGGAGGAGGAGGAAGGG

GAACAGGAGATGGAGCAGGAGCAGGATGAAGAGGAGGAGGAGGCGGAGGCCTCGCCCCGC

GAGATCCCCTTCATGACGTCGGCGGCGGCGGCGGCCACCGCCTCATCGTCCTCCCCGACA

TCGGTCTCCCCTTCCGCCACCGCTTCCGCGGCGGCGTCCACGTCGGCGTCGGGCTCTCCC

TTCCGGTCGAGCGACGGTGCGGGAGCGTCGGGGAGTGGCGGCGGCGGTGGCGGCGAGGAC

GTGGAGGTGATCGAGAAGGAGCACATGTTCGACAAGGTGGTGACGCCGAGCGACGTGGGG

AAGCTGAACCGGCTGGTGATCCCGAAGCAGCACGCCGAGAAGTACTTCCCGCTGGACTCG

GCGGCGAACGAGAAGGGCCTTCTCCTCAGCTTCGAGGACCGAACCGGCAAGCTATGGCGC

TTCCGCTACTCCTACTGGAACAGCAGCCAGAGCTACGTCATGACCAAGGGTTGGAGCCGC

TTCGTCAAGGAGAAGCGCCTCGACGCCGGGGACACCGTCTCCTTCTGCCGCGGCGCCGCC

GAGGCCACCCGCGACCGCCTCTTCATCGACTGGAAGCGCCGCGCCGACGTCCGCGACCCG

CACCGCTTCCAGCGCCTACCGCTCCCCATGACCTCGCCCTACGGCCCGTGGGGCGGCGGC

GCGGGCGCTTCTTCATGCCGCCCGCGCCGCCCGCCACGCTCTACGAGCATCACCGCTTTC

GCCAGGGCTTCGACTTCCGCAACATCAACCCCGCTGTGCCGGCGAGGCAGCTCGTCTTCT

TCGGCTCCCCAGGGACGGGGATTCATCAGCACCCGCCCTTGCCACCGCCGCCGTCGCCAC

CTCCGCCTCCTCACCAACTCCACATTACGGTGCACCACCCGAGCCCCGTAG

SEQ ID NO: 56

MEFATTSSRFSKEEEEEEEGEQEMEQEQDEEEEEAEASPREIPFMTSAAAAATASSSSPT

SVSPSATASAAASTSASGSPFRSSDGAGASGSGGGGGGEDVEVIEKEHMFDKVVTPSDVG

KLNRLVIPKQHAEKYFPLDSAANEKGLLLSFEDRTGKLWRFRYSYWNSSQSYVMTKGWSR

FVKEKRLDAGDTVSFCRGAAEATRDRLFIDWKRRADVRDPHRFQRLPLPMTSPYGPWGGG

AGASSCRPRRPPRSTSITAFARASTSATSTPLCRRGSSSSSAPQGRGFISTRPCHRRRRH

LRLLTNSTLRCTTRAP

Os03g0120900 LOC_Os03g02900
Cover 47% identity 63%
CDS

SEQ ID NO: 57

ATGGAGTTCATCACGCCAATCGTGAGGCCGGCATCGGCGGCGGCGGGCGGCGGCGAGGTG

CAGGAGAGTGGTGGGAGGAGCTTGGCGGCGGTGGAGAAGGAGCACATGTTCGACAAGGTG

GTGACGCCGAGCGACGTGGGGAAGCTGAACCGGCTGGTGATCCCGAAGCAGCACGCGGAG

AAGTACTTCCCGCTGGACGCGCGTCCAACGAGAAGGGGCTCCTGCTCAGCTTCGAGGAC

CGCACGGGGAAGCCATGGCGGTTCCGCTACTCCTACTGGAACAGCAGCCAGAGCTACGTG

ATGACCAAGGGGTGGAGCCGCTTCGTCAAGGAGAAGCGACTCGACGCCGGGGACACCGTC

TCCTTCGGCCGCGGCGTCGGCGAGGCCGCGCGCGGGAGGCTCTTCATCGACTGGCGCCGC

CGCCCCGACGTCGTCGCCGCGCTCCAGCGCCCACGCACCGCTTCGCCCACCACCTCCCT

TCCTCCATCCCCTTCGCTCCCTGGGCGCACCACCACGGACACGGAGCCGCCGCCGCCGCC

GCCGCCGCCGGCGCCAGGTTTCTCCTGCCTCCCTCCTCGACTCCCATCTACGACCAC

CACCGCCGACACGCCCACGCCGTCGGGTACGACGCGTACGCCGCGGCCACCAGCAGGCAG

GTGCTGTTCTACCGGCCGTTGCCGCCGCAGCAGCAGCATCATCCCGCGGTGGTGCTGGAG

TCGGTGCCGGTGCGCATGACGGCGGGGCACGCGGAGCCGCCGTCGGCTCCGTCGAAGCGA

GTTCGGCTGTTCGGGGTGAACCTCGACTGCGCGAATTCCGAACAAGACCACGCCGGCGTG

```
GTCGGGAAGACGGCGCCGCCGCCGCTGCCATCGCCGCCGTCATCATCGTCATCTTCCTCC

GGGAAAGCGAGGTGCTCCTTGAACCTTGACTTGTGA
```

SEQ ID NO: 58

```
MEFITPIVRPASAAAGGGEVQESGGRSLAAVEKEHMFDKVVTPSDVGKLNRLVIPKQHAE

KYFPLDAASNEKGLLLSFEDRTGKPWRFRYSYWNSSQSYVMTKGWSRFVKEKRLDAGDTV

SFGRGVGEAARGRLFIDWRRRPDVVAALQPPTHRFAHHLPSSIPFAPWAHHHGHGAAAAA

AAAAGARFLLPPSSTPIYDHHRRHAHAVGYDAYAAATSRQVLFYRPLPPQQQHHPAVVLE

SVPVRMTAGHAEPPSAPSKRVRLFGVNLDCANSEQDHAGVVGKTAPPPLPSPPSSSSSSS

GKARCSLNLDL

Os01g0693400
Cover 47% identity 63%
CDS
```

SEQ ID NO: 59

```
ATGGACAGCTCCAGCTGCCTGGTGGATGATACCAACAGCGGCGGCTCGTCCACGGACAAG

CTGAGGGCGTTGGCCGCCGCGGCGGCGGAGACGGCGCCGCTGGAGCGCATGGGGAGCGGG

GCGAGCGCGGTGGTGGACGCGGCCGAGCCTGGCGCGGAGGCGGACTCCGGGTCCGGGGGA

CGTGTGTGCGGCGGCGGCGGCGGTGCCGGCGGTGCGGGAGGGAAGCTGCCGTCGTCC

AAGTTCAAGGGCGTCGTGCCGCAGCCCAACGGGAGGTGGGGCGCGCAGATCTACGAGCGG

CACCAGCGGGTGTGGCTCGGCACGTTCGCCGGGGAGGACGACGCCGCGCGCGCCTACGAC

GTCGCCGCGCAGCGCTTCCGCGGCCGCGACGCCGTCACCAACTTCCGCCCGCTCGCCGAG

GCCGACCCGGACGCCGCCGCCGAGCTTCGCTTCCTCGCCACGCGCTCCAAGGCCGAGGTC

GTCGACATGCTCCGCAAGCACACCTACTTCGACGAGCTCGCGCAGAGCAAGCGCACCTTC

GCCGCCTCCACGCCGTCGGCCGCGACCACCACCGCCTCCCTCTCCAACGGCCACCTCTCG

TCGCCCCGCTCCCCCTTCGCGCCCGCCGCGGCGCGCGACCACCTGTTCGACAAGACGGTC

ACCCCGAGCGACGTGGGCAAGCTGAACAGGCTCGTCATACCGAAGCAGCACGCCGAGAAG

CACTTCCCGCTACAGCTCCCGTCCGCCGGCGGCGAGAGCAAGGGTGTCCTCCTCAACTTC

GAGGACGCCGCCGGCAAGGTGTGGCGGTTCCGGTACTCGTACTGGAACAGCAGCCAGAGC

TACGTGCTAACCAAGGGCTGGAGCCGCTTCGTCAAGGAGAAGGGTCTCCACGCCGGCGAC

GTCGTCGGCTTCTACCGCTCCGCCGCCAGTGCCGGCGACGACGGCAAGCTCTTCATCGAC

TGCAAGTTAGTACGGTCGACCGGCGCCGCCCTCGCGTCGCCCGCTGATCAGCCAGCGCCG

TCGCCGGTGAAGGCCGTCAGGCTCTTCGGCGTGGACCTGCTCACGGCGCCGGCGCCGGTC

GAACAGATGGCCGGGTGCAAGAGAGCCAGGGACTTGGCGGCGACGACGCCTCCACAAGCG

GCGGCGTTCAAGAAGCAATGCATAGAGCTGGCACTAGTATAG
```

SEQ ID NO: 49

```
60MDSSSCLVDDTNSGGSSTDKLRALAAAAAETAPLERMGSGASAVVDAAEPGAEADSGSGG

RVCGGGGGAGGAGGKLPSSKFKGVVPQPNGRWGAQIYERHQRVWLGTFAGEDDAARAYD

VAAQRFRGRDAVTNFRPLAEADPDAAAELRFLATRSKAEVVDMLRKHTYFDELAQSKRTF

AASTPSAATTTASLSNGHLSSPRSPFAPAAARDHLFDKTVTPSDVGKLNRLVIPKQHAEK

HFPLQLPSAGGESKGVLLNFEDAAGKVWRFRYSYWNSSQSYVLTKGWSRFVKEKGLHAGD

VVGFYRSAASAGDDGKLFIDCKLVRSTGAALASPADQPAPSPVKAVRLFGVDLLTAPAPV

EQMAGCKRARDLAATTPPQAAAFKKQCIELALV
```

```
Os10g0537100 LOC_Os10g39190
Cover 47% identity 60%
CDS
                                                                              SEQ ID NO: 61
ATGGAGTTCACCCCAATTTCGCCGCCGACGAGGGTCGCCGGCGGTGAGGAGGATTCCGAG

AGGGGGGCGGCGGCGTGGGCGGTGGTGGAGAAGGAGCACATGTTTGAGAAGGTCGTGACG

CCGAGCGACGTGGGGAAGCTGAACCGATTGGTCATCCCCAAGCAGCACGCCGAGAGGTAC

TTCCCGCTCGACGCCGCGGCGGGCGCCGGCGGCGGCGGTGGTGGCGGCGGTGGCGGCGGC

GGGGGGAAGGGGCTGGTGCTGAGCTTCGAGGACAGGACGGGGAAGGCGTGGAGGTTCCGG

TACTCGTACTGGAACAGCAGCCAGAGCTACGTGATGACCAAAGGGTGGAGCCGCTTCGTC

AAGGAGAAGCGCCTCGGCGCCGGCGACACCGTGTCGTTCGGCCGCGGCCTCGGCGACGCC

GCCCGCGGCCGCCTCTTCATCGACTTCCGCCGCCGCCGCCAGGACGCCGGCAGCTTCATG

TTCCCGCCGACGGCGGCGCCGCCGTCGCACTCGCACCACCATCATCAGCGACACCACCCG

CCGCTCCCGTCCGTGCCCCTTTGCCCGTGGCGAGACTACACCACCGCCTATGGCGGCGGC

TACGGCTACGGCTACGGCGGCGGCTCCACCCCGGCGTCCAGCCGCCACGTGCTGTTCCTC

CGGCCGCAGGTGCCGGCCGCTGTGGTGCTCAAGTCGGTGCCGGTGCACGTCGCGGCCACC

TCGGCGGTGCAGGAGGCGGCGACGACGACAAGGCCGAAGCGTGTCCGGCTGTTCGGGGTG

AACCTCGACTGCCCGGCGGCCATGGACGACGACGACGACATCGCCGGAGCGGCGAGCCGG

ACGGCAGCGTCGTCTCTCCTGCAGCTCCCCTCGCCGTCGTCCTCGACGTCGTCGTCGACG

GCGGGGAAGAAGATGTGCTCCTTGGATCTTGGGTTGTGA

SEQ ID NO: 62
MEFTPISPPTRVAGGEEDSERGAAAWAVVEKEHMFEKVVTPSDVGKLNRLVIPKQHAERY

FPLDAAAGAGGGGGGGGGGGGKGLVLSFEDRTGKAWRFRYSYWNSSQSYVMTKGWSRFV

KEKRLGAGDTVSFGRGLGDAARGRLFIDFRRRRQDAGSFMFPPTAAPPSHSHHHHQRHHP

PLPSVPLCPWRDYTTAYGGGYGYGYGGGSTPASSRHVLFLRPQVPAAVVLKSVPVHVAAT

SAVQEAATTTRPKRVRLFGVNLDCPAAMDDDDDIAGAASRTAASSLLQLPSPSSSTSSST

AGKKMCSLDLGL

Glycine max
Loc100795470
Cover 75% identity 53%
                                                                              SEQ ID NO: 63
Msinhysmdlpeptlwwphphhqqqqltlmdpdplrlnlnsddgngndndndenqttttggeqeilddkepmfekpltpsdvgklnr lvipkqhaekyfplsgdsggseckglllsfedesgkcwrfrysywnssqsyvltkgwsryvkdkrldagdvvlferhrvdaqrlfigwrrrrqsd aalppahvssrksgggdgnsnknegwtrgfysahhpypthhlhhhqpspyqqqhdclhagrgsqgqnqrmrpvgnnsssssssrvlrl fgvdmecqpehddsgpstpqcsynsnnmlpstqgtdhshhnfyqqqpsnsnpsphhmmvhhqpyyy CDS
                                                                              SEQ ID NO: 64
ATGTCCATAAACCACTACTCCATGGACCTTCCCGAACCGACACTCTGGTGGCCACACCCA

CACCACCAACAACAACAACTAACCTTAATGGATCCTGACCCTCTCCGTCTCAACCTCAAT

AGCGACGATGGCAATGGCAATGACAACGACAACGACGAAAATCAAACAACCACAACAGGA

GGAGAACAAGAAATATTAGACGATAAAGAACCGATGTTCGAGAAGCCCTTAACCCCGAGC

GACGTGGGGAAGCTGAACCGTCTCGTAATCCCGAAGCAGCACGCGGAGAAGTACTTCCCA

CTGAGTGGTGACTCGGGCGGGAGCGAGTGCAAGGGGCTGTTACTGAGTTTCGAGGACGAG

TCGGGGAAGTGTTGGCGCTTCCGCTACTCGTACTGGAACAGCAGCCAGAGCTACGTGCTC

ACCAAAGGGTGGAGCCGCTACGTCAAGGACAAGCGCCTTGACGCGGGCGACGTCGTTTTG

TTCGAGCGTCACCGCGTCGACGCGCAGCGCCTCTTCATCGGGTGGAGGCGCAGGCGGCAG
```

```
                                     -continued
AGCGATGCCGCCTTGCCGCCTGCGCACGTTAGCAGTAGGAAGAGTGGTGGTGGTGATGGG

AATAGTAATAAGAATGAGGGGTGGACCAGAGGGTTCTATTCTGCGCATCATCCTTATCCT

ACGCATCATCTTCATCATCATCAGCCCTCGCCATACCAACAACAACATGACTGTCTTCAT

GCAGGTAGAGGGTCCCAAGGTCAGAACCAAAGGATGAGACCAGTGGGAAACAACAGTTCT

AGCTCTAGTTCGAGTTCAAGGGTACTTAGGCTGTTCGGGTCGACATGGAATGCCAACCC

GAACATGATGATTCTGGTCCCTCCACACCCCAATGCTCCTACAATAGTAACAACATGTTG

CCATCAACACAGGGCACAGATCATTCCCATCACAATTTCTACCAACAGCAACCTTCTAAT

TCCAATCCTTCCCCTCATCACATGATGGTACATCACCAACCATACTACTACTAG
```

Loc100818164
Cover 50% identity 73%

SEQ ID NO: 65

```
MSTNHYTMDLPEPTLWWPHPHQQQLTLIDPDPLPLNLNNDDNDNGDDNDNDENQTVTTTT

TGGEEEIINNKEPMFEKPLTPSDVGKLNRLVIPKQHAEKYFPLSGGDSGSSECKGLLLSF

EDESGKCWRFRYSYWNSSQSYVLTKGWSRYVKDKRLDAGDVVLFQRHRADAQRLFIGWRR

RRQSDALPPPAHVSSRKSGGDGNSSKNEGDVGVGWTRGFYPAHHPYPTHHHHPSPYHHQQ

DDSLHAVRGSQGQNQRTRPVGNSSSSSSSSSRVLRLFGVNMECQPEHDDSGPSTPQCSYN

TNNILPSTQGTDIHSHLNFYQQQQTSNSKPPPHHMMIRHQPYYY
```

SEQ ID NO: 66

```
ATGTCGACAAACCACTACACCATGGACCTTCCCGAACCAACACTCTGGTGGCCACACCCA

CACCAACAACAACTAACCTTAATAGATCCAGACCCTCTCCCTCTGAACCTCAACAACGAC

GACAACGACAATGGCGACGACAACGACAACGACGAAAACCAAACAGTTACAACAACCACA

ACAGGAGGAGAAGAAGAAATAATAAACAATAAAGAACCGATGTTCGAGAAGCCGCTAACC

CCGAGCGACGTGGGGAAGCTGAACCGCCTCGTAATCCCGAAGCAGCACGCTGAGAAGTAC

TTTCCACTGAGTGGTGGTGACTCGGGCAGTAGCGAGTGCAAGGGGCTGTTACTGAGTTTC

GAGGACGAGTCGGGGAAGTGCTGGCGCTTCCGCTACTCGTACTGGAACAGCAGCCAGAGC

TACGTGCTCACCAAAGGGTGGAGCCGTTACGTGAAGGACAAGCGCCTCGATGCGGGAGAT

GTCGTTTTATTCCAGCGCCACCGCGCCGACGCGCAGCGCCTCTTCATCGGCTGGAGGCGC

AGGCGGCAGAGCGACGCCCTGCCGCCGCCTGCGCACGTTAGCAGCAGGAAGAGTGGTGGT

GATGGGAATAGTAGTAAGAATGAGGGTGATGTGGGCGTGGGCTGGACCAGAGGGTTCTAT

CCTGCGCATCATCCTTATCCTACGCATCATCATCATCCCTCGCCATACCATCACCAACAA

GATGACTCTCTTCATGCAGTTAGAGGGTCCCAAGGTCAGAACCAAAGGACGAGACCAGTG

GGAAACAGCAGTTCTAGTTCGAGTTCGAGTTCAAGGGTACTTAGGCTATTCGGGTCAAC

ATGGAATGCCAACCCGAACATGATGATTCTGGACCCTCCACACCCCAATGCTCCTACAAT

ACTAACAACATATTGCCATCCACACAGGGCACAGATATTCATTCCCATCTCAATTTCTAC

CAACAACAACAAACTTCTAATTCCAAGCCTCCCCCTCATCACATGATGATACGTCACCAA

CCATACTACTACTAG
```

Loc100802734
Cover 77% identity 53%

SEQ ID NO: 67

```
MSSINHYSPETTLYWTNDQQQQAAMWLSNSHTPRFNLNDEEEEEEDDVIVSDKATNNLTQ

EEEKVAMFEKPLTPSDVGKLNRLVIPKQHAEKHFPLDSSAAKGLLLSFEDESGKCWRFRY

SYWNSSQSYVLTKGWSRYVKDKRLHAGDVVLFHRHRSLPQRFFISCSRRQPNPVPAHVST

TRSSASFYSAHPPYPAHHFPFPYQPHSLHAPGGGSQGQNETTPGGNSSSSGSGRVLRLFG

VNMECQPDNHNDSQNSTPECSYTHLYHHQTSSYSSSSNPHHHMVPQQP
```

```
ATGTCATCGATAAACCACTATTCACCGGAAACAACACTATACTGGACCAACGACCAACAG

CAACAAGCCGCCATGTGGCTGAGTAATTCCCACACCCCGCGTTTCAATCTGAACGACGAG

GAGGAGGAGGAGGAAGACGACGTTATCGTTTCGGACAAGGCTACTAATAACTTGACGCAA

GAGGAGGAGAAGGTAGCCATGTTCGAGAAGCCGTTGACGCCGAGCGACGTCGGGAAGCTG

AACCGGCTCGTGATTCCGAAACAGCACGCGGAGAAGCACTTCCCTCTCGACTCGTCGGCG

GCGAAGGGGCTGTTGCTGAGTTTCGAGGACGAGTCCGGGAAGTGTTGGCGCTTCCGTTAC

TCTTATTGGAACAGTAGCCAGAGTTACGTTTTGACCAAAGGATGGAGCCGTTACGTCAAA

GACAAACGCCTCCACGCTGGCGACGTCGTTTTGTTCCACAGACACCGCTCCCTCCCTCAA

CGCTTCTTCATCTCCTGCAGCCGCCGCCAACCCAACCCGGTCCCCGCTCACGTTAGCACC

ACCAGATCCTCCGCTTCCTTCTACTCTGCGCACCCACCTTATCCTGCGCACCACTTCCCC

TTCCCATACCAACCTCACTCTCTTCATGCACCAGGTGGAGGGTCCCAAGGACAGAACGAA

ACGACACCGGGAGGGAACAGTAGTTCAAGTGGCAGTGGCAGGGTGCTGAGGCTCTTTGGT

GTGAACATGGAATGCCAACCTGATAATCATAATGATTCCCAGAACTCCACACCAGAATGC

TCCTACACCCACTTATACCACCATCAAACCTCTTCTTATTCTTCTTCTTCAAACCCTCAC

CATCACATGGTACCTCAACAACCATAA
```

Loc100781489
Cover 49% identity 64%

SEQ ID NO: 69
```
MELMQQVKGNYSDSREEEEEEEAAAITRESESSRLHQQDTASNFGKKLDLMDLSLGSSKE

EEEEGNLQQGGGGVVHHAHQVVEKEHMFEKVATPSDVGKLNRLVIPKQHAEKYFPLDSST

NEKGLLLNFEDRNGKVWRFRYSYWNSSQSYVMTKGWSRFVKEKKLDAGDIVSFQRGLGDL

YRHRLYIDWKRRPDHAHAHPPHHHDPLFLPSIRLYSLPPTMPPRYHHDHHFHHHLNYNNL

FTFQQHQYQQLGAATTTHHNNYGYQNSGSGSLYYLRSSMSMGGGDQNLQGRGSNIVPMII

DSVPVNVAHHNNNRHGNGGITSGGTNCSGKRLRLFGVNMECASSAEDSKELSSGSAAHVT

TAASSSSLHHQRLRVPVPVPLEDPLSSSAAAAARFGDHKGASTGTSLLFDLDPSLQYHRH
```

CDS

SEQ ID NO: 70
```
ATGGAGTTGATGCAACAAGTTAAAGGTAATTATTCTGATAGCAGGGAGGAAGAGGAGGAA

GAGGAAGCTGCAGCAATCACAAGGGAATCAGAAAGCAGCAGGTTACACCAACAAGATACA

GCATCCAATTTTGGAAAGAAGCTAGACTTGATGGACTTGTCACTAGGGAGCAGCAAGGAA

GAGGAAGAGGAAGGGAATTTGCAACAAGGAGGAGGAGGAGTGGTTCATCATGCTCACCAA

GTAGTGGAGAAAGAACACATGTTTGAGAAAGTGGCGACACCGAGCGACGTAGGGAAGCTG

AACAGGCTGGTGATACCGAAGCAGCACGCGGAGAAGTACTTCCCCCTTGACTCCTCAACC

AACGAGAAGGGTCTGCTCCTGAATTTCGAGGACAGGAATGGGAAGGTGTGGCGATTCAGG

TATTCCTATTGGAACAGCAGCCAGAGCTATGTGATGACAAAAGGGTGGAGCCGCTTTGTT

AAGGAGAAGAAGCTGGATGCCGGTGACATTGTCTCCTTCCAGCGTGGCCTTGGGGATTTG

TATAGACATCGGTTGTATATAGATTGGAAGAGAAGGCCCGATCATGCTCATGCTCATCCA

CCTCATCATCACGATCCTTTGTTTCTTCCCTCTATCAGATTGTACTCTCTCCCTCCCACC

ATGCCACCTCGCTACCACCACGATCATCACTTTCACCACCATCTCAATTACAACAACCTC

TTCACTTTTCAGCAACACCAGTACCAGCAGCTTGGTGCTGCCACTACCACTCATCACAAC

AACTATGGTTACCAGAATTCGGGATCTGGTTCACTCTATTACCTAAGGTCCTCTATGTCA

ATGGGTGGTGGTGATCAAAACTTGCAAGGGAGAGGGAGCAACATTGTCCCCATGATCATT
```

```
                                                         -continued
GATTCTGTGCCGGTTAACGTTGCTCATCACAACAACAATCGCCATGGGAATGGGGGCATC

ACGAGTGGTGGTACTAATTGTAGTGGAAAACGACTAAGGCTATTTGGGGTGAACATGGAA

TGCGCTTCTTCGGCAGAAGATTCCAAAGAATTGTCCTCGGGTTCGGCAGCACACGTGACG

ACAGCTGCTTCTTCTTCTTCTCTTCATCATCAGCGCTTGAGGGTGCCAGTGCCAGTGCCA

CTTGAAGATCCACTTTCGTCGTCAGCAGCAGCAGCAAGGTTTGGGGATCACAAAGGG

GCCAGTACTGGGACTTCGCTGCTGTTTGATTTGGATCCCTCTTTGCAGTATCATCGCCAC

TGA
```

Loc100776987
Cover 46% identity 62%

SEQ ID NO: 71

```
MDAISCLDESTTTESLSISQAKPSSTIMSSEKASPSPPPPNRLCRVGSGASAVVDSDGGG

GGGSTEVESRKLPSSKYKGVVPQPNGRWGSQIYEKHQRVWLGTFNEEDEAARAYDVAVQR

FRGKDAVTNFKPLSGTDDDDGESEFLNSHSKSEIVDMLRKHTYNDELEQSKRSRGFVRRR

GSAAGAGNGNSISGACVMKAREQLFQKAVTPSDVGKLNRLVIPKQHAEKHFPLQSAANGV

SATATAAKGVLLNFEDVGGKVWRFRYSYWNSSQSYVLTKGWSRFVKEKNLKAGDTVCFQR

STGPDRQLYIDWKTRNVVNEVALFGPVVEPIQMVRLFGVNILKLPGSDSIANNNNASGCC

NGKRREMELFSLECSKKPKIIGAL
```

CDS

SEQ ID NO: 72

```
ATGGATGCAATTAGTTGCCTGGATGAGAGCACCACCACCGAGTCACTCTCCATAAGTCAG

GCGAAGCCTTCTTCGACGATTATGTCGTCCGAGAAGGCTTCTCCTTCCCCGCCGCCGCCG

AACAGGCTGTGCCGCGTCGGTAGCGGTGCTAGCGCAGTCGTGGATTCCGACGGCGGCGGC

GGGGGTGGCAGCACCGAGGTGGAGTCGCGGAAGCTCCCCTCGTCCAAGTATAAGGGCGTC

GTGCCCCAGCCCAACGGCCGCTGGGGCTCGCAGATTTACGAGAAGCACCAGCGCGTGTGG

CTGGGAACGTTCAACGAGGAAGACGAGGCGGCGCGTGCGTACGACGTCGCCGTGCAGCGA

TTCCGCGGCAAGGACGCCGTCACAAACTTCAAGCCGCTCTCCGGCACCGACGACGACGAC

GGGGAATCGGAGTTTCTCAACTCGCATTCGAAATCCGAGATCGTCGACATGCTGCGTAAG

CATACGTACAATGACGAGCTGGAACAAAGCAAGCGCAGCCGCGGCTTCGTACGTCGGCGC

GGCTCCGCCGCCGGCGCCGGAAACGGAAACTCAATCTCCGGCGCGTGTGTTATGAAGGCG

CGTGAGCAGCTATTCCAGAAGGCCGTTACGCCGAGCGACGTTGGGAAACTGAACCGTTTG

GTGATACCGAAGCAGCACGCGGAGAAGCACTTTCCTTTACAGAGCGCTGCTAACGGCGTT

AGCGCGACGGCGACGGCGGCGAAGGGCGTTTTGTTGAACTTCGAAGACGTTGGAGGGAAA

GTGTGGCGGTTTCGTTACTCGTATTGGAACAGTAGCCAGAGTTACGTCTTGACCAAAGGT

TGGAGCCGGTTCGTTAAGGAGAAGAATCTGAAAGCCGGTGACACGGTTTGTTTTCAACGG

TCCACTGGACCGGACAGGCAGCTTTACATCGATTGGAAGACGAGGAATGTTGTTAACGAG

GTCGCGTTGTTCGGACCGGTTGTCGAACCGATCCAGATGGTTCGGCTCTTTGGTGTTAAC

ATTTTGAAACTACCCGGTTCAGATTCTATCGCCAATAACAATAATGCAAGTGGGTGCTGC

AATGGCAAGAGAAGAGAAATGGAACTCTTTTCATTAGAGTGTAGCAAGAAACCTAAGATT

ATTGGTGCTTTGTAG
```

Loc100778733
Cover 44% identity 64%

SEQ ID NO: 73

```
MELMQEVKGYSDGREEEEEEEAAEEIITREESSRLLHQHQEAAGSNFIINNNHHHHQHH

HHHTTKQLDFMDLSLGSSKDEGNLQGSSSSVYAHHHHAASASSSANGNNNNSSSSNLQQQ

QQQPAEKEHMFDKVVTPSDVGKLNRLVIPKQHAEKYFPLDSSANEKGLLLNFEDRNGKLW
```

RFRYSYWNSSQSYVMTKGWSRFVKEKKLDAGDMVSFQRGVGELYRHRLYIDWWRRPDHHH

HHHHGPDHSTTLFTPFLIPNQPHHLMSIRWGATGRLYSLPSPTPPRHHEHLNYNNNAMYH

PFHHHGAGSGINATTHHYNNYHEMSSTTTSGSAGSVFYHRSTPPISMPLADHQTLNTRQQ

QQQQQQQEGAGNVSLSPMIIDSVPVAHHLHHQQHHGGKSSGPSSTSTSPSTAGKRLRLFG

VNMECASSTSEDPKCFSLLSSSSMANSNSQPPLQLLREDTLSSSSARFGDQRGVGEPSML

FDLDPSLQYRQ

SEQ ID NO: 74

ATGGAGTTGATGCAAGAAGTGAAAGGGTATTCTGATGGCAGAGAGGAGGAGGAGGAGGAA

GAGGAAGCAGCAGAAGAAATCATCACAAGAGAAGAAAGCAGCAGGTTGTTACACCAGCAC

CAGGAGGCAGCAGGTTCCAATTTCATCATCAACAATAATCATCATCATCATCAACATCAC

CACCACCACACAACAAAGCAGCTAGACTTCATGGACTTGTCACTTGGTAGCAGCAAGGAT

GAAGGGAATTTGCAAGGATCATCTTCTTCTGTCTATGCTCATCATCATCATGCAGCAAGT

GCTAGTTCTTCTGCCAATGGTAACAACAACAACAGCAGCAGCAGCAACTTGCAGCAACAG

CAGCAGCAGCCTGCTGAGAAGGAGCACATGTTTGATAAAGTAGTGACACCAAGTGATGTG

GGGAAGCTGAACCGGTTGGTGATACCAAAGCAGCATGCTGAGAAGTATTTCCCTCTTGAT

TCCTCAGCCAATGAGAAGGGTCTGTTGCTGAATTTTGAGGACAGGAATGGTAAGTTGTGG

AGGTTCAGGTACTCCTATTGGAACAGCAGCCAGAGCTATGTGATGACCAAAGGTTGGAGC

CGTTTTGTTAAGGAGAAGAAGCTTGATGCTGGTGACATGGTGTCCTTCCAGCGTGGTGTT

GGGGAGTTGTATAGGCATAGGTTGTACATAGATTGGTGGAGAAGGCCTGATCATCATCAC

CATCACCATCATGGCCCTGACCATTCAACCACACTCTTCACACCTTTCTTAATTCCCAAT

CAGCCTCATCACTTAATGTCCATCAGATGGGGTGCCACTGGCAGATTGTACTCCCTCCCT

TCCCCAACCCCACCACGCCACCATGAACACCTCAATTACAACAATAACGCCATGTATCAT

CCCTTTCATCACCATGGTGCTGGAAGTGGAATTAATGCTACTACTCATCACTACAACAAC

TATCATGAGATGAGTAGTACTACTACTTCAGGATCTGCAGGCTCAGTCTTTTACCACAGG

TCAACACCCCCAATATCAATGCCATTGGCTGACCACCAAACCTTGAACACAAGGCAGCAG

CAACAACAACAACAACAAGAGGGAGCTGGCAATGTTTCTCTTTCCCCTATGATCATT

GATTCTGTTCCAGTTGCTCACCACCTCCATCATCAACAACACCATGGTGGCAAGAGTAGT

GGTCCTAGTAGTACTAGTACTAGTCCTAGCACTGCAGGGAAAAGACTAAGGCTATTTGGG

GTCAACATGGAATGTGCTTCTTCAACATCAGAAGACCCCAAATGCTTCAGCTTGTTGTCC

TCATCTTCAATGGCTAATTCCAATTCACAACCACCACTTCAGCTTTTGAGGGAAGATACA

CTTTCGTCATCATCGGCAAGGTTTGGGGATCAGAGAGGAGTAGGGGAACCTTCAATGCTT

TTTGATCTGGACCCTTCTTTGCAATACCGGCAGTGA

Loc732601
Cover 44% identity 62%

SEQ ID NO: 75

MDGGCVTDETTTSSDSLSVPPPSRVGSVASAVVDPDGCCVSGEAESRKLPSSKYKGVVPQ

PNGRWGAQIYEKHQRVWLGTFNEEDEAARAYDIAALRFRGPDAVTNFKPPAASDDAESEF

LNSHSKFEIVDMLRKHTYDDELQQSTRGGRRRLDADTASSGVFDAKAREQLFEKTVTPSD

VGKLNRLVIPKQHAEKHFPLSGSGDESSPCVAGASAAKGMLLNFEDVGGKVWRFRYSYWN

SSQSYVLTKGWSRFVKEKNLRAGDAVQFFKSTGPDRQLYIDCKARSGEVNNNAGGLFVPI

GPVVEPVQMVRLFGVNLLKLPVPGSDGVGKRKEMELFAFECCKKLKVIGAL

CDS

SEQ ID NO: 76

ATGGATGGAGGCTGTGTCACAGACGAAACCACCACATCCAGCGACTCTCTTTCCGTTCCG

CCGCCCAGCCGCGTCGGCAGCGTTGCAAGCGCCGTCGTCGACCCCGACGGTTGTTGCGTT

TCCGGCGAGGCCGAATCCCGGAAACTCCCTTCGTCGAAATACAAAGGCGTGGTGCCGCAA

CCGAACGGTCGCTGGGGAGCTCAGATTTACGAGAAGCACCAGCGCGTGTGGCTCGGCACT

TTCAACGAGGAAGACGAAGCCGCCAGAGCCTACGACATCGCCGCGCTGCGCTTCCGCGGC

CCCGACGCCGTCACCAACTTCAAGCCTCCCGCCGCCTCCGACGACGCCGAGTCCGAGTTC

CTCAACTCGCATTCCAAGTTCGAGATCGTCGACATGCTCCGCAAGCACACCTACGACGAC

GAGCTCCAGCAGAGCACGCGCGGTGGTAGGCGCCGCCTCGACGCTGACACCGCGTCGAGC

GGTGTGTTCGACGCGAAAGCGCGTGAGCAGCTGTTCGAGAAAACGGTTACGCCGAGCGAC

GTCGGGAAGCTGAATCGATTAGTGATACCGAAGCAGCACGCGGAGAAGCACTTTCCGTTA

AGCGGATCCGGCGACGAAAGCTCGCCGTGCGTGGCGGGGGCTTCGGCGGCGAAGGGAATG

TTGTTGAACTTTGAGGACGTTGGAGGGAAAGTGTGGCGGTTTCGTTACTCTTATTGGAAC

AGTAGCCAGAGCTACGTGCTTACCAAAGGATGGAGCCGGTTCGTTAAGGAGAAGAATCTT

CGAGCCGGTGACGCGGTTCAGTTCTTCAAGTCGACCGGACCGGACCGGCAGCTATATATA

GACTGCAAGGCGAGGAGTGGTGAGGTTAACAATAATGCTGGCGGTTTGTTTGTTCCGATT

GGACCGGTCGTTGAGCCGGTTCAGATGGTTCGGCTTTTCGGGGTCAACCTTTTGAAACTA

CCCGTACCCGGTTCGGATGGTGTAGGGAAGAGAAAAGAGATGGAACTGTTTGCATTTGAA

TGTTGCAAGAAGTTAAAAGTAATTGGAGCTTTGTAA

Loc100801107
Cover 44% identity 61%

SEQ ID NO: 77

MDAISCMDESTTTESLSISLSPTSSSEKAKPSSMITSSEKVSLSPPPSNRLCRVGSGASA

VVDPDGGGSGAEVESRKLPSSKYKGVVPQPNGRWGAQIYEKHQRVWLGTFNEEDEAARAY

DIAAQRFRGKDAVTNFKPLAGADDDDGESEFLNSHSKPEIVDMLRKHTYNDELEQSKRSR

GVVRRRGSAAAGTANSISGACFTKAREQLFEKAVTPSDVGKLNRLVIPKQHAEKHFPLQS

SNGVSATTIAAVTATPTAAKGVLLNFEDVGGKVWRFRYSYWNSSQSYVLTKGWSRFVKEK

NLKAGDTVCFHRSTGPDKQLYIDWKTRNVVNNEVALFGPVGPVVEPIQMVRLFGVNILKL

PGSDTIVGNNNNASGCCNGKRREMELFSLECSKKPKIIGAL

CDS

SEQ ID NO: 78

ATGGATGCAATTAGTTGCATGGATGAGAGCACCACCACTGAGTCACTCTCTATAAGTCTT

TCTCCGACGTCATCGTCGGAGAAAGCGAAGCCTTCTTCGATGATTACATCGTCGGAGAAG

GTTTCTCTGTCCCCGCCGCCGTCAAACAGACTATGCCGTGTTGGAAGCGGCGCGAGCGCA

GTCGTGGATCCTGATGGCGGCGGCAGCGGCGCTGAGGTAGAGTCGCGGAAACTCCCCTCG

TCGAAGTACAAGGGCGTGGTGCCCCAGCCCAACGGCCGCTGGGGTGCGCAGATTTACGAG

AAGCACCAGCGCGTGTGGCTTGGAACGTTCAACGAGGAAGACGAGGCGGCGCGTGCGTAC

GACATCGCCGCGCAGCGGTTCCGCGGCAAGGACGCCGTCACGAACTTCAAGCCGCTCGCC

GGCGCCGACGACGACGACGGAGAATCGGAGTTTCTCAACTCGCATTCCAAACCCGAGATC

GTCGACATGCTGCGAAAGCACACGTACAATGACGAGCTGGAGCAGAGCAAGCGCAGCCGC

GGCGTCGTCCGGCGGCGAGGCTCCGCCGCCGCCGGCACCGCAAACTCAATTTCCGGCGCG

-continued

```
TGCTTTACTAAGGCACGTGAGCAGCTATTCGAGAAGGCTGTTACGCCGAGCGACGTTGGG

AAATTGAACCGTTTGGTGATACCGAAGCAGCACGCGGAGAAGCACTTTCCGTTACAGAGC

TCTAACGGCGTTAGCGCGACGACGATAGCGGCGGTGACGGCGACGCCGACGGCGGCGAAG

GGCGTTTTGTTGAACTTCGAAGACGTTGGAGGGAAAGTGTGGCGGTTTCGTTACTCGTAT

TGGAACAGTAGCCAGAGTTACGTCTTAACCAAAGGTTGGAGCCGGTTCGTTAAGGAGAAG

AATCTGAAAGCTGGTGACACGGTTTGTTTTCACCGGTCCACTGGACCGGACAAGCAGCTT

TACATCGATTGGAAGACGAGGAATGTTGTTAACAACGAGGTCGCGTTGTTCGGACCGGTC

GGACCGGTTGTCGAACCGATCCAGATGGTTCGGCTCTTTGGGGTTAACATTTTGAAACTA

CCCGGTTCAGATACTATTGTTGGCAATAACAATAATGCAAGTGGGTGCTGCAATGGCAAG

AGAAGAGAAATGGAACTGTTCTCGTTAGAGTGTAGCAAGAAACCTAAGATTATTGGTGCT

TTGTAA
```

Loc100789009
Cover 44% identity 62%

SEQ ID NO: 79

```
MDGGSVTDETTTTSNSLSVPANLSPPPLSLVGSGATAVVYPDGCCVSGEAESRKLPSSKY

KGVVPQPNGRWGAQIYEKHQRVWLGTFNEEDEAARAYDIAAHRFRGRDAVTNFKPLAGAD

DAEAEFLSTHSKSEIVDMLRKHTYDNELQQSTRGGRRRRDAETASSGAFDAKAREQLFEK

TVTQSDVGKLNRLVIPKQHAEKHFPLSGSGGGALPCMAAAAGAKGMLLNFEDVGGKVWRF

RYSYWNSSQSYVLTKGWSRFVKEKNLRAGDAVQFFKSTGLDRQLYIDCKARSGKVNNNAA

GLFIPVGPVVEPVQMVRLFGVDLLKLPVPGSDGIGVGCDGKRKEMELFAFECSKKLKVIG

AL
```

SEQ ID NO: 80

```
ATGGATGGAGGCAGTGTCACAGACGAAACCACCACAACCAGCAACTCTCTTTCGGTTCCG

GCGAATCTATCTCCGCCGCCTCTCAGCCTTGTCGGCAGCGGCGCAACCGCCGTCGTCTAC

CCCGACGGTTGTTGCGTCTCCGGCGAAGCCGAATCCCGGAAACTCCCGTCCTCGAAATAC

AAAGGCGTGGTGCCGCAACCGAACGGTCGTTGGGGAGCTCAGATTTACGAGAAGCACCAG

CGCGTGTGGCTCGGCACCTTCAACGAGGAAGACGAAGCCGCCAGAGCCTACGACATCGCC

GCGCATCGCTTCCGCGGCCGCGACGCCGTCACTAACTTCAAGCCTCTCGCCGGCGCCGAC

GACGCCGAAGCCGAGTTCCTCAGCACGCATTCCAAGTCCGAGATCGTCGACATGCTCCGC

AAGCACACCTACGACAACGAGCTCCAGCAGAGCACCCGCGGCGGCAGGCGCCGCCGGGAC

GCCGAAACCGCGTCGAGCGGCGCGTTCGACGCGAAGGCGCGTGAGCAGCTGTTCGAGAAA

ACCGTTACGCAGAGCGACGTCGGGAAGCTGAACCGATTAGTGATACCAAAGCAGCACGCG

GAGAAGCACTTTCCGTTAAGCGGATCCGGCGGCGGAGCCTTGCCGTGCATGGCGGCGGCT

GCGGGGGCGAAGGGAATGTTGCTGAACTTTGAGGACGTTGGAGGGAAAGTGTGGCGGTTC

CGTTACTCGTATTGGAACAGTAGCCAGAGCTACGTGCTTACCAAAGGATGGAGCCGGTTC

GTTAAGGAGAAGAATCTTCGAGCTGGTGACGCGGTTCAGTTCTTCAAGTCGACCGGACTG

GACCGGCAACTATATATAGACTGCAAGGCGAGGAGTGGTAAGGTTAACAATAATGCTGCC

GGTTTGTTTATTCCGGTTGGACCGGTTGTTGAGCCGGTTCAGATGGTACGGCTTTTCGGG

GTCGACCTTTTGAAACTACCCGTACCCGGTTCGGATGGTATTGGGGTTGGCTGTGACGGG

AAGAGAAAAGAGATGGAGCTGTTTGCATTTGAATGTAGCAAGAAGTTAAAAGTAATTGGA

GCTTTGTAA
```

Loc102660503
Cover 36% identity 57%

SEQ ID NO: 81 migvekvticmrievntekgrralmdcwqisgvhessdcseikfafdavykrarheennaaaqkfkgvvsqqngnwgaqiyahqqriwl gtfksereaamaydsasiklrsgechrnfpwndqtvqepqfqshysaetvlnmirdgtypskfatflktrqtqkgvakhiglkgddeeqfcct qlfqkeltpsdvgklnrlvipkkhaysyfpyvggsadesgsvdveavfydklmrlwkfrycywkssqsyvftrgwnrfvkdkklkakdviaffft wgksggegeafalidviynnnaeedskgdtkqvlgnqlqlagseegededanigkdfnaqkglrlfgvcit

CDS

SEQ ID NO: 82 atgattggagttgagaaagtgacaatttgtatgagaatagaggtgaatactgaaaagggaagaagggctttaatggactgttggcaaatatcag gagttcatgaaagttcagattgtagcgaaatcaaatttgcattcgacgcagtagtaaaacgcgcgaggcatgaagagaataatgcagcagcac agaagttcaaaggcgttgtgtctcaacaaaatgggaactggggtgcacagatatatgcacaccagcagagaatctggttggggaccttcaaat ctgaaagagaggctgcaatggcttatgacagcgccagcataaaacttagaagcggagagtgccacagaaactttccatggaacgaccaaaca gttcaagagcctcagttccaaagccattacagcgcagaaacagtgctaaacatgattagagatggcacctatccatcaaaatttgctacatttctc aaaactcgtcaaacccaaaaaggcgttgcgaaacacataggtctgaaggtgatgacgaggaacagttttgttgcacccaacttttttcagaagg aattaacaccaagtgatgtgggcaagctcaacaggcttgtcatcccaagaagcatgcagttagctattttccttacgttggtggcagtgctgatg agagtggtagtgttgacgtggaggctgtgttttatgacaaactcatgcgattgtggaagttccgatactgctattggaagagcagccaaagttacg tgttcaccagaggctggaatcggtttgtgaaggataagaagttgaaggctaaagatgtcattgcgttttttacgtggggaaaaagtggaggaga gggagaagcttttgcattgatcgatgtaatttataataataatgcagaagaagacagcaaggagacaccaaacaagtttgggaaaccaatta caattagctggcagtgaagaaggtgaagatgaagatgcaaacattggaaaggatttcaatgcacaaaagggtctgaggctctttggtgtgtgta tcacctaa

*Hordeum vulgare*
MLOC_66387
Cover 47% identity 64%

SEQ ID NO: 83

MEFTATSSRFSKGEEEVEEEQEEASMREIPFMTPAAATCAAAPPSASASASTPASASGSS

PPFRSGDDAGASGSGAGDGSRSNVAEAVEKEHMFDKVVTPSDVGKLNRLVIPKQYAEKYF

PLDSAANEKGLLLNFEDSAGKPWRFRYSYWNSSQSYVMTKGWSRFVKEKRLDAGDTVSFS

RGAGEAARHRLFIDWKRRADTRDPLRLPRLPLPMPLTSHYSPWGLGAGARGFFMPPSPPA

TLYEHRLRQGFDFRGMNPSYPTMGRQVILFGSAARMPPHGPAPLLVPRPPPPLHFTVQQQ

GSDAGGSVTAGSPVVLDSVPVIESPTTATKKRVRLFGVNLDNPQHPGDGGGESSNYGSAL

PLQMPASAWRPRDHTLRLLEFPSHGAEASSPSSSSSSKREAHSGLDLDL

SEQ ID NO: 84

ATGGAGTTTACTGCGACAAGCAGTAGGTTTTCTAAAGGAGAGGAGGAGGTGGAGGAGGAG

CAGGAGGAGGCGTCGATGCGCGAGATCCCTTTCATGACGCCCGCGGCCGCCACCTGCGCC

GCGGCGCCGCCTTCTGCTTCTGCGTCGGCCTCGACACCCGCGTCAGCGTCTGGAAGTAGC

CCTCCCTTTCGATCTGGGGATGACGCCGGAGCGTCGGGGAGCGGGGCCGGCGACGGCAGC

CGCAGCAACGTGGCGGAGGCCGTGGAGAAGGAGCACATGTTCGACAAAGTGGTGACGCCG

AGCGACGTGGGGAAGCTTAACCGGCTGGTCATCCCCAAGCAGTACGCCGAGAAGTACTTC

CCGCTGGACTCGGCGGCCAACGAGAAGGGCCTTCTGCTCAACTTCGAGGACAGCGCCGGG

AAGCCATGGCGCTTCCGCTATTCCTACTGGAACAGCAGCCAGAGCTACGTCATGACCAAA

GGCTGGAGCCGCTTCGTCAAGGAGAAGCGCCTCGACGCTGGGGACACCGTCTCCTTCTCC

CGCGGCGCCGGTGAGGCCGCGCGCCACCGCCTCTTCATCGACTGGAAGCGCCGAGCCGAC

ACCAGAGACCCGCTCCGCTTGCCCCGCCTCCCGCTCCCGATGCCGCTGACGTCGCACTAC

AGCCCGTGGGGCCTCGGCGCCGGCGCCAGAGGATTCTTCATGCCTCCCTCGCCGCCAGCC

-continued

```
ACGCTCTACGAGCACCGTCTCCGTCAAGGCTTCGACTTCCGCGGCATGAACCCCAGTTAC

CCCACAATGGGGAGACAGGTCATCCTTTTCGGCTCGGCCGCCAGGATGCCTCCGCACGGA

CCAGCACCACTCCTCGTGCCGCGCCCGCCGCCGCCGCTGCACTTCACGGTGCAGCAACAA

GGCAGCGACGCCGGCGGAAGTGTAACCGCAGGATCCCCAGTGGTGCTCGACTCAGTGCCG

GTAATCGAAAGCCCCACGACGGCAACGAAGAAGCGCGTGCGCTTGTTCGGCGTGAACTTG

GACAACCCGCAGCATCCCGGTGATGGCGGGGGCGAATCGAGCAATTATGGCAGTGCACTG

CCATTGCAGATGCCCGCATCAGCATGGCGGCCAAGGGACCATACGCTGAGGCTGCTCGAA

TTCCCCTCGCACGGTGCCGAGGCGTCGTCTCCATCGTCGTCGTCGTCTTCCAAGAGGGAG

GCGCATTCGGGCTTGGATCTCGATCTGTGA
```

MLOC44012
Cover 55% identity 63%

SEQ ID NO: 85
```
MLRKHTYFDELAQSKRAFAASAALSAPTTSGDAGGSASPPSPAAVREHLFDKTVTPSDVG

KLNRLVIPKQNAEKHFPLQLPAGGGESKGLLLNFEDDAGKVWRFRYSYWNSSQSYVLTKG

WSRFVKEKGLGAGDVVGFYRSAAGRTGEDSKFFIDCRLRPNTNTAAEADPVDQSSAPVQK

AVRLFGVDLLAAPEQGMPGGCKRARDLVKPPPPKVAFKKQCIELALA
```

SEQ ID NO: 86
```
ATGCTCCGCAAGCACACCTACTTCGACGAGCTCGCCCAGAGCAAGCGCGCCTTCGCCGCG

TCGGCCGCGCTCTCCGCGCCCACCACCTCGGGCGACGCCGGCGGCAGCGCCTCGCCGCCC

TCCCCGGCCGCCGTGCGCGAGCACCTCTTCGACAAGACCGTCACGCCCAGCGACGTCGGC

AAGCTGAACAGGCTGGTGATACCGAAGCAGAACGCCGAGAAGCACTTCCCGCTGCAGCTC

CCGGCCGGCGGCGGCGAGAGCAAGGGCCTGCTCCTCAACTTCGAGGACGATGCGGGCAAG

GTGTGGCGGTTCCGCTACTCGTACTGGAACAGCAGCCAGAGCTACGTCCTCACCAAGGGC

TGGAGCCGCTTCGTGAAGGAGAAGGGCCTCGGCGCCGGAGACGTCGTCGGGTTCTACCGC

TCCGCCGCCGGGAGGACCGGCGAAGACAGCAAGTTCTTCATTGACTGCAGGCTGCGGCCG

AACACCAACACCGCCGCCGAAGCAGACCCCGTGGACCAGTCGTCGGCGCCCGTGCAGAAG

GCCGTGAGACTCTTCGGCGTCGATCTTCTCGCGGCGCCGGAGCAGGGCATGCCGGGCGGG

TGCAAGAGGGCCAGAGACTTGGTGAAGCCGCCGCCTCCGAAAGTGGCGTTCAAGAAGCAA

TGCATAGAGCTGGCGCTAGCGTAG
```

MLOC_57250
Cover 50% identity 57%

SEQ ID NO: 87
```
MYCSRGRIDPAEEGQVMGGLGVRDASWALFKVLEQSDVQVGQNRLLLTKEAVWGGPIPKL

FPELEELRGDGLNAENRVAVKILDADGCEGDANFRYLNSSKAYRVMGPQWSRLVKETGMC

KGDRLDLYAATATAASSCSGARAAVAPAIPPGAIVKAAGF
```

CDS

SEQ ID NO: 88
```
ATGTATTGTTCCCGCGGCCGCATCGATCCCGCGGAAGAAGGGCAGGTGATGGGCGGCCTC

GGCGTGCGCGACGCCAGCTGGGCGCTGTTCAAGGTGTTGGAGCAGTCCGACGTCCAGGTG

GGGCAGAACCGGCTGCTCCTCACCAAGGAGGCGGTGTGGGGCGGCCCTATCCCCAAGCTT

TTCCCGGAGCTGGAGGAGCTCCGCGGCGACGGCCTCAACGCCGAGAACAGGGTCGCGGTC

AAGATCCTCGACGCCGACGGCTGCGAGGGGGACGCCAACTTCCGCTACCTCAACTCCAGC

AAGGCGTACCGGGTCATGGGGCCTCAGTGGAGCCGGCTCGTGAAGGAGACCGGCATGTGC
```

```
AAGGGAGACCGCCTCGATCTGTACGCGGCAACGGCGACCGCTGCCTCTTCGTGTTCTGGA

GCCAGGGCGGCTGTGGCGCCGGCGATACCTCCCGGAGCAATCGTGAAGGCAGCCGGGTTC

TAA

MLOC_38822
Cover 47% identity 56%                                                                SEQ ID NO: 89

MLRKHIYPDELAQHKRAFFFAAASSPTSSSSPLASPAPSAAAARREHLFDKTVTPSDVGK

LNRLVIPKQHAEKHFPLQLPSASAAVPGECKGVLLNFDDATGKVWRFRYSYWNSSQSYVL

TKGWSRFVKEKGLHAGDAVEFYRAASGNNQLFIDCKLRSKSTTTTTSVNSEAAPSPAPVT

RTVRLFGVDLLIAPAARHAHEHEDYGMAKTNKRTMEASVAAPTPAHAVWKKRCVDFALTY

RLATTPQCPRSRDQLEGVQAAGSTFAL

CDS                                                                                    SEQ ID NO: 90

ATGCTGCGCAAGCACATCTATCCCGACGAGCTCGCGCAGCACAAGCGCGCCTTCTTCTTC

GCCGCGGCGTCGTCCCCTACGTCGTCGTCGTCACCTCTCGCCTCGCCGGCTCCTTCAGCC

GCGGCGGCGCGGCGCGAGCACCTGTTCGACAAGACGGTCACGCCCAGCGACGTGGGAAG

CTGAACCGGCTGGTGATCCCCAAGCAGCACGCCGAGAAGCACTTCCCGCTGCAGCTCCCT

TCTGCCAGCGCCGCCGTGCCAGGCGAGTGCAAGGGCGTGCTGCTCAACTTCGATGACGCG

ACCGGCAAGGTGTGGAGGTTCCGGTACTCCTACTGGAACAGCAGCCAGAGCTACGTGCTC

ACCAAGGGGTGGAGCCGCTTCGTGAAGGAGAAGGGCCTTCACGCCGGCGACGCCGTCGAG

TTCTACCGCGCCGCCTCCGGCAACAACCAGCTCTTCATCGACTGCAAGCTCCGGTCCAAG

AGCACCACGACGACGACCTCCGTCAACTCGGAGGCCGCCCCATCGCCGGCACCCGTGACG

AGGACAGTGCGACTCTTCGGGGTCGACCTTCTCATCGCGCCGGCGGCGAGGCACGCGCAT

GAGCACGAGGACTACGGCATGGCCAAGACAAACAAGAGAACCATGGAGGCCAGCGTAGCG

GCGCCTACTCCGGCGCACGCGGTGTGGAAGAAGCGGTGCGTAGACTTCGCGCTGACCTAC

CGACTTGCCACCACCCCACAGTGCCCGAGGTCAAGAGATCAACTAGAAGGAGTACAAGCA

GCTGGGAGTACATTTGCTCTATAG

MLOC_7940
Cover 49% identity 52%                                                                 SEQ ID NO: 91

MGVEILSSTGEHSSQYSSGAASTATTESGVGGRPPTAPSLPVSIADESATSRSASAQSTS

SRFKGVVPQPNGRWGAQIYERHARVWLGTFPDEDSAARAYDVAALRYRGREAATNFPCAA

AEAELAFLAAHSKAEIVDMLRKHTYTDELRQGLRRGRGMGARAQPTPSWAREPLFEKAVT

PSDVGKLNRLVVPKQHAEKHFPLKRTPETTTTTGKGVLLNFEDGEGKVWRFRYSYWNSSQ

SYVLTKGWSRFVREKGLGAGDSIVFSCSAYGQEKQFFIDCKKNKTMTSCPADDRGAATAS

PPVSEPTKGEQVRVVRLFGVDIAGEKRGRAAPVEQELFKRQCVAHSQHSPALGAFVL

CDS                                                                                    SEQ ID NO: 92

ATGGGGGTGGAGATCCTGAGCTCAACGGGGGAACACTCCTCCCAGTACTCTTCCGGAGCC

GCGTCCACGGCGACGACGGAGTCAGGCGTGGGCGGACGGCCGCCGACTGCGCCGAGCCTA

CCTGTTTCCATCGCCGACGAGTCGGCGACCTCGCGGTCGGCATCGGCGCAGTCGACGTCG

TCGCGGTTCAAGGGCGTGGTGCCGCAGCCCAACGGGCGGTGGGGCGCCCAGATCTACGAG

CGCCACGCCCGCGTCTGGCTCGGCACGTTCCCGGACGAAGACTCTGCGGCGCGCGCCTAC

GACGTGGCCGCGCTCCGGTACCGGGGCCGCGAGGCCGCCACCAACTTCCCGTGCGCGGCC

GCCGAGGCGGAGCTCGCCTTCCTGGCGGCACACTCCAAGGCCGAGATCGTCGACATGCTC
```

```
                                                          -continued
CGGAAGCACACCTACACCGACGAGCTCCGCCAGGGCCTGCGGCGCGGCCGCGGCATGGGG

GCGCGCGCGCAGCCGACGCCGTCGTGGGCGCGGGAGCCCCTTTTCGAGAAGGCCGTGACC

CCGAGCGACGTGGGCAAGCTCAACCGCCTCGTTGTGCCGAAGCAGCACGCCGAGAAGCAC

TTCCCCCTGAAACGCACGCCGGAGACGACAACGACCACCGGCAAGGGGGTGCTTCTCAAC

TTCGAGGATGGCGAGGGGAAAGTGTGGAGGTTCCGGTACTCGTATTGGAACAGCAGCCAG

AGCTACGTGCTCACCAAGGGATGGAGCCGCTTCGTTCGGGAGAAGGGCCTCGGTGCCGGC

GACTCCATCGTGTTCTCCTGCTCGGCGTACGGTCAGGAGAAGCAGTTCTTCATCGACTGC

AAGAAGAACAAGACGATGACGAGCTGCCCCGCCGATGACCGCGGCGCCGCAACAGCGTCG

CCGCCAGTGTCAGAGCCAACAAAGGAGAACAAGTCCGTGTTGTGAGGCTGTTCGGCGTC

GACATCGCCGGAGAGAAGAGGGGGCGAGCGGCGCCGGTGGAGCAGGAGTTGTTCAAGAGG

CAATGCGTGGCACACAGCCAGCACTCTCCAGCCCTAGGTGCCTTCGTCTTATAG
```

MLOC_56567
Cover 42% identity 59%

SEQ ID NO: 93

```
MGVEILSSMVEHSFQYSSGASSATAESGAVGTPPRHLSLPVAIADESLTSRSASSRFKGV

VPQPNGRWGAQIYERHARVWLGTFPDQDSAARAYDVASLRYRGGDAAFNFPCVVVEAELA

FLAAHSKAEIVDMLRKQTYADELRQGLRRGRGMGVRAQPMPSWARVPLFEKAVTPSDVGK

LNRLVVPKQHAEKHFPLKRSPETTTTTGNGVLLNFEDGQGKVWRFRYSYWNSSQSYVLTK

GWSRFVREKGLGAGDSIMFSCSAYGQEKQFFIDCKKNTTVNGGKSASPLQVMEIAKAEQV

RVVRLFGVDIAGVKRERAATAEQGPQGWFKRQCMAHGQHSPALGDFAL
```

SEQ ID NO: 94

```
ATGGGGGTGGAGATCCTGAGCTCCATGGTGGAGCACTCCTTCCAGTACTCTTCGGGCGCG

TCCTCGGCCACCGCGGAGTCAGGCGCCGTCGGAACACCGCCGAGGCATCTGAGCCTACCT

GTCGCCATCGCCGACGAGTCCCTGACCTCACGGTCGGCGTCGTCTCGGTTCAAGGGCGTG

GTGCCGCAGCCCAACGGGCGGTGGGGCGCCCAGATCTACGAGCGCCACGCTCGCGTCTGG

CTCGGCACGTTCCCAGACCAGGACTCGGCGGCGCGCGCCTACGACGTTGCCTCGCTCAGG

TACCGCGGCGGCGACGCCGCCTTCAACTTCCCGTGCGTGGTGGTGGAGGCGGAGCTCGCC

TTCCTGGCGGCGCACTCCAAGGCTGAGATCGTTGACATGCTCCGGAAGCAGACCTACGCC

GATGAACTCCGCCAGGGACTACGGCGCGGCCGTGGCATGGGGGTGCGCGCGCAGCCGATG

CCGTCGTGGGCGCGGGTTCCCCTTTTCGAGAAGGCCGTGACCCCTAGCGATGTCGGCAAG

CTCAATCGCCTGGTGGTGCCGAAGCAGCACGCCGAGAAGCACTTCCCCCTGAAGCGCAGC

CCGGAGACGACGACCACCGGCAACGGCGTACTGCTCAACTTTGAGGACGGCCAGGGA

AAAGTGTGGAGGTTCCGGTACTCATATTGGAACAGCAGCCAGAGCTACGTGCTCACCAAA

GGCTGGAGCCGCTTCGTCCGGGAGAAGGGCCTCGGCGCCGGTGACTCCATCATGTTCTCC

TGCTCGGCGTACGGGCAGGAGAAGCAGTTCTTCATCGACTGCAAGAAGAACACGACCGTG

AACGGAGGCAAATCGGCGTCGCCGCTGCAGGTGATGGAGATTGCCAAAGCAGAACAAGTC

CGCGTCGTTAGACTGTTCGGTGTCGACATCGCCGGGGTGAAGAGGGAGCGAGCGGCGACG

GCGGAGCAAGGCCCGCAGGGGTGGTTCAAGAGGCAATGCATGGCACACGGCCAGCACTCT

CCTGCCCTAGGTGACTTCGCCTTATAG
```

MLOC_75135
Cover 43% identity 57%

SEQ ID NO: 95

```
MGMEILSSTVEHCSQYSSSASTATTESGAAGRSTTALSLPVAITDESVTSRSASAQPASS

RFKGVVPQPNGRWGSQIYERHARVWLGTFPDQDSAARAYDVASLRYRGRDAATNFPCAAA
```

-continued

EAELAFLTAHSKAEIVDMLRKHTYADELRQGLRRGRGMGARAQPTPSWARVPLFEKAVTP
SDVGKLNRLVVPKQHAEKHFPLKCTAETTTTTGNGVLLNFEDGEGKVWRFRYSYWNSSQS
YVLTKGWSSFVREKGLGAGDSIVFSSSAYGQEKQLFINCKKNTTMNGGKTALPLPVVETA
KGEQDHVVKLFGVDIAGVKRVRAATGELGPPELFKRQSVAHGCGRMNYICYSIGTIGPLM
LN

SEQ ID NO: 96

ATGGGGATGGAAATCCTGAGCTCCACGGTGGAGCACTGCTCCCAGTACTCTTCCAGCGCG
TCCACGGCCACAACGGAGTCAGGCGCCGCCGGAAGATCGACGACGGCTCTGAGCCTACCA
GTTGCCATCACCGACGAGTCCGTTACCTCGCGGTCGGCATCGGCGCAGCCGGCGTCATCA
CGGTTCAAGGGCGTGGTGCCGCAGCCCAACGGGCGGTGGGGCTCCCAGATCTACGAGCGC
CACGCTCGCGTCTGGCTCGGCACCTTCCCGGATCAGGACTCGGCGGCGCGTGCCTACGAC
GTTGCCTCGCTCAGGTACCGGGGCCGCGATGCCGCCACCAACTTCCCGTGCGCCGCTGCG
GAAGCGGAGCTCGCCTTCCTGACCGCGCACTCCAAGGCCGAGATCGTCGACATGCTCCGG
AAGCACACCTACGCCGACGAACTCCGCCAGGGCCTGCGGCGCGGCCGCGGCATGGGTGCG
CGCGCGCAGCCGACGCCGTCGTGGGCGCGGGTTCCCCTTTTCGAGAAGGCTGTGACCCCT
AGCGATGTCGGCAAGCTCAATCGCCTGGTGGTGCCGAAGCAGCACGCCGAGAAGCACTTC
CCCCTGAAGTGCACCGCAGAGACGACGACCACCACCGGCAACGGCGTGCTGCTAAACTTC
GAGGATGGTGAGGGGAAGGTGTGGAGGTTCCGGTACTCGTATTGGAACAGTAGCCAGAGC
TACGTGCTCACCAAAGGCTGGAGCAGCTTCGTCCGGGAGAAGGGCCTCGGCGCAGGCGAC
TCCATCGTCTTCTCCTCCTCGGCGTACGGGCAGGAGAAGCAGTTATTCATCAACTGCAAA
AAGAACACGACTATGAACGGCGGCAAAACAGCGTTGCCGCTGCCAGTGGTGGAGACTGCC
AAAGGAGAACAAGACCACGTCGTTAAGTTGTTCGGTGTTGACATCGCCGGTGTGAAGAGG
GTGCGAGCGGCGACGGGGGAGCTAGGCCCGCCGGAGTTGTTCAAGAGACAATCCGTGGCA
CACGGATGCGGAAGGATGAACTACATTTGCTACTCCATAGGGACAATAGGACCTCTTATG
CTCAACTGA

MLOC_63261
Cover 49% identity 51%

SEQ ID NO: 97

MASSKPTNPEVDNDMECSSPESGAEDAVESSSPVAAPSSRFKGVVPQPNGRWGAQIYEKH
SRVWLGTFGDEEAAACAYDVAALRFRGRDAVTNHQRLPAAEGAGWSSTSELAFLADHSKA
EIVDMLRKHTYDDELRQGLRRGHGRAQPTPAWAREFLFEKALTPSDVGKLNRLVVPKQHA
EKHFPPTTAAAAGSDGKGLLLNFEDGQGKVWRFRYSYWNSSQSYVLTKGWSRFVQEKGLC
AGDTVTFSRSAYVMNDTDEQLFIDYKQSSKNDEAADVATADENEAGHVAVKLFGVDIGWA
GMAGSSGG

SEQ ID NO: 98

ATGGCGTCTAGCAAGCCGACAAACCCCGAGGTAGACAATGACATGGAGTGCTCCTCCCCG
GAATCGGGTGCCGAGGACGCCGTGGAGTCGTCGTCGCCGGTGGCAGCGCCATCTTCGCGG
TTCAAGGGCGTCGTGCCGCAGCCTAACGGGCGCTGGGGCGCAGATCTACGAGAAGCAC
TCGCGGGTGTGGCTTGGCACGTTCGGGGACGAGGAAGCCGCCGCGTGCGCCTACGACGTG
GCCGCGCTCCGCTTCCGCGGCCGCGACGCCGTCACCAACCACCAGCGCCTGCCGGCGGCG
GAGGGGGCCGGCTGGTCGTCCACGAGCGAGCTCGCCTTCCTCGCCGACCACTCCAAGGCC
GAGATCGTCGACATGCTCCGGAAGCACACCTACGACGACGAGCTCCGGCAGGGCCTGCGC
CGCGGCCACGGGCGCGCGCAGCCCACGCCGGCGTGGGCGCGAGAGTTCCTCTTCGAGAAG

-continued

```
GCCCTGACCCCGAGCGACGTCGGCAAGCTCAACCGCCTGGTCGTTCCGAAGCAGCACGCC

GAGAAGCACTTCCCCCCGACGACGGCGGCGGCCGCCGGAAGCGACGGCAAGGGCTTGCTG

CTCAACTTCGAGGACGGCCAAGGGAAGGTGTGGAGGTTCCGGTACTCATACTGGAACAGC

AGCCAGAGCTACGTGCTCACCAAGGGCTGGAGCCGCTTCGTCCAAGAAAAGGGCCTCTGC

GCCGGCGACACCGTGACGTTCTCCCGGTCGGCGTACGTGATGAATGACACGGATGAGCAG

CTCTTCATCGACTACAAGCAGAGTAGCAAGAACGACGAAGCGGCCGACGTAGCCACTGCC

GATGAGAATGAGGCCGGCCATGTCGCCGTGAAGCTCTTCGGGGTCGACATTGGCTGGGCT

GGGATGGCGGGATCATCAGGTGGGTGA
```

MLOC_64708
Cover 49% identity 51%

SEQ ID NO: 99

```
MLFDSSVSASLGTMRPLVKKLDMLLAPARGYSTLCKRIKEVMHLLKHDVEEISSYLDELT

EVEDPPPMAKCWMNEARDLSYDMEDYIDSLLFVPPGHFIKKKKKKKKGKKKMVIKKRLK

WCKQIVFTKQVSDHGIKTSKIIHVNVPRLPNKPKVAKIILQFRIYVQEAIERYDKYRLHH

CSTLRRRLLSTGSMLSVPIPYEEAAQIVTDGRMNEFISSLAANNAADQQQLKVVSVLGSG

CLGKTTLANVLYDRIGMQFECRAFIRVSKKPDMKRLFRDLLSQFHQKQPLPTSCNELGIS

DNIIKHLQDKRYLIVIDDLWDLSVWDIIKYAFPKGNHGSRIIITTQIEDVALTCCCDHSE

HVFEMKPLNIGHSRELFFNRLFGSESDCLEEFKRVSNEIVDICGGLPLATINIASHLANQ

ETEVSLDLLTDTRDLLRSCLWSNSTSERTKQVLNLSYSNLPDYLKTCLLYLHMYPVGSII

WKDDLVKQLVAEGFIATREGKDQDQEMIEKAAGLCFDALIDRRFIQPIYTKYNNKVLSCT

VHEVVHDLIAQKSAEENFIVVADHNRKNIALSHKVRRLSLIFGDTIYAKTPANITKSQIR

SFRFFGLFECMPCITEFKVLRVLNLQLSGHRGDNDPIDLTGISELFQLRYLKITSDVCIK

LPNQMQKLQYLETLDIMDAPRVTAVPWDIINLPHLLHLTLPVDTYLLDWISSMTDSVISL

WTLGKLNYLQHLHLTSSSTRPSYHLERSVEALGYLIGGHGKLKTIVVAHVSSAQNTVVRG

APEVTISWDRMSPPPLLQRFECPHSCFIFYRIPKWVTELGNLCILKIAVKELHMICLGTL

RGLHALTDLSLYVETAPIDKIIFDKAGFSVLKYCKLRFAAGIAWLKFEADAMPSLWKLML

VFNAIPRMDQNLVFFHHSRPAMHQRGGAVIIVEHMPGLRVISAKFGGAASDLEYASRTVV

SNHPSNPTINMQLVCYSSNGKRSRKRKQQPYDVVKGQPDEYAKRLERPAEKRISTPTKSS

LRLHVPEITPKPMQITDNNVQRREHMFDTVLTRGDVGMLNRLVVPKKHAEKYFPLDSSST

RTSKAIVLSFEDPAGKSWFFHYSYRSSSQNYVMFKGWTGFVKEKFLEAGDTVSFSRGVGE

ATRGRLFIDCQNEQRYMFERVLTASDMESDGCSLMVPVNLVWPHPGLRKTIKGRHAVLQF

EDGSGNGKVWPFQFEASGQYYLMKGLNYFVNDRDLAAGYTVSFYRAGTRLFVDSGRKDDK

VALGTRSRERIYPKIVRSQ
```

*Brassica rapa*
LOC103849927
Cover 99% ident 80%
CDS

SEQ ID NO: 100

```
ATGTTGTTTGATAGTTCAGTGAGTGCTTCGTTGGGCACCATGAGACCACTIGTCAAGAAG

CTCGACATGCTGCTAGCTCCTGCTCGGGGATACAGTACCTTGTGCAAGAGGATCAAGGAA

GTGATGCACCTTCTCAAACATGATGTTGAAGAGATAAGCTCCTACCTTGATGAACTTACA

GAGGTGGAGGACCCTCCACCAATGGCCAAGTGCTGGATGAACGAGGCACGCGACCTGTCT

TATGATATGGAGGATTACATTGATAGCTTGTTATTTGTGCCACCTGGCCATTTCATCAAG

AAGAAGAAGAAGAAGAAGAAGGGAAAGAAGAAGATGGTGATAAAGAAGAGGCTCAAC

TGGTGCAAACAGATCGTATTCACAAAGCAAGTGTCAGACCATGGTATCAAGACCAGTAAA
```

-continued

```
ATCATTCATGTTAATGTCCCTCGTCTTCCCAATAAGCCCAAGGTTGCAAAAATAATATTA

CAGTTCAGGATCTATGTCCAGGAGGCTATTGAACGGTATGACAAGTATAGGCTTCACCAT

TGCAGCACCTTGAGGCGTAGATTGTTGTCCACTGGTAGTATGCTTTCAGTGCCAATACCC

TATGAAGAAGCTGCCCAAATTGTAACTGATGGCCGGATGAATGAGTTTATCAGCTCACTG

GCTGCTAATAATGCAGCAGATCAGCAGCAGCTCAAGGTGGTATCTGTTCTTGGATCTGGG

TGTCTAGGTAAAACTACGCTTGCGAATGTGTTGTACGACAGAATTGGGATGCAATTCGAA

TGCAGAGCTTTCATTCGAGTGTCCAAAAAGCCTGATATGAAGAGACTTTTCCGTGACTTG

CTCTCGCAATTCCACCAGAAGCAGCCACTGCCTACCAGTTGTAATGAGCTTGGCATAAGT

GACAATATCATCAAACATCTGCAAGATAAAAGGTATCTAATTGTTATTGATGATTTGTGG

GATTTATCAGTATGGGATATTATTAAATATGCTTTTCCAAAGGGAAACCATGGAAGCAGA

ATAATAATAACTACACAGATTGAAGATGTTGCATTAACTTGTTGCTGTGATCACTCGGAG

CATGTTTTCGAGATGAAACCTCTCAACATTGGTCACTCAAGAGAGCTATTTTTTAATAGA

CTTTTTGGTTCTGAAAGTGACTGTCTTGAAGAATTCAAACGAGTTTCAAACGAAATTGTT

GATATATGTGGTGGTTTACCGCTAGCAACAATCAACATAGCTAGTCATTTGGCAAACCAG

GAGACAGAAGTATCATTGGATTTGCTAACAGACACACGTGATTTGTTGAGGTCCTGTTTG

TGGTCAAATTCTACTTCAGAAAGAACAAAACAAGTACTGAACCTCAGCTACAGTAATCTT

CCTGATTATCTGAAGACATGTTTGCTGTATCTTCATATGTATCCAGTGGGCTCCATAATC

TGGAAGGATGATCTGGTGAAGCAATTGGTGGCTGAAGGGTTTATTGCTACAAGAGAAGGG

AAAGACCAAGACCAAGAAATGATAGAGAAAGCTGCAGGACTCTGTTTCGATGCACTTATT

GATAGAAGATTCATCCAGCCTATATATACCAAGTACAACAATAAGGTGTTGTCCTGCACG

GTTCATGAGGTGGTACATGATCTTATTGCCCAAAAGTCTGCTGAAGAGAATTTCATTGTG

GTAGCAGACCACAATCGAAAGAATATAGCACTTTCTCATAAGGTTCGTCGACTATCTCTC

ATCTTTGGCGACACAATATATGCCAAGACACCAGCAAACATCACAAAGTCACAAATTCGG

TCATTCAGATTTTTTGGATTATTCGAGTGTATGCCTTGTATTACAGAGTTCAAGGTTCTC

CGTGTTCTAAACCTTCAACTATCTGGTCATCGTGGGACAATGACCCTATAGACCTCACT

GGGATTTCAGAACTGTTTCAGCTGAGATATTTAAAGATTACAAGTGATGTGTGCATAAAA

CTACCAAATCAAATGCAAAAACTGCAATATTTGGAAACGTTGGACATTATGGATGCACCA

AGAGTCACTGCTGTTCCATGGGATATTATAAATCTCCCACACCTGTTGCACCTGACTCTT

CCTGTTGATACATATCTGCTGGATTGGATTAGCAGCATGACTGACTCCGTCATCAGTCTG

TGGACCCTTGGCAAGCTGAACTACCTGCAGCATCTTCATCTTACTAGTTCTTCTACACGT

CCTTCATACCATCTGGAGAGAAGTGTGGAGGCTCTGGGTTATTTGATCGGAGGACATGGC

AAGCTGAAAACTATAGTAGTCGCTCATGTCTCCTCTGCTCAAAATACTGTGGTTCGTGGC

GCCCCAGAAGTAACCATTTCATGGGATCGTATGTCACCTCCCCCCCTTCTCCAGAGATTC

GAATGCCCACACAGCTGCTTCATATTTTACCGAATTCCTAAGTGGGTTACAGAACTTGGC

AACCTGTGCATTTTGAAGATTGCAGTGAAGGAGCTTCATATGATTTGTCTTGGTACTCTC

AGAGGATTGCATGCCCTCACTGATCTGTCGCTGTATGTGGAGACAGCGCCCATTGACAAG

ATCATCTTTGACAAGGCCGGGTTCTCAGTTCTCAAGTACTGCAAATTGCGCTTCGCGGCT

GGTATAGCTTGGCTGAAATTTGAGGCTGATGCAATGCCTAGTCTATGGAAACTGATGCTA

GTTTTCAACGCCATCCCACGAATGGACCAAAATCTTGTTTTCTTTCACCACAGCCGACCG

GCGATGCATCAACGTGGTGGTGCAGTAATCATTGTCGAGCATATGCCAGGGCTTAGAGTG
```

-continued

```
ATCTCCGCAAAATTTGGGGCGCAGCTTCTGATCTAGAGTATGCTTCGAGGACCGTCGTT

AGTAACCATCCAAGCAATCCTACAATCAACATGCAATTGGTGTGTTATAGTTCCAATGGT

AAGAGAAGCAGAAAAAGGAAACAACAACCTTACGACGTTGTGAAGGGACAACCAGATGAA

TACGCCAAGAGATTGGAGAGACCAGCTGAGAAAAGGATTTCAACGCCGACAAAGTCTTCT

TTGCGTCTGCATGTTCCAGAAATTACACCAAAACCTATGCAGATTACAGACAACAATGTT

CAGAGGAGGGAGCACATGTTCGATACGGTTCTGACTCGGGGGACGTGGGGATGCTGAAC

CGGCTGGTGGTACCGAAGAAGCACGCGGAGAAGTACTTCCCGCTGGACAGTTCCTCCACC

CGCACCAGCAAGGCCATCGTACTCAGCTTTGAGGACCCTGCTGGGAAGTCATGGTTCTTC

CACTACTCCTACCGGAGCAGCAGCCAGAACTACGTCATGTTCAAGGGGTGGACTGGCTTC

GTCAAGGAGAAGTTTCTCGAAGCCGGCGACACCGTCTCCTTCAGCCGCGGCGTCGGGGAG

GCCACGAGGGGGAGGCTCTTCATCGACTGTCAAAATGAGCAGAGGTACATGTTCGAGCGA

GTGCTGACGGCGAGTGATATGGAGTCGGATGGCTGCTCGCTGATGGTCCCAGTGAACTTG

GTGTGGCCGCACCCCGGCCTCCGCAAGACGATCAAGGGGAGGCACGCCGTGCTGCAGTTT

GAGGACGGCAGCGGCAACGGGAAGGTGTGGCCATTTCAGTTTGAGGCCTCCGGCCAATAC

TATCTCATGAAGGGCTTGAACTACTTTGTTAACGACCGCGACCTTGCGGCTGGCTATACC

GTCTCCTTCTACCGCGCCGGCACGCGGTTGTTCGTCGACTCCGGGCGTAAAGATGACAAA

GTAGCCTTGGGAACCAGAAGCCGCGAAAGGATCTATCCTAAGATCGTGCGGTCGCAGTAG
```

LOC103849927

SEQ ID NO: 101

```
msgnhysrdihhntpsvhhhqnyavvdreylfeksltpsdvgklnrlvipkqhaekhfplnnagddvaaaettekgmlltfedesgkcwki rysywnssqsyvltkgwsryvkdkhlhagdvvffqrhrfdlhrvfigwrkrgevssptaysvvsqearvnttaywsglttpyrqvhastssyp nihqeyshygavaeiptvvtgssrtvrlfgvnlechgdvvetppcpdgyngqhfyyystpdpmnisfageameqvgdgrr
```

Bra034828
Cover 100% identity 79%

SEQ ID NO: 102

```
MSVNHYSNTLSSHNHHNEHKESLFEKSLTPSDVGKLNRLVIPKQHAERYLPLNNCGGGGD

VTAESTEKGVLLSFEDESGKSWKFRYSYWNSSQSYVLTKGWSRYVKDKHLNAGDVVLFQR

HRFDIHRLFIGWRRRGEASSSSAVSAVTQDPRANTTAYWNGLTTPYRQVHASTSSYPNNI

HQEYSHYGPVAETPTVAAGSSKTVRLFGVNLECHSDVVEPPPCPDAYNGQHIYYYSTPHP

MNISFAGEAMEQVGDGRG
```

CDS

SEQ ID NO: 103

```
ATGTCAGTCAACCATTACTCAAACACTCTCTCGTCGCACAATCACCACAACGAACATAAA

GAGTCTTTGTTCGAGAAGTCACTCACGCCAAGCGATGTTGGAAAGCTAAACCGTTTAGTC

ATACCAAAACAACACGCCGAGAGATACCTCCCTCTCAATAATTGCGGCGGCGGCGGCGAC

GTGACGGCGGAGTCGACGGAGAAAGGGGTGCTTCTCAGCTTCGAGGACGAGTCGGGAAAA

TCTTGGAAATTCAGATACTCATATTGGAACAGTAGTCAAAGCTACGTGTTGACCAAAGGA

TGGAGCAGGTACGTCAAAGACAAGCACCTCAACGCAGGGGACGTCGTTTTATTTCAACGG

CACCGTTTTGATATTCATAGACTCTTCATTGGCTGGAGGAGACGCGGAGAGGCTTCTTCC

TCTTCCGCCGTTTCCGCCGTGACTCAAGATCCTCGAGCTAACACGACGGCGTACTGGAAC

GGTTTGACTACACCTTATCGTCAAGTACACGCGTCAACTAGTTCTTACCCTAACAACATC

CACCAAGAGTATTCACATTATGGCCCTGTTGCTGAGACACCGACGGTAGCTGCAGGGAGC

TCGAAGACGGTGAGGCTATTTGGAGTTAACCTCGAATGTCACAGTGACGTTGTGGAGCCA
```

-continued

```
CCACCGTGTCCTGACGCCTACAACGGCCAACACATTTACTATTACTCAACTCCACATCCC

ATGAATATCTCATTTGCTGGAGAAGCAATGGAGCAGGTAGGAGATGGACGAGGTTGA
```

Bra005886
Cover 100% identity 79%

SEQ ID NO: 104

```
MSVNHYSTDHHQVHHHHTLFLQNLHTTDTSEPTTTAATSLREDQKEYLFEKSLTPSDVGK

LNRLVIPKQHAEKYFPLNTIISNNAEEKGMLLSFEDESGKCWRFRYSYWNSSQSYVLTKG

WSRYVKDKQLDPADVVFFQRQRSDSRRLFIGWRRRGQGSSSAANTTSYSSSMTAPPYSNY

SNRPAHSEYSHYGAAVATATETHFIPSSSAVGSSRTVRLFGVNLECQMDEDEGDDSVATA

AAAECPRQDSYYDQNMYNYYTPHSSAS
```

CDS

105

```
ATGTCAGTCAACCATTACTCCACGGACCACCACCAGGTCCACCACCACCACACTCTCTTC

TTGCAGAACCTCCACACCACCGACACATCGGAGCCAACCACAACCGCCGCCACATCACTC

CGCGAAGACCAGAAAGAGTATCTCTTCGAGAAATCTCTCACACCAAGCGACGTTGGCAAA

CTCAACCGTCTCGTTATACCAAAACAGCACGCGGAGAAGTACTTCCCTCTCAACACCATC

ATCTCCAATAATGCTGAGGAGAAAGGGATGCTTCTAAGCTTCGAAGACGAGTCAGGCAAG

TGCTGGAGGTTCAGATACTCTTACTGGAACAGCAGTCAAAGCTACGTGTTGACTAAAGGA

TGGAGCAGATACGTCAAAGACAAACAGCTCGACCCAGCCGATGTTGTTTTCTTCCAACGT

CAACGTTCTGATTCCCGGAGACTCTTTATTGGCTGGCGTAGACGCGGTCAAGGCTCCTCC

TCCGCCGCGAATACGACGTCGTATTCTAGTTCCATGACTGCTCCACCGTATAGTAATTAC

TCTAATCGTCCTGCTCACTCAGAGTATTCCCACTATGGCGCCGCCGTAGCAACAGCGACG

GAGACGCACTTCATACCATCGTCTTCCGCCGTCGGGAGCTCGAGGACGGTGAGGCTTTTT

GGTGTGAATTTGGAGTGTCAAATGGATGAAGACGAAGGAGATGATTCGGTTGCCACGGCA

GCCGCCGCTGAGTGTCCTCGTCAGGACAGCTACTACGACCAAAACATGTACAATTATTAC

ACTCCTCACTCCTCAGCCTCATAA
```

Bra005301
Cover 100% identity 58%

SEQ ID NO: 106

```
MSINQYSSDFNYHSLMWQQQQHRHHHHQNDVAEEKEALFEKPLTPSDVGKLNRLVIPKQH

AERYFPLAAAAADAMEKGLLLCFEDEEGKPWRFRYSYWNSSQSYVLTKGWSRYVKEKQLD

AGDVILFHRHRVDGGRFFIGWRRRGNSSSSSDSYRHLQSNASLQYYPHAGVQAVESQRGN

SKTLRLFGVNMECQLDSDLPDPSTPDGSTICPTSHDQFHLYPQQHYPPPYYMDISFTGDV

HQTRSPQG
```

CDS

SEQ ID NO: 107

```
ATGTCAATAAACCAATACTCAAGCGATTTCAACTACCACTCTCTCATGTGGCAACAACAG

CAGCACCGCCACCACCACCATCAAAACGACGTCGCGGAGGAAAAAGAAGCTCTTTTCGAG

AAACCCTTAACCCCAAGTGACGTCGGAAAACTCAACCGCCTCGTCATCCCAAAACAGCAC

GCCGAGAGATACTTCCCTCTCGCAGCAGCCGCCGCAGACGCGATGGAGAAGGGATTACTT

CTCTGCTTCGAGGACGAGGAAGGTAAGCCATGGAGATTCAGATACTCGTATTGGAACAGT

AGCCAGAGTTATGTCTTGACCAAAGGATGGAGCAGATACGTCAAGGAGAAGCAGCTCGAC

GCCGGTGACGTCATTCTCTTCCACCGCCACCGTGTTGACGGAGGAAGATTCTTCATTGGC

TGGAGAAGACGCGGCAACTCTTCCTCCTCTTCCGACTCTTATCGCCATCTTCAGTCCAAT

GCCTCGCTCCAATATTATCCTCATGCAGGAGTTCAAGCGGTGGAGAGCCAGAGAGGGAAT
```

-continued

TCGAAGACATTAAGACTGTTCGGAGTGAACATGGAGTGTCAGCTAGACTCCGACTTGCCC

GATCCATCTACACCAGACGGTTCCACCATATGTCCGACCAGTCACGACCAGTTTCATCTC

TACCCTCAACAACACTATCCTCCTCCGTACTACATGGACATAAGTTTCACAGGAGATGTG

CACCAGACGAGAAGCCCACAAGGATAA

Bra017262
Cover 92% identity 56%

SEQ ID NO: 108

MSINQYSSEFYYHSLMWQQQQHHHQNEVVEEKEALFEKPLTPSDVGKLNRLVIPKQHAE

RYFPLAAAAVDAVEKGLLLCFEDEEGKPWRFRYSYWNSSQSYVLTKGWSRYVKEKQLDAG

DVVLFHRHRADGGRFFIGWRRRGDSSSSSDSYRNLQSNSSLQYYPHAGAQAVENQRGNSK

TLRLFGVNMECQIDSDWSEPSTPDGFTTCPTNHDQFPIYPEHFPPPYYMDVSFTGDVHQT

SSQQG

CDS

SEQ ID NO: 109

ATGTCAATAAATCAATATTCAAGCGAGTTCTACTACCATTCTCTCATGTGGCAACAACAG

CAGCAACACCACCATCAAAACGAAGTCGTGGAGGAAAAAGAAGCTCTTTTCGAGAAACCC

TTAACCCCAAGTGACGTCGGAAAACTAAACCGCCTAGTCATCCCTAAACAGCACGCCGAG

AGATACTTCCCTCTCGCCGCCGCCGCGGTAGACGCCGTGGAGAAGGGATTACTCCTCTGC

TTCGAGGACGAGGAAGGTAAGCCATGGAGATTCAGATACTCTTATTGGAATAGTAGCCAG

AGTTACGTCTTGACCAAAGGATGGAGCAGATATGTTAAAGAGAAGCAACTTGACGCCGGC

GACGTTGTTCTCTTTCATCGCCACCGTGCTGACGGTGGAAGATTCTTCATTGGCTGGAGA

AGACGCGGCGACTCTTCCTCCTCCTCCGACTCTTATCGCAATCTTCAATCTAATTCCTCG

CTCCAATATTATCCTCATGCAGGGGCTCAAGCGGTGGAGAACCAGAGAGGTAACTCCAAG

ACATTGAGACTTTTTGGAGTGAACATGGAGTGCCAGATAGACTCAGACTGGTCCGAGCCA

TCCACACCTGACGGTTTTACCACATGTCCAACCAATCACGACCAGTTTCCTATCTACCCT

GAACACTTTCCTCCTCCGTACTACATGGACGTAAGTTTCACAGGAGATGTGCACCAGACG

AGTAGCCAACAAGGATAG

Bra000434
Cover 96% identity 47%

SEQ ID NO: 110

MMTNLSLAREGEEEEEEAGAKKPTEEVEREHMFDKVVTPSDVGKLNRLVIPKQHAERYFP

LDSSTNEKGLILNFEDLTGKSWRFRYSYWNSSQSYVMTKGWSRFVKDKKLDAGDIVSFLR

CVGDTGRDSRLFIDWRRRPKVPDYTTSTSHFPAGAMFPRFYSFQTATTSTSYNPYNHQQP

RHHHSGYCYPQIPREFGYGYVVRSVDQRAVVADPLVIESVPVMMHGGARVNQAAVGTAGK

RLRLFGVDMECGESGGTNSTEEESSSSGGSLPRGGASPSSSMFQLRLGNSSEDDHLFKKG

KSSLPFNLDQ

SEQ ID NO: 111

ATGATGACAAATTTGTCTCTTGCAAGAGAAGGAGAAGAAGAAGAAGAAGAGGCAGGAGCA

AAGAAGCCCACAGAAGAAGTGGAGAGAGAGCACATGTTCGACAAAGTGGTGACTCCAAGT

GACGTCGGAAAACTAAACCGACTCGTGATCCCAAAGCAACACGCGGAGAGATACTTCCCT

TTAGATTCATCCACAAACGAGAAGGGTTTGATTCTAAACTTCGAAGATCTCACGGGAAAG

TCATGGAGGTTCCGTTACTCTTACTGGAACAGCAGTCAGAGCTATGTCATGACTAAAGGT

TGGAGCCGTTTCGTTAAAGACAAGAAGCTAGACGCTGGAGATATTGTCTCTTTCCTGAGA

TGTGTCGGAGACACAGGAAGGGACAGCCGCTTGTTTATCGATTGGAGGAGACGACCTAAA

GTCCCTGACTACACGACATCGACTTCTCACTTTCCTGCCGGAGCTATGTTCCCTAGGTTT

```
TACAGTTTTCAGACAGCAACTACTTCCACAAGTTACAATCCCTATAATCATCAGCAGCCA

CGTCATCATCACAGTGGTTACTGTTATCCTCAAATCCCGAGAGAATTTGGATATGGGTAT

GTCGTTAGGTCAGTAGATCAGAGGGCGGTGGTGGCTGATCCGTTAGTGATCGAATCTGTG

CCGGTGATGATGCACGGAGGAGCTCGAGTGAACCAGGCGGCTGTTGGAACGGCCGGGAAA

AGGCTGAGGCTTTTTGGAGTCGATATGGAATGTGGCGAGAGTGGAGGAACAAACAGTACG

GAGGAAGAATCTICATCTTCCGGTGGGAGTTTGCCACGTGGCGGTGCTTCTCCGTCTTCC

TCTATGTTTCAGCTGAGGCTTGGAAACAGCAGTGAAGATGATCACTTATTTAAGAAAGGA

AAGTCTTCATTGCCTTTTAATTTGGATCAATAA

Bra040478
Cover 96% identity 48%
```
SEQ ID NO: 112
```
MMTNLSLAREGEAQVKKPIEEVEREHMFDKVVTPSDVGKLNRLVIPKQHAERYFPLDSSS

NEKGLLLNFEDLTGKSWRFRYSYWNSSQSYVMTKGWSRFVKDKKLDAGDIVSFQRCVGDS

RLFIDWRRRPKVPDYPTSTAHFAAGAMFPRFYSFPTATTSTCYDLYNHQPPRHHHIGYGY

PQIPREFGYGYFVRSVDQRAVVADPLVIESVPVMMRGGARVSQEVVGTAGKRLRLFGVDM

EEESSSSGGSLPRAGGGGASSSSSLFQLRLGSSCEDDHFSKKGKSSLPFDLDQ
```
SEQ ID NO: 113
```
ATGATGACCAACTTGTCTCTTGCAAGGGAAGGAGAAGCACAAGTAAAGAAGCCCATAGAA

GAAGTTGAGAGAGAGCACATGTTCGACAAAGTGGTGACTCCAAGCGACGTAGGGAAACTA

AACAGACTCGTGATCCCAAAGCAACACGCAGAGAGATACTTCCCTCTAGATTCATCCTCA

AACGAGAAAGGTTTGCTTCTAAACTTTGAAGATCTAACAGGAAAGTCATGGAGGTTCCGT

TACTCTTACTGGAACAGTAGCCAGAGCTATGTCATGACTAAAGGTTGGAGTCGTTTCGTT

AAAGACAAGAAGCTTGACGCCGGAGATATTGTCTCTTTCCAGAGATGTGTCGGAGACAGC

CGCTTGTTTATCGATTGGAGGAGACGACCTAAAGTCCCTGACTATCCGACATCGACTGCT

CACTTTGCTGCAGGAGCTATGTTCCCTAGGTTTTACAGTTTTCCGACAGCAACTACTTCG

ACATGTTACGATCTGTACAATCATCAGCCGCCACGTCATCATCACATTGGTTACGGTTAT

CCACAGATTCCGAGAGAATTTGGATACGGGTATTTCGTTAGGTCAGTGGACCAGAGAGCG

GTGGTGGCTGATCCGTTGGTGATCGAATCTGTGCCGGTGATGATGCGCGGAGGAGCTCGA

GTTAGTCAGGAGGTTGTTGGAACGGCCGGGAAGAGGCTGAGGCTTTTTGGAGTCGATATG

GAGGAAGAATCTICATCTTCCGGTGGGAGTTTGCCGCGTGCCGGAGGTGGCGGTGCTTCT

TCATCTTCCTCTTTGTTTCAGCTGAGACTTGGGAGCAGCTGTGAAGATGATCACTTCTCT

AAGAAAGGAAAGTCTTCATTGCCTTTTGATTTGGATCAATAA

Bra004501
Cover 74% identity 45%
```
SEQ ID NO: 114
```
MMMTNLSLSREGEEEEEEEQEEAKKPMEEVEREHMFDKVVTPSDVGKLNRLVIPKQYAER

YFPLDSSTNEKGLLLNFEDLAGKSWRFRYSYWNSSQSYVMTKGWSRFVKDKKLDAGDIVS

FQRCVGDSGRDSRLFIDWRRRPKVPDHPTSIAHFAAGSMFPRFYSFPTATSYNLYNYQQP

RHHHHSGYNYPQIPREFGYGYLVDQRAVVADPLVIESVPVMMHGGAQVSQAVVGTAGKRL

RLFGVDMEEESSSSGGSLPRGDASPSSSLFQLRLGSSSEDDHFSKKGKSSLPFDLDQ
```
SEQ ID NO: 133
```
ATGATGATGACAAACTTGTCTCTTTCAAGAGAAGGAGAAGAGGAGGAAGAAGAAGAACAA

GAAGAGGCCAAGAAGCCCATGGAAGAAGTAGAGAGAGAGCACATGTTCGACAAAGTGGTG

ACTCCAAGCGATGTTGGTAAACTAAACCGGCTCGTGATCCCAAAGCAATACGCAGAGAGA

TACTTCCCTTTAGATTCATCCACAAACGAGAAAGGTTTGCTTCTAAACTTCGAAGATCTC
```

-continued

```
GCAGGAAAGTCATGGAGGTTCCGTTACTCTTACTGGAACAGTAGTCAGAGCTATGTCATG

ACTAAAGGTTGGAGCCGTTTCGTTAAAGACAAAAAGCTAGACGCCGGAGATATTGTCTCT

TTCCAGAGATGTGTCGGAGATTCAGGAAGAGACAGCCGCTTGTTTATTGATTGGAGGAGA

AGACCTAAAGTTCCTGACCATCCGACATCGATTGCTCACTTTGCTGCCGGATCTATGTTT

CCTAGGTTTTACAGTTTTCCGACAGCAACTAGTTACAATCTTTACAACTATCAGCAGCCA

CGTCATCATCATCACAGTGGTTATAATTATCCTCAAATTCCGAGAGAATTTGGATACGGG

TACTTGGTGGATCAAAGAGCCGTGGTGGCTGATCCGTTGGTGATTGAATCTGTGCCGGTG

ATGATGCACGGAGGAGCTCAAGTTAGTCAGGCGGTTGTTGGAACGGCCGGGAAGAGGCTG

AGGCTTTTTGGAGTCGATATGGAGGAAGAATCTCATCTTCCGGTGGGAGTTTGCCACGT

GGTGACGCTTCTCCGTCTTCCTCTTTGTTTCAGCTGAGACTTGGAAGCAGCAGTGAAGAT

GATCACTTCTCTAAGAAAGGAAAGTCCTCATTGCCTTTTGATTTGGATCAATAA
```

Bra003482
Cover 79% identity 44%

SEQ ID NO: 115

```
MNQEEENPVEKASSMEREHMFEKVVTPSDVGKLNRLVIPKQHAERYFPLDNNSDSSKGLL

LNFEDRTGNSWRFRYSYWNSSQSYVMTKGWSRFVKDKKLDAGDIVSFQRDPGNKDKLFID

WRRRPKIPDHHQFAGAMFPRFYSFSHPQNLYHRYQQDLGIGYYVSSMERNDPTAVIESV

PLIMQRRAAHVAAIPSSRGEKRLRLFGVDMECGGGGGSVNSTEEESSSGGGGGVSMASV

GSLLQLRLVSSDDESLVAMEAASVDEDHHLFTKKGKSSLSFDLDRK
```

SEQ ID NO: 116

```
ATGAATCAAGAAGAAGAGAATCCTGTGGAAAAAGCCTCTTCAATGGAGAGAGAGCACATG

TTTGAAAAAGTAGTAACACCAAGCGACGTAGGCAAACTAAACCGACTCGTGATCCCAAAG

CAACACGCGGAGAGATACTTCCCTTTAGACAACAATTCTGACAGCAGCAAAGGTTTGCTT

CTAAACTTCGAAGACCGAACAGGAAACTCATGGAGATTCCGTTACTCTTACTGGAACAGT

AGCCAGAGTTATGTCATGACAAAAGGTTGGAGCCGCTTCGTCAAAGACAAGAAGCTTGAT

GCTGGCGACATCGTTTCTTTTCAGAGAGATCCTGGTAATAAAGACAAGCTTTTCATTGAT

TGGAGGAGACGACCAAAGATTCCAGATCATCATCATCAATTCGCTGGAGCTATGTTCCCT

AGGTTTTACTCTTTCTCTCATCCTCAGAACCTTTATCATCGATATCAACAAGATCTTGGA

ATTGGGTATTATGTGAGTTCAATGGAGAGAAATGATCCAACGGCTGTAATTGAATCTGTG

CCGTTGATAATGCAAAGGAGAGCAGCACACGTGGCTGCTATACCTTCATCAAGAGGAGAG

AAGAGGTTAAGGCTGTTTGGAGTGGACATGGAGTGCGGCGGCGGCGGAGGAAGTGTGAAT

AGCACGGAGGAAGAGTCGTCGTCTTCCGGTGGTGGCGGCGGCGTTTCTATGGCTAGTGTT

GGTTCTCTTCTCCAATTGAGGCTAGTGAGCAGTGATGATGAGTCTTTGGTAGCAATGGAA

GCTGCAAGTGTCGATGAGGATCATCACTTGTTTACAAAGAAAGGAAAGTCTTCTTTGTCT

TTCGATTTGGATAGAAAATGA
```

Bra007646
Cover 74% identity 45%

SEQ ID NO: 117

```
MNQENKKPLEEASTSMERENMFDKVVTPSDVGKLNRLVIPKQHAERYFPLDNSSTNNKGL

LLDFEDRTGSSWRFRYSYWNSSQSYVMTKGWSRFVKDKKLDAGDIVSFQRDPCNKDKLYI

DWRRRPKIPDHHQFAGAMFPRFYSFPHPQMPTSFESSHNLYHHRFQRDLGIGYYPTAVIE
```

SVPVIMQRREAQVANMASSRGEKRLRLFGVDVECGGGGGGSVNSTEEESSSSGGSMSRGG

VSMAGVGSLLQLRLVSSDDESLVAMEGATVDEDHHLFTTKKGKSSLSFDLDI

CDS

SEQ ID NO: 118

ATGAATCAAGAAAACAAGAAGCCTTTGGAAGAAGCTTCGACTTCAATGGAGAGAGAGAAC

ATGTTCGACAAAGTAGTAACACCAAGCGACGTAGGGAAACTAAACCGACTCGTGATCCCA

AAGCAACACGCAGAGAGATACTTCCCTTTAGACAACTCCTCAACAAACAACAAAGGGTTG

CTTCTAGACTTCGAAGACCGTACAGGAAGCTCATGGAGATTCCGTTACTCTTACTGGAAC

AGTAGCCAAAGTTATGTCATGACAAAAGGTTGGAGCCGTTTTGTCAAAGACAAGAAGCTT

GATGCTGGTGACATCGTGTCTTTTCAAAGAGATCCCTGTAATAAAGACAAGCTTTACATA

GATTGGAGGAGACGACCAAAGATTCCAGATCATCATCAGTTCGCCGGAGCTATGTTCCCT

AGGTTTTACTCTTTCCCTCACCCTCAGATGCCGACAAGTTTTGAAAGTAGTCACAACCTT

TATCATCATCGGTTTCAACGAGATCTTGGAATTGGGTATTATCCAACGGCTGTGATTGAA

TCTGTGCCGGTGATAATGCAAAGGAGAGAAGCACAAGTGGCTAATATGGCTTCATCAAGA

GGAGAGAAGAGGTTAAGGCTGTTTGGAGTGGACGTGGAGTGCGGCGGCGGAGGAGGAGGA

AGTGTGAATAGCACGGAGGAAGAGTCGTCGTCTTCCGGTGGTAGTATGTCACGTGGCGGC

GTTTCTATGGCTGGTGTTGGTTCTCTCCTTCAGTTGAGGTTAGTGAGCAGTGATGATGAG

TCTTTAGTAGCGATGGAAGGTGCTACTGTCGATGAGGATCATCACTTGTTTACAACTAAG

AAAGGAAAGTCTTCTTTGTCTTTCGATTTGGATATATGA

Bra014415
Cover 48% identity 60%

SEQ ID NO: 119

MERKSNDLERSENIDSQNKKMNLEEERPVQEASSMEREHMFDKVVTPSDVGKLNRLVIPK

QHAERYFPLDNNSSDNNKGLLLNFEDRIGILWSFRYSYWNSSQSYVMTKGWSRFVKDKKL

DAGDIVSFHRGSCNKDKLFIDWKRRPKIPDHQVVGAMFPRFYSYPYPQIQASYERHNLYH

RYQRDIGIGYYVRSMERYDPTAVIESVPVIMQRRAHVATMASSRGEKRLRLFGVDMECVR

GGRGGGGSVNSTEEESSTSGGSISRGGVSMAGVGSPLQLRLVSSDGDDQSLVARGAARVD

EDHHLFTKKGKSSLSFDLDK

CDS

SEQ ID NO: 120

ATGGAGAGGAAGTCCAATGATCTTGAGAGATCTGAGAATATTGATTCTCAAAACAAGAAG

ATGAATCTAGAAGAAGAGAGGCCTGTACAAGAAGCTTCTTCGATGGAGAGAGAGCACATG

TTCGACAAAGTAGTAACACCAAGCGACGTTGGGAAACTAAACCGGCTGGTGATCCCAAAG

CAACACGCAGAGCGATACTTCCCTTTAGACAATAATTCCTCAGACAACAACAAAGGTTTG

CTTCTAAACTTCGAAGATCGAATAGGAATCTTATGGAGTTTCCGTTACTCCTACTGGAAC

AGTAGCCAAAGTTATGTAATGACTAAAGGCTGGAGCCGTTTCGTCAAAGACAAGAAGCTT

GATGCTGGCGACATAGTTTCTTTTCATAGAGGTTCTTGTAATAAAGACAAGCTTTTCATT

GATTGGAAGAGACGACCAAAGATTCCTGATCACCAAGTCGTCGGAGCTATGTTCCCTAGG

TTTTACTCTTACCCTTATCCTCAGATACAGGCTAGTTATGAACGTCACAACCTTTATCAT

CGATATCAACGAGATATAGGAATTGGGTATTATGTGAGGTCAATGGAGAGATATGATCCA

ACGGCTGTAATTGAATCTGTGCCGGTGATAATGCAAAGGAGAGCACATGTGGCTACTATG

GCTTCATCAAGAGGAGAGAAGAGGTTAAGGCTTTTTGGAGTGGATATGGAGTGCGTCAGA

GGCGGCCGAGGAGGAGGAGGAAGTGTGAATAGCACGGAGGAAGAGTCTTCGACTTCCGGT

GGTAGTATCTCACGTGGCGGCGTTTCTATGGCTGGTGTTGGCTCTCCACTCCAGTTGAGG

```
TTAGTGAGCAGTGACGGTGATGATCAGTCTCTAGTAGCTAGGGGAGCTGCTAGGGTTGAT

GAGGATCATCACTTGTTTACAAAGAAAGGAAAGTCTTCTTTGTCTTTCGATTTGGATAAA

TGA
```

Bra038346
Cover 51% identity 57%

SEQ ID NO: 121

```
MVFSCIDESSSTSESFSPATATATATATKFSAPPLPPLRLNRMRSGGSNVVLDSKNGVDI

DSRKLSSSKYKGVVPQPNGRWGAQIYVKHQRVWLGTFCDEEEAAHSYDIAARKFRGRDAV

VNFKTFLASEDDNGELCFLEAHSKAEIVDMLRKHTYADELAQSNKRSGANTNTNTTQSHT

VSRTREVLFEKVVTPSDVGKLNRLVIPKQHAEKYFPLPSLSVTKGVLINFEDVTGKVWRF

RYSYWNSSQSYVLTKGWSRFVKEKNLRAGDVVTFERSTGSDRQLYIDWKIRSGPSKNPVQ

VVVRLFGVDIFNVTSAKPSNVVDACGGKRSRDVDMFALRCSKKHAIINAL
```

CDS

SEQ ID NO: 122

```
ATGGTATTCAGTTGCATAGACGAGAGCTCTTCCACTTCAGAATCTTTTTCACCCGCAACC

GCAACCGCAACCGCAACCGCCACAAAGTTCTCTGCTCCTCCGCTTCCACCGTTACGCCTC

AACCGGATGAGAAGCGGTGGAAGCAACGTCGTGTTGGATTCAAAGAATGGCGTAGATATT

GATTCACGGAAGCTATCGTCGTCAAAGTACAAAGGCGTGGTTCCTCAGCCCAACGGAAGA

TGGGGAGCTCAGATTTACGTGAAGCACCAGCGAGTTTGGCTGGGCACTTTCTGCGATGAA

GAGGAAGCTGCTCACTCCTACGACATAGCCGCCCGTAAATTCCGTGGCCGTGACGCCGTT

GTCAACTTCAAAACCTTCCTCGCCTCAGAGGACGACAACGGCGAGTTATGTTTCCTTGAA

GCTCACTCCAAGGCCGAGATCGTCGACATGTTGAGGAAACACACTTACGCTGACGAGCTT

GCGCAGAGCAATAAACGCAGCGGAGCGAATACGAATACGAATACGACTCAAAGCCACACC

GTTTCGAGAACACGTGAAGTGCTTTTCGAGAAGGTTGTCACGCCTAGCGACGTTGGTAAG

CTAAACCGCCTCGTGATACCTAAACAGCACGCGGAGAAATATTTTCCGTTACCGTCACTG

TCGGTGACTAAAGGCGTTCTGATCAACTTCGAAGACGTGACGGGTAAGGTGTGGCGGTTC

CGTTACTCATACTGGAACAGTAGTCAAAGTTACGTGTTGACCAAGGGATGGAGTCGGTTC

GTTAAGGAGAAGAATCTCCGAGCCGGTGATGTCGTTACTTTCGAGAGATCGACCGGTTCA

GACCGGCAGCTTTATATTGATTGGAAAATCCGGTCTGGTCCGAGCAAAAACCCTGTTCAG

GTTGTGGTTAGGCTTTTCGGAGTTGACATCTTCAACGTGACAAGCGCGAAGCCGAGCAAC

GTTGTAGACGCGTGCGGTGGAAAGAGATCTCGGGATGTTGATATGTTTGCGCTACGGTGT

TCCAAAAAACACGCTATAATCAATGCTTTGTGA
```

*Zea mays*
GRMZM2G053008
Cover 74% identity 47%

SEQ ID NO: 123

```
MAASPSSPLTAPPEPVTPPSPWTITDGAISGTLPAAEAFAVHYPGYPSSPARAARTLGGL

PGLAKVRSSDPGARLELRFRPEDPYCHPAFGQSRASTGLLLRLSKRKGAAAPCAHVVARV

RTAYYFEGMADFQHVVPVHAAQTRKRKHSDSQNDNENFGSDKTGHDEADGDVMMLVPPLF

SVKDRPTKIALVPSSNAISKTMHRGVVQERWEMNVGPTLALPFNTQVVPEKINWEDHIRK

NSVEWGWQMAVCKLFDERPVWPRQSLYERFLDDNVHVSQNQFKRLLFRAGYYFSTGPFGK

FWIRRGYDPRKDSESQIYQRIDFRMPPELRYLLRLKNSESRKWADMCKLETMPSQSFIYL

QLYELKDDFIQAEIRKPSYQSVCSRSTGWFSKPMIKTLRLQVSIRLLSLLHNEEAKNLLR
```

NAHELIERSKKQEALSRSELSIEYNDADQVSAAHTGTEDQVGPNNSDSEDVDDEEEEEL

EGYDSPPMADDIHEFTLGDSYAFGEGFSNGYLEEVLRSLPLQEDGQKKLCDAPINADASD

CDS

SEQ ID NO: 124

ATGGCCGCCTCGCCCTCTTCACCCTTGACAGCGCCGCCAGAGCCGGTGACCCCGCCGTCC

CCATGGACCATCACAGACGGAGCCATCTCTGGCACGCTCCCAGCAGCCGAGGCCTTCGCA

GTGCACTACCCGGGCTACCCCTCCTCTCCCGCCCGCGCCGCCCGCACCCTCGGCGGTCTC

CCCGGCCTCGCCAAGGTCCGGAGTTCCGATCCCGGCGCCCGCCTCGAGCTCCGCTTCCGC

CCCGAGGACCCCTACTGCCATCCAGCCTTTGGCCAGTCCCGCGCCTCCACTGGCCTTCTG

CTGCGCCTCTCCAAGCGCAAAGGAGCTGCGGCACCTTGTGCCCATGTGGTCGCTCGTGTC

CGGACTGCTTACTACTTCGAAGGTATGGCAGATTTTCAACATGTTGTTCCAGTGCATGCT

GCACAAACAAGAAAAAGAAAACACTCAGATTCTCAAAATGATAATGAGAATTTTGGTAGT

GATAAGACAGGACATGATGAAGCAGATGGAGATGTCATGATGTTGGTACCCCCTCTCTTT

TCAGTGAAGGATAGGCCAACAAAGATAGCGCTTGTACCATCGTCCAATGCCATATCTAAA

ACCATGCACAGGGGAGTTGTACAAGAACGGTGGGAGATGAATGTTGGACCAACTCTGGCG

CTTCCGTTCAACACTCAAGTTGTCCCGGAGAAGATTAATTGGGAAGACCACATTAGAAAG

AATTCTGTAGAATGGGGTTGGCAAATGGCTGTTTGCAAATTGTTTGATGAGCGCCCTGTG

TGGCCAAGGCAATCACTTTATGAGCGGTTCCTTGATGATAATGTGCATGTCTCTCAAAAC

CAATTCAAAAGGCTTCTGTTTAGAGCTGGATACTACTTCTCTACTGGACCCTTTGGAAAA

TTTTGGATCAGAAGAGGATATGACCCTCGTAAAGACTCTGAGTCACAAATATATCAGAGA

ATTGATTTTCGCATGCCTCCCGAGCTACGATATCTTCTAAGGCTGAAGAATTCTGAGTCT

CGAAAGTGGGCAGATATGTGCAAGCTTGAAACAATGCCATCACAGAGTTTCATCTACCTG

CAATTATATGAACTGAAGGATGATTTTATTCAAGCAGAAATTCGAAAACCTTCTTATCAA

TCAGTTTGTTCACGTTCTACAGGATGGTTTTCTAAGCCAATGATCAAACCCTGAGGTTG

CAAGTGAGCATAAGGCTCCTCTCTTTATTGCATAATGAAGAGGCTAAAAACTTGTTGAGG

AATGCCCATGAGCTTATTGAAAGGTCCAAGAAGCAGGAAGCCCTTTCGAGATCTGAGCTG

TCAATAGAATATAATGATGCTGATCAAGTTTCTGCCGCACATACTGGAACTGAGGATCAA

GTCGGCCCTAACAACTCTGATAGTGAAGATGTGGATGATGAAGAAGAGGAAGAGGAATTG

GAGGGTTATGATTCTCCACCTATGGCAGATGATATTCATGAGTTCACCTTAGGTGATTCC

TATGCATTTGGTGAAGGCTTCTCGAATGGATACCTCGAAGAAGTACTGCGCAGCTTGCCA

TTGCAGGAAGACGGCCAAAAGAAATTATGTGATGCTCCTATCAACGCTGATGCAAGTGAT

GGAGAGTTTGAAATTTACGAACAGCCCAGTGATGATGAAGATTCTGATGGCTAG

GRMZM2G102059_T01
Cover 47% identity 62%

SEQ ID NO: 125

MEFASSSSRFSREEDEEEEQEEEEEEEEASPREIPFMTAAATADTGAAASSSSPSAAASS

GPAAAPRSSDGAGASGSGGGGSDDVQVIEKEHMFDKVVTPSDVGKLNRLVIPKQHAEKYF

PLDAAANEKGQLLSFEDRAGKLWRFRYSYWNSSQSYVMTKGWSRFVKEKRLDAGDTVSFC

RGAGDTARDRLFIDWKRRADSRDPHRMPRLPLPMAPVASPYGPWGGGGGGAGGFFMPPA

PPATLYEHHRFRQALDFRNINAAAAPARQLLFFGSAGMPPRASMPQQQQPPPPPHPPLHS

IMLVQPSPAPPTASVPMLLDSVPLVNSPTAASKRVRLFGVNLDNPQPGTSAESSQDANAL

SLRTPGWQRPGPLRFFESPQRGAESSAASSPSSSSSSKREAHSSLDLDL

CDS

SEQ ID NO: 126

ATGGAGTTCGCGAGCTCTTCGAGTAGGTTTTCCAGGGAGGAGGACGAGGAGGAAGAGCAG

GAGGAAGAGGAGGAGGAGGAGGAGGCGTCTCCGCGCGAGATCCCCTTCATGACAGCGGCA

GCGACGGCCGACACCGGAGCCGCCGCCTCCTCGTCCTCGCCTTCCGCGGCGGCCTCATCG

GGTCCTGCTGCTGCCCCCCGCTCGAGCGACGGCGCCGGGGCGTCCGGGAGCGGCGGCGGC

GGGAGCGACGACGTGCAGGTGATCGAGAAGGAGCACATGTTCGACAAGGTGGTGACGCCC

AGCGACGTGGGGAAGCTCAACCGGCTGGTGATCCCGAAGCAGCACGCGGAGAAGTACTTC

CCGCTGGACGCGGCGGCCAACGAGAAGGGCCAGCTGCTCAGCTTCGAGGACCGCGCCGGT

AAGCTCTGGCGCTTCCGCTACTCCTACTGGAACAGCAGCCAGAGCTACGTCATGACCAAG

GGCTGGAGCCGCTTCGTCAAGGAGAAGCGCCTCGACGCCGGCGACACCGTCTCCTTCTGC

CGCGGCGCCGGCGACACCGCGCGGGACCGCCTCTTCATCGACTGGAAGCGCCGCGCCGAC

TCCCGCGACCCGCACCGCATGCCGCGCCTCCCGCTCCCCATGGCGCCCGTCGCGTCGCCC

TACGGCCCCTGGGGCGGCGGCGGCGGCGGCGCGGGCGGTTTCTTCATGCCGCCCGCG

CCGCCCGCCACACTCTACGAGCACCACCGCTTCCGCCAGGCCCTCGACTTCCGCAACATC

AACGCCGCGGCCGCGCCGGCCAGGCAGCTCCTCTTCTTCGGCTCAGCCGGCATGCCCCCG

CGCGCGTCCATGCCGCAGCAGCAGCAGCCGCCTCCGCCCCCGCACCCGCCTCTGCACAGC

ATTATGTTGGTGCAACCCAGCCCCGCGCCGCCCACGGCCAGCGTGCCCATGCTTCTCGAC

TCGGTACCGCTCGTCAACAGCCCAACGGCAGCGTCGAAGCGCGTCCGCCTGTTTGGGGTC

AACCTCGACAACCCGCAACCAGGCACAAGTGCGGAGTCAAGCCAAGATGCCAACGCATTG

TCGCTGAGGACACCGGGATGGCAAAGGCCGGGGCCGTTGAGGTTCTTCGAATCGCCTCAA

CGCGGCGCCGAGTCATCTGCAGCCTCCTCGCCGTCGTCATCGTCGTCCTCCAAGAGAGAA

GCGCACTCGTCCTTGGATCTCGATCTGTGA

GRMZM2G098443_T01
Cover 47% identity 63%

SEQ ID NO: 127

MEFTTPPPATRSGGGEERAAAEHNQHHQQQHATVEKEHMFDKVVTPSDVGKLNRLVIPKQ

HAEKYFPLDAAANEKGLLLSFEDRTGKPWRFRYSYWNSSQSYVMTKGWSRFVKEKRLDAG

DTVSFGRGISEAARDRLFIDWRCRPDPPVVHHQYHHRLPLPSAVVPYAPWAAHAHHHHYP

ADGHTEPVTPCLCATLVATEMRASSSQLSLTRSNLSRPPQPRIARVDGAQPRPSSSPRQP

QSLWCRSCQPQPRRTADVP

CDS

SEQ ID NO: 128

ATGGAGTTCACCACTCCCCCGCCCGCGACCCGGTCGGGCGGCGGAGAGGAGAGGGCGGCT

GCTGAGCACAACCAGCACCACCAGCAGCAGCATGCGACGGTGGAGAAGGAGCACATGTTC

GACAAGGTGGTGACGCCGAGCGACGTCGGGAAGCTGAACCGGCTGGTGATCCCGAAGCAG

CACGCGGAGAAGTACTTCCCGCTGGACGCGGCGGCGAACGAGAAGGGCCTCCTGCTCAGC

TTCGAGGACCGCACGGGGAAGCCCTGGCGCTTCCGCTACTCCTACTGGAACAGTAGCCAG

AGCTACGTGATGACCAAGGGCTGGAGCCGCTTCGTCAAGGAGAAGCGCCTCGACGCCGGG

GACACAGTCTCCTTCGGCCGCGGCATCAGCGAGGCGGCGCGCGACAGGCTTTTCATCGAC

TGGCGGTGCCGACCCGACCCGCCCGTCGTGCACCACCAGTACCACCACCGCCTCCCTCTC

CCCTCCGCCGTCGTCCCCTACGCGCCGTGGGCGGCGCACGCGCACCACCACCACTACCCA

```
GCAGATGGGCACACGGAACCAGTAACACCTTGCCTGTGCGCCACACTCGTTGCCACTGAA

ATGAGAGCATCATCTTCGCAACTGTCACTCACACGCTCCAACCTCTCCAGGCCGCCACAA

CCTAGAATAGCCAGAGTCGATGGCGCCCAGCCACGGCCGTCGTCGTCACCACGCCAGCCA

CAGTCGTTGTGGTGCCGGTCGTGCCAACCGCAACCACGGCGAACGGCCGACGTTCCTTGA
```

GRMZM2G082227_T01
Cover 45% identity 64%

SEQ ID NO: 129

```
MEFTAPPPATRSGGGEERAAAEHHQQQQQATVEKEHMFDKVVTPSDVGKLNRLVIPKQHA

ERYFPLDAAANDKGLLLSFEDRAGKPWRFRYSYWNSSQSYVMTKGWSRFVKEKRLDAGDT

VSFGRGVGEAARGRLFIDWRRRPDPPVVHHQYHHHRLPLPSAVVPYAPWAAAAHAHHHHY

PAAGVGAARTTTTTTTTVLHHLPPSPSPLYLDTRRRHVGYDAYGAGTRQLLFYRPHQQPS

TTVMLDSVPVRLPPTPGQHAEPPPPAVASSASKRVRLFGVNLDCAAAAGSEEENVGGWRT

SAPPTQQASSSSSYSSGKARCSLNLDL
```

CDS

SEQ ID NO: 130

```
ATGGAGTTCACCGCTCCCCCGCCCGCGACCCGGTCGGGCGGCGGCGAGGAGAGGGCGGCT

GCTGAGCACCACCAGCAGCAGCAGGCGACGGTGGAGAAGGAGCACATGTTCGACAAG

GTGGTGACGCCGAGCGACGTCGGGAAGCTGAACCGGCTGGTGATCCCGAAGCAGCACGCG

GAGAGGTACTTCCCGCTGGACGCGGCGGCGAACGACAAGGGCCTGCTGCTCAGCTTCGAG

GACCGCGCGGGGAAGCCCTGGCGCTTCCGCTACTCCTACTGGAACAGCAGCCAGAGCTAC

GTGATGACCAAGGGCTGGAGCCGCTTCGTCAAGGAGAAGCGCCTCGACGCCGGGGACACC

GTCTCCTTCGGCCGCGCGTCGGCGAGGCGGCGCGCGGCAGGCTCTTCATCGACTGGCGG

CGCCGACCCGACCCGCCCGTCGTGCACCACCAGTACCACCACCACCGCCTCCCTCTCCCC

TCCGCCGTCGTCCCTACGCGCCGTGGGCGGCGGCGGCGCACGCGCACCACCACCACTAC

CCAGCAGCTGGGGTCGGTGCCGCCAGGACGACGACGACGACGACGACGGTGCTCCAC

CACCTGCCGCCCTCGCCCTCCCCGCTCTACCTTGACACCCGCCGCCGCCACGTCGGCTAC

GACGCCTACGGGGCCGGCACCAGGCAACTTCTCTTCTACAGGCCGCACCAGCAGCCCTCC

ACGACGGTGATGCTGGACTCCGTGCCGGTACGGTTACCGCCAACGCCAGGGCAGCACGCC

GAGCCGCCGCCCCCGCCGTGGCGTCGTCAGCCTCGAAGCGGGTGCGCCTGTTCGGGGTG

AACCTCGACTGCGCCGCCGCCGCCGGCTCAGAGGAGGAGAACGTCGGCGGGTGGAGGACT

AGTGCGCCGCCGACGCAGCAGGCGTCCTCCTCCTCATCCTACTCTTCCGGGAAAGCGAGG

TGCTCCTTGAACCTTGACTTGTGA
```

GRMZM2G024948_T01
Cover 46% identity 63%

SEQ ID NO: 131

```
MDQFAASGRFSREEEADEEQEDASNSMREISFMPPAAASSSAAASASASASTSASACAS

GSSSAPFRSASASGDAAGASGSGGPADADAEAEAVEKEHMFDKVVTPSDVGKLNRLVIPK

QYAEKYFPLDAAANEKGLLLSFEDSAGKHWRFRYSYWNSSQSYVMTKGWSRFVKEKRLVA

GDTVSFSRAAAEDARHRLFIDWKRRVDTRGPLRFSGLALPMPLPSSHYGGPHHYSPWGFG

GGGGGGGGFFMPPSPPATLYEHRLRQGLDFRSMTTTYPAPTVGRQLLFFGSARMPPHHAP
```

```
PPQPRPFSLPLHHYTVQPSAAGVTAASRPVLLDSVPVIESPTTAAKRVRLFGVNLDNNPD
GGGEASHQGDALSLQMPGWQQRTPTLRLLELPRHGGESSAASSPSSSSSSKREARSALDL
DL
```

CDS

SEQ ID NO: 132

```
ATGGACCAGTTCGCCGCGAGCGGGAGGTTCTCTAGAGAGGAGGAGGCGGACGAGGAGCAG
GAGGATGCGTCCAATTCCATGCGCGAGATCTCCTTCATGCCGCCGGCTGCGGCCTCGTCA
TCTTCGGCGGCTGCTTCCGCGTCCGCGTCCGCCTCCACCAGCGCATCCGCGTGTGCATCG
GGAAGCAGCAGCGCCCCCTTCCGCTCCGCCTCCGCGTCGGGGGATGCCGCCGGAGCGTCG
GGGAGCGGCGGCCCAGCGGACGCGGACGCGGAGGCGGAGGCGGTGGAGAAGGAGCACATG
TTCGACAAGGTGGTCACGCCGAGCGACGTGGGGAAGCTCAACCGGCTGGTGATCCCGAAG
CAGTACGCGGAGAAGTACTTCCCGCTGGACGCGGCGGCCAACGAGAAGGGCCTCCTCCTC
AGCTTCGAGGACAGCGCCGGCAAGCACTGGCGCTTCCGCTACTCCTACTGGAACAGCAGC
CAGAGCTACGTCATGACCAAGGGCTGGAGCCGCTTCGTCAAGGAGAAGCGCCTCGTCGCC
GGGGACACCGTCTCCTTCTCCCGCGCCGCCGCCGAGGACGCGCGCCACCGCCTCTTCATC
GACTGGAAGCGCCGGGTCGACACCCGCGGCCCGCTTCGTTTCTCCGGCCTCGCGCTGCCG
ATGCCGCTGCCGTCGTCGCACTACGGCGGCCCCACCACTACAGCCCGTGGGGCTTCGGC
GGCGGCGGCGGCGGCGGCGGATTCTTCATGCCGCCCTCGCCGCCCGCCACGCTCTAC
GAGCACCGCCTCAGACAGGGCCTCGACTTCCGCAGCATGACGACGACCTACCCCGCGCCG
ACCGTGGGGAGGCAGCTCCTGTTTTTCGGCTCGGCCAGGATGCCTCCTCATCACGCGCCG
CCGCCCCAGCCGCGCCCGTTCTCGCTGCCGCTGCATCACTACACGGTGCAACCGAGCGCC
GCCGGCGTCACCGCCGCGTCACGGCCGGTCCTTCTTGACTCGGTGCCGGTCATCGAGAGC
CCGACGACCGCCGCGAAGCGCGTGCGGCTGTTCGGCGTCAACCTGGACAACAACCCAGAT
GGCGGCGGCGAGGCTAGCCATCAGGGCGATGCATTGTCATTGCAGATGCCCGGGTGGCAG
CAAAGGACTCCAACTCTAAGGCTACTAGAATTGCCTCGCCATGGCGGGGAGTCCTCCGCG
GCGTCGTCTCCGTCGTCGTCGTCTTCCTCCAAGAGGGAGGCGCGTTCAGCTTTGGATCTC
GATCTGTGA
```

GRMZM2G328742_T01
Cover 55% identity 64%

SEQ ID NO: 134

```
MATNHLSQGQHQHPQAWPWGVAMYTNLHYHHQQHHHYEKEHLFEKPLTPSDVGKLNRLVI
PKQHAERYFPLSSSGAGDKGLILCFEDDDDDEAAAANKPWRFRYSYWTSSQSYVLTKGWS
RYVKEKQLDAGDVVRFQRMRGFGMPDRLFISHSRRGETTATAATTVPPAAAAVRVVVAPA
QSAGADHQQQQQPSPWSPMCYSTSGSYSYPTSSPANSQHAYHRHSADHDHSNNMQHAGES
QSDRDNRSCSAASAPPPPSRRLRLFGVNLDCGPGPEPETPTAMYGYMHQSPYAYNNWGSP
YQHDEEI
```

CDS

135

```
ATGGCCACGAACCATCTCTCCCAAGGGCAGCACCAGCACCCGCAGGCCTGGCCCTGGGGC
GTGGCCATGTACACCAACCTACACTACCACCACCAGCAGCACCACCACTACGAGAAGGAG
CACCTGTTCGAGAAGCCGCTGACGCCGAGCGACGTGGGCAAGCTCAACAGGCTGGTGATC
CCCAAGCAGCACGCCGAGAGGTACTTCCCTCTCAGCAGCAGCGGCGCCGGCGACAAAGGC
CTCATCCTGTGCTTCGAGGACGACGACGACGACGAGGCTGCCGCCGCCAACAAGCCGTGG
CGGTTCCGCTACTCGTACTGGACCAGCAGCCAGAGCTACGTGCTCACCAAGGGCTGGAGC
```

```
CGCTACGTCAAGGAGAAGCAGCTTGACGCCGGCGACGTCGTGCGCTTCCAGAGGATGCGT

GGTTTCGGCATGCCCGACCGCCTGTTCATCAGCCACAGCCGCCGCGGCGAGACTACTGCT

ACTGCTGCAACAACAGTGCCCCCCGCTGCTGCTGCCGTGCGCGTAGTAGTGGCACCTGCA

CAGAGCGCTGGCGCAGACCACCAGCAGCAGCAGCCGTCGCCTTGGAGCCCAATGTGC

TACAGCACATCAGGCTCGTACTCGTACCCCACCAGCAGCCCAGCCAATTCCCAGCATGCC

TACCACCGCCACTCAGCTGACCATGACCACAGCAACAACATGCAACATGCAGGAGAATCT

CAGTCCGACAGAGACAACAGGAGCTGCAGTGCAGCTTCGGCACCGCCGCCACCGTCGCGG

CGGCTCCGGCTGTTCGGCGTAAACCTCGACTGCGGCCCGGGGCCGGAGCCGGAGACACCA

ACGGCGATGTACGGCTACATGCACCAAAGCCCCTACGCTTACAACAACTGGGGCAGTCCA

TACCAGCATGACGAGGAGATTTAA
```

GRMZM2G142999_T01
Cover 44% identity 64%

SEQ ID NO: 136

```
MEFTPAHAHARVVEDSERPRGGVAWVEKEHMFEKVVTPSDVGKLNRLVIPKQHAERYFPA

LDASSAAAAAAAAAGGGKGLVLSFEDRAGKAWRFRYSYWNSSQSYVMTKGWSRFVKEKR

LGAGDTVLFARGAGGARGRFFIDFRRRRQDLAFLQPTLASAQRLLPLPSVPICPWQDYGA

SAPAPNRHVLFLRPQVPAAVVLKSVPVHVAASAVEATMSKRVRLFGVNLDCPPDAEDSAT

VPRGRAASTTLLQLPSPSSSTSSSTAGKDVCCLDLGL
```

CDS

SEQ ID NO: 137

```
ATGGAGTTCACGCCCGCGCATGCGCATGCCCGTGTCGTTGAGGATTCCGAGAGGCCTCGC

GGCGGCGTGGCCTGGGTGGAGAAGGAGCACATGTTCGAGAAGGTGGTCACCCCCGAGCGAC

GTGGGGAAGCTCAATCGCCTGGTCATCCCAAAGCAGCACGCGGAGCGCTACTTCCCCGCG

CTGGACGCCTCGTCCGCCGCGGCGGCGGCGGCAGCAGCCGCGGGAGGCGGGAAGGGG

CTGGTGCTCAGCTTCGAGGACCGGGCGGGGAAGGCGTGGCGCTTCCGCTACTCGTACTGG

AACAGCAGCCAGAGCTACGTGATGACCAAAGGTTGGAGCCGCTTCGTGAAGGAGAAGCGC

CTCGGTGCCGGGGACACAGTCTTGTTCGCGCGCGGCGCGGGCGGCGCGCGCGGCCGCTTC

TTCATCGATTTCCGCCGCCGTCGCCAGGATCTCGCGTTCCTGCAGCCGACGCTGGCGTCT

GCGCAGCGACTCCTGCCGCTGCCGTCGGTGCCCATCTGCCCGTGGCAGGACTACGGCGCC

TCGGCTCCGGCGCCCAACCGGCACGTGCTGTTCCTGCGGCCGCAGGTGCCGGCCGCCGTA

GTGCTCAAGTCGGTCCCCGTGCACGTTGCTGCATCCGCGGTGGAGGCGACCATGTCGAAG

CGCGTCCGCCTGTTCGGGGTGAACCTCGACTGCCCGCCGGACGCCGAAGACAGCGCCACA

GTCCCCCGGGGCCGGGCGGCGTCGACGACGCTTCTGCAACTGCCCTCGCCATCGTCGTCA

ACATCCTCCTCGACGGCAGGGAAGGACGTGTGCTGTTTGGATCTTGGACTGTGA
```

GRMZM2G125095_T01
Cover 85% identity 40%

SEQ ID NO: 138

```
MEFRPAHARVFEDSERPRGGVAWLEKEHMFEKVVTPSDVGKLNRLVIPKQHAERYFPALD

ASAAAASASASAGGGKAGLVLSFEDRAGKAWRFRYSYWNSSQSYVMTKGWSRFVKEKRLG

AGDTVLFARGAGATRGRFFIDFRRRRHELAFLQPPLASAQRLLPLPSVPICPWQGYGASA
```

PAPSRHVLFLRPQVPAAVVLTSVPVRVAASAVEEATRSKRVRLFGVNLDCPPDAEDGATA

TRTPSTLLQLPSPSSSTSSSTGGKDVRSLDLGL

CDS

SEQ ID NO: 139

ATGGAGTTCAGGCCCGCGCATGCCCGTGTCTTCGAGGATTCCGAGAGGCCTCGCGGCGGC

GTGGCGTGGCTGGAGAAGGAGCACATGTTCGAGAAAGTGGTCACCCCGAGCGACGTGGGG

AAGCTCAATCGCCTGGTCATCCCGAAGCAGCACGCCGAGCGCTACTTCCCCGCGCTGGAC

GCCTCGGCCGCCGCGGCGTCGGCATCGGCGTCGGCGGGCGGCGGGAAGGCGGGGCTGGTG

CTCAGCTTCGAGGACCGGGCGGGGAAGGCGTGGCGCTTCCGCTACTCGTACTGGAACAGC

AGCCAGAGCTACGTGATGACCAAGGGATGGAGCCGCTTCGTGAAAGAGAAGCGCCTCGGT

GCCGGGGACACGGTATTGTTCGCGCGCGGCGCGGGCGCCACGCGCGGCCGCTTCTTCATC

GATTTCCGCCGCCGCCGCCACGAGCTCGCGTTCCTGCAGCCGCCGCTGGCGTCTGCGCAG

CGCCTCCTGCCGCTCCCGTCGGTGCCCATCTGCCCGTGGCAGGGCTACGGCGCCTCCGCT

CCGGCGCCAAGCCGGCACGTGCTGTTCCTGCGGCCGCAGGTGCCGGCCGCCGTAGTGCTC

ACGTCGGTGCCCGTGCGCGTCGCCGCATCCGCGGTGGAGGAGGCGACGAGGTCGAAGCGC

GTCCGCCTGTTCGGGGTGAACCTCGACTGCCCGCCGGACGCCGAAGACGGTGCCACAGCC

ACCCGGACGCCGTCGACGCTTCTGCAGCTGCCCTCGCCATCGTCGTCAACATCCTCCTCC

ACGGGAGGCAAGGATGTGCGTTCTTTGGATCTTGGACTTTGA

*Tricum aeseirum*
TRAES3BF098300010CFD_t1
Cover: 42% ident 60%
SEQ ID NO: 140
MGVEILSSMVEHSFQYSSGVSTATTESGTAGTPPRPLSLPVAIADESVTSRSASSRFKGVVPQPNGRWGAQIYERH

ARVWLGTFPDQDSAARAYDVASLRYRGRDVAFNFPCAAVEGELAFLAAHSKAEIVDMLRKQTYADELRQGLRRG

RGMGARAQPTPSWAREPLFEKAVTPSDVGKLNRLVVPKQHAEKHFPLKRTPETPTTTGKGVLLNFEDGEGKVWR

FRYSYWNSSQSYVLTKGWSRFVREKGLGAGDSILFSCSLYEQEKQFFIDCKKNTSMNGGKSASPLPVGVTTKGEQV

RVVRLFGVDISGVKRGRAATATAEQGLQELFKRQCVAPGQHSPALGAFAL

CDS

SEQ ID NO: 141

ATGGGGGTGGAAATCCTGAGCTCCATGGTGGAGCACTCCTTCCAGTACTCTTCCGGCGTG

TCCACGGCCACGACGGAGTCAGGCACCGCCGGAACACCGCCGAGGCCTTTGAGCCTACCT

GTCGCCATCGCCGACGAGTCCGTGACCTCGCGGTCGGCGTCGTCTCGGTTCAAGGGCGTG

GTGCCGCAGCCAAACGGGCGATGGGGCGCCCAGATCTACGAGCGCCACGCTCGCGTCTGG

CTCGGCACGTTCCCAGACCAGGACTCGGCGGCGCGCGCCTACGACGTAGCCTCGCTCAGG

TACCGCGGCCGCGACGTCGCCTTCAACTTCCCGTGCGCGGCCGTGGAGGGGGAGCTCGCC

TTCCTGGCGGCGCACTCCAAGGCTGAGATAGTGGACATGCTCCGGAAGCAGACCTACGCC

GATGAACTCCGCCAGGGCCTGCGGCGCGGCCGTGGCATGGGGGCGCGCGCGCAGCCGACG

CCGTCGTGGGCGCGGGAGCCCCTTTTCGAGAAGGCCGTGACCCCTAGCGATGTCGGCAAG

CTCAATCGCCTCGTAGTGCCGAAGCAGCACGCCGAGAAGCACTTCCCCCTGAAGCGCACG

CCGGAGACGCCGACCACCACCGGCAAGGGCGTGCTGCTCAACTTCGAGGACGGCGAGGGG

AAGGTGTGGAGGTTCCGGTACTCGTACTGGAACAGCAGCCAGAGCTACGTGCTCACCAAA

GGCTGGAGCCGCTTCGTCCGGGAGAAGGGCCTAGGTGCCGGCGACTCCATCCTATTCTCG

TGCTCGCTGTACGAACAGGAGAAGCAGTTCTTCATCGACTGCAAGAAGAACACTAGCATG

AACGGAGGCAAATCGGCGTCGCCGCTGCCAGTGGGGGTGACTACCAAAGGAGAACAAGTT

-continued

CGCGTCGTTAGGCTATTCGGTGTCGACATCTCGGGAGTGAAGAGGGGGCGAGCGGCGACG

GCAACGGCGGAGCAAGGCCTGCAGGAGTTGTTCAAGAGGCAATGCGTGGCACCCGGCCAG

CACTCTCCTGCCCTAGGTGCCTTCGCCTTATAG

TRAES3BF062700040CFD_t1
Cover 47% ident 55%

SEQ ID NO: 142

MASGKPTNHGMEDDNDMEYSSAESGAEDAAEPSSSPVLAPPRAAPSSRFKGVVPQPNGRW

GAQIYEKHSRVWLGTFPDEDAAVRAYDVAALRFRGPDAVINHQRPTAAEEAGSSSSRSEL

DPELGFLADHSKAEIVDMLRKHTYDDELRQGLRRGRGRAQPTPAWARELLFEKAVTPSDV

GKLNRLVVPKQQAEKHFPPTTAAATGSNGKGVLLNFEDGEGKVWRFRYSYWNSSQSYVLT

KGWSRFVKETGLRAGDTVAFYRSAYGNDTEDQLFIDYKKMNKNDDAADAAISDENETGHV

AVKLFGVDIAGGGMAGSSGG

CDS

SEQ ID NO: 143

ATGGCATCTGGCAAGCCGACAAACCACGGGATGGAGGACGACAACGACATGGAGTACTCC

TCCGCGGAATCGGGGGCCGAGGACGCGGCGGAGCCGTCGTCGTCGCCGGTGCTGGCGCCG

CCCCGGGCGGCTCCATCGTCGCGGTTCAAGGGCGTCGTGCCGCAGCCCAACGGGCGGTGG

GGAGCGCAGATCTACGAGAAGCACTCGCGGGTGTGGCTCGGAACGTTCCCCGACGAGGAC

GCCGCCGTGCGCGCCTACGACGTGGCCGCGCTCCGCTTCCGCGGCCCGGACGCCGTCATC

AACCACCAGCGACCGACGGCCGCGGAGGAGGCCGGCTCGTCGTCGTCCAGGAGCGAGCTG

GATCCAGAGCTCGGCTTCCTTGCCGACCACTCCAAGGCCGAGATCGTCGACATGCTCCGG

AAGCACACCTACGACGACGAGCTCCGTCAGGGCCTGCGCCGCGGCCGCGGGCGCGCGCAG

CCGACGCCGGCGTGGGCACGAGAGCTCCTCTTCGAGAAGGCCGTGACCCCGAGCGACGTC

GGCAAGCTCAACCGCCTCGTGGTGCCGAAGCAGCAGGCCGAGAAGCACTTCCCTCCGACC

ACTGCGGCGGCCACCGGCAGCAACGGCAAGGGCGTGCTGCTCAACTTCGAGGACGGCGAA

GGGAAGGTGTGGCGCTTCCGGTACTCGTACTGGAACAGCAGCCAGAGCTACGTGCTCACC

AAGGGCTGGAGCCGCTTCGTCAAGGAGACGGGCCTCCGCGCCGGCGACACCGTGGCGTTC

TACCGGTCGGCGTACGGGAATGACACGGAGGATCAGCTCTTCATCGACTACAAGAAGATG

AACAAGAATGACGATGCTGCGGACGCGGCGATTTCCGATGAGAATGAGACAGGCCATGTC

GCCGTCAAGCTCTTCGGCGTTGACATTGCCGGTGGAGGGATGGCGGGATCATCAGGTGGC

TGA

TRAES3BF062600010CFD_t1
Cover 43% ident 58%

SEQ ID NO: 144

MASGKPTNHGMEDDNDMEYSSAESGAEDAAEPSSSPVLAPPRAAPSSRFKGVVPQPNGRW

GAQIYEKHSRVWLGTFPDEDAAARAYDVAALRFRGPDAVINHQRPTAAEEAGSSSSRSEL

DPELGFLADHSKAEIVDMLRKHTYDDELRQGLRRGRGRAQPTPAWARELLFEKAVTPSDV

GKLNRLVVPKQQAEKHFPPTTAAATGSNGKGVLLNFEDGEGKVWRFRYSYWNSSQSYVLT

KGWSRFVKETGLRAGDTVAFYRSAYGNDTEDQLFIDYKKMNKNDDAADAAISDENETGHV

AVKLFGVDIAGGGMAGSSGG

CDS

SEQ ID NO: 145

ATGGCATCTGGCAAGCCGACAAACCACGGGATGGAGGACGACAACGACATGGAGTACTCC

TCCGCGGAATCGGGGGCCGAGGACGCGGCGGAGCCGTCGTCGTCGCCGGTGCTGGCGCCG

CCCCGGGCGGCTCCATCGTCGCGGTTCAAGGGCGTCGTGCCGCAGCCCAACGGGCGGTGG

GGAGCGCAGATCTACGAGAAGCACTCGCGGGTGTGGCTCGGAACGTTCCCCGACGAGGAC

GCCGCCGCGCGCCTACGACGTGGCCGCGCTCCGCTTCCGCGGCCCGGACGCCGTCATC

AACCACCAGCGACCGACGGCCGCGGAGGAGGCCGGCTCGTCGTCGTCCAGGAGCGAGCTG

GATCCAGAGCTCGGCTTCCTCGCCGACCACTCCAAGGCCGAGATCGTCGACATGCTCCGG

AAGCACACCTACGACGACGAGCTCCGTCAGGGCCTGCGCCGCGGCCGCGGGCGCGCGCAG

CCGACGCCGGCGTGGGCACGAGAGCTCCTCTTCGAGAAGGCCGTGACCCCGAGCGACGTC

GGCAAGCTCAACCGCCTCGTGGTGCCGAAGCAGCAGGCCGAGAAGCACTTCCCTCCGACC

ACTGCGGCGGCCACCGGCAGCAACGGCAAGGGCGTGCTGCTCAACTTCGAGGACGGCGAA

GGGAAGGTGTGGCGCTTCCGGTACTCGTACTGGAACAGCAGCCAGAGCTACGTGCTCACC

AAGGGCTGGAGCCGCTTCGTCAAGGAGACGGGCCTCCGCGCCGGCGACACCGTGGCGTTC

TACCGGTCGGCGTACGGGAATGACACGGAGGATCAGCTCTTCATCGACTACAAGAAGATG

AACAAGAATGACGATGCTGCGGACGCGGCGATTTCCGATGAGAATGAGACAGGCCATGTC

GCCGTCAAGCTCTTCGGCGTTGACATTGCCGGTGGAGGGATGGCGGGATCATCAGGTGGC

TGA

---

The invention claimed is:

1. A plant comprising:
   i) reduced or abolished expression of a nucleic acid sequence encoding a NGAL2 polypeptide or reduced or abolished activity of a NGAL2 polypeptide compared to the expression or activity of said nucleic acid or polypeptide in a control plant; and
   ii) reduced or abolished expression of a nucleic acid sequence encoding a NGAL3 polypeptide or reduced or abolished activity of a NGAL3 polypeptide compared to the expression or activity of said nucleic acid or polypeptide in a control plant;
   wherein said reduced expression or activity of NGAL2 and NGAL3 nucleic acid sequences or polypeptides is caused by a mutation introduced in the promoter of said nucleic acids, by a mutation introduced in said nucleic acids that reduces activity or expression of the encoded polypeptides compared to expression of a control plant or activity of a wild-type polypeptide, or by introduction and expression of a silencing or co-suppressing nucleic acid into the plant that targets and silences or suppresses said NGAL2 and NGAL3 nucleic acid sequences; and wherein a) said NGAL2 nucleic acid molecule comprises SEQ ID NO: 1 or 2 or a sequence having at least 95% identity to SEQ ID NO: 1 or 2, and said NGAL3 nucleic acid molecule comprises SEQ ID NO: 4 or a sequence having at least 95% identity to SEQ ID NO: 4; or b) said NGAL2 polypeptide comprises SEQ ID NO: 3 or a polypeptide having at least 95% identity to SEQ ID NO: 3, and said NGAL3 polypeptide comprises SEQ ID NO: 5 or a polypeptide having at least 95% identity to SEQ ID NO: 5.

2. The plant according to claim 1, wherein said sequence having at least 95% identity to SEQ ID NO: 3 comprises a mutation in the region of the sequence aligning with SEQ ID NO: 260 or 7 or both.

3. The plant according to claim 1, wherein said sequence encoding a NGAL2 polypeptide comprises SEQ ID NO: 1 or 2, or a sequence having at least 95% identity to SEQ ID NO: 1 or 2.

4. The plant according to claim 1, wherein said polypeptide having at least 95% identity to SEQ ID NO: 5 comprises SEQ ID NO: 6 or 7 or both.

5. The plant according to claim 1, wherein the NGAL3 nucleic acid sequence encoding a NGAL3 polypeptide comprises SEQ ID NO: 4, or a sequence having at least 95% identity to SEQ ID NO: 4.

6. The plant according to claim 1, wherein said NGAL2 and NGAL3 nucleic acid sequences or their promoters comprise a mutation introduced in said nucleic acid sequences or promoters that reduces activity or expression of the polypeptides encoded by nucleic acids compared to expression of a control plant or activity of a wild-type NGAL2 or NGAL3 polypeptide.

7. The plant according to claim 1 wherein said plant comprises an RNA interference construct that targets said NGAL2 and NGAL3 nucleic acid sequences and reduces the expression of said NGLA2 and NGAL3 polypeptides.

8. A method for altering a plant phenotype comprising- reducing or abolishing the expression of a nucleic acid sequence encoding a NGAL2 polypeptide or reducing or abolishing the activity of a NGAL2 polypeptide, and reducing or abolishing the expression of a nucleic acid sequence encoding a NGAL3 polypeptide, or reducing or abolishing the activity of a NGAL3 polypeptide, relative to the expression or activity of a control plant, wherein said reducing or abolishing of expression or activity of said NGAL2 and NGAL3 nucleic acid sequences or polypeptides is by introduction of a mutation in the promoter of said nucleic acids, by introduction of a mutation in said nucleic acids that reduces activity or expression of the encoded polypeptides compared to expression of a control plant or activity of a wild-type polypeptide, or by introduction and expression of a silencinq or co-suppressinq nucleic acid into the plant that targets and silences or suppresses said NGAL2 and NGAL3 nucleic acid sequences, and wherein a) said NGAL2 nucleic acid molecule comprises SEQ ID NO: 1 or 2 or a sequence having at least 95% identity to SEQ ID NO: 1 or 2 and said NGAL3 nucleic acid molecule comprises SEQ ID NO: 4 or a sequence having at least 95% identity SEQ ID NO: 4, or b) said NGAL2 polypeptide comprises SEQ ID NO: 3 or a polypeptide having at least 95% identity to SEQ ID NO: 3, and said NGAL3 polypeptide comprises SEQ ID NO: 5 or a polypeptide having at least 95% identity to SEQ ID NO: 5.

9. The method according to claim 8, wherein said sequence having at least 95% identity to SEQ ID NO: 3 or 5 comprises a mutation in the region of the sequence aligning with SEQ ID NO: 260 or 7 or both.

10. The method according to claim 8, wherein the nucleic acid sequence encoding a NGAL2 polypeptide comprises SEQ ID NO: 1 or 2 or a sequence having at least 95% identity to SEQ ID NO: 1 or 2.

11. The method according to claim 8 wherein the NGAL3 nucleic acid sequence encoding a NGAL3 polypeptide comprises SEQ ID NO: 4 or a sequence having at least 95% identity to SEQ ID NO: 4.

12. The method according to claim 8, wherein said phenotype is characterised by increased seed size relative to a control plant.

13. The plant according to claim 1, wherein expression of said NGAL2 and NGAL3 nucleic acid sequence is silenced by introduction and expression of a silencinq nucleic acid into the plant that tarqets and silences or suppresses said NGAL2 and NGAL3 nucleic acid sequences.

14. The plant of claim 1, wherein said NGAL2 and NGAL3 nucleic acid molecule is mutated, co-suppressed, silenced or mutated by targeted genome editing of said NGAL2 and NGAL3 nucleic acid molecule, or any combination thereof.

15. The plant of claim 1, wherein said NGAL2 and NGAL3 polypeptide having 95% identity to SEQ ID NO: 3 or 5 comprises a mutation in the region of the sequence aligning with SEQ ID NO: 260 or 7 or both.

16. The plant of claim 1, wherein said NGAL2 polypeptide comprises SEQ ID NO: 3 and said NGAL3 polypeptide comprises SEQ ID NO: 5.

* * * * *

SEQUENCE LISTING

<160> NUMBER OF SEQ ID NOS: 272

<210> SEQ ID NO 1
<211> LENGTH: 804
<212> TYPE: DNA
<213> ORGANISM: Artificial Sequence
<220> FEATURE:
<223> OTHER INFORMATION: cDNA

<400> SEQUENCE: 1
atgtcagtca accattacca caacactctc tcgttgcatc atcaccacca aaacgacgta      60
gctatagcac aacgagagtc tttgttcgag aaatcactca caccaagcga cgtcggaaag     120
ctaaaccgct tagtcatacc aaaacaacac gccgagaaat acttccctct caataataat     180
aataataatg gcggcagcgg agatgacgtg gcgacgacgg agaaagggat gcttcttagc     240
ttcgaggatg agtcaggcaa gtgttggaaa ttcagatact cttattggaa cagtagccaa     300
agctacgtgt tgaccaaagg atggagcagg tacgtcaaag acaaacacct cgacgcaggc     360
gacgttgttt tctttcaacg tcaccgtttt gatctccata gactcttcat tggctggcgg     420
agacgcggtg aagcttcttc ctctcccgct gtctccgttg tgtctcaaga agctctagtt     480
aatacgacgg cgtattggag cggcttgact acaccttatc gtcaagtaca cgcgtcaact     540
acttacccta atattcacca agagtattca cactatggcg ccgtcgttga tcatgctcag     600
tcgataccac cggtggtcgc aggtagctcg aggacggtga ggcttttttgg cgtgaacctc     660 gaatgtcatg gtgatgccgt cgagccacca ccgcgtcctg atgtctataa tgaccaacac     720
atttactatt actcaactcc tcatcccatg aatatatcat tgctgggga agcattggag     780 caggtaggag atggacgagg ttga                                            804

<210> SEQ ID NO 2
<211> LENGTH: 4285
<212> TYPE: DNA
<213> ORGANISM: Arabidopsis thaliana

<400> SEQUENCE: 2
ttgtttcggc tatttgttat actattgtta taacagtcac aagacttgac ctcaacgaaa      60

-continued

```
acttttacaa aacgtgaatt ggaaatttt acaaaatatg ctcttaatcg ttaatgcttc    120
ccaattaggt gagttaaatt gtgagaggaa ccatttctta gaggaaatgg ttcatgaaaa    180
caaatatgaa atagtatcac tagtcttagt tttgcgagaa aattaggaaa aatagaaacg    240
tgtaagcacc aatgatattc ctgaaagcac gtgacagata tttcatgatc ctataattaa    300
caagtgataa agatattaaa taaaattaac gatacttgag aaattcgtca aataaaatag    360
aagaggacca ctcacgtaac catttgcacg tcccattgat ttttgtggta gacttggtat    420
gttatattac ttatattcac agaattatat acgaaactca cgacttaaga tgcacggtaa    480
taactacaga tggaaattta cccatcaaac aagaaaacaa catttactca agcatctagc    540
tagaccaaaa tgtttgttta cttgttgact tgcgatccat agatatatta gttagaactt    600
tttcttctac aattgatcaa atgtttcaca ctgttctcaa tttctcatct agattcatga    660
cttatatgtt tggtcaaata tcacagcttg atgagcatta aatagcgtcg aagtatagga    720
tggttacgtt gttcaatatt gtaaaggaaa aaaagagaaa gagtgccaaa aggtcaagtc    780
gatttcacaa ataaatcttg aagtctttat ccctctcgat tataaaatga ttaggaaaag    840
aaaaagagag aataaaatgt agataaagag aaagagaaag agagagagga acataaggga    900
tggtatgaag tagaagtgaa gatgcatgcg atggtgtgtc ggaaaggcaa agcacatgct    960
acacaacttg agcttctcac ttgcgtcagg gataagtatc ctctgtacct tcttactttt   1020
gcgtaatatg taccacctca cttctcaacc gtttgatctt taatccttca ttatttcttc   1080
attaccttct cttttgttt ttgttttcgt tttcaatttc tcatagattc atttacaaac   1140
taaatatcat aggaaggtgt tatctctagt taatttctta tcctacttta acaaaattta   1200
attgtcaaaa gattattttt acgtttatag acaaagagata ctgacacatc aattccacga   1260
accaaatggt tgagaaaaac aaaacgacta tctttgtctt gcaaataaat taatggcagt   1320
tagtaagatt ctcagctgaa aattcataca agagtaaatg atcaaataac catttatgag   1380
agaaatttaa tccttcagaa accaatgagg atctgatcaa gtaattgcaa accacatgag   1440
tccatgataa aggattgttt gacttacgca atccacatat ttatggctgc ttgatatgta   1500
aggtttatct gctttgacag tctatagaat cttgctaatc aatacgtcat atccggtgaa   1560
tactgaaact ttttaatta agaaaacaca aatcatcttt tctccggagg atttcgaatt   1620
tagttccggc aatgctgaaa taacatatgt tgaacttata acattccaag acatcaaatt   1680
ttactaatat ataaataatt acatattctt cttctacatg atcaaaacct tttcaacttt   1740
aattaaaggg ttacgtcgcg gcgttttgtg tggcttactc tttttttaca ctataactat   1800
agaacactcg tggatccaat gccgtttagg acaagatttt atcagacgag aaaaaaaaaa   1860
acaataccac atttttaaat atatatggat tatggactgc aacaacaata tagaaaagaa   1920
gagaaaaaaa taaaaataat gattgaaagg aaatatcatc acgcaaaacc ttaaaagtac   1980
tatcggtatc gtgtcgtcct ctcctcatca aatagttccc acagttttca catcaattta   2040
accattttca atttttttca ctctctgtct ctctcctttg tataatacta tattagtacc   2100
attacccatc tctctttcac caccaaacca acacctgcaa atcctctctc tctctctcac   2160
tccaagaaac caaaaaaaaa gatgtcagtc aaccattacc acaacactct ctcgttgcat   2220
catcaccacc aaaacgacgt agctatagca caacgagagt ctttgttcga gaaatcactc   2280
acaccaagcg acgtcggaaa gctaaaccgc ttagtcatac caaaacaaca cgccgagaaa   2340
tacttccctc tcaataataa taataataat ggcggcagcg gagatgacgt ggcgacgacg   2400
```

```
gagaaaggga tgcttcttag cttcgaggat gagtcaggca agtgttggaa attcagatac    2460
tcttattgga acagtagcca aagctacgtg ttgaccaaag gatggagcag gtacgtcaaa    2520
gacaaacacc tcgacgcagg cgacgttgtt ttctttcaac gtcaccgttt tgatctccat    2580
agactcttca ttggctggcg gagacgcggt gaagcttctt cctctcccgc tgtctccgtt    2640
gtgtctcaag aagctctagt taatacgacg gcgtattgga gcggcttgac tacaccttat    2700
cgtcaagtac acgcgtcaac tacttaccct aatattcacc aagagtattc acactatggt    2760
aaattcaaac cctttatttc ctcttttgtt ttttctttct ctcttatcta tatgtcagat    2820
ttatactcct ctctgttctc ttttaagatt tgtcttttc ataaaaatag atgattcgta    2880
atttgtattg catatttaca tgttctctta aaaaagtaa tagagattaa tattttatgc    2940
atggtatttt agattatctg cctactttat atggtagtaa acaagaacat tcatctttat    3000
ttggttttat aaacaaaata tgagaatttt taaaggttag ggcaagcact tggaaagctc    3060 aaccattta gttagctggt ggaatatctt tcttataaaa agcaaatgag ttatctaaaa     3120
ctatatgaca attattttag ttgcgtgtgt aatgtatata aaataacaac atgaaataac    3180
attttgtctt ttattttgt cattcttatt atttaatttt ggacccgaca atttcaaata     3240
atcttctcca agttgtaact aatccgttac atgcgcgtga ggaaccgt ccaatccact       3300 tagactaacg tgcccttat ttcttccttt taattctatg ttaaaaaaac aatttaacta     3360
aaagatgcgc acgtgtcttg acggtggaaa aaaattgtag gcgccgtcgt tgatcatgct    3420
cagtcgatac caccggtggt cgcaggtagc tcgaggacgg tgaggctttt tggcgtgaac    3480
ctcgaatgtc atggtgatgc cgtcgagcca ccaccgcgtc ctgatgtcta taatgaccaa    3540
cacatttact attactcaac tcctcatccc atggtaaata tttttttttt ttacattttt    3600
gtcagattca aatttttgct tacgtatgat ataattatta aacagatgtc gtggctgttt    3660
ctcgagacga gacagatgaa aattagtaat tttaaaatag acctgaaaga gattttatg     3720 tttaataaat tatataaagg aggaatcaga gagaataata ctatacactt gactgtaaaa    3780
ccacatggcc aatttggttt ttatttgatt actttgattt gttttgttta ctcttttgtc    3840
tctgtagcct ccttttgttc attaattaat atcagccgta agtatatagt ttcctgtgaa    3900
aacagtctct attttggttt tactattcta atttgttagg caccgtcagt tttttttgtg    3960
aaaccaaatt attgactaat aagctggaaa gcaaaactga ctaaaagcat acaaactta    4020 tcaatgacat aagttttgaa tttattacca tgttttgtaa tgttcagata taatttgaaa    4080
tgcttagaat tatatatttg tatacttaaa ttaatgaaat aaagtgaata ctaaagatag   4140
ttttattttt catattattc tatacaattc ggtgtacaat ttgttttga tgataataaa    4200 aataataaaa ttgcgtgttg gaattgtgaa acagaatata tcatttgctg gggaagcatt   4260
ggagcaggta ggagatggac gaggt                                         4285
```

<210> SEQ ID NO 3
<211> LENGTH: 267
<212> TYPE: PRT
<213> ORGANISM: Arabidopsis thaliana

<400> SEQUENCE: 3

Met Ser Val Asn His Tyr His Asn Thr Leu Ser Leu His His His
1               5                   10                  15

Gln Asn Asp Val Ala Ile Ala Gln Arg Glu Ser Leu Phe Glu Lys Ser
            20                  25                  30

Leu Thr Pro Ser Asp Val Gly Lys Leu Asn Arg Leu Val Ile Pro Lys

```
                    35                  40                  45
Gln His Ala Glu Lys Tyr Phe Pro Leu Asn Asn Asn Asn Asn Gly
 50                  55                  60

Gly Ser Gly Asp Asp Val Ala Thr Thr Glu Lys Gly Met Leu Leu Ser
 65                  70                  75                  80

Phe Glu Asp Glu Ser Gly Lys Cys Trp Lys Phe Arg Tyr Ser Tyr Trp
                 85                  90                  95

Asn Ser Ser Gln Ser Tyr Val Leu Thr Lys Gly Trp Ser Arg Tyr Val
                100                 105                 110

Lys Asp Lys His Leu Asp Ala Gly Asp Val Val Phe Gln Arg His
                115                 120                 125

Arg Phe Asp Leu His Arg Leu Phe Ile Gly Trp Arg Arg Gly Glu
 130                 135                 140

Ala Ser Ser Ser Pro Ala Val Ser Val Val Ser Gln Glu Ala Leu Val
145                 150                 155                 160

Asn Thr Thr Ala Tyr Trp Ser Gly Leu Thr Thr Pro Tyr Arg Gln Val
                165                 170                 175

His Ala Ser Thr Thr Tyr Pro Asn Ile His Gln Glu Tyr Ser His Tyr
                180                 185                 190

Gly Ala Val Val Asp His Ala Gln Ser Ile Pro Val Val Ala Gly
                195                 200                 205

Ser Ser Arg Thr Val Arg Leu Phe Gly Val Asn Leu Glu Cys His Gly
210                 215                 220

Asp Ala Val Glu Pro Pro Arg Pro Asp Val Tyr Asn Asp Gln His
225                 230                 235                 240

Ile Tyr Tyr Tyr Ser Thr Pro His Pro Met Asn Ile Ser Phe Ala Gly
                245                 250                 255

Glu Ala Leu Glu Gln Val Gly Asp Gly Arg Gly
            260                 265
```

<210> SEQ ID NO 4
<211> LENGTH: 849
<212> TYPE: DNA
<213> ORGANISM: Artificial Sequence
<220> FEATURE:
<223> OTHER INFORMATION: cDNA

<400> SEQUENCE: 4

```
atgtcagtca accattactc cacagaccac caccacactc tcttgtggca gcaacagcaa    60
caccgccaca ccaccgacac atcggagaca accaccaccg ccacatggct ccacgacgac   120
ctaaaagagt cactcttcga gaagtctctc acaccaagcg acgtcgggaa actcaaccgc   180
ctcgtcatac caaacaaca cgcagagaaa tacttccctc tcaatgccgt cctagtctcc    240
tctgctgctg ctgacacgtc atcttcggag aaagggatgc ttctaagctt tgaagacgag   300
tcaggcaagt catggaggtt cagatactct tactggaaca gcagtcaaag ctatgtcttg   360
actaaaggat ggagcagatt tgtcaaagac aaacagctcg atccaggcga cgttgttttc   420
ttccaacgac accgttctga ttctaggaga ctcttcattg gctggcgcag acgtggacaa   480
ggctcctcat cctccgtcgc ggccactaac tccgccgtga atacgagttc tatgggagct   540
ctttcttatc atcaaatcca cgccactagt aattactcta atcctccctc tcactcagag   600
tattcccact atggagccgc cgtagcaaca gcggctgaga ctcacagcac accgtcgtct   660
tccgtcgtcg ggagctcaag gacggtgagg cttttcggtg tgaatctgga gtgtcaaatg   720
gatgaaaacg acggagatga ttctgttgca gttgccacca ccgttgaatc tcccgacggt   780
```

```
tactacggcc aaaacatgta ctattattac tctcatcctc ataacatggt aattttaact    840
cttttataa                                                            849
```

<210> SEQ ID NO 5
<211> LENGTH: 282
<212> TYPE: PRT
<213> ORGANISM: Arabidopsis thaliana

<400> SEQUENCE: 5

```
Met Ser Val Asn His Tyr Ser Thr Asp His His Thr Leu Leu Trp
1               5                   10                  15

Gln Gln Gln Gln His Arg His Thr Thr Asp Thr Ser Glu Thr Thr Thr
            20                  25                  30

Thr Ala Thr Trp Leu His Asp Asp Leu Lys Glu Ser Leu Phe Glu Lys
        35                  40                  45

Ser Leu Thr Pro Ser Asp Val Gly Lys Leu Asn Arg Leu Val Ile Pro
    50                  55                  60

Lys Gln His Ala Glu Lys Tyr Phe Pro Leu Asn Ala Val Leu Val Ser
65                  70                  75                  80

Ser Ala Ala Ala Asp Thr Ser Ser Glu Lys Gly Met Leu Leu Ser
                85                  90                  95

Phe Glu Asp Glu Ser Gly Lys Ser Trp Arg Phe Arg Tyr Ser Tyr Trp
            100                 105                 110

Asn Ser Ser Gln Ser Tyr Val Leu Thr Lys Gly Trp Ser Arg Phe Val
        115                 120                 125

Lys Asp Lys Gln Leu Asp Pro Gly Asp Val Val Phe Phe Gln Arg His
    130                 135                 140

Arg Ser Asp Ser Arg Arg Leu Phe Ile Gly Trp Arg Arg Arg Gly Gln
145                 150                 155                 160

Gly Ser Ser Ser Ser Val Ala Ala Thr Asn Ser Ala Val Asn Thr Ser
                165                 170                 175

Ser Met Gly Ala Leu Ser Tyr His Gln Ile His Ala Thr Ser Asn Tyr
            180                 185                 190

Ser Asn Pro Pro Ser His Ser Glu Tyr Ser His Tyr Gly Ala Ala Val
        195                 200                 205

Ala Thr Ala Ala Glu Thr His Ser Thr Pro Ser Ser Ser Val Val Gly
    210                 215                 220

Ser Ser Arg Thr Val Arg Leu Phe Gly Val Asn Leu Glu Cys Gln Met
225                 230                 235                 240

Asp Glu Asn Asp Gly Asp Asp Ser Val Ala Val Ala Thr Thr Val Glu
                245                 250                 255

Ser Pro Asp Gly Tyr Tyr Gly Gln Asn Met Tyr Tyr Tyr Ser His
            260                 265                 270

Pro His Asn Met Val Ile Leu Thr Leu Leu
        275                 280
```

<210> SEQ ID NO 6
<211> LENGTH: 33
<212> TYPE: PRT
<213> ORGANISM: Artificial Sequence
<220> FEATURE:
<223> OTHER INFORMATION: domain

<400> SEQUENCE: 6

```
Ser Asn Asn Asn Asn Asn Asn Gly Gly Ser Gly Asp Asp Val Ala Cys
1               5                   10                  15
```

```
His Phe Gln Arg Phe Asp Leu His Arg Leu Phe Ile Gly Trp Arg Gly
            20                  25                  30

Glu

<210> SEQ ID NO 7
<211> LENGTH: 9
<212> TYPE: PRT
<213> ORGANISM: Artificial Sequence
<220> FEATURE:
<223> OTHER INFORMATION: domain

<400> SEQUENCE: 7

Val Arg Leu Phe Gly Val Asn Leu Glu
1               5

<210> SEQ ID NO 8
<211> LENGTH: 21
<212> TYPE: DNA
<213> ORGANISM: Artificial Sequence
<220> FEATURE:
<223> OTHER INFORMATION: primer

<400> SEQUENCE: 8
accatgacat tcgaggttca c                                           21

<210> SEQ ID NO 9
<211> LENGTH: 21
<212> TYPE: DNA
<213> ORGANISM: Artificial Sequence
<220> FEATURE:
<223> OTHER INFORMATION: primer

<400> SEQUENCE: 9
atcaccacca aaacgacgta g                                           21

<210> SEQ ID NO 10
<211> LENGTH: 21
<212> TYPE: DNA
<213> ORGANISM: Artificial Sequence
<220> FEATURE:
<223> OTHER INFORMATION: primer

<400> SEQUENCE: 10
tacgtcatgc ttcaaatcgt g                                           21

<210> SEQ ID NO 11
<211> LENGTH: 21
<212> TYPE: DNA
<213> ORGANISM: Artificial Sequence
<220> FEATURE:
<223> OTHER INFORMATION: primer

<400> SEQUENCE: 11
aggacacgaa caattcattc g                                           21

<210> SEQ ID NO 12
<211> LENGTH: 29
<212> TYPE: DNA
<213> ORGANISM: Artificial Sequence
<220> FEATURE:
<223> OTHER INFORMATION: primer

<400> SEQUENCE: 12
tacgaataag agcgtccatt ttagagtga                                   29
```

```
<210> SEQ ID NO 13
<211> LENGTH: 21
<212> TYPE: DNA
<213> ORGANISM: Artificial Sequence
<220> FEATURE:
<223> OTHER INFORMATION: primer

<400> SEQUENCE: 13
acccaaagaa cagcaatcat g                                             21

<210> SEQ ID NO 14
<211> LENGTH: 21
<212> TYPE: DNA
<213> ORGANISM: Artificial Sequence
<220> FEATURE:
<223> OTHER INFORMATION: primer

<400> SEQUENCE: 14
aaaacactcc gccattaaac c                                             21

<210> SEQ ID NO 15
<211> LENGTH: 24
<212> TYPE: DNA
<213> ORGANISM: Artificial Sequence
<220> FEATURE:
<223> OTHER INFORMATION: primer

<400> SEQUENCE: 15
cgagtatcaa tggaaactta accg                                          24

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
aacggagagt ggcttgagat                                               20

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
tggcccttat ggtttctgca                                               20

<210> SEQ ID NO 18
<211> LENGTH: 15
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t
```

```
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 18
ntcgantntn gngtt                                                      15

<210> SEQ ID NO 19
<211> LENGTH: 21
<212> TYPE: DNA
<213> ORGANISM: Artificial Sequence
<220> FEATURE:
<223> OTHER INFORMATION: primer

<400> SEQUENCE: 19
atgtcagtca accattacca c                                               21

<210> SEQ ID NO 20
<211> LENGTH: 24
<212> TYPE: DNA
<213> ORGANISM: Artificial Sequence
<220> FEATURE:
<223> OTHER INFORMATION: primer

<400> SEQUENCE: 20
caggtaggag atggacgagg ttga                                            24

<210> SEQ ID NO 21
<211> LENGTH: 23
<212> TYPE: DNA
<213> ORGANISM: Artificial Sequence
<220> FEATURE:
<223> OTHER INFORMATION: primer

<400> SEQUENCE: 21
tgagaggaac catttcttag agg                                             23

<210> SEQ ID NO 22
<211> LENGTH: 22
<212> TYPE: DNA
<213> ORGANISM: Artificial Sequence
<220> FEATURE:
<223> OTHER INFORMATION: primer

<400> SEQUENCE: 22
acctcgtcca tctcctacct gc                                              22

<210> SEQ ID NO 23
<211> LENGTH: 22
<212> TYPE: DNA
<213> ORGANISM: Artificial Sequence
<220> FEATURE:
<223> OTHER INFORMATION: primer

<400> SEQUENCE: 23
aaacacgtca aatataacga at                                              22

<210> SEQ ID NO 24
<211> LENGTH: 33
<212> TYPE: DNA
<213> ORGANISM: Artificial Sequence
<220> FEATURE:
```

```
<223> OTHER INFORMATION: primer

<400> SEQUENCE: 24
cttttttttg gtttcttgga gtgagagaga gag                              33

<210> SEQ ID NO 25
<211> LENGTH: 29
<212> TYPE: DNA
<213> ORGANISM: Artificial Sequence
<220> FEATURE:
<223> OTHER INFORMATION: primer

<400> SEQUENCE: 25
agtctgggcc catgtcagtc aaccattac                                   29

<210> SEQ ID NO 26
<211> LENGTH: 29
<212> TYPE: DNA
<213> ORGANISM: Artificial Sequence
<220> FEATURE:
<223> OTHER INFORMATION: primer

<400> SEQUENCE: 26
gcgactagtt tataaaagag ttaaaatta                                   29

<210> SEQ ID NO 27
<211> LENGTH: 24
<212> TYPE: DNA
<213> ORGANISM: Artificial Sequence
<220> FEATURE:
<223> OTHER INFORMATION: primer

<400> SEQUENCE: 27
cgggatcctc agtcaaccat tacc                                        24

<210> SEQ ID NO 28
<211> LENGTH: 28
<212> TYPE: DNA
<213> ORGANISM: Artificial Sequence
<220> FEATURE:
<223> OTHER INFORMATION: primer

<400> SEQUENCE: 28
actagtcgac tcaacctcgt ccatctcc                                    28

<210> SEQ ID NO 29
<211> LENGTH: 20
<212> TYPE: DNA
<213> ORGANISM: Artificial Sequence
<220> FEATURE:
<223> OTHER INFORMATION: primer

<400> SEQUENCE: 29
gaaatcacag cacttgcacc                                             20

<210> SEQ ID NO 30
<211> LENGTH: 20
<212> TYPE: DNA
<213> ORGANISM: Artificial Sequence
<220> FEATURE:
<223> OTHER INFORMATION: primer

<400> SEQUENCE: 30
aagcctttga tcttgagagc                                             20
```

```
<210> SEQ ID NO 31
<211> LENGTH: 18
<212> TYPE: DNA
<213> ORGANISM: Artificial Sequence
<220> FEATURE:
<223> OTHER INFORMATION: primer

<400> SEQUENCE: 31
gcgacgacgg agaaaggg                                                 18

<210> SEQ ID NO 32
<211> LENGTH: 18
<212> TYPE: DNA
<213> ORGANISM: Artificial Sequence
<220> FEATURE:
<223> OTHER INFORMATION: primer

<400> SEQUENCE: 32
acgacggcgc catagtgt                                                 18

<210> SEQ ID NO 33
<211> LENGTH: 22
<212> TYPE: DNA
<213> ORGANISM: Artificial Sequence
<220> FEATURE:
<223> OTHER INFORMATION: primer

<400> SEQUENCE: 33
tttgaagacg agtcaggcaa gt                                            22

<210> SEQ ID NO 34
<211> LENGTH: 20
<212> TYPE: DNA
<213> ORGANISM: Artificial Sequence
<220> FEATURE:
<223> OTHER INFORMATION: primer

<400> SEQUENCE: 34
tacggcggct ccatagtggg                                               20

<210> SEQ ID NO 35
<211> LENGTH: 24
<212> TYPE: DNA
<213> ORGANISM: Artificial Sequence
<220> FEATURE:
<223> OTHER INFORMATION: primer

<400> SEQUENCE: 35
gtattggagc ggcttgacta cacc                                          24

<210> SEQ ID NO 36
<211> LENGTH: 22
<212> TYPE: DNA
<213> ORGANISM: Artificial Sequence
<220> FEATURE:
<223> OTHER INFORMATION: primer

<400> SEQUENCE: 36
gacggcatca ccatgacatt cg                                            22

<210> SEQ ID NO 37
<211> LENGTH: 24
<212> TYPE: DNA
<213> ORGANISM: Artificial Sequence
<220> FEATURE:
<223> OTHER INFORMATION: primer
```

```
<400> SEQUENCE: 37
tgattctgac atgattgctg ttct                                          24

<210> SEQ ID NO 38
<211> LENGTH: 23
<212> TYPE: DNA
<213> ORGANISM: Artificial Sequence
<220> FEATURE:
<223> OTHER INFORMATION: primer

<400> SEQUENCE: 38
tcgcaactgt atctgtccct cta                                           23

<210> SEQ ID NO 39
<211> LENGTH: 25
<212> TYPE: DNA
<213> ORGANISM: Artificial Sequence
<220> FEATURE:
<223> OTHER INFORMATION: primer

<400> SEQUENCE: 39
cgtttcgctt tccttagtgt tagct                                         25

<210> SEQ ID NO 40
<211> LENGTH: 27
<212> TYPE: DNA
<213> ORGANISM: Artificial Sequence
<220> FEATURE:
<223> OTHER INFORMATION: primer

<400> SEQUENCE: 40
agcgaacgga tctagagact caccttg                                       27

<210> SEQ ID NO 41
<211> LENGTH: 23
<212> TYPE: DNA
<213> ORGANISM: Artificial Sequence
<220> FEATURE:
<223> OTHER INFORMATION: primer

<400> SEQUENCE: 41
caggcctaag cctaacagta gac                                           23

<210> SEQ ID NO 42
<211> LENGTH: 23
<212> TYPE: DNA
<213> ORGANISM: Artificial Sequence
<220> FEATURE:
<223> OTHER INFORMATION: primer

<400> SEQUENCE: 42
tgtactagga tttatttacg tag                                           23

<210> SEQ ID NO 43
<211> LENGTH: 24
<212> TYPE: DNA
<213> ORGANISM: Artificial Sequence
<220> FEATURE:
<223> OTHER INFORMATION: primer

<400> SEQUENCE: 43
tattgttcat agaaaccctg caaa                                          24

<210> SEQ ID NO 44
<211> LENGTH: 24
```

-continued

```
<212> TYPE: DNA
<213> ORGANISM: Artificial Sequence
<220> FEATURE:
<223> OTHER INFORMATION: primer

<400> SEQUENCE: 44
agtcaatggt ttaatggcgg agtg                                        24

<210> SEQ ID NO 45
<211> LENGTH: 23
<212> TYPE: DNA
<213> ORGANISM: Artificial Sequence
<220> FEATURE:
<223> OTHER INFORMATION: primer

<400> SEQUENCE: 45
ttctactaca cttgctctct gta                                         23

<210> SEQ ID NO 46
<211> LENGTH: 23
<212> TYPE: DNA
<213> ORGANISM: Artificial Sequence
<220> FEATURE:
<223> OTHER INFORMATION: primer

<400> SEQUENCE: 46
tacagagagc aagtgtagta gaa                                         23

<210> SEQ ID NO 47
<211> LENGTH: 23
<212> TYPE: DNA
<213> ORGANISM: Artificial Sequence
<220> FEATURE:
<223> OTHER INFORMATION: primer

<400> SEQUENCE: 47
ttctactaac acctctctct gta                                         23

<210> SEQ ID NO 48
<211> LENGTH: 23
<212> TYPE: DNA
<213> ORGANISM: Artificial Sequence
<220> FEATURE:
<223> OTHER INFORMATION: primer

<400> SEQUENCE: 48
tacagagaga ggtgttagta gaa                                         23

<210> SEQ ID NO 49
<211> LENGTH: 192
<212> TYPE: PRT
<213> ORGANISM: Oryza sativa

<400> SEQUENCE: 49
```

Met Ala Met His Ala Gly His Ala Trp Trp Gly Val Ala Met Tyr Thr
 1               5                  10                  15

Asn His Tyr His His His Tyr Arg His Lys Thr Ser Asp Val Gly Lys
                20                  25                  30

Asn Arg Val Lys His Ala Arg Tyr Gly Gly Gly Asp Ser Gly Lys Gly
            35                  40                  45

Ser Asp Ser Gly Lys Trp Arg Arg Tyr Ser Tyr Trp Thr Ser Ser Ser
        50                  55                  60

Tyr Val Thr Lys Gly Trp Ser Arg Tyr Val Lys Lys Arg Asp Ala Gly
65                  70                  75                  80

```
Asp Val Val His Arg Val Arg Gly Gly Ala Ala Asp Arg Gly Cys Arg
                85                  90                  95

Arg Arg Gly Ser Ala Ala Val Arg Val Thr Ala Asn Gly Gly Trp
           100                 105                 110

Ser Met Cys Tyr Ser Thr Ser Gly Ser Ser Tyr Asp Ser Ala Asn
           115                 120                 125

Ser Tyr Ala Tyr His Arg Ser Val Asp Asp His Ser Asp His Ala Gly
           130                 135                 140

Ser Arg Ala Asp Ala Lys Ser Ser Ala Ser Ala Ser Arg Arg
145                 150                 155                 160

Arg Gly Val Asn Asp Cys Gly Ala Asp Ala Thr Ala Met Tyr Gly Tyr
                165                 170                 175

Met His His Ser Tyr Ala Ala Val Ser Thr Val Asn Tyr Trp Ser Val
                180                 185                 190

<210> SEQ ID NO 50
<211> LENGTH: 834
<212> TYPE: DNA
<213> ORGANISM: Oryza sativa

<400> SEQUENCE: 50
atggccatgc accctctcgc ccaggggcac ccccaggcgt ggccatgggg tgtagccatg      60
tacaccaacc tgcactacca ccaccactac gagagggagc acctgttcga aagccgctg     120 acgccgagcg acgtcggcaa gctcaacagg ctggtgatcc caagcagca cgccgagagg     180 tacttcccgc tcggcggcgg cgactccggt gagaagggcc tcctcctctc cttcgaggac     240
gagtccggca agccatggcg gttccgctac tcctactgga ccagcagcca gagctacgtg     300
ctcaccaagg gctggagccg ctacgtcaag gagaagcgcc tcgacgccgg cgacgtcgtc     360
cacttcgagc gcgtccgcgg cctcggcgcc gccgaccgcc tcttcatcgg ctgcaggcgc     420
cgcggcgaga gcgcgcccgc gccgccgccc gccgttcgcg tcacgccgca gccgcctgcc     480
ctcaacggcg gcgagcagca gccgtggagc ccaatgtgtt acagcacgtc gggctcgtcc     540
tacgacccta ccagccctgc caattcatat gcctaccatc gctccgtaga ccaagatcac     600
agcgacatac tacacgcagg agagtcgcag agagaagcag acgccaagag cagcagcgcg     660
gcgtcggcgc cgccgccgtc gaggcggctc aggctgttcg cgttaacct cgactgcggc     720 ccggagccgg aggcggatca ggcgacggca atgtacggct acatgcacca ccagagcccc     780
tacgccgcag tgtctacagt gccaaattac tggtcagtat tttttcagtt ttaa           834

<210> SEQ ID NO 51
<211> LENGTH: 279
<212> TYPE: PRT
<213> ORGANISM: Oryza sativa

<400> SEQUENCE: 51

Met Ala Met Asn His Pro Leu Phe Ser Gln Glu Gln Pro Gln Ser Trp
1               5                   10                  15

Pro Trp Gly Val Ala Met Tyr Ala Asn Phe His Tyr His His Tyr
            20                  25                  30

Glu Lys Glu His Met Phe Glu Lys Pro Leu Thr Pro Ser Asp Val Gly
        35                  40                  45

Lys Leu Asn Arg Leu Val Ile Pro Lys Gln His Ala Glu Arg Tyr Phe
    50                  55                  60

Pro Leu Gly Ala Gly Asp Ala Ala Asp Lys Gly Leu Ile Leu Ser Phe
```

```
                65                  70                  75                  80
Glu Asp Glu Ala Gly Ala Pro Trp Arg Phe Arg Tyr Ser Tyr Trp Thr
                        85                  90                  95
Ser Ser Gln Ser Tyr Val Leu Thr Lys Gly Trp Ser Arg Tyr Val Lys
                100                 105                 110
Glu Lys Arg Leu Asp Ala Gly Asp Val Val His Phe Glu Arg Val Arg
            115                 120                 125
Gly Ser Phe Gly Val Gly Asp Arg Leu Phe Ile Gly Cys Arg Arg Arg
        130                 135                 140
Gly Asp Ala Ala Ala Gln Thr Pro Ala Pro Pro Ala Val Arg
145                 150                 155                 160
Val Ala Pro Ala Ala Gln Asn Ala Gly Glu Gln Gln Pro Trp Ser Pro
                165                 170                 175
Met Cys Tyr Ser Thr Ser Gly Gly Ser Tyr Pro Thr Ser Pro Ala
            180                 185                 190
Asn Ser Tyr Ala Tyr Arg Arg Ala Ala Asp His Asp His Gly Asp Met
                195                 200                 205
His His Ala Asp Glu Ser Pro Arg Asp Thr Asp Ser Pro Ser Phe Ser
        210                 215                 220
Ala Gly Ser Ala Pro Ser Arg Arg Leu Arg Leu Phe Gly Val Asn Leu
225                 230                 235                 240
Asp Cys Gly Pro Glu Pro Glu Ala Asp Thr Thr Ala Ala Ala Thr Met
                245                 250                 255
Tyr Gly Tyr Met His Gln Gln Ser Ser Tyr Ala Ala Met Ser Ala Val
            260                 265                 270
Pro Ser Tyr Trp Gly Asn Ser
        275

<210> SEQ ID NO 52
<211> LENGTH: 840
<212> TYPE: DNA
<213> ORGANISM: Oryza sativa

<400> SEQUENCE: 52
atggccatga accaccctct cttctcccag gagcaacccc agtcctggcc atggggtgtg        60
gccatgtacg ccaacttcca ctaccaccac cactacgaga aggagcacat gtttgagaag       120
cccctgacgc ccagtgacgt ggggaagctg aaccggctgg tgatcccaa gcagcacgcc        180 gagaggtact tccccctcgg cgccggcgac gccgccgaca agggcctgat cctgtcgttc       240
gaggacgagg ccggcgcgcc gtggcggttc aggtactcct actggacgag cagccagagc       300
tacgtgctca ccaagggctg gagccgctac gtcaaggaga gcgcctcga cgccggcgac       360 gtcgtgcact cgagagggt gcgcggctcc ttcggcgtcg cgaccgtct cttcatcggc         420 tgcaggcgcc gcggcgacgc cgccgccgcg caaacacccg caccgccgcc gccgtgcgc        480 gtcgccccgg ctgcacagaa cgccggcgag cagcagccgt ggagcccaat gtgttacagc      540
acgtcgggcg gcggctcata ccctaccagc ccagccaact cctacgccta ccgccgcgca      600
gcagatcatg atcacgggga catgcaccat gcagacgagt ctccgcgcga cacggacagc      660
ccaagcttca gtgcaggctc ggcgccatcg aggcggctca ggctgttcgg cgtcaacctc      720
gactgcgggc cagagccgga ggcagacacc acggcagcgg caacaatgta cggctacatg      780
caccagcaga gctcctatgc tgccatgtct gcagtaccca gttactgggg caattcataa      840

<210> SEQ ID NO 53
```

```
<211> LENGTH: 412
<212> TYPE: PRT
<213> ORGANISM: Oryza sativa

<400> SEQUENCE: 53

Met Glu Phe Thr Thr Ser Ser Arg Phe Ser Lys Glu Glu Asp Glu
1               5                   10                  15

Glu Gln Asp Glu Ala Gly Arg Arg Glu Ile Pro Phe Met Thr Ala Thr
            20                  25                  30

Ala Glu Ala Ala Pro Ala Pro Thr Ser Ser Ser Ser Pro Ala His
        35                  40                  45

His Ala Ala Ser Ala Ser Ala Ser Ala Ser Gly Ser Ser Thr
    50                  55                  60

Pro Phe Arg Ser Asp Asp Gly Ala Gly Ala Ser Gly Ser Gly Gly Gly
65                  70                  75                  80

Gly Gly Gly Gly Gly Glu Ala Glu Val Val Glu Lys Glu His Met Phe
                85                  90                  95

Asp Lys Val Val Thr Pro Ser Asp Val Gly Lys Leu Asn Arg Leu Val
            100                 105                 110

Ile Pro Lys Gln Tyr Ala Glu Lys Tyr Phe Pro Leu Asp Ala Ala Ala
        115                 120                 125

Asn Glu Lys Gly Leu Leu Leu Asn Phe Glu Asp Arg Ala Gly Lys Pro
    130                 135                 140

Trp Arg Phe Arg Tyr Ser Tyr Trp Asn Ser Ser Gln Ser Tyr Val Met
145                 150                 155                 160

Thr Lys Gly Trp Ser Arg Phe Val Lys Glu Lys Arg Leu Asp Ala Gly
                165                 170                 175

Asp Thr Val Ser Phe Ser Arg Gly Ile Gly Asp Glu Ala Ala Arg His
            180                 185                 190

Arg Leu Phe Ile Asp Trp Lys Arg Arg Ala Asp Thr Arg Asp Pro Leu
        195                 200                 205

Arg Leu Pro Arg Gly Leu Pro Leu Pro Met Pro Leu Thr Ser His Tyr
    210                 215                 220

Ala Pro Trp Gly Ile Gly Gly Gly Gly Phe Phe Val Gln Pro Ser
225                 230                 235                 240

Pro Pro Ala Thr Leu Tyr Glu His Arg Leu Arg Gln Gly Leu Asp Phe
                245                 250                 255

Arg Ala Phe Asn Pro Ala Ala Ala Met Gly Arg Gln Val Leu Leu Phe
            260                 265                 270

Gly Ser Ala Arg Ile Pro Pro Gln Ala Pro Leu Leu Ala Arg Ala Pro
        275                 280                 285

Ser Pro Leu His His His Tyr Thr Leu Gln Pro Ser Gly Asp Gly Val
    290                 295                 300

Arg Ala Ala Gly Ser Pro Val Val Leu Asp Ser Val Pro Val Ile Glu
305                 310                 315                 320

Ser Pro Thr Thr Ala Ala Lys Arg Val Arg Leu Phe Gly Val Asn Leu
                325                 330                 335

Asp Asn Pro His Ala Gly Gly Gly Gly Ala Ala Ala Gly Glu Ser
            340                 345                 350

Ser Asn His Gly Asn Ala Leu Ser Leu Gln Thr Pro Ala Trp Met Arg
        355                 360                 365

Arg Asp Pro Thr Leu Arg Leu Leu Glu Leu Pro Pro His His His His
    370                 375                 380

Gly Ala Glu Ser Ser Ala Ala Ser Ser Pro Ser Ser Ser Ser Ser
```

| | | | | |
|---|---|---|---|---|
| 385 | 390 | 395 | 400 | |

Lys Arg Asp Ala His Ser Ala Leu Asp Leu Asp Leu
                    405                 410

<210> SEQ ID NO 54
<211> LENGTH: 1239
<212> TYPE: DNA
<213> ORGANISM: Oryza sativa

<400> SEQUENCE: 54

| | |
|---|---|
| atggagttca ctacaagcag taggttttct aaagaagagg aggacgagga gcaggatgag | 60 |
| gcggaaggc gagagatccc cttcatgacg gccacggccg aagccgcgcc tgcgcccacg | 120 |
| tcgtcgtcgt cgtctcctgc tcatcacgcg gcttccgcgt cggcgtcggc gtctgcgtca | 180 |
| gggagcagca ctccctttcg ctccgacgat ggcgccgggg cgtctgggag cggcggcggc | 240 |
| ggcggcggcg gcggagaagc ggaggtggtg gagaaggagc acatgttcga caaggtggtg | 300 |
| acgccgagcg acgttgggaa gctgaaccgg ctggtgatcc cgaagcagta cgccgagaag | 360 |
| tacttcccgc tggacgcggc ggcgaacgag aagggcctcc tgctcaactt cgaggaccgc | 420 |
| gcggggaagc catggcggtt ccgctactcc tactggaaca gcagccagag ctacgtgatg | 480 |
| accaaggggt ggagccgctt cgtcaaggag aagcgcctcg acgccgggga caccgtctcc | 540 |
| ttctcccgcg catcggcga cgaggcggcg cggcaccgcc tcttcatcga ctggaagcgc | 600 |
| cgcgccgaca cccgcgaccc gctccggctg ccccgcgggc tgccgctccc gatgccgctc | 660 |
| acgtcgcact acgcccgtg ggggatcggc ggcggagggg gattcttcgt gcagccctcg | 720 |
| ccgccggcca cgctctacga gcaccgcctc aggcaaggcc tcgacttccg cgccttcaac | 780 |
| cccgccgccg cgatggggag gcaggtcctc ctgttcggct cggcgaggat cctccgcaa | 840 |
| gcaccactgc tggcgcgcgc gccgtcgccg ctgcaccacc actacacgct gcagccgagc | 900 |
| ggcgatggtg taagggcggc gggctcaccg gtggtgctcg actcggttcc ggtcatcgag | 960 |
| agccccacga cggccgcgaa gcgcgtgcgg ctgttcggcg tgaacctcga caacccgcat | 1020 |
| gccggcggcg gcggcggcgc cgccgccggc gagtcgagca atcatggcaa tgcactgtca | 1080 |
| ttgcagacgc ccgcgtggat gaggagggat ccaacactgc ggctgctgga attgcctcct | 1140 |
| caccaccacc atggcgccga gtcgtccgct gcatcgtctc cgtcgtcgtc gtcttcctcc | 1200 |
| aagagggacg cgcattcggc cttggatctc gatctgtag | 1239 |

<210> SEQ ID NO 55
<211> LENGTH: 951
<212> TYPE: DNA
<213> ORGANISM: Oryza sativa

<400> SEQUENCE: 55

| | |
|---|---|
| atggagtttg ctacaacgag tagtaggttt tccaaggaag aggaggagga ggaggaaggg | 60 |
| gaacaggaga tggagcagga gcaggatgaa gaggaggagg aggcggaggc ctcgccccgc | 120 |
| gagatcccct tcatgacgtc ggcggcggcg gcggccaccg cctcatcgtc ctccccgaca | 180 |
| tcggtctccc cttccgccac cgcttccgcg gcggcgtcca cgtcggcgtc gggctctccc | 240 |
| ttccggtcga gcgacggtgc gggagcgtcg gggagtggcg gcggcggtgg cggcgaggac | 300 |
| gtggaggtga tcgagaagga gcacatgttc gacaaggtgg tgacgccgag cgacgtgggg | 360 |
| aagctgaacc ggctggtgat cccgaagcag cacgccgaga agtacttccc gctggactcg | 420 |
| gcggcgaacg agaagggcct tctcctcagc ttcgaggacc gaaccggcaa gctatggcgc | 480 |

-continued

```
ttccgctact cctactggaa cagcagccag agctacgtca tgaccaaggg ttggagccgc    540
ttcgtcaagg agaagcgcct cgacgccggg gacaccgtct ccttctgccg cggcgccgcc    600
gaggccaccc gcgaccgcct cttcatcgac tggaagcgcc gcgccgacgt ccgcgacccg    660
caccgcttcc agcgcctacc gctccccatg acctcgccct acggcccgtg gggcggcggc    720
gcgggcgctt cttcatgccg cccgcgccgc ccgccacgct ctacgagcat caccgctttc    780
gccagggctt cgacttccgc aacatcaacc ccgctgtgcc ggcgaggcag ctcgtcttct    840
tcggctcccc agggacgggg attcatcagc accgcccttg ccaccgccg ccgtcgccac    900 ctccgcctcc tcaccaactc cacattacgg tgcaccaccc gagccccgta g            951
```

<210> SEQ ID NO 56
<211> LENGTH: 316
<212> TYPE: PRT
<213> ORGANISM: Oryza sativa

<400> SEQUENCE: 56

```
Met Glu Phe Ala Thr Thr Ser Ser Arg Phe Ser Lys Glu Glu Glu
1               5                   10                  15

Glu Glu Glu Gly Glu Gln Glu Met Glu Gln Glu Gln Asp Glu Glu
            20                  25                  30

Glu Glu Ala Glu Ala Ser Pro Arg Glu Ile Pro Phe Met Thr Ser Ala
        35                  40                  45

Ala Ala Ala Thr Ala Ser Ser Ser Pro Thr Ser Val Ser Pro
    50                  55                  60

Ser Ala Thr Ala Ser Ala Ala Ser Thr Ser Ala Ser Gly Ser Pro
65                  70                  75                  80

Phe Arg Ser Ser Asp Gly Ala Gly Ala Ser Gly Ser Gly Gly Gly
                85                  90                  95

Gly Gly Glu Asp Val Glu Val Ile Glu Lys Glu His Met Phe Asp Lys
            100                 105                 110

Val Val Thr Pro Ser Asp Val Gly Lys Leu Asn Arg Leu Val Ile Pro
        115                 120                 125

Lys Gln His Ala Glu Lys Tyr Phe Pro Leu Asp Ser Ala Ala Asn Glu
    130                 135                 140

Lys Gly Leu Leu Leu Ser Phe Glu Asp Arg Thr Gly Lys Leu Trp Arg
145                 150                 155                 160

Phe Arg Tyr Ser Tyr Trp Asn Ser Ser Gln Ser Tyr Val Met Thr Lys
                165                 170                 175

Gly Trp Ser Arg Phe Val Lys Glu Lys Arg Leu Asp Ala Gly Asp Thr
            180                 185                 190

Val Ser Phe Cys Arg Gly Ala Ala Glu Ala Thr Arg Asp Arg Leu Phe
        195                 200                 205

Ile Asp Trp Lys Arg Arg Ala Asp Val Arg Asp Pro His Arg Phe Gln
    210                 215                 220

Arg Leu Pro Leu Pro Met Thr Ser Pro Tyr Gly Pro Trp Gly Gly Gly
225                 230                 235                 240

Ala Gly Ala Ser Ser Cys Arg Pro Arg Pro Arg Ser Thr Ser
                245                 250                 255

Ile Thr Ala Phe Ala Arg Ala Ser Ser Ala Thr Ser Thr Pro Leu
            260                 265                 270

Cys Arg Arg Gly Ser Ser Ser Ser Ala Pro Gln Gly Arg Gly Phe
        275                 280                 285

Ile Ser Thr Arg Pro Cys His Arg Arg Arg Arg His Leu Arg Leu Leu
```

```
                290                 295                 300
Thr Asn Ser Thr Leu Arg Cys Thr Thr Arg Ala Pro
305                 310                 315

<210> SEQ ID NO 57
<211> LENGTH: 936
<212> TYPE: DNA
<213> ORGANISM: Oryza sativa

<400> SEQUENCE: 57
atggagttca tcacgccaat cgtgaggccg gcatcggcgg cggcgggcgg cggcgaggtg      60
caggagagtg gtgggaggag cttggcggcg gtggagaagg agcacatgtt cgacaaggtg     120
gtgacgccga gcgacgtggg gaagctgaac cggctggtga tcccgaagca gcacgcggag     180
aagtacttcc cgctggacgc ggcgtccaac gagaaggggc tcctgctcag cttcgaggac     240
cgcacgggga agccatggcg gttccgctac tcctactgga acagcagcca gagctacgtg     300
atgaccaagg gctggagccg cttcgtcaag gagaagcgac tcgacgccgg gacaccgtc     360 tccttcggcc gcggcgtcgg cgaggccgcg cgcgggaggc tcttcatcga ctggcgccgc     420
cgccccgacg tcgtcgccgc gctccagccg cccacgcacc gcttcgccca ccacctccct     480
tcctccatcc ccttcgctcc ctgggcgcac caccacggac acggagccgc cgccgccgcc     540
gccgccgccg ccgcgccag gtttctcctg cctccctcct cgactcccat ctacgaccac     600
caccgccgac acgcccacgc cgtcgggtac gacgcgtacg ccgcggccac cagcaggcag     660
gtgctgttct accggccgtt gccgccgcag cagcagcatc atcccgcggt ggtgctggag     720
tcggtgccgg tgcgcatgac ggcggggcac gcggagccgc cgtcggctcc gtcgaagcga     780
gttcggctgt tcggggtgaa cctcgactgc gcgaattccg aacaagacca cgccggcgtg     840
gtcgggaaga cggcgccgcc gccgctgcca tcgccgccgt catcatcgtc atcttcctcc     900
gggaaagcga ggtgctcctt gaaccttgac ttgtga                              936

<210> SEQ ID NO 58
<211> LENGTH: 311
<212> TYPE: PRT
<213> ORGANISM: Oryza sativa

<400> SEQUENCE: 58

Met Glu Phe Ile Thr Pro Ile Val Arg Pro Ala Ser Ala Ala Gly
1               5                   10                  15

Gly Gly Glu Val Gln Glu Ser Gly Gly Arg Ser Leu Ala Ala Val Glu
            20                  25                  30

Lys Glu His Met Phe Asp Lys Val Thr Pro Ser Asp Val Gly Lys
        35                  40                  45

Leu Asn Arg Leu Val Ile Pro Lys Gln His Ala Glu Lys Tyr Phe Pro
    50                  55                  60

Leu Asp Ala Ala Ser Asn Glu Lys Gly Leu Leu Leu Ser Phe Glu Asp
65                  70                  75                  80

Arg Thr Gly Lys Pro Trp Arg Phe Arg Tyr Ser Tyr Trp Asn Ser Ser
                85                  90                  95

Gln Ser Tyr Val Met Thr Lys Gly Trp Ser Arg Phe Val Lys Glu Lys
            100                 105                 110

Arg Leu Asp Ala Gly Asp Thr Val Ser Phe Gly Arg Gly Val Gly Glu
        115                 120                 125

Ala Ala Arg Gly Arg Leu Phe Ile Asp Trp Arg Arg Pro Asp Val
    130                 135                 140
```

```
Val Ala Ala Leu Gln Pro Pro Thr His Arg Phe Ala His His Leu Pro
145                 150                 155                 160

Ser Ser Ile Pro Phe Ala Pro Trp Ala His His Gly His Gly Ala
                165                 170                 175

Ala Ala Ala Ala Ala Ala Ala Gly Ala Arg Phe Leu Leu Pro Pro
            180                 185                 190

Ser Ser Thr Pro Ile Tyr Asp His His Arg Arg His Ala His Ala Val
            195                 200                 205

Gly Tyr Asp Ala Tyr Ala Ala Ala Thr Ser Arg Gln Val Leu Phe Tyr
            210                 215                 220

Arg Pro Leu Pro Pro Gln Gln Gln His His Pro Ala Val Val Leu Glu
225                 230                 235                 240

Ser Val Pro Val Arg Met Thr Ala Gly His Ala Glu Pro Pro Ser Ala
                245                 250                 255

Pro Ser Lys Arg Val Arg Leu Phe Gly Val Asn Leu Asp Cys Ala Asn
                260                 265                 270

Ser Glu Gln Asp His Ala Gly Val Val Gly Lys Thr Ala Pro Pro
            275                 280                 285

Leu Pro Ser Pro Pro Ser Ser Ser Ser Ser Ser Gly Lys Ala Arg
            290                 295                 300

Cys Ser Leu Asn Leu Asp Leu
305                 310
```

<210> SEQ ID NO 59
<211> LENGTH: 1182
<212> TYPE: DNA
<213> ORGANISM: Oryza sativa

<400> SEQUENCE: 59

```
atggacagct ccagctgcct ggtggatgat accaacagcg gcggctcgtc cacggacaag      60
ctgagggcgt ggccgccgc ggcggcggag acggcgccgc tggagcgcat ggggagcggg      120
gcgagcgcgg tggtggacgc ggcccgagcct ggcgcggagg cggactccgg gtccggggga    180
cgtgtgtgcg gcggcggcgg cggcggtgcc ggcggtgcgg gagggaagct gccgtcgtcc      240
aagttcaagg gcgtcgtgcc gcagcccaac gggaggtggg gcgcgcagat ctacgagcgg     300
caccagcggg tgtggctcgg cacgttcgcc ggggaggacg acgccgcgcg cgcctacgac     360
gtcgccgcgc agcgcttccg cggccgcgac gccgtcacca acttccgccc gctcgccgag    420
gccgacccgg acgccgccgc cgagcttcgc ttcctcgcca cgcgctccaa ggccgaggtc    480
gtcgacatgc tccgcaagca cacctacttc gacgagctcg cgcagagcaa gcgcaccttc    540
gccgcctcca cgccgtcggc cgcgaccacc accgcctccc tctccaacgg ccacctctcg    600
tcgccccgct ccccttcgc gcccgccgcg gcgcgcgacc acctgttcga caagacggtc   660
acccccgagcg acgtgggcaa gctgaacagg ctcgtcatac cgaagcagca cgccgagaag    720
cacttcccgc tacagctccc gtccgccggc ggcgagagca agggtgtcct cctcaacttc    780
gaggacgccg ccggcaaggt gtggcggttc cggtactcgt actggaacag cagccagagc    840
tacgtgctaa ccaagggctg gagccgcttc gtcaaggaga agggtctcca cgccggcgac    900
gtcgtcggct tctaccgctc cgccgccagt gccggcgacg acggcaagct cttcatcgac    960
tgcaagttag tacggtcgac cggcgccgcc ctcgcgtcgc ccgctgatca gccagcgccg   1020
tcgcggtga aggccgtcag gctcttcggc gtggacctgc tcacggcgcc ggcgccggtc   1080
gaacagatgg ccgggtgcaa gagagccagg gacttggcgg cgacgacgcc tccacaagcg   1140
```
gcggcgttca agaagcaatg catagagctg gcactagtat ag					1182

<210> SEQ ID NO 60
<211> LENGTH: 393
<212> TYPE: PRT
<213> ORGANISM: Oryza sativa

<400> SEQUENCE: 60

| Met | Asp | Ser | Ser | Cys | Leu | Val | Asp | Thr | Asn | Ser | Gly | Gly | Ser |
|-----|-----|-----|-----|-----|-----|-----|-----|-----|-----|-----|-----|-----|-----|
| 1   |     |     |     | 5   |     |     |     |     | 10  |     |     |     | 15  |

Ser Thr Asp Lys Leu Arg Ala Leu Ala Ala Ala Ala Glu Thr Ala
            20                  25                  30

Pro Leu Glu Arg Met Gly Ser Gly Ala Ser Ala Val Val Asp Ala Ala
        35                  40                  45

Glu Pro Gly Ala Glu Ala Asp Ser Gly Ser Gly Gly Arg Val Cys Gly
    50                  55                  60

Gly Gly Gly Gly Gly Ala Gly Gly Ala Gly Gly Lys Leu Pro Ser Ser
65                  70                  75                  80

Lys Phe Lys Gly Val Val Pro Gln Pro Asn Gly Arg Trp Gly Ala Gln
                85                  90                  95

Ile Tyr Glu Arg His Gln Arg Val Trp Leu Gly Thr Phe Ala Gly Glu
            100                 105                 110

Asp Asp Ala Ala Arg Ala Tyr Asp Val Ala Ala Gln Arg Phe Arg Gly
        115                 120                 125

Arg Asp Ala Val Thr Asn Phe Arg Pro Leu Ala Glu Ala Asp Pro Asp
    130                 135                 140

Ala Ala Ala Glu Leu Arg Phe Leu Ala Thr Arg Ser Lys Ala Glu Val
145                 150                 155                 160

Val Asp Met Leu Arg Lys His Thr Tyr Phe Asp Glu Leu Ala Gln Ser
                165                 170                 175

Lys Arg Thr Phe Ala Ala Ser Thr Pro Ser Ala Ala Thr Thr Thr Ala
            180                 185                 190

Ser Leu Ser Asn Gly His Leu Ser Ser Pro Arg Ser Pro Phe Ala Pro
        195                 200                 205

Ala Ala Ala Arg Asp His Leu Phe Asp Lys Thr Val Thr Pro Ser Asp
    210                 215                 220

Val Gly Lys Leu Asn Arg Leu Val Ile Pro Lys Gln His Ala Glu Lys
225                 230                 235                 240

His Phe Pro Leu Gln Leu Pro Ser Ala Gly Gly Glu Ser Lys Gly Val
                245                 250                 255

Leu Leu Asn Phe Glu Asp Ala Ala Gly Lys Val Trp Arg Phe Arg Tyr
            260                 265                 270

Ser Tyr Trp Asn Ser Ser Gln Ser Tyr Val Leu Thr Lys Gly Trp Ser
        275                 280                 285

Arg Phe Val Lys Glu Lys Gly Leu His Ala Gly Asp Val Val Gly Phe
    290                 295                 300

Tyr Arg Ser Ala Ala Ser Ala Gly Asp Asp Gly Lys Leu Phe Ile Asp
305                 310                 315                 320

Cys Lys Leu Val Arg Ser Thr Gly Ala Ala Leu Ala Ser Pro Ala Asp
                325                 330                 335

Gln Pro Ala Pro Ser Pro Val Lys Ala Val Arg Leu Phe Gly Val Asp
            340                 345                 350

Leu Leu Thr Ala Pro Ala Pro Val Glu Gln Met Ala Gly Cys Lys Arg
        355                 360                 365

```
Ala Arg Asp Leu Ala Ala Thr Thr Pro Pro Gln Ala Ala Ala Phe Lys
    370                 375                 380

Lys Gln Cys Ile Glu Leu Ala Leu Val
385                 390
```

<210> SEQ ID NO 61
<211> LENGTH: 939
<212> TYPE: DNA
<213> ORGANISM: Oryza sativa

<400> SEQUENCE: 61

```
atggagttca ccccaatttc gccgccgacg agggtcgccg gcggtgagga ggattccgag      60
agggggcgg cggcgtgggc ggtggtggag aaggagcaca tgtttgagaa ggtcgtgacg     120
ccgagcgacg tggggaagct gaaccgattg gtcatcccca gcagcacgc cgagaggtac     180
ttcccgctcg acgccgcggc gggcgccggc ggcggcggtg gtggcggcgg tggcggcggc     240
ggggggaagg gctggtgct gagcttcgag gacaggacgg gaaggcgtg gaggttccgg      300
tactcgtact ggaacagcag ccagagctac gtgatgacca agggtggag ccgcttcgtc      360
aaggagaagc gcctcggcgc cggcgacacc gtgtcgttcg ccgcggcct cggcgacgcc     420
gcccgcggcc gcctcttcat cgacttccgc cgccgccgcc aggacgccgg cagcttcatg     480
ttcccgccga cggcggcgcc gccgtcgcac tcgcaccacc atcatcagcg acaccacccg     540
ccgctcccgt ccgtgcccct tgcccgtgg cgagactaca ccaccgccta tggcggcggc     600
tacggctacg gctacggcgg cggctccacc ccggcgtcca gccgccacgt gctgttcctc     660
cggccgcagg tgccggccgc tgtggtgctc aagtcggtgc cggtgcacgt cgcggccacc     720
tcggcggtgc aggaggcggc gacgacgaca aggccgaagc gtgtccggct gttcggggtg     780
aacctcgact gcccggcggc catggacgac gacgacgaca tcgccggagc ggcgagccgg     840
acggcagcgt cgtctctcct gcagctcccc tcgccgtcgt cctcgacgtc gtcgtcgacg     900
gcggggaaga agatgtgctc cttggatctt gggttgtga                           939
```

<210> SEQ ID NO 62
<211> LENGTH: 312
<212> TYPE: PRT
<213> ORGANISM: Oryza sativa

<400> SEQUENCE: 62

```
Met Glu Phe Thr Pro Ile Ser Pro Pro Thr Arg Val Ala Gly Gly Glu
1               5                   10                  15

Glu Asp Ser Glu Arg Gly Ala Ala Trp Ala Val Val Glu Lys Glu
            20                  25                  30

His Met Phe Glu Lys Val Val Thr Pro Ser Asp Val Gly Lys Leu Asn
        35                  40                  45

Arg Leu Val Ile Pro Lys Gln His Ala Glu Arg Tyr Phe Pro Leu Asp
    50                  55                  60

Ala Ala Ala Gly Ala Gly Gly Gly Gly Gly Gly Gly Gly Gly Gly Gly
65                  70                  75                  80

Gly Gly Lys Gly Leu Val Leu Ser Phe Glu Asp Arg Thr Gly Lys Ala
            85                  90                  95

Trp Arg Phe Arg Tyr Ser Tyr Trp Asn Ser Ser Gln Ser Tyr Val Met
            100                 105                 110

Thr Lys Gly Trp Ser Arg Phe Val Lys Glu Lys Arg Leu Gly Ala Gly
            115                 120                 125
```

```
Asp Thr Val Ser Phe Gly Arg Gly Leu Gly Asp Ala Ala Arg Gly Arg
            130                 135                 140

Leu Phe Ile Asp Phe Arg Arg Arg Gln Asp Ala Gly Ser Phe Met
145                 150                 155                 160

Phe Pro Pro Thr Ala Ala Pro Pro Ser His Ser His His His Gln
                165                 170                 175

Arg His His Pro Pro Leu Pro Ser Val Pro Leu Cys Pro Trp Arg Asp
                180                 185                 190

Tyr Thr Thr Ala Tyr Gly Gly Tyr Gly Tyr Gly Tyr Gly Gly Gly
            195                 200                 205

Ser Thr Pro Ala Ser Ser Arg His Val Leu Phe Leu Arg Pro Gln Val
210                 215                 220

Pro Ala Ala Val Val Leu Lys Ser Val Pro Val His Val Ala Ala Thr
225                 230                 235                 240

Ser Ala Val Gln Glu Ala Ala Thr Thr Thr Arg Pro Lys Arg Val Arg
                245                 250                 255

Leu Phe Gly Val Asn Leu Asp Cys Pro Ala Ala Met Asp Asp Asp
            260                 265                 270

Asp Ile Ala Gly Ala Ala Ser Arg Thr Ala Ala Ser Ser Leu Leu Gln
            275                 280                 285

Leu Pro Ser Pro Ser Ser Ser Thr Ser Ser Ser Thr Ala Gly Lys Lys
290                 295                 300

Met Cys Ser Leu Asp Leu Gly Leu
305                 310

<210> SEQ ID NO 63
<211> LENGTH: 337
<212> TYPE: PRT
<213> ORGANISM: Glycine max

<400> SEQUENCE: 63

Met Ser Ile Asn His Tyr Ser Met Asp Leu Pro Glu Pro Thr Leu Trp
1               5                   10                  15

Trp Pro His Pro His His Gln Gln Gln Gln Leu Thr Leu Met Asp Pro
                20                  25                  30

Asp Pro Leu Arg Leu Asn Leu Asn Ser Asp Asp Gly Asn Gly Asn Asp
            35                  40                  45

Asn Asp Asn Asp Glu Asn Gln Thr Thr Thr Gly Gly Glu Gln Glu
50                  55                  60

Ile Leu Asp Asp Lys Glu Pro Met Phe Glu Lys Pro Leu Thr Pro Ser
65                  70                  75                  80

Asp Val Gly Lys Leu Asn Arg Leu Val Ile Pro Lys Gln His Ala Glu
                85                  90                  95

Lys Tyr Phe Pro Leu Ser Gly Asp Ser Gly Ser Glu Cys Lys Gly
                100                 105                 110

Leu Leu Leu Ser Phe Glu Asp Glu Ser Gly Lys Cys Trp Arg Phe Arg
            115                 120                 125

Tyr Ser Tyr Trp Asn Ser Ser Gln Ser Tyr Val Leu Thr Lys Gly Trp
            130                 135                 140

Ser Arg Tyr Val Lys Asp Lys Arg Leu Asp Ala Gly Asp Val Val Leu
145                 150                 155                 160

Phe Glu Arg His Arg Val Asp Ala Gln Arg Leu Phe Ile Gly Trp Arg
                165                 170                 175

Arg Arg Arg Gln Ser Asp Ala Ala Leu Pro Pro Ala His Val Ser Ser
                180                 185                 190
```

```
Arg Lys Ser Gly Gly Asp Gly Asn Ser Asn Lys Asn Glu Gly Trp
            195                 200                 205

Thr Arg Gly Phe Tyr Ser Ala His His Pro Tyr Pro Thr His His Leu
        210                 215                 220

His His His Gln Pro Ser Pro Tyr Gln Gln Gln His Asp Cys Leu His
225                 230                 235                 240

Ala Gly Arg Gly Ser Gln Gly Gln Asn Gln Arg Met Arg Pro Val Gly
                245                 250                 255

Asn Asn Ser Ser Ser Ser Ser Ser Ser Arg Val Leu Arg Leu Phe
            260                 265                 270

Gly Val Asp Met Glu Cys Gln Pro Glu His Asp Asp Ser Gly Pro Ser
        275                 280                 285

Thr Pro Gln Cys Ser Tyr Asn Ser Asn Asn Met Leu Pro Ser Thr Gln
        290                 295                 300

Gly Thr Asp His Ser His His Asn Phe Tyr Gln Gln Gln Pro Ser Asn
305                 310                 315                 320

Ser Asn Pro Ser Pro His His Met Met Val His His Gln Pro Tyr Tyr
                325                 330                 335

Tyr

<210> SEQ ID NO 64
<211> LENGTH: 1014
<212> TYPE: DNA
<213> ORGANISM: Glycine max

<400> SEQUENCE: 64
atgtccataa accactactc catggaccct cccgaaccga cactctggtg gccacaccca      60
caccaccaac aacaacaact aaccttaatg gatcctgacc ctctccgtct caacctcaat     120
agcgacgatg gcaatggcaa tgacaacgac aacgacgaaa atcaaacaac cacaacagga     180
ggagaacaag aaatattaga cgataaagaa ccgatgttcg agaagccctt aaccccgagc     240
gacgtgggga agctgaaccg tctcgtaatc ccgaagcagc acgcggagaa gtacttccca     300
ctgagtggtg actcgggcgg gagcgagtgc aaggggctgt tactgagttt cgaggacgag     360
tcggggaagt gttggcgctt ccgctactcg tactggaaca gcagccagag ctacgtgctc     420
accaaagggt ggagccgcta cgtcaaggac aagcgccttg acgcgggcga cgtcgttttg     480
ttcgagcgtc accgcgtcga cgcgcagcgc ctcttcatcg ggtggaggcg caggcggcag     540
agcgatgccg ccttgccgcc tgcgcacgtt agcagtagga agagtggtgg tggtgatggg     600
aatagtaata agaatgaggg gtggaccaga gggttctatt ctgcgcatca tccttatcct     660
acgcatcatc ttcatcatca tcagccctcg ccataccaac aacaacatga ctgtcttcat     720
gcaggtagag ggtcccaagg tcagaaccaa aggatgagac cagtgggaaa caacagttct     780
agctctagtt cgagttcaag ggtacttagg ctgttcgggg tcgacatgga atgccaaccc     840
gaacatgatg attctggtcc ctccacaccc aatgctcct acaatagtaa caacatgttg     900
ccatcaacac agggcacaga tcattcccat cacaatttct accaacagca accttctaat     960
tccaatcctt cccctcatca catgatggta catcaccaac catactacta ctag          1014

<210> SEQ ID NO 65
<211> LENGTH: 344
<212> TYPE: PRT
<213> ORGANISM: Glycine max

<400> SEQUENCE: 65
```

```
Met Ser Thr Asn His Tyr Thr Met Asp Leu Pro Glu Pro Thr Leu Trp
1               5                   10                  15

Trp Pro His Pro His Gln Gln Gln Leu Thr Leu Ile Asp Pro Asp Pro
                20                  25                  30

Leu Pro Leu Asn Leu Asn Asn Asp Asp Asn Asp Asn Gly Asp Asp Asn
            35                  40                  45

Asp Asn Asp Glu Asn Gln Thr Val Thr Thr Thr Thr Thr Gly Gly Glu
        50                  55                  60

Glu Glu Ile Ile Asn Asn Lys Glu Pro Met Phe Glu Lys Pro Leu Thr
65                  70                  75                  80

Pro Ser Asp Val Gly Lys Leu Asn Arg Leu Val Ile Pro Lys Gln His
                85                  90                  95

Ala Glu Lys Tyr Phe Pro Leu Ser Gly Gly Asp Ser Gly Ser Ser Glu
                100                 105                 110

Cys Lys Gly Leu Leu Leu Ser Phe Glu Asp Glu Ser Gly Lys Cys Trp
                115                 120                 125

Arg Phe Arg Tyr Ser Tyr Trp Asn Ser Ser Gln Ser Tyr Val Leu Thr
            130                 135                 140

Lys Gly Trp Ser Arg Tyr Val Lys Asp Lys Arg Leu Asp Ala Gly Asp
145                 150                 155                 160

Val Val Leu Phe Gln Arg His Arg Ala Asp Ala Gln Arg Leu Phe Ile
                165                 170                 175

Gly Trp Arg Arg Arg Arg Gln Ser Asp Ala Leu Pro Pro Pro Ala His
                180                 185                 190

Val Ser Ser Arg Lys Ser Gly Gly Asp Gly Asn Ser Ser Lys Asn Glu
                195                 200                 205

Gly Asp Val Gly Val Gly Trp Thr Arg Gly Phe Tyr Pro Ala His His
            210                 215                 220

Pro Tyr Pro Thr His His His His Pro Ser Pro Tyr His His Gln Gln
225                 230                 235                 240

Asp Asp Ser Leu His Ala Val Arg Gly Ser Gln Gly Gln Asn Gln Arg
                245                 250                 255

Thr Arg Pro Val Gly Asn Ser Ser Ser Ser Ser Ser Ser Ser Ser Arg
                260                 265                 270

Val Leu Arg Leu Phe Gly Val Asn Met Glu Cys Gln Pro Glu His Asp
                275                 280                 285

Asp Ser Gly Pro Ser Thr Pro Gln Cys Ser Tyr Asn Thr Asn Asn Ile
            290                 295                 300

Leu Pro Ser Thr Gln Gly Thr Asp Ile His Ser His Leu Asn Phe Tyr
305                 310                 315                 320

Gln Gln Gln Gln Thr Ser Asn Ser Lys Pro Pro Pro His His Met Met
                325                 330                 335

Ile Arg His Gln Pro Tyr Tyr Tyr
            340
```

<210> SEQ ID NO 66
<211> LENGTH: 1035
<212> TYPE: DNA
<213> ORGANISM: Glycine max

<400> SEQUENCE: 66
atgtcgacaa accactacac catggacctt cccgaaccaa cactctggtg gccacaccca      60
caccaacaac aactaacctt aatagatcca gaccctctcc ctctgaacct caacaacgac     120

```
gacaacgaca atggcgacga caacgacaac gacgaaaacc aaacagttac aacaaccaca    180
acaggaggag aagaagaaat aataaacaat aaagaaccga tgttcgagaa gccgctaacc    240
ccgagcgacg tgggaagct  gaaccgcctc gtaatcccga agcagcacgc tgagaagtac    300
tttccactga gtggtggtga ctcgggcagt agcgagtgca aggggctgtt actgagtttc    360
gaggacgagt cggggaagtg ctggcgcttc cgctactcgt actggaacag cagccagagc    420
tacgtgctca ccaaagggtg gagccgttac gtgaaggaca agcgcctcga tgcgggagat    480
gtcgttttat tccagcgcca ccgcgccgac gcgcagcgcc tcttcatcgg ctggaggcgc    540
aggcggcaga gcgacgcect gccgccgcct gcgcacgtta gcagcaggaa gagtggtggt    600
gatgggaata gtagtaagaa tgagggtgat gtgggcgtgg gctggaccag agggttctat    660
cctgcgcatc atccttatcc tacgcatcat catcatccct cgccatacca tcaccaacaa    720
gatgactctc ttcatgcagt tagagggtcc caaggtcaga accaaaggac gagaccagtg    780
ggaaacagca gttctagttc gagttcgagt tcaagggtac ttaggctatt cggggtcaac    840
atggaatgcc aacccgaaca tgatgattct ggaccctcca caccccaatg ctcctacaat    900
actaacaaca tattgccatc cacacagggc acagatattc attcccatct caatttctac    960
caacaacaac aaacttctaa ttccaagcct ccccctcatc acatgatgat acgtcaccaa   1020
ccatactact actag                                                   1035
```

<210> SEQ ID NO 67
<211> LENGTH: 288
<212> TYPE: PRT
<213> ORGANISM: Glycine max

<400> SEQUENCE: 67

```
Met Ser Ser Ile Asn His Tyr Ser Pro Glu Thr Thr Leu Tyr Trp Thr
1               5                   10                  15

Asn Asp Gln Gln Gln Gln Ala Ala Met Trp Leu Ser Asn Ser His Thr
            20                  25                  30

Pro Arg Phe Asn Leu Asn Asp Glu Glu Glu Glu Glu Asp Asp Val
        35                  40                  45

Ile Val Ser Asp Lys Ala Thr Asn Asn Leu Thr Gln Glu Glu Glu Lys
    50                  55                  60

Val Ala Met Phe Glu Lys Pro Leu Thr Pro Ser Asp Val Gly Lys Leu
65                  70                  75                  80

Asn Arg Leu Val Ile Pro Lys Gln His Ala Glu Lys His Phe Pro Leu
                85                  90                  95

Asp Ser Ser Ala Ala Lys Gly Leu Leu Leu Ser Phe Glu Asp Glu Ser
            100                 105                 110

Gly Lys Cys Trp Arg Phe Arg Tyr Ser Tyr Trp Asn Ser Ser Gln Ser
        115                 120                 125

Tyr Val Leu Thr Lys Gly Trp Ser Arg Tyr Val Lys Asp Lys Arg Leu
    130                 135                 140

His Ala Gly Asp Val Val Leu Phe His Arg His Arg Ser Leu Pro Gln
145                 150                 155                 160

Arg Phe Phe Ile Ser Cys Ser Arg Arg Gln Pro Asn Pro Val Pro Ala
                165                 170                 175

His Val Ser Thr Thr Arg Ser Ser Ala Ser Phe Tyr Ser Ala His Pro
            180                 185                 190

Pro Tyr Pro Ala His His Phe Pro Phe Pro Tyr Gln Pro His Ser Leu
        195                 200                 205
```

```
His Ala Pro Gly Gly Gly Ser Gln Gly Gln Asn Glu Thr Thr Pro Gly
        210                 215                 220
Gly Asn Ser Ser Ser Gly Ser Gly Arg Val Leu Arg Leu Phe Gly
225                 230                 235                 240
Val Asn Met Glu Cys Gln Pro Asp Asn His Asn Asp Ser Gln Asn Ser
                245                 250                 255
Thr Pro Glu Cys Ser Tyr Thr His Leu Tyr His Gln Thr Ser Ser
                260                 265                 270
Tyr Ser Ser Ser Asn Pro His His His Met Val Pro Gln Gln Pro
        275                 280                 285
```

<210> SEQ ID NO 68
<211> LENGTH: 867
<212> TYPE: DNA
<213> ORGANISM: Glycine max

<400> SEQUENCE: 68

```
atgtcatcga taaaccacta ttcaccggaa acaacactat actggaccaa cgaccaacag      60
caacaagccg ccatgtggct gagtaattcc cacaccccgc gtttcaatct gaacgacgag     120
gaggaggagg aggaagacga cgttatcgtt tcggacaagg ctactaataa cttgacgcaa     180
gaggaggaga aggtagccat gttcgagaag ccgttgacgc cgagcgacgt cgggaagctg     240
aaccggctcg tgattccgaa acagcacgcg gagaagcact ccctctcga ctcgtcggcg      300
gcgaaggggc tgttgctgag tttcgaggac gagtccggga agtgttggcg cttccgttac     360
tcttattgga acagtagcca gagttacgtt ttgaccaaag gatggagccg ttacgtcaaa     420
gacaaacgcc tccacgctgg cgacgtcgtt ttgttccaca gacaccgctc cctccctcaa     480
cgcttcttca tctcctgcag ccgccgccaa cccaacccgg tccccgctca cgttagcacc     540
accagatcct ccgcttcctt ctactctgcg cacccacctt atcctgcgca ccacttcccc     600
ttcccatacc aacctcactc tcttcatgca ccaggtggag ggtcccaagg acagaacgaa     660
acgacaccgg gagggaacag tagttcaagt ggcagtggca gggtgctgag gctctttggt     720
gtgaacatgg aatgccaacc tgataatcat aatgattccc agaactccac accagaatgc     780
tcctacaccc acttatacca ccatcaaacc tcttcttatt cttcttcttc aaaccctcac     840
catcacatgg tacctcaaca accataa                                        867
```

<210> SEQ ID NO 69
<211> LENGTH: 420
<212> TYPE: PRT
<213> ORGANISM: Glycine max

<400> SEQUENCE: 69

```
Met Glu Leu Met Gln Gln Val Lys Gly Asn Tyr Ser Asp Ser Arg Glu
1               5                   10                  15
Glu Glu Glu Glu Glu Glu Ala Ala Ile Thr Arg Glu Ser Glu Ser
            20                  25                  30
Ser Arg Leu His Gln Gln Asp Thr Ala Ser Asn Phe Gly Lys Lys Leu
        35                  40                  45
Asp Leu Met Asp Leu Ser Leu Gly Ser Ser Lys Glu Glu Glu Glu Glu
    50                  55                  60
Gly Asn Leu Gln Gln Gly Gly Gly Val Val His Ala His Gln
65                  70                  75                  80
Val Val Glu Lys Glu His Met Phe Glu Lys Val Ala Thr Pro Ser Asp
                85                  90                  95
```

Val Gly Lys Leu Asn Arg Leu Val Ile Pro Lys Gln His Ala Glu Lys
            100                 105                 110

Tyr Phe Pro Leu Asp Ser Ser Thr Asn Glu Lys Gly Leu Leu Leu Asn
        115                 120                 125

Phe Glu Asp Arg Asn Gly Lys Val Trp Arg Phe Arg Tyr Ser Tyr Trp
130                 135                 140

Asn Ser Ser Gln Ser Tyr Val Met Thr Lys Gly Trp Ser Arg Phe Val
145                 150                 155                 160

Lys Glu Lys Lys Leu Asp Ala Gly Asp Ile Val Ser Phe Gln Arg Gly
                165                 170                 175

Leu Gly Asp Leu Tyr Arg His Arg Leu Tyr Ile Asp Trp Lys Arg Arg
            180                 185                 190

Pro Asp His Ala His Ala His Pro His His His Asp Pro Leu Phe
        195                 200                 205

Leu Pro Ser Ile Arg Leu Tyr Ser Leu Pro Pro Thr Met Pro Pro Arg
210                 215                 220

Tyr His His Asp His His Phe His His His Leu Asn Tyr Asn Asn Leu
225                 230                 235                 240

Phe Thr Phe Gln Gln His Gln Tyr Gln Gln Leu Gly Ala Ala Thr Thr
                245                 250                 255

Thr His His Asn Asn Tyr Gly Tyr Gln Asn Ser Gly Ser Gly Ser Leu
            260                 265                 270

Tyr Tyr Leu Arg Ser Ser Met Ser Met Gly Gly Asp Gln Asn Leu
        275                 280                 285

Gln Gly Arg Gly Ser Asn Ile Val Pro Met Ile Ile Asp Ser Val Pro
290                 295                 300

Val Asn Val Ala His His Asn Asn Asn Arg His Gly Asn Gly Gly Ile
305                 310                 315                 320

Thr Ser Gly Gly Thr Asn Cys Ser Gly Lys Arg Leu Arg Leu Phe Gly
                325                 330                 335

Val Asn Met Glu Cys Ala Ser Ser Ala Glu Asp Ser Lys Glu Leu Ser
            340                 345                 350

Ser Gly Ser Ala Ala His Val Thr Thr Ala Ala Ser Ser Ser Leu
        355                 360                 365

His His Gln Arg Leu Arg Val Pro Val Pro Val Pro Leu Glu Asp Pro
370                 375                 380

Leu Ser Ser Ser Ala Ala Ala Ala Arg Phe Gly Asp His Lys Gly
385                 390                 395                 400

Ala Ser Thr Gly Thr Ser Leu Leu Phe Asp Leu Asp Pro Ser Leu Gln
                405                 410                 415

Tyr His Arg His
            420

<210> SEQ ID NO 70
<211> LENGTH: 1263
<212> TYPE: DNA
<213> ORGANISM: Glycine max

<400> SEQUENCE: 70
atggagttga tgcaacaagt taaaggtaat tattctgata gcagggagga agaggaggaa     60
gaggaagctg cagcaatcac aagggaatca gaaagcagca ggttacacca acaagataca    120
gcatccaatt ttggaaagaa gctagacttg atggacttgt cactaggag cagcaaggaa     180 gaggaagagg aagggaattt gcaacaagga ggaggaggag tggttcatca tgctcaccaa    240

```
gtagtggaga aagaacacat gtttgagaaa gtggcgacac cgagcgacgt agggaagctg      300
aacaggctgg tgataccgaa gcagcacgcg gagaagtact tcccccttga ctcctcaacc      360
aacgagaagg gtctgctcct gaatttcgag gacaggaatg ggaaggtgtg gcgattcagg      420
tattcctatt ggaacagcag ccagagctat gtgatgacaa aagggtggag ccgctttgtt      480
aaggagaaga agctggatgc cggtgacatt gtctccttcc agcgtggcct tggggatttg      540
tatagacatc ggttgtatat agattggaag agaaggcccg atcatgctca tgctcatcca      600
cctcatcatc acgatccttt gtttcttccc tctatcagat tgtactctct ccctcccacc      660
atgccacctc gctaccacca cgatcatcac tttcaccacc atctcaatta caacaacctc      720 ttcactttc agcaacacca gtaccagcag cttggtgctg ccactaccac tcatcacaac      780
aactatggtt accagaattc gggatctggt tcactctatt acctaaggtc ctctatgtca      840
atgggtggtg gtgatcaaaa cttgcaaggg agagggagca acattgtccc catgatcatt      900
gattctgtgc cggttaacgt tgctcatcac aacaacaatc gccatgggaa tgggggcatc      960
acgagtggtg gtactaattg tagtggaaaa cgactaaggc tatttggggt gaacatggaa     1020
tgcgcttctt cggcagaaga ttccaaagaa ttgtcctcgg gttcggcagc acacgtgacg     1080
acagctgctt cttcttcttc tcttcatcat cagcgcttga gggtgccagt gccagtgcca     1140
cttgaagatc cactttcgtc gtcagcagca gcagcagcaa ggtttgggga tcacaaaggg     1200
gccagtactg ggacttcgct gctgtttgat ttggatccct ctttgcagta tcatcgccac     1260
tga                                                                   1263
```

<210> SEQ ID NO 71
<211> LENGTH: 384
<212> TYPE: PRT
<213> ORGANISM: Glycine max

<400> SEQUENCE: 71

```
Met Asp Ala Ile Ser Cys Leu Asp Glu Ser Thr Thr Thr Glu Ser Leu
1               5                   10                  15

Ser Ile Ser Gln Ala Lys Pro Ser Ser Thr Ile Met Ser Ser Glu Lys
            20                  25                  30

Ala Ser Pro Ser Pro Pro Pro Asn Arg Leu Cys Arg Val Gly Ser
        35                  40                  45

Gly Ala Ser Ala Val Val Asp Ser Asp Gly Gly Gly Gly Gly Ser
    50                  55                  60

Thr Glu Val Glu Ser Arg Lys Leu Pro Ser Ser Lys Tyr Lys Gly Val
65                  70                  75                  80

Val Pro Gln Pro Asn Gly Arg Trp Gly Ser Gln Ile Tyr Glu Lys His
                85                  90                  95

Gln Arg Val Trp Leu Gly Thr Phe Asn Glu Glu Asp Glu Ala Ala Arg
            100                 105                 110

Ala Tyr Asp Val Ala Val Gln Arg Phe Arg Gly Lys Asp Ala Val Thr
        115                 120                 125

Asn Phe Lys Pro Leu Ser Gly Thr Asp Asp Asp Gly Glu Ser Glu
    130                 135                 140

Phe Leu Asn Ser His Ser Lys Ser Glu Ile Val Asp Met Leu Arg Lys
145                 150                 155                 160

His Thr Tyr Asn Asp Glu Leu Glu Gln Ser Lys Arg Ser Arg Gly Phe
                165                 170                 175

Val Arg Arg Arg Gly Ser Ala Ala Gly Ala Gly Asn Gly Asn Ser Ile
            180                 185                 190
```

Ser Gly Ala Cys Val Met Lys Ala Arg Glu Gln Leu Phe Gln Lys Ala
    195                 200                 205

Val Thr Pro Ser Asp Val Gly Lys Leu Asn Arg Leu Val Ile Pro Lys
    210                 215                 220

Gln His Ala Glu Lys His Phe Pro Leu Gln Ser Ala Ala Asn Gly Val
225                 230                 235                 240

Ser Ala Thr Ala Thr Ala Ala Lys Gly Val Leu Leu Asn Phe Glu Asp
                245                 250                 255

Val Gly Gly Lys Val Trp Arg Phe Arg Tyr Ser Tyr Trp Asn Ser Ser
            260                 265                 270

Gln Ser Tyr Val Leu Thr Lys Gly Trp Ser Arg Phe Val Lys Glu Lys
        275                 280                 285

Asn Leu Lys Ala Gly Asp Thr Val Cys Phe Gln Arg Ser Thr Gly Pro
    290                 295                 300

Asp Arg Gln Leu Tyr Ile Asp Trp Lys Thr Arg Asn Val Val Asn Glu
305                 310                 315                 320

Val Ala Leu Phe Gly Pro Val Val Glu Pro Ile Gln Met Val Arg Leu
                325                 330                 335

Phe Gly Val Asn Ile Leu Lys Leu Pro Gly Ser Asp Ser Ile Ala Asn
            340                 345                 350

Asn Asn Asn Ala Ser Gly Cys Cys Asn Gly Lys Arg Arg Glu Met Glu
        355                 360                 365

Leu Phe Ser Leu Glu Cys Ser Lys Lys Pro Lys Ile Ile Gly Ala Leu
    370                 375                 380

<210> SEQ ID NO 72
<211> LENGTH: 1155
<212> TYPE: DNA
<213> ORGANISM: Glycine max

<400> SEQUENCE: 72
atggatgcaa ttagttgcct ggatgagagc accaccaccg agtcactctc cataagtcag      60
gcgaagcctt cttcgacgat tatgtcgtcc gagaaggctt ctccttcccc gccgccgccg     120
aacaggctgt gccgcgtcgg tagcggtgct agcgcagtcg tggattccga cggcggcggc     180
gggggtggca gcaccgaggt ggagtcgcgg aagctccccct cgtccaagta aagggcgtc     240 gtgccccagc ccaacggccg ctggggctcg cagatttacg agaagcacca gcgcgtgtgg     300
ctgggaacgt tcaacgagga agacgaggcg gcgcgtgcgt acgacgtcgc cgtgcagcga     360
ttccgcggca aggacgccgt cacaaacttc aagccgctct ccggcaccga cgacgacgac     420
ggggaatcgg agtttctcaa ctcgcattcg aaatccgaga tcgtcgacat gctgcgtaag     480
catacgtaca atgacgagct ggaacaaagc aagcgcagcc gcggcttcgt acgtcggcgc     540
ggctccgccg ccggcgccgg aaacggaaac tcaatctccg gcgcgtgtgt tatgaaggcg     600
cgtgagcagc tattccagaa ggccgttacg ccgagcgacg ttgggaaact gaaccgtttg     660
gtgataccga agcagcacgc ggagaagcac tttcctttac agagcgctgc taacggcgtt     720
agcgcgacgg cgacggcggc gaagggcgtt ttgttgaact tcgaagacgt tggagggaaa     780
gtgtggcggt tcgttactc gtattggaac agtagccaga gttacgtctt gaccaaaggt     840
tggagccggt tcgttaagga agaatctg aaagccggtg acacggtttg ttttcaacgg     900
tccactggac cggacaggca gctttacatc gattggaaga cgaggaatgt tgttaacgag     960
gtcgcgttgt tcggaccggt tgtcgaaccg atccagatgg ttcggctctt tggtgttaac    1020

-continued

```
attttgaaac tacccggttc agattctatc gccaataaca ataatgcaag tgggtgctgc   1080
aatggcaaga gaagagaaat ggaactcttt tcattagagt gtagcaagaa acctaagatt   1140
attggtgctt tgtag                                                    1155
```

<210> SEQ ID NO 73
<211> LENGTH: 491
<212> TYPE: PRT
<213> ORGANISM: Glycine max

<400> SEQUENCE: 73

```
Met Glu Leu Met Gln Glu Val Lys Gly Tyr Ser Asp Gly Arg Glu Glu
1               5                   10                  15

Glu Glu Glu Glu Glu Ala Ala Glu Glu Ile Ile Thr Arg Glu Glu
            20                  25                  30

Ser Ser Arg Leu Leu His Gln His Gln Glu Ala Ala Gly Ser Asn Phe
        35                  40                  45

Ile Ile Asn Asn Asn His His His Gln His His His His Thr
    50                  55                  60

Thr Lys Gln Leu Asp Phe Met Asp Leu Ser Leu Gly Ser Ser Lys Asp
65                  70                  75                  80

Glu Gly Asn Leu Gln Gly Ser Ser Ser Val Tyr Ala His His His
                85                  90                  95

His Ala Ala Ser Ala Ser Ser Ser Ala Asn Gly Asn Asn Asn Asn Ser
            100                 105                 110

Ser Ser Ser Asn Leu Gln Gln Gln Gln Gln Gln Pro Ala Glu Lys Glu
        115                 120                 125

His Met Phe Asp Lys Val Val Thr Pro Ser Asp Val Gly Lys Leu Asn
    130                 135                 140

Arg Leu Val Ile Pro Lys Gln His Ala Glu Lys Tyr Phe Pro Leu Asp
145                 150                 155                 160

Ser Ser Ala Asn Glu Lys Gly Leu Leu Leu Asn Phe Glu Asp Arg Asn
                165                 170                 175

Gly Lys Leu Trp Arg Phe Arg Tyr Ser Tyr Trp Asn Ser Ser Gln Ser
            180                 185                 190

Tyr Val Met Thr Lys Gly Trp Ser Arg Phe Val Lys Glu Lys Lys Leu
        195                 200                 205

Asp Ala Gly Asp Met Val Ser Phe Gln Arg Gly Val Gly Glu Leu Tyr
    210                 215                 220

Arg His Arg Leu Tyr Ile Asp Trp Trp Arg Arg Pro Asp His His His
225                 230                 235                 240

His His His His Gly Pro Asp His Ser Thr Thr Leu Phe Thr Pro Phe
                245                 250                 255

Leu Ile Pro Asn Gln Pro His His Leu Met Ser Ile Arg Trp Gly Ala
            260                 265                 270

Thr Gly Arg Leu Tyr Ser Leu Pro Ser Pro Thr Pro Arg His His
        275                 280                 285

Glu His Leu Asn Tyr Asn Asn Asn Ala Met Tyr His Pro Phe His His
    290                 295                 300

His Gly Ala Gly Ser Gly Ile Asn Ala Thr Thr His Tyr Asn Asn
305                 310                 315                 320

Tyr His Glu Met Ser Ser Thr Thr Thr Ser Gly Ser Ala Gly Ser Val
                325                 330                 335

Phe Tyr His Arg Ser Thr Pro Pro Ile Ser Met Pro Leu Ala Asp His
            340                 345                 350
```

```
Gln Thr Leu Asn Thr Arg Gln Gln Gln Gln Gln Gln Gln Glu
        355                 360                 365

Gly Ala Gly Asn Val Ser Leu Ser Pro Met Ile Ile Asp Ser Val Pro
370                 375                 380

Val Ala His His Leu His His Gln Gln His His Gly Gly Lys Ser Ser
385                 390                 395                 400

Gly Pro Ser Ser Thr Ser Thr Ser Pro Ser Thr Ala Gly Lys Arg Leu
                405                 410                 415

Arg Leu Phe Gly Val Asn Met Glu Cys Ala Ser Ser Thr Ser Glu Asp
                420                 425                 430

Pro Lys Cys Phe Ser Leu Leu Ser Ser Ser Met Ala Asn Ser Asn
        435                 440                 445

Ser Gln Pro Pro Leu Gln Leu Leu Arg Glu Asp Thr Leu Ser Ser Ser
        450                 455                 460

Ser Ala Arg Phe Gly Asp Gln Arg Gly Val Gly Glu Pro Ser Met Leu
465                 470                 475                 480

Phe Asp Leu Asp Pro Ser Leu Gln Tyr Arg Gln
                485                 490

<210> SEQ ID NO 74
<211> LENGTH: 1476
<212> TYPE: DNA
<213> ORGANISM: Glycine max

<400> SEQUENCE: 74
atggagttga tgcaagaagt gaaagggtat tctgatggca gagaggagga ggaggaggaa    60
gaggaagcag cagaagaaat catcacaaga gaagaaagca gcaggttgtt acaccagcac   120
caggaggcag caggttccaa tttcatcatc aacaataatc atcatcatca tcaacatcac   180
caccaccaca caacaaagca gctagacttc atggacttgt cacttggtag cagcaaggat   240
gaagggaatt gcaaggatc atcttcttct gtctatgctc atcatcatca tgcagcaagt   300
gctagttctt ctgccaatgg taacaacaac aacagcagca gcagcaactt gcagcaacag   360
cagcagcagc ctgctgagaa ggagcacatg tttgataaag tagtgacacc aagtgatgtg   420
gggaagctga accggttggt gataccaaag cagcatgctg agaagtattt ccctcttgat   480
tcctcagcca atgagaaggg tctgttgctg aattttgagg acaggaatgg taagttgtgg   540
aggttcaggt actcctattg aacagcagca cagagctatg tgatgaccaa aggttggagc   600
cgttttgtta aggagaagaa gcttgatgct ggtgacatgg tgtccttcca gcgtggtgtt   660
ggggagttgt ataggcatag gttgtacata gattggtgga aaggcctga tcatcatcac   720 catcaccatc atggccctga ccattcaacc acactcttca ccctttcttc aattcccaat   780
cagcctcatc acttaatgtc catcagatgg ggtgccactg gcagattgta ctccctccct   840
tccccaaccc caccacgcca ccatgaacac ctcaattaca caataacgc catgtatcat   900 cccttcatc accatggtgc tggaagtgga attaatgcta ctactcatca ctacaacaac   960
tatcatgaga tgagtagtac tactacttca ggatctgcag gctcagtctt ttaccacagg  1020 tcaacaccc caatatcaat gccattggct gaccaccaaa ccttgaacac aaggcagcag  1080
caacaacaac aacaacaaca agagggagct ggcaatgttt ctctttcccc tatgatcatt  1140
gattctgttc cagttgctca ccacctccat catcaacaac accatggtgg caagagtagt  1200
ggtcctagta gtactagtac tagtcctagc actgcaggga aaagactaag gctatttggg  1260
gtcaacatgg aatgtgcttc ttcaacatca gaagacccca aatgcttcag cttgttgtcc  1320
```
tcatcttcaa tggctaattc caattcacaa ccaccacttc agcttttgag ggaagataca    1380
ctttcgtcat catcggcaag gtttggggat cagagaggag tagggaacc ttcaatgctt    1440 tttgatctgg acccttcttt gcaataccgg cagtga                              1476

<210> SEQ ID NO 75
<211> LENGTH: 351
<212> TYPE: PRT
<213> ORGANISM: Glycine max

<400> SEQUENCE: 75

```
Met Asp Gly Gly Cys Val Thr Asp Glu Thr Thr Ser Ser Asp Ser
1               5                   10                  15

Leu Ser Val Pro Pro Ser Arg Val Gly Ser Val Ala Ser Ala Val
                20                  25                  30

Val Asp Pro Asp Gly Cys Cys Val Ser Gly Glu Ala Glu Ser Arg Lys
                35                  40                  45

Leu Pro Ser Ser Lys Tyr Lys Gly Val Val Pro Gln Pro Asn Gly Arg
 50                  55                  60

Trp Gly Ala Gln Ile Tyr Glu Lys His Gln Arg Val Trp Leu Gly Thr
 65                  70                  75                  80

Phe Asn Glu Glu Asp Glu Ala Ala Arg Ala Tyr Asp Ile Ala Ala Leu
                85                  90                  95

Arg Phe Arg Gly Pro Asp Ala Val Thr Asn Phe Lys Pro Ala Ala
                100                 105                 110

Ser Asp Asp Ala Glu Ser Glu Phe Leu Asn Ser His Ser Lys Phe Glu
                115                 120                 125

Ile Val Asp Met Leu Arg Lys His Thr Tyr Asp Asp Glu Leu Gln Gln
130                 135                 140

Ser Thr Arg Gly Gly Arg Arg Leu Asp Ala Asp Thr Ala Ser Ser
145                 150                 155                 160

Gly Val Phe Asp Ala Lys Ala Arg Glu Gln Leu Phe Glu Lys Thr Val
                165                 170                 175

Thr Pro Ser Asp Val Gly Lys Leu Asn Arg Leu Val Ile Pro Lys Gln
                180                 185                 190

His Ala Glu Lys His Phe Pro Leu Ser Gly Ser Gly Asp Glu Ser Ser
                195                 200                 205

Pro Cys Val Ala Gly Ala Ser Ala Ala Lys Gly Met Leu Leu Asn Phe
                210                 215                 220

Glu Asp Val Gly Gly Lys Val Trp Arg Phe Arg Tyr Ser Tyr Trp Asn
225                 230                 235                 240

Ser Ser Gln Ser Tyr Val Leu Thr Lys Gly Trp Ser Arg Phe Val Lys
                245                 250                 255

Glu Lys Asn Leu Arg Ala Gly Asp Ala Val Gln Phe Phe Lys Ser Thr
                260                 265                 270

Gly Pro Asp Arg Gln Leu Tyr Ile Asp Cys Lys Ala Arg Ser Gly Glu
                275                 280                 285

Val Asn Asn Asn Ala Gly Gly Leu Phe Val Pro Ile Gly Pro Val Val
                290                 295                 300

Glu Pro Val Gln Met Val Arg Leu Phe Gly Val Asn Leu Leu Lys Leu
305                 310                 315                 320

Pro Val Pro Gly Ser Asp Gly Val Gly Lys Arg Lys Glu Met Glu Leu
                325                 330                 335

Phe Ala Phe Glu Cys Cys Lys Lys Leu Lys Val Ile Gly Ala Leu
```

<210> SEQ ID NO 76
<211> LENGTH: 1056
<212> TYPE: DNA
<213> ORGANISM: Glycine max

<400> SEQUENCE: 76

```
atggatggag gctgtgtcac agacgaaacc accacatcca gcgactctct ttccgttccg      60
ccgcccagcc gcgtcggcag cgttgcaagc gccgtcgtcg accccgacgg ttgttgcgtt     120
tccggcgagg ccgaatcccg gaaactccct tcgtcgaaat acaaaggcgt ggtgccgcaa     180
ccgaacggtc gctggggagc tcagatttac gagaagcacc agcgcgtgtg gctcggcact     240
ttcaacgagg aagacgaagc cgccagagcc tacgacatcg ccgcgctgcg cttccgcggc     300
cccgacgccg tcaccaactt caagcctccc gccgcctccg acgacgccga gtccgagttc     360
ctcaactcgc attccaagtt cgagatcgtc gacatgctcc gcaagcacac ctacgacgac     420
gagctccagc agagcacgcg cggtggtagg cgccgcctcg acgctgacac cgcgtcgagc     480
ggtgtgttcg acgcgaaagc gcgtgagcag ctgttcgaga aacggttac gccgagcgac     540
gtcgggaagc tgaatcgatt agtgataccg aagcagcacg cggagaagca ctttccgtta     600
agcggatccg cgacgaaaag ctcgccgtgc gtggcggggg cttcggcggc aagggaatg     660
ttgttgaact tgaggacgt tggagggaaa gtgtggcggt tcgttactc ttattggaac     720
agtagccaga gctacgtgct taccaaagga tggagccggt tcgttaagga agaatcctt     780
cgagccggtg acgcggttca gttcttcaag tcgaccggac cggaccggca gctatatata     840
gactgcaagg cgaggagtgg tgaggttaac aataatgctg gcggtttgtt tgttccgatt     900
ggaccggtcg ttgagccggt tcagatggtt cggcttttcg gggtcaacct tttgaaacta     960
cccgtacccg gttcggatgg tgtagggaag agaaaagaga tggaactgtt tgcatttgaa    1020
tgttgcaaga agttaaaagt aattggagct ttgtaa                              1056
```

<210> SEQ ID NO 77
<211> LENGTH: 401
<212> TYPE: PRT
<213> ORGANISM: Glycine max

<400> SEQUENCE: 77

```
Met Asp Ala Ile Ser Cys Met Asp Glu Ser Thr Thr Thr Glu Ser Leu
1               5                   10                  15

Ser Ile Ser Leu Ser Pro Thr Ser Ser Glu Lys Ala Lys Pro Ser
            20                  25                  30

Ser Met Ile Thr Ser Ser Glu Lys Val Ser Leu Ser Pro Pro Pro Ser
        35                  40                  45

Asn Arg Leu Cys Arg Val Gly Ser Ala Ser Ala Val Val Asp Pro
    50                  55                  60

Asp Gly Gly Gly Ser Gly Ala Glu Val Glu Ser Arg Lys Leu Pro Ser
65                  70                  75                  80

Ser Lys Tyr Lys Gly Val Val Pro Gln Pro Asn Gly Arg Trp Gly Ala
                85                  90                  95

Gln Ile Tyr Glu Lys His Gln Arg Val Trp Leu Gly Thr Phe Asn Glu
            100                 105                 110

Glu Asp Glu Ala Ala Arg Ala Tyr Asp Ile Ala Ala Gln Arg Phe Arg
        115                 120                 125

Gly Lys Asp Ala Val Thr Asn Phe Lys Pro Leu Ala Gly Ala Asp Asp
```

```
                130             135             140
Asp Asp Gly Glu Ser Glu Phe Leu Asn Ser His Ser Lys Pro Glu Ile
145                 150                 155                 160

Val Asp Met Leu Arg Lys His Thr Tyr Asn Asp Glu Leu Glu Gln Ser
                165                 170                 175

Lys Arg Ser Arg Gly Val Val Arg Arg Gly Ser Ala Ala Ala Gly
                180                 185                 190

Thr Ala Asn Ser Ile Ser Gly Ala Cys Phe Thr Lys Ala Arg Glu Gln
                195                 200                 205

Leu Phe Glu Lys Ala Val Thr Pro Ser Asp Val Gly Lys Leu Asn Arg
210                 215                 220

Leu Val Ile Pro Lys Gln His Ala Glu Lys His Phe Pro Leu Gln Ser
225                 230                 235                 240

Ser Asn Gly Val Ser Ala Thr Thr Ile Ala Ala Val Thr Ala Thr Pro
                245                 250                 255

Thr Ala Ala Lys Gly Val Leu Leu Asn Phe Glu Asp Val Gly Gly Lys
                260                 265                 270

Val Trp Arg Phe Arg Tyr Ser Tyr Trp Asn Ser Ser Gln Ser Tyr Val
                275                 280                 285

Leu Thr Lys Gly Trp Ser Arg Phe Val Lys Glu Lys Asn Leu Lys Ala
                290                 295                 300

Gly Asp Thr Val Cys Phe His Arg Ser Thr Gly Pro Asp Lys Gln Leu
305                 310                 315                 320

Tyr Ile Asp Trp Lys Thr Arg Asn Val Val Asn Asn Glu Val Ala Leu
                325                 330                 335

Phe Gly Pro Val Gly Pro Val Val Glu Pro Ile Gln Met Val Arg Leu
                340                 345                 350

Phe Gly Val Asn Ile Leu Lys Leu Pro Gly Ser Asp Thr Ile Val Gly
                355                 360                 365

Asn Asn Asn Ala Ser Gly Cys Cys Asn Gly Lys Arg Arg Glu Met
                370                 375                 380

Glu Leu Phe Ser Leu Glu Cys Ser Lys Lys Pro Lys Ile Ile Gly Ala
385                 390                 395                 400

Leu

<210> SEQ ID NO 78
<211> LENGTH: 1206
<212> TYPE: DNA
<213> ORGANISM: Glycine max

<400> SEQUENCE: 78
atggatgcaa ttagttgcat ggatgagagc accaccactg agtcactctc tataagtctt    60
tctccgacgt catcgtcgga gaaagcgaag ccttcttcga tgattacatc gtcggagaag   120
gtttctctgt ccccgccgcc gtcaaacaga ctatgccgtg ttggaagcgg cgcgagcgca   180
gtcgtggatc ctgatggcgg cggcagcggc gctgaggtag agtcgcggaa actcccctcg   240
tcgaagtaca agggcgtggt gccccagccc aacggccgct ggggtgcgca gatttacgag   300
aagcaccagc gcgtgtggct tggaacgttc aacgaggaag acgaggcggc gcgtgcgtac   360
gacatcgccg cgcagcggtt ccgcggcaag gacgccgtca cgaacttcaa gccgctcgcc   420
ggcgccgacg acgacgacgg agaatcggag tttctcaact cgcattccaa acccgagatc   480
gtcgacatgc tgcgaaagca cacgtacaat gacgagctgg agcagagcaa gcgcagccgc   540
ggcgtcgtcc ggcggcgagg ctccgccgcc gccggcaccg caaactcaat tccggcgcg    600
```

```
tgctttacta aggcacgtga gcagctattc gagaaggctg ttacgccgag cgacgttggg    660
aaattgaacc gtttggtgat accgaagcag cacgcggaga agcactttcc gttacagagc    720
tctaacggcg ttagcgcgac gacgatagcg gcggtgacgg cgacgccgac ggcggcgaag    780
ggcgttttgt tgaacttcga agacgttgga gggaaagtgt ggcggtttcg ttactcgtat    840
tggaacagta gccagagtta cgtcttaacc aaaggttgga gccggttcgt taaggagaag    900
aatctgaaag ctggtgacac ggtttgtttt caccggtcca ctggaccgga caagcagctt    960
tacatcgatt ggaagacgag gaatgttgtt aacaacgagg tcgcgttgtt cggaccggtc   1020
ggaccggttg tcgaaccgat ccagatggtt cggctctttg gggttaacat tttgaaacta   1080
cccggttcag atactattgt tggcaataac aataatgcaa gtgggtgctg caatggcaag   1140
agaagagaaa tggaactgtt ctcgttagag tgtagcaaga aacctaagat tattggtgct   1200
ttgtaa                                                              1206
```

<210> SEQ ID NO 79
<211> LENGTH: 362
<212> TYPE: PRT
<213> ORGANISM: Glycine max

<400> SEQUENCE: 79

```
Met Asp Gly Gly Ser Val Thr Asp Glu Thr Thr Thr Ser Asn Ser
1               5                   10                  15

Leu Ser Val Pro Ala Asn Leu Ser Pro Pro Leu Ser Leu Val Gly
                20                  25                  30

Ser Gly Ala Thr Ala Val Val Tyr Pro Asp Gly Cys Cys Val Ser Gly
            35                  40                      45

Glu Ala Glu Ser Arg Lys Leu Pro Ser Ser Lys Tyr Lys Gly Val Val
50                  55                      60

Pro Gln Pro Asn Gly Arg Trp Gly Ala Gln Ile Tyr Glu Lys His Gln
65                      70                  75                  80

Arg Val Trp Leu Gly Thr Phe Asn Glu Glu Asp Ala Ala Arg Ala
                85                  90                  95

Tyr Asp Ile Ala Ala His Arg Phe Arg Gly Arg Asp Ala Val Thr Asn
            100                 105                     110

Phe Lys Pro Leu Ala Gly Ala Asp Asp Ala Glu Ala Glu Phe Leu Ser
        115                 120                 125

Thr His Ser Lys Ser Glu Ile Val Asp Met Leu Arg Lys His Thr Tyr
    130                 135                 140

Asp Asn Glu Leu Gln Gln Ser Thr Arg Gly Arg Arg Arg Arg Asp
145                 150                 155                 160

Ala Glu Thr Ala Ser Ser Gly Ala Phe Asp Ala Lys Ala Arg Glu Gln
                165                 170                 175

Leu Phe Glu Lys Thr Val Thr Gln Ser Asp Val Gly Lys Leu Asn Arg
            180                 185                 190

Leu Val Ile Pro Lys Gln His Ala Glu Lys His Phe Pro Leu Ser Gly
        195                 200                 205

Ser Gly Gly Gly Ala Leu Pro Cys Met Ala Ala Ala Gly Ala Lys
    210                 215                 220

Gly Met Leu Leu Asn Phe Glu Asp Val Gly Gly Lys Val Trp Arg Phe
225                 230                 235                 240

Arg Tyr Ser Tyr Trp Asn Ser Gln Ser Tyr Val Leu Thr Lys Gly
                245                 250                 255
```

```
Trp Ser Arg Phe Val Lys Glu Lys Asn Leu Arg Ala Gly Asp Ala Val
            260                 265                 270

Gln Phe Phe Lys Ser Thr Gly Leu Asp Arg Gln Leu Tyr Ile Asp Cys
        275                 280                 285

Lys Ala Arg Ser Gly Lys Val Asn Asn Asn Ala Gly Leu Phe Ile
    290                 295                 300

Pro Val Gly Pro Val Val Glu Pro Val Gln Met Val Arg Leu Phe Gly
305                 310                 315                 320

Val Asp Leu Leu Lys Leu Pro Val Pro Gly Ser Asp Gly Ile Gly Val
                325                 330                 335

Gly Cys Asp Gly Lys Arg Lys Glu Met Glu Leu Phe Ala Phe Glu Cys
            340                 345                 350

Ser Lys Lys Leu Lys Val Ile Gly Ala Leu
            355                 360

<210> SEQ ID NO 80
<211> LENGTH: 1089
<212> TYPE: DNA
<213> ORGANISM: Glycine max

<400> SEQUENCE: 80
atggatggag gcagtgtcac agacgaaacc accacaacca gcaactctct ttcggttccg      60
gcgaatctat ctccgccgcc tctcagcctt gtcggcagcg gcgcaaccgc cgtcgtctac     120
cccgacggtt gttgcgtctc cggcgaagcc gaatcccgga actcccgtc ctcgaaatac      180 aaaggcgtgg tgccgcaacc gaacggtcgt tggggagctc agatttacga aagcaccag      240 cgcgtgtggc tcggcacctt caacgaggaa gacgaagccg ccagagccta cgacatcgcc     300
gcgcatcgct ccgcggccg cgacgccgtc actaacttca gcctctcgc cggcgccgac      360 gacgccgaag ccgagttcct cagcacgcat tccaagtccg agatcgtcga catgctccgc     420
aagcacacct acgacaacga gctccagcag agcacccgcg gcggcaggcg ccgccgggac     480
gccgaaaccg cgtcgagcgg cgcgttcgac gcgaaggcgc gtgagcagct gttcgagaaa     540
accgttacgc agagcgacgt cgggaagctg aaccgattag tgataccaaa gcagcacgcg     600
gagaagcact ttccgttaag cggatccggc ggcggagcct tgccgtgcat ggcggcggct     660 gcggggggcga agggaatgtt gctgaacttt gaggacgttg gagggaaagt gtggcggttc     720
cgttactcgt attggaacag tagccagagc tacgtgctta ccaaaggatg gagccggttc     780
gttaaggaga agaatcttcg agctggtgac gcggttcagt tcttcaagtc gaccggactg     840
gaccggcaac tatatatag ctgcaaggcg aggagtggta aggttaacaa taatgctgcc      900
ggtttgttta ttccggttgg accggttgtt gagccggttc agatggtacg gcttttcggg     960
gtcgaccttt tgaaactacc cgtacccggt tcggatggta ttggggttgg ctgtgacggg    1020
aagagaaaag agatggagct gtttgcattt gaatgtagca agaagttaaa agtaattgga    1080
gctttgtaa                                                            1089

<210> SEQ ID NO 81
<211> LENGTH: 347
<212> TYPE: PRT
<213> ORGANISM: Glycine max

<400> SEQUENCE: 81

Met Ile Gly Val Glu Lys Val Thr Ile Cys Met Arg Ile Glu Val Asn
1               5                   10                  15

Thr Glu Lys Gly Arg Arg Ala Leu Met Asp Cys Trp Gln Ile Ser Gly
```

|  |  | 20 |  |  | 25 |  |  | 30 |  |  |  |
|---|---|---|---|---|---|---|---|---|---|---|---|
| Val | His | Glu | Ser | Ser | Asp | Cys | Ser | Glu | Ile | Lys | Phe Ala Phe Asp Ala |

Val Val Lys Arg Ala Arg His Glu Glu Asn Asn Ala Ala Ala Gln Lys
  50                          55                  60

Phe Lys Gly Val Val Ser Gln Gln Asn Gly Asn Trp Gly Ala Gln Ile
65                        70                      75                        80

Tyr Ala His Gln Gln Arg Ile Trp Leu Gly Thr Phe Lys Ser Glu Arg
                      85                      90                      95

Glu Ala Ala Met Ala Tyr Asp Ser Ala Ser Ile Lys Leu Arg Ser Gly
              100                   105                 110

Glu Cys His Arg Asn Phe Pro Trp Asn Asp Gln Thr Val Gln Glu Pro
              115                   120                 125

Gln Phe Gln Ser His Tyr Ser Ala Glu Thr Val Leu Asn Met Ile Arg
              130                   135                 140

Asp Gly Thr Tyr Pro Ser Lys Phe Ala Thr Phe Leu Lys Thr Arg Gln
145                        150                      155                      160

Thr Gln Lys Gly Val Ala Lys His Ile Gly Leu Lys Gly Asp Asp Glu
              165                   170                 175

Glu Gln Phe Cys Cys Thr Gln Leu Phe Gln Lys Glu Leu Thr Pro Ser
              180                   185                 190

Asp Val Gly Lys Leu Asn Arg Leu Val Ile Pro Lys Lys His Ala Val
              195                   200                 205

Ser Tyr Phe Pro Tyr Val Gly Gly Ser Ala Asp Glu Ser Gly Ser Val
              210                   215                 220

Asp Val Glu Ala Val Phe Tyr Asp Lys Leu Met Arg Leu Trp Lys Phe
225                        230                      235                      240

Arg Tyr Cys Tyr Trp Lys Ser Ser Gln Ser Tyr Val Phe Thr Arg Gly
              245                   250                 255

Trp Asn Arg Phe Val Lys Asp Lys Lys Leu Lys Ala Lys Asp Val Ile
              260                   265                 270

Ala Phe Phe Thr Trp Gly Lys Ser Gly Gly Glu Gly Glu Ala Phe Ala
              275                   280                 285

Leu Ile Asp Val Ile Tyr Asn Asn Asn Ala Glu Glu Asp Ser Lys Gly
              290                   295                 300

Asp Thr Lys Gln Val Leu Gly Asn Gln Leu Gln Leu Ala Gly Ser Glu
305                        310                      315                      320

Glu Gly Glu Asp Glu Asp Ala Asn Ile Gly Lys Asp Phe Asn Ala Gln
              325                   330                 335

Lys Gly Leu Arg Leu Phe Gly Val Cys Ile Thr
              340                   345

<210> SEQ ID NO 82
<211> LENGTH: 1044
<212> TYPE: DNA
<213> ORGANISM: Glycine max

<400> SEQUENCE: 82

```
atgattggag ttgagaaagt gacaatttgt atgagaatag aggtgaatac tgaaaaggga    60
agaagggctt taatggactg ttggcaaata tcaggagttc atgaaagttc agattgtagc   120
gaaatcaaat ttgcattcga cgcagtagta aaacgcgcga ggcatgaaga gaataatgca   180
gcagcacaga agttcaaagg cgttgtgtct caacaaaatg ggaactgggg tgcacagata   240
tatgcacacc agcagagaat ctggttgggg accttcaaat ctgaaagaga ggctgcaatg   300
```

```
gcttatgaca gcgccagcat aaaacttaga agcggagagt gccacagaaa ctttccatgg    360
aacgaccaaa cagttcaaga gcctcagttc caaagccatt acagcgcaga aacagtgcta    420
aacatgatta gagatggcac ctatccatca aaatttgcta catttctcaa aactcgtcaa    480
acccaaaaag gcgttgcgaa acacataggt ctgaagggtg atgacgagga acagttttgt    540
tgcacccaac ttttcagaa ggaattaaca ccaagtgatg tgggcaagct caacaggctt    600
gtcatcccaa agaagcatgc agttagctat tttccttacg ttggtggcag tgctgatgag    660
agtggtagtg ttgacgtgga ggctgtgttt tatgacaaac tcatgcgatt gtggaagttc    720
cgatactgct attggaagag cagccaaagt tacgtgttca ccagaggctg aatcggtttt    780
gtgaaggata agaagttgaa ggctaaagat gtcattgcgt tttttacgtg gggaaaaagt    840
ggaggagagg gagaagcttt tgcattgatc gatgtaattt ataataataa tgcagaagaa    900
gacagcaagg gagacaccaa acaagttttg ggaaaccaat tacaattagc tggcagtgaa    960
gaaggtgaag atgaagatgc aaacattgga aaggatttca atgcacaaaa gggtctgagg   1020
ctctttggtg tgtgtatcac ctaa                                          1044
```

<210> SEQ ID NO 83
<211> LENGTH: 409
<212> TYPE: PRT
<213> ORGANISM: Hordeum vulgare

<400> SEQUENCE: 83

```
Met Glu Phe Thr Ala Thr Ser Ser Arg Phe Ser Lys Gly Glu Glu
 1               5                  10                  15

Val Glu Glu Glu Gln Glu Ala Ser Met Arg Glu Ile Pro Phe Met
                20                  25                  30

Thr Pro Ala Ala Thr Cys Ala Ala Pro Ser Ala Ser Ala
                35                  40                  45

Ser Ala Ser Thr Pro Ala Ser Ala Ser Gly Ser Ser Pro Pro Phe Arg
 50                  55                  60

Ser Gly Asp Asp Ala Gly Ala Ser Gly Ser Gly Ala Gly Asp Gly Ser
 65                  70                  75                  80

Arg Ser Asn Val Ala Glu Ala Val Glu Lys Glu His Met Phe Asp Lys
                 85                  90                  95

Val Val Thr Pro Ser Asp Val Gly Lys Leu Asn Arg Leu Val Ile Pro
                100                 105                 110

Lys Gln Tyr Ala Glu Lys Tyr Phe Pro Leu Asp Ser Ala Ala Asn Glu
            115                 120                 125

Lys Gly Leu Leu Leu Asn Phe Glu Asp Ser Ala Gly Lys Pro Trp Arg
130                 135                 140

Phe Arg Tyr Ser Tyr Trp Asn Ser Ser Gln Ser Tyr Val Met Thr Lys
145                 150                 155                 160

Gly Trp Ser Arg Phe Val Lys Glu Lys Arg Leu Asp Ala Gly Asp Thr
                165                 170                 175

Val Ser Phe Ser Arg Gly Ala Gly Glu Ala Ala Arg His Arg Leu Phe
            180                 185                 190

Ile Asp Trp Lys Arg Arg Ala Asp Thr Arg Asp Pro Leu Arg Leu Pro
        195                 200                 205

Arg Leu Pro Leu Pro Met Pro Leu Thr Ser His Tyr Ser Pro Trp Gly
    210                 215                 220

Leu Gly Ala Gly Ala Arg Gly Phe Phe Met Pro Pro Ser Pro Pro Ala
225                 230                 235                 240
```

```
Thr Leu Tyr Glu His Arg Leu Arg Gln Gly Phe Asp Phe Arg Gly Met
                245                 250                 255
Asn Pro Ser Tyr Pro Thr Met Gly Arg Gln Val Ile Leu Phe Gly Ser
            260                 265                 270
Ala Ala Arg Met Pro Pro His Gly Pro Ala Pro Leu Leu Val Pro Arg
        275                 280                 285
Pro Pro Pro Leu His Phe Thr Val Gln Gln Gln Gly Ser Asp Ala
    290                 295                 300
Gly Gly Ser Val Thr Ala Gly Ser Pro Val Val Leu Asp Ser Val Pro
305                 310                 315                 320
Val Ile Glu Ser Pro Thr Thr Ala Thr Lys Lys Arg Val Arg Leu Phe
                325                 330                 335
Gly Val Asn Leu Asp Asn Pro Gln His Pro Gly Asp Gly Gly Gly Glu
            340                 345                 350
Ser Ser Asn Tyr Gly Ser Ala Leu Pro Leu Gln Met Pro Ala Ser Ala
        355                 360                 365
Trp Arg Pro Arg Asp His Thr Leu Arg Leu Leu Glu Phe Pro Ser His
    370                 375                 380
Gly Ala Glu Ala Ser Ser Pro Ser Ser Ser Ser Ser Lys Arg Glu
385                 390                 395                 400
Ala His Ser Gly Leu Asp Leu Asp Leu
                405

<210> SEQ ID NO 84
<211> LENGTH: 1230
<212> TYPE: DNA
<213> ORGANISM: Hordeum vulgare

<400> SEQUENCE: 84
atggagttta ctgcgacaag cagtaggttt tctaaaggag aggaggaggt ggaggaggag      60
caggaggagg cgtcgatgcg cgagatccct ttcatgacgc ccgcggccgc cacctgcgcc     120
gcggcgccgc cttctgcttc tgcgtcggcc tcgacacccg cgtcagcgtc tggaagtagc     180
cctccctttc gatctgggga tgacgccgga gcgtcgggga gcggggccgg cgacggcagc     240
cgcagcaacg tggcggaggc cgtggagaag gagcacatgt tcgacaaagt ggtgacgccg     300
agcgacgtgg ggaagcttaa ccggctggtc atccccaagc agtacgccga agtacttc     360
ccgctggact cggcggccaa cgagaagggc cttctgctca acttcgagga cagcgccggg     420
aagccatggc gcttccgcta ttcctactgg aacagcagcc agagctacgt catgaccaaa     480
ggctggagcc gcttcgtcaa ggagaagcgc ctcgacgctg ggacaccgt ctccttctcc     540
cgcggcgccg gtgaggccgc gcgccaccgc ctcttcatcg actggaagcg ccgagccgac     600
accagagacc cgctccgctt gccccgcctc ccgctcccga tgccgctgac gtcgcactac     660
agcccgtggg gcctcggcgc cggcgccaga ggattcttca tgcctccctc gccgccagcc     720
acgctctacg agcaccgtct ccgtcaaggc ttcgacttcc gcggcatgaa ccccagttac     780
cccacaatgg ggagacaggt catcctttc ggctcggccg ccaggatgcc tccgcacgga     840
ccagcaccac tcctcgtgcc gcgccgcgcc ccgccgctgc acttcacggt gcagcaacaa     900
ggcagcgacg ccggcggaag tgtaaccgca ggatcccag tggtgctcga ctcagtgccg     960
gtaatcgaaa gccccacgac ggcaacgaag aagcgcgtgc gcttgttcgg cgtgaacttg    1020
gacaaccccg cgcatcccgg tgatggcggg gcgaatcga gcaattatgg cagtgcactg    1080
ccattgcaga tgcccgcatc agcatggcgg ccaagggacc atacgctgag gctgctcgaa    1140
```

```
ttccctcgc acggtgccga ggcgtcgtct ccatcgtcgt cgtcgtcttc caagagggag    1200
gcgcattcgg gcttggatct cgatctgtga                                    1230
```

<210> SEQ ID NO 85
<211> LENGTH: 227
<212> TYPE: PRT
<213> ORGANISM: Hordeum vulgare

<400> SEQUENCE: 85

```
Met Leu Arg Lys His Thr Tyr Phe Asp Glu Leu Ala Gln Ser Lys Arg
1               5                   10                  15

Ala Phe Ala Ala Ser Ala Ala Leu Ser Ala Pro Thr Thr Ser Gly Asp
            20                  25                  30

Ala Gly Gly Ser Ala Ser Pro Pro Ser Pro Ala Ala Val Arg Glu His
        35                  40                  45

Leu Phe Asp Lys Thr Val Thr Pro Ser Asp Val Gly Lys Leu Asn Arg
    50                  55                  60

Leu Val Ile Pro Lys Gln Asn Ala Glu Lys His Phe Pro Leu Gln Leu
65                  70                  75                  80

Pro Ala Gly Gly Gly Glu Ser Lys Gly Leu Leu Asn Phe Glu Asp
                85                  90                  95

Asp Ala Gly Lys Val Trp Arg Phe Arg Tyr Ser Tyr Trp Asn Ser Ser
            100                 105                 110

Gln Ser Tyr Val Leu Thr Lys Gly Trp Ser Arg Phe Val Lys Glu Lys
        115                 120                 125

Gly Leu Gly Ala Gly Asp Val Val Gly Phe Tyr Arg Ser Ala Ala Gly
    130                 135                 140

Arg Thr Gly Glu Asp Ser Lys Phe Phe Ile Asp Cys Arg Leu Arg Pro
145                 150                 155                 160

Asn Thr Asn Thr Ala Ala Glu Ala Asp Pro Val Asp Gln Ser Ser Ala
                165                 170                 175

Pro Val Gln Lys Ala Val Arg Leu Phe Gly Val Asp Leu Leu Ala Ala
            180                 185                 190

Pro Glu Gln Gly Met Pro Gly Gly Cys Lys Arg Ala Arg Asp Leu Val
        195                 200                 205

Lys Pro Pro Pro Pro Lys Val Ala Phe Lys Lys Gln Cys Ile Glu Leu
    210                 215                 220

Ala Leu Ala
225
```

<210> SEQ ID NO 86
<211> LENGTH: 684
<212> TYPE: DNA
<213> ORGANISM: Hordeum vulgare

<400> SEQUENCE: 86

```
atgctccgca agcacaccta cttcgacgag ctcgcccaga gcaagcgcgc cttcgccgcg    60
tcggccgcgc tctccgcgcc caccacctcg ggcgacgccg gcggcagcgc ctcgccgccc   120
tccccggccg ccgtgcgcga gcacctcttc gacaagaccg tcacgcccag cgacgtcggc   180
aagctgaaca ggctggtgat accgaagcag aacgccgaga agcacttccc gctgcagctc   240
ccggccggcg gcggcgagag caagggcctg ctcctcaact tcgaggacga tgcgggcaag   300
gtgtggcggt tccgctactc gtactggaac agcagccaga gctacgtcct caccaagggc   360
tggagccgct tcgtgaagga gaagggcctc ggcgccggag acgtcgtcgg gttctaccgc   420
```

```
tccgccgccg ggaggaccgg cgaagacagc aagttcttca ttgactgcag gctgcggccg      480
aacaccaaca ccgccgccga agcagacccc gtggaccagt cgtcggcgcc cgtgcagaag      540
gccgtgagac tcttcggcgt cgatcttctc gcggcgccgg agcagggcat gccgggcggg      600
tgcaagaggg ccagagactt ggtgaagccg ccgcctccga agtggcgtt caagaagcaa       660 tgcatagagc tggcgctagc gtag                                             684
```

<210> SEQ ID NO 87
<211> LENGTH: 160
<212> TYPE: PRT
<213> ORGANISM: Hordeum vulgare

<400> SEQUENCE: 87

```
Met Tyr Cys Ser Arg Gly Arg Ile Asp Pro Ala Glu Glu Gly Gln Val
1               5                   10                  15

Met Gly Gly Leu Gly Val Arg Asp Ala Ser Trp Ala Leu Phe Lys Val
            20                  25                  30

Leu Glu Gln Ser Asp Val Gln Val Gly Gln Asn Arg Leu Leu Leu Thr
        35                  40                  45

Lys Glu Ala Val Trp Gly Gly Pro Ile Pro Lys Leu Phe Pro Glu Leu
    50                  55                  60

Glu Glu Leu Arg Gly Asp Gly Leu Asn Ala Glu Asn Arg Val Ala Val
65                  70                  75                  80

Lys Ile Leu Asp Ala Asp Gly Cys Glu Gly Asp Ala Asn Phe Arg Tyr
                85                  90                  95

Leu Asn Ser Ser Lys Ala Tyr Arg Val Met Gly Pro Gln Trp Ser Arg
            100                 105                 110

Leu Val Lys Glu Thr Gly Met Cys Lys Gly Asp Arg Leu Asp Leu Tyr
        115                 120                 125

Ala Ala Thr Ala Thr Ala Ala Ser Ser Cys Ser Gly Ala Arg Ala Ala
    130                 135                 140

Val Ala Pro Ala Ile Pro Pro Gly Ala Ile Val Lys Ala Ala Gly Phe
145                 150                 155                 160
```

<210> SEQ ID NO 88
<211> LENGTH: 483
<212> TYPE: DNA
<213> ORGANISM: Hordeum vulgare

<400> SEQUENCE: 88

```
atgtattgtt cccgcggccg catcgatccc gcggaagaag gcaggtgat gggcggcctc        60 ggcgtgcgcg acgccagctg ggcgctgttc aaggtgttgg agcagtccga cgtccaggtg     120
gggcagaacc ggctgctcct caccaaggag gcggtgtggg gcggccctat ccccaagctt     180
ttcccggagc tggaggagct ccgcggcgac ggcctcaacg ccgagaacag gtcgcggtc      240 aagatcctcg acgccgacgg ctgcgagggg acgccaact tccgctacct caactccagc      300
aaggcgtacc gggtcatggg gcctcagtgg agccggctcg tgaaggagac cggcatgtgc     360
aagggagacc gcctcgatct gtacgcggca acggcgaccg ctgcctcttc gtgttctgga     420
gccagggcgg ctgtggcgcc ggcgatacct cccggagcaa tcgtgaaggc agccgggttc     480
taa                                                                    483
```

<210> SEQ ID NO 89
<211> LENGTH: 267
<212> TYPE: PRT

<213> ORGANISM: Hordeum vulgare

<400> SEQUENCE: 89

```
Met Leu Arg Lys His Ile Tyr Pro Asp Glu Leu Ala Gln His Lys Arg
1               5                   10                  15
Ala Phe Phe Ala Ala Ala Ser Ser Pro Thr Ser Ser Ser Ser Ser Pro
            20                  25                  30
Leu Ala Ser Pro Ala Pro Ser Ala Ala Ala Arg Arg Glu His Leu
        35                  40                  45
Phe Asp Lys Thr Val Thr Pro Ser Asp Val Gly Lys Leu Asn Arg Leu
    50                  55                  60
Val Ile Pro Lys Gln His Ala Glu Lys His Phe Pro Leu Gln Leu Pro
65                  70                  75                  80
Ser Ala Ser Ala Ala Val Pro Gly Glu Cys Lys Gly Val Leu Leu Asn
                85                  90                  95
Phe Asp Asp Ala Thr Gly Lys Val Trp Arg Phe Arg Tyr Ser Tyr Trp
            100                 105                 110
Asn Ser Ser Gln Ser Tyr Val Leu Thr Lys Gly Trp Ser Arg Phe Val
        115                 120                 125
Lys Glu Lys Gly Leu His Ala Gly Asp Ala Val Glu Phe Tyr Arg Ala
    130                 135                 140
Ala Ser Gly Asn Asn Gln Leu Phe Ile Asp Cys Lys Leu Arg Ser Lys
145                 150                 155                 160
Ser Thr Thr Thr Thr Thr Ser Val Asn Ser Glu Ala Ala Pro Ser Pro
                165                 170                 175
Ala Pro Val Thr Arg Thr Val Arg Leu Phe Gly Val Asp Leu Leu Ile
            180                 185                 190
Ala Pro Ala Ala Arg His Ala His Glu His Asp Tyr Gly Met Ala
        195                 200                 205
Lys Thr Asn Lys Arg Thr Met Glu Ala Ser Val Ala Ala Pro Thr Pro
    210                 215                 220
Ala His Ala Val Trp Lys Lys Arg Cys Val Asp Phe Ala Leu Thr Tyr
225                 230                 235                 240
Arg Leu Ala Thr Thr Pro Gln Cys Pro Arg Ser Arg Asp Gln Leu Glu
                245                 250                 255
Gly Val Gln Ala Ala Gly Ser Thr Phe Ala Leu
            260                 265
```

<210> SEQ ID NO 90
<211> LENGTH: 804
<212> TYPE: DNA
<213> ORGANISM: Hordeum vulgare

<400> SEQUENCE: 90

```
atgctgcgca agcacatcta tcccgacgag ctcgcgcagc acaagcgcgc cttcttcttc      60
gccgcggcgt cgtccctac gtcgtcgtcg tcacctctcg cctcgccggc tccttcagcc     120
gcggcggcgc ggcgcgagca cctgttcgac aagacggtca cgcccagcga cgtggggaag     180
ctgaaccggc tggtgatccc caagcagcac gccgagaagc acttcccgct gcagctccct     240
tctgccagcg ccgccgtgcc aggcgagtgc aagggcgtgc tgctcaactt cgatgacgcg     300
accggcaagg tgtggaggtt ccggtactcc tactggaaca gcagccagag ctacgtgctc     360
accaaggggt ggagccgctt cgtgaaggag aagggccttc acgccggcga cgccgtcgag     420
ttctaccgcg ccgcctccgg caacaaccag ctcttcatcg actgcaagct ccggtccaag     480
```

```
agcaccacga cgacgacctc cgtcaactcg gaggccgccc catcgccggc acccgtgacg    540
aggacagtgc gactcttcgg ggtcgacctt ctcatcgcgc cggcggcgag gcacgcgcat    600
gagcacgagg actacggcat ggccaagaca aacaagagaa ccatggaggc cagcgtagcg    660
gcgcctactc cggcgcacgc ggtgtggaag aagcggtgcg tagacttcgc gctgacctac    720
cgacttgcca ccaccccaca gtgcccgagg tcaagagatc aactagaagg agtacaagca    780
gctgggagta catttgctct atag                                           804
```

<210> SEQ ID NO 91
<211> LENGTH: 357
<212> TYPE: PRT
<213> ORGANISM: Hordeum vulgare

<400> SEQUENCE: 91

| | | | | | | | | | | | | |
|---|---|---|---|---|---|---|---|---|---|---|---|---|
| Met | Gly | Val | Glu | Ile | Leu | Ser | Ser | Thr | Gly | Glu | His | Ser | Ser | Gln | Tyr |
| 1 | | | | 5 | | | | | 10 | | | | | 15 | |

| Ser | Ser | Gly | Ala | Ala | Ser | Thr | Ala | Thr | Thr | Glu | Ser | Gly | Val | Gly | Gly |
| | | | | 20 | | | | | 25 | | | | | 30 | |

| Arg | Pro | Pro | Thr | Ala | Pro | Ser | Leu | Pro | Val | Ser | Ile | Ala | Asp | Glu | Ser |
| | | | | 35 | | | | | 40 | | | | | 45 | |

| Ala | Thr | Ser | Arg | Ser | Ala | Ser | Ala | Gln | Ser | Thr | Ser | Ser | Arg | Phe | Lys |
| | 50 | | | | | 55 | | | | | 60 | | | | |

| Gly | Val | Val | Pro | Gln | Pro | Asn | Gly | Arg | Trp | Gly | Ala | Gln | Ile | Tyr | Glu |
| 65 | | | | | 70 | | | | | 75 | | | | | 80 |

| Arg | His | Ala | Arg | Val | Trp | Leu | Gly | Thr | Phe | Pro | Asp | Glu | Asp | Ser | Ala |
| | | | | 85 | | | | | 90 | | | | | 95 | |

| Ala | Arg | Ala | Tyr | Asp | Val | Ala | Ala | Leu | Arg | Tyr | Arg | Gly | Arg | Glu | Ala |
| | | | | 100 | | | | | 105 | | | | | 110 | |

| Ala | Thr | Asn | Phe | Pro | Cys | Ala | Ala | Ala | Glu | Ala | Glu | Leu | Ala | Phe | Leu |
| | | | | 115 | | | | | 120 | | | | | 125 | |

| Ala | Ala | His | Ser | Lys | Ala | Glu | Ile | Val | Asp | Met | Leu | Arg | Lys | His | Thr |
| | 130 | | | | | 135 | | | | | 140 | | | | |

| Tyr | Thr | Asp | Glu | Leu | Arg | Gln | Gly | Leu | Arg | Arg | Gly | Arg | Gly | Met | Gly |
| 145 | | | | | 150 | | | | | 155 | | | | | 160 |

| Ala | Arg | Ala | Gln | Pro | Thr | Pro | Ser | Trp | Ala | Arg | Glu | Pro | Leu | Phe | Glu |
| | | | | 165 | | | | | 170 | | | | | 175 | |

| Lys | Ala | Val | Thr | Pro | Ser | Asp | Val | Gly | Lys | Leu | Asn | Arg | Leu | Val | Val |
| | | | | 180 | | | | | 185 | | | | | 190 | |

| Pro | Lys | Gln | His | Ala | Glu | Lys | His | Phe | Pro | Leu | Lys | Arg | Thr | Pro | Glu |
| | | | | 195 | | | | | 200 | | | | | 205 | |

| Thr | Thr | Thr | Thr | Thr | Gly | Lys | Gly | Val | Leu | Leu | Asn | Phe | Glu | Asp | Gly |
| | 210 | | | | | 215 | | | | | 220 | | | | |

| Glu | Gly | Lys | Val | Trp | Arg | Phe | Arg | Tyr | Ser | Tyr | Trp | Asn | Ser | Ser | Gln |
| 225 | | | | | 230 | | | | | 235 | | | | | 240 |

| Ser | Tyr | Val | Leu | Thr | Lys | Gly | Trp | Ser | Arg | Phe | Val | Arg | Glu | Lys | Gly |
| | | | | 245 | | | | | 250 | | | | | 255 | |

| Leu | Gly | Ala | Gly | Asp | Ser | Ile | Val | Phe | Ser | Cys | Ser | Ala | Tyr | Gly | Gln |
| | | | | 260 | | | | | 265 | | | | | 270 | |

| Glu | Lys | Gln | Phe | Phe | Ile | Asp | Cys | Lys | Lys | Asn | Lys | Thr | Met | Thr | Ser |
| | | | | 275 | | | | | 280 | | | | | 285 | |

| Cys | Pro | Ala | Asp | Asp | Arg | Gly | Ala | Ala | Thr | Ala | Ser | Pro | Pro | Val | Ser |
| | 290 | | | | | 295 | | | | | 300 | | | | |

| Glu | Pro | Thr | Lys | Gly | Glu | Gln | Val | Arg | Val | Val | Arg | Leu | Phe | Gly | Val |
| 305 | | | | | 310 | | | | | 315 | | | | | 320 |

```
Asp Ile Ala Gly Glu Lys Arg Gly Arg Ala Ala Pro Val Glu Gln Glu
                325                 330                 335

Leu Phe Lys Arg Gln Cys Val Ala His Ser Gln His Ser Pro Ala Leu
            340                 345                 350

Gly Ala Phe Val Leu
        355

<210> SEQ ID NO 92
<211> LENGTH: 1074
<212> TYPE: DNA
<213> ORGANISM: Hordeum vulgare

<400> SEQUENCE: 92
atgggggtgg agatcctgag ctcaacgggg aacactcct  cccagtactc ttccggagcc    60
gcgtccacgg cgacgacgga gtcaggcgtg ggcggacggc cgccgactgc gccgagccta   120 cctgttttcca tcgccgacga gtcggcgacc tcgcggtcgg catcggcgca gtcgacgtcg   180
tcgcggttca agggcgtggt gccgcagccc aacgggcggt ggggcgccca gatctacgag   240
cgccacgccc gcgtctggct cggcacgttc ccggacgaag actctgcggc gcgcgcctac   300
gacgtggccc gctccggta ccggggccgc gaggccgcca ccaacttccc gtgcgcggcc    360
gccgaggcgg agctcgcctt cctggcggca cactccaagg ccgagatcgt cgacatgctc   420
cggaagcaca cctacaccga cgagctccgc cagggcctgc ggcgcggccg cggcatgggg   480
gcgcgcgcgc agccgacgcc gtcgtgggcg cgggagcccc ttttcgagaa ggccgtgacc   540
ccgagcgacg tgggcaagct caaccgcctc gttgtgccga agcagcacgc cgagaagcac   600 ttcccccctga acgcacgcc ggagacgaca acgaccaccg gcaaggggggt gcttctcaac   660 ttcgaggatg gcgaggggaa agtgtggagg ttccggtact cgtattggaa cagcagccag   720
agctacgtgc tcaccaaggg atggagccgc ttcgttcggg agaagggcct cggtgccggc   780
gactccatcg tgttctcctg ctcggcgtac ggtcaggaga gcagttctt  catcgactgc   840 aagaagaaca agacgatgac gagctgcccc gccgatgacc gcggcgccgc aacagcgtcg   900
ccgccagtgt cagagccaac aaaaggagaa caagtccgtg ttgtgaggct gttcggcgtc   960
gacatcgccg agagaagag ggggcgagcg cgccggtgg agcaggagtt gttcaagagg    1020
caatgcgtgg cacacagcca gcactctcca gccctaggtg ccttcgtctt atag         1074

<210> SEQ ID NO 93
<211> LENGTH: 348
<212> TYPE: PRT
<213> ORGANISM: Hordeum vulgare

<400> SEQUENCE: 93

Met Gly Val Glu Ile Leu Ser Ser Met Val Glu His Ser Phe Gln Tyr
1               5                   10                  15

Ser Ser Gly Ala Ser Ser Ala Thr Ala Glu Ser Gly Ala Val Gly Thr
            20                  25                  30

Pro Pro Arg His Leu Ser Leu Pro Val Ala Ile Ala Asp Glu Ser Leu
        35                  40                  45

Thr Ser Arg Ser Ala Ser Ser Arg Phe Lys Gly Val Val Pro Gln Pro
    50                  55                  60

Asn Gly Arg Trp Gly Ala Gln Ile Tyr Glu Arg His Ala Arg Val Trp
65                  70                  75                  80

Leu Gly Thr Phe Pro Asp Gln Asp Ser Ala Ala Arg Ala Tyr Asp Val
                85                  90                  95
```

```
Ala Ser Leu Arg Tyr Arg Gly Gly Asp Ala Ala Phe Asn Phe Pro Cys
                100                 105                 110

Val Val Val Glu Ala Glu Leu Ala Phe Leu Ala Ala His Ser Lys Ala
            115                 120                 125

Glu Ile Val Asp Met Leu Arg Lys Gln Thr Tyr Ala Asp Glu Leu Arg
    130                 135                 140

Gln Gly Leu Arg Arg Gly Arg Gly Met Gly Val Arg Ala Gln Pro Met
145                 150                 155                 160

Pro Ser Trp Ala Arg Val Pro Leu Phe Glu Lys Ala Val Thr Pro Ser
                165                 170                 175

Asp Val Gly Lys Leu Asn Arg Leu Val Val Pro Lys Gln His Ala Glu
            180                 185                 190

Lys His Phe Pro Leu Lys Arg Ser Pro Glu Thr Thr Thr Thr Thr Gly
    195                 200                 205

Asn Gly Val Leu Leu Asn Phe Glu Asp Gly Gln Gly Lys Val Trp Arg
210                 215                 220

Phe Arg Tyr Ser Tyr Trp Asn Ser Ser Gln Ser Tyr Val Leu Thr Lys
225                 230                 235                 240

Gly Trp Ser Arg Phe Val Arg Glu Lys Gly Leu Gly Ala Gly Asp Ser
                245                 250                 255

Ile Met Phe Ser Cys Ser Ala Tyr Gly Gln Glu Lys Gln Phe Phe Ile
            260                 265                 270

Asp Cys Lys Lys Asn Thr Thr Val Asn Gly Gly Lys Ser Ala Ser Pro
    275                 280                 285

Leu Gln Val Met Glu Ile Ala Lys Ala Glu Gln Val Arg Val Val Arg
290                 295                 300

Leu Phe Gly Val Asp Ile Ala Gly Val Lys Arg Glu Arg Ala Ala Thr
305                 310                 315                 320

Ala Glu Gln Gly Pro Gln Gly Trp Phe Lys Arg Gln Cys Met Ala His
                325                 330                 335

Gly Gln His Ser Pro Ala Leu Gly Asp Phe Ala Leu
            340                 345

<210> SEQ ID NO 94
<211> LENGTH: 1047
<212> TYPE: DNA
<213> ORGANISM: Hordeum vulgare

<400> SEQUENCE: 94
atgggggtgg agatcctgag ctccatggtg gagcactcct tccagtactc ttcgggcgcg      60
tcctcggcca ccgcggagtc aggcgccgtc ggaacaccgc cgaggcatct gagcctacct     120
gtcgccatcg ccgacgagtc cctgacctca cggtcggcgt cgtctcggtt caagggcgtg     180
gtgccgcagc ccaacgggcg gtggggcgcc cagatctacg agcgccacgc tcgcgtctgg     240
ctcggcacgt tccagaccca ggactcggcg gcgcgcgcct acgacgttgc ctcgctcagg     300
taccgcggcg gcgacgccgc cttcaacttc ccgtgcgtgg tggtggaggc ggagctcgcc     360
ttcctggcgg cgcactccaa ggctgagatc gttgacatgc tccggaagca gacctacgcc     420
gatgaactcc gccagggact acggcgcggc cgtggcatgg gggtgcgcgc gcagccgatg     480
ccgtcgtggg cgcgggttcc ccttttcgag aaggccgtga ccctagcga  tgtcggcaag     540 ctcaatcgcc tggtggtgcc gaagcagcac gccgagaagc acttcccct  gaagcgcagc     600 ccggagacga cgaccaccac cggcaacggc gtactgctca actttgagga cggccaggga     660
```

```
aaagtgtgga ggttccggta ctcatattgg aacagcagcc agagctacgt gctcaccaaa    720
ggctggagcc gcttcgtccg ggagaagggc ctcggcgccg gtgactccat catgttctcc    780
tgctcggcgt acgggcagga gaagcagttc ttcatcgact gcaagaagaa cacgaccgtg    840
aacggaggca atcggcgtc gccgctgcag gtgatggaga ttgccaaagc agaacaagtc    900
cgcgtcgtta gactgttcgg tgtcgacatc gccggggtga gagggagcg agcggcgacg    960 gcggagcaag gcccgcaggg gtggttcaag aggcaatgca tggcacacgg ccagcactct   1020
cctgccctag gtgacttcgc cttatag                                        1047
```

<210> SEQ ID NO 95
<211> LENGTH: 362
<212> TYPE: PRT
<213> ORGANISM: Hordeum vulgare

<400> SEQUENCE: 95

```
Met Gly Met Glu Ile Leu Ser Ser Thr Val Glu His Cys Ser Gln Tyr
 1               5                  10                  15

Ser Ser Ser Ala Ser Thr Ala Thr Thr Glu Ser Gly Ala Ala Gly Arg
             20                  25                  30

Ser Thr Thr Ala Leu Ser Leu Pro Val Ala Ile Thr Asp Glu Ser Val
         35                  40                  45

Thr Ser Arg Ser Ala Ser Ala Gln Pro Ala Ser Arg Phe Lys Gly
     50                  55                  60

Val Val Pro Gln Pro Asn Gly Arg Trp Gly Ser Gln Ile Tyr Glu Arg
 65                  70                  75                  80

His Ala Arg Val Trp Leu Gly Thr Phe Pro Gln Asp Ser Ala Ala
                 85                  90                  95

Arg Ala Tyr Asp Val Ala Ser Leu Arg Tyr Arg Gly Arg Asp Ala Ala
            100                 105                 110

Thr Asn Phe Pro Cys Ala Ala Ala Glu Ala Glu Leu Ala Phe Leu Thr
        115                 120                 125

Ala His Ser Lys Ala Glu Ile Val Asp Met Leu Arg Lys His Thr Tyr
    130                 135                 140

Ala Asp Glu Leu Arg Gln Gly Leu Arg Arg Gly Arg Gly Met Gly Ala
145                 150                 155                 160

Arg Ala Gln Pro Thr Pro Ser Trp Ala Arg Val Pro Leu Phe Glu Lys
                165                 170                 175

Ala Val Thr Pro Ser Asp Val Gly Lys Leu Asn Arg Leu Val Val Pro
            180                 185                 190

Lys Gln His Ala Glu Lys His Phe Pro Leu Lys Cys Thr Ala Glu Thr
        195                 200                 205

Thr Thr Thr Thr Gly Asn Gly Val Leu Leu Asn Phe Glu Asp Gly Glu
    210                 215                 220

Gly Lys Val Trp Arg Phe Arg Tyr Ser Tyr Trp Asn Ser Ser Gln Ser
225                 230                 235                 240

Tyr Val Leu Thr Lys Gly Trp Ser Ser Phe Val Arg Glu Lys Gly Leu
                245                 250                 255

Gly Ala Gly Asp Ser Ile Val Phe Ser Ser Ser Ala Tyr Gly Gln Glu
            260                 265                 270

Lys Gln Leu Phe Ile Asn Cys Lys Lys Asn Thr Thr Met Asn Gly Gly
        275                 280                 285

Lys Thr Ala Leu Pro Leu Pro Val Val Glu Thr Ala Lys Gly Glu Gln
    290                 295                 300
```

Asp His Val Val Lys Leu Phe Gly Val Asp Ile Ala Gly Val Lys Arg
305                 310                 315                 320

Val Arg Ala Ala Thr Gly Glu Leu Gly Pro Pro Glu Leu Phe Lys Arg
                325                 330                 335

Gln Ser Val Ala His Gly Cys Gly Arg Met Asn Tyr Ile Cys Tyr Ser
                340                 345                 350

Ile Gly Thr Ile Gly Pro Leu Met Leu Asn
                355                 360

<210> SEQ ID NO 96
<211> LENGTH: 1089
<212> TYPE: DNA
<213> ORGANISM: Hordeum vulgare

<400> SEQUENCE: 96

| | |
|---|---|
| atggggatgg aaatcctgag ctccacggtg gagcactgct cccagtactc ttccagcgcg | 60 |
| tccacggcca caacggagtc aggcgccgcc ggaagatcga cgacggctct gagcctacca | 120 |
| gttgccatca ccgacgagtc cgttacctcg cggtcggcat cggcgcagcc ggcgtcatca | 180 |
| cggttcaagg gcgtggtgcc gcagcccaac gggcggtggg gctcccagat ctacgagcgc | 240 |
| cacgctcgcg tctggctcgg caccttcccg gatcaggact cggcggcgcg tgcctacgac | 300 |
| gttgcctcgc tcaggtaccg gggccgcgat gccgccacca acttcccgtg cgccgctgcg | 360 |
| gaagcggagc tcgccttcct gaccgcgcac tccaaggccg agatcgtcga catgctccgg | 420 |
| aagcacacct acgccgacga actccgccag ggcctgcggc gcggccgcgg catgggtgcg | 480 |
| cgcgcgcagc cgacgccgtc gtgggcgcgg gttccccttt tcgagaaggc tgtgaccccc | 540 |
| agcgatgtcg gcaagctcaa tcgcctggtg gtgccgaagc agcacgccga aagcacttc | 600 |
| cccctgaagt gcaccgcaga acgacgacc accaccggca acggcgtgct gctaaacttc | 660 |
| gaggatggtg aggggaaggt gtggaggttc cggtactcgt attggaacag tagccagagc | 720 |
| tacgtgctca ccaaaggctg gagcagcttc gtccgggaga agggcctcgg cgcaggcgac | 780 |
| tccatcgtct tctcctcctc ggcgtacggg caggagaagc agttattcat caactgcaaa | 840 |
| aagaacacga ctatgaacgg cggcaaaaca gcgttgccgc tgccagtggt ggagactgcc | 900 |
| aaaggagaac aagaccacgt cgttaagttg ttcggtgttg acatcgccgg tgtgaagagg | 960 |
| gtgcgagcgg cgacggggga gctaggcccg ccggagttgt tcaagagaca atccgtggca | 1020 |
| cacggatgcg gaaggatgaa ctacatttgc tactccatag gacaataggg acctcttatg | 1080 |
| ctcaactga | 1089 |

<210> SEQ ID NO 97
<211> LENGTH: 308
<212> TYPE: PRT
<213> ORGANISM: Hordeum vulgare

<400> SEQUENCE: 97

Met Ala Ser Ser Lys Pro Thr Asn Pro Glu Val Asp Asn Asp Met Glu
1               5                   10                  15

Cys Ser Ser Pro Glu Ser Gly Ala Glu Asp Ala Val Glu Ser Ser Ser
                20                  25                  30

Pro Val Ala Ala Pro Ser Ser Arg Phe Lys Gly Val Pro Gln Pro
                35                  40                  45

Asn Gly Arg Trp Gly Ala Gln Ile Tyr Glu Lys His Ser Arg Val Trp
            50                  55                  60

Leu Gly Thr Phe Gly Asp Glu Glu Ala Ala Ala Cys Ala Tyr Asp Val

```
                65                  70                  75                  80
Ala Ala Leu Arg Phe Arg Gly Arg Asp Ala Val Thr Asn His Gln Arg
                    85                  90                  95
Leu Pro Ala Ala Glu Gly Ala Gly Trp Ser Ser Thr Ser Glu Leu Ala
               100                 105                 110
Phe Leu Ala Asp His Ser Lys Ala Glu Ile Val Asp Met Leu Arg Lys
               115                 120                 125
His Thr Tyr Asp Asp Glu Leu Arg Gln Gly Leu Arg Arg Gly His Gly
           130                 135                 140
Arg Ala Gln Pro Thr Pro Ala Trp Ala Arg Glu Phe Leu Phe Glu Lys
145                 150                 155                 160
Ala Leu Thr Pro Ser Asp Val Gly Lys Leu Asn Arg Leu Val Val Pro
                   165                 170                 175
Lys Gln His Ala Glu Lys His Phe Pro Pro Thr Thr Ala Ala Ala Ala
                   180                 185                 190
Gly Ser Asp Gly Lys Gly Leu Leu Leu Asn Phe Glu Asp Gly Gln Gly
               195                 200                 205
Lys Val Trp Arg Phe Arg Tyr Ser Tyr Trp Asn Ser Ser Gln Ser Tyr
           210                 215                 220
Val Leu Thr Lys Gly Trp Ser Arg Phe Val Gln Lys Gly Leu Cys
225                 230                 235                 240
Ala Gly Asp Thr Val Thr Phe Ser Arg Ser Ala Tyr Val Met Asn Asp
                   245                 250                 255
Thr Asp Glu Gln Leu Phe Ile Asp Tyr Lys Gln Ser Ser Lys Asn Asp
                   260                 265                 270
Glu Ala Ala Asp Val Ala Thr Ala Asp Glu Asn Glu Ala Gly His Val
               275                 280                 285
Ala Val Lys Leu Phe Gly Val Asp Ile Gly Trp Ala Gly Met Ala Gly
           290                 295                 300
Ser Ser Gly Gly
305

<210> SEQ ID NO 98
<211> LENGTH: 927
<212> TYPE: DNA
<213> ORGANISM: Hordeum vulgare

<400> SEQUENCE: 98
atggcgtcta gcaagccgac aaaccccgag gtagacaatg acatggagtg ctcctccccg      60
gaatcgggtg ccgaggacgc cgtggagtcg tcgtcgccgg tggcagcgcc atcttcgcgg     120
ttcaagggcg tcgtgccgca gcctaacggg cgctggggcg cgcagatcta cgagaagcac     180
tcgcgggtgt ggcttggcac gttcggggac gaggaagccg ccgcgtgcgc ctacgacgtg     240
gccgcgctcc gcttccgcgg ccgcgacgcc gtcaccaacc accagcgcct gccggcggcg     300
gagggggccg gctggtcgtc cacgagcgag ctcgccttcc tcgccgacca ctccaaggcc     360
gagatcgtcg acatgctccg gaagcacacc tacgacgacg agctccggca gggcctgcgc     420
cgcggccacg gcgcgcgcca gcccacgccg cgtgggcgc gagagttcct cttcgagaag     480
gccctgaccc cgagcgacgt cggcaagctc aaccgcctgg tcgttccgaa gcagcacgcc     540
gagaagcact ccccccgac gacggcggcg gccgccggaa gcgacggcaa gggcttgctg     600
ctcaacttcg aggacggcca agggaaggtg tggaggttcc ggtactcata ctggaacagc     660
agccagagct acgtgctcac caagggctgg agccgcttcg tccaagaaaa gggcctctgc     720
```

```
gccggcgaca ccgtgacgtt ctcccggtcg gcgtacgtga tgaatgacac ggatgagcag    780
ctcttcatcg actacaagca gagtagcaag aacgacgaag cggccgacgt agccactgcc    840
gatgagaatg aggccggcca tgtcgccgtg aagctcttcg gggtcgacat tggctgggct    900
gggatggcgg gatcatcagg tgggtga                                         927
```

<210> SEQ ID NO 99
<211> LENGTH: 1279
<212> TYPE: PRT
<213> ORGANISM: Hordeum vulgare

<400> SEQUENCE: 99

```
Met Leu Phe Asp Ser Ser Val Ser Ala Ser Leu Gly Thr Met Arg Pro
1               5                   10                  15

Leu Val Lys Lys Leu Asp Met Leu Leu Ala Pro Ala Arg Gly Tyr Ser
            20                  25                  30

Thr Leu Cys Lys Arg Ile Lys Glu Val Met His Leu Leu Lys His Asp
        35                  40                  45

Val Glu Glu Ile Ser Ser Tyr Leu Asp Glu Leu Thr Glu Val Glu Asp
    50                  55                  60

Pro Pro Pro Met Ala Lys Cys Trp Met Asn Glu Ala Arg Asp Leu Ser
65                  70                  75                  80

Tyr Asp Met Glu Asp Tyr Ile Asp Ser Leu Leu Phe Val Pro Pro Gly
                85                  90                  95

His Phe Ile Lys Lys Lys Lys Lys Lys Gly Lys Lys Lys
            100                 105                 110

Met Val Ile Lys Lys Arg Leu Lys Trp Cys Lys Gln Ile Val Phe Thr
            115                 120                 125

Lys Gln Val Ser Asp His Gly Ile Lys Thr Ser Lys Ile Ile His Val
    130                 135                 140

Asn Val Pro Arg Leu Pro Asn Lys Pro Lys Val Ala Lys Ile Ile Leu
145                 150                 155                 160

Gln Phe Arg Ile Tyr Val Gln Glu Ala Ile Glu Arg Tyr Asp Lys Tyr
                165                 170                 175

Arg Leu His His Cys Ser Thr Leu Arg Arg Arg Leu Leu Ser Thr Gly
            180                 185                 190

Ser Met Leu Ser Val Pro Ile Pro Tyr Glu Glu Ala Ala Gln Ile Val
            195                 200                 205

Thr Asp Gly Arg Met Asn Glu Phe Ile Ser Ser Leu Ala Ala Asn Asn
    210                 215                 220

Ala Ala Asp Gln Gln Gln Leu Lys Val Val Ser Val Leu Gly Ser Gly
225                 230                 235                 240

Cys Leu Gly Lys Thr Thr Leu Ala Asn Val Leu Tyr Asp Arg Ile Gly
                245                 250                 255

Met Gln Phe Glu Cys Arg Ala Phe Ile Arg Val Ser Lys Lys Pro Asp
            260                 265                 270

Met Lys Arg Leu Phe Arg Asp Leu Leu Ser Gln Phe His Gln Lys Gln
            275                 280                 285

Pro Leu Pro Thr Ser Cys Asn Glu Leu Gly Ile Ser Asp Asn Ile Ile
    290                 295                 300

Lys His Leu Gln Asp Lys Arg Tyr Leu Ile Val Ile Asp Asp Leu Trp
305                 310                 315                 320

Asp Leu Ser Val Trp Asp Ile Ile Lys Tyr Ala Phe Pro Lys Gly Asn
                325                 330                 335
```

```
His Gly Ser Arg Ile Ile Ile Thr Thr Gln Ile Glu Asp Val Ala Leu
                340                 345                 350

Thr Cys Cys Cys Asp His Ser Glu His Val Phe Glu Met Lys Pro Leu
                355                 360                 365

Asn Ile Gly His Ser Arg Glu Leu Phe Phe Asn Arg Leu Phe Gly Ser
                370                 375                 380

Glu Ser Asp Cys Leu Glu Glu Phe Lys Arg Val Ser Asn Glu Ile Val
385                 390                 395                 400

Asp Ile Cys Gly Gly Leu Pro Leu Ala Thr Ile Asn Ile Ala Ser His
                405                 410                 415

Leu Ala Asn Gln Glu Thr Glu Val Ser Leu Asp Leu Leu Thr Asp Thr
                420                 425                 430

Arg Asp Leu Leu Arg Ser Cys Leu Trp Ser Asn Ser Thr Ser Glu Arg
                435                 440                 445

Thr Lys Gln Val Leu Asn Leu Ser Tyr Ser Asn Leu Pro Asp Tyr Leu
                450                 455                 460

Lys Thr Cys Leu Leu Tyr Leu His Met Tyr Pro Val Gly Ser Ile Ile
465                 470                 475                 480

Trp Lys Asp Asp Leu Val Lys Gln Leu Val Ala Glu Gly Phe Ile Ala
                485                 490                 495

Thr Arg Glu Gly Lys Asp Gln Asp Gln Glu Met Ile Glu Lys Ala Ala
                500                 505                 510

Gly Leu Cys Phe Asp Ala Leu Ile Asp Arg Arg Phe Ile Gln Pro Ile
                515                 520                 525

Tyr Thr Lys Tyr Asn Asn Lys Val Leu Ser Cys Thr Val His Glu Val
                530                 535                 540

Val His Asp Leu Ile Ala Gln Lys Ser Ala Glu Glu Asn Phe Ile Val
545                 550                 555                 560

Val Ala Asp His Asn Arg Lys Asn Ile Ala Leu Ser His Lys Val Arg
                565                 570                 575

Arg Leu Ser Leu Ile Phe Gly Asp Thr Ile Tyr Ala Lys Thr Pro Ala
                580                 585                 590

Asn Ile Thr Lys Ser Gln Ile Arg Ser Phe Arg Phe Phe Gly Leu Phe
                595                 600                 605

Glu Cys Met Pro Cys Ile Thr Glu Phe Lys Val Leu Arg Val Leu Asn
                610                 615                 620

Leu Gln Leu Ser Gly His Arg Gly Asp Asn Asp Pro Ile Asp Leu Thr
625                 630                 635                 640

Gly Ile Ser Glu Leu Phe Gln Leu Arg Tyr Leu Lys Ile Thr Ser Asp
                645                 650                 655

Val Cys Ile Lys Leu Pro Asn Gln Met Gln Lys Leu Gln Tyr Leu Glu
                660                 665                 670

Thr Leu Asp Ile Met Asp Ala Pro Arg Val Thr Ala Val Pro Trp Asp
                675                 680                 685

Ile Ile Asn Leu Pro His Leu Leu His Leu Thr Leu Pro Val Asp Thr
                690                 695                 700

Tyr Leu Leu Asp Trp Ile Ser Ser Met Thr Asp Ser Val Ile Ser Leu
705                 710                 715                 720

Trp Thr Leu Gly Lys Leu Asn Tyr Leu Gln His Leu His Leu Thr Ser
                725                 730                 735

Ser Ser Thr Arg Pro Ser Tyr His Leu Glu Arg Ser Val Glu Ala Leu
                740                 745                 750

Gly Tyr Leu Ile Gly Gly His Gly Lys Leu Lys Thr Ile Val Val Ala
```

```
                755                 760                 765
His Val Ser Ser Ala Gln Asn Thr Val Val Arg Gly Ala Pro Glu Val
    770                 775                 780

Thr Ile Ser Trp Asp Arg Met Ser Pro Pro Leu Leu Gln Arg Phe
785                 790                 795                 800

Glu Cys Pro His Ser Cys Phe Ile Phe Tyr Arg Ile Pro Lys Trp Val
                805                 810                 815

Thr Glu Leu Gly Asn Leu Cys Ile Leu Lys Ile Ala Val Lys Glu Leu
            820                 825                 830

His Met Ile Cys Leu Gly Thr Leu Arg Gly Leu His Ala Leu Thr Asp
        835                 840                 845

Leu Ser Leu Tyr Val Glu Thr Ala Pro Ile Asp Lys Ile Ile Phe Asp
    850                 855                 860

Lys Ala Gly Phe Ser Val Leu Lys Tyr Cys Lys Leu Arg Phe Ala Ala
865                 870                 875                 880

Gly Ile Ala Trp Leu Lys Phe Glu Ala Asp Ala Met Pro Ser Leu Trp
                885                 890                 895

Lys Leu Met Leu Val Phe Asn Ala Ile Pro Arg Met Asp Gln Asn Leu
            900                 905                 910

Val Phe Phe His His Ser Arg Pro Ala Met His Gln Arg Gly Gly Ala
        915                 920                 925

Val Ile Ile Val Glu His Met Pro Gly Leu Arg Val Ile Ser Ala Lys
    930                 935                 940

Phe Gly Gly Ala Ala Ser Asp Leu Glu Tyr Ala Ser Arg Thr Val Val
945                 950                 955                 960

Ser Asn His Pro Ser Asn Pro Thr Ile Asn Met Gln Leu Val Cys Tyr
                965                 970                 975

Ser Ser Asn Gly Lys Arg Ser Arg Lys Arg Lys Gln Gln Pro Tyr Asp
            980                 985                 990

Val Val Lys Gly Gln Pro Asp Glu Tyr Ala Lys Arg Leu Glu Arg Pro
        995                 1000                1005

Ala Glu Lys Arg Ile Ser Thr Pro Thr Lys Ser Ser Leu Arg Leu
    1010                1015                1020

His Val Pro Glu Ile Thr Pro Lys Pro Met Gln Ile Thr Asp Asn
    1025                1030                1035

Asn Val Gln Arg Arg Glu His Met Phe Asp Thr Val Leu Thr Arg
    1040                1045                1050

Gly Asp Val Gly Met Leu Asn Arg Leu Val Val Pro Lys Lys His
    1055                1060                1065

Ala Glu Lys Tyr Phe Pro Leu Asp Ser Ser Ser Thr Arg Thr Ser
    1070                1075                1080

Lys Ala Ile Val Leu Ser Phe Glu Asp Pro Ala Gly Lys Ser Trp
    1085                1090                1095

Phe Phe His Tyr Ser Tyr Arg Ser Ser Ser Gln Asn Tyr Val Met
    1100                1105                1110

Phe Lys Gly Trp Thr Gly Phe Val Lys Glu Lys Phe Leu Glu Ala
    1115                1120                1125

Gly Asp Thr Val Ser Phe Ser Arg Gly Val Gly Glu Ala Thr Arg
    1130                1135                1140

Gly Arg Leu Phe Ile Asp Cys Gln Asn Glu Gln Arg Tyr Met Phe
    1145                1150                1155

Glu Arg Val Leu Thr Ala Ser Asp Met Glu Ser Asp Gly Cys Ser
    1160                1165                1170
```

```
Leu Met Val Pro Val Asn Leu Val Trp Pro His Pro Gly Leu Arg
    1175            1180                1185
Lys Thr Ile Lys Gly Arg His Ala Val Leu Gln Phe Glu Asp Gly
    1190            1195                1200
Ser Gly Asn Gly Lys Val Trp Pro Phe Gln Phe Glu Ala Ser Gly
    1205            1210                1215
Gln Tyr Tyr Leu Met Lys Gly Leu Asn Tyr Phe Val Asn Asp Arg
    1220            1225                1230
Asp Leu Ala Ala Gly Tyr Thr Val Ser Phe Tyr Arg Ala Gly Thr
    1235            1240                1245
Arg Leu Phe Val Asp Ser Gly Arg Lys Asp Asp Lys Val Ala Leu
    1250            1255                1260
Gly Thr Arg Ser Arg Glu Arg Ile Tyr Pro Lys Ile Val Arg Ser
    1265            1270                1275
Gln

<210> SEQ ID NO 100
<211> LENGTH: 3840
<212> TYPE: DNA
<213> ORGANISM: Brassica rapa

<400> SEQUENCE: 100
atgttgtttg atagttcagt gagtgcttcg ttgggcacca tgagaccact tgtcaagaag      60
ctcgacatgc tgctagctcc tgctcgggga tacagtacct tgtgcaagag gatcaaggaa     120
gtgatgcacc ttctcaaaca tgatgttgaa gagataagct cctaccttga tgaacttaca     180
gaggtggagg accctccacc aatggccaag tgctggatga cgaggcacg cgacctgtct      240
tatgatatgg aggattacat tgatagcttg ttatttgtgc cacctggcca tttcatcaag     300
aagaagaaga agaagaagaa gaagggaaag aagaagatgg tgataaagaa gaggctcaag     360
tggtgcaaac agatcgtatt cacaaagcaa gtgtcagacc atggtatcaa gaccagtaaa     420
atcattcatg ttaatgtccc tcgtcttccc aataagccca aggttgcaaa ataatatta      480
cagttcagga tctatgtcca ggaggctatt gaacggtatg acaagtatag gcttcaccat     540
tgcagcacct tgaggcgtag attgttgtcc actggtagta tgctttcagt gccaataccc     600
tatgaagaag ctgcccaaat tgtaactgat ggccggatga atgagtttat cagctcactg     660
gctgctaata atgcagcaga tcagcagcag ctcaaggtgg tatctgttct tggatctggg     720
tgtctaggta aaactacgct tgcgaatgtg ttgtacgaca gaattgggat gcaattcgaa     780
tgcagagctt tcattcgagt gtccaaaaag cctgatatga agagactttt ccgtgacttg     840
ctctcgcaat tccaccagaa gcagccactg cctaccagtt gtaatgagct tggcataagt     900
gacaatatca tcaaacatct gcaagataaa aggtatctaa ttgttattga tgatttgtgg     960
gatttatcag tatgggatat tattaaatat gcttttccaa agggaaacca tggaagcaga    1020
ataataataa ctacacagat tgaagatgtt gcattaactt gttgctgtga tcactcggag    1080
catgttttcg agatgaaacc tctcaacatt ggtcactcaa gagagctatt ttttaataga    1140
cttttttggtt ctgaaagtga ctgtcttgaa gaattcaaac gagtttcaaa cgaaattgtt    1200
gatatatgtg gtggtttacc gctagcaaca atcaacatag ctagtcattt ggcaaaccag    1260
gagacagaag tatcattgga tttgctaaca gacacacgtg atttgttgag gtcctgtttg    1320
tggtcaaatt ctacttcaga aagaacaaaa caagtactga acctcagcta cagtaatctt    1380
cctgattatc tgaagacatg tttgctgtat cttcatatgt atccagtggg ctccataatc    1440
```

```
tggaaggatg atctggtgaa gcaattggtg gctgaagggt ttattgctac aagagaaggg    1500
aaagaccaag accaagaaat gatagagaaa gctgcaggac tctgtttcga tgcacttatt    1560
gatagaagat tcatccagcc tatatatacc aagtacaaca ataaggtgtt gtcctgcacg    1620
gttcatgagg tggtacatga tcttattgcc caaaagtctg ctgaagagaa tttcattgtg    1680
gtagcagacc acaatcgaaa gaatatagca ctttctcata aggttcgtcg actatctctc    1740
atctttggcg acacaatata tgccaagaca ccagcaaaca tcacaaagtc acaaattcgg    1800
tcattcagat tttttggatt attcgagtgt atgccttgta ttacagagtt caaggttctc    1860
cgtgttctaa accttcaact atctggtcat cgtggggaca atgaccctat agacctcact    1920
gggatttcag aactgtttca gctgagatat ttaaagatta caagtgatgt gtgcataaaa    1980
ctaccaaatc aaatgcaaaa actgcaatat ttggaaacgt tggacattat ggatgcacca    2040
agagtcactg ctgttccatg ggatattata aatctcccac acctgttgca cctgactctt    2100
cctgttgata catatctgct ggattggatt agcagcatga ctgactccgt catcagtctg    2160
tggacccttg gcaagctgaa ctacctgcag catcttcatc ttactagttc ttctacacgt    2220
ccttcatacc atctggagag aagtgtggag gctctgggtt atttgatcgg aggacatggc    2280
aagctgaaaa ctatagtagt cgctcatgtc tcctctgctc aaaatactgt ggttcgtggc    2340
gccccagaag taaccatttc atgggatcgt atgtcacctc ccccccttct ccagagattc    2400
gaatgcccac acagctgctt catattttac cgaattccta agtgggttac agaacttggc    2460
aacctgtgca ttttgaagat tgcagtgaag gagcttcata tgatttgtct tggtactctc    2520
agaggattgc atgccctcac tgatctgtcg ctgtatgtgg agacagcgcc cattgacaag    2580
atcatctttg acaaggccgg gttctcagtt ctcaagtact gcaaattgcg cttcgcggct    2640
ggtatagctt ggctgaaatt tgaggctgat gcaatgccta gtctatggaa actgatgcta    2700
gttttcaacg ccatcccacg aatggaccaa aatcttgttt tctttcacca cagccgaccg    2760
gcgatgcatc aacgtggtgg tgcagtaatc attgtcgagc atatgccagg gcttagagtg    2820
atctccgcaa aatttgggg gcgcagcttct gatctagagt atgcttcgag gaccgtcgtt    2880
agtaaccatc caagcaatcc tacaatcaac atgcaattgg tgtgttatag ttccaatggt    2940
aagagaagca gaaaaaggaa acaacaacct tacgacgttg tgaagggaca accagatgaa    3000
tacgccaaga gattggagag accagctgag aaaaggattt caacgccgac aaagtcttct    3060
ttgcgtctgc atgttccaga aattacacca aaacctatgc agattacaga caacaatgtt    3120
cagaggaggg agcacatgtt cgatacggtt ctgactcggg gggacgtggg gatgctgaac    3180
cggctggtgg taccgaagaa gcacgcggag aagtacttcc cgctggacag ttcctccacc    3240
cgcaccagca aggccatcgt actcagcttt gaggaccctg ctgggaagtc atggttcttc    3300
cactactcct accggagcag cagccagaac tacgtcatgt tcaaggggtg gactggcttc    3360
gtcaaggaga agtttctcga agccggcgac accgtctcct tcagccgcgg cgtcggggag    3420
gccacgaggg ggaggctctt catcgactgt caaaatgagc agaggtacat gttcgagcga    3480
gtgctgacgg cgagtgatat ggagtcggat ggctgctcgc tgatggtccc agtgaacttg    3540
gtgtggccgc accccggcct ccgcaagacg atcaagggga ggcacgccgt gctgcagttt    3600
gaggacggca gcggcaacgg gaaggtgtgg ccatttcagt ttgaggcctc cggccaatac    3660
tatctcatga agggcttgaa ctactttgtt aacgaccgcg accttgcggc tggctatacc    3720
gtctccttct accgcgccgg cacgcggttg ttcgtcgact ccgggcgtaa agatgacaaa    3780
```
gtagccttgg gaaccagaag ccgcgaaagg atctatccta agatcgtgcg gtcgcagtag   3840

<210> SEQ ID NO 101
<211> LENGTH: 264
<212> TYPE: PRT
<213> ORGANISM: Brassica rapa

<400> SEQUENCE: 101

Met Ser Gly Asn His Tyr Ser Arg Asp Ile His His Asn Thr Pro Ser
1               5                   10                  15

Val His His Gln Asn Tyr Ala Val Val Asp Arg Glu Tyr Leu Phe
            20                  25                  30

Glu Lys Ser Leu Thr Pro Ser Asp Val Gly Lys Leu Asn Arg Leu Val
        35                  40                  45

Ile Pro Lys Gln His Ala Glu Lys His Phe Pro Leu Asn Asn Ala Gly
    50                  55                  60

Asp Asp Val Ala Ala Ala Glu Thr Thr Glu Lys Gly Met Leu Leu Thr
65                  70                  75                  80

Phe Glu Asp Glu Ser Gly Lys Cys Trp Lys Phe Arg Tyr Ser Tyr Trp
                85                  90                  95

Asn Ser Ser Gln Ser Tyr Val Leu Thr Lys Gly Trp Ser Arg Tyr Val
            100                 105                 110

Lys Asp Lys His Leu His Ala Gly Asp Val Val Phe Phe Gln Arg His
        115                 120                 125

Arg Phe Asp Leu His Arg Val Phe Ile Gly Trp Arg Lys Arg Gly Glu
    130                 135                 140

Val Ser Ser Pro Thr Ala Val Ser Val Val Ser Gln Glu Ala Arg Val
145                 150                 155                 160

Asn Thr Thr Ala Tyr Trp Ser Gly Leu Thr Thr Pro Tyr Arg Gln Val
                165                 170                 175

His Ala Ser Thr Ser Ser Tyr Pro Asn Ile His Gln Glu Tyr Ser His
            180                 185                 190

Tyr Gly Ala Val Ala Glu Ile Pro Thr Val Val Thr Gly Ser Ser Arg
        195                 200                 205

Thr Val Arg Leu Phe Gly Val Asn Leu Glu Cys His Gly Asp Val Val
    210                 215                 220

Glu Thr Pro Pro Cys Pro Asp Gly Tyr Asn Gly Gln His Phe Tyr Tyr
225                 230                 235                 240

Tyr Ser Thr Pro Asp Pro Met Asn Ile Ser Phe Ala Gly Glu Ala Met
                245                 250                 255

Glu Gln Val Gly Asp Gly Arg Arg
            260

<210> SEQ ID NO 102
<211> LENGTH: 258
<212> TYPE: PRT
<213> ORGANISM: Brassica rapa

<400> SEQUENCE: 102

Met Ser Val Asn His Tyr Ser Asn Thr Leu Ser Ser His Asn His His
1               5                   10                  15

Asn Glu His Lys Glu Ser Leu Phe Glu Lys Ser Leu Thr Pro Ser Asp
            20                  25                  30

Val Gly Lys Leu Asn Arg Leu Val Ile Pro Lys Gln His Ala Glu Arg
        35                  40                  45

Tyr Leu Pro Leu Asn Asn Cys Gly Gly Gly Gly Asp Val Thr Ala Glu

```
                50                  55                  60
Ser Thr Glu Lys Gly Val Leu Leu Ser Phe Glu Asp Glu Ser Gly Lys
 65                  70                  75                  80

Ser Trp Lys Phe Arg Tyr Ser Tyr Trp Asn Ser Ser Gln Ser Tyr Val
                 85                  90                  95

Leu Thr Lys Gly Trp Ser Arg Tyr Val Lys Asp Lys His Leu Asn Ala
                100                 105                 110

Gly Asp Val Val Leu Phe Gln Arg His Arg Phe Asp Ile His Arg Leu
            115                 120                 125

Phe Ile Gly Trp Arg Arg Gly Glu Ala Ser Ser Ser Ala Val
            130                 135                 140

Ser Ala Val Thr Gln Asp Pro Arg Ala Asn Thr Thr Ala Tyr Trp Asn
145                 150                 155                 160

Gly Leu Thr Thr Pro Tyr Arg Gln Val His Ala Ser Ser Ser Tyr
                165                 170                 175

Pro Asn Asn Ile His Gln Glu Tyr Ser His Tyr Gly Pro Val Ala Glu
                180                 185                 190

Thr Pro Thr Val Ala Ala Gly Ser Ser Lys Thr Val Arg Leu Phe Gly
                195                 200                 205

Val Asn Leu Glu Cys His Ser Asp Val Val Glu Pro Pro Cys Pro
        210                 215                 220

Asp Ala Tyr Asn Gly Gln His Ile Tyr Tyr Ser Thr Pro His Pro
225                 230                 235                 240

Met Asn Ile Ser Phe Ala Gly Glu Ala Met Glu Gln Val Gly Asp Gly
                245                 250                 255

Arg Gly
```

<210> SEQ ID NO 103
<211> LENGTH: 777
<212> TYPE: DNA
<213> ORGANISM: Brassica rapa

<400> SEQUENCE: 103

```
atgtcagtca accattactc aaacactctc tcgtcgcaca atcaccacaa cgaacataaa      60
gagtctttgt tcgagaagtc actcacgcca agcgatgttg aaagctaaa  ccgtttagtc     120
ataccaaaac aacacgccga gagatacctc cctctcaata ttgcggcgg  cggcggcgac     180
gtgacggcgg agtcgacgga gaaggggtg  cttctcagct cgaggacga  gtcgggaaaa     240
tcttggaaat tcagatactc atattggaac agtagtcaaa gctacgtgtt gaccaaagga     300
tggagcaggt acgtcaaaga caagcacctc aacgcagggg acgtcgtttt atttcaacgg     360
caccgttttg atattcatag actcttcatt ggctggagga gacgcggaga ggcttcttcc     420
tcttccgccg tttccgccgt gactcaagat cctcgagcta cacgacggc  gtactggaac     480
ggtttgacta caccttatcg tcaagtacac gcgtcaacta gttcttaccc taacaacatc     540
caccaagagt attcacatta tggccctgtt gctgagacac cgacggtagc tgcagggagc     600
tcgaagacgg tgaggctatt tggagttaac ctcgaatgtc acagtgacgt tgtggagcca     660
ccaccgtgtc ctgacgccta caacggccaa cacatttact attactcaac tccacatccc     720
atgaatatct catttgctgg agaagcaatg gagcaggtag gagatggacg aggttga       777
```

<210> SEQ ID NO 104
<211> LENGTH: 267
<212> TYPE: PRT
<213> ORGANISM: Brassica rapa

<400> SEQUENCE: 104

Met Ser Val Asn His Tyr Ser Thr Asp His Gln Val His His His
1               5                   10                  15

His Thr Leu Phe Leu Gln Asn Leu His Thr Thr Asp Thr Ser Glu Pro
            20                  25                  30

Thr Thr Thr Ala Ala Thr Ser Leu Arg Glu Asp Gln Lys Glu Tyr Leu
        35                  40                  45

Phe Glu Lys Ser Leu Thr Pro Ser Asp Val Gly Lys Leu Asn Arg Leu
50                  55                  60

Val Ile Pro Lys Gln His Ala Glu Lys Tyr Phe Pro Leu Asn Thr Ile
65                  70                  75                  80

Ile Ser Asn Asn Ala Glu Glu Lys Gly Met Leu Leu Ser Phe Glu Asp
                85                  90                  95

Glu Ser Gly Lys Cys Trp Arg Phe Arg Tyr Ser Tyr Trp Asn Ser Ser
            100                 105                 110

Gln Ser Tyr Val Leu Thr Lys Gly Trp Ser Arg Tyr Val Lys Asp Lys
        115                 120                 125

Gln Leu Asp Pro Ala Asp Val Val Phe Phe Gln Arg Gln Arg Ser Asp
130                 135                 140

Ser Arg Arg Leu Phe Ile Gly Trp Arg Arg Gly Gln Gly Ser Ser
145                 150                 155                 160

Ser Ala Ala Asn Thr Thr Ser Tyr Ser Ser Ser Met Thr Ala Pro Pro
                165                 170                 175

Tyr Ser Asn Tyr Ser Asn Arg Pro Ala His Ser Glu Tyr Ser His Tyr
            180                 185                 190

Gly Ala Ala Val Ala Thr Ala Thr Glu Thr His Phe Ile Pro Ser Ser
        195                 200                 205

Ser Ala Val Gly Ser Ser Arg Thr Val Arg Leu Phe Gly Val Asn Leu
210                 215                 220

Glu Cys Gln Met Asp Glu Asp Glu Gly Asp Ser Val Ala Thr Ala
225                 230                 235                 240

Ala Ala Ala Glu Cys Pro Arg Gln Asp Ser Tyr Tyr Asp Gln Asn Met
                245                 250                 255

Tyr Asn Tyr Tyr Thr Pro His Ser Ser Ala Ser
            260                 265

<210> SEQ ID NO 105
<211> LENGTH: 804
<212> TYPE: DNA
<213> ORGANISM: Brassica rapa

<400> SEQUENCE: 105
atgtcagtca accattactc cacggaccac caccaggtcc accaccacca cactctcttc      60
ttgcagaacc tccacaccac cgacacatcg gagccaacca caaccgccgc cacatcactc     120
cgcgaagacc agaaagagta tctcttcgag aaatctctca caccaagcga cgttggcaaa     180
ctcaaccgtc tcgttatacc aaaacagcac gcggagaagt acttccctct caacaccatc     240
atctccaata atgctgagga gaaagggatg cttctaagct tcgaagacga gtcaggcaag     300
tgctggaggt tcagatactc ttactggaac agcagtcaaa gctacgtgtt gactaaagga     360
tggagcagat acgtcaaaga caaacagctc gacccagccg atgttgtttt cttccaacgt     420
caacgttctg attcccggag actctttatt ggctggcgta gacgcggtca aggctcctcc     480
tccgccgcga atacgacgtc gtattctagt tccatgactg ctccaccgta tagtaattac     540

```
tctaatcgtc ctgctcactc agagtattcc cactatggcg ccgccgtagc aacagcgacg    600
gagacgcact tcataccatc gtcttccgcc gtcgggagct cgaggacggt gaggcttttt    660
ggtgtgaatt tggagtgtca aatggatgaa gacgaaggag atgattcggt tgccacggca    720
gccgccgctg agtgtcctcg tcaggacagc tactacgacc aaaacatgta caattattac    780
actcctcact cctcagcctc ataa                                           804
```

<210> SEQ ID NO 106
<211> LENGTH: 248
<212> TYPE: PRT
<213> ORGANISM: Brassica rapa

<400> SEQUENCE: 106

```
Met Ser Ile Asn Gln Tyr Ser Ser Asp Phe Asn Tyr His Ser Leu Met
1               5                   10                  15

Trp Gln Gln Gln His Arg His His His Gln Asn Asp Val Ala
            20                  25                  30

Glu Glu Lys Glu Ala Leu Phe Glu Lys Pro Leu Thr Pro Ser Asp Val
        35                  40                  45

Gly Lys Leu Asn Arg Leu Val Ile Pro Lys Gln His Ala Glu Arg Tyr
    50                  55                  60

Phe Pro Leu Ala Ala Ala Ala Asp Ala Met Glu Lys Gly Leu Leu
65                  70                  75                  80

Leu Cys Phe Glu Asp Glu Gly Lys Pro Trp Arg Phe Arg Tyr Ser
                85                  90                  95

Tyr Trp Asn Ser Ser Gln Ser Tyr Val Leu Thr Lys Gly Trp Ser Arg
            100                 105                 110

Tyr Val Lys Glu Lys Gln Leu Asp Ala Gly Asp Val Ile Leu Phe His
        115                 120                 125

Arg His Arg Val Asp Gly Gly Arg Phe Phe Ile Gly Trp Arg Arg Arg
    130                 135                 140

Gly Asn Ser Ser Ser Ser Asp Ser Tyr Arg His Leu Gln Ser Asn
145                 150                 155                 160

Ala Ser Leu Gln Tyr Tyr Pro His Ala Gly Val Gln Ala Val Glu Ser
                165                 170                 175

Gln Arg Gly Asn Ser Lys Thr Leu Arg Leu Phe Gly Val Asn Met Glu
            180                 185                 190

Cys Gln Leu Asp Ser Asp Leu Pro Asp Pro Ser Thr Pro Asp Gly Ser
        195                 200                 205

Thr Ile Cys Pro Thr Ser His Asp Gln Phe His Leu Tyr Pro Gln Gln
    210                 215                 220

His Tyr Pro Pro Pro Tyr Tyr Met Asp Ile Ser Phe Thr Gly Asp Val
225                 230                 235                 240

His Gln Thr Arg Ser Pro Gln Gly
                245
```

<210> SEQ ID NO 107
<211> LENGTH: 747
<212> TYPE: DNA
<213> ORGANISM: Brassica rapa

<400> SEQUENCE: 107

```
atgtcaataa accaatactc aagcgatttc aactaccact ctctcatgtg gcaacaacag    60
cagcaccgcc accaccacca tcaaaacgac gtcgcggagg aaaagaagc tcttttcgag    120
```

```
aaacccttaa ccccaagtga cgtcggaaaa ctcaaccgcc tcgtcatccc aaaacagcac      180
gccgagagat acttccctct cgcagcagcc gccgcagacg cgatggagaa gggattactt      240
ctctgcttcg aggacgagga aggtaagcca tggagattca gatactcgta ttggaacagt      300
agccagagtt atgtcttgac caaaggatgg agcagatacg tcaaggagaa gcagctcgac      360
gccggtgacg tcattctctt ccaccgccac cgtgttgacg aggaagatt  cttcattggc      420 tggagaagac gcggcaactc ttcctcctct tccgactctt atcgccatct tcagtccaat      480
gcctcgctcc aatattatcc tcatgcagga gttcaagcgg tggagagcca gagagggaat      540
tcgaagacat taagactgtt cggagtgaac atggagtgtc agctagactc cgacttgccc      600
gatccatcta caccagacgg ttccaccata tgtccgacca gtcacgacca gtttcatctc      660
taccctcaac aacactatcc tcctccgtac tacatggaca aagtttcac aggagatgtg      720 caccagacga gaagcccaca aggataa                                          747
```

<210> SEQ ID NO 108
<211> LENGTH: 245
<212> TYPE: PRT
<213> ORGANISM: Brassica rapa

<400> SEQUENCE: 108

```
Met Ser Ile Asn Gln Tyr Ser Ser Glu Phe Tyr Tyr His Ser Leu Met
1               5                   10                  15

Trp Gln Gln Gln Gln His His His Gln Asn Glu Val Val Glu Glu
            20                  25                  30

Lys Glu Ala Leu Phe Glu Lys Pro Leu Thr Pro Ser Asp Val Gly Lys
        35                  40                  45

Leu Asn Arg Leu Val Ile Pro Lys Gln His Ala Glu Arg Tyr Phe Pro
    50                  55                  60

Leu Ala Ala Ala Val Asp Ala Val Glu Lys Gly Leu Leu Leu Cys
65                  70                  75                  80

Phe Glu Asp Glu Glu Gly Lys Pro Trp Arg Phe Arg Tyr Ser Tyr Trp
                85                  90                  95

Asn Ser Ser Gln Ser Tyr Val Leu Thr Lys Gly Trp Ser Arg Tyr Val
            100                 105                 110

Lys Glu Lys Gln Leu Asp Ala Gly Asp Val Val Leu Phe His Arg His
        115                 120                 125

Arg Ala Asp Gly Gly Arg Phe Phe Ile Gly Trp Arg Arg Gly Asp
    130                 135                 140

Ser Ser Ser Ser Asp Ser Tyr Arg Asn Leu Gln Ser Asn Ser Ser
145                 150                 155                 160

Leu Gln Tyr Tyr Pro His Ala Gly Ala Gln Ala Val Glu Asn Gln Arg
                165                 170                 175

Gly Asn Ser Lys Thr Leu Arg Leu Phe Gly Val Asn Met Glu Cys Gln
            180                 185                 190

Ile Asp Ser Asp Trp Ser Glu Pro Ser Thr Pro Asp Gly Phe Thr Thr
        195                 200                 205

Cys Pro Thr Asn His Asp Gln Phe Pro Ile Tyr Pro Glu His Phe Pro
    210                 215                 220

Pro Pro Tyr Tyr Met Asp Val Ser Phe Thr Gly Asp Val His Gln Thr
225                 230                 235                 240

Ser Ser Gln Gln Gly
            245
```

<210> SEQ ID NO 109
<211> LENGTH: 738
<212> TYPE: DNA
<213> ORGANISM: Brassica rapa

<400> SEQUENCE: 109

```
atgtcaataa atcaatattc aagcgagttc tactaccatt ctctcatgtg gcaacaacag      60
cagcaacacc accatcaaaa cgaagtcgtg gaggaaaaag aagctctttt cgagaaaccc     120
ttaaccccaa gtgacgtcgg aaaactaaac cgcctagtca tccctaaaca gcacgccgag     180
agatacttcc ctctcgccgc cgccgcggta gacgccgtgg agaagggatt actcctctgc     240
ttcgaggacg aggaaggtaa gccatggaga ttcagatact cttattggaa tagtagccag     300
agttacgtct tgaccaaagg atggagcaga tatgttaaag agaagcaact tgacgccggc     360
gacgttgttc tctttcatcg ccaccgtgct gacggtggaa gattcttcat ggctggagaa     420
gacgcggcg actcttcctc ctcctccgac tcttatcgca atcttcaatc taattcctcg     480
ctccaatatt atcctcatgc aggggctcaa gcggtggaga accagagagg taactccaag     540
acattgagac tttttggagt gaacatggag tgccagatag actcagactg gtccgagcca     600
tccacacctg acggttttac acatgtccca accaatcacg accagtttcc tatctaccct     660
gaacactttc ctcctccgta ctacatggac gtaagtttca caggagatgt gcaccagacg     720
agtagccaac aaggatag                                                   738
```

<210> SEQ ID NO 110
<211> LENGTH: 310
<212> TYPE: PRT
<213> ORGANISM: Brassica rapa

<400> SEQUENCE: 110

```
Met Met Thr Asn Leu Ser Leu Ala Arg Glu Gly Glu Glu Glu Glu
 1               5                  10                  15

Glu Ala Gly Ala Lys Lys Pro Thr Glu Glu Val Glu Arg Glu His Met
            20                  25                  30

Phe Asp Lys Val Val Thr Pro Ser Asp Val Gly Lys Leu Asn Arg Leu
        35                  40                  45

Val Ile Pro Lys Gln His Ala Glu Arg Tyr Phe Pro Leu Asp Ser Ser
    50                  55                  60

Thr Asn Glu Lys Gly Leu Ile Leu Asn Phe Glu Asp Leu Thr Gly Lys
65                  70                  75                  80

Ser Trp Arg Phe Arg Tyr Ser Tyr Trp Asn Ser Ser Gln Ser Tyr Val
                85                  90                  95

Met Thr Lys Gly Trp Ser Arg Phe Val Lys Asp Lys Lys Leu Asp Ala
            100                 105                 110

Gly Asp Ile Val Ser Phe Leu Arg Cys Val Gly Asp Thr Gly Arg Asp
        115                 120                 125

Ser Arg Leu Phe Ile Asp Trp Arg Arg Pro Lys Val Pro Asp Tyr
    130                 135                 140

Thr Thr Ser Thr Ser His Phe Pro Ala Gly Ala Met Phe Pro Arg Phe
145                 150                 155                 160

Tyr Ser Phe Gln Thr Ala Thr Ser Thr Ser Tyr Asn Pro Tyr Asn
                165                 170                 175

His Gln Gln Pro Arg His His His Ser Gly Tyr Cys Tyr Pro Gln Ile
            180                 185                 190

Pro Arg Glu Phe Gly Tyr Gly Tyr Val Val Arg Ser Val Asp Gln Arg
        195                 200                 205
```

```
Ala Val Val Ala Asp Pro Leu Val Ile Glu Ser Val Pro Val Met Met
        210                 215                 220

His Gly Gly Ala Arg Val Asn Gln Ala Ala Val Gly Thr Ala Gly Lys
225                 230                 235                 240

Arg Leu Arg Leu Phe Gly Val Asp Met Glu Cys Gly Glu Ser Gly Gly
                245                 250                 255

Thr Asn Ser Thr Glu Glu Glu Ser Ser Ser Gly Gly Ser Leu Pro
            260                 265                 270

Arg Gly Gly Ala Ser Pro Ser Ser Ser Met Phe Gln Leu Arg Leu Gly
                275                 280                 285

Asn Ser Ser Glu Asp Asp His Leu Phe Lys Lys Gly Lys Ser Ser Leu
            290                 295                 300

Pro Phe Asn Leu Asp Gln
305                 310

<210> SEQ ID NO 111
<211> LENGTH: 933
<212> TYPE: DNA
<213> ORGANISM: Brassica rapa

<400> SEQUENCE: 111
atgatgacaa atttgtctct tgcaagagaa ggagaagaag aagaagaaga ggcaggagca      60
aagaagccca cagaagaagt ggagagagag cacatgttcg acaaagtggt gactccaagt     120
gacgtcggga aactaaaccg actcgtgatc ccaaagcaac acgcggagag atacttccct     180
ttagattcat ccacaaacga aagggtttg attctaaact tcgaagatct cacgggaaag      240
tcatggaggt tccgttactc ttactggaac agcagtcaga gctatgtcat gactaaaggt     300
tggagccgtt tcgttaaaga caagaagcta gacgctggag atattgtctc tttcctgaga     360
tgtgtcggag acacaggaag ggacagccgc ttgtttatcg attggaggag acgacctaaa     420
gtccctgact acgacatcga cttctcac tttcctgccg gagctatgtt ccctaggttt       480
tacagttttc agacagcaac tacttccaca agttacaatc cctataatca tcagcagcca     540
cgtcatcatc acagtggtta ctgttatcct caaatcccga gagaatttgg atatgggtat     600
gtcgttaggt cagtagatca gagggcggtg gtggctgatc cgttagtgat cgaatctgtg     660
ccggtgatga tgcacggagg agctcgagtg aaccaggcgg ctgttggaac ggccgggaaa     720
aggctgaggc tttttggagt cgatatggaa tgtggcgaga gtggaggaac aaacagtacg     780
gaggaagaat cttcatcttc cggtgggagt ttgccacgtg gcggtgcttc tccgtcttcc     840
tctatgtttc agctgaggct tggaaacagc agtgaagatg atcacttatt taagaaagga     900
aagtcttcat tgcctttaa tttggatcaa taa                                   933

<210> SEQ ID NO 112
<211> LENGTH: 293
<212> TYPE: PRT
<213> ORGANISM: Brassica rapa

<400> SEQUENCE: 112

Met Met Thr Asn Leu Ser Leu Ala Arg Glu Gly Glu Ala Gln Val Lys
1               5                   10                  15

Lys Pro Ile Glu Glu Val Glu Arg Glu His Met Phe Asp Lys Val Val
            20                  25                  30

Thr Pro Ser Asp Val Gly Lys Leu Asn Arg Leu Val Ile Pro Lys Gln
        35                  40                  45
```

| | | | | | | | | | | | | |
|---|---|---|---|---|---|---|---|---|---|---|---|---|
|His|Ala|Glu|Arg|Tyr|Phe|Pro|Leu|Asp|Ser|Ser|Asn|Glu|Lys|Gly|
| |50| | | |55| | | |60| | | |

His Ala Glu Arg Tyr Phe Pro Leu Asp Ser Ser Asn Glu Lys Gly
 50                  55                  60

Leu Leu Leu Asn Phe Glu Asp Leu Thr Gly Lys Ser Trp Arg Phe Arg
 65                  70                  75                  80

Tyr Ser Tyr Trp Asn Ser Ser Gln Ser Tyr Val Met Thr Lys Gly Trp
                 85                  90                  95

Ser Arg Phe Val Lys Asp Lys Lys Leu Asp Ala Gly Asp Ile Val Ser
             100                 105                 110

Phe Gln Arg Cys Val Gly Asp Ser Arg Leu Phe Ile Asp Trp Arg Arg
         115                 120                 125

Arg Pro Lys Val Pro Asp Tyr Pro Thr Ser Thr Ala His Phe Ala Ala
    130                 135                 140

Gly Ala Met Phe Pro Arg Phe Tyr Ser Phe Pro Thr Ala Thr Thr Ser
145                 150                 155                 160

Thr Cys Tyr Asp Leu Tyr Asn His Gln Pro Pro Arg His His His Ile
                165                 170                 175

Gly Tyr Gly Tyr Pro Gln Ile Pro Arg Glu Phe Gly Tyr Gly Tyr Phe
            180                 185                 190

Val Arg Ser Val Asp Gln Arg Ala Val Val Ala Asp Pro Leu Val Ile
        195                 200                 205

Glu Ser Val Pro Val Met Met Arg Gly Gly Ala Arg Val Ser Gln Glu
    210                 215                 220

Val Val Gly Thr Ala Gly Lys Arg Leu Arg Leu Phe Gly Val Asp Met
225                 230                 235                 240

Glu Glu Glu Ser Ser Ser Gly Gly Ser Leu Pro Arg Ala Gly Gly
                245                 250                 255

Gly Gly Ala Ser Ser Ser Ser Ser Leu Phe Gln Leu Arg Leu Gly Ser
            260                 265                 270

Ser Cys Glu Asp Asp His Phe Ser Lys Lys Gly Lys Ser Ser Leu Pro
    275                 280                 285

Phe Asp Leu Asp Gln
    290

<210> SEQ ID NO 113
<211> LENGTH: 882
<212> TYPE: DNA
<213> ORGANISM: Brassica rapa

<400> SEQUENCE: 113

```
atgatgacca acttgtctct tgcaagggaa ggagaagcac aagtaaagaa gcccatagaa      60
gaagttgaga gagagcacat gttcgacaaa gtggtgactc caagcgacgt agggaaacta     120
aacagactcg tgatcccaaa gcaacacgca gagagatact ccctctaga  ttcatcctca     180
aacgagaaag gtttgcttct aaactttgaa gatctaacag gaaagtcatg gaggttccgt     240
tactcttact ggaacagtag ccagagctat gtcatgacta aggttggag  tcgtttcgtt     300
aaagacaaga agcttgacgc cggagatatt gtctctttcc agagatgtgt cggagacagc     360
cgcttgttta tcgattggag agacgacct  aaagtccctg actatccgac atcgactgct     420
cactttgctg caggagctat gttccctagg ttttacagtt ttccgacagc aactacttcg     480
acatgttacg atctgtacaa tcatcagccg ccacgtcatc atcacattgg ttacggttat     540
ccacagattc cgagagaatt tggatacggg tatttcgtta ggtcagtgga ccagagagcg     600
gtggtggctg atccgttggt gatcgaatct gtgccggtga tgatgcgcgg aggagctcga     660
gttagtcagg aggttgttgg aacggccggg aagaggctga ggcttttttgg agtcgatatg    720
```

```
gaggaagaat cttcatcttc cggtgggagt ttgccgcgtg ccggaggtgg cggtgcttct    780
tcatcttcct ctttgtttca gctgagactt gggagcagct gtgaagatga tcacttctct    840
aagaaaggaa agtcttcatt gccttttgat ttggatcaat aa                       882
```

<210> SEQ ID NO 114
<211> LENGTH: 297
<212> TYPE: PRT
<213> ORGANISM: Brassica rapa

<400> SEQUENCE: 114

```
Met Met Met Thr Asn Leu Ser Leu Ser Arg Glu Gly Glu Glu Glu
1               5                   10                  15

Glu Glu Glu Gln Glu Glu Ala Lys Lys Pro Met Glu Glu Val Glu Arg
            20                  25                  30

Glu His Met Phe Asp Lys Val Val Thr Pro Ser Asp Val Gly Lys Leu
        35                  40                  45

Asn Arg Leu Val Ile Pro Lys Gln Tyr Ala Glu Arg Tyr Phe Pro Leu
    50                  55                  60

Asp Ser Ser Thr Asn Glu Lys Gly Leu Leu Leu Asn Phe Glu Asp Leu
65                  70                  75                  80

Ala Gly Lys Ser Trp Arg Phe Arg Tyr Ser Tyr Trp Asn Ser Ser Gln
                85                  90                  95

Ser Tyr Val Met Thr Lys Gly Trp Ser Arg Phe Val Lys Asp Lys Lys
            100                 105                 110

Leu Asp Ala Gly Asp Ile Val Ser Phe Gln Arg Cys Val Gly Asp Ser
        115                 120                 125

Gly Arg Asp Ser Arg Leu Phe Ile Asp Trp Arg Arg Arg Pro Lys Val
    130                 135                 140

Pro Asp His Pro Thr Ser Ile Ala His Phe Ala Ala Gly Ser Met Phe
145                 150                 155                 160

Pro Arg Phe Tyr Ser Phe Pro Thr Ala Thr Tyr Asn Leu Tyr Asn
                165                 170                 175

Tyr Gln Gln Pro Arg His His His Ser Gly Tyr Asn Tyr Pro Gln
            180                 185                 190

Ile Pro Arg Glu Phe Gly Tyr Gly Tyr Leu Val Asp Gln Arg Ala Val
        195                 200                 205

Val Ala Asp Pro Leu Val Ile Glu Ser Val Pro Val Met Met His Gly
    210                 215                 220

Gly Ala Gln Val Ser Gln Ala Val Val Gly Thr Ala Gly Lys Arg Leu
225                 230                 235                 240

Arg Leu Phe Gly Val Asp Met Glu Glu Glu Ser Ser Ser Gly Gly
                245                 250                 255

Ser Leu Pro Arg Gly Asp Ala Ser Pro Ser Ser Leu Phe Gln Leu
            260                 265                 270

Arg Leu Gly Ser Ser Ser Glu Asp Asp His Phe Ser Lys Lys Gly Lys
        275                 280                 285

Ser Ser Leu Pro Phe Asp Leu Asp Gln
    290                 295
```

<210> SEQ ID NO 115
<211> LENGTH: 894
<212> TYPE: DNA
<213> ORGANISM: Brassica rapa

<400> SEQUENCE: 115

-continued

```
atgatgatga caaacttgtc tctttcaaga gaaggagaag aggaggaaga agaagaacaa    60
gaagaggcca agaagcccat ggaagaagta gagagagagc acatgttcga caaagtggtg   120
actccaagcg atgttggtaa actaaaccgg ctcgtgatcc caaagcaata cgcagagaga   180
tacttcccct tagattcatc cacaaacgag aaaggtttgc ttctaaactt cgaagatctc   240
gcaggaaagt catggaggtt ccgttactct tactggaaca gtagtcagag ctatgtcatg   300
actaaaggtt ggagccgttt cgttaaagac aaaaagctag acgccggaga tattgtctct   360
ttccagagat gtgtcggaga ttcaggaaga gacagccgct tgtttattga ttggaggaga   420
agacctaaag ttcctgacca tccgacatcg attgctcact tgctgccgg atctatgttt    480
cctaggtttt acagtttcc gacagcaact agttacaatc tttacaacta tcagcagcca   540
cgtcatcatc atcacagtgg ttataattat cctcaaattc gagagaatt tggatacggg    600
tacttggtgg atcaaagagc cgtggtggct gatccgttgg tgattgaatc tgtgccggtg   660
atgatgcacg gaggagctca agttagtcag gcggttgttg aacggccgg aagaggctg    720
aggctttttg gagtcgatat ggaggaagaa tcttcatctt ccggtgggag tttgccacgt   780
ggtgacgctt ctccgtcttc ctctttgttt cagctgagac ttggaagcag cagtgaagat   840
gatcacttct ctaagaaagg aaagtcctca ttgccttttg atttggatca ataa          894
```

<210> SEQ ID NO 116
<211> LENGTH: 286
<212> TYPE: PRT
<213> ORGANISM: Brassica rapa

<400> SEQUENCE: 116

```
Met Asn Gln Glu Glu Glu Asn Pro Val Glu Lys Ala Ser Ser Met Glu
1               5                   10                  15

Arg Glu His Met Phe Glu Lys Val Val Thr Pro Ser Asp Val Gly Lys
                20                  25                  30

Leu Asn Arg Leu Val Ile Pro Lys Gln His Ala Glu Arg Tyr Phe Pro
            35                  40                  45

Leu Asp Asn Asn Ser Asp Ser Ser Lys Gly Leu Leu Leu Asn Phe Glu
        50                  55                  60

Asp Arg Thr Gly Asn Ser Trp Arg Phe Arg Tyr Ser Tyr Trp Asn Ser
65                  70                  75                  80

Ser Gln Ser Tyr Val Met Thr Lys Gly Trp Ser Arg Phe Val Lys Asp
                85                  90                  95

Lys Lys Leu Asp Ala Gly Asp Ile Val Ser Phe Gln Arg Asp Pro Gly
            100                 105                 110

Asn Lys Asp Lys Leu Phe Ile Asp Trp Arg Arg Arg Pro Lys Ile Pro
        115                 120                 125

Asp His His His Gln Phe Ala Gly Ala Met Phe Pro Arg Phe Tyr Ser
    130                 135                 140

Phe Ser His Pro Gln Asn Leu Tyr His Arg Tyr Gln Gln Asp Leu Gly
145                 150                 155                 160

Ile Gly Tyr Tyr Val Ser Ser Met Glu Arg Asn Asp Pro Thr Ala Val
                165                 170                 175

Ile Glu Ser Val Pro Leu Ile Met Gln Arg Arg Ala Ala His Val Ala
            180                 185                 190

Ala Ile Pro Ser Ser Arg Gly Glu Lys Arg Leu Arg Leu Phe Gly Val
        195                 200                 205

Asp Met Glu Cys Gly Gly Gly Gly Gly Ser Val Asn Ser Thr Glu Glu
```

```
                    210                 215                 220
Glu Ser Ser Ser Gly Gly Gly Gly Val Ser Met Ala Ser Val
225                 230                 235                 240

Gly Ser Leu Leu Gln Leu Arg Leu Val Ser Ser Asp Asp Glu Ser Leu
                245                 250                 255

Val Ala Met Glu Ala Ala Ser Val Asp Glu Asp His His Leu Phe Thr
            260                 265                 270

Lys Lys Gly Lys Ser Ser Leu Ser Phe Asp Leu Asp Arg Lys
            275                 280                 285

<210> SEQ ID NO 117
<211> LENGTH: 861
<212> TYPE: DNA
<213> ORGANISM: Brassica rapa

<400> SEQUENCE: 117
atgaatcaag aagaagagaa tcctgtggaa aaagcctctt caatggagag agagcacatg     60
tttgaaaaag tagtaacacc aagcgacgta ggcaaactaa accgactcgt gatcccaaag    120
caacacgcgg agagatactt ccctttagac aacaattctg acagcagcaa aggtttgctt    180
ctaaacttcg aagaccgaac aggaaactca tggagattcc gttactctta ctggaacagt    240
agccagagtt atgtcatgac aaaaggttgg agccgcttcg tcaaagacaa gaagcttgat    300
gctggcgaca tcgtttcttt tcagagagat cctggtaata agacaagct tttcattgat    360 tggaggagac gaccaaagat tccagatcat catcatcaat tcgctggagc tatgttccct    420 aggtttact ctttctctca tcctcagaac ctttatcatc gatatcaaca agatcttgga    480
attgggtatt atgtgagttc aatggagaga atgatccaa cggctgtaat tgaatctgtg    540
ccgttgataa tgcaaaggag agcagcacac gtggctgcta ccttcatc aagaggagag    600 aagaggttaa ggctgtttgg agtggacatg gagtgcggcg gcggcggagg aagtgtgaat    660
agcacggagg aagagtcgtc gtcttccggt ggtggcggcg gcgtttctat ggctagtgtt    720
ggttctcttc tccaattgag gctagtgagc agtgatgatg agtctttggt agcaatggaa    780
gctgcaagtg tcgatgagga tcatcacttg tttacaaaga aggaaagtc ttctttgtct    840 ttcgatttgg atagaaaatg a                                              861

<210> SEQ ID NO 118
<211> LENGTH: 292
<212> TYPE: PRT
<213> ORGANISM: Brassica rapa

<400> SEQUENCE: 118

Met Asn Gln Glu Asn Lys Lys Pro Leu Glu Glu Ala Ser Thr Ser Met
1               5                   10                  15

Glu Arg Glu Asn Met Phe Asp Lys Val Val Thr Pro Ser Asp Val Gly
            20                  25                  30

Lys Leu Asn Arg Leu Val Ile Pro Lys Gln His Ala Glu Arg Tyr Phe
        35                  40                  45

Pro Leu Asp Asn Ser Thr Asn Asn Lys Gly Leu Leu Leu Asp Phe
    50                  55                  60

Glu Asp Arg Thr Gly Ser Ser Trp Arg Phe Tyr Ser Tyr Trp Asn
65                  70                  75                  80

Ser Ser Gln Ser Tyr Val Met Thr Lys Gly Trp Ser Arg Phe Val Lys
                85                  90                  95

Asp Lys Lys Leu Asp Ala Gly Asp Ile Val Ser Phe Gln Arg Asp Pro
```

```
            100                 105                 110
Cys Asn Lys Asp Lys Leu Tyr Ile Asp Trp Arg Arg Arg Pro Lys Ile
        115                 120                 125

Pro Asp His His Gln Phe Ala Gly Ala Met Pro Arg Phe Tyr Ser
130                 135                 140

Phe Pro His Pro Gln Met Pro Thr Ser Phe Glu Ser Ser His Asn Leu
145                 150                 155                 160

Tyr His His Arg Phe Gln Arg Asp Leu Gly Ile Gly Tyr Tyr Pro Thr
                165                 170                 175

Ala Val Ile Glu Ser Val Pro Val Ile Met Gln Arg Arg Glu Ala Gln
            180                 185                 190

Val Ala Asn Met Ala Ser Ser Arg Gly Glu Lys Arg Leu Arg Leu Phe
        195                 200                 205

Gly Val Asp Val Glu Cys Gly Gly Gly Gly Gly Ser Val Asn Ser
210                 215                 220

Thr Glu Glu Glu Ser Ser Ser Gly Gly Ser Met Ser Arg Gly Gly
225                 230                 235                 240

Val Ser Met Ala Gly Val Gly Ser Leu Leu Gln Leu Arg Leu Val Ser
                245                 250                 255

Ser Asp Asp Glu Ser Leu Val Ala Met Glu Gly Ala Thr Val Asp Glu
            260                 265                 270

Asp His His Leu Phe Thr Thr Lys Lys Gly Lys Ser Ser Leu Ser Phe
        275                 280                 285

Asp Leu Asp Ile
    290
```

<210> SEQ ID NO 119
<211> LENGTH: 879
<212> TYPE: DNA
<213> ORGANISM: Brassica rapa

<400> SEQUENCE: 119

```
atgaatcaag aaaacaagaa gcctttggaa gaagcttcga cttcaatgga gagagagaac    60
atgttcgaca agtagtaac accaagcgac gtagggaaac taaaccgact cgtgatccca   120
aagcaacacg cagagagata cttcccttta gacaactcct caacaaacaa caaagggttg   180
cttctagact tcgaagaccg tacaggaagc tcatggagat tccgttactc ttactgaac    240
agtagccaaa gttatgtcat gacaaaaggt tggagccgtt ttgtcaaaga caagaagctt   300
gatgctggtg acatcgtgtc ttttcaaaga gatccctgta ataaagacaa gctttacata   360
gattggagga cgaccaaa gattccagat catcatcagt tcgccggagc tatgttccct    420
aggttttact ctttccctca ccctcagatg ccgacaagtt ttgaaagtag tcacaacctt   480
tatcatcatc ggtttcaacg agatcttgga attgggtatt atccaacggc tgtgattgaa   540
tctgtgccgg tgataatgca aggagagaa gcacaagtgg ctaatatggc ttcatcaaga   600
ggagagaaga ggttaaggct gtttggagtg gacgtggagt gcggcggcgg aggaggagga   660
agtgtgaata gcacggagga agagtcgtcg tcttccggtg gtagtatgtc acgtggcggc   720
gtttctatgg ctggtgttgg ttctctcctt cagttgaggt tagtgagcag tgatgatgag   780
tctttagtag cgatggaagg tgctactgtc gatgaggatc atcacttgtt tacaactaag   840
aaaggaaagt cttctttgtc tttcgatttg gatatatga                           879
```

<210> SEQ ID NO 120
<211> LENGTH: 320

<212> TYPE: PRT
<213> ORGANISM: Brassica rapa

<400> SEQUENCE: 120

Met Glu Arg Lys Ser Asn Asp Leu Glu Arg Ser Glu Asn Ile Asp Ser
1               5                   10                  15

Gln Asn Lys Lys Met Asn Leu Glu Glu Arg Pro Val Gln Glu Ala
            20                  25                  30

Ser Ser Met Glu Arg Glu His Met Phe Asp Lys Val Val Thr Pro Ser
        35                  40                  45

Asp Val Gly Lys Leu Asn Arg Leu Val Ile Pro Lys Gln His Ala Glu
    50                  55                  60

Arg Tyr Phe Pro Leu Asp Asn Ser Ser Asp Asn Asn Lys Gly Leu
65                  70                  75                  80

Leu Leu Asn Phe Glu Asp Arg Ile Gly Ile Leu Trp Ser Phe Arg Tyr
                85                  90                  95

Ser Tyr Trp Asn Ser Ser Gln Ser Tyr Val Met Thr Lys Gly Trp Ser
            100                 105                 110

Arg Phe Val Lys Asp Lys Lys Leu Asp Ala Gly Asp Ile Val Ser Phe
        115                 120                 125

His Arg Gly Ser Cys Asn Lys Asp Lys Leu Phe Ile Asp Trp Lys Arg
    130                 135                 140

Arg Pro Lys Ile Pro Asp His Gln Val Val Gly Ala Met Phe Pro Arg
145                 150                 155                 160

Phe Tyr Ser Tyr Pro Tyr Pro Gln Ile Gln Ala Ser Tyr Glu Arg His
                165                 170                 175

Asn Leu Tyr His Arg Tyr Gln Arg Asp Ile Gly Ile Gly Tyr Tyr Val
            180                 185                 190

Arg Ser Met Glu Arg Tyr Asp Pro Thr Ala Val Ile Glu Ser Val Pro
        195                 200                 205

Val Ile Met Gln Arg Arg Ala His Val Ala Thr Met Ala Ser Ser Arg
    210                 215                 220

Gly Glu Lys Arg Leu Arg Leu Phe Gly Val Asp Met Glu Cys Val Arg
225                 230                 235                 240

Gly Gly Arg Gly Gly Gly Ser Val Asn Ser Thr Glu Glu Ser
                245                 250                 255

Ser Thr Ser Gly Gly Ser Ile Ser Arg Gly Val Ser Met Ala Gly
        260                 265                 270

Val Gly Ser Pro Leu Gln Leu Arg Leu Val Ser Ser Asp Gly Asp Asp
    275                 280                 285

Gln Ser Leu Val Ala Arg Gly Ala Ala Arg Val Asp Glu Asp His His
    290                 295                 300

Leu Phe Thr Lys Lys Gly Lys Ser Ser Leu Ser Phe Asp Leu Asp Lys
305                 310                 315                 320

<210> SEQ ID NO 121
<211> LENGTH: 963
<212> TYPE: DNA
<213> ORGANISM: Brassica rapa

<400> SEQUENCE: 121
atggagagga agtccaatga tcttgagaga tctgagaata ttgattctca aaacaagaag    60
atgaatctag aagaagagag gcctgtacaa gaagcttctt cgatggagag agagcacatg   120
ttcgacaaag tagtaacacc aagcgacgtt gggaaactaa accggctggt gatcccaaag   180

-continued

```
caacacgcag agcgatactt cccttttagac aataattcct cagacaacaa caaaggtttg    240
cttctaaact tcgaagatcg aataggaatc ttatggagtt tccgttactc ctactggaac    300
agtagccaaa gttatgtaat gactaaaggc tggagccgtt tcgtcaaaga caagaagctt    360
gatgctggcg acatagtttc ttttcataga ggttcttgta ataaagacaa gcttttcatt    420
gattggaaga gacgaccaaa gattcctgat caccaagtcg tcggagctat gttccctagg    480
ttttactctt acccttatcc tcagatacag gctagttatg aacgtcacaa cctttatcat    540
cgatatcaac gagatatagg aattgggtat tatgtgaggt caatggagag atatgatcca    600
acggctgtaa ttgaatctgt gccggtgata atgcaaagga gcacatgt ggctactatg     660 gcttcatcaa gaggagagaa gaggttaagg ctttttggag tggatatgga gtgcgtcaga    720
ggcggccgag gaggaggagg aagtgtgaat agcacggagg aagagtcttc gacttccggt    780
ggtagtatct cacgtggcgg cgtttctatg gctggtgttg gctctccact ccagttgagg    840
ttagtgagca gtgacggtga tgatcagtct ctagtagcta ggggagctgc tagggttgat    900
gaggatcatc acttgtttac aaagaaagga aagtcttctt tgtctttcga tttggataaa    960
tga                                                                    963
```

<210> SEQ ID NO 122
<211> LENGTH: 350
<212> TYPE: PRT
<213> ORGANISM: Brassica rapa
<400> SEQUENCE: 122

```
Met Val Phe Ser Cys Ile Asp Glu Ser Ser Thr Ser Glu Ser Phe
1               5                   10                  15

Ser Pro Ala Thr Ala Thr Ala Thr Ala Thr Lys Phe Ser Ala
                20                  25                  30

Pro Pro Leu Pro Pro Leu Arg Leu Asn Arg Met Arg Ser Gly Gly Ser
            35                  40                  45

Asn Val Val Leu Asp Ser Lys Asn Gly Val Asp Ile Asp Ser Arg Lys
    50                  55                  60

Leu Ser Ser Ser Lys Tyr Lys Gly Val Val Pro Gln Pro Asn Gly Arg
65                  70                  75                  80

Trp Gly Ala Gln Ile Tyr Val Lys His Gln Arg Val Trp Leu Gly Thr
                85                  90                  95

Phe Cys Asp Glu Glu Glu Ala Ala His Ser Tyr Asp Ile Ala Ala Arg
            100                 105                 110

Lys Phe Arg Gly Arg Asp Ala Val Val Asn Phe Lys Thr Phe Leu Ala
        115                 120                 125

Ser Glu Asp Asp Asn Gly Glu Leu Cys Phe Leu Glu Ala His Ser Lys
    130                 135                 140

Ala Glu Ile Val Asp Met Leu Arg Lys His Thr Tyr Ala Asp Glu Leu
145                 150                 155                 160

Ala Gln Ser Asn Lys Arg Ser Gly Ala Asn Thr Asn Thr Asn Thr Thr
                165                 170                 175

Gln Ser His Thr Val Ser Arg Thr Arg Glu Val Leu Phe Glu Lys Val
            180                 185                 190

Val Thr Pro Ser Asp Val Gly Lys Leu Asn Arg Leu Val Ile Pro Lys
        195                 200                 205

Gln His Ala Glu Lys Tyr Phe Pro Leu Pro Ser Leu Ser Val Thr Lys
    210                 215                 220

Gly Val Leu Ile Asn Phe Glu Asp Val Thr Gly Lys Val Trp Arg Phe
```

```
                225                 230                 235                 240
Arg Tyr Ser Tyr Trp Asn Ser Ser Gln Ser Tyr Val Leu Thr Lys Gly
                    245                 250                 255

Trp Ser Arg Phe Val Lys Glu Lys Asn Leu Arg Ala Gly Asp Val Val
                260                 265                 270

Thr Phe Glu Arg Ser Thr Gly Ser Asp Arg Gln Leu Tyr Ile Asp Trp
            275                 280                 285

Lys Ile Arg Ser Gly Pro Ser Lys Asn Pro Val Gln Val Val Arg
        290                 295                 300

Leu Phe Gly Val Asp Ile Phe Asn Val Thr Ser Ala Lys Pro Ser Asn
305                 310                 315                 320

Val Val Asp Ala Cys Gly Gly Lys Arg Ser Arg Asp Val Asp Met Phe
                325                 330                 335

Ala Leu Arg Cys Ser Lys Lys His Ala Ile Ile Asn Ala Leu
                340                 345                 350

<210> SEQ ID NO 123
<211> LENGTH: 1053
<212> TYPE: DNA
<213> ORGANISM: Brassica rapa

<400> SEQUENCE: 123
atggtattca gttgcataga cgagagctct tccacttcag aatctttttc acccgcaacc        60
gcaaccgcaa ccgcaaccgc cacaaagttc tctgctcctc cgcttccacc gttacgcctc       120
aaccggatga aagcggtgg aagcaacgtc gtgttggatt caaagaatgg cgtagatatt        180
gattcacgga agctatcgtc gtcaaagtac aaaggcgtgg ttcctcagcc caacggaaga       240
tggggagctc agatttacgt gaagcaccag cgagtttggc tgggcacttt ctgcgatgaa       300
gaggaagctg ctcactccta cgacatagcc gcccgtaaat tccgtggccg tgacgccgtt       360
gtcaacttca aaaccttcct cgcctcagag gacgacaacg gcgagttatg tttccttgaa       420
gctcactcca aggccgagat cgtcgacatg ttgaggaaac acacttacgc tgacgagctt       480
gcgcagagca taaacgcag cggagcgaat acgaatacga atacgactca aagccacacc       540
gtttcgagaa cacgtgaagt gcttttcgag aaggttgtca cgcctagcga cgttggtaag       600
ctaaaccgcc tcgtgatacc taaacagcac gcggagaaat attttccgtt accgtcactg       660
tcggtgacta aaggcgttct gatcaacttc gaagacgtga cgggtaaggt gtggcggttc       720
cgttactcat actggaacag tagtcaaagt tacgtgttga ccaagggatg gagtcggttc       780
gttaaggaga agaatctccg agccggtgat gtcgttactt cgagagatc gaccggttca       840 gaccggcagc tttatattga ttggaaaatc cggtctggtc cgagcaaaaa ccctgttcag       900
gttgtggtta ggcttttcgg agttgacatc ttcaacgtga caagcgcgaa gccgagcaac       960
gttgtagacg cgtgcggtgg aaagagatct cgggatgttg atatgtttgc gctacggtgt      1020
tccaaaaaac acgctataat caatgctttg tga                                    1053

<210> SEQ ID NO 124
<211> LENGTH: 540
<212> TYPE: PRT
<213> ORGANISM: Zea mays

<400> SEQUENCE: 124

Met Ala Ala Ser Pro Ser Ser Pro Leu Thr Ala Pro Pro Glu Pro Val
1               5                   10                  15

Thr Pro Pro Ser Pro Trp Thr Ile Thr Asp Gly Ala Ile Ser Gly Thr
```

```
                    20                  25                  30
Leu Pro Ala Ala Glu Ala Phe Ala Val His Tyr Pro Gly Tyr Pro Ser
                35                  40                  45
Ser Pro Ala Arg Ala Ala Arg Thr Leu Gly Gly Leu Pro Gly Leu Ala
            50                  55                  60
Lys Val Arg Ser Ser Asp Pro Gly Ala Arg Leu Glu Leu Arg Phe Arg
 65                  70                  75                  80
Pro Glu Asp Pro Tyr Cys His Pro Ala Phe Gly Gln Ser Arg Ala Ser
                85                  90                  95
Thr Gly Leu Leu Leu Arg Leu Ser Lys Arg Lys Gly Ala Ala Ala Pro
            100                 105                 110
Cys Ala His Val Val Ala Arg Val Arg Thr Ala Tyr Tyr Phe Glu Gly
            115                 120                 125
Met Ala Asp Phe Gln His Val Val Pro Val His Ala Ala Gln Thr Arg
            130                 135                 140
Lys Arg Lys His Ser Asp Ser Gln Asn Asp Asn Glu Asn Phe Gly Ser
145                 150                 155                 160
Asp Lys Thr Gly His Asp Glu Ala Asp Gly Asp Val Met Met Leu Val
                165                 170                 175
Pro Pro Leu Phe Ser Val Lys Asp Arg Pro Thr Lys Ile Ala Leu Val
            180                 185                 190
Pro Ser Ser Asn Ala Ile Ser Lys Thr Met His Arg Gly Val Val Gln
            195                 200                 205
Glu Arg Trp Glu Met Asn Val Gly Pro Thr Leu Ala Leu Pro Phe Asn
            210                 215                 220
Thr Gln Val Val Pro Glu Lys Ile Asn Trp Glu Asp His Ile Arg Lys
225                 230                 235                 240
Asn Ser Val Glu Trp Gly Trp Gln Met Ala Val Cys Lys Leu Phe Asp
                245                 250                 255
Glu Arg Pro Val Trp Pro Arg Gln Ser Leu Tyr Glu Arg Phe Leu Asp
            260                 265                 270
Asp Asn Val His Val Ser Gln Asn Gln Phe Lys Arg Leu Leu Phe Arg
            275                 280                 285
Ala Gly Tyr Tyr Phe Ser Thr Gly Pro Phe Gly Lys Phe Trp Ile Arg
            290                 295                 300
Arg Gly Tyr Asp Pro Arg Lys Asp Ser Glu Ser Gln Ile Tyr Gln Arg
305                 310                 315                 320
Ile Asp Phe Arg Met Pro Pro Glu Leu Arg Tyr Leu Arg Leu Lys
                325                 330                 335
Asn Ser Glu Ser Arg Lys Trp Ala Asp Met Cys Lys Leu Glu Thr Met
            340                 345                 350
Pro Ser Gln Ser Phe Ile Tyr Leu Gln Leu Tyr Glu Leu Lys Asp Asp
            355                 360                 365
Phe Ile Gln Ala Glu Ile Arg Lys Pro Ser Tyr Gln Ser Val Cys Ser
            370                 375                 380
Arg Ser Thr Gly Trp Phe Ser Lys Pro Met Ile Lys Thr Leu Arg Leu
385                 390                 395                 400
Gln Val Ser Ile Arg Leu Leu Ser Leu Leu His Asn Glu Glu Ala Lys
                405                 410                 415
Asn Leu Leu Arg Asn Ala His Glu Leu Ile Glu Arg Ser Lys Lys Gln
            420                 425                 430
Glu Ala Leu Ser Arg Ser Glu Leu Ser Ile Glu Tyr Asn Asp Ala Asp
            435                 440                 445
```

```
Gln Val Ser Ala Ala His Thr Gly Thr Glu Asp Gln Val Gly Pro Asn
    450                 455                 460

Asn Ser Asp Ser Glu Asp Val Asp Asp Glu Glu Glu Glu Glu Glu Leu
465                 470                 475                 480

Glu Gly Tyr Asp Ser Pro Pro Met Ala Asp Asp Ile His Glu Phe Thr
                485                 490                 495

Leu Gly Asp Ser Tyr Ala Phe Gly Glu Gly Phe Ser Asn Gly Tyr Leu
            500                 505                 510

Glu Glu Val Leu Arg Ser Leu Pro Leu Gln Glu Asp Gly Gln Lys Lys
        515                 520                 525

Leu Cys Asp Ala Pro Ile Asn Ala Asp Ala Ser Asp
    530                 535                 540

<210> SEQ ID NO 125
<211> LENGTH: 1674
<212> TYPE: DNA
<213> ORGANISM: Zea mays

<400> SEQUENCE: 125
```

| | | | | | |
|---|---|---|---|---|---|
| atggccgcct | cgccctcttc | acccttgaca | gcgccgccag | agccggtgac | cccgccgtcc | 60 |
| ccatggacca | tcacagacgg | agccatctct | ggcacgctcc | cagcagccga | ggccttcgca | 120 |
| gtgcactacc | cgggctaccc | ctcctctccc | gcccgcgccg | cccgcaccct | cggcggtctc | 180 |
| cccggcctcg | ccaaggtccg | gagttccgat | cccggcgccc | gcctcgagct | ccgcttccgc | 240 |
| cccgaggacc | cctactgcca | tccagccttt | ggccagtccc | gcgcctccac | tggccttctg | 300 |
| ctgcgcctct | ccaagcgcaa | aggagctgcg | gcaccttgtg | cccatgtggt | cgctcgtgtc | 360 |
| cggactgctt | actacttcga | aggtatggca | gattttcaac | atgttgttcc | agtgcatgct | 420 |
| gcacaaacaa | gaaaagaaa | acactcagat | tctcaaaatg | ataatgagaa | ttttggtagt | 480 |
| gataagacag | gacatgatga | agcagatgga | gatgtcatga | tgttggtacc | ccctctcttt | 540 |
| tcagtgaagg | ataggccaac | aaagatagcg | cttgtaccat | cgtccaatgc | catatctaaa | 600 |
| accatgcaca | ggggagttgt | acaagaacg | tgggagatga | atgttggacc | aactctggcg | 660 |
| cttccgttca | acactcaagt | tgtcccggag | aagattaatt | gggaagacca | cattagaaag | 720 |
| aattctgtag | aatggggttg | gcaaatggct | gtttgcaaat | tgtttgatga | gcgccctgtg | 780 |
| tggccaaggc | aatcactta | tgagcggttc | cttgatgata | tgtgcatgt | ctctcaaaac | 840 |
| caattcaaaa | ggcttctgtt | tagagctgga | tactacttct | ctactggacc | ctttggaaaa | 900 |
| ttttggatca | gaagaggata | tgaccctcgt | aaagactctg | agtcacaaat | atatcagaga | 960 |
| attgatttc | gcatgcctcc | cgagctacga | tatcttctaa | ggctgaagaa | ttctgagtct | 1020 |
| cgaaagtggg | cagatatgtg | caagcttgaa | acaatgccat | cacagagttt | catctacctg | 1080 |
| caattatatg | aactgaagga | tgattttatt | caagcagaaa | ttcgaaaacc | ttcttatcaa | 1140 |
| tcagtttgtt | cacgttctac | aggatggttt | tctaagccaa | tgatcaaaac | cctgaggttg | 1200 |
| caagtgagca | taaggctcct | ctctttattg | cataatgaag | aggctaaaaa | cttgttgagg | 1260 |
| aatgcccatg | agcttattga | aaggtccaag | aagcaggaag | ccctttcgag | atctgagctg | 1320 |
| tcaatagaat | ataatgatgc | tgatcaagtt | tctgccgcac | atactggaac | tgaggatcaa | 1380 |
| gtcggcccta | caactctga | tagtgaagat | gtggatgatg | aagaagagga | agaggaattg | 1440 |
| gagggttatg | attctccacc | tatggcagat | gatattcatg | agttcacctt | aggtgattcc | 1500 |
| tatgcatttg | gtgaaggctt | ctcgaatgga | tacctcgaag | aagtactgcg | cagcttgcca | 1560 |

```
ttgcaggaag acggccaaaa gaaattatgt gatgctccta tcaacgctga tgcaagtgat    1620
ggagagtttg aaatttacga acagcccagt gatgatgaag attctgatgg ctag          1674
```

<210> SEQ ID NO 126
<211> LENGTH: 409
<212> TYPE: PRT
<213> ORGANISM: Zea mays

<400> SEQUENCE: 126

```
Met Glu Phe Ala Ser Ser Ser Arg Phe Ser Arg Glu Glu Asp Glu
 1               5                  10                  15

Glu Glu Glu Gln Glu Glu Glu Glu Glu Glu Glu Ala Ser Pro Arg
                20                  25                  30

Glu Ile Pro Phe Met Thr Ala Ala Thr Ala Asp Thr Gly Ala Ala
                35                  40                  45

Ala Ser Ser Ser Pro Ser Ala Ala Ser Ser Gly Pro Ala Ala
        50                  55                  60

Ala Pro Arg Ser Ser Asp Gly Ala Gly Ala Ser Gly Ser Gly Gly
65                  70                  75                  80

Gly Ser Asp Asp Val Gln Val Ile Glu Lys Glu His Met Phe Asp Lys
                85                  90                  95

Val Val Thr Pro Ser Asp Val Gly Lys Leu Asn Arg Leu Val Ile Pro
                100                 105                 110

Lys Gln His Ala Glu Lys Tyr Phe Pro Leu Asp Ala Ala Asn Glu
        115                 120                 125

Lys Gly Gln Leu Leu Ser Phe Glu Asp Arg Ala Gly Lys Leu Trp Arg
        130                 135                 140

Phe Arg Tyr Ser Tyr Trp Asn Ser Ser Gln Ser Tyr Val Met Thr Lys
145                 150                 155                 160

Gly Trp Ser Arg Phe Val Lys Glu Lys Arg Leu Asp Ala Gly Asp Thr
                165                 170                 175

Val Ser Phe Cys Arg Gly Ala Gly Asp Thr Ala Arg Asp Arg Leu Phe
                180                 185                 190

Ile Asp Trp Lys Arg Arg Ala Asp Ser Arg Asp Pro His Arg Met Pro
        195                 200                 205

Arg Leu Pro Leu Pro Met Ala Pro Val Ala Ser Pro Tyr Gly Pro Trp
210                 215                 220

Gly Gly Gly Gly Gly Gly Ala Gly Gly Phe Met Pro Pro Ala
225                 230                 235                 240

Pro Pro Ala Thr Leu Tyr Glu His His Arg Phe Arg Gln Ala Leu Asp
                245                 250                 255

Phe Arg Asn Ile Asn Ala Ala Ala Ala Pro Ala Arg Gln Leu Leu Phe
                260                 265                 270

Phe Gly Ser Ala Gly Met Pro Pro Arg Ala Ser Met Pro Gln Gln Gln
        275                 280                 285

Gln Pro Pro Pro Pro His Pro Pro Leu His Ser Ile Met Leu Val
        290                 295                 300

Gln Pro Ser Pro Ala Pro Pro Thr Ala Ser Val Pro Met Leu Leu Asp
305                 310                 315                 320

Ser Val Pro Leu Val Asn Ser Pro Thr Ala Ala Ser Lys Arg Val Arg
                325                 330                 335

Leu Phe Gly Val Asn Leu Asp Asn Pro Gln Pro Gly Thr Ser Ala Glu
                340                 345                 350

Ser Ser Gln Asp Ala Asn Ala Leu Ser Leu Arg Thr Pro Gly Trp Gln
```

```
                 355                 360                 365
Arg Pro Gly Pro Leu Arg Phe Phe Glu Ser Pro Gln Arg Gly Ala Glu
        370                 375                 380

Ser Ser Ala Ala Ser Ser Pro Ser Ser Ser Ser Ser Lys Arg Glu
385                 390                 395                 400

Ala His Ser Ser Leu Asp Leu Asp Leu
                405

<210> SEQ ID NO 127
<211> LENGTH: 259
<212> TYPE: PRT
<213> ORGANISM: Zea mays

<400> SEQUENCE: 127

Met Glu Phe Thr Thr Pro Pro Ala Thr Arg Ser Gly Gly Gly Glu
1               5                   10                  15

Glu Arg Ala Ala Ala Glu His Asn Gln His Gln Gln Gln His Ala
            20                  25                  30

Thr Val Glu Lys Glu His Met Phe Asp Lys Val Val Thr Pro Ser Asp
        35                  40                  45

Val Gly Lys Leu Asn Arg Leu Val Ile Pro Lys Gln His Ala Glu Lys
50                  55                  60

Tyr Phe Pro Leu Asp Ala Ala Asn Glu Lys Gly Leu Leu Leu Ser
65                  70                  75                  80

Phe Glu Asp Arg Thr Gly Lys Pro Trp Arg Phe Arg Tyr Ser Tyr Trp
                85                  90                  95

Asn Ser Ser Gln Ser Tyr Val Met Thr Lys Gly Trp Ser Arg Phe Val
            100                 105                 110

Lys Glu Lys Arg Leu Asp Ala Gly Asp Thr Val Ser Phe Gly Arg Gly
        115                 120                 125

Ile Ser Glu Ala Ala Arg Asp Arg Leu Phe Ile Asp Trp Arg Cys Arg
    130                 135                 140

Pro Asp Pro Pro Val Val His His Gln Tyr His His Arg Leu Pro Leu
145                 150                 155                 160

Pro Ser Ala Val Val Pro Tyr Ala Pro Trp Ala Ala His Ala His His
                165                 170                 175

His His Tyr Pro Ala Asp Gly His Thr Glu Pro Val Thr Pro Cys Leu
            180                 185                 190

Cys Ala Thr Leu Val Ala Thr Glu Met Arg Ala Ser Ser Ser Gln Leu
        195                 200                 205

Ser Leu Thr Arg Ser Asn Leu Ser Arg Pro Pro Gln Pro Arg Ile Ala
    210                 215                 220

Arg Val Asp Gly Ala Gln Pro Arg Pro Ser Ser Pro Arg Gln Pro
225                 230                 235                 240

Gln Ser Leu Trp Cys Arg Ser Cys Gln Pro Gln Pro Arg Arg Thr Ala
                245                 250                 255

Asp Val Pro

<210> SEQ ID NO 128
<211> LENGTH: 780
<212> TYPE: DNA
<213> ORGANISM: Zea mays

<400> SEQUENCE: 128
atggagttca ccactccccc gcccgcgacc cggtcgggcg gcggagagga gagggcggct    60
```

```
gctgagcaca accagcacca ccagcagcag catgcgacgg tggagaagga gcacatgttc    120
gacaaggtgg tgacgccgag cgacgtcggg aagctgaacc ggctggtgat cccgaagcag    180
cacgcggaga agtacttccc gctggacgcg gcggcgaacg agaagggcct cctgctcagc    240
ttcgaggacc gcacggggaa gccctggcgc ttccgctact cctactggaa cagtagccag    300
agctacgtga tgaccaaggg ctggagccgc ttcgtcaagg agaagcgcct cgacgccggg    360
gacacagtct ccttcggccg cggcatcagc gaggcggcgc gcgacaggct tttcatcgac    420
tggcggtgcc gacccgaccc gccgtcgtg caccaccagt accaccaccg cctccctctc    480
ccctccgccg tcgtccccta cgcgccgtgg cggcgcacg cgcaccacca ccactaccca    540
gcagatgggc acacggaacc agtaacacct tgcctgtgcg ccacactcgt tgccactgaa    600
atgagagcat catcttcgca actgtcactc acacgctcca acctctccag gccgccacaa    660
cctagaatag ccagagtcga tggcgcccag ccacggccgt cgtcgtcacc acgccagcca    720
cagtcgttgt ggtgccggtc gtgccaaccg caaccacggc gaacggccga cgttccttga    780
```

<210> SEQ ID NO 129
<211> LENGTH: 327
<212> TYPE: PRT
<213> ORGANISM: Zea mays

<400> SEQUENCE: 129

```
Met Glu Phe Thr Ala Pro Pro Ala Thr Arg Ser Gly Gly Gly Glu
1               5                   10                  15

Glu Arg Ala Ala Ala Glu His His Gln Gln Gln Gln Gln Ala Thr Val
            20                  25                  30

Glu Lys Glu His Met Phe Asp Lys Val Val Thr Pro Ser Asp Val Gly
        35                  40                  45

Lys Leu Asn Arg Leu Val Ile Pro Lys Gln His Ala Glu Arg Tyr Phe
    50                  55                  60

Pro Leu Asp Ala Ala Ala Asn Asp Lys Gly Leu Leu Leu Ser Phe Glu
65                  70                  75                  80

Asp Arg Ala Gly Lys Pro Trp Arg Phe Arg Tyr Ser Tyr Trp Asn Ser
                85                  90                  95

Ser Gln Ser Tyr Val Met Thr Lys Gly Trp Ser Arg Phe Val Lys Glu
            100                 105                 110

Lys Arg Leu Asp Ala Gly Asp Thr Val Ser Phe Gly Arg Gly Val Gly
        115                 120                 125

Glu Ala Ala Arg Gly Arg Leu Phe Ile Asp Trp Arg Arg Pro Asp
    130                 135                 140

Pro Pro Val Val His His Gln Tyr His His His Arg Leu Pro Leu Pro
145                 150                 155                 160

Ser Ala Val Val Pro Tyr Ala Pro Trp Ala Ala Ala His Ala His
                165                 170                 175

His His His Tyr Pro Ala Ala Gly Val Gly Ala Ala Arg Thr Thr Thr
            180                 185                 190

Thr Thr Thr Thr Thr Val Leu His His Leu Pro Pro Ser Pro Ser Pro
        195                 200                 205

Leu Tyr Leu Asp Thr Arg Arg Arg His Val Gly Tyr Asp Ala Tyr Gly
    210                 215                 220

Ala Gly Thr Arg Gln Leu Leu Phe Tyr Arg Pro His Gln Gln Pro Ser
225                 230                 235                 240

Thr Thr Val Met Leu Asp Ser Val Pro Val Arg Leu Pro Pro Thr Pro
                245                 250                 255
```

```
Gly Gln His Ala Glu Pro Pro Pro Ala Val Ala Ser Ser Ala Ser
            260                 265                 270

Lys Arg Val Arg Leu Phe Gly Val Asn Leu Asp Cys Ala Ala Ala
        275                 280                 285

Gly Ser Glu Glu Glu Asn Val Gly Gly Trp Arg Thr Ser Ala Pro Pro
    290                 295                 300

Thr Gln Gln Ala Ser Ser Ser Ser Tyr Ser Gly Lys Ala Arg
305                 310                 315                 320

Cys Ser Leu Asn Leu Asp Leu
                325
```

<210> SEQ ID NO 130
<211> LENGTH: 984
<212> TYPE: DNA
<213> ORGANISM: Zea mays

<400> SEQUENCE: 130

```
atggagttca ccgctccccc gcccgcgacc cggtcgggcg gcggcgagga gagggcggct    60
gctgagcacc accagcagca gcagcaggcg acggtggaga aggagcacat gttcgacaag   120
gtggtgacgc cgagcgacgt cgggaagctg aaccggctgg tgatcccgaa gcagcacgcg   180
gagaggtact cccgctgga cgcggcggcg aacgacaagg gcctgctgct cagcttcgag   240
gaccgcgcgg ggaagcccctg gcgcttccgc tactcctact ggaacagcag ccagagctac   300
gtgatgacca agggctggag ccgcttcgtc aaggagaagc gcctcgacgc cggggacacc   360
gtctccttcg gccgcggcgt cggcgaggcg gcgcgcggca ggctcttcat cgactggcgg   420
cgccgacccg accccgccgt cgtgcaccac cagtaccacc accaccgcct ccctctcccc   480
tccgccgtcg tccctacgc gccgtgggcg gcggcggcgc acgcgcacca ccaccactac   540
ccagcagctg ggtcggtgc cgccaggacg acgacgacga cgacgacgac ggtgctccac   600
cacctgccgc cctcgccctc cccgctctac cttgacaccc gccgccgcca cgtcggctac   660
gacgcctacg gggccggcac caggcaactt ctcttctaca ggccgcacca gcagccctcc   720
acgacggtga tgctggactc cgtgccggta cggttaccgc caacgccagg gcagcacgcc   780
gagccgccgc cccccgccgt ggcgtcgtca gcctcgaagc gggtgcgcct gttcggggtg   840
aacctcgact cgccgccgc cgccggctca gaggaggaga acgtcggcgg gtggaggact   900
agtgcgccgc cgacgcagca ggcgtcctcc tcctcatcct actcttccgg gaaagcgagg   960
tgctccttga accttgactt gtga                                         984
```

<210> SEQ ID NO 131
<211> LENGTH: 422
<212> TYPE: PRT
<213> ORGANISM: Zea mays

<400> SEQUENCE: 131

```
Met Asp Gln Phe Ala Ala Ser Gly Arg Phe Ser Arg Glu Glu Ala
1               5                   10                  15

Asp Glu Glu Gln Glu Asp Ala Ser Asn Ser Met Arg Glu Ile Ser Phe
            20                  25                  30

Met Pro Pro Ala Ala Ala Ser Ser Ser Ala Ala Ser Ala Ser
        35                  40                  45

Ala Ser Ala Ser Thr Ser Ala Ser Ala Cys Ala Ser Gly Ser Ser Ser
    50                  55                  60

Ala Pro Phe Arg Ser Ala Ser Ala Ser Gly Asp Ala Ala Gly Ala Ser
```

```
                65                  70                  75                  80
Gly Ser Gly Gly Pro Ala Asp Ala Asp Ala Glu Ala Glu Ala Val Glu
                    85                  90                  95
Lys Glu His Met Phe Asp Lys Val Val Thr Pro Ser Asp Val Gly Lys
                100                 105                 110
Leu Asn Arg Leu Val Ile Pro Lys Gln Tyr Ala Glu Lys Tyr Phe Pro
                115                 120                 125
Leu Asp Ala Ala Ala Asn Glu Lys Gly Leu Leu Leu Ser Phe Glu Asp
            130                 135                 140
Ser Ala Gly Lys His Trp Arg Phe Arg Tyr Ser Tyr Trp Asn Ser Ser
145                 150                 155                 160
Gln Ser Tyr Val Met Thr Lys Gly Trp Ser Arg Phe Val Lys Glu Lys
                    165                 170                 175
Arg Leu Val Ala Gly Asp Thr Val Ser Phe Ser Arg Ala Ala Ala Glu
                180                 185                 190
Asp Ala Arg His Arg Leu Phe Ile Asp Trp Lys Arg Val Asp Thr
                195                 200                 205
Arg Gly Pro Leu Arg Phe Ser Gly Leu Ala Leu Pro Met Pro Leu Pro
            210                 215                 220
Ser Ser His Tyr Gly Gly Pro His His Tyr Ser Pro Trp Gly Phe Gly
225                 230                 235                 240
Gly Gly Gly Gly Gly Gly Gly Phe Phe Met Pro Pro Ser Pro Pro
                    245                 250                 255
Ala Thr Leu Tyr Glu His Arg Leu Arg Gln Gly Leu Asp Phe Arg Ser
                260                 265                 270
Met Thr Thr Thr Tyr Pro Ala Pro Thr Val Gly Arg Gln Leu Leu Phe
            275                 280                 285
Phe Gly Ser Ala Arg Met Pro Pro His His Ala Pro Pro Gln Pro
290                 295                 300
Arg Pro Phe Ser Leu Pro Leu His His Tyr Thr Val Gln Pro Ser Ala
305                 310                 315                 320
Ala Gly Val Thr Ala Ala Ser Arg Pro Val Leu Leu Asp Ser Val Pro
                325                 330                 335
Val Ile Glu Ser Pro Thr Thr Ala Ala Lys Arg Val Arg Leu Phe Gly
                340                 345                 350
Val Asn Leu Asp Asn Asn Pro Asp Gly Gly Glu Ala Ser His Gln
                355                 360                 365
Gly Asp Ala Leu Ser Leu Gln Met Pro Gly Trp Gln Gln Arg Thr Pro
            370                 375                 380
Thr Leu Arg Leu Leu Glu Leu Pro Arg His Gly Gly Glu Ser Ser Ala
385                 390                 395                 400
Ala Ser Ser Pro Ser Ser Ser Ser Ser Lys Arg Glu Ala Arg Ser
                    405                 410                 415
Ala Leu Asp Leu Asp Leu
                420

<210> SEQ ID NO 132
<211> LENGTH: 1269
<212> TYPE: DNA
<213> ORGANISM: Zea mays

<400> SEQUENCE: 132
atggaccagt cgccgcgag cgggaggttc tctagagagg aggaggcgga cgaggagcag      60
gaggatgcgt ccaattccat gcgcgagatc tccttcatgc cgccggctgc ggcctcgtca     120
```

```
tcttcggcgg ctgcttccgc gtccgcgtcc gcctccacca gcgcatccgc gtgtgcatcg      180
ggaagcagca gcgccccctt ccgctccgcc tccgcgtcgg gggatgccgc cggagcgtcg      240
gggagcggcg gcccagcgga cgcggacgcg gaggcggagg cggtggagaa ggagcacatg      300
ttcgacaagg tggtcacgcc gagcgacgtg gggaagctca accggctggt gatcccgaag      360
cagtacgcgg agaagtactt cccgctggac gcggcggcca acgagaaggg cctcctcctc      420
agcttcgagg acagcgccgg caagcactgg cgcttccgct actcctactg gaacagcagc      480
cagagctacg tcatgaccaa gggctggagc cgcttcgtca aggagaagcg cctcgtcgcc      540
ggggacaccg tctccttctc ccgcgccgcc gccgaggacg cgcgccaccg cctcttcatc      600
gactggaagc gccgggtcga cacccgcggc ccgcttcgtt tctccggcct cgcgctgccg      660
atgccgctgc cgtcgtcgca ctacggcggg ccccaccact acagcccgtg gggcttcggc      720
ggcggcggcg gcggcggcgg cggattcttc atgccgccct cgccgcccgc cacgctctac      780
gagcaccgcc tcagacaggg cctcgacttc gcagcatga cgacgaccta ccccgcgccg      840
accgtgggga ggcagctcct gttttcggc tcggccagga tgcctcctca tcacgcgccg      900
ccgccccagc cgcgcccgtt ctcgctgccg ctgcatcact acacggtgca accgagcgcc      960
gccggcgtca ccgccgcgtc acggccggtc cttcttgact cggtgccggt catcgagagc     1020
ccgacgaccg ccgcgaagcg cgtgcggctg ttcggcgtca acctggacaa caacccagat     1080
ggcggcggcg aggctagcca tcagggcgat gcattgtcat tgcagatgcc cgggtggcag     1140
caaaggactc caactctaag gctactagaa ttgcctcgcc atggcgggga gtcctccgcg     1200
gcgtcgtctc cgtcgtcgtc gtcttcctcc aagagggagg cgcgttcagc tttggatctc     1260
gatctgtga                                                             1269
```

<210> SEQ ID NO 133
<211> LENGTH: 894
<212> TYPE: DNA
<213> ORGANISM: Brassica rapa

<400> SEQUENCE: 133

```
atgatgatga caaacttgtc tctttcaaga gaaggagaag aggaggaaga agaagaacaa       60
gaagaggcca agaagcccat ggaagaagta gagagagagc acatgttcga caaagtggtg      120
actccaagcg atgttggtaa actaaaccgg ctcgtgatcc caaagcaata cgcagagaga      180
tacttccctt tagattcatc cacaaacgag aaaggtttgc ttctaaactt cgaagatctc      240
gcaggaaagt catggaggtt ccgttactct tactggaaca gtagtcagag ctatgtcatg      300
actaaaggtt ggagccgttt cgttaaagac aaaaagctag acgccggaga tattgtctct      360
ttccagagat gtgtcggaga ttcaggaaga cagccgct tgtttattga ttggaggaga      420
agacctaaag ttcctgacca tccgacatcg attgctcact tgctgccgg atctatgttt      480 cctaggtttt acagttttcc gacagcaact agttacaatc tttacaacta tcagcagcca      540
cgtcatcatc atcacagtgg ttataattat cctcaaattc cgagagaatt tggatacggg      600
tacttggtgg atcaaagagc cgtggtggct gatccgttgg tgattgaatc tgtgccggtg      660
atgatgcacg gaggagctca agttagtcag gcggttgttg aacggccgg aagaggctg      720 aggcttttg gagtcgatat ggaggaagaa tcttcatctt ccggtgggag tttgccacgt      780
ggtgacgctt ctccgtcttc ctctttgttt cagctgagac ttggaagcag cagtgaagat      840
gatcacttct ctaagaaagg aaagtcctca ttgccttttg atttggatca ataa            894
```

<210> SEQ ID NO 134
<211> LENGTH: 307
<212> TYPE: PRT
<213> ORGANISM: Zea mays

<400> SEQUENCE: 134

```
Met Ala Thr Asn His Leu Ser Gln Gly Gln His Gln His Pro Gln Ala
1               5                   10                  15

Trp Pro Trp Gly Val Ala Met Tyr Thr Asn Leu His Tyr His His Gln
            20                  25                  30

Gln His His His Tyr Glu Lys Glu His Leu Phe Glu Lys Pro Leu Thr
        35                  40                  45

Pro Ser Asp Val Gly Lys Leu Asn Arg Leu Val Ile Pro Lys Gln His
    50                  55                  60

Ala Glu Arg Tyr Phe Pro Leu Ser Ser Ser Gly Ala Gly Asp Lys Gly
65                  70                  75                  80

Leu Ile Leu Cys Phe Glu Asp Asp Asp Asp Glu Ala Ala Ala
                85                  90                  95

Asn Lys Pro Trp Arg Phe Arg Tyr Ser Tyr Trp Thr Ser Gln Ser
            100                 105                 110

Tyr Val Leu Thr Lys Gly Trp Ser Arg Tyr Val Lys Glu Lys Gln Leu
        115                 120                 125

Asp Ala Gly Asp Val Val Arg Phe Gln Arg Met Arg Gly Phe Gly Met
    130                 135                 140

Pro Asp Arg Leu Phe Ile Ser His Ser Arg Arg Gly Glu Thr Thr Ala
145                 150                 155                 160

Thr Ala Ala Thr Thr Val Pro Pro Ala Ala Ala Val Arg Val Val
                165                 170                 175

Val Ala Pro Ala Gln Ser Ala Gly Ala Asp His Gln Gln Gln Gln
            180                 185                 190

Pro Ser Pro Trp Ser Pro Met Cys Tyr Ser Thr Ser Gly Ser Tyr Ser
        195                 200                 205

Tyr Pro Thr Ser Ser Pro Ala Asn Ser Gln His Ala Tyr His Arg His
    210                 215                 220

Ser Ala Asp His Asp His Ser Asn Asn Met Gln His Ala Gly Glu Ser
225                 230                 235                 240

Gln Ser Asp Arg Asp Asn Arg Ser Cys Ser Ala Ser Ala Pro Pro
                245                 250                 255

Pro Pro Ser Arg Arg Leu Arg Leu Phe Gly Val Asn Leu Asp Cys Gly
            260                 265                 270

Pro Gly Pro Glu Pro Glu Thr Pro Thr Ala Met Tyr Gly Tyr Met His
        275                 280                 285

Gln Ser Pro Tyr Ala Tyr Asn Asn Trp Gly Ser Pro Tyr Gln His Asp
    290                 295                 300

Glu Glu Ile
305
```

<210> SEQ ID NO 135
<211> LENGTH: 924
<212> TYPE: DNA
<213> ORGANISM: Zea mays

<400> SEQUENCE: 135

| | | |
|---|---|---|
| atggccacga accatctctc ccaagggcag caccagcacc cgcaggcctg gccctggggc | | 60 |
| gtggccatgt acaccaacct acactaccac caccagcagc accaccacta cgagaaggag | | 120 |

```
cacctgttcg agaagccgct gacgccgagc gacgtgggca agctcaacag gctggtgatc    180
cccaagcagc acgccgagag gtacttccct ctcagcagca gcggcgccgg cgacaaaggc    240
ctcatcctgt gcttcgagga cgacgacgac gacgaggctg ccgccgccaa caagccgtgg    300
cggttccgct actcgtactg gaccagcagc cagagctacg tgctcaccaa gggctggagc    360
cgctacgtca aggagaagca gcttgacgcc ggcgacgtcg tgcgcttcca gaggatgcgt    420
ggtttcggca tgcccgaccg cctgttcatc agccacagcc gccgcggcga gactactgct    480
actgctgcaa caacagtgcc ccccgctgct gctgccgtgc gcgtagtagt ggcacctgca    540
cagagcgctg gcgcagacca ccagcagcag cagcagccgt cgccttggag cccaatgtgc    600
tacagcacat caggctcgta ctcgtacccc accagcagcc cagccaattc ccagcatgcc    660
taccaccgcc actcagctga ccatgaccac agcaacaaca tgcaacatgc aggagaatct    720
cagtccgaca gagacaacag gagctgcagt gcagcttcgg caccgccgcc accgtcgcgg    780
cggctccggc tgttcggcgt aaacctcgac tgcggcccgg ggccggagcc ggagacacca    840
acggcgatgt acggctacat gcaccaaagc ccctacgctt acaacaactg gggcagtcca    900
taccagcatg acgaggagat ttaa                                            924
```

<210> SEQ ID NO 136
<211> LENGTH: 277
<212> TYPE: PRT
<213> ORGANISM: Zea mays

<400> SEQUENCE: 136

```
Met Glu Phe Thr Pro Ala His Ala His Ala Arg Val Val Glu Asp Ser
1               5                   10                  15
Glu Arg Pro Arg Gly Gly Val Ala Trp Val Glu Lys Glu His Met Phe
            20                  25                  30
Glu Lys Val Val Thr Pro Ser Asp Val Gly Lys Leu Asn Arg Leu Val
        35                  40                  45
Ile Pro Lys Gln His Ala Glu Arg Tyr Phe Pro Ala Leu Asp Ala Ser
    50                  55                  60
Ser Ala Ala Ala Ala Ala Ala Ala Ala Gly Gly Gly Lys Gly
65                  70                  75                  80
Leu Val Leu Ser Phe Glu Asp Arg Ala Gly Lys Ala Trp Arg Phe Arg
                85                  90                  95
Tyr Ser Tyr Trp Asn Ser Ser Gln Ser Tyr Val Met Thr Lys Gly Trp
            100                 105                 110
Ser Arg Phe Val Lys Glu Lys Arg Leu Gly Ala Gly Asp Thr Val Leu
        115                 120                 125
Phe Ala Arg Gly Ala Gly Gly Arg Gly Arg Phe Phe Ile Asp Phe
    130                 135                 140
Arg Arg Arg Arg Gln Asp Leu Ala Phe Leu Gln Pro Thr Leu Ala Ser
145                 150                 155                 160
Ala Gln Arg Leu Leu Pro Leu Pro Ser Val Pro Ile Cys Pro Trp Gln
                165                 170                 175
Asp Tyr Gly Ala Ser Ala Pro Ala Pro Asn Arg His Val Leu Phe Leu
            180                 185                 190
Arg Pro Gln Val Pro Ala Ala Val Leu Lys Ser Val Pro Val His
        195                 200                 205
Val Ala Ala Ser Ala Val Glu Thr Met Ser Lys Arg Val Arg Leu
    210                 215                 220
```

```
Phe Gly Val Asn Leu Asp Cys Pro Pro Asp Ala Glu Asp Ser Ala Thr
225                 230                 235                 240

Val Pro Arg Gly Arg Ala Ala Ser Thr Thr Leu Leu Gln Leu Pro Ser
            245                 250                 255

Pro Ser Ser Ser Thr Ser Ser Ser Thr Ala Gly Lys Asp Val Cys Cys
        260                 265                 270

Leu Asp Leu Gly Leu
        275

<210> SEQ ID NO 137
<211> LENGTH: 834
<212> TYPE: DNA
<213> ORGANISM: Zea mays

<400> SEQUENCE: 137
atggagttca cgcccgcgca tgcgcatgcc cgtgtcgttg aggattccga gaggcctcgc      60
ggcggcgtgg cctgggtgga gaaggagcac atgttcgaga aggtggtcac cccgagcgac     120
gtggggaagc tcaatcgcct ggtcatccca aagcagcacg cggagcgcta cttccccgcg     180
ctggacgcct cgtccgccgc ggcggcggcg gcggcagcag ccgcgggagg cgggaagggg     240
ctggtgctca gcttcgagga ccgggcgggg aaggcgtggc gcttccgcta ctcgtactgg     300
aacagcagcc agagctacgt gatgaccaaa ggttggagcc gcttcgtgaa ggagaagcgc     360
ctcggtgccg ggacacagt cttgttcgcg cgcggcgcgg gcggcgcgcg cggccgcttc     420
ttcatcgatt ccgccgccg tcgccaggat ctcgcgttcc tgcagccgac gctggcgtct     480
gcgcagcgac tcctgccgct gccgtcggtg cccatctgcc cgtggcagga ctacggcgcc     540
tcggctccgg cgcccaaccg gcacgtgctg ttcctgcggc cgcaggtgcc ggccgccgta     600
gtgctcaagt cggtccccgt gcacgttgct gcatccgcgg tggaggcgac catgtcgaag     660
cgcgtccgcc tgttcggggt gaacctcgac tgcccgccgg acgccaagga cagcgccaca     720
gtccccggg gccgggcggc gtcgacgacg cttctgcaac tgccctcgcc atcgtcgtca     780
acatcctcct cgacggcagg gaaggacgtg tgctgtttgg atcttggact gtga           834

<210> SEQ ID NO 138
<211> LENGTH: 273
<212> TYPE: PRT
<213> ORGANISM: Zea mays

<400> SEQUENCE: 138

Met Glu Phe Arg Pro Ala His Ala Arg Val Phe Glu Asp Ser Glu Arg
1               5                   10                  15

Pro Arg Gly Gly Val Ala Trp Leu Glu Lys Glu His Met Phe Glu Lys
            20                  25                  30

Val Val Thr Pro Ser Asp Val Gly Lys Leu Asn Arg Leu Val Ile Pro
        35                  40                  45

Lys Gln His Ala Glu Arg Tyr Phe Pro Ala Leu Asp Ala Ser Ala Ala
    50                  55                  60

Ala Ala Ser Ala Ser Ala Ser Ala Gly Gly Gly Lys Ala Gly Leu Val
65                  70                  75                  80

Leu Ser Phe Glu Asp Arg Ala Gly Lys Ala Trp Arg Phe Arg Tyr Ser
                85                  90                  95

Tyr Trp Asn Ser Ser Gln Ser Tyr Val Met Thr Lys Gly Trp Ser Arg
            100                 105                 110

Phe Val Lys Glu Lys Arg Leu Gly Ala Gly Asp Thr Val Leu Phe Ala
        115                 120                 125
```

```
Arg Gly Ala Gly Ala Thr Arg Gly Arg Phe Phe Ile Asp Phe Arg Arg
        130                 135                 140

Arg Arg His Glu Leu Ala Phe Leu Gln Pro Pro Leu Ala Ser Ala Gln
145                 150                 155                 160

Arg Leu Leu Pro Leu Pro Ser Val Pro Ile Cys Pro Trp Gln Gly Tyr
                165                 170                 175

Gly Ala Ser Ala Pro Ala Pro Ser Arg His Val Leu Phe Leu Arg Pro
            180                 185                 190

Gln Val Pro Ala Ala Val Val Leu Thr Ser Val Pro Val Arg Val Ala
        195                 200                 205

Ala Ser Ala Val Glu Glu Ala Thr Arg Ser Lys Arg Val Arg Leu Phe
    210                 215                 220

Gly Val Asn Leu Asp Cys Pro Pro Asp Ala Glu Asp Gly Ala Thr Ala
225                 230                 235                 240

Thr Arg Thr Pro Ser Thr Leu Leu Gln Leu Pro Ser Pro Ser Ser Ser
                245                 250                 255

Thr Ser Ser Ser Thr Gly Gly Lys Asp Val Arg Ser Leu Asp Leu Gly
            260                 265                 270

Leu
```

<210> SEQ ID NO 139
<211> LENGTH: 822
<212> TYPE: DNA
<213> ORGANISM: Zea mays

<400> SEQUENCE: 139

```
atggagttca ggcccgcgca tgcccgtgtc ttcgaggatt ccgagaggcc tcgcggcggc    60
gtggcgtggc tggagaagga gcacatgttc gagaaagtgg tcaccccgag cgacgtgggg   120
aagctcaatc gcctggtcat cccgaagcag cacgccgagc gctacttccc cgcgctggac   180
gcctcggccg ccgcggcgtc ggcatcgggc tcggcgggcg cgggaaggcc ggggctggtg   240
ctcagcttcg aggaccgggc ggggaaggcg tggcgcttcc gctactcgta ctggaacagc   300
agccagagct acgtgatgac caagggatgg agccgcttcg tgaaagagaa cgcctcggt   360
gccggggaca cggtattgtt cgcgcgcggc gcgggcgcca cgcgcggccg cttcttcatc   420
gatttccgcc gccgccgcca cgagctcgcg ttcctgcagc cgccgctggc gtctgcgcag   480
cgcctcctgc cgctcccgtc ggtgcccatc tgcccgtggc agggctacgg cgcctccgct   540
ccggcgccaa gccggcacgt gctgttcctg cggccgcagg tgccggccgc cgtagtgctc   600
acgtcggtgc ccgtgcgcgt cgccgcatcc gcggtggagg aggcgacgag gtcgaagcgc   660
gtccgcctgt tcggggtgaa cctcgactgc ccgccgacg ccgaagacgg tgccacagcc   720
acccggacgc cgtcgacgct tctgcagctg ccctcgccat cgtcgtcaac atcctcctcc   780
acgggaggca aggatgtgcg ttctttggat cttggacttt ga                      822
```

<210> SEQ ID NO 140
<211> LENGTH: 350
<212> TYPE: PRT
<213> ORGANISM: Triticum aestivum

<400> SEQUENCE: 140

```
Met Gly Val Glu Ile Leu Ser Ser Met Val Glu His Ser Phe Gln Tyr
1               5                   10                  15

Ser Ser Gly Val Ser Thr Ala Thr Thr Glu Ser Gly Thr Ala Gly Thr
            20                  25                  30
```

```
Pro Pro Arg Pro Leu Ser Leu Pro Val Ala Ile Ala Asp Glu Ser Val
        35                  40                  45

Thr Ser Arg Ser Ala Ser Ser Arg Phe Lys Gly Val Val Pro Gln Pro
 50                  55                  60

Asn Gly Arg Trp Gly Ala Gln Ile Tyr Glu Arg His Ala Arg Val Trp
 65                  70                  75                  80

Leu Gly Thr Phe Pro Asp Gln Asp Ser Ala Ala Arg Ala Tyr Asp Val
                 85                  90                  95

Ala Ser Leu Arg Tyr Arg Gly Arg Asp Val Ala Phe Asn Phe Pro Cys
            100                 105                 110

Ala Ala Val Glu Gly Glu Leu Ala Phe Leu Ala Ala His Ser Lys Ala
        115                 120                 125

Glu Ile Val Asp Met Leu Arg Lys Gln Thr Tyr Ala Asp Glu Leu Arg
    130                 135                 140

Gln Gly Leu Arg Arg Gly Arg Gly Met Gly Ala Arg Ala Gln Pro Thr
145                 150                 155                 160

Pro Ser Trp Ala Arg Glu Pro Leu Phe Glu Lys Ala Val Thr Pro Ser
                165                 170                 175

Asp Val Gly Lys Leu Asn Arg Leu Val Val Pro Lys Gln His Ala Glu
            180                 185                 190

Lys His Phe Pro Leu Lys Arg Thr Pro Glu Thr Pro Thr Thr Thr Gly
        195                 200                 205

Lys Gly Val Leu Leu Asn Phe Glu Asp Gly Glu Gly Lys Val Trp Arg
    210                 215                 220

Phe Arg Tyr Ser Tyr Trp Asn Ser Ser Gln Ser Tyr Val Leu Thr Lys
225                 230                 235                 240

Gly Trp Ser Arg Phe Val Arg Glu Lys Gly Leu Gly Ala Gly Asp Ser
                245                 250                 255

Ile Leu Phe Ser Cys Ser Leu Tyr Glu Gln Glu Lys Gln Phe Phe Ile
            260                 265                 270

Asp Cys Lys Lys Asn Thr Ser Met Asn Gly Gly Lys Ser Ala Ser Pro
        275                 280                 285

Leu Pro Val Gly Val Thr Thr Lys Gly Glu Gln Val Arg Val Val Arg
    290                 295                 300

Leu Phe Gly Val Asp Ile Ser Gly Val Lys Arg Gly Arg Ala Ala Thr
305                 310                 315                 320

Ala Thr Ala Glu Gln Gly Leu Gln Glu Leu Phe Lys Arg Gln Cys Val
                325                 330                 335

Ala Pro Gly Gln His Ser Pro Ala Leu Gly Ala Phe Ala Leu
            340                 345                 350

<210> SEQ ID NO 141
<211> LENGTH: 1053
<212> TYPE: DNA
<213> ORGANISM: Triticum aestivum

<400> SEQUENCE: 141
atgggggtgg aaatcctgag ctccatggtg gagcactcct tccagtactc ttccggcgtg     60
tccacggcca cgacggagtc aggcaccgcc ggaacaccgc cgaggccttt gagcctacct    120
gtcgccatcg ccgacgagtc cgtgaccctc ggtcggcgt cgtctcggtt caagggcgtg    180
gtgccgcagc caaacgggcg atggggcgcc cagatctacg agcgccacgc tcgcgtctgg    240
ctcggcacgt tccagaccca ggactcggcg gcgcgcgcct acgacgtagc ctcgctcagg    300
```

```
taccgcggcc gcgacgtcgc cttcaacttc ccgtgcgcgg ccgtggaggg ggagctcgcc    360
ttcctggcgg cgcactccaa ggctgagata gtggacatgc tccggaagca gacctacgcc    420
gatgaactcc gccagggcct gcggcgcggc cgtggcatgg gggcgcgcgc gcagccgacg    480
ccgtcgtggg cgcgggagcc cctttcgag aaggccgtga ccctagcga tgtcggcaag     540
ctcaatcgcc tcgtagtgcc gaagcagcac gccgagaagc acttccccct gaagcgcacg    600
ccggagacgc cgaccaccac cggcaagggc gtgctgctca acttcgagga cggcgagggg    660
aaggtgtgga ggttccggta ctcgtactgg aacagcagcc agagctacgt gctcaccaaa    720
ggctggagcc gcttcgtccg ggagaagggc ctaggtgccg cgactccat cctattctcg     780
tgctcgctgt acgaacagga gaagcagttc ttcatcgact gcaagaagaa cactagcatg    840
aacggaggca aatcggcgtc gccgctgcca gtggggtga ctaccaaagg agaacaagtt     900
cgcgtcgtta ggctattcgg tgtcgacatc tcggagtga agaggggcg agcggcgacg      960
gcaacggcgg agcaaggcct gcaggagttg ttcaagaggc aatgcgtggc acccggccag    1020
cactctcctg ccctaggtgc cttcgcctta tag                                 1053
```

<210> SEQ ID NO 142
<211> LENGTH: 320
<212> TYPE: PRT
<213> ORGANISM: Triticum aestivum

<400> SEQUENCE: 142

```
Met Ala Ser Gly Lys Pro Thr Asn His Gly Met Glu Asp Asp Asn Asp
1               5                   10                  15

Met Glu Tyr Ser Ser Ala Glu Ser Gly Ala Glu Asp Ala Ala Glu Pro
            20                  25                  30

Ser Ser Ser Pro Val Leu Ala Pro Pro Arg Ala Ala Pro Ser Ser Arg
        35                  40                  45

Phe Lys Gly Val Val Pro Gln Pro Asn Gly Arg Trp Gly Ala Gln Ile
    50                  55                  60

Tyr Glu Lys His Ser Arg Val Trp Leu Gly Thr Phe Pro Asp Glu Asp
65                  70                  75                  80

Ala Ala Val Arg Ala Tyr Asp Val Ala Ala Leu Arg Phe Arg Gly Pro
                85                  90                  95

Asp Ala Val Ile Asn His Gln Arg Pro Thr Ala Ala Glu Glu Ala Gly
            100                 105                 110

Ser Ser Ser Ser Arg Ser Glu Leu Asp Pro Glu Leu Gly Phe Leu Ala
        115                 120                 125

Asp His Ser Lys Ala Glu Ile Val Asp Met Leu Arg Lys His Thr Tyr
    130                 135                 140

Asp Asp Glu Leu Arg Gln Gly Leu Arg Arg Gly Arg Gly Arg Ala Gln
145                 150                 155                 160

Pro Thr Pro Ala Trp Ala Arg Glu Leu Leu Phe Glu Lys Ala Val Thr
                165                 170                 175

Pro Ser Asp Val Gly Lys Leu Asn Arg Leu Val Val Pro Lys Gln Gln
            180                 185                 190

Ala Glu Lys His Phe Pro Pro Thr Thr Ala Ala Thr Gly Ser Asn
        195                 200                 205

Gly Lys Gly Val Leu Leu Asn Phe Glu Asp Gly Glu Gly Lys Val Trp
    210                 215                 220

Arg Phe Arg Tyr Ser Tyr Trp Asn Ser Ser Gln Ser Tyr Val Leu Thr
225                 230                 235                 240
```

```
Lys Gly Trp Ser Arg Phe Val Lys Glu Thr Gly Leu Arg Ala Gly Asp
            245                 250                 255

Thr Val Ala Phe Tyr Arg Ser Ala Tyr Gly Asn Asp Thr Glu Asp Gln
        260                 265                 270

Leu Phe Ile Asp Tyr Lys Lys Met Asn Lys Asn Asp Asp Ala Ala Asp
    275                 280                 285

Ala Ala Ile Ser Asp Glu Asn Glu Thr Gly His Val Ala Val Lys Leu
290                 295                 300

Phe Gly Val Asp Ile Ala Gly Gly Met Ala Gly Ser Ser Gly Gly
305                 310                 315                 320
```

<210> SEQ ID NO 143
<211> LENGTH: 963
<212> TYPE: DNA
<213> ORGANISM: Triticum aestivum

<400> SEQUENCE: 143

```
atggcatctg gcaagccgac aaaccacggg atggaggacg acaacgacat ggagtactcc    60
tccgcggaat cggggGccga ggacgcggcg gagccgtcgt cgtcgccggt gctggcgccg   120
ccccgggcgg ctccatcgtc gcggttcaag ggcgtcgtgc cgcagcccaa cgggcggtgg   180
ggagcgcaga tctacgagaa gcactcgcgg gtgtggctcg gaacgttccc cgacgaggac   240
gccgccgtgc cgcgcctacga cgtggccgcg ctccgcttcc gcggcccgga cgccgtcatc   300
aaccaccagc gaccgacggc gcggaggag gccggctcgt cgtcgtccag gagcgagctg   360
gatccagagc tcggcttcct tgccgaccac tccaaggccg agatcgtcga catgctccgg   420
aagcacacct acgacgacga gctccgtcag ggcctgcgcc gcggccgcgg gcgcgcgcag   480
ccgacgccgg cgtgggcacg agagctcctc ttcgagaagg ccgtgacccc gagcgacgtc   540
ggcaagctca accgcctcgt ggtgccgaag cagcaggccg agaagcactt ccctccgacc   600
actgcggcgg ccaccggcag caacggcaag ggcgtgctgc tcaacttcga ggacggcgaa   660
gggaaggtgt ggcgcttccg gtactcgtac tggaacagca gccagagcta cgtgctcacc   720
aagggctgga ccgcttcgt caaggagacg gccctccgcg ccggcgacac cgtggcgttc   780
taccggtcgg cgtacgggaa tgacacggag gatcagctct tcatcgacta caagaagatg   840
aacaagaatg acgatgctgc ggacgcggcg atttccgatg agaatgagac aggccatgtc   900
gccgtcaagc tcttcggcgt tgacattgcc ggtggaggga tggcgggatc atcaggtggc   960
tga                                                                963
```

<210> SEQ ID NO 144
<211> LENGTH: 320
<212> TYPE: PRT
<213> ORGANISM: Triticum aestivum

<400> SEQUENCE: 144

```
Met Ala Ser Gly Lys Pro Thr Asn His Gly Met Glu Asp Asp Asn Asp
1               5                   10                  15

Met Glu Tyr Ser Ser Ala Glu Ser Gly Ala Glu Asp Ala Ala Glu Pro
            20                  25                  30

Ser Ser Ser Pro Val Leu Ala Pro Arg Ala Ala Pro Ser Ser Arg
        35                  40                  45

Phe Lys Gly Val Val Pro Gln Pro Asn Gly Arg Trp Gly Ala Gln Ile
    50                  55                  60

Tyr Glu Lys His Ser Arg Val Trp Leu Gly Thr Phe Pro Asp Glu Asp
65                  70                  75                  80
```

```
Ala Ala Ala Arg Ala Tyr Asp Val Ala Leu Arg Phe Arg Gly Pro
            85                  90                  95

Asp Ala Val Ile Asn His Gln Arg Pro Thr Ala Ala Glu Glu Ala Gly
            100                 105                 110

Ser Ser Ser Ser Arg Ser Glu Leu Asp Pro Glu Leu Gly Phe Leu Ala
            115                 120                 125

Asp His Ser Lys Ala Glu Ile Val Asp Met Leu Arg Lys His Thr Tyr
        130                 135                 140

Asp Asp Glu Leu Arg Gln Gly Leu Arg Arg Gly Arg Gly Arg Ala Gln
145                 150                 155                 160

Pro Thr Pro Ala Trp Ala Arg Glu Leu Leu Phe Glu Lys Ala Val Thr
                165                 170                 175

Pro Ser Asp Val Gly Lys Leu Asn Arg Leu Val Val Pro Lys Gln Gln
            180                 185                 190

Ala Glu Lys His Phe Pro Pro Thr Ala Ala Thr Gly Ser Asn
        195                 200                 205

Gly Lys Gly Val Leu Leu Asn Phe Glu Asp Gly Glu Gly Lys Val Trp
        210                 215                 220

Arg Phe Arg Tyr Ser Tyr Trp Asn Ser Ser Gln Ser Tyr Val Leu Thr
225                 230                 235                 240

Lys Gly Trp Ser Arg Phe Val Lys Glu Thr Gly Leu Arg Ala Gly Asp
                245                 250                 255

Thr Val Ala Phe Tyr Arg Ser Ala Tyr Gly Asn Asp Thr Glu Asp Gln
            260                 265                 270

Leu Phe Ile Asp Tyr Lys Lys Met Asn Lys Asn Asp Asp Ala Ala Asp
        275                 280                 285

Ala Ala Ile Ser Asp Glu Asn Glu Thr Gly His Val Ala Val Lys Leu
        290                 295                 300

Phe Gly Val Asp Ile Ala Gly Gly Met Ala Gly Ser Ser Gly Gly
305                 310                 315                 320

<210> SEQ ID NO 145
<211> LENGTH: 963
<212> TYPE: DNA
<213> ORGANISM: Triticum aestivum

<400> SEQUENCE: 145
atggcatctg gcaagccgac aaaccacggg atggaggacg acaacgacat ggagtactcc    60
tccgcggaat cggggccgga ggacgcggcg gagccgtcgt cgtcgccggt gctggcgccg   120
ccccgggcgg ctccatcgtc gcggttcaag ggcgtcgtgc cgcagcccaa cgggcggtgg   180
ggagcgcaga tctacgagaa gcactcgcgg gtgtggctcg gaacgttccc cgacgaggac   240
gccgccgcgc gcgcctacga cgtggccgcg ctccgcttcc gcggcccgga cgccgtcatc   300
aaccaccagc gaccgacggc cgcggaggag gccggctcgt cgtcgtccag gagcgagctg   360
gatccagagc tcggcttcct cgccgaccac tccaaggccg agatcgtcga catgctccgg   420
aagcacacct acgacgacga gctccgtcag ggcctgcgcc gcggccgcgg gcgcgcgcag   480
ccgacgccgg cgtgggcacg agagctcctc ttcgagaagg ccgtgacccc gagcgacgtc   540
ggcaagctca accgcctcgt ggtgccgaag cagcaggccg agaagcactt ccctccgacc   600
actgcggcgg ccaccggcag caacggcaag ggcgtgctgc tcaacttcga ggacggcgaa   660
gggaaggtgt ggcgcttccg gtactcgtac tggaacagca gcagagctac gtgctcacc    720 aagggctgga gccgcttcgt caaggagacg ggcctccgcg ccggcgacac cgtggcgttc   780
```

```
taccggtcgg cgtacgggaa tgacacggag gatcagctct tcatcgacta caagaagatg    840
aacaagaatg acgatgctgc ggacgcggcg atttccgatg agaatgagac aggccatgtc    900
gccgtcaagc tcttcggcgt tgacattgcc ggtggaggga tggcgggatc atcaggtggc    960
tga                                                                  963
```

<210> SEQ ID NO 146
<211> LENGTH: 488
<212> TYPE: DNA
<213> ORGANISM: Artificial Sequence
<220> FEATURE:
<223> OTHER INFORMATION: gRNA sequence

<400> SEQUENCE: 146

```
gacggccagt gccaagcttc tcggatccac tagtaacggc cgccagtgtg ctggaattgc     60
ccttggatca tgaaccaacg gcctggctgt atttggtggt tgtgtaggga gatggggaga    120
agaaaagccc gattctcttc gctgtgatgg gctggatgca tgcggggggag cgggaggccc    180 aagtacgtgc acggtgagcg gcccacaggg cgagtgtgag cgcgagaggc gggaggaaca    240
gtttagtacc acattgccca gctaactcga acgcgaccaa cttataaacc cgcgcgctgt    300
cgcttgtgtg ggaaggaaga gacagattgg ttttagagct agaaatagca agttaaaata    360
aggctagtcc gttatcaact tgaaaaagtg gcaccgagtc ggtgcttttt ttgtcccttc    420
gaagggcaat tctgcagata tccatcacac tggcggccgc tcgaggtcga agcttgcatg    480
cctgcagg                                                            488
```

<210> SEQ ID NO 147
<211> LENGTH: 41
<212> TYPE: DNA
<213> ORGANISM: Artificial Sequence
<220> FEATURE:
<223> OTHER INFORMATION: primer

<400> SEQUENCE: 147

```
ggactggggt tgctcctggg acacaagcga cagcgcgcgg g                         41
```

<210> SEQ ID NO 148
<211> LENGTH: 41
<212> TYPE: DNA
<213> ORGANISM: Artificial Sequence
<220> FEATURE:
<223> OTHER INFORMATION: primer

<400> SEQUENCE: 148

```
cccaggagca accccagtcc gttttagagc tagaaatagc a                         41
```

<210> SEQ ID NO 149
<211> LENGTH: 42
<212> TYPE: DNA
<213> ORGANISM: Artificial Sequence
<220> FEATURE:
<223> OTHER INFORMATION: primer

<400> SEQUENCE: 149

```
tgctatttct agctctaaaa cacacaagcg acagcgcgcg gg                        42
```

<210> SEQ ID NO 150
<211> LENGTH: 41
<212> TYPE: DNA
<213> ORGANISM: Artificial Sequence
<220> FEATURE:

<223> OTHER INFORMATION: primer

<400> SEQUENCE: 150
gcccctgacg cccagtgacg gttttagagc tagaaatagc a   41

<210> SEQ ID NO 151
<211> LENGTH: 41
<212> TYPE: DNA
<213> ORGANISM: Artificial Sequence
<220> FEATURE:
<223> OTHER INFORMATION: primer

<400> SEQUENCE: 151
gggggtgccc ctgggcgaga acacaagcga cagcgcgcgg g   41

<210> SEQ ID NO 152
<211> LENGTH: 41
<212> TYPE: DNA
<213> ORGANISM: Artificial Sequence
<220> FEATURE:
<223> OTHER INFORMATION: primer

<400> SEQUENCE: 152
tctcgcccag gggcaccccc gttttagagc tagaaatagc a   41

<210> SEQ ID NO 153
<211> LENGTH: 41
<212> TYPE: DNA
<213> ORGANISM: Artificial Sequence
<220> FEATURE:
<223> OTHER INFORMATION: primer

<400> SEQUENCE: 153
ctcgtagtgg tggtggtagt acacaagcga cagcgcgcgg g   41

<210> SEQ ID NO 154
<211> LENGTH: 41
<212> TYPE: DNA
<213> ORGANISM: Artificial Sequence
<220> FEATURE:
<223> OTHER INFORMATION: primer

<400> SEQUENCE: 154
actaccacca ccactacgag gttttagagc tagaaatagc a   41

<210> SEQ ID NO 155
<211> LENGTH: 15681
<212> TYPE: DNA
<213> ORGANISM: Artificial Sequence
<220> FEATURE:
<223> OTHER INFORMATION: vector
<220> FEATURE:
<221> NAME/KEY: misc_feature
<222> LOCATION: (5964)..(5984)
<223> OTHER INFORMATION: /note="target sequence"
<220> FEATURE:
<221> NAME/KEY: misc_feature
<222> LOCATION: (6617)..(6637)
<223> OTHER INFORMATION: /note="target sequence"

<400> SEQUENCE: 155
aattcccgat ctagtaacat agatgacacc gcgcgcgata atttatccta gtttgcgcgc   60
tatattttgt tttctatcgc gtattaaatg tataattgcg ggactctaat cataaaaacc   120
catctcataa ataacgtcat gcattacatg ttaattatta catgcttaac gtaattcaac   180
agaaattata tgataatcat cgcaagaccg gcaacaggat tcaatcttaa gaaactttat   240

```
tgccaaatgt tgaacgatc ggggaaattc gagctctatc gatcaatcag gatccttact    300
ttttcttttt tgcctggccg gccttttcg tggccgccgg ccttttgtcg cctcccagct    360
gagacaggtc gatccgtgtc tcgtacaggc cggtgatgct ctggtggatc agggtggcgt    420
ccagcacctc tttggtgctg gtgtacctct tccggtcgat ggtggtgtca aagtacttga    480
aggcggcagg ggctcccaga ttggtcaggg taaacaggtg gatgatattc tcggcctgct    540
ctctgatggg cttatcccgg tgcttgttgt aggcggacag cactttgtcc agattagcgt    600
cggccaggat cactctcttg gagaactcgc tgatctgctc gatgatctcg tccaggtagt    660
gcttgtgctg ttccacaaac agctgtttct gctcattatc ctcggggag cccttcagct    720 tctcatagtg gctggccagg tacaggaagt tcacatattt ggagggcagg gccagttcgt    780
ttcccttctg cagttcgccg gcagaggcca gcattctctt ccggccgttt tccagctcga    840
acagggagta cttaggcagc ttgatgatca ggtccttttt cacttctttg tagcccttgg    900
cttccagaaa gtcgatggga ttcttctcga agctgcttct ttccatgatg gtgatcccca    960
gcagctcttt cacactcttc agtttcttgg acttgcccctt ttccactttg gccaccacca    1020
gcacagaata ggccacggtg gggctgtcga agccgccgta cttcttaggg tcccagtcct    1080
tctttctggc gatcagctta tcgctgttcc tcttgggcag gatagactct ttgctgaagc    1140
cgcctgtctg cacctcggtc tttttcacga tattcacttg gggcatgctc agcactttcc    1200
gcacggtggc aaaatcccgg cccttatccc acacgatctc cccggtttcg ccgtttgtct    1260
cgatcagagg ccgcttccgg atctcgccgt tggccaggt aatctcggtc ttgaaaaagt    1320
tcatgatgtt gctgtagaag aagtacttgg cggtagcctt gccgatttcc tgctcgctct    1380
tggcgatcat cttccgcacg tcgtacacct tgtagtcgcc gtacacgaac tcgctttcca    1440
gcttagggta cttttgatc agggcggttc ccacgacggc gttcaggtag gcgtcgtggg    1500
cgtggtggta gttgttgatc tcgcgcactt tgtaaaactg gaaatccttc cggaaatcgg    1560
acaccagctt ggacttcagg gtgatcactt tcacttcccg gatcagcttg tcattctcgt    1620
cgtacttagt gttcatccgg gagtccagga tctgtgccac gtgctttgtg atctgccggg    1680
tttccaccag ctgtctcttg atgaagccgg ccttatccag ttcgctcagg ccgctctct    1740 cggccttggt cagattgtcg aactttctct gggtaatcag cttggcgttc agcagctgcc    1800
gccagtagtt cttcatcttc ttcacgacct cttcggaggg cacgttgtcg ctcttgcccc    1860
ggttcttgtc gcttctggtc agcaccttgt tgtcgatgga gtcgtccttc agaaagctct    1920
gaggcacgat atggtccaca tcgtagtcgg acagccggtt gatgtccagt tcctggtcca    1980
cgtacatatc ccgcccattc tgcaggtagt acaggtacag cttctcgttc tgcagctggg    2040
tgttttccac ggggtgttct ttcaggatct ggctgcccag ctctttgatg ccctcttcga    2100
tccgcttcat tctctcgcgg ctgttcttct gtcccttctg ggtggtctgg ttctctctgg    2160
ccatttcgat cacgatgttc tcgggcttgt gccggcccat cactttcacg agctcgtcca    2220
ccaccttcac tgtctgcagg atgcccttct taatggcggg gctgccggcc agattggcaa    2280
tgtgctcgtg caggctatcg ccctggccgg acacctgggc tttctggatg tcctcttaa    2340 aggtcaggct gtcgtcgtgg atcagctgca tgaagtttct gttggcgaag ccgtcggact    2400
tcaggaaatc caggattgtc ttgccggact gcttgtcccg gatgccgttg atcagcttcc    2460
ggctcagcct gccccagccg gtgtatctcc gccgcttcag ctgcttcatc actttgtcgt    2520
cgaacaggtg ggcataggtt ttcagccgtt cctcgatcat ctctctgtcc tcaaacagtg    2580
```

```
tcagggtcag cacgatatct tccagaatgt cctcgttttc ctcattgtcc aggaagtcct    2640
tgtccttgat aattttcagc agatcgtggt atgtgcccag ggaggcgttg aaccgatctt    2700
ccacgccgga gatttccacg gagtcgaagc actcgatttt cttgaagtag tcctctttca    2760
gctgcttcac ggtcactttc cggttggtct tgaacagcag gtccacgatg cctttttct     2820
gctcgccgct caggaaggcg ggctttctca ttccctcggt cacgtatttc actttggtca    2880
gctcgttata cacggtgaag tactcgtaca gcaggctgtg cttgggcagc accttctcgt    2940
tgggcaggtt cttatcgaag ttggtcatcc gctcgatgaa gctctgggcg aagcgccct     3000
tgtccaccac ttcctcgaag ttccagggg tgatggtttc ctcgctcttt ctggtcatcc     3060
aggcgaatct gctgtttccc ctggccagag ggcccacgta gtaggggatg cggaaggtca    3120
ggatcttctc gatcttttcc cggttgtcct tcaggaatgg gtaaaaatct tcctgccgcc    3180
gcagaatggc gtgcagctct cccaggtgga tctggtgggg gatgctgccg ttgtcgaagg    3240
tccgctgctt ccgcagcagg tcctctctgt tcagcttcac gagcagttcc tcggtgccgt    3300
ccatcttttc caggatgggc ttgatgaact tgtagaactc ttcctggctg gctccgccgt    3360
caatgtagcc ggcgtagccg ttcttgctct ggtcgaagaa aatctctttg tacttctcag    3420
gcagctgctg ccgcacgaga gctttcagca gggtcaggtc ctggtggtgc tcgtcgtatc    3480
tcttgatcat agaggcgctc aggggggcct tggtgatctc ggtgttcact ctcaggatgt    3540
cgctcagcag gatggcgtcg acaggttct tggcggccag aaacaggtcg cgtactggt      3600
cgccgatctg ggccagcagg ttgtccaggt cgtcgtcgta ggtgtccttg ctcagctgca    3660
gtttggcatc ctcggccagg tcgaagttgc tcttgaagtt gggggtcagg cccaggctca    3720
ggcaatcag gtttccgaac aggccattct tcttctcgcc gggcagctgg gcgatcagat     3780
tttccagccg tctgctcttg ctcagtctgg cagacaggat ggccttggcg tccacgccgc    3840
tggcgttgat ggggttttcc tcgaacagct ggttgtaggt ctgcaccagc tggatgaaca    3900
gcttgtccac gtcgctgttg tcggggttca ggtcgccctc gatcaggaag tggccccgga    3960
acttgatcat gtgggccagg gccagataga tcagccgcag gtcggccttg tcggtgctgt    4020
ccaccagttt ctttctcagg tggtagatgg tggggtactt ctcgtggtag gccacctcgt    4080
ccacgatgtt gccgaagatg gggtgccgct cgtgcttctt atcctcttcc accaggaagg    4140
actcttccag tctgtggaag aagctgtcgt ccaccttggc catctcgttg ctgaagatct    4200
cttgcagata gcagatccgg ttcttccgtc tggtgtatct tcttctggcg gttctcttca    4260
gccgggtggc ctcggctgtt tcgccgctgt cgaacagcag gctccgatc aggttcttct     4320
tgatgctgtg ccggtcggtg ttgcccagca ccttgaattt cttgctgggc accttgtact    4380
cgtcggtgat cacggcccag cccacagagt tggtgccgat gtccaggccg atgctgtact    4440
tcttgtcggc tgctgggact ccgtggatac cgaccttccg cttcttcttt ggggccatct    4500
tatcgtcatc gtctttgtaa tcaatatcat gatccttgta gtctccgtcg tggtccttat    4560
agtccatctc gagtatcgtt cgtaaatggt gaaaattttc agaaaattgc ttttgcttta    4620
aaagaaatga tttaaattgc tgcaatagaa gtagaatgct tgattgcttg agattcgttt    4680
gttttgtata tgttgtgttg aggtcgaggt cctctccaaa tgaaatgaac ttccttatat    4740
agaggaaggg tcttgcgaag gatagtggga ttgtgcgtca tcccttacgt cagtggagat    4800
atcacatcaa tccacttgct ttgaagacgt ggttggaacg tcttcttttt ccacgatgct    4860
cctcgtgggt gggggtccat cttttgggacc actgtcggca gaggcatctt caacgatggc    4920
cttccttta tcgcaatgat ggcatttgta ggagccacct tccttttcca ctatcttcac      4980
```

```
aataaagtga cagatagctg ggcaatggaa tccgaggagg tttccggata tcaccctttg   5040
ttgaaaagtc tcaattgccc tttggtcttc tgagactgta tctttgatat ttttggagta   5100
gacaagtgtg tcgtgctcca ccatgttatc acatcaatcc acttgctttg aagacgtggt   5160
tggaacgtct tcttttttcca cgatgctcct cgtgggtggg ggtccatctt tgggaccact   5220
gtcggcagag gcatcttcaa cgatggcctt tcctttatcg caatgatggc atttgtagga   5280
gccaccttcc ttttccacta tcttcacaat aaagtgacag atagctgggc aatggaatcc   5340
gaggaggttt ccggatatta cccttttgttg aaaagtctca attgcccttt ggtcttctga   5400
gactgtatct ttgatatttt tggagtagac aagtgtgtcg tgctccacca tgttgacctg   5460
caggcatgcc tcggatccac tagtaacggc cgccagtgtg ctggaattgc ccttaagctt   5520
cgttgaacaa cggaaactcg acttgccttc cgcacaatac atcatttctt cttagctttt   5580
tttcttcttc ttcgttcata cagttttttt ttgtttatca gcttacattt tcttgaaccg   5640
tagctttcgt tttcttcttt ttaactttcc attcggagtt tttgtatctt gtttcatagt   5700
ttgtcccagg attagaatga ttaggcatcg aaccttcaag aatttgattg aataaaacat   5760
cttcattctt aagatatgaa gataatcttc aaaaggcccc tgggaatctg aaagaagaga   5820
agcaggccca tttatatggg aaagaacaat agtatttctt ataggccc atttaagttg     5880
aaaacaatct tcaaaagtcc cacatcgctt agataagaaa acgaagctga gtttatatac   5940
agctagagtc gaagtagtga tttccccacg tcactgggcg tcgttttaga gctagaaata   6000
gcaagttaaa ataaggctag tccgttatca acttgaaaaa gtggcaccga gtcggtgctt   6060
tttttgtccc ttcgaagggc ctttctcaga tatccatcac actggcggcc gctcgaggtc   6120
gctcggatcc actagtaacg gccgccagtg tgctggaatt gcccttaagc ttcgttgaac   6180
aacggaaact cgacttgcct tccgcacaat acatcatttc ttcttagctt ttttttcttct   6240
tcttcgttca tacagttttt ttttgtttat cagcttacat tttcttgaac cgtagctttc   6300
gttttcttct ttttaacttt ccattcggag ttttttgtatc ttgtttcata gtttgtccca   6360
ggattagaat gattaggcat cgaaccttca agaatttgat tgaataaaac atcttcattc   6420
ttaagatatg aagataatct tcaaaaggcc cctgggaatc tgaaagaaga gaagcaggcc   6480
catttatatg ggaaagaaca atagtatttc ttatataggc ccatttaagt tgaaaacaat   6540
cttcaaaagt cccacatcgc ttagataaga aaacgaagct gagtttatat acagctagag   6600
tcgaagtagt gattcacacc ccatggccag gactgtttta gagctagaaa tagcaagtta   6660
aaataaggct agtccgttat caacttgaaa aagtggcacc gagtcggtgc tttttttgtc   6720
ccttcgaagg gcctttctca gatatccatc acactggcgg ccgctcgagg tcgaagcttg   6780
gcactggccg tcgttttaca acgtcgtgac tgggaaaacc ctggcgttac ccaacttaat   6840
cgccttgcag cacatccccc tttcgccagc tggcgtaata gcgaagaggc ccgcaccgat   6900
cgcccttccc aacagttgcg cagcctgaat ggcgaatgct agagcagctt gagcttggat   6960
cagattgtcg tttcccgcct tcagtttaaa ctatcagtgt ttgacaggat atattggcgg   7020
gtaaacctaa gagaaaagag cgtttattag aataacggat attttaaagg gcgtgaaaag   7080
gtttatccgt tcgtccattt gtatgtgcat gccaaccaca gggttcccct cgggatcaaa   7140
gtactttgat ccaacccctc cgctgctata gtgcagtcgg cttctgacgt tcagtgcagc   7200
cgtcttctga aaacgacatg tcgcacaagt cctaagttac gcgacaggct gccgccctgc   7260
ccttttcctg gcgttttctt gtcgcgtgtt ttagtcgcat aaagtagaat acttgcgact   7320
```

```
agaaccggag acattacgcc atgaacaaga gcgccgccgc tggcctgctg ggctatgccc    7380
gcgtcagcac cgacgaccag gacttgacca accaacgggc cgaactgcac gcggccggct    7440
gcaccaagct gttttccgag aagatcaccg gcaccaggcg cgaccgcccg gagctggcca    7500
ggatgcttga ccacctacgc cctggcgacg ttgtgacagt gaccaggcta gaccgcctgg    7560
cccgcagcac ccgcgaccta ctggacattg ccgagcgcat ccaggaggcc ggcgcgggcc    7620
tgcgtagcct ggcagagccg tgggccgaca ccaccacgcc ggccggccgc atggtgttga    7680
ccgtgttcgc cggcattgcc gagttcgagc gttccctaat catcgaccgc acccggagcg    7740
ggcgcgaggc cgccaaggcc cgaggcgtga agtttggccc ccgccctacc ctcaccccgg    7800
cacagatcgc gcacgcccgc gagctgatcg accaggaagg ccgcaccgtg aaagaggcgg    7860
ctgcactgct tggcgtgcat cgctcgaccc tgtaccgcgc acttgagcgc agcgaggaag    7920
tgacgcccac cgaggccagg cggcgcggtg ccttccgtga ggacgcattg accgaggccg    7980
acgccctggc ggccgccgag aatgaacgcc aagaggaaca agcatgaaac cgcaccagga    8040
cggccaggac gaaccgtttt tcattaccga agagatcgag gcggagatga tcgcggccgg    8100
gtacgtgttc gagccgcccg cgcacgtctc aaccgtgcgg ctgcatgaaa tcctggccgg    8160
tttgtctgat gccaagctgg cggcctggcc ggccagcttg gccgctgaag aaaccgagcg    8220
ccgccgtcta aaaggtgat gtgtatttga gtaaaacagc ttgcgtcatg cggtcgctgc    8280
gtatatgatg cgatgagtaa ataaacaaat acgcaagggg aacgcatgaa ggttatcgct    8340
gtacttaacc agaaaggcgg gtcaggcaag acgaccatcg caacccatct agcccgcgcc    8400
ctgcaactcg ccggggccga tgttctgtta gtcgattccg atcccaggg cagtgcccgc    8460
gattgggcgg ccgtgcggga agatcaaccg ctaaccgttg tcggcatcga ccgcccgacg    8520
attgaccgcg acgtgaaggc catcggccgg cgcgacttcg tagtgatcga cggagcgccc    8580
caggcggcgg acttggctgt gtccgcgatc aaggcagccg acttcgtgct gattccggtg    8640
cagccaagcc cttacgacat atgggccacc gccgacctgg tggagctggt taagcagcgc    8700
attgaggtca cggatggaag gctacaagcg gcctttgtcg tgtcgcgggc gatcaaaggc    8760
acgcgcatcg gcgtgaggt tgccgaggcg ctggccgggt acgagctgcc cattcttgag    8820
tcccgtatca cgcagcgcgt gagctaccca ggcactgccg ccgccggcac aaccgttctt    8880
gaatcagaac ccgagggcga cgctgcccgc gaggtccagg cgctggccgc tgaaattaaa    8940
tcaaaactca tttgagttaa tgaggtaaag agaaaatgag caaaagcaca aacacgctaa    9000
gtgccggccg tccgagcgca cgcagcagca aggctgcaac gttggccagc ctggcagaca    9060
cgccagccat gaagcgggtc aactttcagt tgccggcgga ggatcacacc aagctgaaga    9120
tgtacgcggt acgccaaggc aagaccatta ccgagctgct atctgaatac atcgcgcagc    9180
taccagagta aatgagcaaa tgaataaatg agtagatgaa tttagcggc taaaggaggc    9240
ggcatggaaa atcaagaaca accaggcacc gacgccgtgg aatgccccat gtgtggagga    9300
acgggcggtt ggccaggcgt aagcggctgg gttgtctgcc ggcctgcaa tggcactgga    9360
acccccaagc ccgaggaatc ggcgtgacgg tcgcaaacca tccggcccgg tacaaatcgg    9420
cgcggcgctg ggtgatgacc tggtggagaa gttgaaggcc gcgcaggccg cccagcggca    9480
acgcatcgag gcagaagcac gccccggtga atcgtggcaa gcggccgctg atcgaatccg    9540
caaagaatcc cggcaaccgc cggcagccgg tgcgccgtcg attaggaagc cgcccaaggg    9600
cgacgagcaa ccagattttt tcgttccgat gctctatgac gtgggcaccc gcgatagtcg    9660
cagcatcatg gacgtggccg ttttccgtct gtcgaagcgt gaccgacgag ctggcgaggt    9720
```

```
gatccgctac gagcttccag acgggcacgt agaggtttcc gcagggccgg ccggcatggc   9780
cagtgtgtgg gattacgacc tggtactgat ggcggtttcc catctaaccg aatccatgaa   9840
ccgataccgg gaagggaagg gagacaagcc cggccgcgtg ttccgtccac acgttgcgga   9900
cgtactcaag ttctgccggc gagccgatgg cggaaagcag aaagacgacc tggtagaaac   9960
ctgcattcgg ttaaacacca cgcacgttgc catgcagcgt acgaagaagg ccaagaacgg  10020
ccgcctggtg acggtatccg agggtgaagc cttgattagc cgctacaaga tcgtaaagag  10080
cgaaaccggg cggccggagt acatcgagat cgagctagct gattggatgt accgcgagat  10140
cacagaaggc aagaacccgg acgtgctgac ggttcacccc gattactttt tgatcgatcc  10200
cggcatcggc cgttttctct accgcctggc acgccgcgcc gcaggcaagg cagaagccag  10260
atggttgttc aagacgatct acgaacgcag tggcagcgcc ggagagttca agaagttctg  10320
tttcaccgtg cgcaagctga tcgggtcaaa tgacctgccg gagtacgatt tgaaggagga  10380
ggcggggcag gctggcccga tcctagtcat gcgctaccgc aacctgatcg agggcgaagc  10440
atccgccggt tcctaatgta cggagcagat gctagggcaa attgccctag caggggaaaa  10500
aggtcgaaaa ggtctctttc ctgtggatag cacgtacatt gggaacccaa agccgtacat  10560
tgggaaccgg aacccgtaca ttgggaaccc aaagccgtac attgggaacc ggtcacacat  10620
gtaagtgact gatataaaag agaaaaaagg cgattttttcc gcctaaaact ctttaaaact  10680
tattaaaact cttaaaaccc gcctggcctg tgcataactg tctggccagc gcacagccga  10740
agagctgcaa aaagcgccta cccttcggtc gctgcgctcc ctacgccccg ccgcttcgcg  10800
tcggcctatc gcggccgctg gccgctcaaa aatggctggc ctacggccag gcaatctacc  10860
agggcgcgga caagccgcgc cgtcgccact cgaccgccgg cgcccacatc aaggcaccct  10920
gcctcgcgcg tttcggtgat gacggtgaaa acctctgaca catgcagctc ccggagacgg  10980
tcacagcttg tctgtaagcg gatgccggga gcagacaagc ccgtcagggc gcgtcagcgg  11040
gtgttggcgg gtgtcggggc gcagccatga cccagtcacg tagcgatagc ggagtgtata  11100
ctggcttaac tatgcggcat cagagcagat tgtactgaga gtgcaccata tgcggtgtga  11160
aataccgcac agatgcgtaa ggagaaaata ccgcatcagg cgctcttccg cttcctcgct  11220
cactgactcg ctgcgctcgg tcgttcggct gcggcgagcg gtatcagctc actcaaaggc  11280
ggtaatacgg ttatccacag aatcagggga taacgcagga agaacatgt  gagcaaaagg  11340
ccagcaaaag gccaggaacc gtaaaaaggc cgcgttgctg gcgttttccc ataggctccg  11400
ccccctgac gagcatcaca aaaatcgacg ctcaagtcag aggtggcgaa acccgacagg  11460
actataaaga taccaggcgt ttccccctgg aagctccctc gtgcgctctc ctgttccgac  11520
cctgccgctt accggatacc tgtccgcctt tctcccttcg ggaagcgtgg cgctttctca  11580
tagctcacgc tgtaggtatc tcagttcggt gtaggtcgtt cgctccaagc tgggctgtgt  11640
gcacgaaccc cccgttcagc ccgaccgctg cgccttatcc ggtaactatc gtcttgagtc  11700
caacccggta agacacgact tatcgccact ggcagcagcc actggtaaca ggattagcag  11760
agcgaggtat gtaggcggtg ctacagagtt cttgaagtgg tggcctaact acggctacac  11820
tagaaggaca gtatttggta tctgcgctct gctgaagcca gttaccttcg gaaaaagagt  11880
tggtagctct tgatccggca acaaaccac cgctggtagc ggtggttttt tgtttgcaa   11940
gcagcagatt acgcgcagaa aaaaaggatc tcaagaagat cctttgatct tttctacggg  12000
gtctgacgct cagtggaacg aaaactcacg ttaagggatt ttggtcatgc attctaggta  12060
```

```
ctaaaacaat tcatccagta aaatataata ttttattttc tcccaatcag gcttgatccc    12120
cagtaagtca aaaaatagct cgacatactg ttcttccccg atatcctccc tgatcgaccg    12180
gacgcagaag gcaatgtcat accacttgtc cgccctgccg cttctcccaa gatcaataaa    12240
gccacttact ttgccatctt tcacaaagat gttgctgtct cccaggtcgc cgtgggaaaa    12300
gacaagttcc tcttcgggct tttccgtctt taaaaaatca tacagctcgc gcggatcttt    12360
aaatggagtg tcttcttccc agttttcgca atccacatcg gccagatcgt tattcagtaa    12420
gtaatccaat tcggctaagc ggctgtctaa gctattcgta tagggacaat ccgatatgtc    12480
gatggagtga agagcctga tgcactccgc atacagctcg ataatctttt cagggctttg     12540
ttcatcttca tactcttccg agcaaaggac gccatcggcc tcactcatga gcagattgct    12600
ccagccatca tgccgttcaa agtgcaggac ctttggaaca ggcagctttc cttccagcca    12660
tagcatcatg tcctttccc gttccacatc ataggtggtc cctttatacc ggctgtccgt     12720 cattttaaa tataggtttt cattttctcc caccagctta tataccttag caggagacat     12780
tccttccgta tcttttacgc agcggtattt ttcgatcagt ttttcaatt ccggtgatat     12840 tctcatttta gccatttatt atttccttcc tcttttctac agtatttaaa gatacccccaa   12900 gaagctaatt ataacaagac gaactccaat tcactgttcc ttgcattcta aaaccttaaa   12960
taccagaaaa cagcttttc aaagttgttt tcaaagttgg cgtataacat agtatcgacg     13020
gagccgattt tgaaaccgcg gtgatcacag gcagcaacgc tctgtcatcg ttacaatcaa    13080
catgctaccc tccgcgagat catccgtgtt tcaaacccgg cagcttagtt gccgttcttc    13140
cgaatagcat cggtaacatg agcaaagtct gccgccttac aacggctctc ccgctgacgc    13200
cgtcccggac tgatgggctg cctgtatcga gtggtgattt tgtgccgagc tgccggtcgg    13260
ggagctgttg gctggctggt ggcaggatat attgtggtgt aaacaaattg acgcttagac    13320
aacttaataa cacattgcgg acgtttttaa tgtactgaat taacgccgaa ttaattcggg    13380
ggatctggat tttagtactg gattttggtt ttaggaatta gaaattttat tgatagaagt    13440
attttacaaa tacaaataca tactaagggt ttcttatatg ctcaacacat gagcgaaacc    13500
ctataggaac cctaattccc ttatctggga actactcaca cattattatg gagaaactcg    13560
agcttgtcga tcgacagatc cggtcggcat ctactctatt tctttgccct cggacgagtg    13620
ctggggcgtc ggtttccact atcggcgagt acttctacac agccatcggt ccagacggcc    13680
gcgcttctgc gggcgatttg tgtacgcccg acagtcccgg ctccggatcg gacgattgcg    13740
tcgcatcgac cctgcgccca agctgcatca tcgaaattgc cgtcaaccaa gctctgatag    13800
agttggtcaa gaccaatgcg gagcatatac gcccggagtc gtggcgatcc tgcaagctcc    13860
ggatgcctcc gctcgaagta gcgcgtctgc tgctccatac aagccaacca cggcctccag    13920
aagaagatgt tggcgacctc gtattgggaa tccccgaaca tcgcctcgct ccagtcaatg    13980
accgctgtta tgcggccatt gtccgtcagg acattgttgg agccgaaatc cgcgtgcacg    14040
aggtgccgga cttcggggca gtcctcggcc caaagcatca gctcatcgag agcctgcgcg    14100
acggacgcac tgacggtgtc gtccatcaca gtttgccagt gatacacatg gggatcagca    14160
atcgcgcata tgaaatcacg ccatgtagtg tattgaccga ttccttgcgg tccgaatggg    14220
ccgaacccgc tcgtctggct aagatcggcc gcagcgatcg catccatagc ctccgcgacc    14280
ggttgtagaa cagcgggcag ttcggtttca ggcaggtctt gcaacgtgac accctgtgca    14340
cggcgggaga tgcaataggt caggctctcg ctaaactccc caatgtcaag cacttccgga    14400
atcgggagcg cggccgatgc aaagtgccga taaacataac gatctttgta gaaaccatcg    14460
```

```
gcgcagctat ttacccgcag gacatatcca cgccctccta catcgaagct gaaagcacga    14520
gattcttcgc cctccgagag ctgcatcagg tcggagacgc tgtcgaactt ttcgatcaga    14580
aacttctcga cagacgtcgc ggtgagttca ggcttttttca tatctcattg cccccccggga   14640 tctgcgaaag ctcgagagag atagatttgt agagagagac tggtgatttc agcgtgtcct    14700
ctccaaatga aatgaacttc cttatataga ggaaggtctt gcgaaggata gtgggattgt    14760
gcgtcatccc ttacgtcagt ggagatatca catcaatcca cttgctttga agacgtggtt    14820
ggaacgtctt cttttccac gatgctcctc gtgggtgggg gtccatcttt gggaccactg     14880
tcggcagagg catcttgaac gatagccttt cctttatcgc aatgatggca tttgtaggtg    14940
ccaccttcct tttctactgt ccttttgatg aagtgacaga tagctgggca atggaatccg    15000
aggaggtttc ccgatattac cctttgttga aaagtctcaa tagccctttg gtcttctgag    15060
actgtatctt tgatattctt ggagtagacg agagtgtcgt gctccaccat gttatcacat    15120
caatccactt gctttgaaga cgtggttgga acgtcttctt tttccacgat gctcctcgtg    15180
ggtgggggtc catctttggg accactgtcg gcagaggcat cttgaacgat agccttttcct   15240 ttatcgcaat gatggcattt gtaggtgcca ccttcctttt ctactgtcct tttgatgaag    15300
tgacagatag ctgggcaatg gaatccgagg aggtttcccg atattaccct ttgttgaaaa    15360
gtctcaatag ccctttggtc ttctgagact gtatctttga tattcttgga gtagacgaga    15420
gtgtcgtgct ccaccatgtt ggcaagctgc tctagccaat acgcaaaccg cctctccccg    15480
cgcgttggcc gattcattaa tgcagctggc acgacaggtt tcccgactgg aaagcgggca    15540
gtgagcgcaa cgcaattaat gtgagttagc tcactcatta ggcacccag gctttacact     15600 ttatgcttcc ggctcgtatg ttgtgtggaa ttgtgagcgg ataacaattt cacacaggaa    15660
acagctatga ccatgattac g                                                15681

<210> SEQ ID NO 156
<211> LENGTH: 15681
<212> TYPE: DNA
<213> ORGANISM: Artificial Sequence
<220> FEATURE:
<223> OTHER INFORMATION: vector
<220> FEATURE:
<221> NAME/KEY: misc_feature
<222> LOCATION: (5964)..(5984)
<223> OTHER INFORMATION: /note="target sequence"
<220> FEATURE:
<221> NAME/KEY: misc_feature
<222> LOCATION: (6617)..(6637)
<223> OTHER INFORMATION: /note="target sequence"

<400> SEQUENCE: 156
aattcccgat ctagtaacat agatgacacc gcgcgcgata atttatccta gtttgcgcgc      60
tatattttgt tttctatcgc gtattaaatg tataattgcg ggactctaat cataaaaacc     120
catctcataa ataacgtcat gcattacatg ttaattatta catgcttaac gtaattcaac     180
agaaattata tgataatcat cgcaagaccg gcaacaggat tcaatcttaa gaaactttat     240
tgccaaatgt ttgaacgatc ggggaaattc gagctctatc gatcaatcag gatccttact     300
ttttcttttt tgcctggccg gcctttttcg tggccgccgg cctttttgtcg cctcccagct    360 gagacaggtc gatccgtgtc tcgtacaggc cggtgatgct ctggtggatc agggtggcgt    420
ccagcacctc tttggtgctg gtgtacctct tccggtcgat ggtggtgtca aagtacttga    480
aggcggcagg ggctcccaga ttggtcaggg taaacaggtg gatgatattc tcggcctgct    540
```

```
ctctgatggg cttatcccgg tgcttgttgt aggcggacag cactttgtcc agattagcgt    600
cggccaggat cactctcttg gagaactcgc tgatctgctc gatgatctcg tccaggtagt    660
gcttgtgctg ttccacaaac agctgtttct gctcattatc ctcgggggag cccttcagct    720
tctcatagtg gctggccagg tacaggaagt tcacatattt ggagggcagg ccagttcgt    780
ttcccttctg cagttcgccg gcagaggcca gcattctctt ccggccgttt ccagctcga    840
acagggagta cttaggcagc ttgatgatca ggtcctttt cacttctttg tagcccttgg    900
cttccagaaa gtcgatggga ttcttctcga agctgcttct ttccatgatg gtgatcccca    960
gcagctcttt cacactcttc agtttcttgg acttgccctt ttccactttg gccaccacca   1020
gcacagaata ggccacggtg gggctgtcga agccgccgta cttcttaggg tcccagtcct   1080
tctttctggc gatcagctta tcgctgttcc tcttgggcag gatagactct ttgctgaagc   1140
cgcctgtctg cacctcggtc ttttttcacga tattcacttg gggcatgctc agcactttcc   1200
gcacggtggc aaaatcccgg cccttatccc acacgatctc cccggtttcg ccgtttgtct   1260
cgatcagagg ccgcttccgg atctcgccgt tggccagggt aatctcggtc ttgaaaaagt   1320
tcatgatgtt gctgtagaag aagtacttgg cggtagcctt gccgattccc tgctcgctct   1380
tggcgatcat cttccgcacg tcgtacacct tgtagtcgcc gtacacgaac tcgctttcca   1440
gcttagggta ctttttgatc agggcggttc ccacgacggc gttcaggtag gcgtcgtggg   1500
cgtggtggta gttgttgatc tcgcgcactt tgtaaaactg gaaatccttc cggaaatcgg   1560
acaccagctt ggacttcagg gtgatcactt tcacttcccg gatcagcttg tcattctcgt   1620
cgtacttagt gttcatccgg gagtccagga tctgtgccac gtgctttgtg atctgccggg   1680
tttccaccag ctgtctcttg atgaagccgg ccttatccag ttcgctcagg ccgcctctct   1740
cggccttggt cagattgtcg aactttctct gggtaatcag cttggcgttc agcagctgcc   1800
gccagtagtt cttcatcttc ttcacgacct cttcggaggg cacgttgtcg ctcttgcccc   1860
ggttcttgtc gcttctggtc agcaccttgt tgtcgatgga gtcgtccttc agaaagctct   1920
gaggcacgat atggtccaca tcgtagtcgg acagccggtt gatgtccagt tcctggtcca   1980
cgtacatatc ccgcccattc tgcaggtagt acaggtacag cttctcgttc tgcagctggg   2040
tgttttccac ggggtgttct ttcaggatct ggctgcccag ctctttgatg ccctcttcga   2100
tccgcttcat tctctcgcgg ctgttcttct gtcccttctg ggtggtctgg ttctctctgg   2160
ccatttcgat cacgatgttc tcgggcttgt gccggcccat cactttcacg agctcgtcca   2220
ccaccttcac tgtctgcagg atgcccttct taatggcggg gctgccggcc agattggcaa   2280
tgtgctcgtg caggctatcg ccctggccgg acacctgggc tttctggatg tcctctttaa   2340
aggtcaggct gtcgtcgtgg atcagctgca tgaagtttct gttggcgaag ccgtcggact   2400
tcaggaaatc caggattgtc ttgccggact gcttgtcccg gatgccgttg atcagcttcc   2460
ggctcagcct gccccagccg gtgtatctcc gccgcttcag ctgcttcatc actttgtcgt   2520
cgaacaggtg ggcataggtt ttcagccgtt cctcgatcat ctctctgtcc tcaaacagtg   2580
tcagggtcag cacgatatct tccagaatgt cctcgttttc ctcattgtcc aggaagtcct   2640
tgtccttgat aattttcagc agatcgtggt atgtgcccag ggaggcgttg aaccgatctt   2700
ccacgccgga gatttccacg gagtcgaagc actcgatttt cttgaagtag tcctctttca   2760
gctgcttcac ggtcactttc cggttggtct tgaacagcag gtccacgatg gccttttct   2820
gctcgccgct caggaaggcg ggcttctcca ttccctcggt cacgtatttc actttggtca   2880
gctcgttata cacggtgaag tactcgtaca gcaggctgtg cttgggcagc accttctcgt   2940
```

```
tgggcaggtt cttatcgaag ttggtcatcc gctcgatgaa gctctgggcg aagcgccct    3000 tgtccaccac ttcctcgaag ttccagggggg tgatggtttc ctcgctcttt ctggtcatcc   3060
aggcgaatct gctgtttccc ctggccagag ggcccacgta gtaggggatg cggaaggtca   3120
ggatcttctc gatcttttcc cggttgtcct tcaggaatgg gtaaaaatct tcctgccgcc   3180
gcagaatggc gtgcagctct cccaggtgga tctggtgggg gatgctgccg ttgtcgaagg   3240
tccgctgctt ccgcagcagg tcctctctgt tcagcttcac gagcagttcc tcggtgccgt   3300
ccatcttttc caggatgggc ttgatgaact gtagaactc ttcctggctg gctccgccgt    3360
caatgtagcc ggcgtagccg ttcttgctct ggtcgaagaa aatctctttg tacttctcag   3420
gcagctgctg ccgcacgaga gctttcagca gggtcaggtc ctggtggtgc tcgtcgtatc   3480
tcttgatcat agaggcgctc agggggggcct tggtgatctc ggtgttcact ctcaggatgt   3540
cgctcagcag gatggcgtcg acaggttct ggcggccag aaacaggtcg gcgtactggt     3600
cgccgatctg ggccagcagg ttgtccaggt cgtcgtcgta ggtgtccttg ctcagctgca   3660
gtttggcatc ctcggccagg tcgaagttgc tcttgaagtt gggggtcagg cccaggctca   3720
gggcaatcag gttccgaac aggccattct tcttctcgcc gggcagctgg gcgatcagat     3780
tttccagccg tctgctcttg ctcagtctgg cagacaggat ggccttggcg tccacgccgc   3840
tggcgttgat ggggttttcc tcgaacagct ggttgtaggt ctgcaccagc tggatgaaca   3900
gcttgtccac gtcgctgttg tcggggttca ggtcgccctc gatcaggaag tggccccgga   3960
acttgatcat gtgggccagg gccagataga tcagccgcag gtcggccttg tcggtgctgt   4020
ccaccagttt ctttctcagg tggtagatgg tggggtactt ctcgtggtag gccacctcgt   4080
ccacgatgtt gccgaagatg gggtgccgct cgtgcttctt atcctcttcc accaggaagg   4140
actcttccag tctgtggaag aagctgtcgt ccaccttggc catctcgttg ctgaagatct   4200
cttgcagata gcagatccgg ttcttccgtc tggtgtatct tcttctgcg gttctcttca    4260 gccgggtggc ctcggctgtt tcgccgctgt cgaacagcag ggctccgatc aggttcttct   4320
tgatgctgtg ccggtcggtg ttgcccagca ccttgaattt cttgctgggc accttgtact   4380
cgtcggtgat cacggcccag cccacagagt tggtgccgat gtccaggccg atgctgtact   4440
tcttgtcggc tgctgggact ccgtggatac cgaccttccg cttcttcttt ggggccatct   4500
tatcgtcatc gtctttgtaa tcaatatcat gatccttgta gtctccgtcg tggtccttat   4560
agtccatctc gagtatcgtt cgtaaatggt gaaaattttc agaaaattgc ttttgcttta   4620
aaagaaatga tttaaattgc tgcaatagaa gtagaatgct tgattgcttg agattcgttt   4680
gttttgtata tgttgtgttg aggtcgaggt cctctccaaa tgaaatgaac ttccttatat   4740
agaggaaggg tcttgcgaag gatagtggga ttgtgcgtca tcccttacgt cagtggagat   4800
atcacatcaa tccacttgct ttgaagacgt ggttggaacg tcttctttttt ccacgatgct   4860 cctcgtgggt ggggtccat ctttgggacc actgtcggca gaggcatctt caacgatggc    4920 cttttccttta tcgcaatgat ggcatttgta ggagccacct tccttttcca ctatcttcac   4980
aataaagtga cagatagctg ggcaatggaa tccgaggagg tttccggata tcaccctttg   5040
ttgaaaagtc tcaattgccc tttggtcttc tgagactgta tctttgatat ttttggagta   5100
gacaagtgtg tcgtgctcca ccatgttatc acatcaatcc acttgctttg aagacgtggt   5160
tggaacgtct tctttttcca cgatgctcct cgtgggtggg ggtccatctt tgggaccact   5220
gtcggcagag gcatcttcaa cgatggcctt tcctttatcg caatgatggc atttgtagga   5280
```

-continued

```
gccaccttcc ttttccacta tcttcacaat aaagtgacag atagctgggc aatggaatcc   5340
gaggaggttt ccggatatta ccctttgttg aaaagtctca attgccctt ggtcttctga    5400 gactgtatct ttgatatttt tggagtagac aagtgtgtcg tgctccacca tgttgacctg   5460
caggcatgcc tcgatccac tagtaacggc cgccagtgtg ctggaattgc ccttaagctt    5520
cgttgaacaa cggaaactcg acttgccttc cgcacaatac atcatttctt cttagctttt   5580
tttcttcttc ttcgttcata cagttttttt ttgtttatca gcttacattt tcttgaaccg   5640
tagctttcgt tttcttcttt ttaactttcc attcggagtt tttgtatctt gtttcatagt   5700
ttgtcccagg attagaatga ttaggcatcg aaccttcaag aatttgattg aataaaacat   5760
cttcattctt aagatatgaa gataatcttc aaaaggcccc tgggaatctg aaagaagaga   5820
agcaggccca tttatatggg aaagaacaat agtatttctt atataggccc atttaagttg   5880
aaaacaatct tcaaaagtcc cacatcgctt agataagaaa acgaagctga gtttatatac   5940
agctagagtc gaagtagtga ttgcggagac tcgtctacag ttgttttaga gctagaaata   6000
gcaagttaaa ataaggctag tccgttatca acttgaaaaa gtggcaccga gtcggtgctt   6060
tttttgtccc ttcgaagggc ctttctcaga tatccatcac actggcggcc gctcgaggtc   6120
gctcggatcc actagtaacg gccgccagtg tgctggaatt gcccttaagc ttcgttgaac   6180
aacggaaact cgacttgcct tccgcacaat acatcatttc ttcttagctt ttttttcttct  6240 tcttcgttca tacagttttt ttttgtttat cagcttacat tttcttgaac cgtagctttc   6300
gttttcttct ttttaacttt ccattcggag ttttttgtatc ttgtttcata gtttgtccca  6360
ggattagaat gattaggcat cgaaccttca agaatttgat tgaataaaac atcttcattc   6420
ttaagatatg aagataatct tcaaaaggcc ctgggaatc tgaaagaaga gaagcaggcc    6480
catttatatg ggaaagaaca atagtatttc ttatataggc ccatttaagt tgaaaacaat   6540
cttcaaaagt cccacatcgc ttagataaga aaacgaagct gagtttatat acagctagag   6600
tcgaagtagt gattatgtgt tacagcacgt cggggtttta gagctagaaa tagcaagtta   6660
aaataaggct agtccgttat caacttgaaa agtggcacc gagtcggtgc ttttttttgtc   6720 ccttcgaagg gccttttctca gatatccatc acactggcgg ccgctcgagg tcgaagcttg   6780
gcactggccg tcgttttaca acgtcgtgac tgggaaaacc ctggcgttac ccaacttaat   6840
cgccttgcag cacatccccc tttcgccagc tggcgtaata gcgaagaggc ccgcaccgat   6900
cgcccttccc aacagttgcg cagcctgaat ggcgaatgct agagcagctt gagcttggat   6960
cagattgtcg tttcccgcct tcagtttaaa ctatcagtgt ttgacaggat atattggcgg   7020
gtaaacctaa gagaaaagag cgtttattag aataacggat atttaaaagg gcgtgaaaag   7080
gtttatccgt tcgtccattt gtatgtgcat gccaaccaca gggttcccct cgggatcaaa   7140
gtactttgat ccaaccccctc cgctgctata gtgcagtcgg cttctgacgt tcagtgcagc   7200
cgtcttctga aaacgacatg tcgcacaagt cctaagttac gcgacaggct gccgccctgc   7260 cctttcctg gcgttttctt gtcgcgtgtt ttagtcgcat aaagtagaat acttgcgact   7320
agaaccggag acattacgcc atgaacaaga gcgccgccgc tggcctgctg ggctatgccc   7380
gcgtcagcac cgacgaccag gacttgacca accaacgggc cgaactgcac gcggccggct   7440
gcaccaagct gttttccgag aagatcaccg gcaccaggcg cgaccgcccg gagctggcca   7500
ggatgcttga ccacctacgc cctggcgacg ttgtgacagt gaccaggcta gaccgcctgg   7560
cccgcagcac ccgcgaccta ctggacattg ccgagcgcat ccaggaggcc ggcgcgggc    7620 tgcgtagcct ggcagagccg tgggccgaca ccaccacgcc ggccggccgc atggtgttga   7680
```

```
ccgtgttcgc cggcattgcc gagttcgagc gttccctaat catcgaccgc acccggagcg   7740
ggcgcgaggc cgccaaggcc cgaggcgtga agtttggccc ccgccctacc ctcaccccgg   7800
cacagatcgc gcacgcccgc gagctgatcg accaggaagg ccgcaccgtg aaagaggcgg   7860
ctgcactgct tggcgtgcat cgctcgaccc tgtaccgcgc acttgagcgc agcgaggaag   7920
tgacgcccac cgaggccagg cggcgcggtg ccttccgtga ggacgcattg accgaggccg   7980
acgccctggc ggccgccgag aatgaacgcc aagaggaaca agcatgaaac cgcaccagga   8040
cggccaggac gaaccgtttt tcattaccga agagatcgag gcggagatga tcgcggccgg   8100
gtacgtgttc gagccgcccg cgcacgtctc aaccgtgcgg ctgcatgaaa tcctggccgg   8160
tttgtctgat gccaagctgg cggcctggcc ggccagcttg gccgctgaag aaaccgagcg   8220
ccgccgtcta aaaggtgat gtgtatttga gtaaaacagc ttgcgtcatg cggtcgctgc   8280
gtatatgatg cgatgagtaa ataaacaaat acgcaagggg aacgcatgaa ggttatcgct   8340
gtacttaacc agaaaggcgg gtcaggcaag acgaccatcg caacccatct agcccgcgcc   8400
ctgcaactcg ccggggccga tgttctgtta gtcgattccg atccccaggg cagtgcccgc   8460
gattgggcgg ccgtgcggga agatcaaccg ctaaccgttg tcggcatcga ccgcccgacg   8520
attgaccgcg acgtgaaggc catcggccgg cgcgacttcg tagtgatcga cggagcgccc   8580
caggcggcgg acttggctgt gtccgcgatc aaggcagccg acttcgtgct gattccggtg   8640
cagccaagcc cttacgacat atgggccacc gccgacctgg tggagctggt taagcagcgc   8700
attgaggtca cggatggaag gctacaagcg gcctttgtcg tgtcgcgggc gatcaaaggc   8760
acgcgcatcg gcggtgaggt tgccgaggcg ctggccgggt acgagctgcc cattcttgag   8820
tcccgtatca cgcagcgcgt gagctaccca ggcactgccg ccgccggcac aaccgttctt   8880
gaatcagaac ccgagggcga cgctgcccgc gaggtccagg cgctggccgc tgaaattaaa   8940
tcaaaactca tttgagttaa tgaggtaaag agaaaatgag caaaagcaca aacacgctaa   9000
gtgccggccg tccgagcgca cgcagcagca aggctgcaac gttggccagc ctggcagaca   9060
cgccagccat gaagcgggtc aactttcagt tgccggcgga ggatcacacc aagctgaaga   9120
tgtacgcggt acgccaaggc aagaccatta ccgagctgct atctgaatac atcgcgcagc   9180
taccagagta aatgagcaaa tgaataaatg agtagatgaa ttttagcggc taaaggaggc   9240
ggcatggaaa atcaagaaca accaggcacc gacgccgtgg aatgccccat gtgtggagga   9300
acgggcggtt ggccaggcgt aagcggctgg gttgtctgcc ggccctgcaa tggcactgga   9360 accccaagc cgaggaatc ggcgtgacgg tcgcaaacca tccggcccgg tacaaatcgg   9420
cgcggcgctg ggtgatgacc tggtggagaa gttgaaggcc gcgcaggccg cccagcggca   9480
acgcatcgag gcagaagcac gccccggtga atcgtggcaa gcggccgctg atcgaatccg   9540
caaagaatcc cggcaaccgc cggcagccgg tgcgccgtcg attaggaagc cgcccaaggg   9600
cgacgagcaa ccagatttt tcgttccgat gctctatgac gtgggcaccc gcgatagtcg   9660
cagcatcatg gacgtggccg ttttccgtct gtcgaagcgt gaccgacgag ctggcgaggt   9720
gatccgctac gagcttccag acgggcacgt agaggtttcc gcaggccgg ccggcatggc   9780 cagtgtgtgg gattacgacc tggtactgat ggcggttttcc catctaaccg aatccatgaa   9840
ccgataccgg gaagggaagg gagacaagcc cggccgcgtg ttccgtccac acgttgcgga   9900
cgtactcaag ttctgccggc gagccgatgg cggaaagcag aaagacgacc tggtagaaac   9960
ctgcattcgg ttaaacacca cgcacgttgc catgcagcgt acgaagaagg ccaagaacgg  10020
```

```
ccgcctggtg acggtatccg agggtgaagc cttgattagc cgctacaaga tcgtaaagag   10080
cgaaaccggg cggccggagt acatcgagat cgagctagct gattggatgt accgcgagat   10140
cacagaaggc aagaacccgg acgtgctgac ggttcacccc gattactttt tgatcgatcc   10200
cggcatcggc cgttttctct accgcctggc acgccgcgcc gcaggcaagg cagaagccag   10260
atggttgttc aagacgatct acgaacgcag tggcagcgcc ggagagttca agaagttctg   10320
tttcaccgtg cgcaagctga tcgggtcaaa tgacctgccg gagtacgatt tgaaggagga   10380
ggcggggcag gctggcccga tcctagtcat gcgctaccgc aacctgatcg agggcgaagc   10440
atccgccggt tcctaatgta cggagcagat gctagggcaa attgccctag caggggaaaa   10500
aggtcgaaaa ggtctctttc ctgtggatag cacgtacatt gggaacccaa agccgtacat   10560
tgggaaccgg aacccgtaca ttgggaaccc aaagccgtac attgggaacc ggtcacacat   10620
gtaagtgact gatataaaag agaaaaaagg cgattttttcc gcctaaaact ctttaaaact   10680
tattaaaact cttaaaaccc gcctggcctg tgcataactg tctggccagc gcacagccga   10740
agagctgcaa aaagcgccta cccttcggtc gctgcgctcc ctacgccccg ccgcttcgcg   10800
tcggcctatc gcggccgctg gccgctcaaa aatggctggc ctacggccag gcaatctacc   10860
agggcgcgga caagccgcgc cgtcgccact cgaccgccgg cgcccacatc aaggcaccct   10920
gcctcgcgcg tttcggtgat gacggtgaaa acctctgaca catgcagctc ccggagacgg   10980
tcacagcttg tctgtaagcg gatgccggga gcagacaagc cgtcagggc gcgtcagcgg   11040 gtgttggcgg gtgtcgggc gcagccatga cccagtcacg tagcgatagc ggagtgtata   11100
ctggcttaac tatgcggcat cagagcagat tgtactgaga gtgcaccata tgcggtgtga   11160
aataccgcac agatgcgtaa ggagaaaata ccgcatcagg cgctcttccg cttcctcgct   11220
cactgactcg ctgcgctcgg tcgttcggct gcggcgagcg gtatcagctc actcaaaggc   11280
ggtaatacgg ttatccacag aatcagggga taacgcagga agaacatgt gagcaaaagg   11340 ccagcaaaag gccaggaacc gtaaaaaggc cgcgttgctg gcgttttttcc ataggctccg   11400 ccccccctgac gagcatcaca aaaatcgacg ctcaagtcag aggtggcgaa acccgacagg   11460
actataaaga taccaggcgt ttccccctgg aagctccctc gtgcgctctc ctgttccgac   11520
cctgccgctt accggatacc tgtccgcctt tctcccttcg ggaagcgtgg cgctttctca   11580
tagctcacgc tgtaggtatc tcagttcggt gtaggtcgtt cgctccaagc tgggctgtgt   11640
gcacgaaccc cccgttcagc ccgaccgctg cgccttatcc ggtaactatc gtcttgagtc   11700
caacccggta agacacgact tatcgccact ggcagcagcc actggtaaca ggattagcag   11760
agcgaggtat gtaggcggtg ctacagagtt cttgaagtgg tggcctaact acggctacac   11820
tagaaggaca gtatttggta tctgcgctct gctgaagcca gttaccttcg gaaaagagt   11880 tggtagctct tgatccggca acaaaccac cgctggtagc ggtggttttt ttgtttgcaa   11940
gcagcagatt acgcgcagaa aaaaggatc tcaagaagat ccttgatcct tttctacggg   12000
gtctgacgct cagtggaacg aaaactcacg ttaagggatt ttggtcatgc attctaggta   12060
ctaaaacaat tcatccagta aaatataata ttttattttc tcccaatcag gcttgatccc   12120
cagtaagtca aaaatagct cgacatactg ttcttcccg atatcctccc tgatcgaccg   12180
gacgcagaag gcaatgtcat accacttgtc cgccctgccg cttctcccaa gatcaataaa   12240
gccacttact tgccatcttt cacaaagat gttgctgtct cccaggtcgc cgtgggaaaa   12300
gacaagttcc tcttcgggct tttccgtctt taaaaaatca tacagctcgc gcggatcttt   12360
aaatggagtg tcttcttccc agttttcgca atccacatcg ccagatcgt tattcagtaa   12420
```

```
gtaatccaat tcggctaagc ggctgtctaa gctattcgta tagggacaat ccgatatgtc   12480
gatggagtga aagagcctga tgcactccgc atacagctcg ataatctttt cagggctttg   12540
ttcatcttca tactcttccg agcaaaggac gccatcggcc tcactcatga gcagattgct   12600
ccagccatca tgccgttcaa agtgcaggac ctttggaaca ggcagctttc cttccagcca   12660
tagcatcatg tccttttccc gttccacatc ataggtggtc cctttatacc ggctgtccgt   12720
catttttaaa tataggtttt cattttctcc caccagctta tataccttag caggagacat   12780
tccttccgta tcttttacgc agcggtattt ttcgatcagt ttttcaatt ccggtgatat   12840 tctcattta gccatttatt atttccttcc tcttttctac agtatttaaa gatacccaa    12900 gaagctaatt ataacaagac gaactccaat tcactgttcc ttgcattcta aaaccttaaa   12960
taccagaaaa cagcttttc aaagttgttt tcaaagttgg cgtataacat agtatcgacg    13020
gagccgattt tgaaaccgcg gtgatcacag gcagcaacgc tctgtcatcg ttacaatcaa   13080
catgctaccc tccgcgagat catccgtgtt tcaaacccgg cagcttagtt gccgttcttc   13140
cgaatagcat cggtaacatg agcaaagtct gccgccttac aacggctctc ccgctgacgc   13200
cgtcccggac tgatgggctg cctgtatcga gtggtgattt tgtgccgagc tgccggtcgg   13260
ggagctgttg gctggctggt ggcaggatat attgtggtgt aaacaaattg acgcttagac   13320
aacttaataa cacattgcgg acgttttta tgtactgaat taacgccgaa ttaattcggg    13380
ggatctggat tttagtactg gattttggtt ttaggaatta gaaattttat tgatagaagt   13440
attttacaaa tacaaataca tactaagggt ttcttatatg ctcaacacat gagcgaaacc   13500
ctataggaac cctaattccc ttatctggga actactcaca cattattatg gagaaactcg   13560
agcttgtcga tcgacagatc cggtcggcat ctactctatt tctttgccct cggacgagtg   13620
ctggggcgtc ggtttccact atcggcgagt acttctacac agccatcggt ccagacggcc   13680
gcgcttctgc gggcgatttg tgtacgcccg acagtcccgg ctccggatcg gacgattgcg   13740
tcgcatcgac cctgcgccca agctgcatca tcgaaattgc cgtcaaccaa gctctgatag   13800
agttggtcaa gaccaatgcg gagcatatac gcccggagtc gtggcgatcc tgcaagctcc   13860
ggatgcctcc gctcgaagta gcgcgtctgc tgctccatac aagccaacca cggcctccag   13920
aagaagatgt tggcgacctc gtattgggaa tccccgaaca tcgcctcgct ccagtcaatg   13980
accgctgtta tgcggccatt gtccgtcagg acattgttgg agccgaaatc cgcgtgcacg   14040
aggtgccgga cttcggggca gtcctcggcc caaagcatca gctcatcgag agcctgcgcg   14100
acggacgcac tgacggtgtc gtccatcaca gtttgccagt gatacacatg gggatcagca   14160
atcgcgcata tgaaatcacg ccatgtagtg tattgaccga ttccttgcgg tccgaatggg   14220
ccgaacccgc tcgtctggct aagatcggcc gcagcgatcg catccatagc ctccgcgacc   14280
ggttgtagaa cagcgggcag ttcggtttca ggcaggtctt gcaacgtgac accctgtgca   14340
cggcgggaga tgcaataggt caggctctcg ctaaactccc caatgtcaag cacttccgga   14400
atcgggagcg cggccgatgc aaagtgccga taaacataac gatctttgta gaaaccatcg   14460
gcgcagctat ttacccgcag gacatatcca cgccctccta catcgaagct gaaagcacga   14520
gattcttcgc cctccgagag ctgcatcagg tcggagacgc tgtcgaactt ttcgatcaga   14580
aacttctcga cagacgtcgc ggtgagttca ggctttttca tatctcattg ccccccggga   14640
tctgcgaaag ctcgagagag atagatttgt agagagagac tggtgatttc agcgtgtcct   14700
ctccaaatga aatgaacttc cttatataga ggaaggtctt gcgaaggata gtgggattgt   14760
```

```
gcgtcatccc ttacgtcagt ggagatatca catcaatcca cttgctttga agacgtggtt    14820
ggaacgtctt cttttttccac gatgctcctc gtgggtgggg gtccatcttt gggaccactg   14880
tcggcagagg catcttgaac gatagccttt cctttatcgc aatgatggca tttgtaggtg    14940
ccaccttcct tttctactgt cctttttgatg aagtgacaga tagctgggca atggaatccg   15000
aggaggtttc ccgatattac cctttgttga aaagtctcaa tagcccttg gtcttctgag     15060 actgtatctt tgatattctt ggagtagacg agagtgtcgt gctccaccat gttatcacat    15120
caatccactt gctttgaaga cgtggttgga acgtcttctt tttccacgat gctcctcgtg    15180
ggtgggggtc catctttggg accactgtcg gcagaggcat cttgaacgat agccttttcct  15240 ttatcgcaat gatggcattt gtaggtgcca ccttcctttt ctactgtcct tttgatgaag    15300
tgacagatag ctgggcaatg gaatccgagg aggtttccg atattaccct ttgttgaaaa     15360
gtctcaatag ccctttggtc ttctgagact gtatctttga tattcttgga gtagacgaga    15420
gtgtcgtgct ccaccatgtt ggcaagctgc tctagccaat acgcaaaccg cctctccccg    15480
cgcgttggcc gattcattaa tgcagctggc acgacaggtt tcccgactgg aaagcgggca    15540
gtgagcgcaa cgcaattaat gtgagttagc tcactcatta ggcaccccag gctttacact    15600
ttatgcttcc ggctcgtatg ttgtgtggaa ttgtgagcgg ataacaattt cacacaggaa    15660
acagctatga ccatgattac g                                              15681

<210> SEQ ID NO 157
<211> LENGTH: 15681
<212> TYPE: DNA
<213> ORGANISM: Artificial Sequence
<220> FEATURE:
<223> OTHER INFORMATION: vector
<220> FEATURE:
<221> NAME/KEY: misc_feature
<222> LOCATION: (5964)..(5984)
<223> OTHER INFORMATION: /note="target sequence"
<220> FEATURE:
<221> NAME/KEY: misc_feature
<222> LOCATION: (6617)..(6637)
<223> OTHER INFORMATION: /note="target sequence"

<400> SEQUENCE: 157
aattcccgat ctagtaacat agatgacacc gcgcgcgata atttatccta gtttgcgcgc     60
tatattttgt tttctatcgc gtattaaatg tataattgcg ggactctaat cataaaaacc    120
catctcataa ataacgtcat gcattacatg ttaattatta catgcttaac gtaattcaac    180
agaaattata tgataatcat cgcaagaccg gcaacaggat tcaatcttaa gaaactttat    240
tgccaaatgt ttgaacgatc ggggaaattc gagctctatc gatcaatcag gatccttact    300
tttctttttt tgcctggccg gccttttttcg tggccgccgg ccttttgtcg cctcccagct    360
gagacaggtc gatccgtgtc tcgtacaggc cggtgatgct ctggtggatc agggtggcgt    420
ccagcacctc tttggtgctg gtgtacctct tccggtcgat ggtggtgtca aagtacttga    480
aggcggcagg ggctcccaga ttggtcaggg taaacaggtg gatgatattc tcggcctgct    540
ctctgatggg cttatcccgg tgcttgttgt aggcggacag cactttgtcc agattagcgt    600
cggccaggat cactctcttg gagaactcgc tgatctgctc gatgatctcg tccaggtagt    660
gcttgtgctg ttccacaaac agctgtttct gctcattatc ctcggggag cccttcagct    720 tctcatagtg gctggccagg tacaggaagt tcacatattt ggagggcagg gccagttcgt    780
ttcccttctg cagttcgccg gcagaggcca gcattctctt ccggccgttt tccagctcga    840
acagggagta cttaggcagc ttgatgatca ggtccttttt cacttctttg tagcccttgg    900
```

```
cttccagaaa gtcgatggga ttcttctcga agctgcttct ttccatgatg gtgatcccca    960
gcagctcttt cacactcttc agtttcttgg acttgccctt ttccactttg gccaccacca   1020
gcacagaata ggccacggtg gggctgtcga agccgccgta cttcttaggg tcccagtcct   1080
tctttctggc gatcagctta tcgctgttcc tcttgggcag gatagactct ttgctgaagc   1140
cgcctgtctg cacctcggtc tttttcacga tattcacttg gggcatgctc agcactttcc   1200
gcacggtggc aaaatcccgg cccttatccc acacgatctc cccggtttcg ccgtttgtct   1260
cgatcagagg ccgcttccgg atctcgccgt tggccagggt aatctcggtc ttgaaaaagt   1320
tcatgatgtt gctgtagaag aagtacttgg cggtagcctt gccgatttcc tgctcgctct   1380
tggcgatcat cttccgcacg tcgtacacct tgtagtcgcc gtacacgaac tcgctttcca   1440
gcttagggta ctttttgatc agggcggttc ccacgacggc gttcaggtag gcgtcgtggg   1500
cgtggtggta gttgttgatc tcgcgcactt tgtaaaactg gaaatccttc cggaaatcgg   1560
acaccagctt ggacttcagg gtgatcactt tcacttcccg gatcagcttg tcattctcgt   1620
cgtacttagt gttcatccgg gagtccagga tctgtgccac gtgctttgtg atctgccggg   1680
tttccaccag ctgtctcttg atgaagccgg cctatccag ttcgctcagg ccgcctctct    1740
cggccttggt cagattgtcg aactttctct gggtaatcag cttggcgttc agcagctgcc   1800
gccagtagtt cttcatcttc ttcacgacct cttcggaggg cacgttgtcg ctcttgcccc   1860
ggttcttgtc gcttctggtc agcaccttgt tgtcgatgga gtcgtccttc agaaagctct   1920
gaggcacgat atggtccaca tcgtagtcgg acagccggtt gatgtccagt tcctggtcca   1980
cgtacatatc ccgcccattc tgcaggtagt acaggtacag cttctcgttc tgcagctggg   2040
tgttttccac ggggtgttct ttcaggatct ggctgcccag ctctttgatg ccctcttcga   2100
tccgcttcat tctctcgcgg ctgttcttct gtcccttctg ggtggtctgg ttctctctgg   2160
ccatttcgat cacgatgttc tcgggcttgt gccggcccat cactttcacg agctcgtcca   2220
ccaccttcac tgtctgcagg atgcccttct taatggcggg gctgccggcc agattggcaa   2280
tgtgctcgtg caggctatcg ccctggccgg acacctgggc tttctggatg tcctcttta   2340 aggtcaggct gtcgtcgtgg atcagctgca tgaagtttct gttggcgaag ccgtcggact   2400
tcaggaaatc caggattgtc ttgccggact gcttgtcccg gatgccgttg atcagcttcc   2460
ggctcagcct gccccagccg gtgtatctcc gccgcttcag ctgcttcatc actttgtcgt   2520
cgaacaggtg ggcataggtt ttcagccgtt cctcgatcat ctctctgtcc tcaaacagtg   2580
tcagggtcag cacgatatct tccagaatgt cctcgttttc ctcattgtcc aggaagtcct   2640
tgtccttgat aattttcagc agatcgtggt atgtgcccag ggaggcgttg aaccgatctt   2700
ccacgccgga gatttccacg gagtcgaagc actcgatttt cttgaagtag tcctcttca   2760 gctgcttcac ggtcactttc cggttggtct tgaacagcag gtccacgatg gcctttttct   2820
gctcgccgct caggaaggcg ggcttttctca ttccctcggt cacgtatttc actttggtca   2880
gctcgttata cacggtgaag tactcgtaca gcaggctgtg cttgggcagc accttctcgt   2940
tgggcaggtt cttatcgaag ttggtcatcc gctcgatgaa gctctgggcg gaagcgccct   3000
tgtccaccac ttcctcgaag ttccaggggg tgatggtttc ctcgctcttt ctggtcatcc   3060
aggcgaatct gctgtttccc ctggccagag ggcccacgta gtagggatg cggaaggtca    3120 ggatcttctc gatctttcc cggttgtcct tcaggaatgg gtaaaaatct tcctgccgcc    3180
gcagaatggc gtgcagctct cccaggtgga tctggtgggg gatgctgccg ttgtcgaagg   3240
```

```
tccgctgctt ccgcagcagg tcctctctgt tcagcttcac gagcagttcc tcggtgccgt    3300
ccatctttc  caggatgggc ttgatgaact tgtagaactc ttcctggctg gctccgccgt    3360
caatgtagcc ggcgtagccg ttcttgctct ggtcgaagaa aatctctttg tacttctcag    3420
gcagctgctg ccgcacgaga gctttcagca gggtcaggtc ctggtggtgc tcgtcgtatc    3480
tcttgatcat agaggcgctc aggggggcct tggtgatctc ggtgttcact ctcaggatgt    3540
cgctcagcag gatggcgtcg gacaggttct tggcggccag aaacaggtcg gcgtactggt    3600
cgccgatctg ggccagcagg ttgtccaggt cgtcgtcgta ggtgtccttg ctcagctgca    3660
gtttggcatc ctcggccagg tcgaagttgc tcttgaagtt gggggtcagg cccaggctca    3720
gggcaatcag gtttccgaac aggccattct tcttctcgcc gggcagctgg gcgatcagat    3780
tttccagccg tctgctcttg ctcagtctgg cagacaggat ggccttggcg tccacgccgc    3840
tggcgttgat ggggtttcc  tcgaacagct ggttgtaggt ctgcaccagc tggatgaaca    3900
gcttgtccac gtcgctgttg tcggggttca ggtcgccctc gatcaggaag tggccccgga    3960
acttgatcat gtgggccagg gccagataga tcagccgcag gtcggccttg tcggtgctgt    4020
ccaccagttt cttctcagg  tggtagatgg tggggtactt ctcgtggtag gccacctcgt    4080
ccacgatgtt gccgaagatg gggtgccgct cgtgcttctt atcctcttcc accaggaagg    4140
actcttccag tctgtggaag aagctgtcgt ccaccttggc catctcgttg ctgaagatct    4200
cttgcagata gcagatccgg ttcttccgtc tggtgtatct tcttctggcg ttctcttca    4260
gccgggtggc ctcggctgtt tcgccgctgt cgaacagcag ggctccgatc aggttcttct    4320
tgatgctgtg ccggtcggtg ttgcccagca ccttgaattt cttgctgggc accttgtact    4380
cgtcggtgat cacggcccag cccacagagt tggtgccgat gtccaggccg atgctgtact    4440
tcttgtcggc tgctgggact ccgtggatac cgaccttccg cttcttcttt ggggccatct    4500
tatcgtcatc gtctttgtaa tcaatatcat gatccttgta gtctccgtcg tggtccttat    4560
agtccatctc gagtatcgtt cgtaaatggt gaaaattttc agaaaattgc ttttgcttta    4620
aaagaaatga tttaaattgc tgcaatagaa gtagaatgct tgattgcttg agattcgttt    4680
gttttgtata tgttgtgttg aggtcgaggt cctctccaaa tgaaatgaac ttccttatat    4740
agaggaaggg tcttgcgaag gatagtggga ttgtgcgtca tcccttacgt cagtggagat    4800
atcacatcaa tccacttgct ttgaagacgt ggttggaacg tcttcttttt ccacgatgct    4860
cctcgtgggt gggggtccat ctttgggacc actgtcggca gaggcatctt caacgatggc    4920
cttcccttta tcgcaatgat ggcatttgta ggagccacct tccttttcca ctatcttcac    4980
aataaagtga cagatagctg gcaatggaa  tccgaggagg tttccggata tcacccttg    5040
ttgaaaagtc tcaattgccc tttggtcttc tgagactgta tctttgatat ttttggagta    5100
gacaagtgtg tcgtgctcca ccatgttatc acatcaatcc acttgctttg aagacgtggt    5160
tggaacgtct tcttttcca  cgatgctcct cgtgggtggg ggtccatctt tgggaccact    5220
gtcggcagag gcatcttcaa cgatggcctt tcctttatcg caatgatggc atttgtagga    5280
gccaccttcc ttttccacta tcttcacaat aaagtgacag atagctgggc aatggaatcc    5340
gaggagggttt ccggatatta cccttgttg  aaaagtctca attgcccttt ggtcttctga    5400
gactgtatct ttgatatttt tggagtagac aagtgtgtcg tgctccacca tgttgacctg    5460
caggcatgcc tcggatccac tagtaacggc cgccagtgtg ctggaattgc ccttaagctt    5520
cgttgaacaa cggaaactcg acttgccttc cgcacaatac atcatttctt cttagctttt    5580
ttcttcttc  ttcgttcata cagtttttt  ttgtttatca gcttacattt tcttgaaccg    5640
```

```
tagctttcgt tttcttcttt ttaactttcc attcggagtt tttgtatctt gtttcatagt    5700
ttgtcccagg attagaatga ttaggcatcg aaccttcaag aatttgattg aataaaacat    5760
cttcattctt aagatatgaa gataatcttc aaaaggcccc tgggaatctg aaagaagaga    5820
agcaggccca tttatatggg aaagaacaat agtatttctt atataggccc atttaagttg    5880
aaaacaatct tcaaaagtcc cacatcgctt agataagaaa acgaagctga gtttatatac    5940
agctagagtc gaagtagtga ttgcggagac tcgtctacag ttgttttaga gctagaaata    6000
gcaagttaaa ataaggctag tccgttatca acttgaaaaa gtggcaccga gtcggtgctt    6060
tttttgtccc ttcgaagggc ctttctcaga tatccatcac actggcggcc gctcgaggtc    6120
gctcggatcc actagtaacg gccgccagtg tgctggaatt gcccttaagc ttcgttgaac    6180
aacggaaact cgacttgcct tccgcacaat acatcatttc ttcttagctt ttttctttct    6240
tcttcgttca tacagttttt ttttgtttat cagcttacat tttcttgaac cgtagctttc    6300
gttttcttct ttttaacttt ccattcggag tttttgtatc ttgtttcata gtttgtccca    6360
ggattagaat gattaggcat cgaaccttca agaatttgat tgaataaaac atcttcattc    6420
ttaagatatg aagataatct tcaaaaggcc cctgggaatc tgaaagaaga gaagcaggcc    6480
catttatatg ggaaagaaca atagtatttc ttatataggc ccatttaagt tgaaaacaat    6540
cttcaaaagt cccacatcgc ttagataaga aaacgaagct gagtttatat acagctagag    6600
tcgaagtagt gattttggtc tacggagcga tggtgtttta gagctagaaa tagcaagtta    6660
aaataaggct agtccgttat caacttgaaa aagtggcacc gagtcggtgc ttttttttgtc    6720
ccttcgaagg gccttttctca gatatccatc acactggcgg ccgctcgagg tcgaagcttg    6780
gcactggccg tcgttttaca acgtcgtgac tgggaaaacc ctggcgttac ccaacttaat    6840
cgccttgcag cacatccccc tttcgccagc tggcgtaata gcgaagaggc ccgcaccgat    6900
cgcccttccc aacagttgcg cagcctgaat ggcgaatgct agagcagctt gagcttggat    6960
cagattgtcg tttcccgcct tcagtttaaa ctatcagtgt ttgacaggat atattggcgg    7020
gtaaacctaa gagaaaagag cgtttattag aataacggat atttaaaagg gcgtgaaaag    7080
gtttatccgt tcgtccattt gtatgtgcat gccaaccaca gggttcccct cgggatcaaa    7140
gtactttgat ccaacccctc cgctgctata gtgcagtcgg cttctgacgt tcagtgcagc    7200
cgtcttctga aaacgacatg tcgcacaagt cctaagttac gcgacaggct gccgccctgc    7260
ccttttcctg gcgttttctt gtcgcgtgtt ttagtcgcat aaagtagaat acttgcgact    7320
agaaccggag acattacgcc atgaacaaga gcgccgccgc tggcctgctg ggctatgccc    7380
gcgtcagcac cgacgaccag gacttgacca accaacgggc cgaactgcac gcggccggct    7440
gcaccaagct gttttccgag aagatcaccg gcaccaggcg cgaccgcccg gagctggcca    7500
ggatgcttga ccacctacgc cctggcgacg ttgtgacagt gaccaggcta gaccgcctgg    7560
cccgcagcac ccgcgaccta ctggacattg ccgagcgcat ccaggaggcc ggcgcgggcc    7620
tgcgtagcct ggcagagccg tgggccgaca ccaccacgcc ggccggccgc atggtgttga    7680
ccgtgttcgc cggcattgcc gagttcgagc gttccctaat catcgaccgc acccggagcg    7740
ggcgcgaggc cgccaaggcc cgaggcgtga agtttggccc ccgccctacc ctcacccctgg   7800
cacagatcgc gcacgcccgc gagctgatcg accaggaagg ccgcaccgtg aaagaggcgg    7860
ctgcactgct ggcgtgcat cgctcgacct gtaccgcgc acttgagcgc agcgaggaag    7920
tgacgcccac cgaggccagg cggcgcggtg ccttccgtga ggacgcattg accgaggccg    7980
```

```
acgccctggc ggccgccgag aatgaacgcc aagaggaaca agcatgaaac cgcaccagga    8040
cggccaggac gaaccgtttt tcattaccga agagatcgag gcggagatga tcgcggccgg    8100
gtacgtgttc gagccgcccg cgcacgtctc aaccgtgcgg ctgcatgaaa tcctggccgg    8160
tttgtctgat gccaagctgg cggcctggcc ggccagcttg gccgctgaag aaaccgagcg    8220
ccgccgtcta aaaggtgat gtgtatttga gtaaaacagc ttgcgtcatg cggtcgctgc    8280
gtatatgatg cgatgagtaa ataaacaaat acgcaagggg aacgcatgaa ggttatcgct    8340
gtacttaacc agaaaggcgg gtcaggcaag acgaccatcg caacccatct agcccgcgcc    8400
ctgcaactcg ccggggccga tgttctgtta gtcgattccg atcccagggg cagtgcccgc    8460
gattgggcgg ccgtgcggga agatcaaccg ctaaccgttg tcggcatcga ccgcccgacg    8520
attgaccgcg acgtgaaggc catcggccgg cgcgacttcg tagtgatcga cggagcgccc    8580
caggcggcgg acttggctgt gtccgcgatc aaggcagccg acttcgtgct gattccggtg    8640
cagccaagcc cttacgacat atgggccacc gccgacctgg tggagctggt taagcagcgc    8700
attgaggtca cggatggaag gctacaagcg gcctttgtcg tgtcgcgggc gatcaaaggc    8760
acgcgcatcg gcggtgaggt tgccgaggcg ctggccgggt acgagctgcc cattcttgag    8820
tcccgtatca cgcagcgcgt gagctaccca ggcactgccg ccgccggcac aaccgttctt    8880
gaatcagaac ccgagggcga cgctgcccgc gaggtccagg cgctggccgc tgaaattaaa    8940
tcaaaactca tttgagttaa tgaggtaaag agaaaatgag caaaagcaca aacacgctaa    9000
gtgccggccg tccgagcgca cgcagcagca aggctgcaac gttggccagc ctggcagaca    9060
cgccagccat gaagcgggtc aactttcagt tgccggcgga ggatcacacc aagctgaaga    9120
tgtacgcggt acgccaaggc aagaccatta ccgagctgct atctgaatac atcgcgcagc    9180
taccagagta aatgagcaaa tgaataaatg agtagatgaa ttttagcggc taaaggaggc    9240
ggcatggaaa atcaagaaca accaggcacc gacgccgtgg aatgccccat gtgtggagga    9300
acgggcggtt ggccaggcgt aagcggctgg gttgtctgcc ggccctgcaa tggcactgga    9360
acccccaagc ccgaggaatc ggcgtgacgg tcgcaaacca tccggcccgg tacaaatcgg    9420
cgcggcgctg ggtgatgacc tggtggagaa gttgaaggcc gcgcaggccg cccagcggca    9480
acgcatcgag gcagaagcac gccccggtga atcgtggcaa gcggccgctg atcgaatccg    9540
caaagaatcc cggcaaccgc cggcagccgg tgcgccgtcg attaggaagc cgcccaaggg    9600
cgacgagcaa ccagattttt tcgttccgat gctctatgac gtgggcaccc gcgatagtcg    9660
cagcatcatg gacgtggccg ttttccgtct gtcgaagcgt gaccgacgag ctggcgaggt    9720
gatccgctac gagcttccag acgggcacgt agaggtttcc gcagggccgg ccggcatggc    9780
cagtgtgtgg gattacgacc tggtactgat ggcggttttcc catctaaccg aatccatgaa    9840
ccgataccgg gaagggaagg gagacaagcc cggccgcgtg ttccgtccac acgttgcgga    9900
cgtactcaag ttctgccggc gagccgatgg cggaaagcag aaagacgacc tggtagaaac    9960
ctgcattcgg ttaaacacca cgcacgttgc catgcagcgt acgaagaagg ccaagaacgg   10020
ccgcctggtg acggtatccg agggtgaagc cttgattagc cgctacaaga tcgtaaagag   10080
cgaaaccggg cggccggagt acatcgagat cgagctagct gattggatgt accgcgagat   10140
cacagaaggc aagaacccgg acgtgctgac ggttcacccc gattactttt tgatcgatcc   10200
cggcatcggc cgttttctct accgcctggc acgccgcgcc gcaggcaagg cagaagccag   10260
atggttgttc aagacgatct acgaacgcag tggcagcgcc ggagagttca agaagttctg   10320
tttcaccgtg cgcaagctga tcgggtcaaa tgacctgccg gagtacgatt tgaaggagga   10380
```

```
ggcggggcag gctggcccga tcctagtcat gcgctaccgc aacctgatcg agggcgaagc   10440
atccgccggt tcctaatgta cggagcagat gctagggcaa attgccctag caggggaaaa   10500
aggtcgaaaa ggtctctttc ctgtggatag cacgtacatt gggaacccaa agccgtacat   10560
tgggaaccgg aacccgtaca ttgggaaccc aaagccgtac attgggaacc ggtcacacat   10620
gtaagtgact gatataaaag agaaaaaagg cgattttcc gcctaaaact ctttaaaact    10680
tattaaaact cttaaaaccc gcctggcctg tgcataactg tctggccagc gcacagccga   10740
agagctgcaa aaagcgccta cccttcggtc gctgcgctcc ctacgccccg ccgcttcgcg   10800
tcggcctatc gcgccgctg gccgctcaaa aatggctggc ctacgccag gcaatctacc     10860 agggcgcgga caagccgcgc cgtcgccact cgaccgccgg cgcccacatc aaggcaccct   10920
gcctcgcgcg tttcggtgat gacggtgaaa acctctgaca catgcagctc ccggagacgg   10980
tcacagcttg tctgtaagcg gatgccggga gcagacaagc ccgtcagggc gcgtcagcgg   11040
gtgttggcgg gtgtcgggc gcagccatga cccagtcacg tagcgatagc ggagtgtata    11100
ctggcttaac tatgcggcat cagagcagat tgtactgaga gtgcaccata tgcggtgtga   11160
aataccgcac agatgcgtaa ggagaaaata ccgcatcagg cgctcttccg cttcctcgct   11220
cactgactcg ctgcgctcgg tcgttcggct gcggcgagcg gtatcagctc actcaaaggc   11280
ggtaatacgg ttatccacag aatcagggga taacgcagga agaacatgt gagcaaaagg    11340 ccagcaaaag gccaggaacc gtaaaaaggc cgcgttgctg gcgttttcc ataggctccg     11400 cccccctgac gagcatcaca aaaatcgacg ctcaagtcag aggtggcgaa acccgacagg   11460
actataaaga taccaggcgt ttccccctgg aagctccctc gtgcgctctc ctgttccgac   11520
cctgccgctt accggatacc tgtccgcctt tctcccttcg ggaagcgtgg cgctttctca    11580
tagctcacgc tgtaggtatc tcagttcggt gtaggtcgtt cgctccaagc tgggctgtgt   11640
gcacgaaccc cccgttcagc ccgaccgctg cgccttatcc ggtaactatc gtcttgagtc    11700
caacccggta agacacgact tatcgccact ggcagcagcc actggtaaca ggattagcag   11760
agcgaggtat gtaggcggtg ctacagagtt cttgaagtgg tggcctaact acggctacac    11820
tagaaggaca gtatttggta tctgcgctct gctgaagcca gttaccttcg gaaaaagagt   11880
tggtagctct tgatccggca acaaaccac cgctggtagc ggtggttttt tgtttgcaa    11940 gcagcagatt acgcgcagaa aaaaggatc tcaagaagat cctttgatct tttctacggg    12000
gtctgacgct cagtggaacg aaaactcacg ttaagggatt ttggtcatgc attctaggta   12060 ctaaacaat tcatccagta aaatataata ttttatttc tcccaatcag gcttgatccc    12120
cagtaagtca aaaatagct cgacatactg ttcttccccg atatcctccc tgatcgaccg    12180
gacgcagaag gcaatgtcat accacttgtc cgccctgccg cttctcccaa gatcaataaa   12240
gccacttact ttgccatctt tcacaaagat gttgctgtct cccaggtcgc cgtgggaaaa    12300
gacaagttcc tcttcgggct tttcgtctt taaaaaatca tacagctcgc gcggatcttt     12360
aaatggagtg tcttcttccc agttttcgca atccacatcg gccagatcgt tattcagtaa   12420
gtaatccaat tcggctaagc ggctgtctaa gctattcgta tagggacaat ccgatatgtc   12480
gatggagtga aagagcctga tgcactccgc atacagctcg ataatctttt cagggctttg    12540
ttcatcttca tactcttccg agcaaaggac gccatcggcc tcactcatga gcagattgct   12600
ccagccatca tgccgttcaa agtgcaggac ctttggaaca gcagctttc cttccagcca    12660 tagcatcatg tcctttttccc gttccacatc ataggtggtc cctttatacc ggctgtccgt   12720
```

```
cattttttaaa tataggtttt cattttctcc caccagctta tataccttag caggagacat   12780
tccttccgta tcttttacgc agcggtattt ttcgatcagt ttttttcaatt ccggtgatat   12840 tctcatttta gccatttatt atttccttcc tcttttctac agtatttaaa gataccccaa   12900
gaagctaatt ataacaagac gaactccaat tcactgttcc ttgcattcta aaaccttaaa   12960
taccagaaaa cagcttttc aaagttgttt tcaaagttgg cgtataacat agtatcgacg   13020
gagccgattt tgaaaccgcg gtgatcacag gcagcaacgc tctgtcatcg ttacaatcaa   13080
catgctaccc tccgcgagat catccgtgtt tcaaacccgg cagcttagtt gccgttcttc   13140
cgaatagcat cggtaacatg agcaaagtct gccgccttac aacggctctc ccgctgacgc   13200
cgtcccggac tgatgggctg cctgtatcga gtggtgattt tgtgccgagc tgccggtcgg   13260
ggagctgttg gctggctggt ggcaggatat attgtggtgt aaacaaattg acgcttagac   13320
aacttaataa cacattgcgg acgtttttaa tgtactgaat taacgccgaa ttaattcggg   13380
ggatctggat tttagtactg gattttggtt ttaggaatta gaaattttat tgatagaagt   13440
attttacaaa tacaaataca tactaagggt ttcttatatg ctcaacacat gagcgaaacc   13500
ctataggaac cctaattccc ttatctggga actactcaca cattattatg gagaaactcg   13560
agcttgtcga tcgacagatc cggtcggcat ctactctatt tctttgccct cggacgagtg   13620
ctggggcgtc ggtttccact atcggcgagt acttctacac agccatcggt ccagacggcc   13680
gcgcttctgc gggcgatttg tgtacgcccg acagtcccgg ctccggatcg gacgattgcg   13740
tcgcatcgac cctgcgccca agctgcatca tcgaaattgc cgtcaaccaa gctctgatag   13800
agttggtcaa gaccaatgcg gagcatatac gcccggagtc gtggcgatcc tgcaagctcc   13860
ggatgcctcc gctcgaagta gcgcgtctgc tgctccatac aagccaacca cggcctccag   13920
aagaagatgt tggcgacctc gtattgggaa tccccgaaca tcgcctcgct ccagtcaatg   13980
accgctgtta tgcggccatt gtccgtcagg acattgttgg agccgaaatc cgcgtgcacg   14040
aggtgccgga cttcggggca gtcctcggcc caaagcatca gctcatcgag agcctgcgcg   14100
acggacgcac tgacggtgtc gtccatcaca gtttgccagt gatacacatg gggatcagca   14160
atcgcgcata tgaaatcacg ccatgtagtg tattgaccga ttccttgcgg tccgaatggg   14220
ccgaacccgc tcgtctggct aagatcggcc gcagcgatcg catccatagc ctccgcgacc   14280
ggttgtagaa cagcgggcag ttcggtttca ggcaggtctt gcaacgtgac accctgtgca   14340
cggcgggaga tgcaataggt caggctctcg ctaaactccc caatgtcaag cacttccgga   14400
atcgggagcg cggccgatgc aaagtgccga taaacataac gatctttgta gaaaccatcg   14460
gcgcagctat ttacccgcag gacatatcca cgccctccta catcgaagct gaaagcacga   14520
gattcttcgc cctccgagag ctgcatcagg tcggagacgc tgtcgaactt ttcgatcaga   14580
aacttctcga cagacgtcgc ggtgagttca ggcttttttca tatctcattg ccccccggga   14640
tctgcgaaag ctcgagagag atagatttgt agagagagac tggtgatttc agcgtgtcct   14700
ctccaaatga aatgaacttc cttatataga ggaaggtctt gcgaaggata gtgggattgt   14760
gcgtcatccc ttacgtcagt ggagatatca catcaatcca cttgctttga agacgtggtt   14820
ggaacgtctt ctttttccac gatgctcctc gtgggtgggg gtccatcttt gggaccactg   14880
tcggcagagg catcttgaac gatagccttt cctttatcgc aatgatggca tttgtaggtg   14940
ccaccttcct tttctactgt cctttttgatg aagtgacaga tagctgggca atggaatccg   15000
aggaggtttc ccgatattac cctttgttga aaagtctcaa tagcccttg gtcttctgag   15060 actgtatctt tgatattctt ggagtagacg agagtgtcgt gctccaccat gttatcacat   15120
```

-continued

```
caatccactt gctttgaaga cgtggttgga acgtcttctt tttccacgat gctcctcgtg    15180
ggtgggggtc catctttggg accactgtcg gcagaggcat cttgaacgat agcctttcct    15240
ttatcgcaat gatggcattt gtaggtgcca ccttcctttt ctactgtcct tttgatgaag    15300
tgacagatag ctgggcaatg gaatccgagg aggtttcccg atattaccct ttgttgaaaa    15360
gtctcaatag ccctttggtc ttctgagact gtatctttga tattcttgga gtagacgaga    15420
gtgtcgtgct ccaccatgtt ggcaagctgc tctagccaat acgcaaaccg cctctccccg    15480
cgcgttggcc gattcattaa tgcagctggc acgacaggtt cccgactgg aaagcgggca     15540 gtgagcgcaa cgcaattaat gtgagttagc tcactcatta ggcacccag gctttacact     15600 ttatgcttcc ggctcgtatg ttgtgtggaa ttgtgagcgg ataacaattt cacacaggaa    15660
acagctatga ccatgattac g                                              15681
```

<210> SEQ ID NO 158
<211> LENGTH: 15681
<212> TYPE: DNA
<213> ORGANISM: Artificial Sequence
<220> FEATURE:
<223> OTHER INFORMATION: vector
<220> FEATURE:
<221> NAME/KEY: misc_feature
<222> LOCATION: (5964)..(5984)
<223> OTHER INFORMATION: /note="target sequence"
<220> FEATURE:
<221> NAME/KEY: misc_feature
<222> LOCATION: (6617)..(6637)
<223> OTHER INFORMATION: /note="target sequence"

<400> SEQUENCE: 158

```
aattcccgat ctagtaacat agatgacacc gcgcgcgata atttatccta gtttgcgcgc      60
tatattttgt tttctatcgc gtattaaatg tataattgcg ggactctaat cataaaaacc     120
catctcataa ataacgtcat gcattacatg ttaattatta catgcttaac gtaattcaac     180
agaaattata tgataatcat cgcaagaccg gcaacaggat tcaatcttaa gaaactttat     240
tgccaaatgt ttgaacgatc ggggaaattc gagctctatc gatcaatcag gatccttact     300
ttttcttttt tgcctggccg gccttttcg tggccgccgg ccttttgtcg cctcccagct      360
gagacaggtc gatccgtgtc tcgtacaggc cggtgatgct ctggtggatc agggtggcgt     420
ccagcaccct tttggtgctg gtgtacctct tccggtcgat ggtggtgtca agtacttga      480 aggcggcagg ggctcccaga ttggtcaggg taaacaggtg gatgatattc tcggcctgct    540
ctctgatggg cttatcccgg tgcttgttgt aggcggacag cactttgtcc agattagcgt    600
cggccaggat cactctcttg gagaactcgc tgatctgctc gatgatctcg tccaggtagt    660
gcttgtgctg ttccacaaac agctgtttct gctcattatc ctcggggag cccttcagct    720 tctcatagtg gctggccagg tacaggaagt tcacatattt ggagggcagg gccagttcgt    780
ttcccttctg cagttcgccg gcagaggcca gcattctctt ccggccgttt ccagctcga    840 acagggagta cttaggcagc ttgatgatca ggtccttttt cacttctttg tagcccttgg    900
cttccagaaa gtcgatggga ttcttctcga agctgcttct ttccatgatg gtgatcccca    960
gcagctcttt cacactcttc agtttcttgg acttgccctt ttccactttg gccaccacca   1020
gcacagaata ggccacggtg gggctgtcga agccgccgta cttcttaggg tcccagtcct   1080
tctttctggc gatcagctta tcgctgttcc tcttgggcag gatagactct ttgctgaagc   1140
cgcctgtctg cacctcggtc tttttcacga tattcacttg gggcatgctc agcactttcc   1200
```

```
gcacggtggc aaaatcccgg cccttatccc acacgatctc cccggtttcg ccgtttgtct    1260
cgatcagagg ccgcttccgg atctcgccgt tggccaggga aatctcggtc ttgaaaaagt    1320
tcatgatgtt gctgtagaag aagtacttgg cggtagcctt gccgatttcc tgctcgctct    1380
tggcgatcat cttccgcacg tcgtacacct tgtagtcgcc gtacacgaac tcgctttcca    1440
gcttagggta cttttgatc agggcggttc ccacgacggc gttcaggtag cgtcgtggg     1500
cgtggtggta gttgttgatc tcgcgcactt tgtaaaactg gaaatccttc cggaaatcgg    1560
acaccagctt ggacttcagg gtgatcactt tcacttcccg gatcagcttg tcattctcgt    1620
cgtacttagt gttcatccgg gagtccagga tctgtgccac gtgctttgtg atctgccggg    1680
tttccaccag ctgtctcttg atgaagccgg ccttatccag ttcgctcagg ccgctctct    1740
cggccttggt cagattgtcg aactttctct gggtaatcag cttggcgttc agcagctgcc    1800
gccagtagtt cttcatcttc ttcacgacct cttcggaggg cacgttgtcg ctcttgcccc    1860
ggttcttgtc gcttctggtc agcaccttgt tgtcgatgga gtcgtccttc agaaagctct    1920
gaggcacgat atggtccaca tcgtagtcgg acagccggtt gatgtccagt tcctggtcca    1980
cgtacatatc ccgcccattc tgcaggtagt acaggtacag cttctcgttc tgcagctggg    2040
tgttttccac ggggtgttct ttcaggatct ggctgcccag ctctttgatg ccctcttcga    2100
tccgcttcat tctctcgcgg ctgttcttct gtcccttctg ggtggtctgg ttctctctgg    2160
ccatttcgat cacgatgttc tcgggcttgt gccggcccat cactttcacg agctcgtcca    2220
ccaccttcac tgtctgcagg atgcccttct taatggcggg gctgccggcc agattggcaa    2280
tgtgctcgtg caggctatcg ccctggccgg cacctgggc tttctggatg tcctctttaa    2340
aggtcaggct gtcgtcgtgg atcagctgca tgaagtttct gttggcgaag ccgtcggact    2400
tcaggaaatc caggattgtc ttgccggact gcttgtcccg gatgccgttg atcagcttcc    2460
ggctcagcct gccccagccg gtgtatctcc gccgcttcag ctgcttcatc actttgtcgt    2520
cgaacaggtg gcataggtt ttcagccgtt cctcgatcat ctctctgtcc tcaaacagtg    2580
tcagggtcag cacgatatct tccagaatgt cctcgttttc ctcattgtcc aggaagtcct    2640
tgtccttgat aattttcagc agatcgtggt atgtgcccag ggaggcgttg aaccgatctt    2700
ccacgccgga gatttccacg gagtcgaagc actcgatttt cttgaagtag tcctctttca    2760
gctgcttcac ggtcactttc cggttggtct tgaacagcag gtccacgatg gcttttttct    2820
gctcgccgct caggaaggcg ggcttctca ttccctcggt cacgtatttc actttggtca    2880
gctcgttata cacggtgaag tactcgtaca gcaggctgtg cttgggcagc accttctcgt    2940
tgggcaggtt cttatcgaag ttggtcatcc gctcgatgaa gctctgggcg aagcgccct    3000
tgtccaccac ttcctcgaag ttccaggggg tgatggtttc ctcgctcttt ctggtcatcc    3060
aggcgaatct gctgtttccc ctggccagag ggcccacgta gtagggatg cggaaggtca    3120
ggatcttctc gatcttttcc cggttgtcct tcaggaatgg gtaaaaatct tcctgccgcc    3180
gcagaatggc gtgcagctct cccaggtgga tctggtgggg gatgctgccg ttgtcgaagg    3240
tccgctgctt ccgcagcagg tcctctctgt tcagcttcac gagcagttcc tcggtgccgt    3300
ccatctttc caggatgggc ttgatgaact tgtagaactc ttcctggctg gctccgccgt    3360
caatgtagcc ggcgtagccg ttcttgctct ggtcgaagaa aatctctttg tacttctcag    3420
gcagctgctg ccgcacgaga gctttcagca gggtcaggtc ctggtggtgc tgtcgtatc    3480
tcttgatcat agaggcgctc agggggggcct tggtgatctc ggtgttcact ctcaggatgt    3540
cgctcagcag gatggcgtcg gacaggttct tggcggccag aaacaggtcg gcgtactggt    3600
```

```
cgccgatctg ggccagcagg ttgtccaggt cgtcgtcgta ggtgtccttg ctcagctgca   3660
gtttggcatc ctcggccagg tcgaagttgc tcttgaagtt gggggtcagg cccaggctca   3720
gggcaatcag gtttccgaac aggccattct tcttctcgcc gggcagctgg gcgatcagat   3780
tttccagccg tctgctcttg ctcagtctgg cagacaggat ggccttggcg tccacgccgc   3840
tggcgttgat ggggttttcc tcgaacagct ggttgtaggt ctgcaccagc tggatgaaca   3900
gcttgtccac gtcgctgttg tcggggttca gtcgccctc gatcaggaag tggccccgga    3960
acttgatcat gtgggccagg gccagataga tcagccgcag gtcggccttg tcggtgctgt   4020
ccaccagttt ctttctcagg tggtagatgg tggggtactt ctcgtggtag gccacctcgt   4080
ccacgatgtt gccgaagatg gggtgccgct cgtgcttctt atcctcttcc accaggaagg   4140
actcttccag tctgtggaag aagctgtcgt ccaccttggc catctcgttg ctgaagatct   4200
cttgcagata gcagatccgg ttcttccgtc tggtgtatct tcttctggcg gttctcttca   4260
gccgggtggc ctcggctgtt tcgccgctgt cgaacagcag ggctccgatc aggttcttct   4320
tgatgctgtg ccggtcggtg ttgcccagca ccttgaattt cttgctgggc accttgtact   4380
cgtcggtgat cacggcccag cccacagagt tggtgccgat gtccaggccg atgctgtact   4440
tcttgtcggc tgctgggact ccgtggatac cgaccttccg cttcttcttt ggggccatct   4500
tatcgtcatc gtctttgtaa tcaatatcat gatccttgta gtctccgtcg tggtccttat   4560
agtccatctc gagtatcgtt cgtaaatggt gaaaattttc agaaaattgc ttttgcttta   4620
aaagaaatga tttaaattgc tgcaatagaa gtagaatgct tgattgcttg agattcgttt   4680
gttttgtata tgttgtgttg aggtcgaggt cctctccaaa tgaaatgaac ttccttatat   4740
agaggaaggg tcttgcgaag gatagtggga ttgtgcgtca tcccttacgt cagtggagat   4800
atcacatcaa tccacttgct ttgaagacgt ggttggaacg tcttcttttt ccacgatgct   4860
cctcgtgggt gggggtccat ctttgggacc actgtcggca gaggcatctt caacgatggc   4920 cttccttta tcgcaatgat ggcatttgta ggagccacct tccttttcca ctatcttcac    4980
aataaagtga cagatagctg ggcaatgaa tccgaggagg tttccggata tcaccctttg     5040
ttgaaaagtc tcaattgccc tttggtcttc tgagactgta tctttgatat ttttggagta   5100
gacaagtgtg tcgtgctcca ccatgttatc acatcaatcc acttgctttg aagacgtggt   5160
tggaacgtct tctttttcca cgatgctcct cgtgggtggg ggtccatctt tgggaccact   5220
gtcggcagag gcatcttcaa cgatggcctt tcctttatcg caatgatggc atttgtagga   5280
gccaccttcc ttttccacta tcttcacaat aaagtgacag atagctgggc aatggaatcc   5340
gaggaggttt ccggatatta ccctttgttg aaaagtctca attgcccttt ggtcttctga   5400
gactgtatct ttgatatttt tggagtagac aagtgtgtcg tgctccacca tgttgacctg   5460
caggcatgcc tcggatccac tagtaacggc cgccagtgtg ctggaattgc ccttaagctt   5520
cgttgaacaa cggaaactcg acttgccttc cgcacaatac atcatttctt cttagctttt   5580
tttcttcttc ttcgttcata cagttttttt ttgtttatca gcttacattt tcttgaaccg   5640
tagctttcgt tttcttcttt ttaactttcc attcggagtt tttgtatctt gtttcatagt   5700
ttgtcccagg attagaatga ttaggcatcg aaccttcaag aatttgattg aataaaacat   5760
cttcattctt aagatatgaa gataatcttc aaaaggcccc tgggaatctg aaagaagaga   5820
agcaggccca tttatatggg aaagaacaat agtatttctt atataggccc atttaagttg   5880
aaaacaatct tcaaaagtcc cacatcgctt agataagaaa acgaagctga gtttatatac   5940
```

```
agctagagtc gaagtagtga tttccccacg tcactgggcg tcgttttaga gctagaaata    6000
gcaagttaaa ataaggctag tccgttatca acttgaaaaa gtggcaccga gtcggtgctt    6060
tttttgtccc ttcgaagggc ctttctcaga tatccatcac actggcggcc gctcgaggtc    6120
gctcggatcc actagtaacg gccgccagtg tgctggaatt gcccttaagc ttcgttgaac    6180
aacggaaact cgacttgcct tccgcacaat acatcatttc ttcttagctt ttttctcttct    6240 tcttcgttca tacagttttt ttttgtttat cagcttacat tttcttgaac cgtagctttc    6300
gttttcttct ttttaacttt ccattcggag tttttgtatc ttgtttcata gtttgtccca    6360
ggattagaat gattaggcat cgaaccttca agaatttgat tgaataaaac atcttcattc    6420
ttaagatatg aagataatct tcaaaaggcc cctgggaatc tgaaagaaga gaagcaggcc    6480
catttatatg ggaaagaaca atagtatttc ttatataggc ccatttaagt tgaaaacaat    6540
cttcaaaagt cccacatcgc ttagataaga aaacgaagct gagtttatat acagctagag    6600
tcgaagtagt gattttggtc tacggagcga tggtgtttta gagctagaaa tagcaagtta    6660
aaataaggct agtccgttat caacttgaaa aagtggcacc gagtcggtgc ttttttttgtc    6720 ccttcgaagg gcctttctca gatatccatc acactggcgg ccgctcgagg tcgaagcttg    6780
gcactggccg tcgttttaca acgtcgtgac tgggaaaacc ctggcgttac ccaacttaat    6840
cgccttgcag cacatccccc tttcgccagc tggcgtaata gcgaagaggc ccgcaccgat    6900
cgcccttccc aacagttgcg cagcctgaat ggcgaatgct agagcagctt gagcttggat    6960
cagattgtcg tttcccgcct tcagtttaaa ctatcagtgt ttgacaggat atattggcgg    7020
gtaaacctaa gagaaaagag cgtttattag aataacggat attttaaagg gcgtgaaaag    7080
gtttatccgt tcgtccattt gtatgtgcat gccaaccaca gggttcccct cgggatcaaa    7140
gtactttgat ccaacccctc cgctgctata gtgcagtcgg cttctgacgt tcagtgcagc    7200
cgtcttctga aaacgacatg tcgcacaagt cctaagttac gcgacaggct gccgccctgc    7260
ccttttcctg gcgttttctt gtcgcgtgtt ttagtcgcat aaagtagaat acttgcgact    7320
agaaccggag acattacgcc atgaacaaga gcgccgccgc tggcctgctg ggctatgccc    7380
gcgtcagcac cgacgaccag gacttgacca accaacgggc cgaactgcac gcggccggct    7440
gcaccaagct gttttccgag aagatcaccg gcaccaggcg cgaccgcccg gagctggcca    7500
ggatgcttga ccacctacgc cctggcgacg ttgtgacagt gaccaggcta gaccgcctgg    7560
cccgcagcac ccgcgaccta ctggacattg ccgagcgcat ccaggaggcc ggcgcgggcc    7620
tgcgtagcct ggcagagccg tgggccgaca ccaccacgcc ggccggccgc atggtgttga    7680
ccgtgttcgc cggcattgcc gagttcgagc gttccctaat catcgaccgc acccggagcg    7740
ggcgcgaggc cgccaaggcc cgaggcgtga agtttggccc ccgccctacc ctcaccccgg    7800
cacagatcgc gcacgcccgc gagctgatcg accaggaagg ccgcaccgtg aaagaggcgg    7860
ctgcactgct tggcgtgcat cgctcgaccc tgtaccgcgc acttgagcgc agcgaggaag    7920
tgacgcccac cgaggccagg cggcgcgtg ccttccgtga ggacgcattg accgaggccg    7980
acgccctggc ggccgccgag aatgaacgcc aagaggaaca agcatgaaac cgcaccagga    8040
cggccaggac gaaccgtttt tcattaccga agagatcgag gcggagatga tcgcggccgg    8100
gtacgtgttc gagccgcccg cgcacgtctc aaccgtgcgg ctgcatgaaa tcctggccgg    8160
tttgtctgat gccaagctgg cggcctggcc ggccagcttg gccgctgaag aaaccgagcg    8220
ccgccgtcta aaaaggtgat gtgtatttga gtaaaacagc ttgcgtcatg cggtcgctgc    8280
gtatatgatg cgatgagtaa ataaacaaat acgcaagggg aacgcatgaa ggttatcgct    8340
```

```
gtacttaacc agaaaggcgg gtcaggcaag acgaccatcg caacccatct agcccgcgcc    8400
ctgcaactcg ccggggccga tgttctgtta gtcgattccg atccccaggg cagtgcccgc    8460
gattgggcgg ccgtgcggga agatcaaccg ctaaccgttg tcggcatcga ccgcccgacg    8520
attgaccgcg acgtgaaggc catcggccgg cgcgacttcg tagtgatcga cggagcgccc    8580
caggcggcgg acttggctgt gtccgcgatc aaggcagccg acttcgtgct gattccggtg    8640
cagccaagcc cttacgacat atgggccacc gccgacctgg tggagctggt taagcagcgc    8700
attgaggtca cggatggaag gctacaagcg gcctttgtcg tgtcgcgggc gatcaaaggc    8760
acgcgcatcg gcgtgaggt  tgccgaggcg ctggccgggt acgagctgcc cattcttgag    8820
tcccgtatca cgcagcgcgt gagctaccca ggcactgccg ccgccggcac aaccgttctt    8880
gaatcagaac ccgagggcga cgctgcccgc gaggtccagg cgctggccgc tgaaattaaa    8940
tcaaaactca tttgagttaa tgaggtaaag agaaaatgag caaaagcaca aacacgctaa    9000
gtgccggccg tccgagcgca cgcagcagca aggctgcaac gttggccagc ctggcagaca    9060
cgccagccat gaagcgggtc aactttcagt tgccggcgga ggatcacacc aagctgaaga    9120
tgtacgcggt acgccaaggc aagaccatta ccgagctgct atctgaatac atcgcgcagc    9180
taccagagta aatgagcaaa tgaataaatg agtagatgaa ttttagcggc taaaggaggc    9240
ggcatggaaa atcaagaaca accaggcacc gacgccgtgg aatgccccat gtgtggagga    9300
acgggcggtt ggccaggcgt aagcggctgg gttgtctgcc ggcctgcaa tggcactgga    9360 accccaagc  ccgaggaatc ggcgtgacgg tcgcaaacca tccggcccgg tacaaatcgg    9420
cgcggcgctg ggtgatgacc tggtggagaa gttgaaggcc gcgcaggccg cccagcggca    9480
acgcatcgag gcagaagcac gccccggtga atcgtggcaa gcggccgctg atcgaatccg    9540
caaagaatcc cggcaaccgc cggcagccgg tgcgccgtcg attaggaagc cgcccaaggg    9600
cgacgagcaa ccagattttt tcgttccgat gctctatgac gtgggcaccc gcgatagtcg    9660
cagcatcatg gacgtggccg ttttccgtct gtcgaagcgt gaccgacgag ctggcgaggt    9720
gatccgctac gagcttccag acgggcacgt agaggtttcc gcaggccgg  ccggcatggc    9780 cagtgtgtgg gattacgacc tggtactgat ggcggtttcc catctaaccg aatccatgaa    9840
ccgataccgg gaagggaagg gagacaagcc cggccgcgtg ttccgtccac acgttgcgga    9900
cgtactcaag ttctgccggc gagccgatgg cggaaagcag aaagacgacc tggtagaaac    9960
ctgcattcgg ttaaacacca cgcacgttgc catgcagcgt acgaagaagg ccaagaacgg    10020
ccgcctggtg acggtatccg agggtgaagc cttgattagc cgctacaaga tcgtaaagag    10080
cgaaaccggg cggccggagt acatcgagat cgagctagct gattggatgt accgcgagat    10140
cacagaaggc aagaacccgg acgtgctgac ggttcacccc gattactttt tgatcgatcc    10200
cggcatcggc cgttttctct accgcctggc acgccgcgcc gcaggcaagg cagaagccag    10260
atggttgttc aagacgatct acgaacgcag tggcagcgcc ggagagttca agaagttctg    10320
tttcaccgtg cgcaagctga tcgggtcaaa tgacctgccg gagtacgatt tgaaggagga    10380
ggcggggcag gctggcccga tcctagtcat gcgctaccgc aacctgatcg agggcgaagc    10440
atccgccggt tcctaatgta cggagcagat gctagggcaa attgccctag caggggaaaa    10500
aggtcgaaaa ggtctctttc ctgtggatag cacgtacatt gggaacccaa agccgtacat    10560
tgggaaccgg aacccgtaca ttgggaaccc aaagccgtac attgggaacc ggtcacacat    10620
gtaagtgact gatataaaag agaaaaaagg cgatttttcc gcctaaaact ctttaaaact    10680
```

```
tattaaaact cttaaaaccc gcctggcctg tgcataactg tctggccagc gcacagccga   10740
agagctgcaa aaagcgccta cccttcggtc gctgcgctcc ctacgccccg ccgcttcgcg   10800
tcggcctatc gcggccgctg gccgctcaaa aatggctggc ctacggccag gcaatctacc   10860
agggcgcgga caagccgcgc cgtcgccact cgaccgccgg cgcccacatc aaggcaccct   10920
gcctcgcgcg tttcggtgat gacggtgaaa acctctgaca catgcagctc ccggagacgg   10980
tcacagcttg tctgtaagcg gatgccggga gcagacaagc ccgtcagggc gcgtcagcgg   11040
gtgttggcgg gtgtcggggc gcagccatga cccagtcacg tagcgatagc ggagtgtata   11100
ctggcttaac tatgcggcat cagagcagat tgtactgaga gtgcaccata tgcggtgtga   11160
aataccgcac agatgcgtaa ggagaaaata ccgcatcagg cgctcttccg cttcctcgct   11220
cactgactcg ctgcgctcgg tcgttcggct gcggcgagcg gtatcagctc actcaaaggc   11280
ggtaatacgg ttatccacag aatcagggga taacgcagga agaacatgt gagcaaaagg   11340
ccagcaaaag gccaggaacc gtaaaaaggc cgcgttgctg gcgttttcc ataggctccg   11400
cccccctgac gagcatcaca aaaatcgacg ctcaagtcag aggtggcgaa acccgacagg   11460
actataaaga taccaggcgt ttccccctgg aagctccctc gtgcgctctc ctgttccgac   11520
cctgccgctt accggatacc tgtccgcctt tctcccttcg ggaagcgtgg cgctttctca   11580
tagctcacgc tgtaggtatc tcagttcggt gtaggtcgtt cgctccaagc tgggctgtgt   11640
gcacgaaccc cccgttcagc ccgaccgctg cgccttatcc ggtaactatc gtcttgagtc   11700
caacccggta agacacgact tatcgccact ggcagcagcc actggtaaca ggattagcag   11760
agcgaggtat gtaggcggtg ctacagagtt cttgaagtgg tggcctaact acggctacac   11820
tagaaggaca gtatttggta tctgcgctct gctgaagcca gttaccttcg gaaaaagagt   11880
tggtagctct tgatccggca acaaaccac cgctggtagc ggtggttttt tgtttgcaa    11940
gcagcagatt acgcgcagaa aaaaggatc tcaagaagat cctttgatct tttctacggg   12000
gtctgacgct cagtggaacg aaaactcacg ttaagggatt ttggtcatgc attctaggta   12060
ctaaaacaat tcatccagta aaatataata ttttatttc tcccaatcag gcttgatccc   12120
cagtaagtca aaaaatagct cgacatactg ttcttcccccg atatcctccc tgatcgaccg   12180
gacgcagaag gcaatgtcat accacttgtc cgccctgccg cttctcccaa gatcaataaa   12240
gccacttact ttgccatctt tcacaaagat gttgctgtct cccaggtcgc cgtgggaaaa   12300
gacaagttcc tcttcgggct tttccgtctt taaaaaatca tacagctcgc gcggatcttt   12360
aaatggagtg tcttccttcccc agttttcgca atccacatcg ccagatcgt tattcagtaa   12420
gtaatccaat tcggctaagc ggctgtctaa gctattcgta tagggacaat ccgatatgtc   12480
gatggagtga aagagcctga tgcactccgc atacagctcg ataatctttt cagggctttg   12540
ttcatcttca tactcttccg agcaaaggac gccatcggcc tcactcatga gcagattgct   12600
ccagccatca tgccgttcaa agtgcaggac ctttggaaca gcagctttc cttccagcca   12660
tagcatcatg tccttttccc gttccacatc ataggtggtc cctttatacc ggctgtccgt   12720
cattttttaaa tataggtttt catttctcc caccagctta tatccttag caggagacat   12780
tccttccgta tcttttacgc agcggtattt ttcgatcagt ttttcaatt ccggtgatat   12840
tctcatttta gccatttatt atttccttcc tcttttctac agtatttaaa gatacccaa    12900
gaagctaatt ataacaagac gaactccaat tcactgttcc ttgcattcta aaaccttaaa   12960
taccagaaaa cagcttttc aaagttgttt tcaaagttgg cgtataacat agtatcgacg   13020
gagccgattt tgaaaccgcg gtgatcacag gcagcaacgc tctgtcatcg ttacaatcaa   13080
```

```
catgctaccc tccgcgagat catccgtgtt tcaaacccgg cagcttagtt gccgttcttc   13140
cgaatagcat cggtaacatg agcaaagtct gccgccttac aacggctctc ccgctgacgc   13200
cgtcccggac tgatgggctg cctgtatcga gtggtgattt tgtgccgagc tgccggtcgg   13260
ggagctgttg gctggctggt ggcaggatat attgtggtgt aaacaaattg acgcttagac   13320
aacttaataa cacattgcgg acgtttttaa tgtactgaat taacgccgaa ttaattcggg   13380
ggatctggat tttagtactg gattttggtt ttaggaatta gaaattttat tgatagaagt   13440
attttacaaa tacaaataca tactaagggt ttcttatatg ctcaacacat gagcgaaacc   13500
ctataggaac cctaattccc ttatctggga actactcaca cattattatg gagaaactcg   13560
agcttgtcga tcgacagatc cggtcggcat ctactctatt tctttgccct cggacgagtg   13620
ctggggcgtc ggtttccact atcggcgagt acttctacac agccatcggt ccagacggcc   13680
gcgcttctgc gggcgatttg tgtacgcccg acagtcccgg ctccggatcg gacgattgcg   13740
tcgcatcgac cctgcgccca agctgcatca tcgaaattgc cgtcaaccaa gctctgatag   13800
agttggtcaa gaccaatgcg gagcatatac gcccggagtc gtggcgatcc tgcaagctcc   13860
ggatgcctcc gctcgaagta gcgcgtctgc tgctccatac aagccaacca cggcctccag   13920
aagaagatgt tggcgacctc gtattgggaa tccccgaaca tcgcctcgct ccagtcaatg   13980
accgctgtta tgcggccatt gtccgtcagg acattgttgg agccgaaatc cgcgtgcacg   14040
aggtgccgga cttcggggca gtcctcggcc caaagcatca gctcatcgag agcctgcgcg   14100
acggacgcac tgacggtgtc gtccatcaca gtttgccagt gatacacatg gggatcagca   14160
atcgcgcata tgaaatcacg ccatgtagtg tattgaccga ttccttgcgg tccgaatggg   14220
ccgaacccgc tcgtctggct aagatcggcc gcagcgatcg catccatagc ctccgcgacc   14280
ggttgtagaa cagcgggcag ttcggtttca ggcaggtctt gcaacgtgac accctgtgca   14340
cggcgggaga tgcaataggt caggctctcg ctaaactccc caatgtcaag cacttccgga   14400
atcgggagcg cggccgatgc aaagtgccga taaacataac gatctttgta gaaaccatcg   14460
gcgcagctat ttacccgcag gacatatcca cgccctccta catcgaagct gaaagcacga   14520
gattcttcgc cctccgagag ctgcatcagg tcggagacgt tgtcgaactt ttcgatcaga   14580
aacttctcga cagacgtcgc ggtgagttca ggcttttttca tatctcattg ccccccggga   14640
tctgcgaaag ctcgagagag atagatttgt agagagagac tggtgatttc agcgtgtcct   14700
ctccaaatga aatgaacttc cttatataga ggaaggtctt gcgaaggata gtgggattgt   14760
gcgtcatccc ttacgtcagt ggagatatca catcaatcca cttgctttga agacgtggtt   14820
ggaacgtctt cttttccac gatgctcctc gtgggtgggg gtccatcttt gggaccactg   14880
tcggcagagg catcttgaac gatagccttt cctttatcgc aatgatggca tttgtaggtg   14940
ccaccttcct tttctactgt cctttttgatg aagtgacaga tagctgggca atggaatccg   15000
aggaggtttc ccgatattac cctttgttga aaagtctcaa tagcccttttg gtcttctgag   15060 actgtatctt tgatattctt ggagtagacg agagtgtcgt gctccaccat gttatcacat   15120
caatccactt gctttgaaga cgtggttgga acgtcttctt tttccacgat gctcctcgtg   15180
ggtgggggtc catctttggg accactgtcg gcagaggcat cttgaacgat agcctttcct   15240
ttatcgcaat gatggcattt gtaggtgcca ccttcctttt ctactgtcct tttgatgaag   15300
tgacagatag ctgggcaatg gaatccgagg aggtttcccg atattaccct tgttgaaaa   15360 gtctcaatag ccctttggtc ttctgagact gtatctttga tattcttgga gtagacgaga   15420
```

-continued

```
gtgtcgtgct ccaccatgtt ggcaagctgc tctagccaat acgcaaaccg cctctccccg    15480
cgcgttggcc gattcattaa tgcagctggc acgacaggtt tcccgactgg aaagcgggca    15540
gtgagcgcaa cgcaattaat gtgagttagc tcactcatta ggcaccccag gctttacact    15600
ttatgcttcc ggctcgtatg ttgtgtggaa ttgtgagcgg ataacaattt cacacaggaa    15660
acagctatga ccatgattac g                                              15681
```

<210> SEQ ID NO 159
<211> LENGTH: 20
<212> TYPE: DNA
<213> ORGANISM: Artificial Sequence
<220> FEATURE:
<223> OTHER INFORMATION: target site

<400> SEQUENCE: 159
tccccacgtc actgggcgtc                                                20

<210> SEQ ID NO 160
<211> LENGTH: 20
<212> TYPE: DNA
<213> ORGANISM: Artificial Sequence
<220> FEATURE:
<223> OTHER INFORMATION: target site

<400> SEQUENCE: 160
cacaccccat ggccaggact                                                20

<210> SEQ ID NO 161
<211> LENGTH: 20
<212> TYPE: DNA
<213> ORGANISM: Artificial Sequence
<220> FEATURE:
<223> OTHER INFORMATION: target site

<400> SEQUENCE: 161
gcggagactc gtctacagtt                                                20

<210> SEQ ID NO 162
<211> LENGTH: 20
<212> TYPE: DNA
<213> ORGANISM: Artificial Sequence
<220> FEATURE:
<223> OTHER INFORMATION: target site

<400> SEQUENCE: 162
atgtgttaca gcacgtcggg                                                20

<210> SEQ ID NO 163
<211> LENGTH: 20
<212> TYPE: DNA
<213> ORGANISM: Artificial Sequence
<220> FEATURE:
<223> OTHER INFORMATION: vector

<400> SEQUENCE: 163
ttggtctacg gagcgatggt                                                20

<210> SEQ ID NO 164
<211> LENGTH: 10
<212> TYPE: PRT
<213> ORGANISM: Artificial Sequence
<220> FEATURE:
<223> OTHER INFORMATION: alignment

<400> SEQUENCE: 164

```
Asp Arg Leu Phe Ile Asp Trp Lys Arg Arg
1               5                   10
```

<210> SEQ ID NO 165
<211> LENGTH: 9
<212> TYPE: PRT
<213> ORGANISM: Artificial Sequence
<220> FEATURE:
<223> OTHER INFORMATION: alignment

<400> SEQUENCE: 165

```
Leu Arg Leu Phe Gly Val Asp Val Glu
1               5
```

<210> SEQ ID NO 166
<211> LENGTH: 9
<212> TYPE: PRT
<213> ORGANISM: Artificial Sequence
<220> FEATURE:
<223> OTHER INFORMATION: alignment

<400> SEQUENCE: 166

```
Leu Arg Leu Phe Gly Val Asp Met Glu
1               5
```

<210> SEQ ID NO 167
<211> LENGTH: 9
<212> TYPE: PRT
<213> ORGANISM: Artificial Sequence
<220> FEATURE:
<223> OTHER INFORMATION: alignment

<400> SEQUENCE: 167

```
Leu Arg Leu Phe Gly Val Asp Met Glu
1               5
```

<210> SEQ ID NO 168
<211> LENGTH: 9
<212> TYPE: PRT
<213> ORGANISM: Artificial Sequence
<220> FEATURE:
<223> OTHER INFORMATION: alignment

<400> SEQUENCE: 168

```
Leu Arg Leu Phe Gly Val Asp Met Glu
1               5
```

<210> SEQ ID NO 169
<211> LENGTH: 9
<212> TYPE: PRT
<213> ORGANISM: Artificial Sequence
<220> FEATURE:
<223> OTHER INFORMATION: alignment

<400> SEQUENCE: 169

```
Leu Arg Leu Phe Gly Val Asp Met Glu
1               5
```

<210> SEQ ID NO 170
<211> LENGTH: 9
<212> TYPE: PRT
<213> ORGANISM: Artificial Sequence
<220> FEATURE:
<223> OTHER INFORMATION: alignment

<400> SEQUENCE: 170

```
Leu Arg Leu Phe Gly Val Asp Met Glu
1               5

<210> SEQ ID NO 171
<211> LENGTH: 9
<212> TYPE: PRT
<213> ORGANISM: Artificial Sequence
<220> FEATURE:
<223> OTHER INFORMATION: alignment

<400> SEQUENCE: 171

Leu Arg Leu Phe Gly Val Asp Met Glu
1               5

<210> SEQ ID NO 172
<211> LENGTH: 9
<212> TYPE: PRT
<213> ORGANISM: Artificial Sequence
<220> FEATURE:
<223> OTHER INFORMATION: alignment

<400> SEQUENCE: 172

Leu Arg Leu Phe Gly Val Asn Met Glu
1               5

<210> SEQ ID NO 173
<211> LENGTH: 9
<212> TYPE: PRT
<213> ORGANISM: Artificial Sequence
<220> FEATURE:
<223> OTHER INFORMATION: alignment

<400> SEQUENCE: 173

Leu Arg Leu Phe Gly Val Asn Met Glu
1               5

<210> SEQ ID NO 174
<211> LENGTH: 9
<212> TYPE: PRT
<213> ORGANISM: Artificial Sequence
<220> FEATURE:
<223> OTHER INFORMATION: alignment

<400> SEQUENCE: 174

Leu Arg Leu Phe Gly Val Asn Met Glu
1               5

<210> SEQ ID NO 175
<211> LENGTH: 9
<212> TYPE: PRT
<213> ORGANISM: Artificial Sequence
<220> FEATURE:
<223> OTHER INFORMATION: alignment

<400> SEQUENCE: 175

Leu Arg Leu Phe Gly Val Asn Met Glu
1               5

<210> SEQ ID NO 176
<211> LENGTH: 9
<212> TYPE: PRT
<213> ORGANISM: Artificial Sequence
<220> FEATURE:
<223> OTHER INFORMATION: alignment

<400> SEQUENCE: 176

Leu Arg Leu Phe Gly Val Asn Met Glu
```

```
1               5
```

<210> SEQ ID NO 177
<211> LENGTH: 9
<212> TYPE: PRT
<213> ORGANISM: Artificial Sequence
<220> FEATURE:
<223> OTHER INFORMATION: alignment

<400> SEQUENCE: 177

```
Leu Arg Leu Phe Gly Val Asn Met Glu
1               5
```

<210> SEQ ID NO 178
<211> LENGTH: 9
<212> TYPE: PRT
<213> ORGANISM: Artificial Sequence
<220> FEATURE:
<223> OTHER INFORMATION: alignment

<400> SEQUENCE: 178

```
Leu Arg Leu Phe Gly Val Cys Ile Thr
1               5
```

<210> SEQ ID NO 179
<211> LENGTH: 9
<212> TYPE: PRT
<213> ORGANISM: Artificial Sequence
<220> FEATURE:
<223> OTHER INFORMATION: alignment

<400> SEQUENCE: 179

```
Val Arg Leu Phe Gly Val Asp Ile Ala
1               5
```

<210> SEQ ID NO 180
<211> LENGTH: 9
<212> TYPE: PRT
<213> ORGANISM: Artificial Sequence
<220> FEATURE:
<223> OTHER INFORMATION: alignment

<400> SEQUENCE: 180

```
Val Arg Leu Phe Gly Val Asp Ile Ala
1               5
```

<210> SEQ ID NO 181
<211> LENGTH: 9
<212> TYPE: PRT
<213> ORGANISM: Artificial Sequence
<220> FEATURE:
<223> OTHER INFORMATION: alignment

<400> SEQUENCE: 181

```
Val Arg Leu Phe Gly Val Asp Ile Phe
1               5
```

<210> SEQ ID NO 182
<211> LENGTH: 9
<212> TYPE: PRT
<213> ORGANISM: Artificial Sequence
<220> FEATURE:
<223> OTHER INFORMATION: alignment

<400> SEQUENCE: 182

```
Val Arg Leu Phe Gly Val Asp Ile Ser
1               5
```

```
<210> SEQ ID NO 183
<211> LENGTH: 9
<212> TYPE: PRT
<213> ORGANISM: Artificial Sequence
<220> FEATURE:
<223> OTHER INFORMATION: alignment

<400> SEQUENCE: 183

Val Arg Leu Phe Gly Val Asn Ile Leu
1               5

<210> SEQ ID NO 184
<211> LENGTH: 9
<212> TYPE: PRT
<213> ORGANISM: Artificial Sequence
<220> FEATURE:
<223> OTHER INFORMATION: alignment

<400> SEQUENCE: 184

Val Arg Leu Phe Gly Val Asn Ile Leu
1               5

<210> SEQ ID NO 185
<211> LENGTH: 9
<212> TYPE: PRT
<213> ORGANISM: Artificial Sequence
<220> FEATURE:
<223> OTHER INFORMATION: alignment

<400> SEQUENCE: 185

Val Arg Leu Phe Gly Val Asp Leu Leu
1               5

<210> SEQ ID NO 186
<211> LENGTH: 9
<212> TYPE: PRT
<213> ORGANISM: Artificial Sequence
<220> FEATURE:
<223> OTHER INFORMATION: alignment

<400> SEQUENCE: 186

Val Arg Leu Phe Gly Val Asp Leu Leu
1               5

<210> SEQ ID NO 187
<211> LENGTH: 9
<212> TYPE: PRT
<213> ORGANISM: Artificial Sequence
<220> FEATURE:
<223> OTHER INFORMATION: alignment

<400> SEQUENCE: 187

Val Arg Leu Phe Gly Val Asp Leu Leu
1               5

<210> SEQ ID NO 188
<211> LENGTH: 9
<212> TYPE: PRT
<213> ORGANISM: Artificial Sequence
<220> FEATURE:
<223> OTHER INFORMATION: alignment

<400> SEQUENCE: 188

Val Arg Leu Phe Gly Val Asp Leu Leu
1               5
```

```
<210> SEQ ID NO 189
<211> LENGTH: 9
<212> TYPE: PRT
<213> ORGANISM: Artificial Sequence
<220> FEATURE:
<223> OTHER INFORMATION: alignment

<400> SEQUENCE: 189

Val Arg Leu Phe Gly Val Asn Leu Leu
1               5

<210> SEQ ID NO 190
<211> LENGTH: 9
<212> TYPE: PRT
<213> ORGANISM: Artificial Sequence
<220> FEATURE:
<223> OTHER INFORMATION: alignment

<400> SEQUENCE: 190

Val Arg Leu Phe Gly Val Asn Leu Glu
1               5

<210> SEQ ID NO 191
<211> LENGTH: 9
<212> TYPE: PRT
<213> ORGANISM: Artificial Sequence
<220> FEATURE:
<223> OTHER INFORMATION: alignment

<400> SEQUENCE: 191

Val Arg Leu Phe Gly Val Asn Leu Glu
1               5

<210> SEQ ID NO 192
<211> LENGTH: 9
<212> TYPE: PRT
<213> ORGANISM: Artificial Sequence
<220> FEATURE:
<223> OTHER INFORMATION: alignment

<400> SEQUENCE: 192

Val Arg Leu Phe Gly Val Asn Leu Glu
1               5

<210> SEQ ID NO 193
<211> LENGTH: 9
<212> TYPE: PRT
<213> ORGANISM: Artificial Sequence
<220> FEATURE:
<223> OTHER INFORMATION: alignment

<400> SEQUENCE: 193

Val Arg Leu Phe Gly Val Asn Leu Glu
1               5

<210> SEQ ID NO 194
<211> LENGTH: 9
<212> TYPE: PRT
<213> ORGANISM: Artificial Sequence
<220> FEATURE:
<223> OTHER INFORMATION: alignment

<400> SEQUENCE: 194

Val Arg Leu Phe Gly Val Asn Leu Glu
1               5
```

-continued

```
<210> SEQ ID NO 195
<211> LENGTH: 9
<212> TYPE: PRT
<213> ORGANISM: Artificial Sequence
<220> FEATURE:
<223> OTHER INFORMATION: alignment

<400> SEQUENCE: 195

Leu Arg Leu Phe Gly Val Asn Leu Asp
1               5

<210> SEQ ID NO 196
<211> LENGTH: 9
<212> TYPE: PRT
<213> ORGANISM: Artificial Sequence
<220> FEATURE:
<223> OTHER INFORMATION: alignment

<400> SEQUENCE: 196

Leu Arg Leu Phe Gly Val Asn Leu Asp
1               5

<210> SEQ ID NO 197
<211> LENGTH: 9
<212> TYPE: PRT
<213> ORGANISM: Artificial Sequence
<220> FEATURE:
<223> OTHER INFORMATION: alignment

<400> SEQUENCE: 197

Val Arg Leu Phe Gly Val Asn Leu Asp
1               5

<210> SEQ ID NO 198
<211> LENGTH: 9
<212> TYPE: PRT
<213> ORGANISM: Artificial Sequence
<220> FEATURE:
<223> OTHER INFORMATION: alignment

<400> SEQUENCE: 198

Val Arg Leu Phe Gly Val Asn Leu Asp
1               5

<210> SEQ ID NO 199
<211> LENGTH: 9
<212> TYPE: PRT
<213> ORGANISM: Artificial Sequence
<220> FEATURE:
<223> OTHER INFORMATION: alignment

<400> SEQUENCE: 199

Val Arg Leu Phe Gly Val Asn Leu Asp
1               5

<210> SEQ ID NO 200
<211> LENGTH: 9
<212> TYPE: PRT
<213> ORGANISM: Artificial Sequence
<220> FEATURE:
<223> OTHER INFORMATION: alignment

<400> SEQUENCE: 200

Val Arg Leu Phe Gly Val Asn Leu Asp
1               5

<210> SEQ ID NO 201
```

```
<211> LENGTH: 9
<212> TYPE: PRT
<213> ORGANISM: Artificial Sequence
<220> FEATURE:
<223> OTHER INFORMATION: alignment

<400> SEQUENCE: 201

Val Arg Leu Phe Gly Val Asn Leu Asp
1               5

<210> SEQ ID NO 202
<211> LENGTH: 9
<212> TYPE: PRT
<213> ORGANISM: Artificial Sequence
<220> FEATURE:
<223> OTHER INFORMATION: alignment

<400> SEQUENCE: 202

Val Arg Leu Phe Gly Val Asn Leu Asp
1               5

<210> SEQ ID NO 203
<211> LENGTH: 9
<212> TYPE: PRT
<213> ORGANISM: Artificial Sequence
<220> FEATURE:
<223> OTHER INFORMATION: alignment

<400> SEQUENCE: 203

Val Arg Leu Phe Gly Val Asn Leu Asp
1               5

<210> SEQ ID NO 204
<211> LENGTH: 9
<212> TYPE: PRT
<213> ORGANISM: Artificial Sequence
<220> FEATURE:
<223> OTHER INFORMATION: alignment

<400> SEQUENCE: 204

Val Arg Leu Phe Gly Val Asn Leu Asp
1               5

<210> SEQ ID NO 205
<211> LENGTH: 9
<212> TYPE: PRT
<213> ORGANISM: Artificial Sequence
<220> FEATURE:
<223> OTHER INFORMATION: alignment

<400> SEQUENCE: 205

Val Arg Leu Phe Gly Val Asn Leu Asp
1               5

<210> SEQ ID NO 206
<211> LENGTH: 894
<212> TYPE: DNA
<213> ORGANISM: Brassica rapa

<400> SEQUENCE: 206
atgatgatga caaacttgtc tctttcaaga gaaggagaag aggaggaaga agaagaacaa      60
gaagaggcca agaagcccat ggaagaagta gagagagagc acatgttcga caaagtggtg     120
actccaagcg atgttggtaa actaaaccgg ctcgtgatcc caaagcaata cgcagagaga     180
tacttcccct tagattcatc cacaaacgag aaaggtttgc ttctaaactt cgaagatctc     240
```

-continued

```
gcaggaaagt catggaggtt ccgttactct tactggaaca gtagtcagag ctatgtcatg      300
actaaaggtt ggagccgttt cgttaaagac aaaaagctag acgccggaga tattgtctct      360
ttccagagat gtgtcggaga ttcaggaaga gacagccgct tgtttattga ttggaggaga      420
agacctaaag ttcctgacca tccgacatcg attgctcact ttgctgccgg atctatgttt      480
cctaggtttt acagttttcc gacagcaact agttacaatc tttacaacta tcagcagcca      540
cgtcatcatc atcacagtgg ttataattat cctcaaattc cgagagaatt tggatacggg      600
tacttggtgg atcaaagagc cgtggtggct gatccgttgg tgattgaatc tgtgccggtg      660
atgatgcacg gaggagctca agttagtcag gcggttgttg aacggccgg gaagaggctg       720 aggcttttg gagtcgatat ggaggaagaa tcttcatctt ccggtgggag tttgccacgt       780
ggtgacgctt ctccgtcttc ctctttgttt cagctgagac ttggaagcag cagtgaagat      840
gatcacttct ctaagaaagg aaagtcctca ttgccttttg atttggatca ataa            894
```

<210> SEQ ID NO 207
<211> LENGTH: 540
<212> TYPE: PRT
<213> ORGANISM: Artificial Sequence
<220> FEATURE:
<223> OTHER INFORMATION: alignment

<400> SEQUENCE: 207

```
Met Ala Ala Ser Pro Ser Ser Pro Leu Thr Ala Pro Pro Glu Pro Val
 1               5                  10                  15

Thr Pro Pro Ser Pro Trp Thr Ile Thr Asp Gly Ala Ile Ser Gly Thr
             20                  25                  30

Leu Pro Ala Ala Glu Ala Phe Ala Val His Tyr Pro Gly Tyr Pro Ser
         35                  40                  45

Ser Pro Ala Arg Ala Ala Arg Thr Leu Gly Gly Leu Pro Gly Leu Ala
     50                  55                  60

Lys Val Arg Ser Ser Asp Pro Gly Ala Arg Leu Glu Leu Arg Phe Arg
 65                  70                  75                  80

Pro Glu Asp Pro Tyr Cys His Pro Ala Phe Gly Gln Ser Arg Ala Ser
                 85                  90                  95

Thr Gly Leu Leu Leu Arg Leu Ser Lys Arg Lys Gly Ala Ala Ala Pro
            100                 105                 110

Cys Ala His Val Val Ala Arg Val Arg Thr Ala Tyr Tyr Phe Glu Gly
        115                 120                 125

Met Ala Asp Phe Gln His Val Val Pro Val His Ala Ala Gln Thr Arg
    130                 135                 140

Lys Arg Lys His Ser Asp Ser Gln Asn Asp Asn Glu Asn Phe Gly Ser
145                 150                 155                 160

Asp Lys Thr Gly His Asp Glu Ala Asp Gly Asp Val Met Met Leu Val
                165                 170                 175

Pro Pro Leu Phe Ser Val Lys Asp Arg Pro Thr Lys Ile Ala Leu Val
            180                 185                 190

Pro Ser Ser Asn Ala Ile Ser Lys Thr Met His Arg Gly Val Val Gln
        195                 200                 205

Glu Arg Trp Glu Met Asn Val Gly Pro Thr Leu Ala Leu Pro Phe Asn
    210                 215                 220

Thr Gln Val Val Pro Glu Lys Ile Asn Trp Glu Asp His Ile Arg Lys
225                 230                 235                 240

Asn Ser Val Glu Trp Gly Trp Gln Met Ala Val Cys Lys Leu Phe Asp
                245                 250                 255
```

```
Glu Arg Pro Val Trp Pro Arg Gln Ser Leu Tyr Glu Arg Phe Leu Asp
            260                 265                 270

Asp Asn Val His Val Ser Gln Asn Gln Phe Lys Arg Leu Leu Phe Arg
            275                 280                 285

Ala Gly Tyr Tyr Phe Ser Thr Gly Pro Phe Gly Lys Phe Trp Ile Arg
            290                 295                 300

Arg Gly Tyr Asp Pro Arg Lys Asp Ser Glu Ser Gln Ile Tyr Gln Arg
305                 310                 315                 320

Ile Asp Phe Arg Met Pro Pro Glu Leu Arg Tyr Leu Arg Leu Lys
                325                 330                 335

Asn Ser Glu Ser Arg Lys Trp Ala Asp Met Cys Lys Leu Glu Thr Met
            340                 345                 350

Pro Ser Gln Ser Phe Ile Tyr Leu Gln Leu Tyr Glu Leu Lys Asp Asp
            355                 360                 365

Phe Ile Gln Ala Glu Ile Arg Lys Pro Ser Tyr Gln Ser Val Cys Ser
            370                 375                 380

Arg Ser Thr Gly Trp Phe Ser Lys Pro Met Ile Lys Thr Leu Arg Leu
385                 390                 395                 400

Gln Val Ser Ile Arg Leu Leu Ser Leu Leu His Asn Glu Glu Ala Lys
            405                 410                 415

Asn Leu Leu Arg Asn Ala His Glu Leu Ile Glu Arg Ser Lys Lys Gln
            420                 425                 430

Glu Ala Leu Ser Arg Ser Glu Leu Ser Ile Glu Tyr Asn Asp Ala Asp
            435                 440                 445

Gln Val Ser Ala Ala His Thr Gly Thr Glu Asp Gln Val Gly Pro Asn
            450                 455                 460

Asn Ser Asp Ser Glu Asp Val Asp Asp Glu Glu Glu Glu Glu Glu Leu
465                 470                 475                 480

Glu Gly Tyr Asp Ser Pro Pro Met Ala Asp Asp Ile His Glu Phe Thr
                485                 490                 495

Leu Gly Asp Ser Tyr Ala Phe Gly Glu Gly Phe Ser Asn Gly Tyr Leu
            500                 505                 510

Glu Glu Val Leu Arg Ser Leu Pro Leu Gln Glu Asp Gly Gln Lys Lys
            515                 520                 525

Leu Cys Asp Ala Pro Ile Asn Ala Asp Ala Ser Asp
            530                 535                 540

<210> SEQ ID NO 208
<211> LENGTH: 160
<212> TYPE: PRT
<213> ORGANISM: Artificial Sequence
<220> FEATURE:
<223> OTHER INFORMATION: alignment

<400> SEQUENCE: 208

Met Tyr Cys Ser Arg Gly Arg Ile Asp Pro Ala Glu Glu Gly Gln Val
1               5                   10                  15

Met Gly Gly Leu Gly Val Arg Asp Ala Ser Trp Ala Leu Phe Lys Val
            20                  25                  30

Leu Glu Gln Ser Asp Val Gln Val Gly Gln Asn Arg Leu Leu Leu Thr
            35                  40                  45

Lys Glu Ala Val Trp Gly Gly Pro Ile Pro Lys Leu Phe Pro Glu Leu
        50                  55                  60

Glu Glu Leu Arg Gly Asp Gly Leu Asn Ala Glu Asn Arg Val Ala Val
65              70                  75                  80
```

-continued

```
Lys Ile Leu Asp Ala Asp Gly Cys Glu Gly Asp Ala Asn Phe Arg Tyr
                85                  90                  95

Leu Asn Ser Ser Lys Ala Tyr Arg Val Met Gly Pro Gln Trp Ser Arg
            100                 105                 110

Leu Val Lys Glu Thr Gly Met Cys Lys Gly Asp Arg Leu Asp Leu Tyr
        115                 120                 125

Ala Ala Thr Ala Thr Ala Ala Ser Ser Cys Ser Gly Ala Arg Ala Ala
    130                 135                 140

Val Ala Pro Ala Ile Pro Pro Gly Ala Ile Val Lys Ala Ala Gly Phe
145                 150                 155                 160
```

<210> SEQ ID NO 209
<211> LENGTH: 192
<212> TYPE: PRT
<213> ORGANISM: Artificial Sequence
<220> FEATURE:
<223> OTHER INFORMATION: alignment

<400> SEQUENCE: 209

```
Met Ala Met His Ala Gly His Ala Trp Trp Gly Val Ala Met Tyr Thr
1               5                   10                  15

Asn His Tyr His His Tyr Arg His Lys Thr Ser Asp Val Gly Lys
                20                  25                  30

Asn Arg Val Lys His Ala Arg Tyr Gly Gly Asp Ser Gly Lys Gly
            35                  40                  45

Ser Asp Ser Gly Lys Trp Arg Arg Tyr Ser Tyr Trp Thr Ser Ser Ser
    50                  55                  60

Tyr Val Thr Lys Gly Trp Ser Arg Tyr Val Lys Lys Arg Asp Ala Gly
65                  70                  75                  80

Asp Val Val His Arg Val Arg Gly Gly Ala Ala Asp Arg Gly Cys Arg
                85                  90                  95

Arg Arg Gly Ser Ala Ala Ala Val Arg Val Thr Ala Asn Gly Gly Trp
            100                 105                 110

Ser Met Cys Tyr Ser Thr Ser Gly Ser Ser Tyr Asp Thr Ser Ala Asn
        115                 120                 125

Ser Tyr Ala Tyr His Arg Ser Val Asp Asp His Ser Asp His Ala Gly
    130                 135                 140

Ser Arg Ala Asp Ala Lys Ser Ser Ser Ala Ala Ser Ala Ser Arg Arg
145                 150                 155                 160

Arg Gly Val Asn Asp Cys Gly Ala Asp Ala Thr Ala Met Tyr Gly Tyr
                165                 170                 175

Met His His Ser Tyr Ala Ala Val Ser Thr Val Asn Tyr Trp Ser Val
            180                 185                 190
```

<210> SEQ ID NO 210
<211> LENGTH: 491
<212> TYPE: PRT
<213> ORGANISM: Artificial Sequence
<220> FEATURE:
<223> OTHER INFORMATION: alignment

<400> SEQUENCE: 210

```
Met Glu Leu Met Gln Glu Val Lys Gly Tyr Ser Asp Gly Arg Glu Glu
1               5                   10                  15

Glu Glu Glu Glu Glu Glu Ala Ala Glu Ile Ile Thr Arg Glu Glu
                20                  25                  30

Ser Ser Arg Leu Leu His Gln His Gln Glu Ala Ala Gly Ser Asn Phe
```

```
                35                  40                  45
Ile Ile Asn Asn Asn His His His Gln His His His His Thr
            50                  55                  60
Thr Lys Gln Leu Asp Phe Met Asp Leu Ser Leu Gly Ser Ser Lys Asp
65                      70                  75                  80
Glu Gly Asn Leu Gln Gly Ser Ser Ser Val Tyr Ala His His
                    85                  90                  95
His Ala Ala Ser Ala Ser Ser Ser Ala Asn Gly Asn Asn Asn Ser
                100                 105                 110
Ser Ser Ser Asn Leu Gln Gln Gln Gln Gln Pro Ala Glu Lys Glu
            115                 120                 125
His Met Phe Asp Lys Val Val Thr Pro Ser Asp Val Gly Lys Leu Asn
    130                 135                 140
Arg Leu Val Ile Pro Lys Gln His Ala Glu Lys Tyr Phe Pro Leu Asp
145                 150                 155                 160
Ser Ser Ala Asn Glu Lys Gly Leu Leu Leu Asn Phe Glu Asp Arg Asn
                165                 170                 175
Gly Lys Leu Trp Arg Phe Arg Tyr Ser Tyr Trp Asn Ser Ser Gln Ser
            180                 185                 190
Tyr Val Met Thr Lys Gly Trp Ser Arg Phe Val Lys Glu Lys Lys Leu
        195                 200                 205
Asp Ala Gly Asp Met Val Ser Phe Gln Arg Gly Val Gly Glu Leu Tyr
    210                 215                 220
Arg His Arg Leu Tyr Ile Asp Trp Trp Arg Arg Pro Asp His His His
225                 230                 235                 240
His His His His Gly Pro Asp His Ser Thr Thr Leu Phe Thr Pro Phe
                245                 250                 255
Leu Ile Pro Asn Gln Pro His His Leu Met Ser Ile Arg Trp Gly Ala
            260                 265                 270
Thr Gly Arg Leu Tyr Ser Leu Pro Ser Pro Thr Pro Arg His His
        275                 280                 285
Glu His Leu Asn Tyr Asn Asn Asn Ala Met Tyr His Pro Phe His His
    290                 295                 300
His Gly Ala Gly Ser Gly Ile Asn Ala Thr Thr His Tyr Asn Asn
305                 310                 315                 320
Tyr His Glu Met Ser Ser Thr Thr Thr Ser Gly Ser Ala Gly Ser Val
                325                 330                 335
Phe Tyr His Arg Ser Thr Pro Pro Ile Ser Met Pro Leu Ala Asp His
            340                 345                 350
Gln Thr Leu Asn Thr Arg Gln Gln Gln Gln Gln Gln Gln Gln Glu
        355                 360                 365
Gly Ala Gly Asn Val Ser Leu Ser Pro Met Ile Ile Asp Ser Val Pro
    370                 375                 380
Val Ala His His Leu His His Gln Gln His His Gly Gly Lys Ser Ser
385                 390                 395                 400
Gly Pro Ser Ser Thr Ser Thr Ser Pro Ser Thr Ala Gly Lys Arg Leu
                405                 410                 415
Arg Leu Phe Gly Val Asn Met Glu Cys Ala Ser Ser Thr Ser Glu Asp
            420                 425                 430
Pro Lys Cys Phe Ser Leu Leu Ser Ser Ser Met Ala Asn Ser Asn
        435                 440                 445
Ser Gln Pro Pro Leu Gln Leu Leu Arg Glu Asp Thr Leu Ser Ser Ser
    450                 455                 460
```

-continued

Ser Ala Arg Phe Gly Asp Gln Arg Gly Val Gly Glu Pro Ser Met Leu
465                 470                 475                 480

Phe Asp Leu Asp Pro Ser Leu Gln Tyr Arg Gln
                485                 490

<210> SEQ ID NO 211
<211> LENGTH: 297
<212> TYPE: PRT
<213> ORGANISM: Artificial Sequence
<220> FEATURE:
<223> OTHER INFORMATION: alignment

<400> SEQUENCE: 211

Met Met Met Thr Asn Leu Ser Leu Ser Arg Glu Gly Glu Glu Glu Glu
1               5                   10                  15

Glu Glu Glu Gln Glu Glu Ala Lys Lys Pro Met Glu Glu Val Glu Arg
                20                  25                  30

Glu His Met Phe Asp Lys Val Val Thr Pro Ser Asp Val Gly Lys Leu
            35                  40                  45

Asn Arg Leu Val Ile Pro Lys Gln Tyr Ala Glu Arg Tyr Phe Pro Leu
        50                  55                  60

Asp Ser Ser Thr Asn Glu Lys Gly Leu Leu Leu Asn Phe Glu Asp Leu
65                  70                  75                  80

Ala Gly Lys Ser Trp Arg Phe Arg Tyr Ser Tyr Trp Asn Ser Ser Gln
                85                  90                  95

Ser Tyr Val Met Thr Lys Gly Trp Ser Arg Phe Val Lys Asp Lys Lys
            100                 105                 110

Leu Asp Ala Gly Asp Ile Val Ser Phe Gln Arg Cys Val Gly Asp Ser
        115                 120                 125

Gly Arg Asp Ser Arg Leu Phe Ile Asp Trp Arg Arg Pro Lys Val
        130                 135                 140

Pro Asp His Pro Thr Ser Ile Ala His Phe Ala Ala Gly Ser Met Phe
145                 150                 155                 160

Pro Arg Phe Tyr Ser Phe Pro Thr Ala Thr Ser Tyr Asn Leu Tyr Asn
                165                 170                 175

Tyr Gln Gln Pro Arg His His His Ser Gly Tyr Asn Tyr Pro Gln
            180                 185                 190

Ile Pro Arg Glu Phe Gly Tyr Gly Tyr Leu Val Asp Gln Arg Ala Val
        195                 200                 205

Val Ala Asp Pro Leu Val Ile Glu Ser Val Pro Val Met Met His Gly
    210                 215                 220

Gly Ala Gln Val Ser Gln Ala Val Val Gly Thr Ala Gly Lys Arg Leu
225                 230                 235                 240

Arg Leu Phe Gly Val Asp Met Glu Glu Glu Ser Ser Ser Ser Gly Gly
                245                 250                 255

Ser Leu Pro Arg Gly Asp Ala Ser Pro Ser Ser Leu Phe Gln Leu
            260                 265                 270

Arg Leu Gly Ser Ser Ser Glu Asp Asp His Phe Ser Lys Lys Gly Lys
        275                 280                 285

Ser Ser Leu Pro Phe Asp Leu Asp Gln
        290                 295

<210> SEQ ID NO 212
<211> LENGTH: 310
<212> TYPE: PRT
<213> ORGANISM: Artificial Sequence
<220> FEATURE:
<223> OTHER INFORMATION: alignment

<400> SEQUENCE: 212

Met Met Thr Asn Leu Ser Leu Ala Arg Glu Gly Glu Glu Glu Glu
1               5                   10                  15

Glu Ala Gly Ala Lys Lys Pro Thr Glu Val Glu Arg Glu His Met
                20                  25                  30

Phe Asp Lys Val Val Thr Pro Ser Asp Val Gly Lys Leu Asn Arg Leu
                35                  40                  45

Val Ile Pro Lys Gln His Ala Glu Arg Tyr Phe Pro Leu Asp Ser Ser
50                  55                  60

Thr Asn Glu Lys Gly Leu Ile Leu Asn Phe Glu Asp Leu Thr Gly Lys
65                  70                  75                  80

Ser Trp Arg Phe Arg Tyr Ser Tyr Trp Asn Ser Ser Gln Ser Tyr Val
                85                  90                  95

Met Thr Lys Gly Trp Ser Arg Phe Val Lys Asp Lys Lys Leu Asp Ala
                100                 105                 110

Gly Asp Ile Val Ser Phe Leu Arg Cys Val Gly Asp Thr Gly Arg Asp
                115                 120                 125

Ser Arg Leu Phe Ile Asp Trp Arg Arg Pro Lys Val Pro Asp Tyr
130                 135                 140

Thr Thr Ser Thr Ser His Phe Pro Ala Gly Ala Met Phe Pro Arg Phe
145                 150                 155                 160

Tyr Ser Phe Gln Thr Ala Thr Thr Ser Thr Tyr Asn Pro Tyr Asn
                165                 170                 175

His Gln Gln Pro Arg His His His Ser Gly Tyr Cys Tyr Pro Gln Ile
                180                 185                 190

Pro Arg Glu Phe Gly Tyr Gly Tyr Val Val Arg Ser Val Asp Gln Arg
                195                 200                 205

Ala Val Val Ala Asp Pro Leu Val Ile Glu Ser Val Pro Val Met Met
                210                 215                 220

His Gly Gly Ala Arg Val Asn Gln Ala Ala Val Gly Thr Ala Gly Lys
225                 230                 235                 240

Arg Leu Arg Leu Phe Gly Val Asp Met Glu Cys Gly Glu Ser Gly Gly
                245                 250                 255

Thr Asn Ser Thr Glu Glu Glu Ser Ser Ser Gly Gly Ser Leu Pro
                260                 265                 270

Arg Gly Gly Ala Ser Pro Ser Ser Ser Met Phe Gln Leu Arg Leu Gly
                275                 280                 285

Asn Ser Ser Glu Asp Asp His Leu Phe Lys Lys Gly Lys Ser Ser Leu
                290                 295                 300

Pro Phe Asn Leu Asp Gln
305                 310

<210> SEQ ID NO 213
<211> LENGTH: 293
<212> TYPE: PRT
<213> ORGANISM: Artificial Sequence
<220> FEATURE:
<223> OTHER INFORMATION: alignment

<400> SEQUENCE: 213

Met Met Thr Asn Leu Ser Leu Ala Arg Glu Gly Glu Ala Gln Val Lys
1               5                   10                  15

Lys Pro Ile Glu Glu Val Glu Arg Glu His Met Phe Asp Lys Val Val

```
            20                  25                  30
Thr Pro Ser Asp Val Gly Lys Leu Asn Arg Leu Val Ile Pro Lys Gln
        35                  40                  45

His Ala Glu Arg Tyr Phe Pro Leu Asp Ser Ser Asn Glu Lys Gly
    50                  55                  60

Leu Leu Leu Asn Phe Glu Asp Leu Thr Gly Lys Ser Trp Arg Phe Arg
65                  70                  75                  80

Tyr Ser Tyr Trp Asn Ser Ser Gln Ser Tyr Val Met Thr Lys Gly Trp
                85                  90                  95

Ser Arg Phe Val Lys Asp Lys Lys Leu Asp Ala Gly Asp Ile Val Ser
            100                 105                 110

Phe Gln Arg Cys Val Gly Asp Ser Arg Leu Phe Ile Asp Trp Arg Arg
        115                 120                 125

Arg Pro Lys Val Pro Asp Tyr Pro Thr Ser Thr Ala His Phe Ala Ala
    130                 135                 140

Gly Ala Met Phe Pro Arg Phe Tyr Ser Phe Pro Thr Ala Thr Thr Ser
145                 150                 155                 160

Thr Cys Tyr Asp Leu Tyr Asn His Gln Pro Pro Arg His His His Ile
                165                 170                 175

Gly Tyr Gly Tyr Pro Gln Ile Pro Arg Glu Phe Gly Tyr Gly Tyr Phe
            180                 185                 190

Val Arg Ser Val Asp Gln Arg Ala Val Ala Asp Pro Leu Val Ile
        195                 200                 205

Glu Ser Val Pro Val Met Met Arg Gly Gly Ala Arg Val Ser Gln Glu
    210                 215                 220

Val Val Gly Thr Ala Gly Lys Arg Leu Arg Leu Phe Gly Val Asp Met
225                 230                 235                 240

Glu Glu Glu Ser Ser Ser Ser Gly Gly Ser Leu Pro Arg Ala Gly Gly
                245                 250                 255

Gly Gly Ala Ser Ser Ser Ser Ser Leu Phe Gln Leu Arg Leu Gly Ser
            260                 265                 270

Ser Cys Glu Asp Asp His Phe Ser Lys Lys Gly Lys Ser Ser Leu Pro
        275                 280                 285

Phe Asp Leu Asp Gln
    290

<210> SEQ ID NO 214
<211> LENGTH: 320
<212> TYPE: PRT
<213> ORGANISM: Artificial Sequence
<220> FEATURE:
<223> OTHER INFORMATION: alignment

<400> SEQUENCE: 214

Met Glu Arg Lys Ser Asn Asp Leu Glu Arg Ser Glu Asn Ile Asp Ser
1               5                   10                  15

Gln Asn Lys Lys Met Asn Leu Glu Glu Arg Pro Val Gln Glu Ala
            20                  25                  30

Ser Ser Met Glu Arg Glu His Met Phe Asp Lys Val Val Thr Pro Ser
        35                  40                  45

Asp Val Gly Lys Leu Asn Arg Leu Val Ile Pro Lys Gln His Ala Glu
    50                  55                  60

Arg Tyr Phe Pro Leu Asp Asn Asn Ser Ser Asp Asn Lys Gly Leu
65                  70                  75                  80

Leu Leu Asn Phe Glu Asp Arg Ile Gly Ile Leu Trp Ser Phe Arg Tyr
```

```
            85                  90                  95
Ser Tyr Trp Asn Ser Ser Gln Ser Tyr Val Met Thr Lys Gly Trp Ser
            100                 105                 110

Arg Phe Val Lys Asp Lys Lys Leu Asp Ala Gly Asp Ile Val Ser Phe
            115                 120                 125

His Arg Gly Ser Cys Asn Lys Asp Lys Leu Phe Ile Asp Trp Lys Arg
            130                 135                 140

Arg Pro Lys Ile Pro Asp His Gln Val Gly Ala Met Phe Pro Arg
145                 150                 155                 160

Phe Tyr Ser Tyr Pro Tyr Pro Gln Ile Gln Ala Ser Tyr Glu Arg His
                    165                 170                 175

Asn Leu Tyr His Arg Tyr Gln Arg Asp Ile Gly Ile Gly Tyr Tyr Val
                180                 185                 190

Arg Ser Met Glu Arg Tyr Asp Pro Thr Ala Val Ile Glu Ser Val Pro
            195                 200                 205

Val Ile Met Gln Arg Arg Ala His Val Ala Thr Met Ala Ser Ser Arg
210                 215                 220

Gly Glu Lys Arg Leu Arg Leu Phe Gly Val Asp Met Glu Cys Val Arg
225                 230                 235                 240

Gly Gly Arg Gly Gly Gly Ser Val Asn Ser Thr Glu Glu Ser
                    245                 250                 255

Ser Thr Ser Gly Gly Ser Ile Ser Arg Gly Gly Val Ser Met Ala Gly
                260                 265                 270

Val Gly Ser Pro Leu Gln Leu Arg Leu Val Ser Ser Asp Gly Asp Asp
                275                 280                 285

Gln Ser Leu Val Ala Arg Gly Ala Arg Val Asp Glu Asp His His
        290                 295                 300

Leu Phe Thr Lys Lys Gly Lys Ser Ser Leu Ser Phe Asp Leu Asp Lys
305                 310                 315                 320

<210> SEQ ID NO 215
<211> LENGTH: 286
<212> TYPE: PRT
<213> ORGANISM: Artificial Sequence
<220> FEATURE:
<223> OTHER INFORMATION: alignment

<400> SEQUENCE: 215

Met Asn Gln Glu Glu Glu Asn Pro Val Glu Lys Ala Ser Ser Met Glu
1               5                   10                  15

Arg Glu His Met Phe Gly Lys Val Thr Pro Ser Asp Val Gly Lys
            20                  25                  30

Leu Asn Arg Leu Val Ile Pro Lys Gln His Ala Glu Arg Tyr Phe Pro
        35                  40                  45

Leu Asp Asn Asn Ser Asp Ser Ser Lys Gly Leu Leu Leu Asn Phe Glu
    50                  55                  60

Asp Arg Thr Gly Asn Ser Trp Arg Phe Arg Tyr Ser Tyr Trp Asn Ser
65                  70                  75                  80

Ser Gln Ser Tyr Val Met Thr Lys Gly Trp Ser Arg Phe Val Lys Asp
                85                  90                  95

Lys Lys Leu Asp Ala Gly Asp Ile Val Ser Phe Gln Arg Asp Pro Gly
            100                 105                 110

Asn Lys Asp Lys Leu Phe Ile Asp Trp Arg Arg Arg Pro Lys Ile Pro
        115                 120                 125

Asp His His His Gln Phe Ala Gly Ala Met Phe Pro Arg Phe Tyr Ser
```

```
              130                 135                 140
Phe Ser His Pro Gln Asn Leu Tyr His Arg Tyr Gln Gln Asp Leu Gly
145                 150                 155                 160

Ile Gly Tyr Tyr Val Ser Ser Met Glu Arg Asn Asp Pro Thr Ala Val
                165                 170                 175

Ile Glu Ser Val Pro Leu Ile Met Gln Arg Arg Ala Ala His Val Ala
                180                 185                 190

Ala Ile Pro Ser Ser Arg Gly Glu Lys Arg Leu Arg Leu Phe Gly Val
                195                 200                 205

Asp Met Glu Cys Gly Gly Gly Gly Ser Val Asn Ser Thr Glu Glu
                210                 215                 220

Glu Ser Ser Ser Gly Gly Gly Gly Val Ser Met Ala Ser Val
225                 230                 235                 240

Gly Ser Leu Leu Gln Leu Arg Leu Val Ser Ser Asp Asp Glu Ser Leu
                245                 250                 255

Val Ala Met Glu Ala Ala Ser Val Asp Glu Asp His His Leu Phe Thr
                260                 265                 270

Lys Lys Gly Lys Ser Ser Leu Ser Phe Asp Leu Asp Arg Lys
                275                 280                 285
```

<210> SEQ ID NO 216
<211> LENGTH: 292
<212> TYPE: PRT
<213> ORGANISM: Artificial Sequence
<220> FEATURE:
<223> OTHER INFORMATION: alignment

<400> SEQUENCE: 216

```
Met Asn Gln Glu Asn Lys Lys Pro Leu Glu Ala Ser Thr Ser Met
1               5                   10                  15

Glu Arg Glu Asn Met Phe Asp Lys Val Val Thr Pro Ser Asp Val Gly
                20                  25                  30

Lys Leu Asn Arg Leu Val Ile Pro Lys Gln His Ala Glu Arg Tyr Phe
                35                  40                  45

Pro Leu Asp Asn Ser Ser Thr Asn Asn Lys Gly Leu Leu Leu Asp Phe
50                  55                  60

Glu Asp Arg Thr Gly Ser Ser Trp Arg Phe Arg Tyr Ser Tyr Trp Asn
65                  70                  75                  80

Ser Ser Gln Ser Tyr Val Met Thr Lys Gly Trp Ser Arg Phe Val Lys
                85                  90                  95

Asp Lys Lys Leu Asp Ala Gly Asp Ile Val Ser Phe Gln Arg Asp Pro
                100                 105                 110

Cys Asn Lys Asp Lys Leu Tyr Ile Asp Trp Arg Arg Arg Pro Lys Ile
                115                 120                 125

Pro Asp His His Gln Phe Ala Gly Ala Met Phe Pro Arg Phe Tyr Ser
                130                 135                 140

Phe Pro His Pro Gln Met Pro Thr Ser Phe Glu Ser Ser His Asn Leu
145                 150                 155                 160

Tyr His His Arg Phe Gln Arg Asp Leu Gly Ile Gly Tyr Tyr Pro Thr
                165                 170                 175

Ala Val Ile Glu Ser Val Pro Val Ile Met Gln Arg Arg Glu Ala Gln
                180                 185                 190

Val Ala Asn Met Ala Ser Ser Arg Gly Glu Lys Arg Leu Arg Leu Phe
                195                 200                 205

Gly Val Asp Val Glu Cys Gly Gly Gly Gly Gly Ser Val Asn Ser
```

```
                210                 215                 220
Thr Glu Glu Glu Ser Ser Ser Gly Gly Ser Met Ser Arg Gly Gly
225                 230                 235                 240

Val Ser Met Ala Gly Val Gly Ser Leu Leu Gln Leu Arg Leu Val Ser
                245                 250                 255

Ser Asp Asp Glu Ser Leu Val Ala Met Glu Gly Ala Thr Val Asp Glu
                260                 265                 270

Asp His His Leu Phe Thr Thr Lys Lys Gly Lys Ser Ser Leu Ser Phe
                275                 280                 285

Asp Leu Asp Ile
            290

<210> SEQ ID NO 217
<211> LENGTH: 420
<212> TYPE: PRT
<213> ORGANISM: Artificial Sequence
<220> FEATURE:
<223> OTHER INFORMATION: alignment

<400> SEQUENCE: 217

Met Glu Leu Met Gln Gln Val Lys Gly Asn Tyr Ser Asp Ser Arg Glu
1               5                   10                  15

Glu Glu Glu Glu Glu Ala Ala Ala Ile Thr Arg Glu Ser Glu Ser
                20                  25                  30

Ser Arg Leu His Gln Gln Asp Thr Ala Ser Asn Phe Gly Lys Lys Leu
            35                  40                  45

Asp Leu Met Asp Leu Ser Leu Gly Ser Ser Lys Glu Glu Glu Glu Glu
    50                  55                  60

Gly Asn Leu Gln Gln Gly Gly Gly Val Val His His Ala His Gln
65                  70                  75                  80

Val Val Glu Lys Glu His Met Phe Glu Lys Val Ala Thr Pro Ser Asp
                85                  90                  95

Val Gly Lys Leu Asn Arg Leu Val Ile Pro Lys Gln His Ala Glu Lys
                100                 105                 110

Tyr Phe Pro Leu Asp Ser Ser Thr Asn Glu Lys Gly Leu Leu Leu Asn
            115                 120                 125

Phe Glu Asp Arg Asn Gly Lys Val Trp Arg Phe Arg Tyr Ser Tyr Trp
    130                 135                 140

Asn Ser Ser Gln Ser Tyr Val Met Thr Lys Gly Trp Ser Arg Phe Val
145                 150                 155                 160

Lys Glu Lys Lys Leu Asp Ala Gly Asp Ile Val Ser Phe Gln Arg Gly
                165                 170                 175

Leu Gly Asp Leu Tyr Arg His Arg Leu Tyr Ile Asp Trp Lys Arg Arg
            180                 185                 190

Pro Asp His Ala His Ala His Pro Pro His His Asp Pro Leu Phe
    195                 200                 205

Leu Pro Ser Ile Arg Leu Tyr Ser Leu Pro Thr Met Pro Pro Arg
    210                 215                 220

Tyr His His Asp His His Phe His His Leu Asn Tyr Asn Asn Leu
225                 230                 235                 240

Phe Thr Phe Gln Gln His Gln Tyr Gln Gln Leu Gly Ala Ala Thr Thr
                245                 250                 255

Thr His His Asn Asn Tyr Gly Tyr Gln Asn Ser Gly Ser Gly Ser Leu
            260                 265                 270

Tyr Tyr Leu Arg Ser Ser Met Ser Met Gly Gly Gly Asp Gln Asn Leu
```

```
                275                 280                 285
Gln Gly Arg Gly Ser Asn Ile Val Pro Met Ile Ile Asp Ser Val Pro
290                 295                 300

Val Asn Val Ala His His Asn Asn Arg His Gly Asn Gly Gly Ile
305                 310                 315                 320

Thr Ser Gly Gly Thr Asn Cys Ser Gly Lys Arg Leu Arg Leu Phe Gly
                325                 330                 335

Val Asn Met Glu Cys Ala Ser Ser Ala Glu Asp Ser Lys Glu Leu Ser
            340                 345                 350

Ser Gly Ser Ala Ala His Val Thr Thr Ala Ala Ser Ser Ser Ser Leu
                355                 360                 365

His His Gln Arg Leu Arg Val Pro Val Pro Val Pro Leu Glu Asp Pro
370                 375                 380

Leu Ser Ser Ser Ala Ala Ala Ala Arg Phe Gly Asp His Lys Gly
385                 390                 395                 400

Ala Ser Thr Gly Thr Ser Leu Leu Phe Asp Leu Asp Pro Ser Leu Gln
                405                 410                 415

Tyr His Arg His
        420

<210> SEQ ID NO 218
<211> LENGTH: 422
<212> TYPE: PRT
<213> ORGANISM: Artificial Sequence
<220> FEATURE:
<223> OTHER INFORMATION: alignment

<400> SEQUENCE: 218

Met Asp Gln Phe Ala Ala Ser Gly Arg Phe Ser Arg Glu Glu Glu Ala
1               5                   10                  15

Asp Glu Glu Gln Glu Asp Ala Ser Asn Ser Met Arg Glu Ile Ser Phe
                20                  25                  30

Met Pro Pro Ala Ala Ala Ser Ser Ser Ala Ala Ser Ala Ser
            35                  40                  45

Ala Ser Ala Ser Thr Ser Ala Ser Ala Cys Ala Ser Gly Ser Ser Ser
50                  55                  60

Ala Pro Phe Arg Ser Ala Ser Ala Ser Gly Asp Ala Ala Gly Ala Ser
65                  70                  75                  80

Gly Ser Gly Gly Pro Ala Asp Ala Asp Ala Glu Ala Glu Ala Val Glu
                85                  90                  95

Lys Glu His Met Phe Asp Lys Val Val Thr Pro Ser Asp Val Gly Lys
            100                 105                 110

Leu Asn Arg Leu Val Ile Pro Lys Gln Tyr Ala Glu Lys Tyr Phe Pro
        115                 120                 125

Leu Asp Ala Ala Ala Asn Glu Lys Gly Leu Leu Ser Phe Glu Asp
        130                 135                 140

Ser Ala Gly Lys His Trp Arg Phe Arg Tyr Ser Tyr Trp Asn Ser Ser
145                 150                 155                 160

Gln Ser Tyr Val Met Thr Lys Gly Trp Ser Arg Phe Val Lys Glu Lys
                165                 170                 175

Arg Leu Val Ala Gly Asp Thr Val Ser Phe Ser Arg Ala Ala Glu
            180                 185                 190

Asp Ala Arg His Arg Leu Phe Ile Asp Trp Lys Arg Arg Val Asp Thr
        195                 200                 205

Arg Gly Pro Leu Arg Phe Ser Gly Leu Ala Leu Pro Met Pro Leu Pro
```

```
                210                 215                 220
Ser Ser His Tyr Gly Gly Pro His His Tyr Ser Pro Trp Gly Phe Gly
225                 230                 235                 240

Gly Gly Gly Gly Gly Gly Gly Phe Phe Met Pro Pro Ser Pro Pro
                245                 250                 255

Ala Thr Leu Tyr Glu His Arg Leu Arg Gln Gly Leu Asp Phe Arg Ser
                260                 265                 270

Met Thr Thr Thr Tyr Pro Ala Pro Thr Val Gly Arg Gln Leu Leu Phe
                275                 280                 285

Phe Gly Ser Ala Arg Met Pro Pro His His Ala Pro Pro Gln Pro
                290                 295                 300

Arg Pro Phe Ser Leu Pro Leu His His Tyr Thr Val Gln Pro Ser Ala
305                 310                 315                 320

Ala Gly Val Thr Ala Ala Ser Arg Pro Val Leu Leu Asp Ser Val Pro
                325                 330                 335

Val Ile Glu Ser Pro Thr Thr Ala Ala Lys Arg Val Arg Leu Phe Gly
                340                 345                 350

Val Asn Leu Asp Asn Asn Pro Asp Gly Gly Glu Ala Ser His Gln
                355                 360                 365

Gly Asp Ala Leu Ser Leu Gln Met Pro Gly Trp Gln Gln Arg Thr Pro
370                 375                 380

Thr Leu Arg Leu Leu Glu Leu Pro Arg His Gly Gly Glu Ser Ser Ala
385                 390                 395                 400

Ala Ser Ser Pro Ser Ser Ser Ser Ser Lys Arg Glu Ala Arg Ser
                405                 410                 415

Ala Leu Asp Leu Asp Leu
                420

<210> SEQ ID NO 219
<211> LENGTH: 412
<212> TYPE: PRT
<213> ORGANISM: Artificial Sequence
<220> FEATURE:
<223> OTHER INFORMATION: alignment

<400> SEQUENCE: 219

Met Glu Phe Thr Thr Ser Ser Arg Phe Ser Lys Glu Glu Asp Glu
1               5                   10                  15

Glu Gln Asp Glu Ala Gly Arg Arg Glu Ile Pro Phe Met Thr Ala Thr
                20                  25                  30

Ala Glu Ala Ala Pro Ala Pro Thr Ser Ser Ser Ser Pro Ala His
                35                  40                  45

His Ala Ala Ser Ala Ser Ala Ser Ala Ser Gly Ser Ser Thr
            50                  55                  60

Pro Phe Arg Ser Asp Asp Gly Ala Gly Ala Ser Gly Ser Gly Gly Gly
65                  70                  75                  80

Gly Gly Gly Gly Gly Glu Ala Glu Val Val Glu Lys Glu His Met Phe
                85                  90                  95

Asp Lys Val Val Thr Pro Ser Asp Val Gly Lys Leu Asn Arg Leu Val
                100                 105                 110

Ile Pro Lys Gln Tyr Ala Glu Lys Tyr Phe Pro Leu Asp Ala Ala Ala
                115                 120                 125

Asn Glu Lys Gly Leu Leu Leu Asn Phe Glu Asp Arg Ala Gly Lys Pro
                130                 135                 140

Trp Arg Phe Arg Tyr Ser Tyr Trp Asn Ser Ser Gln Ser Tyr Val Met
```

```
                145                 150                 155                 160
Thr Lys Gly Trp Ser Arg Phe Val Lys Glu Lys Arg Leu Asp Ala Gly
                165                 170                 175

Asp Thr Val Ser Phe Ser Arg Gly Ile Gly Asp Glu Ala Ala Arg His
                180                 185                 190

Arg Leu Phe Ile Asp Trp Lys Arg Arg Ala Asp Thr Arg Asp Pro Leu
                195                 200                 205

Arg Leu Pro Arg Gly Leu Pro Leu Pro Met Pro Leu Thr Ser His Tyr
                210                 215                 220

Ala Pro Trp Gly Ile Gly Gly Gly Gly Phe Phe Val Gln Pro Ser
225                 230                 235                 240

Pro Pro Ala Thr Leu Tyr Glu His Arg Leu Arg Gln Gly Leu Asp Phe
                245                 250                 255

Arg Ala Phe Asn Pro Ala Ala Met Gly Arg Gln Val Leu Leu Phe
                260                 265                 270

Gly Ser Ala Arg Ile Pro Pro Gln Ala Pro Leu Leu Ala Arg Ala Pro
                275                 280                 285

Ser Pro Leu His His His Tyr Thr Leu Gln Pro Ser Gly Asp Gly Val
                290                 295                 300

Arg Ala Ala Gly Ser Pro Val Val Leu Asp Ser Val Pro Val Ile Glu
305                 310                 315                 320

Ser Pro Thr Thr Ala Ala Lys Arg Val Arg Leu Phe Gly Val Asn Leu
                325                 330                 335

Asp Asn Pro His Ala Gly Gly Gly Gly Ala Ala Gly Glu Ser
                340                 345                 350

Ser Asn His Gly Asn Ala Leu Ser Leu Gln Thr Pro Ala Trp Met Arg
                355                 360                 365

Arg Asp Pro Thr Leu Arg Leu Leu Glu Leu Pro Pro His His His His
                370                 375                 380

Gly Ala Glu Ser Ser Ala Ala Ser Ser Pro Ser Ser Ser Ser Ser Ser
385                 390                 395                 400

Lys Arg Asp Ala His Ser Ala Leu Asp Leu Asp Leu
                405                 410

<210> SEQ ID NO 220
<211> LENGTH: 409
<212> TYPE: PRT
<213> ORGANISM: Artificial Sequence
<220> FEATURE:
<223> OTHER INFORMATION: alignment

<400> SEQUENCE: 220

Met Glu Phe Thr Ala Thr Ser Ser Arg Phe Ser Lys Gly Glu Glu
1               5                   10                  15

Val Glu Glu Glu Gln Glu Glu Ala Ser Met Arg Glu Ile Pro Phe Met
                20                  25                  30

Thr Pro Ala Ala Thr Cys Ala Ala Pro Ser Ala Ser Ala
                35                  40                  45

Ser Ala Ser Thr Pro Ala Ser Ala Ser Gly Ser Ser Pro Pro Phe Arg
                50                  55                  60

Ser Gly Asp Asp Ala Gly Ala Ser Gly Ser Ala Gly Asp Gly Ser
65                  70                  75                  80

Arg Ser Asn Val Ala Glu Ala Val Glu Lys Glu His Met Phe Asp Lys
                85                  90                  95

Val Val Thr Pro Ser Asp Val Gly Lys Leu Asn Arg Leu Val Ile Pro
```

```
                100             105             110
Lys Gln Tyr Ala Glu Lys Tyr Phe Pro Leu Asp Ser Ala Ala Asn Glu
            115             120             125

Lys Gly Leu Leu Leu Asn Phe Glu Asp Ser Ala Gly Lys Pro Trp Arg
130             135             140

Phe Arg Tyr Ser Tyr Trp Asn Ser Ser Gln Ser Tyr Val Met Thr Lys
145             150             155             160

Gly Trp Ser Arg Phe Val Lys Glu Lys Arg Leu Asp Ala Gly Asp Thr
                165             170             175

Val Ser Phe Ser Arg Gly Ala Gly Glu Ala Ala Arg His Arg Leu Phe
            180             185             190

Ile Asp Trp Lys Arg Arg Ala Asp Thr Arg Asp Pro Leu Arg Leu Pro
        195             200             205

Arg Leu Pro Leu Pro Met Pro Leu Thr Ser His Tyr Ser Pro Trp Gly
    210             215             220

Leu Gly Ala Gly Ala Arg Gly Phe Phe Met Pro Pro Ser Pro Pro Ala
225             230             235             240

Thr Leu Tyr Glu His Arg Leu Arg Gln Gly Phe Asp Phe Arg Gly Met
                245             250             255

Asn Pro Ser Tyr Pro Thr Met Gly Arg Gln Val Ile Leu Phe Gly Ser
            260             265             270

Ala Ala Arg Met Pro Pro His Gly Pro Ala Pro Leu Leu Val Pro Arg
        275             280             285

Pro Pro Pro Pro Leu His Phe Thr Val Gln Gln Gln Gly Ser Asp Ala
    290             295             300

Gly Gly Ser Val Thr Ala Gly Ser Pro Val Val Leu Asp Ser Val Pro
305             310             315             320

Val Ile Glu Ser Pro Thr Thr Ala Thr Lys Lys Arg Val Arg Leu Phe
                325             330             335

Gly Val Asn Leu Asp Asn Pro Gln His Pro Gly Asp Gly Gly Gly Glu
            340             345             350

Ser Ser Asn Tyr Gly Ser Ala Leu Pro Leu Gln Met Pro Ala Ser Ala
        355             360             365

Trp Arg Pro Arg Asp His Thr Leu Arg Leu Leu Glu Phe Pro Ser His
    370             375             380

Gly Ala Glu Ala Ser Pro Ser Ser Ser Ser Ser Lys Arg Glu
385             390             395             400

Ala His Ser Gly Leu Asp Leu Asp Leu
                405

<210> SEQ ID NO 221
<211> LENGTH: 316
<212> TYPE: PRT
<213> ORGANISM: Artificial Sequence
<220> FEATURE:
<223> OTHER INFORMATION: alignment

<400> SEQUENCE: 221

Met Glu Phe Ala Thr Thr Ser Ser Arg Phe Ser Lys Glu Glu Glu Glu
1               5                   10                  15

Glu Glu Glu Gly Glu Gln Glu Met Gln Glu Gln Asp Glu Glu Glu
            20                  25                  30

Glu Glu Ala Glu Ala Ser Pro Arg Glu Ile Pro Phe Met Thr Ser Ala
        35                  40                  45

Ala Ala Ala Ala Thr Ala Ser Ser Ser Ser Pro Thr Ser Val Ser Pro
```

```
                    50                  55                  60

Ser Ala Thr Ala Ser Ala Ala Ser Thr Ser Ala Ser Gly Ser Pro
 65                  70                  75                  80

Phe Arg Ser Ser Asp Gly Ala Gly Ala Ser Gly Ser Gly Gly Gly
                     85                  90                  95

Gly Gly Glu Asp Val Glu Val Ile Glu Lys Glu His Met Phe Asp Lys
                    100                 105                 110

Val Val Thr Pro Ser Asp Val Gly Lys Leu Asn Arg Leu Val Ile Pro
                115                 120                 125

Lys Gln His Ala Glu Lys Tyr Phe Pro Leu Asp Ser Ala Ala Asn Glu
            130                 135                 140

Lys Gly Leu Leu Leu Ser Phe Glu Asp Arg Thr Gly Lys Leu Trp Arg
145                 150                 155                 160

Phe Arg Tyr Ser Tyr Trp Asn Ser Ser Gln Ser Tyr Val Met Thr Lys
                    165                 170                 175

Gly Trp Ser Arg Phe Val Lys Glu Lys Arg Leu Asp Ala Gly Asp Thr
                180                 185                 190

Val Ser Phe Cys Arg Gly Ala Ala Glu Ala Thr Arg Asp Arg Leu Phe
            195                 200                 205

Ile Asp Trp Lys Arg Arg Ala Asp Val Arg Asp Pro His Arg Phe Gln
210                 215                 220

Arg Leu Pro Leu Pro Met Thr Ser Pro Tyr Gly Pro Trp Gly Gly
225                 230                 235                 240

Ala Gly Ala Ser Ser Cys Arg Pro Arg Pro Pro Arg Ser Thr Ser
                    245                 250                 255

Ile Thr Ala Phe Ala Arg Ala Ser Thr Ser Ala Thr Ser Thr Pro Leu
                260                 265                 270

Cys Arg Arg Gly Ser Ser Ser Ser Ala Pro Gln Gly Arg Gly Phe
                275                 280                 285

Ile Ser Thr Arg Pro Cys His Arg Arg Arg His Leu Arg Leu Leu
            290                 295                 300

Thr Asn Ser Thr Leu Arg Cys Thr Thr Arg Ala Pro
305                 310                 315

<210> SEQ ID NO 222
<211> LENGTH: 409
<212> TYPE: PRT
<213> ORGANISM: Artificial Sequence
<220> FEATURE:
<223> OTHER INFORMATION: alignment

<400> SEQUENCE: 222

Met Glu Phe Ala Ser Ser Ser Arg Phe Ser Arg Glu Glu Asp Glu
 1               5                  10                  15

Glu Glu Glu Gln Glu Glu Glu Glu Glu Glu Glu Ala Ser Pro Arg
                 20                  25                  30

Glu Ile Pro Phe Met Thr Ala Ala Thr Ala Asp Thr Gly Ala Ala
                 35                  40                  45

Ala Ser Ser Ser Pro Ser Ala Ala Ser Ser Gly Pro Ala Ala
     50                  55                  60

Ala Pro Arg Ser Ser Asp Gly Ala Gly Ala Ser Gly Ser Gly Gly
 65                  70                  75                  80

Gly Ser Asp Asp Val Gln Val Ile Glu Lys Glu His Met Phe Asp Lys
                     85                  90                  95

Val Val Thr Pro Ser Asp Val Gly Lys Leu Asn Arg Leu Val Ile Pro
```

```
                100             105             110
Lys Gln His Ala Glu Lys Tyr Phe Pro Leu Asp Ala Ala Asn Glu
            115                 120                 125

Lys Gly Gln Leu Leu Ser Phe Glu Asp Arg Ala Gly Lys Leu Trp Arg
        130                 135                 140

Phe Arg Tyr Ser Tyr Trp Asn Ser Ser Gln Ser Tyr Val Met Thr Lys
145                 150                 155                 160

Gly Trp Ser Arg Phe Val Lys Glu Lys Arg Leu Asp Ala Gly Asp Thr
                165                 170                 175

Val Ser Phe Cys Arg Gly Ala Gly Asp Thr Ala Arg Asp Arg Leu Phe
            180                 185                 190

Ile Asp Trp Lys Arg Arg Ala Asp Ser Arg Asp Pro His Arg Met Pro
        195                 200                 205

Arg Leu Pro Leu Pro Met Ala Pro Val Ala Ser Pro Tyr Gly Pro Trp
    210                 215                 220

Gly Gly Gly Gly Gly Gly Ala Gly Gly Phe Phe Met Pro Pro Ala
225                 230                 235                 240

Pro Pro Ala Thr Leu Tyr Glu His His Arg Phe Arg Gln Ala Leu Asp
                245                 250                 255

Phe Arg Asn Ile Asn Ala Ala Ala Pro Ala Arg Gln Leu Leu Phe
            260                 265                 270

Phe Gly Ser Ala Gly Met Pro Pro Arg Ala Ser Met Pro Gln Gln Gln
        275                 280                 285

Gln Pro Pro Pro Pro His Pro Pro Leu His Ser Ile Met Leu Val
    290                 295                 300

Gln Pro Ser Pro Ala Pro Pro Thr Ala Ser Val Pro Met Leu Leu Asp
305                 310                 315                 320

Ser Val Pro Leu Val Asn Ser Pro Thr Ala Ala Ser Lys Arg Val Arg
                325                 330                 335

Leu Phe Gly Val Asn Leu Asp Asn Pro Gln Pro Gly Thr Ser Ala Glu
            340                 345                 350

Ser Ser Gln Asp Ala Asn Ala Leu Ser Leu Arg Thr Pro Gly Trp Gln
        355                 360                 365

Arg Pro Gly Pro Leu Arg Phe Phe Glu Ser Pro Gln Arg Gly Ala Glu
    370                 375                 380

Ser Ser Ala Ala Ser Ser Pro Ser Ser Ser Ser Lys Arg Glu
385                 390                 395                 400

Ala His Ser Ser Leu Asp Leu Asp Leu
                405

<210> SEQ ID NO 223
<211> LENGTH: 312
<212> TYPE: PRT
<213> ORGANISM: Artificial Sequence
<220> FEATURE:
<223> OTHER INFORMATION: alignment

<400> SEQUENCE: 223

Met Glu Phe Thr Pro Ile Ser Pro Pro Thr Arg Val Ala Gly Gly Glu
1               5                   10                  15

Glu Asp Ser Glu Arg Gly Ala Ala Trp Ala Val Glu Lys Glu
            20                  25                  30

His Met Phe Glu Lys Val Val Thr Pro Ser Asp Val Gly Lys Leu Asn
        35                  40                  45

Arg Leu Val Ile Pro Lys Gln His Ala Glu Arg Tyr Phe Pro Leu Asp
```

```
                    50                  55                  60
Ala Ala Ala Gly Ala Gly Gly Gly Gly Gly Gly Gly Gly Gly Gly Gly
 65                  70                  75                  80

Gly Gly Lys Gly Leu Val Leu Ser Phe Glu Asp Arg Thr Gly Lys Ala
                 85                  90                  95

Trp Arg Phe Arg Tyr Ser Tyr Trp Asn Ser Ser Gln Ser Tyr Val Met
                100                 105                 110

Thr Lys Gly Trp Ser Arg Phe Val Lys Glu Lys Arg Leu Gly Ala Gly
            115                 120                 125

Asp Thr Val Ser Phe Gly Arg Gly Leu Gly Asp Ala Ala Arg Gly Arg
130                 135                 140

Leu Phe Ile Asp Phe Arg Arg Arg Gln Asp Ala Gly Ser Phe Met
145                 150                 155                 160

Phe Pro Pro Thr Ala Ala Pro Pro Ser His Ser His His His His Gln
                165                 170                 175

Arg His His Pro Pro Leu Pro Ser Val Pro Leu Cys Pro Trp Arg Asp
            180                 185                 190

Tyr Thr Thr Ala Tyr Gly Gly Gly Tyr Gly Tyr Gly Tyr Gly Gly Gly
            195                 200                 205

Ser Thr Pro Ala Ser Ser Arg His Val Leu Phe Leu Arg Pro Gln Val
    210                 215                 220

Pro Ala Ala Val Val Leu Lys Ser Val Pro Val His Val Ala Ala Thr
225                 230                 235                 240

Ser Ala Val Gln Glu Ala Ala Thr Thr Arg Pro Lys Arg Val Arg
                245                 250                 255

Leu Phe Gly Val Asn Leu Asp Cys Pro Ala Ala Met Asp Asp Asp
                260                 265                 270

Asp Ile Ala Gly Ala Ala Ser Arg Thr Ala Ala Ser Ser Leu Leu Gln
            275                 280                 285

Leu Pro Ser Pro Ser Ser Thr Ser Ser Thr Ala Gly Lys Lys
            290                 295                 300

Met Cys Ser Leu Asp Leu Gly Leu
305                 310

<210> SEQ ID NO 224
<211> LENGTH: 277
<212> TYPE: PRT
<213> ORGANISM: Artificial Sequence
<220> FEATURE:
<223> OTHER INFORMATION: alignment

<400> SEQUENCE: 224

Met Glu Phe Thr Pro Ala His Ala His Ala Arg Val Val Glu Asp Ser
 1               5                  10                  15

Glu Arg Pro Arg Gly Gly Val Ala Trp Val Glu Lys Glu His Met Phe
                20                  25                  30

Glu Lys Val Val Thr Pro Ser Asp Val Gly Lys Leu Asn Arg Leu Val
            35                  40                  45

Ile Pro Lys Gln His Ala Glu Arg Tyr Phe Pro Ala Leu Asp Ala Ser
     50                  55                  60

Ser Ala Ala Ala Ala Ala Ala Ala Ala Gly Gly Gly Lys Gly
 65                  70                  75                  80

Leu Val Leu Ser Phe Glu Asp Arg Ala Gly Lys Ala Trp Arg Phe Arg
                 85                  90                  95

Tyr Ser Tyr Trp Asn Ser Ser Gln Ser Tyr Val Met Thr Lys Gly Trp
```

```
            100               105               110
Ser Arg Phe Val Lys Glu Lys Arg Leu Gly Ala Gly Asp Thr Val Leu
            115               120               125

Phe Ala Arg Gly Ala Gly Ala Arg Gly Arg Phe Phe Ile Asp Phe
            130               135               140

Arg Arg Arg Arg Gln Asp Leu Ala Phe Leu Gln Pro Thr Leu Ala Ser
145                 150               155               160

Ala Gln Arg Leu Leu Pro Leu Pro Ser Val Pro Ile Cys Pro Trp Gln
                165               170               175

Asp Tyr Gly Ala Ser Ala Pro Ala Pro Asn Arg His Val Leu Phe Leu
            180               185               190

Arg Pro Gln Val Pro Ala Ala Val Leu Lys Ser Val Pro Val His
            195               200               205

Val Ala Ala Ser Ala Val Glu Ala Thr Met Ser Lys Arg Val Arg Leu
            210               215               220

Phe Gly Val Asn Leu Asp Cys Pro Pro Asp Ala Glu Asp Ser Ala Thr
225                 230               235               240

Val Pro Arg Gly Arg Ala Ala Ser Thr Thr Leu Leu Gln Leu Pro Ser
                245               250               255

Pro Ser Ser Ser Thr Ser Ser Ser Thr Ala Gly Lys Asp Val Cys Cys
                260               265               270

Leu Asp Leu Gly Leu
            275

<210> SEQ ID NO 225
<211> LENGTH: 273
<212> TYPE: PRT
<213> ORGANISM: Artificial Sequence
<220> FEATURE:
<223> OTHER INFORMATION: alignment

<400> SEQUENCE: 225

Met Glu Phe Arg Pro Ala His Ala Arg Val Phe Glu Asp Ser Glu Arg
1               5                   10                  15

Pro Arg Gly Gly Val Ala Trp Leu Glu Lys Glu His Met Phe Glu Lys
                20                  25                  30

Val Val Thr Pro Ser Asp Val Gly Lys Leu Asn Arg Leu Val Ile Pro
            35                  40                  45

Lys Gln His Ala Glu Arg Tyr Phe Pro Ala Leu Asp Ala Ser Ala Ala
        50                  55                  60

Ala Ala Ser Ala Ser Ala Ser Ala Gly Gly Lys Ala Gly Leu Val
65                  70                  75                  80

Leu Ser Phe Glu Asp Arg Ala Gly Lys Ala Trp Arg Phe Arg Tyr Ser
                85                  90                  95

Tyr Trp Asn Ser Ser Gln Ser Tyr Val Met Thr Lys Gly Trp Ser Arg
                100                 105                 110

Phe Val Lys Glu Lys Arg Leu Gly Ala Gly Asp Thr Val Leu Phe Ala
            115                 120                 125

Arg Gly Ala Gly Ala Thr Arg Gly Arg Phe Phe Ile Asp Phe Arg Arg
        130                 135                 140

Arg Arg His Glu Leu Ala Phe Leu Gln Pro Leu Ala Ser Ala Gln
145                 150                 155                 160

Arg Leu Leu Pro Leu Pro Ser Val Pro Ile Cys Pro Trp Gln Gly Tyr
                165                 170                 175

Gly Ala Ser Ala Pro Ala Pro Ser Arg His Val Leu Phe Leu Arg Pro
```

```
            180                 185                 190
Gln Val Pro Ala Val Val Leu Thr Ser Val Pro Val Arg Val Ala
            195                 200                 205
Ala Ser Ala Val Glu Glu Ala Thr Arg Ser Lys Arg Val Arg Leu Phe
210                 215                 220
Gly Val Asn Leu Asp Cys Pro Pro Asp Ala Glu Asp Gly Ala Thr Ala
225                 230                 235                 240
Thr Arg Thr Pro Ser Thr Leu Leu Gln Leu Pro Ser Pro Ser Ser Ser
            245                 250                 255
Thr Ser Ser Ser Thr Gly Gly Lys Asp Val Arg Ser Leu Asp Leu Gly
            260                 265                 270
Leu

<210> SEQ ID NO 226
<211> LENGTH: 282
<212> TYPE: PRT
<213> ORGANISM: Artificial Sequence
<220> FEATURE:
<223> OTHER INFORMATION: alignment

<400> SEQUENCE: 226

Met Glu Phe Ile Thr Pro Ile Val Arg Pro Ala Ser Ala Ala Ala Gly
1               5                   10                  15
Gly Gly Glu Val Gln Glu Ser Gly Arg Pro Arg Gly Gly Val Ala Trp
            20                  25                  30
Leu Glu Lys Glu His Met Phe Glu Lys Val Val Thr Pro Ser Asp Val
            35                  40                  45
Gly Lys Leu Asn Arg Leu Val Ile Pro Lys Gln His Ala Glu Arg Tyr
        50                  55                  60
Phe Pro Ala Leu Asp Ala Ser Ala Ala Ala Ser Ala Ser Ala Ser
65                  70                  75                  80
Ala Gly Gly Gly Lys Ala Gly Leu Val Leu Ser Phe Glu Asp Arg Ala
                85                  90                  95
Gly Lys Ala Trp Arg Phe Arg Tyr Ser Tyr Trp Asn Ser Ser Gln Ser
            100                 105                 110
Tyr Val Met Thr Lys Gly Trp Ser Arg Phe Val Lys Glu Lys Arg Leu
            115                 120                 125
Gly Ala Gly Asp Thr Val Leu Phe Ala Arg Gly Ala Gly Ala Thr Arg
        130                 135                 140
Gly Arg Phe Phe Ile Asp Phe Arg Arg Arg His Glu Leu Ala Phe
145                 150                 155                 160
Leu Gln Pro Pro Leu Ala Ser Ala Gln Arg Leu Leu Pro Leu Pro Ser
                165                 170                 175
Val Pro Ile Cys Pro Trp Gln Gly Tyr Gly Ala Ser Ala Pro Ala Pro
            180                 185                 190
Ser Arg His Val Leu Phe Leu Arg Pro Gln Val Pro Ala Ala Val Val
            195                 200                 205
Leu Thr Ser Val Pro Val Arg Val Ala Ala Ser Ala Val Glu Glu Ala
        210                 215                 220
Thr Arg Ser Lys Arg Val Arg Leu Phe Gly Val Asn Leu Asp Cys Pro
225                 230                 235                 240
Pro Asp Ala Glu Asp Gly Ala Thr Ala Thr Arg Thr Pro Ser Thr Leu
                245                 250                 255
Leu Gln Leu Pro Ser Pro Ser Ser Ser Thr Ser Ser Ser Thr Gly Gly
            260                 265                 270
```

```
Lys Asp Val Arg Ser Leu Asp Leu Gly Leu
        275                 280
```

<210> SEQ ID NO 227
<211> LENGTH: 259
<212> TYPE: PRT
<213> ORGANISM: Artificial Sequence
<220> FEATURE:
<223> OTHER INFORMATION: alignment

<400> SEQUENCE: 227

```
Met Glu Phe Thr Thr Pro Pro Ala Thr Arg Ser Gly Gly Gly Glu
1               5                   10                  15

Glu Arg Ala Ala Ala Glu His Asn Gln His His Gln Gln Gln His Ala
            20                  25                  30

Thr Val Glu Lys Glu His Met Phe Asp Lys Val Val Thr Pro Ser Asp
        35                  40                  45

Val Gly Lys Leu Asn Arg Leu Val Ile Pro Lys Gln His Ala Glu Lys
    50                  55                  60

Tyr Phe Pro Leu Asp Ala Ala Asn Glu Lys Gly Leu Leu Leu Ser
65                  70                  75                  80

Phe Glu Asp Arg Thr Gly Lys Pro Trp Arg Phe Arg Tyr Ser Tyr Trp
                85                  90                  95

Asn Ser Ser Gln Ser Tyr Val Met Thr Lys Gly Trp Ser Arg Phe Val
                100                 105                 110

Lys Glu Lys Arg Leu Asp Ala Gly Asp Thr Val Ser Phe Gly Arg Gly
            115                 120                 125

Ile Ser Glu Ala Ala Arg Asp Arg Leu Phe Ile Asp Trp Arg Cys Arg
    130                 135                 140

Pro Asp Pro Pro Val Val His His Gln Tyr His His Arg Leu Pro Leu
145                 150                 155                 160

Pro Ser Ala Val Val Pro Tyr Ala Pro Trp Ala Ala His Ala His His
                165                 170                 175

His His Tyr Pro Ala Asp Gly His Thr Glu Pro Val Thr Pro Cys Leu
            180                 185                 190

Cys Ala Thr Leu Val Ala Thr Glu Met Arg Ala Ser Ser Ser Gln Leu
        195                 200                 205

Ser Leu Thr Arg Ser Asn Leu Ser Arg Pro Pro Gln Pro Arg Ile Ala
    210                 215                 220

Arg Val Asp Gly Ala Gln Pro Arg Pro Ser Ser Ser Pro Arg Gln Pro
225                 230                 235                 240

Gln Ser Leu Trp Cys Arg Ser Cys Gln Pro Gln Pro Arg Arg Thr Ala
                245                 250                 255

Asp Val Pro
```

<210> SEQ ID NO 228
<211> LENGTH: 327
<212> TYPE: PRT
<213> ORGANISM: Artificial Sequence
<220> FEATURE:
<223> OTHER INFORMATION: alignment

<400> SEQUENCE: 228

```
Met Glu Phe Thr Ala Pro Pro Ala Thr Arg Ser Gly Gly Gly Glu
1               5                   10                  15

Glu Arg Ala Ala Ala Glu His His Gln Gln Gln Gln Ala Thr Val
            20                  25                  30
```

Glu Lys Glu His Met Phe Asp Lys Val Val Thr Pro Ser Asp Val Gly
            35                  40                  45

Lys Leu Asn Arg Leu Val Ile Pro Lys Gln His Ala Glu Arg Tyr Phe
 50                  55                  60

Pro Leu Asp Ala Ala Asn Asp Lys Gly Leu Leu Ser Phe Glu
 65                  70                  75                  80

Asp Arg Ala Gly Lys Pro Trp Arg Phe Arg Tyr Ser Tyr Trp Asn Ser
                85                  90                  95

Ser Gln Ser Tyr Val Met Thr Lys Gly Trp Ser Arg Phe Val Lys Glu
                100                 105                 110

Lys Arg Leu Asp Ala Gly Asp Thr Val Ser Phe Gly Arg Gly Val Gly
            115                 120                 125

Glu Ala Ala Arg Gly Arg Leu Phe Ile Asp Trp Arg Arg Arg Pro Asp
130                 135                 140

Pro Pro Val Val His His Gln Tyr His His His Arg Leu Pro Leu Pro
145                 150                 155                 160

Ser Ala Val Val Pro Tyr Ala Pro Trp Ala Ala Ala His Ala His
                165                 170                 175

His His His Tyr Pro Ala Ala Gly Val Gly Ala Ala Arg Thr Thr Thr
            180                 185                 190

Thr Thr Thr Thr Thr Val Leu His His Leu Pro Pro Ser Pro Ser Pro
            195                 200                 205

Leu Tyr Leu Asp Thr Arg Arg Arg His Val Gly Tyr Asp Ala Tyr Gly
            210                 215                 220

Ala Gly Thr Arg Gln Leu Leu Phe Tyr Arg Pro His Gln Gln Pro Ser
225                 230                 235                 240

Thr Thr Val Met Leu Asp Ser Val Pro Val Arg Leu Pro Pro Thr Pro
                245                 250                 255

Gly Gln His Ala Glu Pro Pro Pro Ala Val Ala Ser Ser Ala Ser
                260                 265                 270

Lys Arg Val Arg Leu Phe Gly Val Asn Leu Asp Cys Ala Ala Ala Ala
            275                 280                 285

Gly Ser Glu Glu Glu Asn Val Gly Gly Trp Arg Thr Ser Ala Pro Pro
            290                 295                 300

Thr Gln Gln Ala Ser Ser Ser Ser Tyr Ser Ser Gly Lys Ala Arg
305                 310                 315                 320

Cys Ser Leu Asn Leu Asp Leu
                325

<210> SEQ ID NO 229
<211> LENGTH: 279
<212> TYPE: PRT
<213> ORGANISM: Artificial Sequence
<220> FEATURE:
<223> OTHER INFORMATION: alignment

<400> SEQUENCE: 229

Met Ala Met Asn His Pro Leu Phe Ser Gln Glu Gln Pro Gln Ser Trp
1               5                   10                  15

Pro Trp Gly Val Ala Met Tyr Ala Asn Phe His Tyr His His Tyr
            20                  25                  30

Glu Lys Glu His Met Phe Glu Lys Pro Leu Thr Pro Ser Asp Val Gly
            35                  40                  45

Lys Leu Asn Arg Leu Val Ile Pro Lys Gln His Ala Glu Arg Tyr Phe
 50                  55                  60

```
Pro Leu Gly Ala Gly Asp Ala Asp Lys Gly Leu Ile Leu Ser Phe
 65                  70                  75                  80

Glu Asp Glu Ala Gly Ala Pro Trp Arg Phe Arg Tyr Ser Tyr Trp Thr
                 85                  90                  95

Ser Ser Gln Ser Tyr Val Leu Thr Lys Gly Trp Ser Arg Tyr Val Lys
            100                 105                 110

Glu Lys Arg Leu Asp Ala Gly Asp Val Val His Phe Glu Arg Val Arg
        115                 120                 125

Gly Ser Phe Gly Val Gly Asp Arg Leu Phe Ile Gly Cys Arg Arg Arg
130                 135                 140

Gly Asp Ala Ala Ala Gln Thr Pro Ala Pro Pro Ala Val Arg
145                 150                 155                 160

Val Ala Pro Ala Ala Gln Asn Ala Gly Glu Gln Gln Pro Trp Ser Pro
                165                 170                 175

Met Cys Tyr Ser Thr Ser Gly Gly Ser Tyr Pro Thr Ser Pro Ala
            180                 185                 190

Asn Ser Tyr Ala Tyr Arg Arg Ala Ala Asp His Asp His Gly Asp Met
        195                 200                 205

His His Ala Asp Glu Ser Pro Arg Asp Thr Asp Ser Pro Ser Phe Ser
210                 215                 220

Ala Gly Ser Ala Pro Ser Arg Arg Leu Arg Leu Phe Gly Val Asn Leu
225                 230                 235                 240

Asp Cys Gly Pro Glu Pro Glu Ala Asp Thr Thr Ala Ala Ala Thr Met
                245                 250                 255

Tyr Gly Tyr Met His Gln Gln Ser Ser Tyr Ala Ala Met Ser Ala Val
            260                 265                 270

Pro Ser Tyr Trp Gly Asn Ser
            275

<210> SEQ ID NO 230
<211> LENGTH: 307
<212> TYPE: PRT
<213> ORGANISM: Artificial Sequence
<220> FEATURE:
<223> OTHER INFORMATION: alignment

<400> SEQUENCE: 230

Met Ala Thr Asn His Leu Ser Gln Gly Gln His Gln His Pro Gln Ala
  1               5                  10                  15

Trp Pro Trp Gly Val Ala Met Tyr Thr Asn Leu His Tyr His His Gln
                 20                  25                  30

Gln His His His Tyr Glu Lys Glu His Leu Phe Glu Lys Pro Leu Thr
             35                  40                  45

Pro Ser Asp Val Gly Lys Leu Asn Arg Leu Val Ile Pro Lys Gln His
         50                  55                  60

Ala Glu Arg Tyr Phe Pro Leu Ser Ser Ser Gly Ala Gly Asp Lys Gly
 65                  70                  75                  80

Leu Ile Leu Cys Phe Glu Asp Asp Asp Glu Ala Ala Ala
                 85                  90                  95

Asn Lys Pro Trp Arg Phe Arg Tyr Ser Tyr Trp Thr Ser Ser Gln Ser
            100                 105                 110

Tyr Val Leu Thr Lys Gly Trp Ser Arg Tyr Val Lys Glu Lys Gln Leu
        115                 120                 125

Asp Ala Gly Asp Val Val Arg Phe Gln Arg Met Arg Gly Phe Gly Met
130                 135                 140
```

```
Pro Asp Arg Leu Phe Ile Ser His Ser Arg Gly Glu Thr Thr Ala
145                 150                 155                 160

Thr Ala Ala Thr Thr Val Pro Pro Ala Ala Ala Val Arg Val Val
                165                 170                 175

Val Ala Pro Ala Gln Ser Ala Gly Ala Asp His Gln Gln Gln Gln
            180                 185                 190

Pro Ser Pro Trp Ser Pro Met Cys Tyr Ser Thr Ser Gly Ser Tyr Ser
        195                 200                 205

Tyr Pro Thr Ser Ser Pro Ala Asn Ser Gln His Ala Tyr His Arg His
        210                 215                 220

Ser Ala Asp His Asp His Ser Asn Asn Met Gln His Ala Gly Glu Ser
225                 230                 235                 240

Gln Ser Asp Arg Asp Asn Arg Ser Cys Ser Ala Ala Ser Ala Pro Pro
                245                 250                 255

Pro Pro Ser Arg Arg Leu Arg Leu Phe Gly Val Asn Leu Asp Cys Gly
                260                 265                 270

Pro Gly Pro Glu Pro Glu Thr Pro Thr Ala Met Tyr Gly Tyr Met His
                275                 280                 285

Gln Ser Pro Tyr Ala Tyr Asn Asn Trp Gly Ser Pro Tyr Gln His Asp
        290                 295                 300

Glu Glu Ile
305

<210> SEQ ID NO 231
<211> LENGTH: 288
<212> TYPE: PRT
<213> ORGANISM: Artificial Sequence
<220> FEATURE:
<223> OTHER INFORMATION: alignment

<400> SEQUENCE: 231

Met Ser Ser Ile Asn His Tyr Ser Pro Glu Thr Thr Leu Tyr Trp Thr
1               5                   10                  15

Asn Asp Gln Gln Gln Gln Ala Ala Met Trp Leu Ser Asn Ser His Thr
                20                  25                  30

Pro Arg Phe Asn Leu Asn Asp Glu Glu Glu Glu Glu Asp Asp Val
            35                  40                  45

Ile Val Ser Asp Lys Ala Thr Asn Asn Leu Thr Gln Glu Glu Glu Lys
        50                  55                  60

Val Ala Met Phe Glu Lys Pro Leu Thr Pro Ser Asp Val Gly Lys Leu
65                  70                  75                  80

Asn Arg Leu Val Ile Pro Lys Gln His Ala Glu Lys His Phe Pro Leu
                85                  90                  95

Asp Ser Ser Ala Ala Lys Gly Leu Leu Leu Ser Phe Glu Asp Glu Ser
            100                 105                 110

Gly Lys Cys Trp Arg Phe Arg Tyr Ser Tyr Trp Asn Ser Ser Gln Ser
        115                 120                 125

Tyr Val Leu Thr Lys Gly Trp Ser Arg Tyr Val Lys Asp Lys Arg Leu
130                 135                 140

His Ala Gly Asp Val Val Leu Phe His Arg His Arg Ser Leu Pro Gln
145                 150                 155                 160

Arg Phe Phe Ile Ser Cys Ser Arg Arg Gln Pro Asn Pro Val Pro Ala
                165                 170                 175

His Val Ser Thr Thr Arg Ser Ser Ala Ser Phe Tyr Ser Ala His Pro
            180                 185                 190
```

```
Pro Tyr Pro Ala His His Phe Pro Phe Pro Tyr Gln Pro His Ser Leu
        195                 200                 205

His Ala Pro Gly Gly Gly Ser Gln Gly Gln Asn Glu Thr Thr Pro Gly
    210                 215                 220

Gly Asn Ser Ser Ser Gly Ser Gly Arg Val Leu Arg Leu Phe Gly
225                 230                 235                 240

Val Asn Met Glu Cys Gln Pro Asp Asn His Asn Asp Ser Gln Asn Ser
                245                 250                 255

Thr Pro Glu Cys Ser Tyr Thr His Leu Tyr His Gln Thr Ser Ser
                260                 265                 270

Tyr Ser Ser Ser Asn Pro His His Met Val Pro Gln Gln Pro
        275                 280                 285
```

<210> SEQ ID NO 232
<211> LENGTH: 337
<212> TYPE: PRT
<213> ORGANISM: Artificial Sequence
<220> FEATURE:
<223> OTHER INFORMATION: alignment

<400> SEQUENCE: 232

```
Met Ser Ile Asn His Tyr Ser Met Asp Leu Pro Glu Pro Thr Leu Trp
1               5                   10                  15

Trp Pro His Pro His His Gln Gln Gln Gln Leu Thr Leu Met Asp Pro
            20                  25                  30

Asp Pro Leu Arg Leu Asn Leu Asn Ser Asp Asp Gly Asn Gly Asn Asp
        35                  40                  45

Asn Asp Asn Asp Glu Asn Gln Thr Thr Thr Thr Gly Gly Glu Gln Glu
50                  55                  60

Ile Leu Asp Asp Lys Glu Pro Met Phe Glu Lys Pro Leu Thr Pro Ser
65                  70                  75                  80

Asp Val Gly Lys Leu Asn Arg Leu Val Ile Pro Lys Gln His Ala Glu
                85                  90                  95

Lys Tyr Phe Pro Leu Ser Gly Asp Ser Gly Ser Glu Cys Lys Gly
            100                 105                 110

Leu Leu Leu Ser Phe Glu Asp Glu Ser Gly Lys Cys Trp Arg Phe Arg
        115                 120                 125

Tyr Ser Tyr Trp Asn Ser Ser Gln Ser Tyr Val Leu Thr Lys Gly Trp
        130                 135                 140

Ser Arg Tyr Val Lys Asp Lys Arg Leu Asp Ala Gly Asp Val Val Leu
145                 150                 155                 160

Phe Glu Arg His Arg Val Asp Ala Gln Arg Leu Phe Ile Gly Trp Arg
                165                 170                 175

Arg Arg Arg Gln Ser Asp Ala Ala Leu Pro Pro Ala His Val Ser Ser
            180                 185                 190

Arg Lys Ser Gly Gly Asp Gly Asn Ser Asn Lys Asn Glu Gly Trp
        195                 200                 205

Thr Arg Gly Phe Tyr Ser Ala His Pro Tyr Pro Thr His His Leu
    210                 215                 220

His His His Gln Pro Ser Pro Tyr Gln Gln His Asp Cys Leu His
225                 230                 235                 240

Ala Gly Arg Gly Ser Gln Gly Gln Asn Gln Arg Met Arg Pro Val Gly
                245                 250                 255

Asn Asn Ser Ser Ser Ser Ser Ser Ser Arg Val Leu Arg Leu Phe
            260                 265                 270
```

```
Gly Val Asp Met Glu Cys Gln Pro Glu His Asp Asp Ser Gly Pro Ser
            275                 280                 285

Thr Pro Gln Cys Ser Tyr Asn Ser Asn Asn Met Leu Pro Ser Thr Gln
    290                 295                 300

Gly Thr Asp His Ser His His Asn Phe Tyr Gln Gln Gln Pro Ser Asn
305                 310                 315                 320

Ser Asn Pro Ser Pro His His Met Met Val His His Gln Pro Tyr Tyr
                325                 330                 335

Tyr

<210> SEQ ID NO 233
<211> LENGTH: 344
<212> TYPE: PRT
<213> ORGANISM: Artificial Sequence
<220> FEATURE:
<223> OTHER INFORMATION: alignment

<400> SEQUENCE: 233

Met Ser Thr Asn His Tyr Thr Met Asp Leu Pro Glu Pro Thr Leu Trp
1               5                   10                  15

Trp Pro His Pro His Gln Gln Gln Leu Thr Leu Ile Asp Pro Asp Pro
            20                  25                  30

Leu Pro Leu Asn Leu Asn Asn Asp Asp Asn Asp Asn Gly Asp Asp Asn
        35                  40                  45

Asp Asn Asp Glu Asn Gln Thr Val Thr Thr Thr Thr Gly Gly Glu
    50                  55                  60

Glu Glu Ile Ile Asn Asn Lys Glu Pro Met Phe Glu Lys Pro Leu Thr
65                  70                  75                  80

Pro Ser Asp Val Gly Lys Leu Asn Arg Leu Val Ile Pro Lys Gln His
            85                  90                  95

Ala Glu Lys Tyr Phe Pro Leu Ser Gly Gly Asp Ser Gly Ser Ser Glu
        100                 105                 110

Cys Lys Gly Leu Leu Leu Ser Phe Glu Asp Glu Ser Gly Lys Cys Trp
    115                 120                 125

Arg Phe Arg Tyr Ser Tyr Trp Asn Ser Ser Gln Ser Tyr Val Leu Thr
130                 135                 140

Lys Gly Trp Ser Arg Tyr Val Lys Asp Lys Arg Leu Asp Ala Gly Asp
145                 150                 155                 160

Val Val Leu Phe Gln Arg His Arg Ala Asp Ala Gln Arg Leu Phe Ile
            165                 170                 175

Gly Trp Arg Arg Arg Arg Gln Ser Asp Ala Leu Pro Pro Pro Ala His
        180                 185                 190

Val Ser Ser Arg Lys Ser Gly Gly Asp Gly Asn Ser Ser Lys Asn Glu
    195                 200                 205

Gly Asp Val Gly Val Gly Trp Thr Arg Gly Phe Tyr Pro Ala His His
210                 215                 220

Pro Tyr Pro Thr His His His His Pro Ser Pro Tyr His His Gln Gln
225                 230                 235                 240

Asp Asp Ser Leu His Ala Val Arg Gly Ser Gln Gly Gln Asn Gln Arg
            245                 250                 255

Thr Arg Pro Val Gly Asn Ser Ser Ser Ser Ser Ser Ser Ser Ser Arg
        260                 265                 270

Val Leu Arg Leu Phe Gly Val Asn Met Glu Cys Gln Pro Glu His Asp
    275                 280                 285
```

```
Asp Ser Gly Pro Ser Thr Pro Gln Cys Ser Tyr Asn Thr Asn Asn Ile
    290                 295                 300

Leu Pro Ser Thr Gln Gly Thr Asp Ile His Ser His Leu Asn Phe Tyr
305                 310                 315                 320

Gln Gln Gln Gln Thr Ser Asn Ser Lys Pro Pro His His Met Met
                325                 330                 335

Ile Arg His Gln Pro Tyr Tyr Tyr
                340

<210> SEQ ID NO 234
<211> LENGTH: 245
<212> TYPE: PRT
<213> ORGANISM: Artificial Sequence
<220> FEATURE:
<223> OTHER INFORMATION: alignment

<400> SEQUENCE: 234

Met Ser Ile Asn Gln Tyr Ser Ser Glu Phe Tyr Tyr His Ser Leu Met
1               5                   10                  15

Trp Gln Gln Gln Gln His His Gln Asn Glu Val Val Glu Glu
            20                  25                  30

Lys Glu Ala Leu Phe Glu Lys Pro Leu Thr Pro Ser Asp Val Gly Lys
        35                  40                  45

Leu Asn Arg Leu Val Ile Pro Lys Gln His Ala Glu Arg Tyr Phe Pro
    50                  55                  60

Leu Ala Ala Ala Val Asp Ala Val Glu Lys Gly Leu Leu Leu Cys
65                  70                  75                  80

Phe Glu Asp Glu Glu Gly Lys Pro Trp Arg Phe Arg Tyr Ser Tyr Trp
                85                  90                  95

Asn Ser Ser Gln Ser Tyr Val Leu Thr Lys Gly Trp Ser Arg Tyr Val
            100                 105                 110

Lys Glu Lys Gln Leu Asp Ala Gly Asp Val Val Leu Phe His Arg His
        115                 120                 125

Arg Ala Asp Gly Gly Arg Phe Phe Ile Gly Trp Arg Arg Gly Asp
    130                 135                 140

Ser Ser Ser Ser Ser Asp Ser Tyr Arg Asn Leu Gln Ser Asn Ser Ser
145                 150                 155                 160

Leu Gln Tyr Tyr Pro His Ala Gly Ala Gln Ala Val Glu Asn Gln Arg
                165                 170                 175

Gly Asn Ser Lys Thr Leu Arg Leu Phe Gly Val Asn Met Glu Cys Gln
            180                 185                 190

Ile Asp Ser Asp Trp Ser Glu Pro Ser Thr Pro Asp Gly Phe Thr Thr
        195                 200                 205

Cys Pro Thr Asn His Asp Gln Phe Pro Ile Tyr Pro Glu His Phe Pro
    210                 215                 220

Pro Pro Tyr Tyr Met Asp Val Ser Phe Thr Gly Asp Val His Gln Thr
225                 230                 235                 240

Ser Ser Gln Gln Gly
                245

<210> SEQ ID NO 235
<211> LENGTH: 244
<212> TYPE: PRT
<213> ORGANISM: Artificial Sequence
<220> FEATURE:
<223> OTHER INFORMATION: alignment

<400> SEQUENCE: 235
```

```
Met Ser Ile Asn Gln Tyr Ser Ser Asp Phe His Tyr His Ser Leu Met
1               5                   10                  15

Trp Gln Gln Gln Gln Gln Gln Gln His Gln Asn Asp Val Val Glu
            20                  25                  30

Glu Lys Glu Ala Leu Phe Glu Lys Pro Leu Thr Pro Ser Asp Val Gly
        35                  40                  45

Lys Leu Asn Arg Leu Val Ile Pro Lys Gln His Ala Glu Arg Tyr Phe
50                  55                  60

Pro Leu Ala Ala Ala Ala Asp Ala Val Glu Lys Gly Leu Leu Leu
65                  70                  75                  80

Cys Phe Glu Asp Glu Glu Gly Lys Pro Trp Arg Phe Arg Tyr Ser Tyr
            85                  90                  95

Trp Asn Ser Ser Gln Ser Tyr Val Leu Thr Lys Gly Trp Ser Arg Tyr
                100                 105                 110

Val Lys Glu Lys His Leu Asp Ala Gly Asp Val Val Leu Phe His Arg
            115                 120                 125

His Arg Ser Asp Gly Gly Arg Phe Phe Ile Gly Trp Arg Arg Gly
        130                 135                 140

Asp Ser Ser Ser Ser Asp Ser Tyr Arg His Val Gln Ser Asn Ala
145                 150                 155                 160

Ser Leu Gln Tyr Tyr Pro His Ala Gly Ala Gln Ala Val Glu Ser Gln
                165                 170                 175

Arg Gly Asn Ser Lys Thr Leu Arg Leu Phe Gly Val Asn Met Glu Cys
            180                 185                 190

Gln Leu Asp Ser Asp Trp Ser Glu Pro Ser Thr Pro Asp Gly Ser Asn
        195                 200                 205

Thr Tyr Thr Thr Asn His Asp Gln Phe His Tyr Pro Gln Gln Gln
210                 215                 220

His Tyr Pro Pro Pro Tyr Tyr Met Asp Ile Ser Phe Thr Gly Asp Met
225                 230                 235                 240

Asn Arg Thr Ser

<210> SEQ ID NO 236
<211> LENGTH: 248
<212> TYPE: PRT
<213> ORGANISM: Artificial Sequence
<220> FEATURE:
<223> OTHER INFORMATION: alignment

<400> SEQUENCE: 236

Met Ser Ile Asn Gln Tyr Ser Ser Asp Phe Asn Tyr His Ser Leu Met
1               5                   10                  15

Trp Gln Gln Gln Gln His Arg His His His Gln Asn Asp Val Ala
            20                  25                  30

Glu Glu Lys Glu Ala Leu Phe Glu Lys Pro Leu Thr Pro Ser Asp Val
        35                  40                  45

Gly Lys Leu Asn Arg Leu Val Ile Pro Lys Gln His Ala Glu Arg Tyr
    50                  55                  60

Phe Pro Leu Ala Ala Ala Ala Ala Asp Ala Met Glu Lys Gly Leu Leu
65                  70                  75                  80

Leu Cys Phe Glu Asp Glu Glu Gly Lys Pro Trp Arg Phe Arg Tyr Ser
            85                  90                  95

Tyr Trp Asn Ser Ser Gln Ser Tyr Val Leu Thr Lys Gly Trp Ser Arg
                100                 105                 110
```

```
Tyr Val Lys Glu Lys Gln Leu Asp Ala Gly Asp Val Ile Leu Phe His
            115                 120                 125
Arg His Arg Val Asp Gly Gly Arg Phe Phe Ile Gly Trp Arg Arg
130                 135                 140
Gly Asn Ser Ser Ser Ser Asp Ser Tyr Arg His Leu Gln Ser Asn
145                 150                 155                 160
Ala Ser Leu Gln Tyr Tyr Pro His Ala Gly Val Gln Ala Val Glu Ser
                165                 170                 175
Gln Arg Gly Asn Ser Lys Thr Leu Arg Leu Phe Gly Val Asn Met Glu
                180                 185                 190
Cys Gln Leu Asp Ser Asp Leu Pro Asp Pro Ser Thr Pro Asp Gly Ser
            195                 200                 205
Thr Ile Cys Pro Thr Ser His Asp Gln Phe His Leu Tyr Pro Gln Gln
            210                 215                 220
His Tyr Pro Pro Pro Tyr Tyr Met Asp Ile Ser Phe Thr Gly Asp Val
225                 230                 235                 240
His Gln Thr Arg Ser Pro Gln Gly
                245

<210> SEQ ID NO 237
<211> LENGTH: 267
<212> TYPE: PRT
<213> ORGANISM: Artificial Sequence
<220> FEATURE:
<223> OTHER INFORMATION: alignment

<400> SEQUENCE: 237

Met Ser Val Asn His Tyr His Asn Thr Leu Ser Leu His His His
1               5                   10                  15
Gln Asn Asp Val Ala Ile Ala Gln Arg Glu Ser Leu Phe Glu Lys Ser
                20                  25                  30
Leu Thr Pro Ser Asp Val Gly Lys Leu Asn Arg Leu Val Ile Pro Lys
            35                  40                  45
Gln His Ala Glu Lys Tyr Phe Pro Leu Asn Asn Asn Asn Asn Gly
        50                  55                  60
Gly Ser Gly Asp Asp Val Ala Thr Thr Glu Lys Gly Met Leu Leu Ser
65                  70                  75                  80
Phe Glu Asp Glu Ser Gly Lys Cys Trp Lys Phe Arg Tyr Ser Tyr Trp
                85                  90                  95
Asn Ser Ser Gln Ser Tyr Val Leu Thr Lys Gly Trp Ser Arg Tyr Val
                100                 105                 110
Lys Asp Lys His Leu Asp Ala Gly Asp Val Val Phe Gln Arg His
            115                 120                 125
Arg Phe Asp Leu His Arg Leu Phe Ile Gly Trp Arg Arg Arg Gly Glu
130                 135                 140
Ala Ser Ser Ser Pro Ala Val Ser Val Val Ser Gln Glu Ala Leu Val
145                 150                 155                 160
Asn Thr Thr Ala Tyr Trp Ser Gly Leu Thr Thr Pro Tyr Arg Gln Val
                165                 170                 175
His Ala Ser Thr Thr Tyr Pro Asn Ile His Gln Glu Tyr Ser His Tyr
                180                 185                 190
Gly Ala Val Val Asp His Ala Gln Ser Ile Pro Pro Val Val Ala Gly
            195                 200                 205
Ser Ser Arg Thr Val Arg Leu Phe Gly Val Asn Leu Glu Cys His Gly
210                 215                 220
```

```
Asp Ala Val Glu Pro Pro Arg Pro Asp Val Tyr Asn Asp Gln His
225                 230                 235                 240

Ile Tyr Tyr Tyr Ser Thr Pro His Pro Met Asn Ile Ser Phe Ala Gly
                245                 250                 255

Glu Ala Leu Glu Gln Val Gly Asp Gly Arg Gly
            260                 265
```

<210> SEQ ID NO 238
<211> LENGTH: 264
<212> TYPE: PRT
<213> ORGANISM: Artificial Sequence
<220> FEATURE:
<223> OTHER INFORMATION: alignment

<400> SEQUENCE: 238

```
Met Ser Gly Asn His Tyr Ser Arg Asp Ile His His Asn Thr Pro Ser
1               5                   10                  15

Val His His Gln Asn Tyr Ala Val Val Asp Arg Glu Tyr Leu Phe
            20                  25                  30

Glu Lys Ser Leu Thr Pro Ser Asp Val Gly Lys Leu Asn Arg Leu Val
            35                  40                  45

Ile Pro Lys Gln His Ala Glu Lys His Phe Pro Leu Asn Asn Ala Gly
50                  55                  60

Asp Val Ala Ala Ala Glu Thr Thr Glu Lys Gly Met Leu Leu Thr
65                  70                  75                  80

Phe Glu Asp Glu Ser Gly Lys Cys Trp Lys Phe Arg Tyr Ser Tyr Trp
                85                  90                  95

Asn Ser Ser Gln Ser Tyr Val Leu Thr Lys Gly Trp Ser Arg Tyr Val
            100                 105                 110

Lys Asp Lys His Leu His Ala Gly Asp Val Val Phe Phe Gln Arg His
            115                 120                 125

Arg Phe Asp Leu His Arg Val Phe Ile Gly Trp Arg Lys Arg Gly Glu
130                 135                 140

Val Ser Ser Pro Thr Ala Val Ser Val Val Ser Gln Glu Ala Arg Val
145                 150                 155                 160

Asn Thr Thr Ala Tyr Trp Ser Gly Leu Thr Thr Pro Tyr Arg Gln Val
                165                 170                 175

His Ala Ser Thr Ser Ser Tyr Pro Asn Ile His Gln Glu Tyr Ser His
            180                 185                 190

Tyr Gly Ala Val Ala Glu Ile Pro Thr Val Thr Gly Ser Ser Arg
            195                 200                 205

Thr Val Arg Leu Phe Gly Val Asn Leu Glu Cys His Gly Asp Val Val
210                 215                 220

Glu Thr Pro Pro Cys Pro Asp Gly Tyr Asn Gly Gln His Phe Tyr Tyr
225                 230                 235                 240

Tyr Ser Thr Pro Asp Pro Met Asn Ile Ser Phe Ala Gly Glu Ala Met
                245                 250                 255

Glu Gln Val Gly Asp Gly Arg Arg
            260
```

<210> SEQ ID NO 239
<211> LENGTH: 258
<212> TYPE: PRT
<213> ORGANISM: Artificial Sequence
<220> FEATURE:
<223> OTHER INFORMATION: alignment

<400> SEQUENCE: 239

Met Ser Val Asn His Tyr Ser Asn Thr Leu Ser Ser His Asn His
1               5                   10                  15

Asn Glu His Lys Glu Ser Leu Phe Glu Lys Ser Leu Thr Pro Ser Asp
                20                  25                  30

Val Gly Lys Leu Asn Arg Leu Val Ile Pro Lys Gln His Ala Glu Arg
            35                  40                  45

Tyr Leu Pro Leu Asn Asn Cys Gly Gly Gly Asp Val Thr Ala Glu
    50                  55                  60

Ser Thr Glu Lys Gly Val Leu Leu Ser Phe Glu Asp Glu Ser Gly Lys
65                  70                  75                  80

Ser Trp Lys Phe Arg Tyr Ser Tyr Trp Asn Ser Ser Gln Ser Tyr Val
                85                  90                  95

Leu Thr Lys Gly Trp Ser Arg Tyr Val Lys Asp Lys His Leu Asn Ala
                100                 105                 110

Gly Asp Val Val Leu Phe Gln Arg His Arg Phe Asp Ile His Arg Leu
            115                 120                 125

Phe Ile Gly Trp Arg Arg Gly Glu Ala Ser Ser Ser Ala Val
130                 135                 140

Ser Ala Val Thr Gln Asp Pro Arg Ala Asn Thr Thr Ala Tyr Trp Asn
145                 150                 155                 160

Gly Leu Thr Thr Pro Tyr Arg Gln Val His Ala Ser Thr Ser Ser Tyr
                165                 170                 175

Pro Asn Asn Ile His Gln Glu Tyr Ser His Tyr Gly Pro Val Ala Glu
                180                 185                 190

Thr Pro Thr Val Ala Ala Gly Ser Ser Lys Thr Val Arg Leu Phe Gly
                195                 200                 205

Val Asn Leu Glu Cys His Ser Asp Val Val Glu Pro Pro Cys Pro
        210                 215                 220

Asp Ala Tyr Asn Gly Gln His Ile Tyr Tyr Ser Thr Pro His Pro
225                 230                 235                 240

Met Asn Ile Ser Phe Ala Gly Glu Ala Met Glu Gln Val Gly Asp Gly
                245                 250                 255

Arg Gly

<210> SEQ ID NO 240
<211> LENGTH: 278
<212> TYPE: PRT
<213> ORGANISM: Artificial Sequence
<220> FEATURE:
<223> OTHER INFORMATION: alignment

<400> SEQUENCE: 240

Met Ser Val Asn His Tyr Ser Thr Asp His His Thr Leu Leu Trp
1               5                   10                  15

Gln Gln Gln Gln His Arg His Thr Thr Asp Thr Ser Glu Thr Thr Thr
                20                  25                  30

Thr Ala Thr Trp Leu His Asp Asp Leu Lys Glu Ser Leu Phe Glu Lys
            35                  40                  45

Ser Leu Thr Pro Ser Asp Val Gly Lys Leu Asn Arg Leu Val Ile Pro
    50                  55                  60

Lys Gln His Ala Glu Lys Tyr Phe Pro Leu Asn Ala Val Leu Val Ser
65                  70                  75                  80

Ser Ala Ala Ala Asp Thr Ser Ser Ser Leu Leu Ser Phe Glu Asp Glu
                85                  90                  95

```
Ser Gly Lys Ser Trp Arg Phe Arg Tyr Ser Tyr Trp Asn Ser Ser Gln
            100                 105                 110

Ser Tyr Val Leu Thr Lys Gly Trp Ser Arg Phe Val Lys Asp Lys Gln
        115                 120                 125

Leu Asp Pro Gly Asp Val Val Phe Phe Gln Arg His Arg Ser Asp Ser
    130                 135                 140

Arg Arg Leu Phe Ile Gly Trp Arg Arg Gly Gln Gly Ser Ser Ser
145                 150                 155                 160

Ser Val Ala Ala Thr Asn Ser Ala Val Asn Thr Ser Ser Met Gly Ala
                165                 170                 175

Leu Ser Tyr His Gln Ile His Ala Thr Ser Asn Tyr Ser Asn Pro Pro
            180                 185                 190

Ser His Ser Glu Tyr Ser His Tyr Gly Ala Ala Val Ala Thr Ala Ala
        195                 200                 205

Glu Thr His Ser Thr Pro Ser Ser Val Val Gly Ser Ser Arg Thr
210                 215                 220

Val Arg Leu Phe Gly Val Asn Leu Glu Cys Gln Met Asp Glu Asn Asp
225                 230                 235                 240

Gly Asp Asp Ser Val Ala Val Ala Thr Val Glu Ser Pro Asp Gly
                245                 250                 255

Tyr Tyr Gly Gln Asn Met Tyr Tyr Tyr Ser His Pro His Asn Met
            260                 265                 270

Val Ile Leu Thr Leu Leu
        275

<210> SEQ ID NO 241
<211> LENGTH: 267
<212> TYPE: PRT
<213> ORGANISM: Artificial Sequence
<220> FEATURE:
<223> OTHER INFORMATION: alignment

<400> SEQUENCE: 241

Met Ser Val Asn His Tyr Ser Thr Asp His His Gln Val His His His
1               5                   10                  15

His Thr Leu Phe Leu Gln Asn Leu His Thr Thr Asp Thr Ser Glu Pro
            20                  25                  30

Thr Thr Thr Ala Ala Thr Ser Leu Arg Glu Asp Gln Lys Glu Tyr Leu
        35                  40                  45

Phe Glu Lys Ser Leu Thr Pro Ser Asp Val Gly Lys Leu Asn Arg Leu
    50                  55                  60

Val Ile Pro Lys Gln His Ala Glu Lys Tyr Phe Pro Leu Asn Thr Ile
65                  70                  75                  80

Ile Ser Asn Asn Ala Glu Glu Lys Gly Met Leu Leu Ser Phe Glu Asp
                85                  90                  95

Glu Ser Gly Lys Cys Trp Arg Phe Arg Tyr Ser Tyr Trp Asn Ser Ser
            100                 105                 110

Gln Ser Tyr Val Leu Thr Lys Gly Trp Ser Arg Tyr Val Lys Asp Lys
        115                 120                 125

Gln Leu Asp Pro Ala Asp Val Val Phe Phe Gln Arg Gln Arg Ser Asp
    130                 135                 140

Ser Arg Arg Leu Phe Ile Gly Trp Arg Arg Gly Gln Gly Ser Ser
145                 150                 155                 160

Ser Ala Ala Asn Thr Thr Ser Tyr Ser Ser Met Thr Ala Pro Pro
                165                 170                 175
```

```
Tyr Ser Asn Tyr Ser Asn Arg Pro Ala His Ser Glu Tyr Ser His Tyr
            180                 185                 190

Gly Ala Ala Val Ala Thr Ala Thr Glu Thr His Phe Ile Pro Ser Ser
            195                 200                 205

Ser Ala Val Gly Ser Ser Arg Thr Val Arg Leu Phe Gly Val Asn Leu
            210                 215                 220

Glu Cys Gln Met Asp Glu Asp Glu Gly Asp Asp Ser Val Ala Thr Ala
225                 230                 235                 240

Ala Ala Ala Glu Cys Pro Arg Gln Asp Ser Tyr Tyr Asp Gln Asn Met
            245                 250                 255

Tyr Asn Tyr Tyr Thr Pro His Ser Ser Ala Ser
            260                 265

<210> SEQ ID NO 242
<211> LENGTH: 347
<212> TYPE: PRT
<213> ORGANISM: Artificial Sequence
<220> FEATURE:
<223> OTHER INFORMATION: alignment

<400> SEQUENCE: 242

Met Ile Gly Val Glu Lys Val Thr Ile Cys Met Arg Ile Glu Val Asn
1               5                   10                  15

Thr Glu Lys Gly Arg Arg Ala Leu Met Asp Cys Trp Gln Ile Ser Gly
            20                  25                  30

Val His Glu Ser Ser Asp Cys Ser Glu Ile Lys Phe Ala Phe Asp Ala
            35                  40                  45

Val Val Lys Arg Ala Arg His Glu Glu Asn Asn Ala Ala Gln Lys
    50                  55                  60

Phe Lys Gly Val Val Ser Gln Gln Asn Gly Asn Trp Gly Ala Gln Ile
65                  70                  75                  80

Tyr Ala His Gln Gln Arg Ile Trp Leu Gly Thr Phe Lys Ser Glu Arg
                85                  90                  95

Glu Ala Ala Met Ala Tyr Asp Ser Ala Ser Ile Lys Leu Arg Ser Gly
            100                 105                 110

Glu Cys His Arg Asn Phe Pro Trp Asn Asp Gln Thr Val Gln Glu Pro
            115                 120                 125

Gln Phe Gln Ser His Tyr Ser Ala Glu Thr Val Leu Asn Met Ile Arg
130                 135                 140

Asp Gly Thr Tyr Pro Ser Lys Phe Ala Thr Phe Leu Lys Thr Arg Gln
145                 150                 155                 160

Thr Gln Lys Gly Val Ala Lys His Ile Gly Leu Lys Gly Asp Asp Glu
            165                 170                 175

Glu Gln Phe Cys Cys Thr Gln Leu Phe Gln Lys Glu Leu Thr Pro Ser
            180                 185                 190

Asp Val Gly Lys Leu Asn Arg Leu Val Ile Pro Lys Lys His Ala Val
            195                 200                 205

Ser Tyr Phe Pro Tyr Val Gly Gly Ser Ala Asp Glu Ser Gly Ser Val
            210                 215                 220

Asp Val Glu Ala Val Phe Tyr Asp Lys Leu Met Arg Leu Trp Lys Phe
225                 230                 235                 240

Arg Tyr Cys Tyr Trp Lys Ser Ser Gln Ser Tyr Val Phe Thr Arg Gly
                245                 250                 255

Trp Asn Arg Phe Val Lys Asp Lys Lys Leu Lys Ala Lys Asp Val Ile
            260                 265                 270
```

Ala Phe Phe Thr Trp Gly Lys Ser Gly Glu Gly Ala Phe Ala
            275                 280                 285

Leu Ile Asp Val Ile Tyr Asn Asn Ala Glu Glu Asp Ser Lys Gly
290                 295                 300

Asp Thr Lys Gln Val Leu Gly Asn Gln Leu Gln Leu Ala Gly Ser Glu
305                 310                 315                 320

Glu Gly Glu Asp Glu Asp Ala Asn Ile Gly Lys Asp Phe Asn Ala Gln
                325                 330                 335

Lys Gly Leu Arg Leu Phe Gly Val Cys Ile Thr
            340                 345

<210> SEQ ID NO 243
<211> LENGTH: 267
<212> TYPE: PRT
<213> ORGANISM: Artificial Sequence
<220> FEATURE:
<223> OTHER INFORMATION: alignment

<400> SEQUENCE: 243

Met Leu Arg Lys His Ile Tyr Pro Asp Glu Leu Ala Gln His Lys Arg
1               5                   10                  15

Ala Phe Phe Phe Ala Ala Ala Ser Ser Pro Thr Ser Ser Ser Ser Pro
                20                  25                  30

Leu Ala Ser Pro Ala Pro Ser Ala Ala Ala Arg Arg Glu His Leu
            35                  40                  45

Phe Asp Lys Thr Val Thr Pro Ser Asp Val Gly Lys Leu Asn Arg Leu
50                  55                  60

Val Ile Pro Lys Gln His Ala Glu Lys His Phe Pro Leu Gln Leu Pro
65                  70                  75                  80

Ser Ala Ser Ala Ala Val Pro Gly Glu Cys Lys Gly Val Leu Leu Asn
                85                  90                  95

Phe Asp Asp Ala Thr Gly Lys Val Trp Arg Phe Arg Tyr Ser Tyr Trp
            100                 105                 110

Asn Ser Ser Gln Ser Tyr Val Leu Thr Lys Gly Trp Ser Arg Phe Val
        115                 120                 125

Lys Glu Lys Gly Leu His Ala Gly Asp Ala Val Glu Phe Tyr Arg Ala
130                 135                 140

Ala Ser Gly Asn Asn Gln Leu Phe Ile Asp Cys Lys Leu Arg Ser Lys
145                 150                 155                 160

Ser Thr Thr Thr Thr Thr Ser Val Asn Ser Glu Ala Ala Pro Ser Pro
                165                 170                 175

Ala Pro Val Thr Arg Thr Val Arg Leu Phe Gly Val Asp Leu Leu Ile
            180                 185                 190

Ala Pro Ala Ala Arg His Ala His Glu His Glu Asp Tyr Gly Met Ala
        195                 200                 205

Lys Thr Asn Lys Arg Thr Met Glu Ala Ser Val Ala Ala Pro Thr Pro
210                 215                 220

Ala His Ala Val Trp Lys Lys Arg Cys Val Asp Phe Ala Leu Thr Tyr
225                 230                 235                 240

Arg Leu Ala Thr Thr Pro Gln Cys Pro Arg Ser Arg Asp Gln Leu Glu
                245                 250                 255

Gly Val Gln Ala Ala Gly Ser Thr Phe Ala Leu
            260                 265

<210> SEQ ID NO 244
<211> LENGTH: 393

<212> TYPE: PRT
<213> ORGANISM: Artificial Sequence
<220> FEATURE:
<223> OTHER INFORMATION: alignment

<400> SEQUENCE: 244

```
Met Asp Ser Ser Ser Cys Leu Val Asp Asp Thr Asn Ser Gly Gly Ser
1               5                   10                  15

Ser Thr Asp Lys Leu Arg Ala Leu Ala Ala Ala Ala Glu Thr Ala
            20                  25                  30

Pro Leu Glu Arg Met Gly Ser Gly Ala Ser Ala Val Val Asp Ala Ala
            35                  40                  45

Glu Pro Gly Ala Glu Ala Asp Ser Gly Ser Gly Arg Val Cys Gly
    50                  55                  60

Gly Gly Gly Gly Ala Gly Gly Ala Gly Gly Lys Leu Pro Ser Ser
65              70                  75                  80

Lys Phe Lys Gly Val Val Pro Gln Pro Asn Gly Arg Trp Gly Ala Gln
                85                  90                  95

Ile Tyr Glu Arg His Gln Arg Val Trp Leu Gly Thr Phe Ala Gly Glu
            100                 105                 110

Asp Asp Ala Ala Arg Ala Tyr Asp Val Ala Ala Gln Arg Phe Arg Gly
            115                 120                 125

Arg Asp Ala Val Thr Asn Phe Arg Pro Leu Ala Glu Ala Asp Pro Asp
130                 135                 140

Ala Ala Ala Glu Leu Arg Phe Leu Ala Thr Arg Ser Lys Ala Glu Val
145                 150                 155                 160

Val Asp Met Leu Arg Lys His Thr Tyr Phe Asp Glu Leu Ala Gln Ser
                165                 170                 175

Lys Arg Thr Phe Ala Ala Ser Thr Pro Ser Ala Ala Thr Thr Thr Ala
            180                 185                 190

Ser Leu Ser Asn Gly His Leu Ser Ser Pro Arg Ser Pro Phe Ala Pro
        195                 200                 205

Ala Ala Ala Arg Asp His Leu Phe Asp Lys Thr Val Thr Pro Ser Asp
210                 215                 220

Val Gly Lys Leu Asn Arg Leu Val Ile Pro Lys Gln His Ala Glu Lys
225                 230                 235                 240

His Phe Pro Leu Gln Leu Pro Ser Ala Gly Gly Glu Ser Lys Gly Val
                245                 250                 255

Leu Leu Asn Phe Glu Asp Ala Ala Gly Lys Val Trp Arg Phe Arg Tyr
            260                 265                 270

Ser Tyr Trp Asn Ser Ser Gln Ser Tyr Val Leu Thr Lys Gly Trp Ser
        275                 280                 285

Arg Phe Val Lys Glu Lys Gly Leu His Ala Gly Asp Val Val Gly Phe
290                 295                 300

Tyr Arg Ser Ala Ala Ser Ala Gly Asp Asp Gly Lys Leu Phe Ile Asp
305                 310                 315                 320

Cys Lys Leu Val Arg Ser Thr Gly Ala Ala Leu Ala Ser Pro Ala Asp
                325                 330                 335

Gln Pro Ala Pro Ser Pro Val Lys Ala Val Arg Leu Phe Gly Val Asp
            340                 345                 350

Leu Leu Thr Ala Pro Ala Pro Val Glu Gln Met Ala Gly Cys Lys Arg
        355                 360                 365

Ala Arg Asp Leu Ala Ala Thr Thr Pro Pro Gln Ala Ala Ala Phe Lys
370                 375                 380
```

```
Lys Gln Cys Ile Glu Leu Ala Leu Val
385                 390

<210> SEQ ID NO 245
<211> LENGTH: 254
<212> TYPE: PRT
<213> ORGANISM: Artificial Sequence
<220> FEATURE:
<223> OTHER INFORMATION: alignment

<400> SEQUENCE: 245

Met Leu Arg Lys His Thr Tyr Phe Asp Glu Leu Ala Gln Ser Lys Arg
1               5                   10                  15

Ala Phe Ala Ala Ser Ala Ala Leu Ser Ala Pro Thr Thr Ser Gly Asp
            20                  25                  30

Ala Gly Gly Ser Ala Ser Pro Pro Ser Pro Ala Ala Val Arg Glu His
        35                  40                  45

Leu Phe Asp Lys Thr Val Thr Pro Ser Asp Val Gly Lys Leu Asn Arg
    50                  55                  60

Leu Val Ile Pro Lys Gln Asn Ala Glu Lys His Phe Pro Leu Gln Leu
65                  70                  75                  80

Pro Ala Gly Gly Gly Glu Ser Lys Gly Leu Leu Asn Phe Glu Asp
                85                  90                  95

Asp Ala Gly Lys Val Trp Arg Phe Arg Tyr Ser Tyr Trp Asn Ser Ser
            100                 105                 110

Gln Ser Tyr Val Leu Thr Lys Gly Trp Ser Arg Phe Val Lys Glu Lys
        115                 120                 125

Gly Leu Gly Ala Gly Asp Val Val Gly Phe Tyr Arg Ser Ala Ala Gly
    130                 135                 140

Arg Thr Gly Glu Asp Ser Lys Phe Phe Ile Asp Cys Arg Leu Arg Pro
145                 150                 155                 160

Asn Thr Asn Thr Ala Ala Glu Ala Asp Pro Val Tyr Gly Asn Asp Thr
                165                 170                 175

Glu Asp Gln Leu Phe Ile Asp Tyr Lys Lys Met Asn Lys Asn Asp Asp
            180                 185                 190

Ala Ala Asp Ala Ala Ile Asp Gln Ser Ser Ala Pro Val Gln Lys Ala
        195                 200                 205

Val Arg Leu Phe Gly Val Asp Leu Leu Ala Ala Pro Glu Gln Gly Met
    210                 215                 220

Pro Gly Gly Cys Lys Arg Ala Arg Asp Leu Val Lys Pro Pro Pro Pro
225                 230                 235                 240

Lys Val Ala Phe Lys Lys Gln Cys Ile Glu Leu Ala Leu Ala
                245                 250

<210> SEQ ID NO 246
<211> LENGTH: 357
<212> TYPE: PRT
<213> ORGANISM: Artificial Sequence
<220> FEATURE:
<223> OTHER INFORMATION: alignment

<400> SEQUENCE: 246

Met Gly Val Glu Ile Leu Ser Thr Gly Glu His Ser Ser Gln Tyr
1               5                   10                  15

Ser Ser Gly Ala Ala Ser Thr Ala Thr Thr Glu Ser Gly Val Gly Gly
            20                  25                  30

Arg Pro Pro Thr Ala Pro Ser Leu Pro Val Ser Ile Ala Asp Glu Ser
        35                  40                  45
```

```
Ala Thr Ser Arg Ser Ala Ser Ala Gln Ser Thr Ser Ser Arg Phe Lys
    50                  55                  60

Gly Val Val Pro Gln Pro Asn Gly Arg Trp Gly Ala Gln Ile Tyr Glu
65                  70                  75                  80

Arg His Ala Arg Val Trp Leu Gly Thr Phe Pro Asp Glu Asp Ser Ala
                85                  90                  95

Ala Arg Ala Tyr Asp Val Ala Ala Leu Arg Tyr Arg Gly Arg Glu Ala
            100                 105                 110

Ala Thr Asn Phe Pro Cys Ala Ala Glu Ala Glu Leu Ala Phe Leu
            115                 120                 125

Ala Ala His Ser Lys Ala Glu Ile Val Asp Met Leu Arg Lys His Thr
    130                 135                 140

Tyr Thr Asp Glu Leu Arg Gln Gly Leu Arg Arg Gly Arg Gly Met Gly
145                 150                 155                 160

Ala Arg Ala Gln Pro Thr Pro Ser Trp Ala Arg Glu Pro Leu Phe Glu
                165                 170                 175

Lys Ala Val Thr Pro Ser Asp Val Gly Lys Leu Asn Arg Leu Val Val
            180                 185                 190

Pro Lys Gln His Ala Glu Lys His Phe Pro Leu Lys Arg Thr Pro Glu
        195                 200                 205

Thr Thr Thr Thr Thr Gly Lys Gly Val Leu Leu Asn Phe Glu Asp Gly
    210                 215                 220

Glu Gly Lys Val Trp Arg Phe Arg Tyr Ser Tyr Trp Asn Ser Ser Gln
225                 230                 235                 240

Ser Tyr Val Leu Thr Lys Gly Trp Ser Arg Phe Val Arg Glu Lys Gly
                245                 250                 255

Leu Gly Ala Gly Asp Ser Ile Val Phe Ser Cys Ser Ala Tyr Gly Gln
            260                 265                 270

Glu Lys Gln Phe Phe Ile Asp Cys Lys Lys Asn Lys Thr Met Thr Ser
        275                 280                 285

Cys Pro Ala Asp Asp Arg Gly Ala Ala Thr Ala Ser Pro Pro Val Ser
    290                 295                 300

Glu Pro Thr Lys Gly Glu Gln Val Arg Val Arg Leu Phe Gly Val
305                 310                 315                 320

Asp Ile Ala Gly Glu Lys Arg Gly Arg Ala Ala Pro Val Glu Gln Glu
                325                 330                 335

Leu Phe Lys Arg Gln Cys Val Ala His Ser Gln His Ser Pro Ala Leu
            340                 345                 350

Gly Ala Phe Val Leu
        355

<210> SEQ ID NO 247
<211> LENGTH: 362
<212> TYPE: PRT
<213> ORGANISM: Artificial Sequence
<220> FEATURE:
<223> OTHER INFORMATION: alignment

<400> SEQUENCE: 247

Met Gly Met Glu Ile Leu Ser Ser Val Glu His Cys Ser Gln Tyr
1               5                   10                  15

Ser Ser Ser Ala Ser Thr Ala Thr Thr Glu Ser Gly Ala Ala Gly Arg
            20                  25                  30

Ser Thr Thr Ala Leu Ser Leu Pro Val Ala Ile Thr Asp Glu Ser Val
        35                  40                  45
```

```
Thr Ser Arg Ser Ala Ser Ala Gln Pro Ala Ser Ser Arg Phe Lys Gly
         50                  55                  60

Val Val Pro Gln Pro Asn Gly Arg Trp Gly Ser Gln Ile Tyr Glu Arg
 65                  70                  75                  80

His Ala Arg Val Trp Leu Gly Thr Phe Pro Asp Gln Asp Ser Ala Ala
                 85                  90                  95

Arg Ala Tyr Asp Val Ala Ser Leu Arg Tyr Arg Gly Arg Asp Ala Ala
                100                 105                 110

Thr Asn Phe Pro Cys Ala Ala Ala Glu Ala Glu Leu Ala Phe Leu Thr
                115                 120                 125

Ala His Ser Lys Ala Glu Ile Val Asp Met Leu Arg Lys His Thr Tyr
        130                 135                 140

Ala Asp Glu Leu Arg Gln Gly Leu Arg Arg Gly Arg Gly Met Gly Ala
145                 150                 155                 160

Arg Ala Gln Pro Thr Pro Ser Trp Ala Arg Val Pro Leu Phe Glu Lys
                165                 170                 175

Ala Val Thr Pro Ser Asp Val Gly Lys Leu Asn Arg Leu Val Val Pro
                180                 185                 190

Lys Gln His Ala Glu Lys His Phe Pro Leu Lys Cys Thr Ala Glu Thr
        195                 200                 205

Thr Thr Thr Thr Gly Asn Gly Val Leu Leu Asn Phe Glu Asp Gly Glu
210                 215                 220

Gly Lys Val Trp Arg Phe Arg Tyr Ser Tyr Trp Asn Ser Ser Gln Ser
225                 230                 235                 240

Tyr Val Leu Thr Lys Gly Trp Ser Ser Phe Val Arg Glu Lys Gly Leu
                245                 250                 255

Gly Ala Gly Asp Ser Ile Val Phe Ser Ser Ala Tyr Gly Gln Glu
                260                 265                 270

Lys Gln Leu Phe Ile Asn Cys Lys Lys Asn Thr Thr Met Asn Gly Gly
        275                 280                 285

Lys Thr Ala Leu Pro Leu Pro Val Glu Thr Ala Lys Gly Glu Gln
290                 295                 300

Asp His Val Val Lys Leu Phe Gly Val Asp Ile Ala Gly Val Lys Arg
305                 310                 315                 320

Val Arg Ala Ala Thr Gly Glu Leu Gly Pro Pro Glu Leu Phe Lys Arg
                325                 330                 335

Gln Ser Val Ala His Gly Cys Gly Arg Met Asn Tyr Ile Cys Tyr Ser
                340                 345                 350

Ile Gly Thr Ile Gly Pro Leu Met Leu Asn
                355                 360
```

<210> SEQ ID NO 248
<211> LENGTH: 351
<212> TYPE: PRT
<213> ORGANISM: Artificial Sequence
<220> FEATURE:
<223> OTHER INFORMATION: alignment

<400> SEQUENCE: 248

```
Met Gly Val Glu Ile Leu Ser Ser Met Val Glu Asp Ser Ser Gln Tyr
 1               5                  10                  15

Ser Ser Gly Ala Ser Thr Ala Thr Thr Glu Ser Gly Thr Thr Gly Arg
                 20                  25                  30

Ala Leu Thr Ala Leu Ser Leu Pro Val Ala Ile Ala Asp Glu Ser Val
                 35                  40                  45
```

Thr Ser Ala Gln Ser Ala Pro Ser Arg Phe Lys Gly Val Val Pro Gln
        50                  55                  60

Pro Asn Gly Arg Trp Gly Ser Gln Ile Tyr Glu Arg His Ala Arg Val
65                  70                  75                  80

Trp Leu Gly Thr Phe Pro Asp Gln Asp Leu Ala Ala Arg Ala Tyr Asp
                85                  90                  95

Val Ala Ala Leu Arg Tyr Arg Gly Arg Asp Ala Ala Thr Asn Phe Pro
            100                 105                 110

Cys Ala Ala Ala Glu Ala Glu Leu Ala Phe Leu Gly Ala His Ser Lys
            115                 120                 125

Ala Glu Ile Val Asp Met Leu Arg Lys His Thr Tyr Ala Asp Glu Leu
        130                 135                 140

Arg Gln Gly Leu Arg Arg Gly Arg Gly Met Gly Ala Arg Ala Gln Pro
145                 150                 155                 160

Thr Pro Ser Trp Ala Arg Glu Pro Leu Phe Glu Lys Ala Val Thr Pro
                165                 170                 175

Ser Asp Val Gly Lys Leu Asn Arg Leu Val Val Pro Lys Gln His Ala
            180                 185                 190

Glu Lys His Phe Pro Leu Lys Arg Thr Pro Glu Arg Thr Thr Thr Thr
        195                 200                 205

Gly Asn Gly Val Leu Leu Asn Phe Glu Asp Gly Glu Gly Lys Val Trp
    210                 215                 220

Arg Phe Arg Tyr Ser Tyr Trp Asn Ser Ser Gln Ser Tyr Val Leu Thr
225                 230                 235                 240

Lys Gly Trp Ser Arg Phe Val Arg Glu Lys Gly Leu Ala Ala Gly Asp
                245                 250                 255

Ser Ile Ile Phe Ser Cys Ser Ala Tyr Gly Gln Glu Lys Gln Leu Phe
            260                 265                 270

Ile Asp Cys Lys Lys Asn Thr Thr Val Asn Ser Gly Lys Ser Ala Ser
        275                 280                 285

Pro Leu Pro Val Val Glu Thr Ala Lys Gly Glu Gln Val Arg Val Val
    290                 295                 300

Arg Leu Phe Gly Val Asp Ile Ala Gly Val Lys Arg Gly Arg Ala Ala
305                 310                 315                 320

Thr Ala Glu Gln Gly Pro Pro Glu Leu Leu Lys Arg Gln Cys Val Pro
                325                 330                 335

Leu Pro His Gly Gln Arg Ser Pro Ala Leu Gly Ala Phe Val Leu
            340                 345                 350

<210> SEQ ID NO 249
<211> LENGTH: 348
<212> TYPE: PRT
<213> ORGANISM: Artificial Sequence
<220> FEATURE:
<223> OTHER INFORMATION: alignment

<400> SEQUENCE: 249

Met Gly Val Glu Ile Leu Ser Ser Met Val Glu His Ser Phe Gln Tyr
1               5                   10                  15

Ser Ser Gly Ala Ser Ser Ala Thr Ala Glu Ser Gly Ala Val Gly Thr
            20                  25                  30

Pro Pro Arg His Leu Ser Leu Pro Val Ala Ile Ala Asp Glu Ser Leu
        35                  40                  45

Thr Ser Arg Ser Ala Ser Ser Arg Phe Lys Gly Val Val Pro Gln Pro
    50                  55                  60

Asn Gly Arg Trp Gly Ala Gln Ile Tyr Glu Arg His Ala Arg Val Trp
 65                  70                  75                  80

Leu Gly Thr Phe Pro Asp Gln Asp Ser Ala Ala Arg Ala Tyr Asp Val
             85                  90                  95

Ala Ser Leu Arg Tyr Arg Gly Gly Asp Ala Ala Phe Asn Phe Pro Cys
            100                 105                 110

Val Val Val Glu Ala Glu Leu Ala Phe Leu Ala Ala His Ser Lys Ala
            115                 120                 125

Glu Ile Val Asp Met Leu Arg Lys Gln Thr Tyr Ala Asp Glu Leu Arg
130                 135                 140

Gln Gly Leu Arg Arg Gly Arg Gly Met Gly Val Arg Ala Gln Pro Met
145                 150                 155                 160

Pro Ser Trp Ala Arg Val Pro Leu Phe Glu Lys Ala Val Thr Pro Ser
                165                 170                 175

Asp Val Gly Lys Leu Asn Arg Leu Val Val Pro Lys Gln His Ala Glu
            180                 185                 190

Lys His Phe Pro Leu Lys Arg Ser Pro Glu Thr Thr Thr Thr Thr Gly
            195                 200                 205

Asn Gly Val Leu Leu Asn Phe Glu Asp Gly Gln Gly Lys Val Trp Arg
210                 215                 220

Phe Arg Tyr Ser Tyr Trp Asn Ser Ser Gln Ser Tyr Val Leu Thr Lys
225                 230                 235                 240

Gly Trp Ser Arg Phe Val Arg Glu Lys Gly Leu Gly Ala Gly Asp Ser
                245                 250                 255

Ile Met Phe Ser Cys Ser Ala Tyr Gly Gln Glu Lys Gln Phe Phe Ile
            260                 265                 270

Asp Cys Lys Lys Asn Thr Thr Val Asn Gly Gly Lys Ser Ala Ser Pro
            275                 280                 285

Leu Gln Val Met Glu Ile Ala Lys Ala Glu Gln Val Arg Val Val Arg
290                 295                 300

Leu Phe Gly Val Asp Ile Ala Gly Val Lys Arg Glu Arg Ala Ala Thr
305                 310                 315                 320

Ala Glu Gln Gly Pro Gly Trp Phe Lys Arg Gln Cys Met Ala His
                325                 330                 335

Gly Gln His Ser Pro Ala Leu Gly Asp Phe Ala Leu
            340                 345

<210> SEQ ID NO 250
<211> LENGTH: 350
<212> TYPE: PRT
<213> ORGANISM: Artificial Sequence
<220> FEATURE:
<223> OTHER INFORMATION: alignment

<400> SEQUENCE: 250

Met Gly Val Glu Ile Leu Ser Ser Met Val Glu His Ser Phe Gln Tyr
1               5                   10                  15

Ser Ser Gly Val Ser Thr Ala Thr Thr Glu Ser Gly Thr Ala Gly Thr
            20                  25                  30

Pro Pro Arg Pro Leu Ser Leu Pro Val Ala Ile Ala Asp Glu Ser Val
            35                  40                  45

Thr Ser Arg Ser Ala Ser Ser Arg Phe Lys Gly Val Val Pro Gln Pro
     50                  55                  60

Asn Gly Arg Trp Gly Ala Gln Ile Tyr Glu Arg His Ala Arg Val Trp
 65                  70                  75                  80

Leu Gly Thr Phe Pro Asp Gln Asp Ser Ala Ala Arg Ala Tyr Asp Val
            85                  90                  95

Ala Ser Leu Arg Tyr Arg Gly Arg Asp Val Ala Phe Asn Phe Pro Cys
            100                 105                 110

Ala Ala Val Glu Gly Glu Leu Ala Phe Leu Ala Ala His Ser Lys Ala
            115                 120                 125

Glu Ile Val Asp Met Leu Arg Lys Gln Thr Tyr Ala Asp Glu Leu Arg
    130                 135                 140

Gln Gly Leu Arg Arg Gly Arg Gly Met Gly Ala Arg Ala Gln Pro Thr
145                 150                 155                 160

Pro Ser Trp Ala Arg Glu Pro Leu Phe Glu Lys Ala Val Thr Pro Ser
                165                 170                 175

Asp Val Gly Lys Leu Asn Arg Leu Val Val Pro Lys Gln His Ala Glu
            180                 185                 190

Lys His Phe Pro Leu Lys Arg Thr Pro Glu Thr Pro Thr Thr Thr Gly
            195                 200                 205

Lys Gly Val Leu Leu Asn Phe Glu Asp Gly Glu Gly Lys Val Trp Arg
    210                 215                 220

Phe Arg Tyr Ser Tyr Trp Asn Ser Ser Gln Ser Tyr Val Leu Thr Lys
225                 230                 235                 240

Gly Trp Ser Arg Phe Val Arg Glu Lys Gly Leu Gly Ala Gly Asp Ser
                245                 250                 255

Ile Leu Phe Ser Cys Ser Leu Tyr Glu Gln Glu Lys Gln Phe Phe Ile
            260                 265                 270

Asp Cys Lys Lys Asn Thr Ser Met Asn Gly Gly Lys Ser Ala Ser Pro
            275                 280                 285

Leu Pro Val Gly Val Thr Thr Lys Gly Glu Gln Val Arg Val Val Arg
    290                 295                 300

Leu Phe Gly Val Asp Ile Ser Gly Val Lys Arg Gly Arg Ala Ala Thr
305                 310                 315                 320

Ala Thr Ala Glu Gln Gly Leu Gln Glu Leu Phe Lys Arg Gln Cys Val
                325                 330                 335

Ala Pro Gly Gln His Ser Pro Ala Leu Gly Ala Phe Ala Leu
            340                 345                 350

<210> SEQ ID NO 251
<211> LENGTH: 308
<212> TYPE: PRT
<213> ORGANISM: Artificial Sequence
<220> FEATURE:
<223> OTHER INFORMATION: alignment

<400> SEQUENCE: 251

Met Ala Ser Ser Lys Pro Thr Asn Pro Glu Val Asp Asn Asp Met Glu
1               5                   10                  15

Cys Ser Ser Pro Glu Ser Gly Ala Glu Asp Ala Val Glu Ser Ser Ser
            20                  25                  30

Pro Val Ala Ala Pro Ser Ser Arg Phe Lys Gly Val Val Pro Gln Pro
        35                  40                  45

Asn Gly Arg Trp Gly Ala Gln Ile Tyr Glu Lys His Ser Arg Val Trp
    50                  55                  60

Leu Gly Thr Phe Gly Asp Glu Glu Ala Ala Cys Ala Tyr Asp Val
65                  70                  75                  80

Ala Ala Leu Arg Phe Arg Gly Arg Asp Ala Val Thr Asn His Gln Arg
            85                  90                  95

```
Leu Pro Ala Ala Glu Gly Ala Gly Trp Ser Ser Thr Ser Glu Leu Ala
            100                 105                 110

Phe Leu Ala Asp His Ser Lys Ala Glu Ile Val Asp Met Leu Arg Lys
        115                 120                 125

His Thr Tyr Asp Asp Glu Leu Arg Gln Gly Leu Arg Arg Gly His Gly
    130                 135                 140

Arg Ala Gln Pro Thr Pro Ala Trp Ala Arg Glu Phe Leu Phe Glu Lys
145                 150                 155                 160

Ala Leu Thr Pro Ser Asp Val Gly Lys Leu Asn Arg Leu Val Val Pro
                165                 170                 175

Lys Gln His Ala Glu Lys His Phe Pro Pro Thr Thr Ala Ala Ala Ala
            180                 185                 190

Gly Ser Asp Gly Lys Gly Leu Leu Leu Asn Phe Glu Asp Gly Gln Gly
        195                 200                 205

Lys Val Trp Arg Phe Arg Tyr Ser Tyr Trp Asn Ser Ser Gln Ser Tyr
    210                 215                 220

Val Leu Thr Lys Gly Trp Ser Arg Phe Val Gln Glu Lys Gly Leu Cys
225                 230                 235                 240

Ala Gly Asp Thr Val Thr Phe Ser Arg Ser Ala Tyr Val Met Asn Asp
                245                 250                 255

Thr Asp Glu Gln Leu Phe Ile Asp Tyr Lys Gln Ser Ser Lys Asn Asp
            260                 265                 270

Glu Ala Ala Asp Val Ala Thr Ala Asp Glu Asn Glu Ala Gly His Val
        275                 280                 285

Ala Val Lys Leu Phe Gly Val Asp Ile Gly Trp Ala Gly Met Ala Gly
    290                 295                 300

Ser Ser Gly Gly
305

<210> SEQ ID NO 252
<211> LENGTH: 293
<212> TYPE: PRT
<213> ORGANISM: Artificial Sequence
<220> FEATURE:
<223> OTHER INFORMATION: alignment

<400> SEQUENCE: 252

Met Ala Ser Gly Lys Pro Thr Asn His Gly Met Glu Asp Asp Asn Asp
1               5                   10                  15

Met Glu Tyr Ser Ser Ala Glu Ser Gly Ala Glu Asp Ala Ala Glu Pro
            20                  25                  30

Ser Ser Ser Pro Val Leu Ala Pro Pro Arg Ala Ala Pro Ser Ser Arg
        35                  40                  45

Phe Lys Gly Val Val Pro Gln Pro Asn Gly Arg Trp Gly Ala Gln Ile
    50                  55                  60

Tyr Glu Lys His Ser Arg Val Trp Leu Gly Thr Phe Pro Asp Glu Asp
65                  70                  75                  80

Ala Ala Val Arg Ala Tyr Asp Val Ala Ala Leu Arg Phe Arg Gly Pro
                85                  90                  95

Asp Ala Val Ile Asn His Gln Arg Pro Thr Ala Glu Glu Ala Gly
            100                 105                 110

Ser Ser Ser Ser Arg Ser Glu Leu Asp Pro Glu Leu Gly Phe Leu Ala
        115                 120                 125

Asp His Ser Lys Ala Glu Ile Val Asp Met Leu Arg Lys His Thr Tyr
    130                 135                 140
```

Asp Asp Glu Leu Arg Gln Gly Leu Arg Arg Gly Arg Gly Arg Ala Gln
145                 150                 155                 160

Pro Thr Pro Ala Trp Ala Arg Glu Leu Leu Phe Glu Lys Ala Val Thr
                165                 170                 175

Pro Ser Asp Val Gly Lys Leu Asn Arg Leu Val Val Pro Lys Gln Gln
            180                 185                 190

Ala Glu Lys His Phe Pro Pro Thr Thr Ala Ala Ala Thr Gly Ser Asn
        195                 200                 205

Gly Lys Gly Val Leu Leu Asn Phe Glu Asp Gly Glu Gly Lys Val Trp
    210                 215                 220

Arg Phe Arg Tyr Ser Tyr Trp Asn Ser Ser Gln Ser Tyr Val Leu Thr
225                 230                 235                 240

Lys Gly Trp Ser Arg Phe Val Lys Glu Thr Gly Leu Arg Ala Gly Asp
                245                 250                 255

Thr Val Ala Phe Tyr Arg Ser Ala Ser Asp Glu Asn Glu Thr Gly His
            260                 265                 270

Val Ala Val Lys Leu Phe Gly Val Asp Ile Ala Gly Gly Met Ala
        275                 280                 285

Gly Ser Ser Gly Gly
    290

<210> SEQ ID NO 253
<211> LENGTH: 320
<212> TYPE: PRT
<213> ORGANISM: Artificial Sequence
<220> FEATURE:
<223> OTHER INFORMATION: alignment

<400> SEQUENCE: 253

Met Ala Ser Gly Lys Pro Thr Asn His Gly Met Glu Asp Asp Asn Asp
1               5                   10                  15

Met Glu Tyr Ser Ser Ala Glu Ser Gly Ala Glu Asp Ala Ala Glu Pro
                20                  25                  30

Ser Ser Ser Pro Val Leu Ala Pro Pro Arg Ala Ala Pro Ser Ser Arg
            35                  40                  45

Phe Lys Gly Val Val Pro Gln Pro Asn Gly Arg Trp Gly Ala Gln Ile
50                  55                  60

Tyr Glu Lys His Ser Arg Val Trp Leu Gly Thr Phe Pro Asp Glu Asp
65                  70                  75                  80

Ala Ala Ala Arg Ala Tyr Asp Val Ala Ala Leu Arg Phe Arg Gly Pro
                85                  90                  95

Asp Ala Val Ile Asn His Gln Arg Pro Thr Ala Ala Glu Glu Ala Gly
            100                 105                 110

Ser Ser Ser Ser Arg Ser Glu Leu Asp Pro Glu Leu Gly Phe Leu Ala
        115                 120                 125

Asp His Ser Lys Ala Glu Ile Val Asp Met Leu Arg Lys His Thr Tyr
    130                 135                 140

Asp Asp Glu Leu Arg Gln Gly Leu Arg Arg Gly Arg Gly Arg Ala Gln
145                 150                 155                 160

Pro Thr Pro Ala Trp Ala Arg Glu Leu Leu Phe Glu Lys Ala Val Thr
                165                 170                 175

Pro Ser Asp Val Gly Lys Leu Asn Arg Leu Val Val Pro Lys Gln Gln
            180                 185                 190

Ala Glu Lys His Phe Pro Pro Thr Thr Ala Ala Ala Thr Gly Ser Asn
        195                 200                 205

Gly Lys Gly Val Leu Leu Asn Phe Glu Asp Gly Gly Lys Val Trp
210                 215                 220

Arg Phe Arg Tyr Ser Tyr Trp Asn Ser Ser Gln Ser Tyr Val Leu Thr
225                 230                 235                 240

Lys Gly Trp Ser Arg Phe Val Lys Glu Thr Gly Leu Arg Ala Gly Asp
                245                 250                 255

Thr Val Ala Phe Tyr Arg Ser Ala Tyr Gly Asn Asp Thr Glu Asp Gln
                260                 265                 270

Leu Phe Ile Asp Tyr Lys Lys Met Asn Lys Asn Asp Ala Ala Asp
        275                 280                 285

Ala Ala Ile Ser Asp Glu Asn Glu Thr Gly His Val Ala Val Lys Leu
290                 295                 300

Phe Gly Val Asp Ile Ala Gly Gly Met Ala Gly Ser Ser Gly Gly
305                 310                 315                 320

<210> SEQ ID NO 254
<211> LENGTH: 350
<212> TYPE: PRT
<213> ORGANISM: Artificial Sequence
<220> FEATURE:
<223> OTHER INFORMATION: alignment

<400> SEQUENCE: 254

Met Val Phe Ser Cys Ile Asp Glu Ser Ser Thr Ser Glu Ser Phe
1               5                   10                  15

Ser Pro Ala Thr Ala Thr Ala Thr Ala Thr Lys Phe Ser Ala
                20                  25                  30

Pro Pro Leu Pro Pro Leu Arg Leu Asn Arg Met Arg Ser Gly Gly Ser
        35                  40                  45

Asn Val Val Leu Asp Ser Lys Asn Gly Val Asp Ile Asp Ser Arg Lys
50                  55                  60

Leu Ser Ser Ser Lys Tyr Lys Gly Val Val Pro Gln Pro Asn Gly Arg
65                  70                  75                  80

Trp Gly Ala Gln Ile Tyr Val Lys His Gln Arg Val Trp Leu Gly Thr
                85                  90                  95

Phe Cys Asp Glu Glu Ala Ala His Ser Tyr Asp Ile Ala Ala Arg
                100                 105                 110

Lys Phe Arg Gly Arg Asp Ala Val Val Asn Phe Lys Thr Phe Leu Ala
        115                 120                 125

Ser Glu Asp Asp Asn Gly Glu Leu Cys Phe Leu Glu Ala His Ser Lys
        130                 135                 140

Ala Glu Ile Val Asp Met Leu Arg Lys His Thr Tyr Ala Asp Glu Leu
145                 150                 155                 160

Ala Gln Ser Asn Lys Arg Ser Gly Ala Asn Thr Asn Thr Asn Thr Thr
                165                 170                 175

Gln Ser His Thr Val Ser Arg Thr Arg Glu Val Leu Phe Glu Lys Val
                180                 185                 190

Val Thr Pro Ser Asp Val Gly Lys Leu Asn Arg Leu Val Ile Pro Lys
        195                 200                 205

Gln His Ala Glu Lys Tyr Phe Pro Leu Pro Ser Leu Ser Val Thr Lys
210                 215                 220

Gly Val Leu Ile Asn Phe Glu Asp Val Thr Gly Lys Val Trp Arg Phe
225                 230                 235                 240

Arg Tyr Ser Tyr Trp Asn Ser Ser Gln Ser Tyr Val Leu Thr Lys Gly
                245                 250                 255

```
Trp Ser Arg Phe Val Lys Glu Lys Asn Leu Arg Ala Gly Asp Val Val
        260                 265                 270

Thr Phe Glu Arg Ser Thr Gly Ser Asp Arg Gln Leu Tyr Ile Asp Trp
            275                 280                 285

Lys Ile Arg Ser Gly Pro Ser Lys Asn Pro Val Gln Val Val Arg
        290                 295                 300

Leu Phe Gly Val Asp Ile Phe Asn Val Thr Ser Ala Lys Pro Ser Asn
305                 310                 315                 320

Val Val Asp Ala Cys Gly Gly Lys Arg Ser Arg Asp Val Asp Met Phe
                325                 330                 335

Ala Leu Arg Cys Ser Lys Lys His Ala Ile Ile Asn Ala Leu
            340                 345                 350

<210> SEQ ID NO 255
<211> LENGTH: 351
<212> TYPE: PRT
<213> ORGANISM: Artificial Sequence
<220> FEATURE:
<223> OTHER INFORMATION: alignment

<400> SEQUENCE: 255

Met Asp Gly Gly Cys Val Thr Asp Glu Thr Thr Thr Ser Ser Asp Ser
1               5                   10                  15

Leu Ser Val Pro Pro Ser Arg Val Gly Ser Val Ala Ser Ala Val
            20                  25                  30

Val Asp Pro Asp Gly Cys Cys Val Ser Gly Glu Ala Glu Ser Arg Lys
            35                  40                  45

Leu Pro Ser Ser Lys Tyr Lys Gly Val Val Pro Gln Pro Asn Gly Arg
    50                  55                  60

Trp Gly Ala Gln Ile Tyr Glu Lys His Gln Arg Val Trp Leu Gly Thr
65                  70                  75                  80

Phe Asn Glu Glu Asp Glu Ala Ala Arg Ala Tyr Asp Ile Ala Ala Leu
                85                  90                  95

Arg Phe Arg Gly Pro Asp Ala Val Thr Asn Phe Lys Pro Pro Ala Ala
            100                 105                 110

Ser Asp Ala Glu Ser Glu Phe Leu Asn Ser His Ser Lys Phe Glu
            115                 120                 125

Ile Val Asp Met Leu Arg Lys His Thr Tyr Asp Asp Glu Leu Gln Gln
        130                 135                 140

Ser Thr Arg Gly Gly Arg Arg Leu Asp Ala Asp Thr Ala Ser Ser
145                 150                 155                 160

Gly Val Phe Asp Ala Lys Ala Arg Glu Gln Leu Phe Glu Lys Thr Val
                165                 170                 175

Thr Pro Ser Asp Val Gly Lys Leu Asn Arg Leu Val Ile Pro Lys Gln
            180                 185                 190

His Ala Glu Lys His Phe Pro Leu Ser Gly Ser Gly Asp Glu Ser Ser
        195                 200                 205

Pro Cys Val Ala Gly Ala Ser Ala Lys Gly Met Leu Leu Asn Phe
    210                 215                 220

Glu Asp Val Gly Gly Lys Val Trp Arg Phe Arg Tyr Ser Tyr Trp Asn
225                 230                 235                 240

Ser Ser Gln Ser Tyr Val Leu Thr Lys Gly Trp Ser Arg Phe Val Lys
                245                 250                 255

Glu Lys Asn Leu Arg Ala Gly Asp Ala Val Gln Phe Phe Lys Ser Thr
            260                 265                 270
```

```
Gly Pro Asp Arg Gln Leu Tyr Ile Asp Cys Lys Ala Arg Ser Gly Glu
            275                 280                 285

Val Asn Asn Ala Gly Gly Leu Phe Val Pro Ile Gly Pro Val Val
        290                 295                 300

Glu Pro Val Gln Met Val Arg Leu Phe Gly Val Asn Leu Leu Lys Leu
305                 310                 315                 320

Pro Val Pro Gly Ser Asp Gly Val Gly Lys Arg Lys Glu Met Glu Leu
                325                 330                 335

Phe Ala Phe Glu Cys Cys Lys Lys Leu Lys Val Ile Gly Ala Leu
            340                 345                 350

<210> SEQ ID NO 256
<211> LENGTH: 362
<212> TYPE: PRT
<213> ORGANISM: Artificial Sequence
<220> FEATURE:
<223> OTHER INFORMATION: alignment

<400> SEQUENCE: 256

Met Asp Gly Gly Ser Val Thr Asp Glu Thr Thr Thr Ser Asn Ser
1               5                   10                  15

Leu Ser Val Pro Ala Asn Leu Ser Pro Pro Leu Ser Leu Val Gly
                20                  25                  30

Ser Gly Ala Thr Ala Val Val Tyr Pro Asp Gly Cys Cys Val Ser Gly
            35                  40                  45

Glu Ala Glu Ser Arg Lys Leu Pro Ser Ser Lys Tyr Lys Gly Val Val
    50                  55                  60

Pro Gln Pro Asn Gly Arg Trp Gly Ala Gln Ile Tyr Glu Lys His Gln
65                  70                  75                  80

Arg Val Trp Leu Gly Thr Phe Asn Glu Glu Asp Glu Ala Ala Arg Ala
                85                  90                  95

Tyr Asp Ile Ala Ala His Arg Phe Arg Gly Arg Asp Ala Val Thr Asn
            100                 105                 110

Phe Lys Pro Leu Ala Gly Ala Asp Asp Ala Glu Ala Glu Phe Leu Ser
        115                 120                 125

Thr His Ser Lys Ser Glu Ile Val Asp Met Leu Arg Lys His Thr Tyr
    130                 135                 140

Asp Asn Glu Leu Gln Gln Ser Thr Arg Gly Gly Arg Arg Arg Arg Asp
145                 150                 155                 160

Ala Glu Thr Ala Ser Ser Gly Ala Phe Asp Ala Lys Ala Arg Glu Gln
                165                 170                 175

Leu Phe Glu Lys Thr Val Thr Gln Ser Asp Val Gly Lys Leu Asn Arg
            180                 185                 190

Leu Val Ile Pro Lys Gln His Ala Glu Lys His Phe Pro Leu Ser Gly
        195                 200                 205

Ser Gly Gly Gly Ala Leu Pro Cys Met Ala Ala Ala Gly Ala Lys
    210                 215                 220

Gly Met Leu Leu Asn Phe Glu Asp Val Gly Gly Lys Val Trp Arg Phe
225                 230                 235                 240

Arg Tyr Ser Tyr Trp Asn Ser Ser Gln Ser Tyr Val Leu Thr Lys Gly
                245                 250                 255

Trp Ser Arg Phe Val Lys Glu Lys Asn Leu Arg Ala Gly Asp Ala Val
            260                 265                 270

Gln Phe Phe Lys Ser Thr Gly Leu Asp Arg Gln Leu Tyr Ile Asp Cys
        275                 280                 285
```

```
Lys Ala Arg Ser Gly Lys Val Asn Asn Ala Ala Gly Leu Phe Ile
    290                 295                 300

Pro Val Gly Pro Val Val Glu Pro Val Gln Met Val Arg Leu Phe Gly
305                 310                 315                 320

Val Asp Leu Leu Lys Leu Pro Val Pro Gly Ser Asp Gly Ile Gly Val
                325                 330                 335

Gly Cys Asp Gly Lys Arg Lys Glu Met Glu Leu Phe Ala Phe Glu Cys
            340                 345                 350

Ser Lys Lys Leu Lys Val Ile Gly Ala Leu
            355                 360

<210> SEQ ID NO 257
<211> LENGTH: 384
<212> TYPE: PRT
<213> ORGANISM: Artificial Sequence
<220> FEATURE:
<223> OTHER INFORMATION: alignment

<400> SEQUENCE: 257

Met Asp Ala Ile Ser Cys Leu Asp Glu Ser Thr Thr Thr Glu Ser Leu
1               5                   10                  15

Ser Ile Ser Gln Ala Lys Pro Ser Ser Thr Ile Met Ser Ser Glu Lys
                20                  25                  30

Ala Ser Pro Ser Pro Pro Pro Asn Arg Leu Cys Arg Val Gly Ser
            35                  40                  45

Gly Ala Ser Ala Val Val Asp Ser Asp Gly Gly Gly Gly Gly Ser
    50                  55                  60

Thr Glu Val Glu Ser Arg Lys Leu Pro Ser Ser Lys Tyr Lys Gly Val
65                  70                  75                  80

Val Pro Gln Pro Asn Gly Arg Trp Gly Ser Gln Ile Tyr Glu Lys His
                85                  90                  95

Gln Arg Val Trp Leu Gly Thr Phe Asn Glu Glu Asp Glu Ala Ala Arg
                100                 105                 110

Ala Tyr Asp Val Ala Val Gln Arg Phe Arg Gly Lys Asp Ala Val Thr
            115                 120                 125

Asn Phe Lys Pro Leu Ser Gly Thr Asp Asp Asp Gly Glu Ser Glu
    130                 135                 140

Phe Leu Asn Ser His Ser Lys Ser Glu Ile Val Asp Met Leu Arg Lys
145                 150                 155                 160

His Thr Tyr Asn Asp Glu Leu Glu Gln Ser Lys Arg Ser Arg Gly Phe
                165                 170                 175

Val Arg Arg Arg Gly Ser Ala Ala Gly Ala Gly Asn Gly Asn Ser Ile
            180                 185                 190

Ser Gly Ala Cys Val Met Lys Ala Arg Glu Gln Leu Phe Gln Lys Ala
        195                 200                 205

Val Thr Pro Ser Asp Val Gly Lys Leu Asn Arg Leu Val Ile Pro Lys
    210                 215                 220

Gln His Ala Glu Lys His Phe Pro Leu Gln Ser Ala Ala Asn Gly Val
225                 230                 235                 240

Ser Ala Thr Ala Thr Ala Ala Lys Gly Val Leu Leu Asn Phe Glu Asp
                245                 250                 255

Val Gly Gly Lys Val Trp Arg Phe Arg Tyr Ser Tyr Trp Asn Ser Ser
            260                 265                 270

Gln Ser Tyr Val Leu Thr Lys Gly Trp Ser Arg Phe Val Lys Glu Lys
        275                 280                 285
```

```
Asn Leu Lys Ala Gly Asp Thr Val Cys Phe Gln Arg Ser Thr Gly Pro
        290                 295                 300

Asp Arg Gln Leu Tyr Ile Asp Trp Lys Thr Arg Asn Val Val Asn Glu
305                 310                 315                 320

Val Ala Leu Phe Gly Pro Val Val Glu Pro Ile Gln Met Val Arg Leu
                325                 330                 335

Phe Gly Val Asn Ile Leu Lys Leu Pro Gly Ser Asp Ser Ile Ala Asn
            340                 345                 350

Asn Asn Asn Ala Ser Gly Cys Cys Asn Gly Lys Arg Arg Glu Met Glu
        355                 360                 365

Leu Phe Ser Leu Glu Cys Ser Lys Lys Pro Lys Ile Ile Gly Ala Leu
    370                 375                 380

<210> SEQ ID NO 258
<211> LENGTH: 401
<212> TYPE: PRT
<213> ORGANISM: Artificial Sequence
<220> FEATURE:
<223> OTHER INFORMATION: alignment

<400> SEQUENCE: 258

Met Asp Ala Ile Ser Cys Met Asp Glu Ser Thr Thr Thr Glu Ser Leu
1               5                   10                  15

Ser Ile Ser Leu Ser Pro Thr Ser Ser Glu Lys Ala Lys Pro Ser
            20                  25                  30

Ser Met Ile Thr Ser Ser Glu Lys Val Ser Leu Ser Pro Pro Pro Ser
            35                  40                  45

Asn Arg Leu Cys Arg Val Gly Ser Gly Ala Ser Ala Val Val Asp Pro
    50                  55                  60

Asp Gly Gly Gly Ser Gly Ala Glu Val Glu Ser Arg Lys Leu Pro Ser
65                  70                  75                  80

Ser Lys Tyr Lys Gly Val Val Pro Gln Pro Asn Gly Arg Trp Gly Ala
                85                  90                  95

Gln Ile Tyr Glu Lys His Gln Arg Val Trp Leu Gly Thr Phe Asn Glu
            100                 105                 110

Glu Asp Glu Ala Ala Arg Ala Tyr Asp Ile Ala Ala Gln Arg Phe Arg
        115                 120                 125

Gly Lys Asp Ala Val Thr Asn Phe Lys Pro Leu Ala Gly Ala Asp Asp
    130                 135                 140

Asp Asp Gly Glu Ser Glu Phe Leu Asn Ser His Ser Lys Pro Glu Ile
145                 150                 155                 160

Val Asp Met Leu Arg Lys His Thr Tyr Asn Asp Glu Leu Glu Gln Ser
                165                 170                 175

Lys Arg Ser Arg Gly Val Val Arg Arg Gly Ser Ala Ala Ala Gly
            180                 185                 190

Thr Ala Asn Ser Ile Ser Gly Ala Cys Phe Thr Lys Ala Arg Glu Gln
        195                 200                 205

Leu Phe Glu Lys Ala Val Thr Pro Ser Asp Val Gly Lys Leu Asn Arg
    210                 215                 220

Leu Val Ile Pro Lys Gln His Ala Glu Lys His Phe Pro Leu Gln Ser
225                 230                 235                 240

Ser Asn Gly Val Ser Ala Thr Thr Ile Ala Ala Val Thr Ala Thr Pro
                245                 250                 255

Thr Ala Ala Lys Gly Val Leu Leu Asn Phe Glu Asp Val Gly Gly Lys
            260                 265                 270
```

```
Val Trp Arg Phe Arg Tyr Ser Tyr Trp Asn Ser Ser Gln Ser Tyr Val
        275                 280                 285

Leu Thr Lys Gly Trp Ser Arg Phe Val Lys Glu Lys Asn Leu Lys Ala
290                 295                 300

Gly Asp Thr Val Cys Phe His Arg Ser Thr Gly Pro Asp Lys Gln Leu
305                 310                 315                 320

Tyr Ile Asp Trp Lys Thr Arg Asn Val Asn Asn Glu Val Ala Leu
                325                 330                 335

Phe Gly Pro Val Gly Pro Val Val Glu Pro Ile Gln Met Val Arg Leu
                340                 345                 350

Phe Gly Val Asn Ile Leu Lys Leu Pro Gly Ser Asp Thr Ile Val Gly
                355                 360                 365

Asn Asn Asn Asn Ala Ser Gly Cys Cys Asn Gly Lys Arg Arg Glu Met
370                 375                 380

Glu Leu Phe Ser Leu Glu Cys Ser Lys Lys Pro Lys Ile Ile Gly Ala
385                 390                 395                 400

Leu

<210> SEQ ID NO 259
<211> LENGTH: 192
<212> TYPE: PRT
<213> ORGANISM: Artificial Sequence
<220> FEATURE:
<223> OTHER INFORMATION: alignment

<400> SEQUENCE: 259

Met Ala Met His Ala Gly His Ala Trp Trp Gly Val Ala Met Tyr Thr
1               5                   10                  15

Asn His Tyr His His Tyr Arg His Lys Thr Ser Asp Val Gly Lys
                20                  25                  30

Asn Arg Val Lys His Ala Arg Tyr Gly Gly Gly Asp Ser Gly Lys Gly
            35                  40                  45

Ser Asp Ser Gly Lys Trp Arg Arg Tyr Ser Tyr Trp Thr Ser Ser Ser
50                  55                  60

Tyr Val Thr Lys Gly Trp Ser Arg Tyr Val Lys Lys Arg Asp Ala Gly
65                  70                  75                  80

Asp Val Val His Arg Val Arg Gly Gly Ala Asp Arg Gly Cys Arg
                85                  90                  95

Arg Arg Gly Ser Ala Ala Ala Val Arg Val Thr Ala Asn Gly Gly Trp
            100                 105                 110

Ser Met Cys Tyr Ser Thr Ser Gly Ser Tyr Asp Thr Ser Ala Asn
            115                 120                 125

Ser Tyr Ala Tyr His Arg Ser Val Asp Asp His Ser Asp His Ala Gly
        130                 135                 140

Ser Arg Ala Asp Ala Lys Ser Ser Ala Ser Ala Ser Arg Arg
145                 150                 155                 160

Arg Gly Val Asn Asp Cys Gly Ala Asp Ala Thr Ala Met Tyr Gly Tyr
                165                 170                 175

Met His His Ser Tyr Ala Ala Val Ser Thr Val Asn Tyr Trp Ser Val
            180                 185                 190

<210> SEQ ID NO 260
<211> LENGTH: 116
<212> TYPE: PRT
<213> ORGANISM: Artificial Sequence
<220> FEATURE:
```

<223> OTHER INFORMATION: alignment

<400> SEQUENCE: 260

Phe Glu Lys Ser Leu Thr Pro Ser Asp Val Gly Lys Leu Asn Arg Leu
1               5                   10                  15

Val Ile Pro Lys Gln His Ala Glu Lys Tyr Phe Pro Leu Asn Asn Asn
            20                  25                  30

Asn Asn Asn Gly Gly Ser Gly Asp Asp Val Ala Thr Thr Glu Lys Gly
        35                  40                  45

Met Leu Leu Ser Phe Glu Asp Glu Ser Gly Lys Cys Trp Lys Phe Arg
    50                  55                  60

Tyr Ser Tyr Trp Asn Ser Ser Gln Ser Tyr Val Leu Thr Lys Gly Trp
65                  70                  75                  80

Ser Arg Tyr Val Lys Asp Lys His Leu Asp Ala Gly Asp Val Val Phe
                85                  90                  95

Phe Gln Arg His Arg Phe Asp Leu His Arg Leu Phe Ile Gly Trp Arg
                100                 105                 110

Arg Arg Gly Glu
        115

<210> SEQ ID NO 261
<211> LENGTH: 114
<212> TYPE: PRT
<213> ORGANISM: Artificial Sequence
<220> FEATURE:
<223> OTHER INFORMATION: alignment

<400> SEQUENCE: 261

Phe Glu Lys Ser Leu Thr Pro Ser Asp Val Gly Lys Leu Asn Arg Leu
1               5                   10                  15

Val Ile Pro Lys Gln His Ala Glu Arg Tyr Leu Pro Leu Asn Asn Cys
            20                  25                  30

Gly Gly Gly Gly Asp Val Thr Ala Glu Ser Thr Glu Lys Gly Val Leu
        35                  40                  45

Leu Ser Phe Glu Asp Glu Ser Gly Lys Ser Trp Lys Phe Arg Tyr Ser
    50                  55                  60

Tyr Trp Asn Ser Ser Gln Ser Tyr Val Leu Thr Lys Gly Trp Ser Arg
65                  70                  75                  80

Tyr Val Lys Asp Lys His Leu Asn Ala Gly Asp Val Val Leu Phe Gln
                85                  90                  95

Arg His Arg Phe Asp Ile His Arg Leu Phe Ile Gly Trp Arg Arg Arg
                100                 105                 110

Gly Glu

<210> SEQ ID NO 262
<211> LENGTH: 106
<212> TYPE: PRT
<213> ORGANISM: Artificial Sequence
<220> FEATURE:
<223> OTHER INFORMATION: alignment

<400> SEQUENCE: 262

Phe Glu Lys Pro Leu Thr Pro Ser Asp Val Gly Lys Leu Asn Arg Leu
1               5                   10                  15

Val Ile Pro Lys Gln His Ala Glu Lys Tyr Phe Pro Leu Ser Gly Asp
            20                  25                  30

Ser Gly Gly Ser Glu Cys Lys Gly Leu Leu Leu Ser Phe Glu Asp Glu
        35                  40                  45

```
Ser Gly Lys Cys Trp Arg Phe Arg Tyr Ser Tyr Trp Asn Ser Ser Gln
    50                  55                  60

Ser Tyr Val Leu Thr Lys Gly Trp Ser Arg Tyr Val Lys Asp Lys Arg
65                  70                  75                  80

Leu Asp Ala Gly Asp Val Val Leu Phe Glu Arg His Arg Val Asp Ala
                85                  90                  95

Gln Arg Leu Phe Ile Gly Trp Arg Arg Arg
            100                 105

<210> SEQ ID NO 263
<211> LENGTH: 107
<212> TYPE: PRT
<213> ORGANISM: Artificial Sequence
<220> FEATURE:
<223> OTHER INFORMATION: alignment

<400> SEQUENCE: 263

Phe Glu Lys Pro Leu Thr Pro Ser Asp Val Gly Lys Leu Asn Arg Leu
1               5                   10                  15

Val Ile Pro Lys Gln His Ala Glu Lys Tyr Phe Pro Leu Ser Gly Gly
            20                  25                  30

Asp Ser Gly Ser Ser Glu Cys Lys Gly Leu Leu Leu Ser Phe Glu Asp
        35                  40                  45

Glu Ser Gly Lys Cys Trp Arg Phe Arg Tyr Ser Tyr Trp Asn Ser Ser
    50                  55                  60

Gln Ser Tyr Val Leu Thr Lys Gly Trp Ser Arg Tyr Val Lys Asp Lys
65                  70                  75                  80

Arg Leu Asp Ala Gly Asp Val Val Leu Phe Gln Arg His Arg Ala Asp
                85                  90                  95

Ala Gln Arg Leu Phe Ile Gly Trp Arg Arg Arg
            100                 105

<210> SEQ ID NO 264
<211> LENGTH: 107
<212> TYPE: PRT
<213> ORGANISM: Artificial Sequence
<220> FEATURE:
<223> OTHER INFORMATION: alignment

<400> SEQUENCE: 264

Phe Glu Lys Pro Leu Thr Pro Ser Asp Val Gly Lys Leu Asn Arg Leu
1               5                   10                  15

Val Ile Pro Lys Gln His Ala Glu Lys Tyr Phe Pro Leu Asp Ser Ser
            20                  25                  30

Gly Gly Asp Ser Ala Ala Ala Lys Gly Leu Leu Leu Ser Phe Glu Asp
        35                  40                  45

Glu Ser Gly Lys Cys Trp Arg Phe Arg Tyr Ser Tyr Trp Asn Ser Ser
    50                  55                  60

Gln Ser Tyr Val Leu Thr Lys Gly Trp Ser Arg Tyr Val Lys Asp Lys
65                  70                  75                  80

Arg Leu His Ala Gly Asp Val Val Leu Phe His Arg His Arg Ala His
                85                  90                  95

Pro Gln Arg Phe Phe Ile Ser Cys Thr Arg His
            100                 105

<210> SEQ ID NO 265
<211> LENGTH: 108
<212> TYPE: PRT
```

-continued

<213> ORGANISM: Artificial Sequence
<220> FEATURE:
<223> OTHER INFORMATION: alignment

<400> SEQUENCE: 265

Phe Glu Lys Pro Leu Thr Pro Ser Asp Val Gly Lys Leu Asn Arg Leu
1               5                   10                  15

Val Ile Pro Lys Gln His Ala Glu Arg Tyr Phe Pro Leu Gly Gly Gly
            20                  25                  30

Asp Ser Gly Glu Lys Gly Leu Leu Leu Ser Phe Glu Asp Glu Ser Gly
        35                  40                  45

Lys Pro Trp Arg Phe Arg Tyr Ser Tyr Trp Thr Ser Ser Gln Ser Tyr
50                  55                  60

Val Leu Thr Lys Gly Trp Ser Arg Tyr Val Lys Glu Lys Arg Leu Asp
65                  70                  75                  80

Ala Gly Asp Val Val His Phe Glu Arg Val Arg Gly Leu Gly Ala Ala
                85                  90                  95

Asp Arg Leu Phe Ile Gly Cys Arg Arg Gly Glu
            100                 105

<210> SEQ ID NO 266
<211> LENGTH: 115
<212> TYPE: PRT
<213> ORGANISM: Artificial Sequence
<220> FEATURE:
<223> OTHER INFORMATION: alignment

<400> SEQUENCE: 266

Phe Glu Lys Ser Leu Thr Pro Ser Asp Val Gly Lys Leu Asn Arg Leu
1               5                   10                  15

Val Ile Pro Lys Gln His Ala Glu Lys Tyr Phe Pro Leu Asn Ala Val
            20                  25                  30

Leu Val Ser Ser Ala Ala Ala Asp Thr Ser Ser Ser Glu Lys Gly Met
        35                  40                  45

Leu Leu Ser Phe Glu Asp Glu Ser Gly Lys Ser Trp Arg Phe Arg Tyr
    50                  55                  60

Ser Tyr Trp Asn Ser Ser Gln Ser Tyr Val Leu Thr Lys Gly Trp Ser
65                  70                  75                  80

Arg Phe Val Lys Asp Lys Gln Leu Asp Pro Gly Asp Val Val Phe Phe
                85                  90                  95

Gln Arg His Arg Ser Asp Ser Arg Arg Leu Phe Ile Gly Trp Arg Arg
            100                 105                 110

Arg Gly Gln
    115

<210> SEQ ID NO 267
<211> LENGTH: 107
<212> TYPE: PRT
<213> ORGANISM: Artificial Sequence
<220> FEATURE:
<223> OTHER INFORMATION: alignment

<400> SEQUENCE: 267

Phe Asp Lys Val Val Thr Pro Ser Asp Val Gly Lys Leu Asn Arg Leu
1               5                   10                  15

Val Ile Pro Lys Gln His Ala Glu Lys Tyr Phe Pro Leu Asp Ala Ala
            20                  25                  30

Ala Asn Glu Lys Gly Leu Leu Leu Ser Phe Glu Asp Arg Gly Gly Lys
        35                  40                  45

Leu Trp Arg Phe Arg Tyr Ser Tyr Trp Asn Ser Ser Gln Ser Tyr Val
        50                  55                  60

Met Thr Lys Gly Trp Ser Arg Phe Val Lys Glu Lys Arg Leu Asp Ala
 65                  70                  75                  80

Gly Asp Thr Val Ser Phe Cys Arg Gly Ala Ala Asp Ala Thr Arg Asp
                 85                  90                  95

Arg Leu Phe Ile Asp Trp Lys Arg Arg Val Glu
            100                 105

<210> SEQ ID NO 268
<211> LENGTH: 105
<212> TYPE: PRT
<213> ORGANISM: Artificial Sequence
<220> FEATURE:
<223> OTHER INFORMATION: alignment

<400> SEQUENCE: 268

Phe Asp Lys Val Val Thr Pro Ser Asp Val Gly Lys Leu Asn Arg Leu
 1               5                  10                  15

Val Ile Pro Lys Gln His Ala Glu Lys Tyr Phe Pro Leu Asp Ala Ala
                20                  25                  30

Ala Asn Glu Lys Gly Leu Leu Leu Ser Phe Glu Asp Arg Ala Gly Lys
             35                  40                  45

Leu Trp Arg Phe Arg Tyr Ser Tyr Trp Asn Ser Ser Gln Ser Tyr Val
        50                  55                  60

Met Thr Lys Gly Trp Ser Arg Phe Val Lys Glu Lys Arg Leu Asp Ala
 65                  70                  75                  80

Gly Asp Thr Val Ser Phe Cys Arg Gly Ala Ala Asp Ala Ala Arg Asp
                 85                  90                  95

Arg Leu Phe Ile Asp Trp Arg Lys Arg
            100                 105

<210> SEQ ID NO 269
<211> LENGTH: 107
<212> TYPE: PRT
<213> ORGANISM: Artificial Sequence
<220> FEATURE:
<223> OTHER INFORMATION: alignment

<400> SEQUENCE: 269

Phe Asp Lys Val Val Thr Pro Ser Asp Val Gly Lys Leu Asn Arg Leu
 1               5                  10                  15

Val Ile Pro Lys Gln His Ala Glu Lys Tyr Phe Pro Leu Asp Ala Ala
                20                  25                  30

Ala Asn Glu Lys Gly Gln Leu Leu Ser Phe Glu Asp Arg Ala Gly Lys
             35                  40                  45

Leu Trp Arg Phe Arg Tyr Ser Tyr Trp Asn Ser Ser Gln Ser Tyr Val
        50                  55                  60

Met Thr Lys Gly Trp Ser Arg Phe Val Lys Glu Lys Arg Leu Asp Ala
 65                  70                  75                  80

Gly Asp Thr Val Ser Phe Cys Arg Gly Ala Gly Asp Thr Ala Arg Asp
                 85                  90                  95

Arg Leu Phe Ile Asp Trp Lys Arg Arg Ala Asp
            100                 105

<210> SEQ ID NO 270
<211> LENGTH: 107
<212> TYPE: PRT

-continued

```
<213> ORGANISM: Artificial Sequence
<220> FEATURE:
<223> OTHER INFORMATION: alignment

<400> SEQUENCE: 270

Phe Asp Lys Val Val Thr Pro Ser Asp Val Gly Lys Leu Asn Arg Leu
1               5                   10                  15

Val Ile Pro Lys Gln His Ala Glu Lys Tyr Phe Pro Leu Asp Ala Ser
            20                  25                  30

Ser Thr Asp Lys Gly Leu Leu Leu Ser Phe Glu Asp Arg Ala Gly Lys
        35                  40                  45

Pro Trp Arg Phe Arg Tyr Ser Tyr Trp Asn Ser Ser Gln Ser Tyr Val
    50                  55                  60

Met Thr Lys Gly Trp Ser Arg Phe Val Lys Glu Lys Arg Leu Asp Ala
65                  70                  75                  80

Gly Asp Thr Val Ser Phe Gly Arg Gly Val Gly Glu Ala Ala Arg Gly
                85                  90                  95

Arg Leu Phe Ile Asp Trp Arg Arg Pro Asp
            100                 105

<210> SEQ ID NO 271
<211> LENGTH: 104
<212> TYPE: PRT
<213> ORGANISM: Artificial Sequence
<220> FEATURE:
<223> OTHER INFORMATION: alignment

<400> SEQUENCE: 271

Phe Glu Lys Ala Val Thr Pro Ser Asp Val Gly Lys Leu Asn Arg Leu
1               5                   10                  15

Val Ile Pro Lys Gln His Ala Glu Lys Tyr Phe Pro Leu Gln Ser Gly
            20                  25                  30

Ser Ala Ser Ser Lys Gly Val Leu Leu Asn Phe Glu Asp Val Thr Gly
        35                  40                  45

Lys Val Trp Arg Phe Arg Tyr Ser Tyr Trp Asn Ser Ser Gln Ser Tyr
    50                  55                  60

Val Leu Ile Lys Gly Trp Ser Arg Phe Val Lys Glu Lys Asn Leu Lys
65                  70                  75                  80

Ala Gly Asp Ile Val Ser Phe Gln Arg Ser Thr Gly Thr Glu Lys Gln
                85                  90                  95

Leu Tyr Ile Asp Trp Lys Ala Arg
            100

<210> SEQ ID NO 272
<211> LENGTH: 102
<212> TYPE: PRT
<213> ORGANISM: Artificial Sequence
<220> FEATURE:
<223> OTHER INFORMATION: alignment

<400> SEQUENCE: 272

Phe Glu Lys Ala Val Thr Pro Ser Asp Val Gly Lys Leu Asn Arg Leu
1               5                   10                  15

Val Val Pro Lys Gln His Ala Glu Lys His Phe Pro Leu Lys Arg Thr
            20                  25                  30

Pro Glu Thr Pro Thr Thr Thr Gly Lys Gly Val Leu Leu Asn Phe Glu
        35                  40                  45

Asp Gly Glu Gly Lys Val Trp Arg Phe Arg Tyr Ser Tyr Trp Asn Ser
    50                  55                  60
```

```
Ser Gln Ser Tyr Val Leu Thr Lys Gly Trp Ser Arg Phe Val Arg Glu
 65                  70                  75                  80

Lys Gly Leu Gly Ala Gly Asp Ser Ile Leu Phe Ser Cys Ser Leu Tyr
                 85                  90                  95

Glu Gln Glu Lys Gln Phe
            100
```